United States Patent
Konieczka et al.

(10) Patent No.: US 9,944,925 B2
(45) Date of Patent: Apr. 17, 2018

(54) PROCESSES AND HOST CELLS FOR GENOME, PATHWAY, AND BIOMOLECULAR ENGINEERING

(71) Applicant: enEvolv, Inc., Cambridge, MA (US)

(72) Inventors: Jay H. Konieczka, Cambridge, MA (US); James E. Spoonamore, Cambridge, MA (US); Ilan N. Wapinski, Cambridge, MA (US); Farren J. Isaacs, Cambridge, MA (US); Gregory B. Foley, Cambridge, MA (US)

(73) Assignee: ENEVOLV, INC., Cambridge ( * ) Notice: Subject to any disclaimer, the term of this patent is extended or adjusted under 35 U.S.C. 154(b) by 120 days.

(21) Appl. No.: 14/909,184

(22) PCT Filed: Aug. 4, 2014

(86) PCT No.: PCT/US2014/049649
§ 371 (c)(1),
(2) Date: Feb. 1, 2016

(87) PCT Pub. No.: WO2015/017866
PCT Pub. Date: Feb. 5, 2015

(65) Prior Publication Data
US 2016/0186168 A1 Jun. 30, 2016

Related U.S. Application Data

(60) Provisional application No. 61/938,933, filed on Feb. 12, 2014, provisional application No. 61/935,265, filed on Feb. 3, 2014, provisional application No. 61/883,131, filed on Sep. 26, 2013, provisional application No. 61/861,805, filed on Aug. 2, 2013.

(51) Int. Cl.
| | | |
|---|---|---|
| *C12Q 1/68* | (2018.01) | |
| *C12N 15/10* | (2006.01) | |
| *C12N 15/85* | (2006.01) | |
| *C12N 15/11* | (2006.01) | |
| *C12N 15/70* | (2006.01) | |
| *C12N 15/81* | (2006.01) | |
| *C12N 15/63* | (2006.01) | |

(52) U.S. Cl.
CPC ..... *C12N 15/1082* (2013.01); *C12N 15/1079* (2013.01); *C12N 15/111* (2013.01); *C12N 15/70* (2013.01); *C12N 15/81* (2013.01); *C12N 15/85* (2013.01); *C12N 15/63* (2013.01); *C12N 2310/10* (2013.01); *C12N 2310/20* (2017.05); *C12N 2330/31* (2013.01)

(58) Field of Classification Search
None
See application file for complete search history.

(56) References Cited

U.S. PATENT DOCUMENTS

| | | | |
|---|---|---|---|
| 5,316,922 A | 5/1994 | Brown et al. | |
| 5,394,537 A | 2/1995 | Courts et al. | |
| 7,144,734 B2 | 12/2006 | Court et al. | |
| 7,521,242 B2 | 4/2009 | Court et al. | |
| 7,674,621 B2 | 3/2010 | Court et al. | |
| 8,153,432 B2 | 4/2012 | Church et al. | |
| 8,541,229 B2 | 9/2013 | Court et al. | |
| 8,569,041 B2 | 10/2013 | Church et al. | |
| 8,697,853 B2 | 4/2014 | Voytas et al. | |
| 8,859,277 B2 | 10/2014 | Court et al. | |
| 9,273,294 B2 | 3/2016 | Yu et al. | |
| 2003/0199091 A1* | 10/2003 | Kmiec et al. | C12P 19/34 435/455 |
| 2007/0243616 A1 | 10/2007 | Church et al. | |
| 2009/0298117 A1 | 12/2009 | Zhang et al. | |
| 2012/0315670 A1 | 12/2012 | Jacobson et al. | |
| 2016/0272965 A1* | 9/2016 | Zhang et al. | C12N 15/1093 |

FOREIGN PATENT DOCUMENTS

WO 2012001352 A1 1/2012

OTHER PUBLICATIONS

Carr, P. A., "Enhanced Multiplex Genome Engineering Through Co-Operative Oligonucleotide Co-Selection," Nucleic Acids Research, 2012, pp. 1-11.
Costantino, N et al., "Enhanced Levels of Lambda Red-Mediated Recombinants in Mismatch Repair Mutants," PNAS, Dec. 23, 2003, vol. 100, No. 26; pp. 15748-15753.
Dicarlo, J.E., "Genome Engineering in *Saccharomyces cerevisiae* using CRISPR-Cas Systems," Nucleic Acids Research, 2013, pp. 1-8.
Dicarlo, J.E., Yeast Oligo-Mediated Genome Engineering (YOGE), Synthetic Biology, 2013, 2, 741-749.
Hartwich, H et al., "An Easy and Versatile 2-Step Protocol for Targeted Modification and Subcloning of DNA from Bacterial Artificial Chromosomes Using Noncommercial Plasmids," BMC Res. Notes, Mar. 20, 2012, vol. 5; No. 156, pp. 1-6.
Holt, N et al., "Zinc Finger Nuclease-Mediated CCR5 Knockout Hematopoietic Stem Cell Transplantation Controls HIV-1 in vivo," Nat. Biotechnology, Aug. 2010, vol. 28, No. 8; pp. 839-847.
PCT International Searching Report PCT/US2014/49649, dated Dec. 24, 2014, 5 pages.
Jiang, W., "RNA-Guided Editing of Bacterial Genomes using CRISPR-Cas Systems," Nature Biotechnology, 2013, pp. 1-9.
Kern, A et al., "Engineering Primary Metabolic Pathways of industrial Micro-organisms," Journal Biotechnol., Mar. 30, 2007, vol. 129, No. 1, pp. 6-29.
Kang, Y et al., "Knock-Out and Pull-Out Recombineering Protocols for Naturally Transformable Burkholdreia thailandensis and Burkholderia pseudomallei," Nat. Protoc., Feb. 5, 2013, vol. 6, No. 8; pp. 1085-1104.
Mosberg J.A., "Improving Lambda Red Genome Engineering in *Escherichia coli* via Rational Removal of Endogenous Nucleases," PLOS ONE, 2012, vol. 7, No. 9, pp. 1-12.

(Continued)

*Primary Examiner* — James S Ketter

(57) ABSTRACT

The present disclosure provides compositions and methods for genomic engineering.

23 Claims, 4 Drawing Sheets

(56) References Cited

OTHER PUBLICATIONS

Oh, J.H., "CRISPR—Cas9-assisted recombineering in Lactobacillus reuteri," Nucleic Acids Research, 2014, vol. 42, No. 17, pp. 1-11.
Van Pijkeren J.P., "Exploring Optimization Parameters to Increase ssDNA Recombineering in Lactococcus Lactis and Lactobacillus Reuteri," Landes Bioscience, Bioengineered 2012, vol. 3 No. 4, pp. 209-217.
Wang, H., "Programming Cells by Multiplex Genome Engineering and Accelerated Evolution," 2009, Nature, vol. 460, pp. 894-899.
Wang, H., Genome-Scale Promoter Engineering by Coselection MAGE, Nature, 2012, pp. 1-6.
Yu, D., et al., Recombineering with Overlapping Single-Stranded DNA Oligonucleotides: Testing a Recombination Intermediate, PNAS, Jun. 10, 2003, vol. 100, No. 12, pp. 7207-7212.
Binder, S., et al "Recombineering in Corynebacterium Glutamicum Combined with Optical Nanosensors: a General Strategy for Fast Producer Strain Generation," Nucleic Acids Research, 2013, vol. 41, No. 12, pp. 6360-6369.

* cited by examiner

PROCESSES AND HOST CELLS FOR GENOME, PATHWAY, AND BIOMOLECULAR ENGINEERING

PRIORITY

This application is the US national stage of International Patent Application No. PCT/US2014/049649, filed Aug. 4, 2014, which claims benefit of and priority to U.S. Provisional Application Nos. 61/861,805 filed Aug. 2, 2013, 61/883,131 filed Sep. 26, 2013, 61/935,265 filed Feb. 3, 2014, and 61/938,933 filed Feb. 12, 2014, each of which is hereby incorporated by reference in its entirety.

FIELD OF THE INVENTION

The invention relates to, inter alia, methods and compositions for genome-scale editing of genetic information.

BACKGROUND

Successful genomic and pathway engineering requires that metabolic flux be increased through select pathways, while not substantially interfering with viability and/or growth of the organism, or a desired phenotype. This can be especially pertinent for substrates or intermediates of the desired pathway that are involved in core or primary metabolism, or for branch intermediates involved in more than one pathway. Stephanopoulos, Metabolic Fluxes and Metabolic Engineering, *Metabolic Engineering* 1, 1-11 (1999). In fact, genetic alterations, or combinations of genetic alterations, that increase metabolic flux through a desired pathway are difficult to predict, limiting the usefulness of rational engineering approaches. Kern A, et al., Engineering primary metabolic pathways of industrial microorganisms, *J. Biotechnology* 129: 6-29 (2007). Further, it is often impractical to generate random and discrete mutational events in vivo and screen or select for improved metabolic flux or biomolecular function.

Methods are needed for screening the genetic space of a host organism to identify changes in endogenous genes and/or heterologous recombinant genes that provide improved phenotypes, such as in metabolic flux and balance, so as to improve or optimize microbial processes, including production of desired chemicals and biomolecules at industrial levels, or bioremediation applications.

SUMMARY OF THE INVENTION

In various aspects, the invention provides methods for genomic and pathway engineering. The methods are useful in *E. coli*, as well as bacterial cells that are harder to genetically manipulate but are otherwise valuable for production of chemicals, including *Bacillus* sp. (e.g., *Bacillus subtilis*), Streptomycetes (e.g., *Streptomyces avermitilis, Streptomyces coelicolor, Streptomyces lividins, Streptomyces cinnamonensis, Streptomyces collinus*, etc.), Cyanobacteria (e.g., *Synechocystis* spp., *Prochlorococcus* spp., *Nostoc punctiforme, Calothrix* spp., *Aphanizomenon flos-aquae, Arthrospira platensis*, etc.), and Corynebacteria (e.g., *Corynebacteria glutamicum, Corynebacteria ammoniagenes*, etc.), among others. The methods are further applicable in some embodiments to Eukaryotic cells, such as yeasts (e.g., *Pichia* sp., *Saccharomyces* sp., *Schizosaccharomyces* sp., *Kluyveromyces* sp, etc.), filamentous fungi (e.g., *Neurospora* sp. and *Aspergillus* sp., *Penicillium*, etc.), algae (e.g., *Botryococcus, Chlorella, Dunaliella, Gracilaria, Pleurochrysis*, and *Sargassum*, etc.), and plants.

In various aspects, the invention is applicable to phenotype engineering, including but not limited to: change in carbon substrate utilization, increased cell growth rate, increased production of a desired chemical, redox cofactor balance, reduced production of one or more undesired byproducts, increased resistance to industrial fermentation, and increased recombinant protein production, among others. In some embodiments, the phenotype relates to pathway engineering, such as where metabolic flux through a core or primary metabolic pathway is significantly altered (e.g., significantly altered as compared to wild type strain, an unengineered strain, or a starting strain), including alteration of metabolic flux through one or more intermediates that represent metabolic branch points. In various embodiments, the invention is applicable to introducing and balancing of heterologous recombinant enzyme activity with endogenous metabolism, to limit effects on viability and growth, for example. In some embodiments, the phenotype relates to engineering alterations among one or more proteins, such as, by way of illustration, enzymes, for improved biochemical or biophysical properties.

In various aspects, the invention provides methods for pathway engineering, in which metabolic flux is altered through one or more intermediates of glycolysis, pentose phosphate pathway, TCA cycle, one or more secondary biosynthesis pathways (e.g., amino acid or nucleotide biosynthesis pathway), the mevalonate or non-mevalonate pathway, pathways involved in sulfur or nitrogen metabolism, and others. The invention relates to, in various embodiments, engineering cells to result in one or more of increased or diversified carbon substrate utilization, increased or maintained growth rate, modified enzyme activity at metabolic branch points, decreased metabolic flux through one or more competing secondary pathways and/or increase in flux through a desired secondary biosynthetic pathway, balanced cellular redox chemistry (e.g., redox cofactor balance), balanced heterologous enzyme activity with the endogenous metabolism, including reduction in toxic intermediates, increased resistance to environmental (e.g., industrial) conditions, increased recombinant protein production, and increased yield of desired product.

In various aspects, the invention engineers cells using one or a combination of recombineering systems. The recombineering systems each offer distinct advantages in engineering cells. In some embodiments, the method produces a library of mutants cells using a ssDNA recombinase system, which may include a single-stranded annealing protein (SSAP), such as the λ Red recombineering system (e.g., Beta protein) or RecET system (e.g., recT), or homologous system, which in some embodiments offers advantages in identifying pathways, genes, or regions of genes for alteration, as well as targeting specific regions for genetic diversification. The λ Red operon encodes ssDNA annealing protein Beta, which promotes annealing of single stranded oligonucleotides at the lagging strand of the replication fork. The λ Red recombineering system, as with other SSAP systems, may further involve a deletion, inactivation, or reduction in mismatch repair (e.g., deletion, inactivation, or reduction in activity or level of mutS). Such a system is useful for engineering *E. coli* and other prokaryotic systems, and may be engineered into other species described herein. Specifically, an oligonucleotide library designed to screen for beneficial mutations (or combinations of mutations) in a target genetic "space" is introduced into the organism, and a desired phenotype identified. The genetic "space" includes identified target pathways (e.g., a primary metabolic pathway and/or one or more secondary competing or biosynthetic pathways), target genes, and the nature and diversity of alterations to screen, including changes to gene regulatory sequences such as promoters and transcriptional enhancer sequences, ribosomal binding sites and other sites relating to the efficiency of transcription, translation, or RNA processing, as well as coding sequence mutations that control the activity, post-translational modification, or turnover of the encoded proteins. Oligonucleotide library design strategies to leverage the power of this method are described in detail herein. In some embodiments, these aspects employ a single stranded DNA annealing protein system with mismatch repair inactivation to identify target genes to be engineered, that is genes that are optimally up- or downregulated in activity or expression. Subsequently target genes or sequences are honed with a more targeted or defined oligonucleotide library, or by a complementary approach to introduce replacement sequences by, for example, producing double-strand breaks in some cases with homologous recombination. Such alternative systems include CRISPR/Cas, ZFNs, BurrH binding domain or BuD, derived nucleases, TALEs, and TALENs, among others, to introduce double-strand breaks at desired location in the host genome to enhance allelic replacement. In this manner, the invention uses both rational and random design aspects to engineer cells toward desired phenotypes.

In some embodiments, the genetic or genomic engineering systems (e.g., recombineering or site-specific programmable nucleases such as Cas, TALENs, ZFNs, or BuDs) are inducible or controlled, such that the engineered strain remains genetically stable.

Other aspects of the invention provides cells that are efficient for recombineering, by targeting the endogenous components of the cell, or providing heterologous components described herein, and screening for increased recombineering efficiency.

In other aspects, the invention is applicable to prokaryotic and eukaryotic organisms that are more difficult to genetically manipulate than *E. coli*. For example, the invention allows for target genes or genomic sequence variants to be introduced into a recombineering- (e.g., MAGE-) competent organism where engineering can be performed, e.g. *E. coli*, using a vector that is compatible for replication in the recombineering or MAGE-competent organism (such as *E. coli*) and replication in the desired host, or replication in the recombineering or MAGE-competent organism and conjugation into the desired host; and after undergoing one or more cycles of engineering in the recombineering or MAGE-competent organism, the engineered vectors are introduced into the host cell of choice. In various aspects, the vector confers one or more selectable markers for both the recombineering or MAGE-competent organism and the target organism, such that following transformation (or transfection, conjugation, etc.), successful transformants can be selected from unsuccessful transformants.

In some aspects and embodiments of the invention employ a vector that encodes a component of a site-specific programmable nuclease system (e.g., CRISPR/Cas9, TALEN, ZFN, BuD, or homologous or analogous system), which is coupled, e.g. in the same vector (e.g., a plasmid), to a donor sequence for a locus targeted by the programmable nuclease. The donor nucleic acids are not susceptible to cutting by the programmable nuclease, described herein, that is introduced into the system. Coupling the site-specific programmable nuclease system to the donor sequence on the same DNA results in a scarless method for selecting recombinants and obviates the need for an additional selectable marker. Thus, recombination with the homologous target region mutated at the wild-type locus targeted by the site-specific nuclease permits the cell to escape restriction by the programmed nuclease system. In other words, recombination with the mutated sequence frees the organism from the genomic instability caused by the programmable site-specific nuclease.

In still other aspects, the invention provides methods for engineering the programmable nuclease system itself by using the recombineering system to replace or alter the subsequence of the vector that specifically targets the host genomic locus (or loci) such that a new genomic locus (or loci) will be targeted by the programmable nuclease (e.g., CRISPR/Cas, ZFNs, BurrH binding domain or BuD, derived nucleases, TALEs, and TALENs).

In various embodiments, the invention provides engineered cells made through the processes described herein, and provides methods of producing desired chemical products through fermentation of the engineered cells. For example, the methods and cells may, in various embodiments, produce a biofuel such as methanol, ethanol, propanol, butanol, or isobutanol, or a compound having a C2 to C6 carbon skeleton (for example) ethylene, acetate, methacrylic acid, acrylate, lactic acid, isoprene, propanoic acid, hydroxypropanoic acid, propylene, propane, propene, butadiene, butanediol, butanone, butyric acid, butyrolactone, butanal, putrescine, fumarate, malate, levulinic acid, pentanoic acid, caproic acid, cyclohexanone, or adipate, among others. In some embodiments, fatty acid derivatives, which may serve as valuable long-chain carbon molecules (e.g., alkanes, alkenes) of high energetic value may be produced. In some embodiments, the compound is a product of secondary metabolism or biosynthetic pathway, and may be a fatty acid, a natural or unnatural amino acid, lipid, lipopeptide, antibiotic, nucleotide, pharmaceutical or intermediate thereof, a polynucleotide (e.g. RNA), or a terpene or terpenoid. In some embodiments, the compound is a recombinant protein such as an antibody or insulin.

Additional aspects and embodiments of the invention will be apparent from the following detailed description.

DETAILED DESCRIPTION OF THE INVENTION

Figure 1:
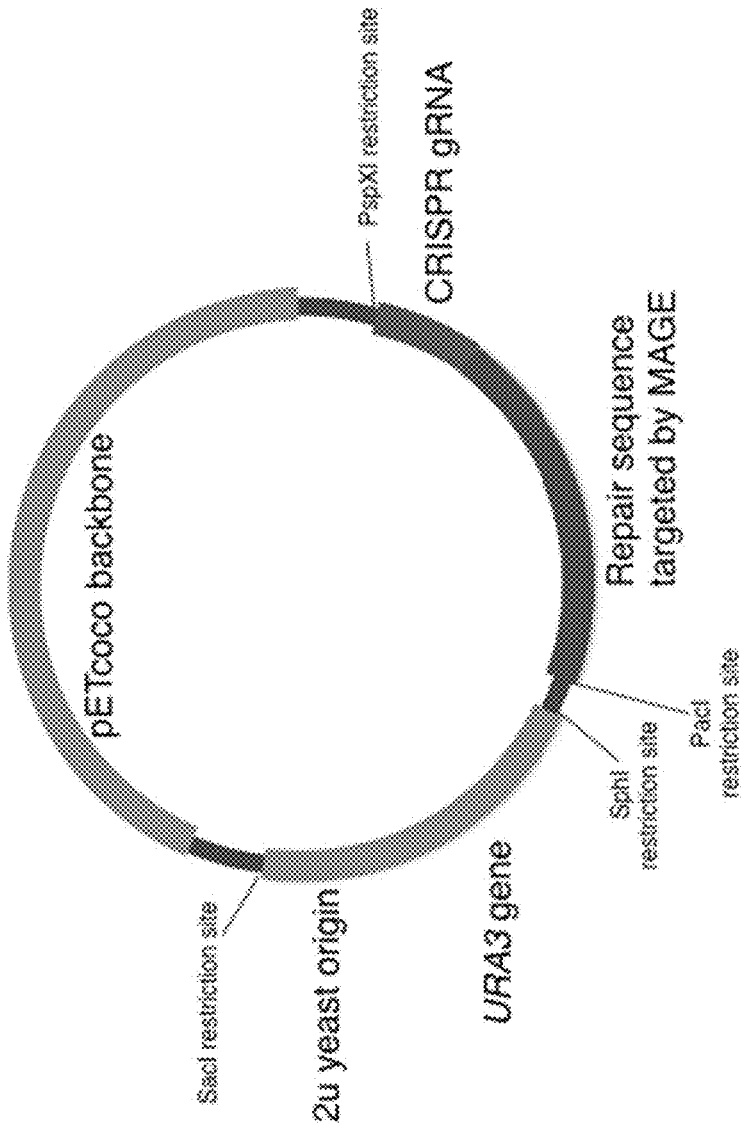
FIG. 1 shows shuttle-MAGE plasmid design. The Shuttle-MAGE plasmid contains origins of replication and selectable marker(s) for the target organism (2u and URA3 in orange), a DNA fragment homologous to the region in the target organism targeted for MAGE mutagenesis (green), and a CRISPR guide RNA expression cassette designed to guide the Cas9 endonuclease to digest the target genome at a specified site (red). The vector backbone (blue) allows the plasmid to be maintained in MAGE-competent *E. coli* cells under a selectable marker.

In various aspects, the invention provides methods for engineering a cell for a desired phenotype. In some embodiments, the method comprises introducing an oligonucleotide library into a population of cells, where the cells express a single-stranded annealing protein (SSAP) system and/or recombinase that promotes recombination of single stranded oligonucleotides. In some embodiments, the oligonucleotide library targets sequences that control gene expression in the cell (e.g., 5' and/or 3' untranslated sequences), and/or may target protein coding sequences (e.g., including start and stop codons). Cells having the desired phenotype may then be screened or selected, and genes with altered expression as a result of oligonucleotide incorporation can be identified for further engineering. Further engineering in various embodiments can be conducted by a second oligonucleotide library designed for diversification of the identified genes, and/or by targeting at least one gene with a gene editing system, such as a programmable nuclease as described herein. With each iterative round (or intermittently in a substantially continuous process), cells are selected having an improvement in the desired phenotype.

While the invention provides for selecting for any desired phenotype, the desired phenotype can be one or more of a change in carbon substrate utilization, increased cell growth rate, increased production of a desired chemical, redox cofactor balance, reduced production of one or more undesired byproducts, increased resistance to industrial fermentation, and increased recombinant protein production, among others.

The various steps for diversifying the genetics of the host cell population can target endogenous genes and/or heterologously expressed genes, including enzymes expressed as part of a biosynthetic pathway or recombinant proteins for production.

As cells with the desired phenotype are selected, genes altered by the first or subsequent oligonucleotide libraries can be identified by transcriptional (e.g., microarray) or translational analysis or by DNA sequencing and compared to a reference genomic sequence (e.g., the starting sequence).

In some embodiments, the desired phenotype is increased production of a desired chemical, and which may be the result of a primary metabolic pathway and a downstream biosynthetic pathway (which may further comprise at least one heterologously expressed gene in some embodiments). In some embodiments, the cell expresses a heterologous biosynthetic pathway that alters flux through one or more of glycolysis, pentose phosphate pathway, TCA cycle, MVA or MEP pathway.

In various aspects, the invention provides methods for genomic and pathway engineering. The invention is applicable to pathway engineering where metabolic flux through a core or primary metabolic pathway is altered (e.g., significantly altered as compared to wild type, unengineered, or starting strain), including where flux at a metabolic branch point is altered. In these or other embodiments, the invention is applicable to balance one or more secondary pathways, that is, to reduce flux from competing secondary pathways while enhancing flux to a desired biosynthetic pathway. In various embodiments, the invention is applicable to introducing and balancing of heterologous recombinant enzyme activity with endogenous metabolism, to limit effects on viability and cell growth (for example). In various aspects, the invention provides methods for pathway engineering, in which metabolic flux is significantly altered through one or more intermediates of glycolysis, pentose phosphate pathway, TCA cycle, one or more biosynthesis pathways (e.g., for production of natural or unnatural amino acids, nucleotides, lipids, fatty acids, antibiotics, among others), the MEP or MVA pathway, pathways involved in sulfur or nitrogen metabolism, and others. Thus, the invention relates to, in various embodiments, engineering cells to increase one or more of carbon substrate utilization, increase or maintain cell growth rate, modify enzyme activity at metabolic branch points, decrease metabolic flux through one or more competing secondary pathways, balance cellular redox chemistry (e.g., redox cofactor balance), balance heterologous enzyme activity with the endogenous metabolism, including reduction in toxic intermediates, increase resistance to environmental (e.g., industrial) conditions, and increase recombinant protein production.

In some embodiments, the invention engineers cells through a SSAP system and/or recombinase that promotes recombination of single stranded oligonucleotides, such as the Beta protein of the λ Red recombineering system or the RecT protein of the homologous RecET system, or a homologous system. In such embodiments, the host cell expresses the ssDNA annealing protein Beta, or derivative or homolog thereof. These proteins promote annealing of single stranded oligonucleotides at the lagging strand of the replication fork. These embodiments may further involve a deletion, inactivation, or reduction in a mismatch repair protein. For example, these embodiments can employ a deletion, inactivation, or reduction in activity or level of mutS, or homolog thereof in the host organism of choice (see, e.g. U.S. Pat. Nos. 7,144,734, 7,521,242, and 7,674, 621 and US Patent Publication No. 2005/0079618, the contents of which are hereby incorporated by reference). This system is useful for engineering *E. coli* and similar bacterial systems. Specifically, an oligonucleotide library designed to screen for beneficial mutations (or combinations of mutations) in a target genetic "space" is introduced into the organism by transformation (e.g., by electroporation (e.g. Lithium Acetate or PolyEthyleneGlycol), chemical transformation, ballistic transformation (e.g. gene gun), pressure induced transformation, mechanical shear forces induced, for example, in microfluids, and carbon nanotubes, nanotube puncture (such as carbon nanotube arrays), induced natural competence mechanisms of an organism, merging of protoplasts, and conjugation with *Agrobacterium*) of a cell population, and a desired phenotype is identified.

The genetic "space" includes selected target pathways, target genes, and the nature and diversity of alterations to screen, including changes to gene regulatory sequences such as promoters and transcriptional enhancer sequences, ribosomal binding sites and other sites relating to the efficiency of transcription, translation, or RNA processing, as well as coding sequence mutations that control the activity, post-translational modification, or turnover of the encoded protein. In some embodiments, the oligonucleotide library targets start and/or stop codons, and splice sites. Alternative genomic engineering platforms that may be used, alternatively or in combination with the λ Red or homologous or analogous system as described herein, include CRISPR/Cas9, ZFNs, BurrH binding domain or BuD, derived nucleases, TALEs, and TALENs.

Thus, in some embodiments, the host cell is an *E. coli* possessing the λ Red recombineering system or the RecET system (e.g., the Beta gene or recT gene) and lacking the mismatch repair gene mutS. The λ Red System has been referred to as Multiplexed Automated Genome Engineering (MAGE) and is a process by which the genome of a cell is reprogrammed to perform desired functions via a form of accelerated, directed evolution (Wang et al., *Nature*, 460: 894-898 (2009); Church et al., U.S. Pat. No. 8,153,432, the contents of which are hereby incorporated by reference in their entireties). During MAGE cycling, Beta proteins recombine oligos designed to target key genomic regions for highly specific mutations. The deletion of mutS may further improve recombination efficiency by avoiding the mismatch repair machinery.

At each round of transformation, without wishing to be bound by theory, protein Beta binds to, protects, and promotes strand annealing of the ssDNA oligomers. This may occur in the lagging strand during DNA replication where the oligomers are thus incorporated into the duplicated genome. Without wishing to be bound by theory, the deletion of the mismatch repair gene mutS in the recombineering strain prevents the reversion of some of the non-homologous genetic changes introduced by the ssDNA oligonucleotide pool. Thus after each cycle of transformation, genetic diversity is greatly increased in focused regions of the genome according to the targeted design of the oligonucleotide pool. After some number of cycles of transformation (determined by the size of the oligomer pool, for example), selection or screening is performed for the desired genomic characteristic and the process is repeated. In some embodiments, the process is conducted in a continuous fashion.

In some embodiments, the host cell or strain has one or more genetic modifications to protect oligos following entry into the cell. Knocking out four potent ssDNA exonucleases in *E. coli* improves oligomediated allelic recombination frequency when low concentrations of oligos are used (Mosberg, J. A., et al., *PloS One*, 7(9), e44638). ExoVII is a nuclease that degrades the ends of single-stranded DNA (ssDNA) oligonucleotides and double-stranded DNA (dsDNA) cassettes. Removing this nuclease improves both recombination frequency and the inheritance of mutations at 3' ends of ssDNA and dsDNA. Removing ExoVII and the set of four exonucleases (RecJ, ExoI, ExoX, and Lambda Exo) may improve recombineering performance. Thus, the host strain may have a deletion or inactivation in ExoVII, and one or more (or all) of RecJ, ExoI, ExoX, and Lambda Exo.

In some embodiments, co-selection will be applied to increase the rate at which surviving cells will contain the desired mutations. This may be executed by including oligos that introduce or revert mutations in a counter-selectable marker positioned in the genome or on a plasmid along with the oligos targeting other genomic location(s). This may include but is not limited to TolC, as described in (Gregg C J, et al. Nucleic Acids Res. 42(7):4779-90 (2014), the contents of which are hereby incorporated by reference).

In some embodiments, the SSAP system and/or recombinase that promotes recombination of single stranded oligonucleotides is first used to identify primary and secondary pathway targets. For example, transcriptional and/or translational sequences can be broadly disrupted and/or enhanced by oligonucleotide design, and the transcriptional and/or translational state of cells showing improvement in the desired phenotype (e.g., chemical production) evaluated to identify genes that are frequently upregulated versus genes that are frequently downregulated or shut off completely, or identify frequent or optimal combinations of the above. Transcriptional effects can be induced with the oligonucleotide library by exchanging or interfering with gene promoters or transcriptional binding sites. Translational effects can be induced by the oligonucleotides by enhancing or interfering with ribosomal binding sites, such as the Shine-Dalgarno sequence, or the Kozak sequence, or DNA sequences 5' or 3' of the ORF that affect RNA degradation rate, as well as start and stop codons. These identified genes, optionally including genes catalyzing adjacent or competing reactions, can be identified by screening or a selection system with a second round to identify more finely tuned expression modulation or amino acid substitution events that increase product yield.

Alternatively or in addition, subsequent rounds employ CRISPR/Cas9, TALENS, ZFNs, BurrH binding domain or BuD, derived nucleases, or homologous or analagous systems for refining selected strains. Such systems can be used to induce double-strand breaks (DSB) and increase homologous recombination efficiency.

For example, a double-strand break (DSB) or single-strand break or nick can be created by a site-specific nuclease such as a zinc-finger nuclease (ZFN) or TAL effector domain nuclease (TALEN) or BurrH binding domain (BuD)-derived nucleases, or using the CRISPR/Cas9 system with an engineered crRNA/tracrRNA (or synthetic guide RNA) to guide specific cleavage. See United States Patent Publications 2003/0232410; 2005/0208489; 200510026157; 2005/0064474; 2006/0188987; 2009/0263900; 200910117617; 2010/0047805; 2011/0207221; 2011/0301073 and International Publication WO 2007/

014275, the disclosures of which are incorporated by reference in their entireties for all purposes. Transgene insertion can be accomplished via homology-directed repair (HDR) processes, which require the inserted transgene to include regions of homology to the site of insertion (cleavage). Alternatively, targeted integration can occur by homology-independent non-homologous end joining (NHEJ) DNA repair machinery. Thus, in these embodiments, the recombineering strain expresses an endogenous or heterologous ZFN, BuD, TALEN, or CRISPR/Cas9. Donor nucleic acid libraries can be designed for this system as described in detail herein.

For example, in certain embodiments, the process employs a double-strand break system as described in US 2013/0326645, which is hereby incorporated by reference in its entirety. In this system, the donor molecules may be integrated into the endogenous locus via homology-independent mechanisms (e.g., NHEJ), and may employ a double-stranded donor comprising a transgene or synthetic DNA of at least 1 kb in length and nuclease target site(s) 3' and/or 5' of the transgene for in vivo cleavage. The nuclease target site(s) used to cleave the donor are not re-created upon integration of the transgene, for example when a spacer between paired target sites is not present in and/or does not exhibit homology to an endogenous locus. The donor molecule may be, for example, a plasmid or a DNA sequence incorporated within a plasmid. In certain embodiments, the donor DNA is integrated following nuclease-mediated cleavage of the endogenous locus. Such processes can employ donor sequences of up to about 20 kb, and in various embodiments employ donor sequences of from about 50 bases to about 10.000 bases, or from about 100 bases to about 5,000 bases, or about 200 bases to about 2,000 bases, or about 200 bases to about 1000 bases.

Double-strand breaks (DSB) or single-strand breaks (nicks) in the genome of the target cell may be created by any mechanism. In certain embodiments, the DSB or nick is created by one or more (e.g., a dimerizing pair of) zinc-finger nucleases (ZFNs), fusion proteins comprising a zinc finger binding domain, which is engineered to bind a sequence within the region of interest, and a cleavage domain or a cleavage half-domain. In other embodiments, the DSB or nick is created by one or more TALE DNA-binding domains (naturally occurring or non-naturally occurring) fused to a nuclease domain (TALENs). In other embodiments, the DSB or nick is created by one or more BurrH binding domains or BuD-derived nucleases, which is engineered to cleave a sequence within the region of interest. In still further embodiments, cleavage or nicking is performed using a nuclease system such as CRISPR/Cas with an engineered crRNA/tracr RNA or crRNA/tracr RNA combined into a single synthetic guide RNA targeting the desired genomic or extra-chromosomal sequence.

The genetic components of CRISPR/Cas9, as well as the structural requirements for the crRNA/tracrRNA or synthetic guide RNA are described in, for example, PCT/US2013/032589, publication number: WO2013176772 (describing, inter alia, the use of CRISPR/Cas9 with a single combined crRNA/tracrRNA system, known as a guide RNA); Jinek, et al. (2012). A programmable dual-RNA-guided DNA endonuclease in adaptive bacterial immunity. *Science,* 337(6096), 816-821; Mali, et al. (2013). CAS9 transcriptional activators for target specificity screening and paired nickases for cooperative genome engineering. *Nature Biotechnology.* doi:10.1038/nbt.2675; Jiang, et al. (2013). RNA-guided editing of bacterial genomes using CRISPR-Cas systems. *Nature Biotechnology.* doi:10.1038/nbt2508; Dicarlo, at al. (2013). Genome engineering in *Saccharomyces cerevisiae* using CRISPR-Cas systems. *Nucleic Acids Research.* doi:10.1093/nar/gkt135; Gong, et al. (2013). Multiplex Genome Engineering Using CRISPR/Cas Systems. *Science,* 339(6121), 819-823. doi:10.1126/science.1231143; Qi, et al.; (2013). Repurposing CRISPR as an RNA-guided platform for sequence-specific control of gene expression. *Cell,* 152(5), 1173-1183. doi:10.1016/j.cell.2013.02.022; Esvelt, at al. (2013). Orthogonal Cas9 proteins for RNA-guided gene regulation and editing. *Nature Methods,* 10(11), 1116-1121. doi:10.1038/nmeth.2681; Gaj, et al. (2013). ZFN, TALEN, and CRISPR/Cas-based methods for genome engineering. *Trends in Biotechnology,* 31(7), 397-405. doi: 10.1016/j.tibtech.2013.04.004, the contents of which are hereby incorporated by reference in their entireties.

In some embodiments, the invention provides a method for engineering a cell for increased recombineering potential (as well as cells provided by such method), comprising: introducing an oligonucleotide library into said cell, and selecting for increased recombineering potential. Increased recombineering potential may be determined, for example, by introducing an oligonucleotide directing entry of a premature stop codon in a marker gene.

Recombineering strains may be created through initial genetic modifications to protect and promote ssDNA annealing or homologous recombination efficiency and avoid the mismatch repair system. The suitability of any particular host cell or strain for recombineering can be assessed using a reporter or selection system. For example, candidate host cells or strains are subjected to cycles of genomic engineering using an oligo-pool or pool of mutants for recombination designed to introduce mutations into endogenous or heterologous genes that control these processes. Exemplary target genes are described below for bacterial and yeast systems for example, and other prokaryotic and eukaryotic counterparts are known. The number of initial cycles can be determined according to the efficiency of the parent strain and the number of allelic targets. To assess recombineering efficiency, one cycle is performed with a single oligo designed to replace a premature stop codon in a gene for one or more selection marker(s) in the host genome or on a plasmid (e.g., a fluorescent or luminescent reporter protein, or other gene creating an easily observable or quantifiable phenotype); and after selection for strains capable of successfully introducing the stop codon, quantifying specificity and efficiency of the replacement. Promising strains, e.g. those demonstrating more efficient allelic replacement than strains from the previous cycle, are then recursively applied to the process. Cycling with oligos targeting genes that effect ssDNA recombination and mismatch repair, or homologous recombination, in the organism of choice, generates a diverse population of organisms with a spectrum of recombineering efficiencies. Selection for strains with increasingly efficient allelic replacement machinery for reintroduction to the pipeline may continue until replacement reaches a plateau, where there is no quantitative improvement in efficiency.

In recombineering strains, recombination may be mediated by phage-derived proteins from the λ Red system or RecE/RecT from the Rac prophage of *E. coli*. The λ Red recombination functions are encoded by an operon containing three genes, gamma, beta, and exo, although only the beta gene is required for oligonucleotide incorporation. The RecET system is a member of the same superfamily, and the λ Red Exo/Beta and RecE/RecT protein pairs are functionally equivalent. Beta and RecT are SSAPs that bind and protect ssDNA, and Beta is capable of efficient recombination with ssDNA oligos by promoting annealing of complementary ssDNA at the replication fork. ssDNA recombinases other than or related to Beta and RecT, have been described. Sequence analysis of diverse SSAPs and/or recombinases shows at least six families among at least three evolutionarily distinct superfamilies: Rad52-like (of which λ Red Beta, Sak, and Erf are members), Rad51-like (e.g., Sak4), and Gp2.5-like, each with distinct sequence profiles and folds. Datta et al., *PNAS USA*, 105:1626-31 (2008); Lopes, A., *Nucleic Acids Research*, 38(12), 3952-3962. doi:10.1093/nar/gkq096, which are hereby incorporated by reference in their entirety. Specifically, recombineering strains can be engineered as follows.

In various embodiments, the host cell or stain encodes and expresses one or more of a SSAP and/or recombinase or variant from the three superfamilies described above. In this context, the term "variant" means that the variant comprises an amino acid sequence with at least about 50%, at least about 60%, at least about 70%, at least about 80%, at least about 85%, at least about 90%, at least about 95%, at least about 96%, at least about 97%, at least about 98%, or at least about 99% identity to at least one of the SSAPs and/or recombinases.

In some embodiments, yeast strains with higher recombineering efficiency with single stranded oligonucleotides are prepared, using a library of oligonucleotides that alter the expression (transcription and/or translation), and/or coding regions, of one or more (or all) of Rad52, Rad51, Rad59, and Rad54, among others genes. Thus, the library of oligonucleotides target for mutations the 5' and/or 3' non-coding sequences, intron sequences (including splice sites), and/or coding sequences of these genes, and the yeast strains selected for recombineering efficiency as described above. In some embodiments, programmable nuclease systems as referenced above are used to target mutations in these genes, for example, as described above by coupling the heterologous system with donor DNA on a single vector.

In yeast, Rad52 may also function independently of the RecA ortholog, Rad51. In yeast, nearly all homologous recombination pathways begin with resection of dsDNA to generate 3'-terminated ssDNA, followed by the binding of RPA and Rad52, and its paralog Rad59. RAD52 binds ssDNA during recombination and also shows a quaternary organization similar to those of RecT/Redβ and ERF, and may be used in the invention in various embodiments.

The RPA-Rad52-Rad59-ssDNA complex can participate in either Rad51-ssDNA filament formation and the canonical gene conversion pathway or Rad52-mediated (and Rad51-independent) single-strand annealing. This choice is primarily controlled by Rad51, but is moderated by Rad59 and other cellular proteins. The competition is dynamic and reversible, and the pathway chosen for DSB repair is likely determined by DNA target availability and protein availability. Rad59 enhances DNA annealing by Rad52 and increases the likelihood of entering the SSA pathway. Overexpression of *S. cerevisiae* wild-type Rad52 increases recombination rates of dsDNA, and it has the opposite effect with single-strand oligo-mediated AR. When Rad51 and Rad54 are overexpressed together, there is a dramatic increase in oligo-mediated AR, which is further elevated in the absence of Rad52. This system may be engineered as described above to improve the host cell's efficiency for recombineering.

In this manner, aspects of the invention allow for essentially any host cell to have recombineering potential. In various embodiments, the cell is a eukaryotic and/or prokaryotic cell, including bacterial, yeast, algal, plant, insect, and/or non-human mammalian cells, or immortal cell lines. For example, the host cell may be *Escherichia coli, Saccharomyces cerevisiae, Pichia pastoris, Saccharomyces castellii, Kluyveromyces lactis, Pichia stipitis, Schizosaccharomyces pombe. Chlamydomonas reinhardtii, Arabidopsis thaliana,* or *Caenorhabditis elegans*. In some embodiments the cell is a bacterial cell, such as *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp. and *Pantoea* spp. In some embodiments the cell is a Cyanobacterial cell, such as *Synechocystis* spp., *Prochlorococcus* spp., *Nostoc punctiforme, Calothrix* spp., *Aphanizomenon flosaquae, Arthrospira platensis*, etc. The bacterial cell can be a Gram-negative cell such as an *E. coli*, or a Gram-positive cell such as a species of *Bacillus*. In other embodiments, the cell is a fungal cell such as a yeast cell, e.g., *Saccharomyces* spp., *Schizosaccharomyces* spp., *Pichia* spp., *Paffia* spp., *Kluyveromyces* spp., *Candida* spp., *Talaromyces* spp., *Brettanomyces* spp., *Pachysolen* spp., *Debaryomyces* spp., *Yarrowia* spp., and industrial polyploid yeast strains. Preferably the yeast strain is a *S. cerevisiae* strain or a *Yarrowia* spp. strain. Other examples of fungi include *Aspergillus* spp., *Pennicilium* spp., *Fusarium* spp., *Rhizopus* spp., *Acremonium* spp., *Neurospora* spp., *Sordaria* spp., *Magnaporthe* spp., *Allomyces* spp., *Ustilago* spp., *Botrytis* spp., and *Trichoderma* spp. In other embodiments, the cell is an algal cell or a plant cell (e.g., *A. thaliana, C. reinhardtii, Arthrospira, P. tricomutum, T. suecica, P. carterae, P. tricomutum, Chlorella* spp., such as *Chlorella vulgaris*). Target cells can include transgenic and recombinant cell lines, including Chinese Hamster Ovary cells (CHO).

In various embodiments, the host cell or strain, in addition to having a SSAP system and/or recombinase that promotes recombination of single stranded oligonucleotides as described, has one or more nucleic acids for inhibiting a mismatch repair system. While these systems can be inactivated by a more permanent genetic deletion or mutation event, alternatively, the systems can be controlled by expressed inhibitor nucleic acid, which in some embodiments is inducible to render recombineering an inducible phenotype. In other embodiments, inhibitory nucleic acids are not encoded by the cell, but are provided exogenously (e.g., transiently) to allow recombineering to take place. Inhibitory nucleic acids include, but are not limited to, antisense oligonucleotides, antagomirs, and RNAi-related sequences (e.g., short hairpin RNA (shRNA), microRNA (miRNA) and small interfering RNA (siRNA)) that target mismatch repair genes within a target cell and thereby decrease expression of the mismatch repair gene in the cell. Mismatch repair genes that can be targeted include but are not limited to, for example, one or more of Msh2, Msh3, Msh6, Mlh1, Mlh2, and/or Pms1.

The mismatch repair (MMR) system is primarily responsible for correcting errors following replication, but it also directly takes part in homologous recombination by rejecting recombination partners with insufficient homology. The proteins responsible for initiation of *E. coli* mismatch repair are MutS and MutL, which function as homo-oligomers. MutS is responsible for mismatch recognition and MutL serves to interface mismatch recognition by MutS to activation of downstream activities. Eukaryotes have at least two MutS heterodimers that share MSH2 as a common subunit: MSH2-MSH6 and MSH2-MSH3. The MSH2-MSH6 heterodimer mainly recognizes single nucleotide substitutions and small loops of 1 or 2 bases, while the MSH2/MSH3 pair has greater affinity for larger loops of 2-5 unpaired nucleotides. Three eukaryotic MutL heterodimeric complexes have been identified with MLH1 serving as a common subunit: MLH1-PMS2, MLH1-PMS1, and MLH1-MLH3. MLH1-PMS2 is the primary MutL activity in human mitotic cells and supports repair initiated by either MutS heterodimer.

Avoidance of the MMR system in *E. coli* recombineering is substantially more effective in strains lacking MMR machinery, at the cost, or benefit depending on perspective, of higher overall mutation rates. See, e.g., and US Patent Publication No. 2005/0079618, the contents of which are hereby incorporated by reference. Indeed temporary suppression of MMR is an effective strategy for enhancing gene-editing efficiency in many cells. Using short-hairpins to suppress MSH2 expression allows for large increases in allelic recombination efficiency. Transient suppression of MSH2 by shRNA is very effective for base substitutions, particularly for the simultaneous substitution of 3-4 bases rather than 1 or 2. Transient knockdown of the downstream MMR gene, Mlh1, rendered ES cells permissive for oligo-mediated single base pair alterations. Other factors at the interface of homologous recombination and mismatch repair may also markedly contribute to increased allelic recombination efficiency. For example, oligo-mediated targeted mutagenesis by Rad51/54 in early mouse embryos is enhanced by inhibition of the homologous recombination partners Ku70/86. Numerous other interactions exist that could potentially offer subtle or even dramatic improvements. For example, disassembly of the Rad51-ssDNA filament is controlled by the Srs2 helicase and Rad52-mediated annealing between divergent homologous sequences is subjected to heteroduplex rejection by the Sgs1 helicase. The connection between these two processes can also explain, without wishing to be bound by theory, why deletion of RAD54, which promotes stabilization of Rad51-ssDNA filaments and DNA strand invasion, also increases SSA efficiency. Furthermore, the Rad52 SSA recombination pathway also depends on MSH2, MSH3 and numerous other components.

In some embodiments one or more inhibitory nucleic acids can be antisense oligonucleotides. Antisense oligonucleotides may be designed to block expression of a DNA or RNA target by binding to the target and halting expression at the level of transcription, translation, or splicing. The antisense oligonucleotides can be complementary nucleic acid sequences, or substantially complementary sequences, designed to hybridize under stringent conditions to a mismatch repair gene. In some instances, one or more inhibitory nucleic acids can be RNAi-related sequences, including but not limited to a small interfering RNA ("siRNA") or short hairpin RNA ("shRNA"). The interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to a nucleotide sequence in a separate target nucleic acid molecule or a portion thereof and the sense region having nucleotide sequence corresponding to the target nucleic acid sequence or a portion thereof. The interfering RNA can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in a target cell to generate an active siRNA molecule capable of mediating RNA interference.

In some instances, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 23 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., Science 296:550-553, (2002); Lee et al, Nature Biotechnol., 20, 500-505, (2002); Miyagishi and Taira, Nature Biotechnol 20:497-500, (2002); Paddison et al. Genes & Dev. 16:948-958, (2002); Paul, Nature Biotechnol, 20, 505-508, (2002); Sui, Proc. Natl. Acad. Sci. USA, 99(6), 5515-5520, (2002); Yu et a). Proc NatlAcadSci USA 99:6047-6052, (2002).

The target RNA cleavage reaction guided by siRNAs is highly sequence specific. In general, siRNA containing a nucleotide sequences identical to a portion of the target nucleic acid (i.e., a mismatch repair gene) are preferred for inhibition. However, 100% sequence identity between the siRNA and the target gene is not required. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general the siRNAs must retain specificity for their target, i.e., must not directly bind to, or directly significantly affect expression levels of, transcripts other than the intended target.

In some embodiments, a one or a plurality of inhibitory nucleic acids are used to target one or more of Msh2, Msh3, Msh6, Mlh1, Mlh2, Mlh 3, and/or Pms1, in *Saccharomyces cerevisiae, Pichia pastoris, Saccharomyces castellii, Kluyveromyces lactis, Pichia stipitis, Schizosaccharomyces pombe. Escherichia coli, Chlamydomonas reinhardtii, Arabidopsis thaliana, Caenorhabditis elegans*, or mammalian (e.g., non-human mammalian cells). For example, a construct for use in *Saccharomyces cerevisiae* can include one or a plurality of inhibitory nucleic acids that target Msh2 (NP 014551.1), Msh3 (NP 010016.2), Msh6 (NP 010382.10), Mlh1 (NP 013890.1), Mlh3 (NP 015161.1), and/or Pms1 (NP 014317.2). In some instances, constructs can include one or a plurality of inhibitory nucleic acids that target different regions within the same gene. For example, in the case of *Saccharomyces cerevisiae*, constructs can include one or a plurality of inhibitory nucleic acids against Msh2 (NP 014551.1), Msh3 (NP 010016.2), Msh6 (NP 010382.10), Mlh1 (NP 013890.1), Mlh3 (NP 015161.1), and/or Pms1 (NP 014317.2). In an equivalent manner, targeting of the following genes can also occur:

bineering phenotype or programmable site-specific nuclease phenotype is reversible, that is, constructs can be removed after performing the recombineering process. In the case where the construct is to be maintained as a plasmid or episome with a selectable marker, the construct can be removed by growth in non-selectable media as is standard practice for the target organism. In the case where the construct is to be integrated into the host genome, the device may include sequence elements to allow for rapid removal (e.g., flanking loxP sequence).

Expression control sequences suitable for regulating expression of a SSAP system and/or recombinase that promotes recombination of single stranded oligonucleotides, programmable nucleases, and optionally one or more inhibitory nucleic acids, can include a promoter and/or enhancer sequence. The promoter and/or the enhancer can be inducible (e.g. chemically or physically regulated). A chemically regulated promoter and/or enhancer can, for example, be regulated by the presence of alcohol, tetracycline, a steroid, or a metal, to name but a few. A physically regulated promoter and/or enhancer can, for example, be regulated by

| | Target gene | | | | | |
|---|---|---|---|---|---|---|
| Target cell | Msh2 | Msh3 | Msh6 | Mlh1 | Mlh3 | Pms1/2 |
| *Saccharomyces cerevisiae* | NP_014551.1 | NP_010016.2 | NP_010382.1 | NP_013890.1 | NP_015161.1 | NP_014317.2 |
| *Pichia pastoris* | XP_002490775.1 | XP_002490502.1 | XP_002490975.1 | XP_002491051.1 | XP_001388013.2 | XP_002493530.1 |
| *Saccharomyces castellii* | CCC67425.1 | CCC70051.1 | CCC68482.1 | CCC69671.1 | CCC69118.1 | CCC71165.1 |
| *Kluyveromyces lactis* | XP_455202.1 | XP_453028.1 | XP_452992.1 | XP_53504.1 | XP_452646.1 | XP_452705.1 |
| *Pichia stipites* | XP 001386399.2 | XP 001384191.2 | XP 001387139.2 | XP 001384344.2 | XP 001388013.2 | XP 001384508.2 |
| *Schizosaccharomyces pombe* | XP_001713136.1 | NP_593952.1 | NP_588344.1 | NP_596199.1 | | NP_594417.1 |
| *Escherichia coli* | NP417213.1 | | | | | |
| *Chlamydomonas reinhardtii* | XP_001698121.1 | XP_001689901.1 | | XP_001690102.1 | | XP_001692227.1 |
| *Arabidopsis thaliana* | NP_566804.3 | NP_194284.2 | NP_192116.1 NP_850630.1 | NP_567345.2 NP_189075.2 | NP_195277.5 | NP_567236.1 |
| *Cacnorhabditis elegans* | NP 491202.1 | | NP 491163.1 | NP 499796.2 | NP 505933.1 | NP 505933.1 |
| *Mus musculus* | NP_032654.1 | NP_034959.2 | NP_034960.1 | NP_081086.1 | NP_780546.1 | NP_032912.2 |

In some embodiments, the host cell or strain has one or more genetic modifications to protect oligos following entry into the cell. Knocking out four potent ssDNA exonucleases in *E. coli* improves oligomediated allelic recombination frequency when low concentrations of oligos are used. ExoVII has been identified as a nuclease which degrades the ends of single-stranded DNA (ssDNA) oligonucleotides and double-stranded DNA (dsDNA) cassettes. Removing this nuclease may improve both recombination frequency and the inheritance of mutations at 3' ends of ssDNA and dsDNA. Removing ExoVII and the set of four exonucleases (RecJ, ExoI, ExoX, and Lambda Exo) improves recombineering performance.

In some embodiments, the host cell or strain provides for controlled activation/termination (e.g. expression of the machinery necessary for recombineering, or double-strand break or nicking by the programmable site-specific recombinase systems described herein, can be controlled). Control of machinery that suppresses the mismatch repair mechanisms of the host cell provides for genomic stability before and after the recombineering process. In some embodiments, expression of constructs can be induced by chemical or thermal means and can remain unexpressed when not induced (or vice versa). In some embodiments, the recomenvironmental factors, such as temperature and light. In some instances, expression control sequences can include copper and nickel dependent promoters such as the Cyc6 promoter (Quinn et al., Eukaryotic cell, 2:995-1002 (2003)). In some instances, expression control sequences can include light induced expression control systems that include. e.g., the CabII-1 promoter. In some instances, expression control sequences can include tetracycline-controlled systems, including Tet-Off and Tet-On (Bujard et al., PNAS USA, 89:5547-51 (1992)).

In some embodiments, the host cell or strain controls localization of recombineering or programmable nuclease effectors within the cell, to thereby control the process in an on or off fashion. For example, the ligand-binding domain (LBD) of the estrogen receptor (ER) can be used to regulate the localization and activity of nuclear proteins in yeast and mammalian cells. Nuclear proteins containing the ER LBD are retained in the cytoplasm until activated by estradiol or the functional estrogen antagonists tamoxifen (TAM) or 4-hydroxy-tamoxifen (4OHT). Upon binding, the ligand displaces Hsp90 and facilitates correct folding of the released fusion protein, which activates the LBD fused nuclear protein and allows translocation to the nucleus. Several ER ligand variants with different activation mechanisms are known. The mouse ER LBD mutant G525R and corresponding human mutant G521R (ERT) exhibit roughly a 1000-fold reduction in 17β-estradiol binding affinity compared to wildtype, yet retain normal affinity for TAM and 4OHT. The 4OHT affinity of the human ER LBD mutant ERT2 (G400V/M543A/L544A) is approximately 4-fold higher than that of ERT. In addition to the Gal4 transcription factor fusion to ER and VP16 (GEV), ectopic DNA enzymes such as Cre, Flp and I-SceI have successfully been controlled by fusion with ERT and other nuclear hormone receptors. These systems can be adapted for host cells of choice, including yeast.

In some embodiments, ER LBD and mutants fused to other yeast nuclear proteins would elicit the same properties of control. For example, fusing these components to various mutant SSAP or SSAP enabling genes allows constitutive expression, whereby the proteins remain inactive (and nonphysiological) in the cytosol until activated prior to transformation. Furthermore, an inducible protein degradation system using the GEV system to activate expression of the Tobacco Etch Virus (TEV) protease is useful in the present invention. TEV specifically degrades proteins with the N-degron peptide sequence. With expression of TEV under tight control of the GEV system. MMR and/or Non-Homologous End Joining (NHEJ) pathway members with N-degron sequences can be degraded concomitant with SSAP activation.

In these or alternative embodiments, the host cell or strain can include one or more nucleic acids encoding one or more CRISPR pathway components e.g., operably linked to expression control sequences. In some instances, expression control sequences for protein beta, one or a plurality of inhibitory nucleic acids, and/or RNAi and/or CRISPR machinery can be distinct and independently controlled. In some instances, expression control sequences for protein beta, one or a plurality of inhibitory nucleic acids, and/or RNAi and/or CRISPR machinery can be the same or can be induced via the same signal.

In some aspects, the invention is applicable to prokaryotic organisms that are more difficult to genetically manipulate than E. coli. For example, the invention allows for target genes to be introduced into E. coli using a vector that is compatible for replication in E. coli and the desired host, and after undergoing rounds of engineering in E. coli, the engineered vectors are introduced in the host cell of choice. For example, in these embodiments the method comprises providing a vector suitable for replication in a target species (e.g. any of the cells disclosed herein) and suitable for replication in a second species (e.g. any of the cells disclosed herein). The second species expresses a SSAP system and/or recombinase that optionally promotes annealing of single stranded oligonucleotides at the lagging strand of the replication fork, or the second species expresses a gene editing system, wherein the vector comprises a target polynucleotide for engineering. The vector is introduced into the second species under conditions suitable for diversification of said target polynucleotide by the SSAP system and/or recombinase, and the vector library isolated and introduced into said target species. The second species may be E. coli, and the target species can be a slow growing organism. In some embodiments, the target species is S. cerevisiae or an actinomycetes and the second species is E. coli, or the target species is a plant and the second species is an agrobacter.

In some embodiments, genome engineering for the target organism is conducted in a MAGE-competent recombineering strain, for example such as an E. coli strain described herein, anlocus (or library thereof) exported to target cells (e.g., non-recombineering or MAGE-competent strains). In certain embodiments, the invention provides a method for multiplex genomic alteration of a target cell population, comprising: (a) generating a combinatorial vector library in a recombineering cell population; and (b) transferring the combinatorial vector library to a target cell population. While genome engineering methods such as MAGE, CRISPR/Cas9, BuDs, ZFNs, TALEs, and TALENs are applicable to many diverse species, multiplex application of these technologies can be hindered in some organisms by the length of time required to execute the sequential rounds of engineering necessary to accumulate the combinatorial diversity in the loci of interest. For example, organisms such as Actinomycetes (e.g. Streptomyces spp.), are relatively slow growing and laboratory techniques used to perform genetic manipulations may take days or weeks. To facilitate application of multiplex genome engineering techniques in slow growing or difficult to manipulate organisms, such as the Actinomycetes, the present invention provides methods and compositions to elaborate the diversity indirectly in a faster growing and easier to manipulate organism, such as E. coli, via a shuttle system. By elaborating the diversity in the shuttle system within the facile E. coli host, then introducing the generated shuttle library into the target organism, extended sequential cycles in the non-facile target organism are avoided. Such methods and compositions are applicable to a variety of multiplex genome engineering techniques (e.g. MAGE, CAGE, CRISPR/Cas9, BuDs, ZFNs, TALEs, and TALENs). In some embodiments the genetic diversity at the desired locus is synthesized and not elaborated with a technique such as MAGE, then cloned directly into the vector (e.g., a plasmid or virus) using standard methods. In still other embodiments the genetic diversity is synthesized and cloned directly into the vector. In still other embodiments the DNA is then further elaborated with a technique such as MAGE.

In some embodiments, the vector possesses one or more selectable markers such that the vector may be selected for in both the recombineering organism and the target organism. In still other embodiments all or a portion of the site-specific programmable nuclease system (e.g., CRISPR/Cas9, TALEN, ZFN, BuD, or homologous or analogous system) is encoded and coupled, e.g. in the same vector. For example, when using the CRISPR/Cas9 system the components of the site-specific programmable nuclease system comprises the gRNA or crRNA and tracrRNA In some embodiments, the gRNA (e.g. synthetic gRNA) is present on the same vector. In some embodiments, the crRNA is present on the same vector. In some embodiments, the crRNA and tracrRNA are present on the same vector. In some embodiments, the Cas9 is present on the same vector. In some embodiments, the same vector encodes one or more TALENs programmed to cut the target sequence. In some embodiments, the same vector encodes one or more ZFNs programmed to cut the target sequence. In some embodiments, the same vector encodes one or more BuDs programmed to cut the target sequence. In some embodiments, the site-specific programmable nuclease system is directly tethered on the same DNA to the repair or donor sequence that is elaborated with a multiplex genome engineering technique (e.g. MAGE, CAGE, CRISPR/Cas9, BuDs, ZFNs, TALEs, and TALENs) (e.g. there is roughly a 1:1:1 ratio of DNA encoding selectable marker for the target organism, the programmable nuclease designed to cut the organism genome and the repair or donor DNA). Also, in some embodiments, there may be one or more (e.g. 1, or 2, or 3, or 4, etc.) of the site-specific programmable nuclease system and repair or donor sequence on the same vector (e.g. one or more gRNA and donor sequence on the same vector (optionally also with Cas9 on the same vector), one or more crRNA and donor sequence on the same vector (optionally also with Cas9 on the same vector), one or more crRNA and tracrRNA and donor sequence on the same vector (optionally also with Cas9 on the same vector), one or more TALENs programmed to cut the target sequence and donor sequence on the same vector, one or more ZFNs programmed to cut the target sequence and donor sequence on the same vector, and one or more BuDs programmed to cut the target sequence and donor sequence on the same vector). In various embodiments, such vectors, each targeting a unique genomic locus, may be transformed together, optionally in a cyclical manner in a similar way as with MAGE (as described herein). In some embodiments, the systems described herein allow selection for the vector DNA, and against wild type genomic locus being targeted by the programmable nuclease, by providing relief from genome cutting through repair by the donor DNA that contains the desired mutation(s).

This approach allows for a scarless method for selecting recombinants and obviates the need for additional or genome integrating selectable markers. In this case, recombination with the homologous target region mutated at the wild-type locus targeted by the site-specific nuclease permits the cell to escape restriction by the programmed nuclease system. In other words, recombination with the mutated sequence frees the organism from the genomic instability caused by the programmable site-specific nuclease. Thus, in some embodiments, a library of plasmids is introduced into a population of host cells, the plasmids encoding and allowing for expression of Cas9 or homologous or analogous CRIPSR enzyme, and a crRNA/tracrRNA or synthetic guide RNA targeting a region of the host cell genome. In still other embodiments, Cas9 is expressed from the genome or separate from the plasmid and the plasmids express only a crRNA/tracrRNA or a single synthetic guide RNA. In still other embodiments, the tracrRNA is also expressed from the genome or separate from the plasmid and only the crRNA is encoded on the plasmid. In still other embodiments, the plasmids encode one or more TALENs, ZFNs, BuDs, or analogous system, each further providing a donor nucleic acid for introduction into the targeted region of the host genome. In this manner, desired donor nucleic acids targeting the particular site can be introduced into the host cell and screened or selected for desired phenotype. In various embodiments, the donor nucleic acids are not susceptible to cutting by the Cas9 and crRNA/tracrRNA (or synthetic guide RNA), or analogous programmable nuclease described herein, that is introduced into the system. The library of vectors may thereby allow for the screening of any number of variant donor nucleic acids, such at least about $10^2$, about $10^3$, about $10^4$, about $10^5$, about $10^6$, about $10^7$, about $10^8$, about $10^9$, about $10^{10}$ or more, without an additional or integrating selectable marker to select for recombination events. In some embodiments, the library varies one or more (or all) of promoter sequences, ribosomal binding sequences, coding region variations, silent codon variations, synthetic scaffold components, and protein tags to select for optimal expression, function, and/or activity of the target.

Cloning methods are known in the art and include, by way of non-limiting example, fusion PCR and assembly PCR see, e.g. Stemmer et al. Gene 164(1): 49-53 (1995), inverse fusion PCR see, e.g. Spiliotis et al. PLoS ONE 7(4): 35407 (2012), site directed mutagenesis see, e.g. Ruvkun et al. Nature 289(5793): 85-88 (1981). Gibson assembly (see, e.g. Gibson et al. Nature Methods 6 (5): 343-345, (2009) the contents of which are hereby incorporated by reference in their entirety), Quickchange see, e.g. Kalnins et al. EMBO 2(4): 593-7 (1983), Gateway see, e.g. Hartley et al. Genome Res. 10(11):1788-95 (2000), Golden Gate see, e.g. Engler et al. Methods Mol Biol. 1116:119-31 (2014), restriction digest and ligation including but not limited to blunt end, sticky end, and TA methods see, e.g. Cohen et al. PNAS 70 (11): 3240-4 (1973).

In some embodiments, the shuttle vector encodes an origin of replication suitable for both the host where the combinatorial vector library is generated (e.g., *E. coli*) as well as an origin of replication of one or more target organisms where the desired mutations are to be introduced. Illustrative origins of replication are known in the art (see, e.g., Bryant et al., J Exp Bot., 52(355):193-202 (2001); Edward et al., Basic Virology Third Edition, Blackwell publishing, ISBN 1-4051-4715-6 (2007); Mott and Berger, Nat. Rev. Microbial., 5 (5): 343-54 (2007); Huberman et al., Cell, 6; 51(3):473-81 (1987); Brewer and Fangman, Cell, November 6; 51(3):463-71 (1987); Kitai et al., J. Virol., 79(10): 5933-5942 (2005); Kelman, Trends Microbial., 12: 399-401 (2004); Nasheuer et al., Prog. Nucleic Acid Res. Mol. Biol., 72: 41-94 (2002), the contents of which are hereby incorporated by reference in their entireties).

In some embodiments, a programmable nuclease is employed in the recombineering or MAGE-competent organism, or organism where the combinatorial shuttle vector library is generated, in order to eliminate those vectors where mutations were not introduced into the desired target sequence of the target organism through the course of engineering. Thus, the final vector library produced is substantially enriched for possession of mutated target sequences to be introduced into the target organism.

In some embodiments, the shuttle vector encodes an origin of replication allowing for tunable control of copy number such as pETcoco-1 or pETcoco2, such that when creating the combinatorial library, a lower plasmid copy number can be utilized to elaborate the genetic diversity at the desired locus (as described herein). As such, the proportion of vectors within the cell population undergoing allelic replacement with an oligonucleotide is increased at each cycle. Furthermore, the copy number can be increased prior to transfer to the target organism, in order to increase yield.

λ RED-mediated (or functionally similar) genetic manipulation of a compound-producing *Actinomycetes* may be undertaken. The strategy employs *E. coli* as a surrogate to enable recombineering with the λ RED cassette. The *E. coli* strain may carry a plasmid expressing λ RED, and a vector containing one or more target genes or regions in the *Actinomycetes* or other non-recombineering cell. Recombineering is used to perform the replacement with an oligo library targeting the *Actinomycetes* gene of interest within the vector. The vector may then be purified and transferred and/or conjugated or used in any other suitable transferring technique. The genetic exchange in *Actinomycetes* is subsequently achieved by homologous recombination between the chromosomal locus and the recombinant vector following conjugation.

The inclusion of oriT (RK2) allows conjugation to introduce the recombineering-modified vector into an *Actinomycete* (e.g. *Streptomyces coelicolor*). Conjugation is more efficient than transformation of protoplasts and is readily applicable to many *actinomycetes*. The potent methyl-specific restriction system of *Actinomycetes* (e.g. *Streptomyces*) is circumvented by passaging the vector DNA through a methylation-deficient *E. coli* host such as, for example, ET12567 and various Dam– Dcm– strains. Alternatively, the recombineering strain itself may be made methylation-deficient.

Vectors with an oriT (RK2) site are transmissable in trans by pUB307 in *E. coli* or the non-transmissible pUZ8002, which lacks a cis-acting function. To adapt the procedure of λ RED-mediated recombination for *Actinomycetes* (e.g. *Streptomyces*), cassettes were constructed that can be selected both in *E. coli* and in *Actinomycetes* (e.g. *Streptomyces*). After a single disruption with an oriT-containing cassette, further disruptions can be performed on the same vector using oriT-free cassettes containing alternative selective markers.

Thus, a MAGE-competent strain of *E. coli* can readily be used to develop a combinatorial library of *Actinomycetes* (e.g. *Streptomyces, S. coelicolor*) vectors targeting one or multiple *Actinomycetes* (e.g. *Streptomyces, S. coelicolor*) genomic loci. The entire *E. coli* library would subsequently be conjugated with *Actinomycetes* (e.g. *Streptomyces, S. coelicolor*) as outlined herein.

The combinatorial vector library can be constructed in multiple ways to facilitate multiplex genome engineering of diverse cells as described herein. In one embodiment, a vector possessing a sequence allowing conjugation with *Streptomyces*, such as oriT, a selectable marker and origin of replication for *E. coli* and one or multiple cassettes is used for construction. In some embodiments, each cassette may be engineered by MAGE (e.g., SSAP system and/or recombinase) to create a diverse combinatorial vector library. In some embodiments, a cassette is a region of homologous DNA, with one or more insertions, deletions, or mutations introduced by MAGE (for example) or synthetic DNA method, designed to target a specific locus of the genome of the *Actinomycete* spp., and/or encodes one or more genes conferring function necessary or useful for one or more cassettes to recombine with its target locus in the genome of the *Actinomycete* spp. In some embodiments, the cassettes are separated by one or more restriction digest sites that enable digestion by an endogenous restriction endonuclease, (e.g., Sau3239I, StuI, or ScoI) or an exogenous restriction endonuclease encoded by one or more of the cassettes, under control of an inducible or constitutive promoter.

In some embodiments, a cassette may possess one or more genetic markers that can be selected in the *Actinomycete* spp. In various embodiments, the marker enables selection of the vector prior to integration and/or the marker is capable of integrating into the genome of the *Actinomycete* spp. together with the region of homologous DNA, with one or more insertions, deletions, or mutations introduced by MAGE or synthetic DNA method. In some embodiments, the marker can be recycled for use in subsequent modifications of the genome of the *Actinomycete* spp. by, for example, flanking the marker sequence with site-specific recombinase recognition targets such as FRT or loxP for example, that can be excised from the genome following expression of Flp or Cre recombinase, respectively, using standard methods.

In some embodiments, the cassette contains one or more genes, under control of an inducible, repressible, or constitutive promoter, that render the recipient strain improved in homologous recombination efficiency, e.g.: the λ RED cassette from phage A; RecE/T; homologs of the Rad52, Red-beta, Erf, Sak, Rad51 superfamily, and/or endogenous or exogenous analogs and Beta from *E. coli*, EF2132 from *E. faecalis*, OrfC from *L. pneumophila*, s065 from *V. cholera*, plu2935 from *P. luminescens*, RecT from *E. coli*, Orf48 from *L. monocytogenes*, Orf245 from *L. lactis*, GP35 from *B. subtilis*, GP61 from *M. smegmatis*, GP20 from *S. aureus* and/or endogenous or exogenous analogs.

In one embodiment, multiple vectors are used for construction. In some embodiments, one or more vectors comprise a sequence allowing conjugation with *Actinomycete* spp. (e.g. *Streptomyces*), such as oriT; and/or a selectable marker and origin or replication for *E. coli*; and/or a cassette.

In some embodiments, one or more vectors optionally further comprises a sequence which encodes a programmable site-specific nuclease system (e.g., TALEN, BuD, or CRISPR/Cas9) as described above, or one or more components of such a system, such as a tracrRNA, crRNA, or synthetic guide RNA, targeting the wild-type locus of a region of the *Actinomycete* spp. genome targeted for diversification by the cassette conferring the homologous sequence, as described herein, where the site-specific nuclease may be under control of an inducible, repressible, or constitutive promoter. In some embodiments, the cassette may be engineered to create a diverse combinatorial vector library using the methods described herein and/or by including synthesized DNA.

In some embodiments, the cassette possesses one or more genetic markers that can be selected in the *Actinomycete* spp. such that, for example, the marker enables selection of the vector prior to integration; or the marker is capable of integrating into the genome of the *Actinomycete* spp. together with the region of homologous DNA, with one or more insertions, deletions, or mutations introduced by MAGE (for example) or synthetic DNA method. In various embodiments, the marker can be recycled for use in subsequent modifications of the genome of the *Actinomycete* spp. by flanking the marker sequence with site-specific recombinase recognition targets such as FRT or loxP for example, that can be excised from the genome following expression of Flp or Cre recombinase, respectively.

In some embodiments, conjugation can then be used to efficiently introduce the modified DNA library into *Actinomycetes* using previously described techniques (see, e.g., Matsushima, incorporated by reference in its entirety). In some embodiments, the modified DNA library can be introduced by means known in the art (by way of non-limiting example, transfection, transformation, phage, electroporation, biolistics etc.).

When selectable markers are used the number of genomic loci targeted for combinatorial mutations can be either 1:1 or 1:greater than 1 (marker:locus/foci). That is, a selection marker may be tied to the targeting of a single site or the same marker may be tied to several targeted sites. When used in a 1:1 manner, the selection ensures that the locus of interest has been modified. When used as 1:greater than 1 the marker ensures that at least one of the targeted loci have been modified. Multiple recovery cycles for the markers will lead to an accumulation of scars on the genome (e.g., loxP, FRT, etc. sites) which may lead to genomic instability, thus decreasing the overall efficiency of the approach(es) due to decreased viability in the population.

Another method of selection includes the use of a site-specific nuclease (such as CRIPSR/Cas9 or a TALEN) programmed to recognize the wildtype sequence of the *Actinomycete* spp genomic region targeted for diversification by the cassette conferring the homologous sequence as described herein. When coupled, e.g. in the same vector, to an individual locus targeted by the cassette, this approach can result in a scarless method for selecting recombinants and obviates the need for a selectable marker. In this case, recombination with the homologous target region mutated at the wild-type locus targeted by the site-specific nuclease, is the only way to escape repeated cutting by the nuclease. In other words, recombination with the mutated sequence frees the organism from the genomic instability caused by the site-specific nuclease.

In some embodiments, the endogenous exonuclease system(s), e.g. RecD, SbcCD, of the host *Actinomycete* spp. are disrupted.

In some embodiments, conjugation is used to transfer the mutated vector or plasmid from a MAGE-competent organism, e.g., *Escherichia coli*, to the host cell. For example the conjugation may employ the oriT system described as above to transform *Streptomyces*. In some embodiments, the plasmid or vector system encodes the T-DNA or analogous system, to enable transfer of the mutated plasmid or vector DNA to plant cells with *Agrobacterium* (e.g., *Agrobacterium tumefaciens*), as anyone skilled in the art will recognize, for the purpose of genetic engineering of plant cells.

These systems thereby expand the engineering approaches to essentially any host cell. For example, host cells can include eukaryotic and/or prokaryotic cells, including bacterial, yeast, algal, plant, insect, and/or non-human mammalian cells, or immortal cell lines. For example, the host cell may be *Escherichia coli, Saccharomyces cerevisiae, Pichia pastoris, Saccharomyces castelli, Kluyveromyces lactis, Pichia stipitis, Schizosaccharomyces pombe, Chlamydomonas reinhardtii, Arabidopsis thaliana*, or *Caenorhabditis elegans*. In some embodiments the cell is a bacterial cell, such as *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp. and *Pantoea* spp. The bacterial cell can be a Gram-negative cell such as an *E. coli*, or a Gram-positive cell such as a species of *Bacillus*. In other embodiments, the cell is a fungal cell such as a yeast cell, e.g., *Saccharomyces* spp., *Schizosaccharomyces* spp., *Pichia* spp., *Paffia* spp., *Kluyveromyces* spp., *Candida* spp., *Talaromyces* spp., *Brettanomyces* spp., *Pachysolen* spp., *Debaryomyces* spp., *Yarrowia* spp., and industrial polyploid yeast strains. Preferably the yeast strain is a *S. cerevisiae* strain or a *Yarrowia* spp. strain. Other examples of fungi include *Aspergillus* spp., *Pennicilium* spp., *Fusarium* spp., *Rhizopus* spp., *Acremonium* spp., *Neurospora* spp., *Sordaria* spp., *Magnaporfthe* spp., *Allomyces* spp., *Ustilago* spp., *Botrytis* spp., and *Trichoderma* spp. In other embodiments, the cell is an algal cell or a plant cell (e.g., *A. thaliana, C. reinhardtii, Arthrospira, P. tricornutum, T. suecica, P. carterae, P. tricomutum, Chlorella* spp., such as *Chlorella vulgaris*). Target cells can include transgenic and recombinant cell lines. In addition, heterologous cell lines can be used, such as Chinese Hamster Ovary cells (CHO).

In some embodiments the cell is a bacterial cell, such as *Bacillus* spp, *Actinomycetes* spp *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp. and *Pantoea* spp. The bacterial cell can be a Gram-negative cell such as an *Escherichia coli* (*E. coli*) cell, or a Gram-positive cell such as a species of *Bacillus*. In other embodiments, the cell is a fungal cell such as a yeast cell, e.g., *Saccharomyces* spp., *Schizosaccharomyces* spp., *Pichia* spp., *Paffia* spp., *Kluyveromyces* spp., *Candida* spp., *Talaromyces* spp., *Brettanomyces* spp., *Pachysolen* spp., *Debaryomyces* spp., *Yarrowia* spp., and industrial polyploid yeast strains. Preferably the yeast strain is a *S. cerevisiae* strain or a *Yarrowia* spp. strain. Other examples of fungi include *Aspergillus* spp., *Pennicilium* spp., *Fusarium* spp., *Rhizopus* spp., *Acremonium* spp., *Neurospora* spp., *Sordaria* spp., *Magnaporthe* spp., *Allomyces* spp., *Ustilago* spp., *Botrytis* spp., and *Trichoderma* spp. In other embodiments, the cell is an algal cell or a plant cell (e.g., *A. thaliana, C. reinhardtii, Arthrospira, P. tricornutum, T. suecica, P. carterae, P. tricomutum, Chlorella* spp., such as *Chlorella vulgaris*). Target cells can include transgenic and recombinant cell lines. In addition, heterologous cell lines can be used, such as Chinese Hamster Ovary cells (CHO). Host cells may be unicellular host cells or multicellular host cells.

In some embodiments, the cell suitable for use in and/or with the compositions and methods described herein is an *Actinomycetes* spp. cell. *Actinomycetes* are a heterogeneous collection of bacteria that form branching filaments which include, for example, *Actinomyces, Actinomadura, Nocardia, Streptomyces* and related genera. In some embodiments, *Actinomyces* comprise *Streptomyces*. In some embodiments, the *Actinomycetes* spp. cell is a *Streptomyces* cell, (e.g. *S. coelicolor*). *Streptomyces* include, by way of non-limiting example, *S. noursei, S. nodosus, S. natalensis, S. venezuelae, S. roseosporus, S. fradiae, S. lincolnensis, S. alboniger, S. griseus, S. rimosus, S. aureofaciens, S. clavuligerus, S. avermitilis, S. platensis, S. verticillus, S. hygroscopicus*, and *S. viridochromeogenes*.

In some embodiments, the cell suitable for use in and/or with the compositions and methods described herein is a *Subtillus* spp. cell. In some embodiments, the *Bacillus* spp. cell is selected from *B. alcalophilus, B. alvei, B. aminovorans, B. amyloliquefaciens, B. aneurinolyticus, B. anthracis, B. aquaemaris, B. atrophaeus, B. boroniphilus, B. brevis, B. caldolyticus, B. centrosporus, B. cereus, B. circulans, B. coagulans, B. firmus, B. flavothermus, B. fusiformis, B. galliciensis, B. globigii, B. infernus, B. larvae, B. laterosporus, B. lentus, B. licheniformis, B. megaterium, B. mesentericus, B. mucilaginosus, B. mycoides, B. natto, B. pantothenticus, B. polymyxa, B. pseudoanthracis, B. pumilus, B. schlegelii, B. sphaericus, B. sporothermodurans, B. stearothermophilus, B. subtilis, B. thermoglucosidasius, B. thuringiensis, B. vulgatis*, and *B. weihenstephanensis*.

In various embodiments, the present invention pertains to probiotics. For example, the present multiplex genome engineering techniques are used to alter probiotic cells to, for example, increase the functionality of the probiotic cells (e.g. increase digestion, synthesize various vitamins or amino acids, decrease pathogens, etc.). Accordingly, various probiotic species are a cell of the present invention. For example, the cell may be *E. coli* Nissle 1917. By way of further illustration, the cell is a *lactobacillus* (e.g. *acidophilus, Lactobacillus brevis, L. bulgaricus, L. plantarum, L.*

*rhamnosus, Rhamnosus L. fermentum, L. caucasicus, L. helveticus, L. lactis, L. reuteri* and *L. casei*) or a bifidobacteria (*Bifidobacterium bifidum, B. infantis*) *Streptococcus* thermophiles, and *Enterococcus faecium*.

In various embodiments, one or more of these processes are used to target regions of the host, including both endogenous and recombinant genes, for diversity. In some embodiments, the genomic engineering methods alter or diversify the suitable feedstock for a host cell. For example, the process may enhance the usage of feedstock selected from industrial or municipal waste, syngas, methane, as well as cellulosic or lignocellulosic feedstocks, such as sugar cane bagasse, wheat straw, corn stover, or other. For example, the feedstock may be processed from cardboard, paper, yard waste and/or other agricultural waste. In some embodiments, the recombineered strain enhances the availability of five and/or six carbon sugars that are available for metabolism.

In some embodiments, the genomic engineering methods alter carbon flux to increase or decrease the level of one or more glycolysis intermediates or products, such as glucose-6-phosphate, fructose-6-phosphate, fructose-1,6-bisphosphate, 3-phosphoglyceraldehyde, dihydroxyacetonephosphate, glycerol, 1,3-bisphosphoglycerate, 3-phosphoglycerate, 2-phospho-glycerate, phosphoenolpyruvate, and pyruvate. In these embodiments, the increase flux may support production of desired chemicals through one or more recombinantly expressed genes or endogenous secondary pathways. In some embodiments, increased flux supports an increase in production of one or more amino acids (including aromatic amino acids and unnatural amino acids), fatty acids, carboxylic acids, nucleotides or nucleotide derivatives, and polysaccharides.

In some embodiments, the genomic engineering methods alter carbon flux to increase or decrease the level of one or more tricarboxylic acid cycle or glyoxylate pathway products or intermediates, such as citrate, cis-aconitate, isocitrate, oxalosuccinate, α-ketoglutarate, succinyl-CoA, succinate, fumarate, L-malate, oxaloacetate, and glyoxylate. In these embodiments, the increase flux may support production of desired chemicals through one or more recombinantly expressed genes or endogenous secondary pathways. In some embodiments, increased flux supports an increase in production of one or more amino acids (natural or unnatural), fatty acids, and carboxylic acids.

In these or other embodiments, the genomic engineering methods alter carbon flux to increase or decrease the level of one or more Entner-Doudoroff intermediates or products, such as 6-phospho-gluconate or 2-keto-3-deoxy-6-phosphogluconate (KDPG).

In these or other embodiments, the genomic engineering methods alter carbon flux to increase or decrease the level of one or more pentose phosphate pathway intermediates or products, such as ribulose, xylulose, fructose, and/or ribose, or phosphorylated form thereof.

In these or other embodiments, the genomic engineering methods alter carbon flux to increase or decrease the level of one or more phosphoketolase pathway intermediates or products, such as 6-phosphoglucolactone, pyruvic acid, lactic acid, acetyl phosphate, acetyl CoA, acetylaldehyde, and/or ethanol.

In these or other embodiments, the genomic engineering methods alter carbon flux to increase or decrease the level of one or more non-mevolonate pathway products or intermediates, such as Isopentenyl diphosphate (IPP), dimethylallyl pyrophosphate DMAPP, 1-deoxy-D-xylulose 5-phosphate (DXP), 2-C-methyl-D-erythritol 4-phosphate, 4-diphospho-cytidyl-2-C-methylerythritol, 4-diphosphocytidyl-2C-methylerythritol 2-phosphate, 2-C-methyl-D-erythritol 2,4-cyclodiphosphate. These intermediates can be used to support production of isoprene or terpenoid compounds in host cells.

In these or other embodiments, the genomic engineering methods alter carbon flux to increase or decrease the level of one or more mevolonate pathway products or intermediates, such as HMG-CoA, mevalonate, 5-phosphomevalonate, 5-pyrophosphomevalonate, 3-isopentyl pyrophosphate, and dimethylallyl pyrophosphate. These intermediates can be used to support production of isoprene or terpenoid compounds in host cells.

In some embodiments, the method targets one or more genes of central metabolism to direct carbon flux to desired carbon skeleton. For example, the method may target one or more genes (e.g., from 1 to 30 genes, or from 1 to 20 genes, or from 1 to 10 genes, including 1, 2, 3, 4, 5, 6, 7, or 8 genes) of microbial central metabolic pathways, including glycolysis, tricarboxylic acid cycle, Embden-Meyerhof-Parnas, Entner-Doudoroff, pentose phosphate, phosphoketolase pathway, and glyoxylate shunt. In some embodiments, the strain producing the desired chemical or product has from 1 to 10 genes (e.g., 1-5 genes, or 1-3 genes, or 5-10 genes) targeted by the processes described herein selected from: hexokinase, isomerase, phosphofructokinase, fructose-1,6-bisphosphate aldolase, triosephosphate isomerase, triosephosphate dehydrogenase, phosphoglycerate kinase, mutase, enolase, pyruvate kinase, transketolase, transaldolase, ribulose phosphate epimerase, phosphatase, lactonase, glucose 6-phosphate dehydrogenase, gluconate dehydrogenase, pentose phosphate isomerase, xyulose epimerase, KDPG aldolase, PGA kinase, citrate synthase, aconitase, isocitrate dehydrogenase, α-ketoglutarate dehydrogenase, succinate thiokinase, succinate dehydrogenase, fumarase, malate dehydrogenase, isocitrate lyase, malate synthase, PEP carboxykinase, and PEP synthetase.

In some embodiments, the compound is a product or intermediate of microbial metabolism, or a derivative thereof produced by the expression of one or more recombinant genes. The compound may be a product of one or more recombinant genes to synthesize and enhance production of a compound not inherently produced, or not produced at significant levels by the host cell. These compounds include compounds having C2-C6 carbon skeletons that are likely to rely largely on primary metabolism.

In some embodiments, the compound has a C2 carbon skeleton, which may be include one or more groups selected from hydroxyl, amino, or oxy. Exemplary compounds include ethylene, ethanol, ethene, ethane, and acetate. In some embodiments, the compound is a C3 carbon skeleton, which may include one or more groups selected from hydroxyl, amino, or oxy. Exemplary compounds include pyruvate, methacrylic acid, acrylate, propanoic acid, hydroxypropanoic acid, propylene, propanol, isopropanol, propane, and propene. In some embodiments, the compound is a C4 carbon skeleton, which may include one or more groups selected from hydroxyl, amino, or oxy. Exemplary compounds include butanol, isobutanol, butadiene, butanediol, butanone, butyric acid, butyrolactone, butanal, putrescine, fumarate, and malate. In some embodiments, the compound is a C5 carbon skeleton which may include one or more groups selected from hydroxyl, amino, or oxy. Exemplary compounds include levulinic acid, pentanoic acid. In some embodiments, the compound is a C6 carbon skeleton, which may include one or more groups selected from hydroxyl, amino, or oxy. Exemplary compounds include caproic acid, cyclohexanone, or adipate.

The invention as described can employ tools that are standard in molecular biology.

In these or other embodiments, from one to about 100 (or more), or from one to about fifty, or from one to about twenty (e.g., from one to ten or from one to five genes) of secondary biosynthetic pathways (such as amino acid biosynthetic pathways) are also targeted for genetic diversity and screened for desired phenotype.

In some embodiments, genetic components that enhance the production of a desired compound are selected in multiple repeating stages. First, an engineering round is conducted to target all genes of one or more pathways, such as one or more (or three, four, five, or more) of glycolysis, tricarboxylic acid cycle, Embden-Meyerhof-Parnas, Entner-Doudoroff, pentose phosphate, phosphoketolase pathway, and glyoxylate pathway (or others described herein). The engineering round is conducted by varying at least one sub-sequence of each enzyme or related genomic target, such as the ribosomal binding sequence, so as to produce an engineered library of mutants with decreases and increases in expression of each enzyme, change in cellular localization with or without respect to other pathway components, functional characteristics of one or more enzymes, as well as additional endogenous components that may affect cellular characteristics affecting the performance of one or more pathway components (e.g., pH, import/export, degradation rates, etc.) and various combinations thereof.

In various embodiments the invention provides methods to employ combinatorial in vivo screening of synthetic scaffolds to a set of enzymes involved in production of a desired target molecule (John E Dueber, Gabriel C Wu, G Reza Malmirchegini, Tae Seok Moon, Christopher J Petzold, Adeeti V Ullal, Kristala L J Prather & Jay D Keasling. (2009) Synthetic protein scaffolds provide modular control over metabolic flux. *Nature Biotechnology* 27 (8): 753-759. Whitaker, W. R., & Dueber, J. E. (2011). *Metabolic Pathway Flux Enhancement by Synthetic Protein Scaffolding*. *Synthetic Biology*, Part A, 1, 447-478, and International Patent Publication No. WO/2009/108774, the contents of which are incorporated by reference in their entirety). Having then generated any number of strains with mutations in these various aspects, these cells are subjected to a selection or screen for the production of a desired compound or intermediate. Any suitable chemical, analytical, biochemical, biophysical, microbiologic, phenotypic screen common in the art may be applied to identify the improved strain. Non-limiting examples of screening methods include chromatographic analysis, spectroscopic analysis, extraction followed by an analytical chromatographic step, chemical chromogenic assay, flow cytometric analysis and sorting, enzymatic activity assay, zone of inhibition assay, auxotrophic reporter strain growth assay, etc. By then determining the incorporated sequences that gave rise to the increased production, further rounds of targeted genomic engineering may be conducted on the identified genes.

Alternatively or in combination, a sensor strategy may be coupled to a selectable marker or system to identify improved strains. A competitive advantage, such as improved growth, can be induced by a system engineered to respond to the phenotypic improvement being sought, such as higher production of a metabolite. See, e.g, Berteis F, Merker H, Kost C (2012) Design and Characterization of Auxotrophy-Based Amino Acid Biosensors. PLoS ONE 7(7): e41349. For instance, a chemical binding transcription factor can be used to drive expression, via its cognate promoter, of a selectable marker, such as TolC. Expression of the selectable marker may be modulated through means such as transcription factor recruitment or mRNA processing (riboswitch) as long as the expression is regulated by the improved phenotype. Non-limiting examples of sensors include LacI for IPTG or a riboswitch for riboflavin.

Additionally, the screening techniques may be used singly or in combination. In one instance, a sensor-selector screen may be applied to identify a series of high producing strains which are then interrogated for best performers by use of a quantitative chromatographic assay.

In some embodiments, the host cell or strain is engineered to enhance the expression or activity of one or more recombinant genes such that genes are regulated and optimized for product development. For example, the target recombinant enzyme may be one or more of an oxidoreductase, transferase, hydrolase, lyase, isomerase, or ligase specific for the desired substrate, and which may be a product of a core metabolic pathway as described, or an endogenous biosynthetic pathway. In some embodiments, at least one enzyme is an endogenous or heterologous cytochrome P450 oxidase enzyme, which may be fused in some embodiments to its reductase partner.

In other aspects, the invention provides engineered cells made through processes described herein, and provides methods of producing these products through fermentation of the engineered cells. For example, the methods and cells may, in various embodiments, produce a biofuel such as methanol, ethanol, propanol, butanol, or isobutanol, or a compound having a C2 to C6 carbon skeleton (for example) ethylene, acetate, methacrylic acid, acrylate, lactic acid, isoprene, propanoic acid, hydroxypropanoic acid, propylene, propane, propene, butadiene, butanediol, butanone, butyric acid, butyrolactone, butanal, putrescine, fumarate, malate, levulinic acid, pentanoic acid, caproic acid, cyclohexanone, or adipate. In some embodiments, the compound is a fatty acid, amino acid, lipopeptide, antibiotic, nucleotide or nucleotide derivative, or terpenoid. Other potential chemical products are disclosed elsewhere herein.

In various embodiments, the present invention provides for, inter alia, methods of making a desired compound and methods of making a cell capable of producing a desired compound. In various embodiments, the present invention provides for, inter alia, methods of targeting synthetic pathways of the desired compound genes and/or secondary pathways that control effect flux through the synthetic pathways for allelic replacement.

In some embodiments, the desired compound is as listed below. In some embodiments, the desired compound includes Formate; Methanoate, Acetate; Ethanoate, Propionate; Propanoate, Butyrate; Butanoate, Valerate; Pentanoate, Capronate; Hexanoate, Enanthate; Heptanoate, Caprylate; Octanoate, Oxalate, Malonate, Succinate, Glutarate, Adipate, Pimelate, Suberic acid, Citrate, Isocitrate, cis-Aconitate, trans-Aconitate, Pyruvate; 2-Oxopropanoate, 2-Oxobutanoate, 2-Oxopentanoic acid, 2-Oxohexanoic acid, Oxaloacetate; 2-Oxobutanedioic acid, 2-Oxoglutarate, 2-Oxoadipate, 2-Oxopimelate, 2-Oxoisovalerate, 4-Methyl-2-oxopentanoate, (S)-3-Methyl-2-oxopentanoic acid, Butyric acid (4:0), Caproic acid (6:0), Caprylic acid (8:0), Capric acid (10:0), Lauric acid (12:0), Myristic acid (14:0), Palmitic acid (16:0), Stearic acid (18:0), Arachidic acid (20:0), Behenic acid (22:0), Lignoceric acid (24:0), Oleic acid (18:1; 9), Elaidic acid (18:1; 9), Icosenoic acid (20:1; 11), Erucic acid (22:1; 13), Nervonic acid (24:1; 15), Linoleic acid (18:2; 9,12), Icosadienoic acid (20:2; 11,14), Docosadienoic acid (22:2; 13,16), gamma-Linolenic acid (18:3; 6,9,12), alpha-Linolenic acid (18:3; 9,12,15), Arachidonic acid (20:4; 5,8,11,14), Eicosapentaenoic acid (20:5; 5,8,11,14,17), Docosahexaenoic acid (22:6; 4,7,10,13,16,19), Glycerol, 1-Monoacylglycerol, 2-Monoacylglycerol, 1,2-Diacylglycerol, 1,3-Diacylglycerol, Triacylglycerol, Phosphatidic acid, Phosphatidylethanolamine, Phosphatidylcholine; Lecithin, Phosphatidylserine, Phosphatidylinositol, 2-Lysolecithin, Plasmenylethanolamine, Plasmenylcholine, Phosphatidylglycerol, Diphosphatidylglycerol; Cardiolipin, Sphingomyelin, Glucosylceramide, Galactosylceramide, Lactosylceramide, GM1, GM2, GM3, Prostanoic acid, Prostaglandin A1, Prostaglandin A2, Prostaglandin B1, Prostaglandin B2, Prostaglandin C1, Prostaglandin C2, Prostaglandin D1, Prostaglandin D2, Prostaglandin E1, Prostaglandin E2, Prostaglandin E3, Prostaglandin F1alpha, Prostaglardin F2alpha, Prostaglandin F2beta, Prostaglandin F3alpha, Prostaglandin G2, Prostaglandin H2, Prostaglandin I2, Prostaglandin J2, Leukotriene A4, Leukotriene B4, Leukotriene C4, Leukotriene D4, Leukotriene E4, Leukotriene F4, 5-HPETE, Thromboxane A2, Thromboxane B2, 11-Dehydro-thromboxane B2, D-Glyceraldehyde, L-Glyceraldehyde, D-Erythrose (Ery), D-Threose (Tho), D-Arabinose (Ara), L-Arabinose, D-Xylose (Xyl), L-Xylose, D-Lyxose (Lyx), L-Lyxose, D-Ribose (Rib), D-Glucose (Glc), D-Galactose (Gal), L-Galactose, D-Mannose (Man), D-Allose (All), D-Altrose (Alt), D-Gulose (Gul), L-Gulose, D-Idose (Ido), D-Talose (Tal), 3,6-Anhydrogalactose, 3,6-Anhydroglucose, Dihydroxyacetone, D-Erythrulose, L-Erythrulose, D-Ribulose, L-Ribulose, D-Xylulose (Xul), L-Xylulose, D-Fructose (Fru); Fruit sugar, L-Fructose, D-Sorbose (Sor), L-Sorbose, D-Tagatose (Tag), D-Psicose, Sedoheptulose (Sed), Coriose, Deoxyribose, D-Fucose (Fuc), L-Fucose, D-Rhamnose (Rha), L-Rhamnose, 2-Deoxy-D-glucose, D-Quinovose (Qui), 2-Deoxy-D-galactose, Abequose, D-Glucosamine (GlcN), D-Galactosamine (GalN), D-Mannosamine (ManN), D-Fucosamine (FucN), D-Quinovosamine (QuiN), Neuraminic acid (Neu), Muramic acid (Mur), N-Acetyl-D-glucosamine (GlcNAc), N-Acetyl-D-galactosamine (GalNAc), N-Acetyl-D-mannosamine (ManNAc), N-Acetyl-D-fucosamine (FucNAc), N-Acetyl-D-quinovosamine (QuiNAc), N-Acetylneuraminic acid (Neu5Ac), N-Acetylmuramic acid (MurNAc), O-Acetylneuraminic acid, N-Glycoloyl-neuraminate, D-Fructuronic acid, D-Tagaturonic acid, D-Glucuronic acid (GlcA), D-Galacturonic acid (GalA), D-Mannuronic acid (ManA), L-Iduronic acid (IdoA), L-Guluronic acid, D-Gluconic acid, D-Glucosaminic acid, 2-Keto-D-gluconic acid, 3-Deoxy-D-manno-octulosonic acid, Sucrose; Cane sugar, Lactose; Milk sugar, Maltose; Malt sugar, Isomaltose, Trehalose, Cellobiose, Gentiobiose, Kojibiose, Laminaribiose, Maltulose, Mannobiose, Melibiose, Melibiulose, Nigerose, Palatinose, Rutinose, Scillabiose, Turanose, Vicianose, Xylobiose, Adenine (Ade), Guanine (Gua), Uracil (Ura), Thymine (Thy), Cytosine (Cyt), Adenosine (A), Guanosine (G), Uridine (U), Cytidine (C), Deoxyadenosine (dA), Deoxyguanosine (dG), Deoxyuridine (dU), Deoxythymidine (dT), Deoxycytidine (dC), AMP, ADP, ATP, GMP, GDP, GTP, UMP, UDP, UTP, CMP, CDP, CTP, dAMP, dADP, dATP, dGMP, dGDP, dGTP, dUMP, dUDP, dUTP, dTMP, dTDP, dTTP, dCMP, dCDP, dCTP, 3',5'-Cyclic AMP, 3',5'-Cyclic GMP, 3',5'-Cyclic IMP, 3',5'-Cyclic dAMP, 3',5'-Cyclic dGMP, 3,5'-Cyclic CMP, 2,3'-Cyclic AMP, 2,3'-Cyclic GMP, 2',3'-Cyclic CMP, 2',3'-Cyclic UMP, Glycine (Gly), Alanine (Ala), Valine (Val), Leucine (Leu), Isoleucine (Ile), Aspartic acid (Asp), Asparagine (Asn), Glutamic acid (Glu), Glutamine (Gln), Serine (Ser), Threonine (Thr), Methionine (Met), Cysteine (Cys), Lysine (Lys), Arginine (Arg), Histidine (His), Proline (Pro), Phenylalanine (Phe), Tyrosine (Tyr), Tryptophan (Trp), Selenocysteine (Sec), Pyrrolysine (Pyl), L-Ornithine, L-Homocysteine, L-Homoserine, L-Citrulline, 3-Sulfino-L-alanine, L-Argininosuccinate, 3,4-Dihydroxy-L-phenylalanine, 3-Iodo-L-tyrosine, 3,5-Diiodo-L-tyrosine, Triiodothyronine, L-Thyroxine, beta-Alanine, gamma-Aminobutyric acid, 3-Aminoisobutyric acid, D-Alanine, D-Valine, D-Leucine, D-Isoleucine, D-Aspartic acid, D-Asparagine, D-Glutamic acid, D-Glutamine, D-Serine, D-Threonine, D-Methionine, D-Cysteine, D-Lysine, D-Arginine, D-Histidine, D-Proline, D-Phenylalanine, D-Tyrosine, D-Tryptophan, Pidolic acid, Hydroxyproline, Cystine, N-Formylmethionine, Ethanolamine, Cysteamine, Aminopropanol, gamma-Aminobutyric acid (GABA), Histamine, Dopamine, Serotonin, Putrescine, S-Adenosylmethioninamine, Tyramine, Phenethylamine, Retinal (Vitamin A), Ergocalciferol (Vitamin D2), Cholecalciferol (Vitamin D3), alpha-Tocopherol (Vitamin E), Phylloquinone (Vitamin K1), Menaquinone (Vitamin K2), Menadione (Vitamin K3), Thiamine (Vitamin B1), Riboflavin (Vitamin B2), Nicotinic acid (Vitamin B3), Nicotinamide (Vitamin B3), Pantothenic acid (Vitamin B5), Pyridoxal (Vitamin B6), Pyridoxine (Vitamin B6), Pyridoxamine (Vitamin B6), Biotin (Vitamin B7), Folic acid (Vitamin B9), Cobalamin(III) (Vitamin B12), Ascorbic acid (Vitamin C), SAM, Coenzyme B, Coenzyme F430, Coenzyme M, Coenzyme Q10, Glutathione, Methanofuran, PAPS, Tetrahydrobiopterin, 5,6,7,8-Tetrahydromethanopterin, Heme A, Heme C, Heme O, Lipoate, Molybdopterin, PQQ, Gonane, 5alpha-Gonane, 5beta-Gonane, Estrane, Allylestrenol, Estradiol-17alpha, Estradiol-17beta, Estriol, Estrone, Epimestrol, Equilin, Equilenin, 5beta-Estrane-3alpha,17beta-diol, Estramustine, 2-Hydroxyestradiol, 6beta-Hydroxyestradiol-17beta, 2-Methoxyestradiol-17beta, Methyltrienolone, Mifepristone, Nandrolone, Trenbolone, 5alpha-Androstane, Adrenosterone, Androsterone, 5beta-Androstane-3,17-dione, Androstanediol, 3-Androstanol, Androstenediol, Androstenedione, 4-Androstenediol, Dehydroepiandrosterone, Dihydrotestosterone, Etiocholanolone, Oxandrolone, Oxymetholone, Stanozolol, Testolactone, Testosterone, Pregnane, Aldosterone, Betamethasone, Beclomethasone, Corticosterone, Cortisol, Cortisone, Danazol, Dexamethasone, 11-Deoxycorticosterone, Ethisterone, Fluocidnolone, Fluocinonide, Fluorometholone 17-acetate, Megestrol, Norethindrone, Norethynodrel, Norgestrel, Prednisolone, Prednisone, Pregnenolone, Progesterone, Spironolactone, Cardanolide, Cymarin, Gitoxin, Neriifolin, Digitoxin, Digoxin, Ouabain, 5alpha-Cholane, Apocholic acid, Chenodeoxycholate, 3-Oxo-5beta-cholanate, Cholic acid, 5beta-Cholanic acid, Dehydrocholic acid, Deoxycholic acid, Glycocholate, Hyodeoxycholate, Lithocholic acid, Taurocholate, Ursodiol, Bufanolide, Bufadienolide, Bufalin, Bufotalin, Cinobufagin, Cinobufotalin, Gamabufogenin, Proscillaridin, Scillarenin, Scilliroside, Telocinobufagin, Cholestane, Allocholesterol, Cholesterol, 7-Dehydrocholesterol, Desmosterol, Ecdysone, Spirostan, Digitogenin, Diosgenin, Gitogenin, Sarsasapogenin, Smilagenin, Tigogenin, Furostan, Nuatigenin, Pseudoligogenin, Pseudosarsasapogenin, Pseudosmilagenin, Ergostane, Ergostanol, alpha-Ergostenol, Ergosterol, Lumisterol, 5alpha-Campestane, Brassinolide, Campestanol, Campesterol, Stigmastane, Fucosterol, Stigmastanol, Stigmasterol, 5alpha-Poriferastane, Poriferasterol, gamma-Sitosterol, Gorgostane, Acanthasterol, Gorgosterol, Sarcoaldesterol A, Prolactin-releasing peptide-31, Prolactin-releasing peptide-20, Thyrotropin-releasing hormone, Gonadotropin-releasing hormone I, Gonadotropin-releasing hormone II, Growth hormone-releasing hormone (1-29), Somatostatin-14, Somatostatin-28, Corticotropin releasing hormone, Gastrin-releasing peptide, Melanin-concentrating hormone, Ghrelin, Oxytocin, Arg-vasopressin, Corticotropin, alpha-Melanotropin, beta-Melanotropin, gamma-Melanotropin, Growth hormone, Prolactin, Thyroid stimulating hormone, Luteinizing hormone, Follicle stimulating hormone, Chorionic gonadotropin, Calcitonin, Parathyroid hormone, Atrial natriuretic peptide, Brain natriuretic peptide, C-Type natriuretic peptide, Endothelin-1, Endothelin-2, Endothelin-3, Glucagon, Insulin, Amylin, Peptide YY, Gastrin-14, Gastrin-17, Gastrin-34, Cholecystokinin-8, Cholecystokinin-33, Motilin, Secretin, Thymosin alpha-1, Thymosin beta-4, Thymosin beta-10, Insulin-like growth factor I, Insulin-like growth factor II, Erythropoietin, Angiotensin I, Angiotensin II, Angiotensin III, Angiotensin IV, Bradykinin, Leptin, Adiponectin, Resistin, 7alpha-Hydroxytestosterone, Dehydroepiandrosterone sulfate, 19-Hydroxytestosterone, Estrone 3-sulfate, 16alpha-Hydroxyestrone, 17alpha-Hydroxyprogesterone, 17alpha-Hydroxypregnenolone, 11-Deoxycortisol, Tetrahydrocortisone, 21-Deoxycortisol, 18-Hydroxycorticosterone, 11-Dehydrocorticosterone, Calcitriol (Vitamin D), Melatonin, Thyroxine, Adrenaline, Noradrenaline, Acetylcholine, Glycine, Aspartate, Glutamate, GABA, Dopa, Epinephrine; Adrenaline, Norepinephrine; Noradrenaline, Penicillin G, Ampicillin, Cephalosporin C, Cephamycin C, Cefazolin, Ceftriaxone, Clavulanic acid, Thienamycin, Imipenem, Nocardicin A, Aztreonam, Streptomycin, Spectinomycin, Kanamycin, Gentamicin C, Neomycin B, Butirosin A, Erythromycin, Oleandomycin, Tylosin, Candicidin D, Geldanamycin, Rifamycin W, Rifampicin, Tetracycline, Adriamycin, Actinorhodine, Tetranactin, Monensin, Griseofulvin, Vancomycin, Teicoplanin A2-2, Bleomycin B2, Bacitracin A, Valinomycin, Polymyxin B, Actinomycin D, Nalidixic acid, Norfloxacin, Nojirimycin, Flavomycin, Cycloserine, Polyoxin B, Cycloheximide, Fusidic acid, Chloramphenicol, Novobiocin, Fosfomycin, Mitomycin, and 2-Oxazolidinone.

In some embodiments, the desired compound is as listed below. In some embodiments, the desired compound is as listed below and obtainable from an Archaea cell. Desired compounds include Acetolactate synthase, Adenosylcobinamide-GDP ribazoletransferase, ADP-specific glucokinase, ADP-specific phosphofructokinase, Aminoimidazolase, 2-Amino-(1,2,3-trihydroxypropyl)-4(1H)-pteridinone; (1'S, 2'R)-form, 3'-O-β-D-Glucopyranoside, Anthranilate phosphoribosyltransferase, Archaeol, Archaeol; 1-O-[α-D-Galactofuranosyl-(1→3)-[β-D-galactopyranosyl-(1→6)]-α-D-mannopyranosyl-(1→2)-α-D-galactopyranoside], Archaeol; 1-O-[α-D-Galactofuranosyl-(1→3)-[3-O-sulfo-β-D-galactopyranosyl-(1→6)]-α-D-mannopyranosyl-(1→2)-α-D-galactopyranoside], Archaeol; 1-O-[β-D-Galactopyranosyl-(1→6)-α-D-glucopyranosyl-(1→2)-α-D-galactopyranoside], Archaeol; 1-O-[β-D-Galactopyranosyl-(1→6)-α-D-mannopyranosyl-(1→2)-α-D-glucopyranoside], Archaeol; 1-O β-D-Glucopyranoside, Archaeol; 1-O-[β-D-Glucopyranosyl-(1→6)-α-D-mannopyranosyl-(1→2)-α-D-glucopyranoside], Archaeol; 1-O-[3-O-Sulfo-β-D-galactopyranosyl-(1→6)-α-D-mannopyranosyl-(1→2)-α-D-glucopyranoside], Archaeol; 1-O-[2-Sulfo-α-D-mannopyranosyl-(1→2)-α-D-glucopyranoside], Argimicin B, Argimicin B; Amide, Argimicin B; 4'-Deoxy, amide, Aromatic amino acid transaminases; Aromatic amino acid transaminase, Astaxanthin; (3S,3'S)-form, Di-O-α-L-rhamnopyranoside, Bacteriorhodopsin, Bacterioruberin; 3"-Deoxy, 2",3"-didehydro, 3-Benzyl-6-(2-methylpropyl)-1,2,4,5-tetrathiane, Bis-γ-glutamylcystine reductase, 3,6-Bis(2-methylpropyl)-1,2,4,5-tetrathiane, 1,2-Bis-O-(3,7,11,15,19-pentamethyleicosyl) glycerol; 3-O-(2-O-α-D-Glucopyranosyl-myo-inosit-1-ylphosphate), 1,2-Bis-O-(3,7,11,15,19-pentamethyleicosyl) glycerol; 3-O-(myo-Inosit-1-ylphosphate), 1,2-Bis-O-(3,7,11,15-tetramethyl-2,6,10-hexadecatrienyl)glycerol, Caldarchaeol, Caldarchaeol; O-(2-Aminoethylphosphoryl), Caldarchaeol; O-(2-Aminoethylphosphoryl), O'-[β-D-glucopyranosyl-(1→6-β-D-glucopyranoside], Caldarchaeol; O-[α-D-Glucopyranosyl-(1→4)-β-D-galactopyranoside], Caldarchaeol; O-[β-D-Glucopyranosyl-(1→6-β-D-glucopyranoside], Caldarchaeol; O-(2-Hydroxymethyl-2,3,4,5-tetrahydroxy)cyclopentyl ether, Caldarchaeol; O-(1-D-myo-Inositylphosphoryl), Caldarchaeol; O-(1-D-myo-Inositylphosphoryl), O'-β-D-galactopyranoside, Caldarchaeol; O-(1-D-myo-Inositylphosphoryl), O'-[α-D-glucopyranosyl-(1→4)-β-D-galactopyranoside], Caldarchaeol; O-(1-D-myo-Inositylphosphoryl), O'-[β-D-glucopyranosyl-(1→6)-β-D-glucopyranoside], Caldarchaeol; O—(O-Serylphosphoryl), O'-[β-D-glucopyranosyl-(1→6)-β-D-glucopyranoside], Caldariellaquinone, Calditol, Coenzyme-B sulfoethylthiotransferase, Coenzyme F420, Cyano-5-hydroxybenzimidazolylcobamide, Cyano-5-methylbenzimidazolylcobamide, dCTP deaminase, 14,22,26,29,33,50,58,62,65,69-Decamethyl-8,11,44,47-tetraoxaheptacyclo[68.2.1.12, 5.118,21.134,37.138,41.154,57]octaheptacontane-10,46-dimethanol, 14,22,26,29,33,50,58,62,65,69-Decamethyl-8,11,44,47-tetraoxaheptacyclo[68.2.1.12,5.118,21.134,37.138, 41.154,57]octaheptacontane-10,46-dimethanol; 10'-O-(2-Hydroxymethyl-2,3,4,5-tetrahydroxycyclopentyl), 2-Dehydro-3-deoxygluconokinase, 2-Deoxy-arabino-hexuronic acid; D-form, 4,7-Dialkyl-1,2,3,5,6-pentathiepanes, 4,7-Dialkyl-1,2,3,5,6-pentathiepanes; 4-Benzyl-7-(2-methylpropyl)-1,2,3,5,6-pentathiepane, 4,7-Dialkyl-1,2,3,5,6-pentathiepanes; 4,7-Bis(2-methylpropyl)-1,2,3,5,6-pentathiepane, 4,7-Dialkyl-1,2,3,5,6-pentathiepanes; 4-Isopropyl-7-(2-methylpropyl)-1,2,3,5,6-pentathiepane, 4,7-Dialkyl-1,2,3,5,6-pentathiepanes; 4-Methyl-7-(2-methylpropyl)-1,2,3,5,6-pentathiepane, 4,7-Dialkyl-1,2,3,5,6-pentathiepanes; 4-(2-Methylpropyl-1,2,3,5,6-pentathiepane, 3,5-Dialkyl-1,2,4-trithiolanes, 3,5-Dialkyl-1,2,4-trithiolanes; 3-Benzyl-5-(2-methylpropyl)-1,2,4-trithiolane, 3,5-Dialkyl-1,2,4-trithiolanes; 3-Benzyl-5-methyl-1,2,4-trithiolane, 3,5-Dialkyl-1,2,4-trithiolanes; 3,5-Bis(2-methylpropyl)-1,2,4-trithiolane, 3,5-Dialkyl-1,2,4-trithiolanes; 3-Ethyl-5-(2-methylpropyl)-1,2,4-trithiolane, 3,5-Dialkyl-1,2,4-trithiolanes; 3-Ethyl-5-methyl-1,2,4-trithiolane, 3,5-Dialkyl-1,2,4-trithiolanes; 3-Isopropyl-5-(2-methylpropyl)-1,2,4-trithiolane, 3,5-Dialkyl-1,2,4-trithiolanes; 3-Methyl-5-(2-methylpropyl)-1,2,4-trithiolane, 3,5-Dialkyl-1,2,4-trithiolanes; 3-(2-Methylpropyl)-1,2,4-trithiolane, 7,8-Didemethyl-8-hydroxy-5-deazariboflavin, 3,4-Dihydro-4,6,7-trimethyl-3-β-D-ribofuranosyl-9H-imidazo[1,2-a]purin-9-one, 3,5-Dimethyl-1,2,4-trithiolane, 2,5-Dioxopiperazine hydrolase, Diphthine, Diphthine; 1'-Amide, 1,2-Diphytanylglycerol 3-phosphoinositol; D-myo-Inositol-form, 1,2-Diphytanylglycerol 3-phosphoinositol; L-myo-Inositol-form, 1,2-Diphytanylglycero-3-phosphoserine, 1,2-Diphytanylglyceryl-3-phosphorylglycerol, 1,2-Diphytanylglyceryl-3-phosphorylglycerol; 3"-(O-Methylphosphate) 1,2-Diphytanylglyceryl-3-phosphorylglycerol; 3"-O-Sulfate, 2,6,9,13,21,30,38,42,45,49,57,66-Dodecamethyl-24,27,60,63-tetraoxapentacyclo[68.2.1.114,17.134,37.150,53]hexaheptacontane-25,61-dimethanol, 2,6,9,13,21,30,38,42,45,49,57,66-Dodecamethyl-24,27,60,63-tetraoxapentacyclo[68.2.1.114, 17.134,37.150,53]hexaheptacontane-25,61-dimethanol; 25'-O-(2-Hydroxymethyl-2,3,4,5-tetrahydroxycyclopentyl), Factor F430, Factor F430; Penta-Me ester, Formylmethanofuran:tetrahydromethanopterin N-formyltransferase, 1,6-α-L-Fucosidase, β-D-Galactopyranosyl-(1→6)-α-D-mannopyranosyl-(1→2)-D-glucose, Geranylgeranylglycerol phosphate geranylgeranyltransferase, Glionitrin A, Glionitrin B, Glucan 1,4-α-maltotriohydrolase, 4-α-Glucanotransferase, 4-α-D-[(1→4)-α-D-Glucano]trehalose trehalohydrolase, α-Glucosidase, Halocins, Halocins; Haloan C8, Halocins; Halocin H1, Halocins; Halocin H4, Halocins; Halocin H6, Halocins; Halocin KPS1, Halocins; Halocin Sech7a, 2-(1,5,9,13,17,21-Hexamethyldocosyl)benzo[1,2-b:4,5-b']dithiophene-4,8-dione, 1,3,4,6-Hexanetetracarboxylic acid, 1,3,4,6-Hexanetetracarboxylic acid; (3RS,4SR)-form, Homoserine kinase, 3-Hydroxybutanoic acid; (R)-form, Tetramer, 3-[[32-[[1-(Hydroxymethyl)-2-(phytanyloxy)ethyl]oxy]diphytanyloxy]-2-phytanyloxy]-1-propanol, 2-(1H-Indol-3-ylmethyl)-1H-indole-3-acetic acid, 4-(3-Indolylmethyl)-7-(2-methylpropyl)-1,2,3,5,6-pentathiepane, 3-(3-Indolylmethyl)-5-(2-methylpropyl)-1,2,4-trithiolane, Isocaldarchaeol, Lipoyl synthase, Methanofuran, Methanofuran b, Methanophosphagen, Methanopterin, Methenyltetrahydrofolate cyclohydrolase, Methylated-DNA-[protein]-cysteine S-methyltransferase, 15-Methyl-5-hexadecenoic acid; (E)-form, Methylhexathiepane, 3-Methyl-8-(2-methylpropyl)-1,2,4,5-tetrathiane, (2-Methylpropyl)heptathiocane, (2-Methylpropyl)hexathiepane, (2-Methylpropyl)pentathiane, S-Methyl-5'-thioadenosine phosphorylase, MJ 0684, NAD(+) kinase, Nicotinamide nucleotide adenylyltransferase, Nicotinate phosphoribosyltransferase, 4-Nitrophenylphosphatase, 22,26,29,33,50,58,62,65,69-Nonamethyl-8,11,44,47-tetraoxaoctacyclo[68.2.1.12,5.114,17.118,21.134,37.138,41.154,57]nonaheptacontane-10,46-dimethanol, 22,26,29,33,50,58,62,65,69-Nonamethyl-8,11,44,47-tetraoxaoctacyclo[68.2.1.12,5.114,17.118,21.134,37.138,41.154,57]nonaheptacontane-10,46-dimethanol; 10'-O-(2-Hydroxymethyl-2,3,4,5-tetrahydroxycyclopentyl), 7,11,15,19,22,26,30,34-Octamethyl-1,4-dioxacyclohexatriacontane-2-methanol, 3,7,11,15,18,22,26,30-Octamethyl-1,32-dotriacontanediol; (3R,7R,11S,15R,18R,22S,26R,30R)-form, 22,26,29,33,58,62,65,69-Octamethyl-8,11,44,47-tetraoxanonacyclo[68.2.1.12,5.114,17.118,21.134,37.138,41.150,53.154,57]octacontane-9,45-dimethanol, 22,26,29,33,58,62,65,69-Octamethyl-8,11,44,47-tetraoxanonacyclo[68.2.1.12.5.114,17.118,21.134,37.138,41.150,53.154.57]octacontane-9,45-dimethanol; 9'-O-(2-Hydroxymethyl-2,3,4,5-tetrahydroxycyclopentyl), 2-Oxo-2H-pyran-4,6-dicarboxylic acid, 5,14,18,22,26,29,33,37,41,50,54,58,62,65,69-Pentadecamethyl-8,11,44,47-tetraoxabicyclo[68.2.1]triheptacontane-10,46-dimethanol, 5,14,18,22,26,29,33,37,41,50,54,58,62,65,69-Pentadecamethyl-8,11,44,47-tetraoxabicyclo[68.2.1]triheptacontane-10,46-dimethanol; 10'-O-(2-Hydroxymethyl-2,3,4,5-tetrahydroxycyclopentyl), 2-O-(3,7,11,15,19-Pentamethyleicosyl)-1-O-(3,7,11,15-tetramethylhexadecyl)glycerol, Phosphoglycerol geranylgeranyltransferase, O-Phosphoserine sulfhydrylase, 2-Phosphosulfolactate phosphatase, 1-Phytanoic acid; (3R,7R,11R)-form, Pyroglutamyl peptidase I, α-L-Rhamnopyranosyl-(1→3)-α-D-galactopyranosyl-(1→3)-L-fucose, Serine C-palmitoyltransferase, Sulfohalopterin 2, Sulfolobicins, Sulfolobusquinone, Sulfolobusquinone; Didehydro, Sulfur reductase, Superoxide reductase, 2,6,9,13,21,30,34,38,42,45,49,53,57,66-Tetradecamethyl-24,27,60,63-tetraoxatricyclo[68.2.1.114,17]tetraheptacontane-25,61-dimethanol, 5,14,18,22,26,29,33,41,50,54,58,62,65,69-Tetradecamethyl-8,11,44,47-tetraoxatricyclo[68.2.1.134,37]tetraheptacontane-10,46-dimethanol, 5,14,18,22,26,29,33,41,50,54,58,62,65,69-Tetradecamethyl-8,11,44,47-tetraoxatricyclo[68.2.1.134,37]tetraheptacontane-10,46-dimethanol; 46'-O-(2-Hydroxymethyl-2,3,4,5-tetrahydroxycyclopentyl), Tetrahydromethanopterin S-methyltransferase, 2,6,9,13,21,30,38,42,45,49,53,57,66-Tridecamethyl-24,27,60,63-tetraoxatetracyclo[68.2.1.114,17.134,37]pentaheptacontane-25,61-dimethanol, 2,6,9,13,21,30,38,42,45,49,53,57,66-Tridecamethyl-24,27,60,63-tetraoxatetracyclo[68.2.1.114,17.134,37]pentaheptacontane-25,61-dimethanol; 25'-O-(2-Hydroxymethyl-2,3,4,5-tetrahydroxycyclopentyl), 6-(3,7,11-Trimethyldodecyl)-5-methylbenzo[b]thiophene-4,7-dione, 6-(3,7,11-Trimethyldodecyl)-5-methylbenzo[b]thiophene-4,7-dione; Homologue (n=3), 6-(3,7,11-Trimethyldodecyl)-5-methylbenzo[b]thiophene-4,7-dione; Homologue (n=4), 14,22,26,29,33,41,50,58,62,65,69-Undecamethyl-8,11,44,47-tetraoxahexacyclo[68.2.1.12,5.118,21.134,37.154,57]heptaheptacontane-10,46-dimethanol, 14,22,26,29,33,41,50,58,62,65,69-Undecamethyl-8,11,44,47-tetraoxahexacyclo[68.2.1.12,5.118,21.134,37.154,57]heptaheptacontane-10,46-dimethanol; 10'-O-(2-Hydroxymethyl-2,3,4,5-tetrahydroxycyclopentyl), Uroporphyrinogen-III C-methyltransferase, Zeaxanthin; (3R,3'R, all-E)-form, Di-O-α-L-rhamnopyranoside, Zeaxanthin; (3R,3'R, all-E)-form, Di-O-β-D-glucopyranoside, Zeaxanthin; (3R,3'R, all-E)-form, 3-O-α-L-Rhamnopyanoside, Zeaxanthin; (3R,3'R, 9Z)-form, Di-O-α-L-rhamnopyranoside, Zeaxanthin; (3R,3'R,9Z)-form, 3-O-α-L-Rhamnopyranoside, Zeaxanthin; (3R,3'R,13Z)-form, 3-O-α-L-Rhamnopyranoside, Zeaxanthin; (3R,3'R,15Z)-form, and 3-O-α-L-Rhamnopyranoside.

In some embodiments, the desired compound is as listed below. In some embodiments, the desired compound is as listed below and obtainable from an Eubacteria cell. Desired compounds include Abaecin, Abequosyltransferase, Abyssomicin B, Abyssomicin C, Abyssomicin C; Atropisomer, Abyssomicin C; 8,9-Dihydro, Abyssomicin D, Abyssomicin G, Acadesine, Acarbose, Acarbose; 7-O-Phosphate, 2-Acetamidobenzoic acid; Amide, Acetan, Acetate CoA-transferase, Acetate kinase, Acetoin:ribose-5-phosphate transaldolase, Acetolactate synthase, Acetoxan, Acetylacetone-cleaving enzyme, N-[2-[4-(Acetylamino)phenyl]-1-(hydroxymethyl)-2-(1H-indol-3-yl)ethyl]-2,2-dichloroacetamide, Acetyl-CoA C-acetyltransferase, Acetyl-CoA C-acyltransferase, 7-Acetyl-3,4-dihydro-3,6-dihydroxy-8-methyl-1(2H)-naphthalenone; (−)-form, Acetylesterase, β-N-Acetylgalactosaminidase, N-Acetylgalactosaminoglycan deacetylase, N-Acetylgalactosaminylproteoglycan 3-β-glucuronosyltransferase, N-Acetylglucosamine kinase, N-Acetylglucosaminyldiphosphoundecaprenol N-acetyl-β-D-mannosaminyltransferase, N-Acetylglucosaminyldiphosphoundecaprenol glucosyltransferase, 6-O-Acetylglucose; D-form, 6-Acetylglucose deacetylase, Acetylglutamate kinase, N-Acetylglycine, N-Acetylhexosamine 1-dehydrogenase, N6-Acetyl-β-lysine transaminase, N-Acetylmuramoyl-L-alanyl-D-glutamyl-γ-diaminoadipic acid, N-Acetylneuraminate synthase, N-Acetylneuraminic acid; α-Pyranose-form, α(2→8)-Homopolymer, N-Acetylornithine carbamoyltransferase, Acetylornithine transaminase, 2-Acetylthiazole, Acetylxylan esterase, Achromobactin, Acidocins, Acidocins; Acidocin 8912, Acidocins; Acidocin A, Acidocins; Acidocin B, Acidocins; Acidocin 1B, Acidocins; Acidocin CH5, Acidocins; Acidocin D20079, Acidocins; Acidocin J1132, Acidocins; Acidocin J1229, Acidocins; Acidocin LCHV, Acidocins; Acidocin LF221A, Acidocins; Acidocin LF221B, Acidophilin, Acidophilin 801, Acidophilucin A, Acinetoferrin, Acireductone synthase, Aclacinomycin M; 10-Epimer, 1-hydroxy, 4C-ketone, Aclacinomycin M; 1-Hydroxy, 4C-ketone, Acnecin, Aconitate methyltransferases; trans-Aconitate 2-methyltransferase, Acrylochlorin, Actagardine A, Actagardine A; N1-Ac, Actagardine A; N1-Ac, mono-Me ester, Actagardine A; N1-L-Alanyl, Actagardine A; 11-L-Glutamine, 19-L-cysteinamide analogue, S,S-dioxide, Actagardine A; 15-L-Leucine, 16-L-valine analogue, Actagardine A; 15-L-Leucine, 16-L-valine analogue, S-deoxo, Actaplanin, Actinobacillin, Actinoidin; Actinoidin A, Actinoidin; Actinoidin B, Actinomycin lactonase, Actinomycin Z1, Actinomycin Z1; 41β-Deoxy, Actinomycin Z1; 41β-Deoxy, 41β-chloro, Actinomycin Z1; Dideoxy, Actinomycin Z1; Dideoxy, 41β-chloro, Actinoplanic acid, Actinoplanic acid B, Actinoplanone D, Actinoplanone D; N-Amino, Actinoplanone D; 11-Chloro, Actinoplanone D; 11-Chloro, N-amino, Actinoplanone D; 11-Chloro, N-(isopropylideneamino), Actinoplanone D; 11-Chloro, N-(3-oxo-2-butenylideneamino), Actinoplanone D; N-(3-Oxo-2-butenylideneamino), Aculeximycin, Acyl-[acyl-carrier-protein]-phospholipid O-acyltransferase, Acyl-[acyl-carrier-protein]:UDP-N-acetylglucosamine O-acyltransferase, [Acyl-carrier-protein] S-acetyltransferase, [Acyl-carrier-protein] S-malonyltransferase, [Acyl-carrier-protein] phosphodiesterase, Acyl-CoA dehydrogenases; cis-2-Enoyl-CoA reductase (NADPH), Acyl-CoA dehydrogenases; trans-2-Enoyl-CoA reductase (NADPH), Acylglycerol kinase, Acylglycerol lipase, 1-Acylglycerol-3-phosphate O-acyltransferase, N-Acylmannosamine kinase, Acyl phosphate hexose phosphotransferase, Adenine deaminase, Adenine phosphoribosyltransferase, Adenosine deaminase, Adenosylcobinamide-GDP ribazoletransferase, Adenosylcobinamide kinase, Adenosylcobinamide phosphate guanylyltransferase, Adenosylhomocysteine nucleosidase, Adenosylmethionine 8-amino-7-oxononanoate transaminase, Adenosylmethionine hydrolase, Adenylyl-[glutamate-ammonia ligase] hydrolase, Adenylyl sulfate kinase, Adonixanthin; 3-O-β-D-Glucopyranoside, ADP-ribosyl-[dinitrogen reductase] hydrolase, ADP-specific glucokinase, ADP-specific phosphofructokinase, Adriamycin; 11-Deoxy, Aerobactin, Aerocavin, Aerocyanidin, Aeroglycan, Aeruginosin B, α-Agarase, β-Agarase, Agelaxanthin A; Deoxy, Agglomerin, Agmatinase, Agmatine deiminase, Agrastatin, Agrobacteriocin I, Agrobactin, Agrochelin, Agrocin 434, Agrocin 84, Agrocin C58, Agrocin D286, Agrocinopin A, Agrocinopin A; De-O-glucopyranosyl, Agrocinopin C, Agrocinopin D, Agropinic acid, Ajudazol B, Ajudazol B; 15,29-Didehydro, Akanthomycin, D-Ala-D-Ala dipeptidase, Alanilin, Alanine carboxypeptidase, Alanine dehydrogenase, D-Alanine 2-hydroxymethyltransferase, β-Alanine pyruvate transaminase, N-Alanylcysteine; D-L-form, Alanylhomoserinylaspartic acid; (all-S)-form, 5-[(Alanylhomoserinyl-β-aspartyl)oxy]-1,2-dihydro-4-hydroxy-3H-pyrazol-3-one, Alanylphosphatidylglycerol synthase, N-Alanylthreonine; L-L-form, N-(2,3-Dihydroxybenzoyl), Albicidin, Albolutein, Albusin B, Alcaligin, Alcaligin; 8,18-Dideoxy, Alcanivorone, Aldose β-D-fructosyltransferase, Alirin B1, Alkaline phosphatase, *Pseudomonas fluorescens* Alkaloid, Alkanal monooxygenase (FMN-linked), Alkane 1-monooxygenase, Alkanesulfonate monooxygenase, Alkene monooxygenase, 2-Alkyl-3,4-dihydroxyquinolines, 3-(2-Alkyl-5-oxazolyl-1H-indoles; 3-(2-Benzyl-5-oxazolyl)-1H-indole, 3-(2-Alkyl-5-oxazolyl)-1H-indoles; 3-(2-Butyl-5-oxazolyl)-1H-indole, 3-(2-Alkyl-5-oxazolyl)-1H-indoles; 3-(2-Ethyl-5-oxazolyl)-1H-indole, 3-(2-Alkyl-5-oxazolyl)-1H-indoles; 3-(2-Methyl-5-oxazolyl)-1H-indole, 3-(2-Alkyl-5-oxazolyl)-1H-indoles; 3-[2-(2-Methylpropyl)-5-oxazolyl]-1H-indole, 3-(2-Alkyl-5-oxazolyl)-1H-indoles; 3-(2-Pentyl-5-oxazolyl)-1H-indole, 3-(2-Alkyl-5-oxazolyl)-1H-indoles; 3-(2-Propyl-5-oxazolyl)-1H-indole, N-Alkylvaline N-butylglucosamine esters, Allantoate deiminase, Allantoicase, Allaric acid; D-form, Allose kinase, Alphostatin, Alteramide A, Alteramide A; 25-Deoxy, Altericidin, Alternan, Alternansucrase, Aterobactin A, Alterobactin B, Althiomycin, Alveicins, Alvein, Ambruticin, Ambruticin, 5-Epimer, Ambruticin VS 5, Ambruticin VS 5; N,N-Di-Me, Ambruticin VS 5; N,N-Di-Me, N-oxide, Ambruticin VS 5; N-Me, Ambruticin VS 5; N,N,N-Tri-Me, Me ester, Ambruticin VS 5; N,N,N-Tri-Me, Amicoumacin B, Amicoumacin B; Amide, Amicoumacin B; Amide, 8'-phosphate, Amicoumacin B; 8'-Phosphate, Amicoumacin C, Amicoumacin C; N—Ac, Amicoumacin C; N-Propanoyl, Amidinoaspartase, Amidophosphoribosyltransferase, 2-Aminoacetophenone, Amino acid dehydrogenases; D-Amino-acid dehydrogenase, Amino acid dehydrogenases; L-Amino-acid dehydrogenase, α-Amino-acid esterase, D-Amino acid transaminase, Aminoacyl-tRNA hydrolase, 2-Amino-5-amidinooxypentanoic acid, α-Amino-5-[[(2-aminocarbonyl-1-carboxyethyl)amino]carbonyl]-2-pyrrolepropanoic acid, 2-Amino-3-O-(3-amino-3,6-dideoxy-β-D-glucopyranosyl)-2-deoxy-D-galactose; N,N'-Di-Ac, 5-Amino-2-(aminomethyl)-2-hydroxyhexanedioic acid; (2S,5S)-form, 5-Amino-2-(aminomethyl)-2-hydroxyhexanedioic acid; (2S,5S)-form, β-Lactam, 2-Amino-5-(aminomethyl)pyrrolo[2,3-d]pyrimidin-4(3H)-one, 2-Amino-4-(aminooxy)-3-butenoic acid; (S,E)-form, N-Formyl, 3-Amino-1-(2-aminophenyl)-1-propanone; N3-Ac, 2-Amino-3-azidopropanoic acid; (S)-form, 35-Amino-30,31,32,33,34-bacteriohopanepentol; (28S,30R,31R,32R,33S,34S)-form, 30-Deoxy, 35-Amino-30,31,32,33,34-bacteriohopanepentol; (28S,30R,31R,32R,33S,34S)-form, 2-Amino-1,4-benzenediol; N—Ac, 2-Aminobenzenesulfonate 2,3-dioxygenase, 2-Aminobenzoic acid; Amide, 2-Amino-8-benzoyl-6-hydroxy-3H-phenoxazin-3-one, 2-Amino-8-benzoyl-6-hydroxy-3H-phenoxazin-3-one; 4'-Hydroxy, 4-Aminobutyrate transaminase, 3-(3-Amino-3-carboxypropyl)uridine, 3-(2-Amino-3-chlorophenyl)-4-chloro-1H-pyrrole, 3-(2-Amino-3-chlorophenyl)-4-chloro-1H-pyrrole; 2-Chloro, 2-Amino-3-cyanopropanoic acid; (S)-form, α-Amino-1,4-cyclohexadiene-1-propanoic acid; (S)-form, 6-Amino-1,2,3,4,5-cyclohexanepentol; (1α,2β,3α,4β,5α,6β)-form, 2-Me, 2-Aminocyclopentanecarboxylic acid; (1R,2S)-form, 2-Amino-2-deoxyaltruronic acid; L-form, 4-Amino-4-deoxyarabinose; D-form, 4-Amino-4-deoxyarabinose; β-L-Pyranose-form, 1-Dihydrogen phosphate, 2-Amino-2-deoxy-α-L-galactopyranuronosyl-(1→3)-2-amino-2-deoxy-α-D-quinovosyl-(1→3)-D-rhamnose; α-Pyranose-form, 2'N,2''N-Di-Ac, 2-Amino-2-deoxygalacturonic acid; D-form, 2-Amino-2-deoxygalacturonic acid; D-form, N-Formyl, 2-Amino-2-deoxygalacturonic acid; D-form, N—Ac, 2-Amino-2-deoxygalacturonic acid; D-form, N—Ac, amide, 2-Amino-2-deoxygalacturonic acid; L-form, N—Ac, 3-Amino-3-deoxy-β-D-glucopyranosyl 3-amino-3-deoxy-α-D-glucopyranoside, 2-Amino-2-deoxy-β-D-glucopyranosyl-(1→3)-2-amino-2-deoxy-β-D-glucopyranosyl-(1→3)-2-amino-2-deoxy-D-glucose, 2-Amino-2-deoxy-β-D-glucopyranosyl-(1→3)-[α-D-galactopyranosyl-(1→4)]-2-amino-2-deoxy-D-mannose; β-Pyranose-form, N,N'-Di-Ac, 2-Amino-2-deoxy-β-D-glucopyranosyl-(1→3)-α-D-galactopyranosyl-(1→4)-L-rhamnose, 3-O-(2-Amino-2-deoxy-β-D-glucopyranosyl)-D-galactose; D-Pyranose-form, N—Ac, 2-Amino-2-deoxy-4-O-α-D-glucopyranosyl-D-mannopyranuronic acid; Pyranose-form, N—Ac, 2-Amino-2-deoxy-β-

D-glucopyranosyl-(1→2)-α-L-rhamnopyranosyl-(1→2)-L-rhamnose, 4-O-(2-Amino-2-deoxy-D-glucopyranosyl)-D-ribitol; N—Ac, 3-Amino-3-deoxyglucose; D-form, 4-Amino-4-deoxyglucose; D-form, 2-Amino-2-deoxyglucuronic acid; D-form, 2-Amino-2-deoxyglucuronic acid; D-form, 4-Me, N—Ac, 7-Amino-7-deoxyguanosine, 2-Amino-2-deoxyguluronic acid; L-form, 2-Amino-2-deoxy-β-D-mannopyranosyl(1→3)-2-amino-2-deoxy-α-L-fucopyranosyl-(1→3)-2-amino-2-deoxy-D-galactose, 2-Amino-2-deoxy-β-D-mannopyranosyl-(1→4)-[α-D-galactopyranosyl-(1→3)]-2-amino-2-deoxy-β-D-glucose; β-D-Pyranose-form, N,N'-Di-Ac, 2-Amino-2-deoxy-β-D-mannopyranosyl-(1→4)-α-D-glucopyranosyl-(1→2)-L-rhamnose, 2-Amino-2-deoxy-β-D-mannopyranosyl(1→4)-α-D-glucopyranosyl-(1→2)-L-rhamnose, 2-Amino-2-deoxy-β-D-mannopyranuronosyl-(1→4)-2-amino-2-deoxy-α-L-fucopyranosyl-(1→3)-2-amino-2-deoxy-L-fucose, 2-Amino-2-deoxy-β-D-mannopyranuronosyl-(1→4)-2-amino-2-deoxy-β-L-fucopyranosyl-(1→3)-2-amino-2-deoxy-L-fucose, 6-(2-Amino-2-deoxy-β-D-mannopyranuronosyl)-D-glucose; Pyranose-form, N—Ac, 6-(2-Amino-2-deoxy-β-D-mannopyranuronosyl)-D-glucose; Pyranose-form, [2-(Octadecanoylamino)ethyl] glycoside, N—Ac, 2-Amino-2-deoxymannose; D-form, 2-Amino-2-deoxymannuronic acid; D-form, N—Ac, 2-Amino-2-deoxy-8-O-methylglucose; D-form, 4-Amino-4-deoxy-α-D-rhamnopyranosyl-(1→2)-4-amino-4-deoxy-α-D-rhamnopyranosyl-(1→2)-4-amino-4-deoxy-D-rhamnose, 4-Amino-4-deoxy-α-D-rhamnopyranosyl-(1→2)-4-amino-deoxy-α-D-rhamnopyranosyl-(1→3)-4-amino-4-deoxy-D-rhamnose, 2-Amino-2,6-dideoxygalactose; D-form, 2-Amino-2,6-dideoxygalactose; D-form, N-Me, N—Ac, 2-Amino-2,6-dideoxygalactose; L-form, 2-Amino-2,6-dideoxygalactose; DL-form, 3-Amino-3,6-dideoxygalactose; D-form, N—Ac, 3-Amino-3,6-dideoxygalactose; D-form, N-Formyl, 3-Amino-3,6-dideoxygalactose; D-form, N-(2S, 3-Dihydroxypropanoyl), 4-Amino-4,6-dideoxygalactose; D-Pyranose-form, 2-Amino-2,6-dideoxyglucose; D-form, 3-Amino-3,6-dideoxyglucose; D-form, 3-Amino-3,6-dideoxyglucose; D-form, N-Formyl, 3-Amino-3,6-dideoxyglucose; D-form, N-(3S-Hydroxybutanoyl), 3-Amino-3,6-dideoxyglucose; D-form, N-(2S-Acetamido-3-hyroxypropanoyl), 3-Amino-3,6-dideoxyglucose; L-form, 3-Amino-3,6-dideoxyglucose; L-form, N—Ac, 4-Amino-4,6-dideoxyglucose; D-form, 4-Amino-4,6-dideoxyglucose; D-form, N—Ac, 2-Amino-2,6-dideoxymannose; L-form, 4-Amino-4,6-dideoxymannose; D-form, 4-Amino-4,6-dideoxymannose; D-form, N—Ac, 4-Amino-4,6-dideoxymannose; D-form, 2-Me, 2-Amino-2,6-dideoxytalose; L-form, 2-Amino-2,6-dideoxytalose; L-form, N—Ac, 3-Aminodihydro-2(3H)-furanone; (8)-form, N-Hexadecanoyl, 3-Aminodihydro-2(3H)-furanone; (S)-form, N-(3-Oxohexanoyl), 3-Aminodihydro-2(3H)-furanone; (S)-form, N-(3R-Hydroxybutanoyl), 3-Aminodihydro-2(3H)-furanone; (S)-form, N-Octanoyl, 3-Aminodihydro-2(3H)-furanone; (S)-form, N-(3R-Hydroxy-7Z-tetradecenoyl), 3-Aminodihydro-2(3H)-furanone; (S)-form, N-Hexanoyl, 3-Aminodihydro-2(3H)-furanone; (S)-form, N-Heptanoyl, 3-Aminodihydro-2(3H)-furanone; (S)-form, N-(3R-Hydroxyhexanoyl), 3-Aminodihydro-2(3H)-furanone; (S)-form, N-(3-Oxooctanoyl), 3-Aminodihydro-2(3H)-furanone; (S)-form, N-Decanoyl, 3-Aminodihydro-2(3H)-furanone; (S)-form, N-(3-Oxodecanoyl), 3-Aminodihydro-2(3H)-furanone; (S)-form, N-Dodecanoyl, 3-Aminodihydro-2(3H)-furanone; (S)-form, N-(3-Oxododecanoyl), 3-Aminodihydro-2(3H)-furanone; (S)-form, N-Tetradecanoyl, 3-Aminodihydro-2(3H)-furanone; (S)-form, N-(7Z-Tetradecenoyl), 3-Aminodihydro-2(3H)-furanone; (S)-form, N-(3-Oxotetradecanoyl), 3-Aminodihydro-2(3H)-furanone; (S)-form, N-(9Z-Hexadecenoyl), 3-Aminodihydro-2(3H)-furanone; (S)-form, N-(3-Oxo-9Z-hexadecenoyl), 3-Aminodihydro-2(3H)-furanone; (S)-form, N-Octadecanoyl, 3-Aminodihydro-2(3H)-furanone; (S)-form, N-Butanoyl, 3-Aminodihydro-2(3H)-furanone; (S)-form, N-(3R-Hydroxydecanoyl), 3-Aminodihydro-2(3H)-furanone; (S)-form, N-(2E,7Z-Tetradecadienoyl), 3-Aminodihydro-2(3H)-furanone; (S)-form, N-(5Z-Dodecenoyl), 3-Aminodihydro-2(3H)-furanone; (S)-form, N-(3-Oxo-5Z-dodecenoyl), 3-Aminodihydro-2(3H)-furanone; (S)-form, N-(5-Methylhexanoyl), 3-Aminodihydro-2(3H)-furanone; (S)-form, N-(5-Methylhexenoyl), 3-Aminodihydro-2(3H)-furanone; (S)-form, N-(3R-Hydroxy-5-methylhexanoyl), 3-Aminodihydro-2(3H)-furanone; (S)-form, N-(3R-Hydroxy-6-methylheptanoyl), 3-Aminodihydro-2(3H)-furanone; (S)-form, N-(7-Methyloctanoyl), 3-Aminodihydro-2(3H)-furanone; (S)-form, N-(3R-Hydroxy-7-methyloctanoyl), 3-Aminodihydro-2(3H)-furanone; (S)-form, N-(2E,9Z-Hexadecadienoyl), 3-Aminodihydro-2(3H)-furanone; (S)-form, N-Nonanoyl, 3-Aminodihydro-2(3H)-furanone; (S)-form, N-Undecanoyl, 3-Aminodihydro-2(3H)-furanone; (S)-form, N-(2E-Dodecenoyl), 3-Aminodihydro-2(3H)furanone; (S)-form, N-Tridecanoyl, 3-Aminodihydro-2(3H)-furanone; (S)-form, N-Pentadecanoyl, 3-Aminodihydro-2(3H)-furanone; (S)-form, N-(3-Oxo-11Z-hexadecenoyl), 3-Aminodihydro-2(3H)-furanone; (S)-form, N-(3-Oxoheptanoyl), 3-Aminodihydro-2(3H)-furanone; (S)-form, N-(3-Oxohexadecanoyl), 3-Aminodihydro-2(3H)-furanone; (S)-form, N-(3R-Hydroxyoctanoyl), 3-Aminodihydro-2(3H)-furanone; (S)-form, N-(3R-Hydroxytetradecanoyl), 3-Aminodihydro-2(3H)-furanone; (S)-form, N-(4-Hydroxy-E-cinnamoyl), 2-Amino-3,4-dihydroxybenzoic acid; 4-Me ether, Me ester, 3-Amino-6,7-dihydroxy-2H-1-benzopyran-2-one; N-Formyl, 2-Amino-3-(3,4-dihydroxyphenyl)propanoic acid; (S)-form, 2-Amino-6-(1,2-dihydroxypropyl)-4(1H)-pteridinone; (1'R,2'S)-form, 2'-O-(2-Acetamido-2-deoxy-β-D-glucopyranoside), 2-Amino-6-(1,2-dihydroxypropyl)-4(1H)-pteridinone; (1'S,2'S)-form, 2'-O-(2-Acetamido-2-deoxy-β-D-glucopyranoside), 2-Amino-4,6-dihydroxypteridine; 6-O-Sulfate, 6-Amino-2,8-dihydroxypurine, 4-Amino-3,6-dihydroxy-1H-pyrazolo[3,4-d]pyrimidine, 6-Amino-1,2-dithiolo[4,3-b]pyrrol-5(4H)-one; N6-Decanoyl, 6-Amino-1,2-dithiolo[4,3-b]pyrrol-5(4H)-one; N6-(3E-Decenoyl), 6-Amino-1,2-dithiolo[4,3-b]pyrrol-5(4H)-one; N6-(4Z-Decenoyl), 6-Amino-1,2-dithiolo[4,3-b]pyrrol-5(4H)-one; N6-Dodecenoyl, 6-Amino-1,2-dithiolo[4,3-b]pyrrol-5(4H)-one; N6-(Z-Hexadecenoyl), 6-Amino-1,2-dithiolo[4,3-b]pyrrol-5(4H)-one; N6-Hexanoyl, 6-Amino-1,2-dithiolo[4,3-b]pyrrol-5(4H)-one; 4-Me, N6-butanoyl, 6-Amino-1,2-dithiolo[4,3-b]pyrrol-5(4H)-one; 4-Me, N6-hexanoyl, 6-Amino-1,2-dithiolo[4,3-b]pyrrol-5(4H)-one; 4-Me, N6-hexanoyl, S1- or S2-dioxide, 6-Amino-1,2-dithiolo[4,3-b]pyrrol-5(4H)-one; 4-Me, N6-hexanoyl, S1- or S2-oxide, 6-Amino-1,2-dithiolo[4,3-b]pyrrol-5(4H)-one; 4-Me, N6-(3-methylbutanoyl), 6-Amino-1,2-dithiolo[4,3-b]pyrrol-5(4H)-one; 4-Me, N6-5-methylhexanoyl), 6-Amino-1,2-dithiolo[4,3-b]pyrrol-5(4H)-one; 4-Me, N6-(5-methylhexanoyl), S1- or S2-dioxide, 6-Amino-1,2-dithiolo[4,3-b]pyrrol-5(4H)-one; 4-Me, N6-(5-methylhexanoyl), S1- or S2-oxide, 6-Amino-1,2-dithiolo[4,3-b]pyrrol-5(4H)-one; N6-(5-Methylhexanoyl), 6-Amino-1,2-dithiolo[4,3-b]pyrrol-5(4H)-one; N6-(5-Methylhexanoyl), S1- or S2-dioxide, 6-Amino-1,2-dithiolo[4,3-b]pyrrol-5(4H)-one; N6-Octanoyl, 6-Amino-1,2-dithiolo[4,3-b]pyrrol-5(4H)- one; N6-Tetradecanoyl, 6-Amino-1,2-dithiolo[4,3-b]pyrrol-5(4H)-one; N6-(E-Tetradecanoyl), 2-Amino-1,1,2-ethanetricarboxylic acid; (±)-form, 2-Aminoethyl dihydrogen phosphate; N—Ac, 2-(2-Aminoethyl)hexahydropyrrolo[1,2-a]pyrazine-1,4-dione; (3S,8aS)-form, 2'-N-Me, 3-(2-Aminoethyl)-2-nitroindole; Nb-Ac, (2-Aminoethyl)phosphonate pyruvate transaminase, 2-Amino-3-(3-formyl-4-hydroxyphenyl)propanoic acid; (S)-form, 2-Amino-3-(3-formyl-4-hydroxyphenyl)propanoic acid; (S)-form, L-Threonyl amide, Aminoglycoside N3'-acetyltransferase, Aminoglycoside N6'-acetyltransferase, 3-Aminoheptanedioic acid; (ξ)-form, Bis(L-phenylalaninamide), 6-Aminohexanoate cyclic dimer hydrolase, 2-Amino-4-hexenoic acid; (S)-(E)-form, 2-Amino-3-hydroxybenzoic acid, 2-Amino-3-hydroxybutanedioic acid; (2S,3S)-form, 2-Amino-4-hydroxybutanoic acid; (S)-form, Et ether, 2-Amino-4-hydroxybutanoic acid; (S)-form, O-Phosphate, 2-Amino-4-hydroxy-6-hydroxymethyldihydropteridine diphosphokinase, 4-Amino-2-hydroxy-5-(hydroxymethyl)pyrimidine; OH-form, 2-Me ether, 2-Amino-3-hydroxy-15-methyl-1-hexadecanesulfonic acid; (2R,3R)-form, 2-Amino-3-hydroxy-15-methyl-1-hexadecanesulfonic acid; (2R,3R)-form, 4,5-Didehydro(E-), N-(3R-hydroxy-15-methylhexadecanoyl), 2-Amino-3-hydroxy-15-methyl-1-hexadecanesulfonic acid; (2R,3R)-form, N-(3R-Hydroxy-15-methylhexadecanoyl), 2-Amino-3-hydroxy-15-methyl-1-hexadecanesulfonic acid; (2R,3R)-form, N-(13-Methyltetradecanoyl), 2-Amino-3-hydroxy-15-methyl-4-hexadecene-1-sulfonic acid; (2S,3R,4E)-form, N-(2R-Hydroxy-13-methyltetradecanoyl), 2-Amino-3-(4-hydroxymethylphenyl)propanoic acid; (S)-form, 5-Amino-6-hydroxy-4-oxohexanoic acid; (+)-form, 5-Amino-4-hydroxypentanoic acid; (S)-form, 2-Amino-6-[3-hydroxy-4-(phosphonooxy)-1-butenyl]-4(1H)-pteridinone, 6-Amino-2-hydroxypurine; 6-N-Me, 4-Amino-3-hydroxy-1H-pyrazolo[3,4-d]pyrimidine, Aminoimidazolase, 5-Aminoimidazole riboside, 5-Aminoimidazole riboside; 5'-Phosphate, 2-Amino-6-(1H-indol-3-ylacetyl)hexanoic acid; (S)-form, N2-Ac, 5-Aminolevulinate synthase, 5-Aminolevulinate transaminase, 2-Amino-4-methoxy-3-butenoic acid; (S)-(E)-form, 35-Amino-3-methyl-30,31,32,33,34-bacteriohopanepentol; (3β,22ξ,30ξ,31ξ,32ξ,33ξ,34ξ)-form, 11,12-Didehydro, 35-Amino-3-methyl-30,31,32,33,34-bacteriohopanepentol; (3β,22ξ,30R,31R,32R,33S,34S)-form, 35-Amino-3-methyl-30,31,32,33,34-bacteriohopanepentol; (3β,22ξ,30R,31R,32R,33S,34S)-form, 30-Deoxy, 2-Amino-3-methylbutanedioic acid; (2S,3S)-form, α-Amino-1-methylcyclopropaneacetic acid; (S)-form, 2-Amino-3-methylhexanoic acid; (2S,3S)-form, 3-Amino-4-methyl-2-oxetanone; (3S,4R)-form, N—Ac, 2-Amino-3-methyl-4-oxopentanoic acid, 4-Amino-5-(methylthio)-1,2,3-cyclopentanetriol; (1R,2R,3R,4S,5R)-form, 4-Amino-6-(methylthio)-1,2,3-cyclopentanetriol; (1R,2R,3R,4S,5R)-form, S-Oxide, Aminomethyltransferase, 3-Amino-1,4-naphthoquinone-2-carboxylic acid, 2-Amino-1-(4-nitrophenyl)-1,3-propanediol; (1R,2R)-form, N—Ac, 2-Amino-1-(4-nitrophenyl)-1,3-propanediol; (1R,2R)-form, N-Propanoyl, 2-Amino-1-(4-nitrophenyl)-1,3-propanediol; (1R,2R)-form, N-(2-Methylpropanoyl), 2-Amino-1-(4-nitrophenyl)-1,3-propanediol; (1R,2R)-form, N,O3-Di-Ac, 2-Amino-1-(4-nitrophenyl)-1,3-propanediol; (1R,2R)-form, N-Propanoyl, O3-Ac, 2-Amino-1,3-octadecanediol; (2S,3R)-form, N-(2R-Hydroxyhexadecanoyl), 2-Amino-4-oxohexanoic acid, 8-Amino-7-oxononanoate synthase, 5-Amino-4-oxopentanoic acid, 2-Amino-5-oxo-5-(2-pyridinyl)pentanoic acid; (S)-form, Aminopeptidase I, Aminopeptidase Y, 7-Amino-1-phenazinecarboxylic acid; N5-Me, betaine, 2-Amino-3H-phenoxazin-3-one, 2-Amino-3H-phenoxazin-3-one; N—Ac, 2-Amino-3H-phenoxazin-3-one; N-β-D-Glucopyranosyl, 2-Amino-3H-phenoxazin-3-one; 6-Hydroxy, 5-(2-Aminophenyl)-5-oxopentanoic acid, 3-(2-Aminophenyl)pyrrole, 2-Amino-2-propenoic acid, N-(3-Aminopropyl)-1,5-pentanediamine, N-(5-Amino-1-β-D-ribofuranosylimidazole-4-carbonyl)-L-aspartic acid 5'-phosphate, 2-Amino-6-(1,2,3,4-tetrahydroxybutyl)-4(1H)-pteridinone; (1'S,2'S,3'R)-form, 2-Amino-3-(2,4,5-trihydroxyphenyl)propanoic acid; (S)-form, 2-Amino-6-(1,2,3-trihydroxypropyl)-4(1H)-pteridinone; (1'S,2'S)-form, 5,6R,7,8-Tetrahydro, 4-Amino-N,N,N-tris(3-aminopropyl)-1-butanaminium, 5-Aminovalerate transaminase, Ammonificin A, Ammonificin A; 4'-Deoxy, 4'-bromo, Ammonigenin, Amonabactin P 693, Amonabactin P 750, Amonabactin T 732, Amonabactin T 789, Amphibactins, Amphibactins; Amphibactin C, Amphibactins; Amphibactin D, Amphibactins; Amphibactin E, Amphibactins; Amphibactin F, Amphibactins; Amphibactin H, Amphisin, Amphisin; 9-L-Glutamic acid analogue, Amphomycin, AMP nucleosidase, α-Amylase, β-Amylase, Amylocyclicin A, Amylosin, Amylosucrase, Amylovoran, Amylovonin L, Analysine, Andrimide, Andrimide; 3-Epimer, 3-hydroxy, Angiolam A, Angiolam A; 9',10'-Dihydro, Angiolam A; 6'-Ketone, Angucyclinone R2, Anguibactin, 3,6-Anhydro-2-deoxyglucose; D-form, Anhydrorhodovibrin, Anhydrorhodovibrin; O-De-Me, O-β-D-glucopyranoside, Anhydrorhodovibrin; O-De-Me, O-[11-methyldodecanoyl-(→6)-β-D-glucopyranoside], Anhydrorhodovibrin; O-De-Me, Ansatrienin B; 20-O-β-D-Glucopyranoside, Ansatrienin B; 4"-Hydroxy, Ansatrienin B; 20,23-Quinone, 19-hydroxy, Ansatrienin B; 20,23-Quinone, 4"-hydroxy, Antascomicin B, Antascomicin B; 30-Deoxy, Antascomicin B; 30-Deoxy, 37-hydroxy, Antascomicin B; Lower homologue, 30-deoxy, Antascomicin B; 31-Me ether, Anthranilate oxygenases; Anthranilate 1,2-dioxygenase (deaminating, decarboxylating), Anthranilate phosphoribosyltransferase, Anthraniloyl-CoA monooxygenase, *Periplaneta americana* Antibacterial peptides, Antibiotic 02-8, Antibiotic 13-384-5, Antibiotic 13-384-5; N-Hydroxy, Antibiotic 1569, Antibiotic 1998, Antibiotic 2725, Antibiotic 30-2, Antibiotic 339-29, Antibiotic 388, Antibiotic 4205, Antibiotic 61-26, Antibiotic 68-1147, Antibiotic 681-17, Antibiotic 696, Antibiotic A 10947, Antibiotic A 12918, Antibiotic 2197A, Antibiotic A 287, Antibiotic A 39893, Antibiotic A 477, Antibiotic 67-121A, Antibiotic 67-121A; N-De-Me, Antibiotic 67-121A; 4'-O-α-D-Mannopyranosyl, Antibiotic A 672, Antibiotic A 6984, Antibiotic A 7413, Antibiotic A 84575, Antibiotic A 17002A, Antibiotic A 80407A, Antibiotic A 80407A; Diastereoisomer, Antibiotic AB 1, Antibiotic AB 102, Antibiotic AB 111, Antibiotic AB 113, Antibiotic A 17002B, Antibiotic AB 2, Antibiotic A 35566B, Antibiotic A 35566B; 4'-Ketone, Antibiotic AC 1, Antibiotic A 2315C, Antibiotic A 7413D, Antibiotic AF 011A1, Antibiotic AF 011A1; Deoxy, Antibiotic AFC-BC11, Antibiotic AH 7, Antibiotic AI 77A, Antibiotic AI 77F, Antibiotic AI 77G, Antibiotic AM 157, Antibiotic A1-RC 262, Antibiotic Az-SA-501, Antibiotic B 1008, Antibiotic 1316B, Antibiotic B 3454, Antibiotic B 42, Antibiotic B 43, Antibiotic B 4317, Antibiotic B 456, Antibiotic B7, Antibiotic B 90063, Antibiotic B 1371A, Antibiotic B 1371A; 2'-Deoxy, 2',3'-didehydro, Antibiotic BA 843, Antibiotic B 1371E, Antibiotic BE 56980, Antibiotic BE 40665A, Antibiotic BE 40665D, Antibiotic BE 13793X, Antibiotic BK 97A, Antibiotic BL-A60, Antibiotic BMY 28190, Antibiotic BN 109, Antibiotic BN 1512, Antibiotic BN 165, Antibiotic BN 175, Antibiotic BN 192, Antibiotic BN 200, Antibiotic BN 225, Antibiotic BN 7, Antibiotic BN 240B, Antibiotic BO 7, Antibiotic BSA, Antibiotic BU 4514N, Antibiotic 6108C, Antibiotic 66-40C, Antibiotic CB 25-1, Antibiotic CB 25-11, Antibiotic C 33196E4, Antibiotic C 33196E6, Antibiotic C 33196E7, Antibiotic C 33196E4R, Antibiotic C 33196E6R, Antibiotic C 33196E7R, Antibiotic C 11924F1, Antibiotic CF 661, Chainia minutisclerotica Antibiotic, Antibiotic CP 37277, Antibiotic CP 37932, Antibiotic CP 40042, Antibiotic CP 41012, Antibiotic CP 41043, Antibiotic CP 41494, Antibiotic CP 42752, Antibiotic CP 43038, Antibiotic CP 43139, Antibiotic CP 43334, Antibiotic CP 43596, Antibiotic CP 44161, Antibiotic CP 48926, Antibiotic CP 48927, Antibiotic 6108D, Antibiotic 67-121D, Antibiotic DC 102; Demethoxy, 12,13-didehydro, Antibiotic DC 5-4, Antibiotic DOB 41, Antibiotic FM 1001, Antibiotic FR 183737, Antibiotic FR 183742, Antibiotic FR 900493, Antibiotic FR 901375, Antibiotic FR 901451, Antibiotic FR 901463, Antibiotic FR 901465, Antibiotic FR 901465; 2-Deoxy, Antibiotic FR 901484, Antibiotic FR 901537, Antibiotic FU 10, Antibiotic G 1499-2, Antibiotic G 2A, Antibiotic GE 2270, Antibiotic GE 2270; Antibiotic GE 2270A, Antibiotic GIF 1, Antibiotic GIF 2, Antibiotic GTRI-BB, Antibiotic H 107, Antibiotic 477-2h, Antibiotic HA 106, Antibiotic HA 135, Antibiotic HA 145, Antibiotic HA 176, Antibiotic HC 62, Antibiotic HM 17, Antibiotic HP 17, Antibiotic 480HS20, Antibiotic HUT 57, Antibiotic 11, Antibiotic IB 96212, Antibiotic I-SKA1, Antibiotic I-SKB1, Antibiotic I-SKB2, Antibiotic JA 20, Antibiotic JI 20A, Antibiotic JI 20B, Antibiotic K 52A, Antibiotic K 252b, Antibiotic K 252b; Me ester, Antibiotic K 52B, Antibiotic KBS, Antibiotic K 144e, Antibiotic K 144g, Antibiotic KG 431A, Antibiotic KM 8, Antibiotic KT 6291, Antibiotic L 13365, Antibiotic L 660631; (1'R,4S,5R)-form, Antibiotic LIA 0371, Antibiotic LIA 0677, Antibiotic LIA 0725, Antibiotic LIA 0185 I, Antibiotic LIA 0725-II, Antibiotic LI-F, Antibiotic LL-AB 664, Antibiotic LL-AB 664; N5-Me, Antibiotic LL-BO 1208α, Antibiotic LL-BO 1208β, Antibiotic LL-D O5139β, Antibiotic LL-EM 0103, Antibiotic LP 1, Antibiotic M 101, Antibiotic M 138, Antibiotic M 27, Antibiotic M 741, Antibiotic M 9026, Antibiotic M 92, Antibiotic MA 18, Antibiotic M 53A2, Antibiotic M 53B1, Antibiotic M 53B2, Antibiotic MBM 1212, Antibiotic MF 205, Antibiotic MM 240, Antibiotic MM 42842, Antibiotic MSD A 63A, Antibiotic MX-A, Antibiotic N 1999A2, Antibiotic NK 11629, Antibiotic NP 023, Antibiotic OM 001, Antibiotic P 19, Antibiotic P 2, Antibiotic P 3, Antibiotic P 4, Antibiotic P 40, Antibiotic PA 2046, Antibiotic PA 5, Antibiotic PA 7, Antibiotic PB 5266A, Antibiotic PB 5582A, Antibiotic PB 52668, Antibiotic PB 5266C, Antibiotic Pep 5, Antibiotic PM 94128, Antibiotic R 176502, Antibiotic RK 0721, Antibiotic S 264; Antibiotic S 264A, Antibiotic S 264; Antibiotic S 2648, Antibiotic S 264; Antibiotic S 264C, Antibiotic S 53210A, Antibiotic S 54832A, Antibiotic SB 219383, Antibiotic Sch 20561, Antibiotic Sch 20561; 32-O-α-D-Glucopyranoside, Antibiotic Sch 23831, Antibiotic Sch 37137, Antibiotic Sch 38519, Antibiotic Sch 40832, Antibiotic Sch 419558, Antibiotic Sch 419559, Antibiotic Sch 42137, Antibiotic Sch 42137; 11-Ac, Antibiotic Sch 42137; 14-Ac, Antibiotic Sch 49088, Antibiotic Sch 54445, Antibiotic Sch 56036, Antibiotic SE 73, Antibiotic SE 74, Antibiotic SE 73-74D, Antibiotic SF 1908, Antibiotic SF 1919, Antibiotic SF 2033, Antibiotic SF 2107, Antibiotic SF 2107; Antibiotic SF 2107A1, Antibiotic SF 2107; Antibiotic SF 2107A2, Antibiotic SF 2107; Antibiotic SF 21078, Antibiotic SF 2107; Antibiotic SF 2107C, Antibiotic SF 2132, Antibiotic SF 2139, Antibiotic SF 2240, Antibiotic SF 2309, Antibiotic SF 2312, Antibiotic SF 2339, Antibiotic SF 2381, Antibiotic SF 2448; Antibiotic SF 2448A, Antibiotic SF 2448; Antibiotic SF 2448B, Antibiotic SF 2448; Antibiotic SF 2448C, Antibiotic SF 2513; Antibiotic SF 2513A, Antibiotic SF 2513; Antibiotic SF 25138, Antibiotic SF 2513; Antibiotic SF 2513C, Antibiotic SF 2423A, Antibiotic SF 21978, Antibiotic SF 23158, Antibiotic SPF 1012, Antibiotic SQ 26180; (R)-form, Antibiotic SQ 28502, Antibiotic SQ 28504, Antibiotic SQ 28516, Antibiotic SQ 28516; 6'-Amide, Antibiotic SQ 28546, Antibiotic SS 237, Antibiotic SS 228B, Antibiotic SS 228Y, Antibiotic SU1, Antibiotic SU2, Antibiotic SU2; 5-Deoxy, Antibiotic SU2; 6'-N-Me, Antibiotic 1024 SY 1, Antibiotic TAN 1054; Antibiotic TAN 1054A, Antibiotic TAN 1054; Antibiotic TAN 1054B, Antibiotic TAN 1511, Antibiotic TAN 1713, Antibiotic TAN 425, Antibiotic TAN 456, Antibiotic TAN 643, Antibiotic TAN 667, Antibiotic TAN 850, Antibiotic TAN 883, Antibiotic TAN 422A, Antibiotic TAN 1057C, Antibiotic TAN 10570; 2-Epimer, Antibiotic TM 743, Antibiotic TP 1161, Antibiotic TPU 0043; Stereoisomer (1), Antibiotic T 23W, Antibiotic UAA3, Antibiotic UFC 3930, Antibiotic UK 68597, Antibiotic WA 3909, Antibiotic WAP 4068A, Antibiotic WAP 8294A, Antibiotic WB 3559A, Antibiotic WB 35598, Antibiotic WB 3559C, Antibiotic WS 790898, Antibiotic WS 79089B; δ-Lactone, 6-Ac, Antibiotic WS 79089B; δ-Lactone, Antibiotic WSS 2217, Antibiotic WSS 2219, Antibiotic WSS 2219; 4"-Deoxy, Antibiotic WSS 2220, Antibiotic WSS 2221, Antibiotic WSS 2222, Antibiotic XK 206, Antibiotic XK 209, Antibiotic Y 1, Antibiotic Y 02039H, Antibiotic Y 02910-Iβ, Antibiotic YI-HU1, Antibiotic YI-HU3, Antibiotic Y 03559J-A, Antibiotic YL 02107Q-A, Antibiotic YL 02107Q-A; 6C-Hydroxy, Antibiotic YL 02107Q-A; 11-O-Deacyl, Antibiotic YL 02107Q-B, Antibiotic YM 47515, Antibiotic Y 05460M-A, Antibiotic YM 32890A, Antibiotic YM 32890A; Δ23,25,27-Isomer, Antibiotic YS 822A, Anticapsin, Streptoverticillium Anticoagulant, Antifungal CB-1, Antifungin, Propionibacterium jensenii Antimicrobial peptide, Antimycin A; Antimycin A18, Antlermicin B, Antlermicin C, Antlermicin D, Apicularen A, Apicularen A; 4-O-(2-Acetamido-2-deoxy-3D-glucopyranoside), 8'-Apo-β-caroten-8'-al; 8'-Carboxylic acid, 8'-Apo-β-caroten-8'-al; 8'-Carboxylic acid, Me ester, 8'-Apo-ψ-caroten-8'-oic acid; (all-E)-form, [12-Methyltetradecanoyl-(→6)-α-D-glucopyranosyl]ester, Apoptolidin A, Apoptolidin A; 6-Demethyl, Apoptolidin A; 16-Deoxy, Apoptolidin A; 16,20-Dideoxy, Apoptolidin A; 2'-Epimer, 16,20-dideoxy, Apoptolidin A; 2'-Epimer, 16,20-dideoxy, 27-O-deglycosyl, Apramycin, Aqabamycin G, Aquachelins, Aqualysin 1, Arabinan endo-1,5-α-L-arabinosidase, Arabinitol; D-form, 1-Phosphate, α-N-Arabinofuranosidase, Arabinogalactan endo-1,4-β-galactosidase, Arabinokinase; D-form, D-Arabinonolactonase, L-Arabinonolactonase, Aralkylamine dehydrogenase, Archaeol; 1-O-[β-D-Galactofuranosyl-(1→6)-D-galactofuranoside], Archaeol; 1-O-α-D-Galactopyranoside, Archaeol; 1-O-[α-D-Glucopyranosyl-(1→2)-(6-O-acetyl-β-D-galactofuranoside)], Archaeol; 1-O-[α-D-Glucopyranosyl-(1→2)-β-D-galactofuranoside], Archaeol; 3'R-Hydroxy, Archaeol; 3"R-Hydroxy, Archaeol; 3"-Hydroxy, 1-O-[β-D-galactopyranosyl-(1→6)-β-D-galactopyranoside], Archaeol; 3"-Hydroxy, 1-O-[β-D-galactopyranosyl-(1→6)-[β-D-glucopyranosyl-(1→3)]-β-D-galactopyranoside], Archaeol; 3"-Hydroxy, 1-O-β-D-glucopyranoside, Archaeol; 1-O-[α-D-Mannopyranosyl-(1→3)-β-D-galactopyranoside], Archaeol; 1-O-[α-D-Mannopyranosyl-(1→2)-α-D-glucopyranoside], Archazolide A, Archazolide A; 15-O-β-D-Glucopyranoside, Archazolide A; 7-O-β-D-Glucopyranoside, Archazolide A; 26-Hydroxy, 7-O-β-D-glucopyranoside, Archazolide B, Archazolide B; Δ3-Isomer(E-), Arcyriaflavin A, Arcyriaflavin A; 2,10-Dihydroxy, Arcyriarubin A, Arginase, D-Arginase, Arginidiene, Arginine; (S)-form, N-Tetradecanoyl, Arginine; (S)-form, N-Pentadecanoyl, Arginine; (S)-form, N-Hexadecanoyl, Arginine; (S)-form, N-(9Z-Hexadecenoyl), Arginine deiminase, Arginine N-succinyltransferase, Argyrins, Argyrins; Argyrin A, Argyrins; Argyrin B, Ariakemicin A, Ariakemicin A; Δ11-Isomer, Aridicin, Aridicin; Aridicin A, 6A-Alcohol, Aridicin B, 6A-Alcohol, Aridicin; Aridicin C1, 6A-Alcohol, Aridicin; Aridicin C2, 6A-Alcohol, Aridicin; Aridicin D, 6A-Alcohol, Aristeromycin, Arizonin C1, Arizonin C1; O7-De-Me, Arizonin C1; O8-De-Me, Arizonin C3, Arizonin C3; 4,8-Di-O-de-Me, Arizonin C3; 4,9-Di-O-de-Me, Arogenic acid, Aromatic amino acid transaminases; Aromatic amino acid transaminase, Arphamenine A, Arphamenine A; 4'-Hydroxy, Arsenate reductases; Arsenate reductase (azurin), Arsenate reductases; Arsenate reductase (donor), Arsenate reductases; Arsenate reductase (glutaredoxin), Arsindoline A, Arthrobacilin; Arthrobacilin A, Arthrobacilin; Arthrobacilin B, Arthrobacilin; Arthrobacilin C, Arthrobacterin, Arthrobactin, Arthrofactin, Arugomycin; 7-(Deglycosyloxy), 3C—O-de-Me, Arylsulfatase, Aryl-sulfate sulfotransferase, A 23S, Asparaginase, Asparagine; (S)-form, N2-(9-Methyldecanoyl), Asparagine; (S)-form, N2-(10-Methylundecanoyl), Asparagine; (S)-form, N2-(11-Methyldodecanoyl), Aspartate carbamoyltransferase, Aspartate kinase, Aspartate oxidases; L-Aspartate oxidase, Aspartate phenylpyruvate transaminase, Aspartate transaminase, Aspartic acid; (S)-form, Aspartyl aminopeptidase, L-Aspartyl-L-N2-hydroxyaspartyl-D-cycloserine, β-Aspartyl peptidase, Astaxanthin; (3S,3'S)-form, 3-O-β-D-Glucopyranoside, ATP phosphoribosyltransferase, Aurachin A, Aurachin A; 3β-Hydroxy, Aurachin B, Aurachin D, Aurachin D; 9'ξ-Hydroxy, Aurachin D; N-Hydroxy, Aurachin E, Aurachin F, Aurachin G, Aurachin G; 1',2'-Dihydro, Aurachin G; 3ξ-Methoxy, 1',2'-dihydro, Aurachin K, Aurachin K; 3,4-Didehydro, 1',2'-dihydro, Aurafurone A, Aurafurone A; 7-Deoxy, 6,7-didehydro(E-), Aurafurone A; 8E-Isomer, 7-deoxy, 6,7-didehydro(E-), Aurantinin A, Aurantinin A; 17-O-(6-Deoxy-β-ribohexopyranos-3-ulosyl), Aureocins; Aureocin A53, Aureocins; Aureocin A70, Aureothin; (R)-form, AUS 1, Autoinducer 2, *Staphylococcus aureus* Autoinducing peptide 1, *Staphylococcus aureus* Autoinducing peptide 2, *Staphylococcus aureus* Autoinducing peptide 3, *Staphylococcus aureus* Autoinducing peptide 4, *Staphylococcus epidermidis* Autoinducing peptide, *Staphylococcus intermedius* Autoinducing peptide, *Staphylococcus lugdunensis* Autoinducing peptide, Avicin A, Avoparcin; β-Avoparcin, O-Demannosyl, O2B-Me, Avoparcin; β-Avoparcin, O2B-Me, AVS, 5-Azacytidine, 8-Azainosine, Azaserine; (S)-form, 2-Azetidinecarboxylic acid; (S)-form, 3-Azetidinone; Covalent hydrate, Azotobactin CCM2798, Azotobactin D, Azotobactin G173, Azotobactin 87-I, Azotobactin 87-I; γ-Lactone, Azotobactin P19, Azotobactin Pch 9446, Azotochelin, Azoverdin A, Azoverdin A; 4'-Amide, Azoverdin G, Azoverdin G; 5β,6-Dihydro, Azoxybacilin; (Z,S)-form, Azureomycin, B 12489, Bac 1829, Bacereutin, Baciferacin, Bacileucine A, Bacileucine B, Bacilipin, Bacillaene, Bacillaene; 14',15'-Dihydro, Bacillaene; 2"-O-β-D-Glucopyranoside, Bacillamide A, Bacillamide A; 15R-Alcohol, Bacillamide A; 15-Deoxo, 15R-acetamido, Bacillibactin, Bacillistatin 1, Bacillistatin 2, Bacillithiol, Bacillocin, Bacillocin 490, Bacillocins; Bacillocin 1580, Bacillocins; Bacillocin 490, Bacillocins; Bacillocin 602, Bacillocins; Bacillocin B37, Bacillocins; Bacillocin Bb, Bacillolysin, Bacillomycin A, Bacillomycin C, Bacillomycin D; Bacillomycin D1, Bacillomycin D; Bacillomycin D2, Bacillomycin D; Bacillomycin D3, Bacillomycin D; Bacillomycin D4, Bacillomycin D; Bacillomycin D5, Bacillomycin F, Bacillomycin Fb, Bacillomycin Fc, Bacillomycin LC, Bacillomycin P; Bacillomycin P1, Bacillomycin P; Bacillomycin P2, Bacillomycin S, Bacillopeptin, Bacilosarcin A, Bacilosarcin B, Bacilysin, Baciphelacin, Bacircines, Bacisubin, Bacitracin, Bacitracin B, Bacitracin C, Bacitracin D, Bacitracin G, Bacterial leucyl aminopeptidase, Bacteriochlorophyll a, Bacteriochlorophyll b, Bacteriochlorophyll b; 10',11'-Didehydro, Bacteriochlorophyll c, Bacteriochlorophyll d, Bacteriochlorophyll e, Bacteriochlorophyll g, Bacteriochlorophyll g; 21-Epimer, Bacteriochlorophyllide a, Bacteriocin 217, Bacteriocin 28, Bacteriocin 31, Bacteriocin 41, Bacteriocin 51, Bacteriocin ABP 118, Bacteriocin AS 48, Bacteriocin 14B, Bacteriocin 28b, Bacteriocin Bc48, Bacteriocin C3603, Bacteriocin E1, Bacteriocin E50-52, Bacteriocin GM005, Bacteriocin HV219, Bacteriocin I1, Bacteriocin J46, Bacteriocin JW 15BZ, Bacteriocin L 1077, Bacteriocin LL 171, Bacteriocin LS 1, Bacteriocin Mc-E22, Bacteriocin MMFII, Bacteriocin N5, Bacteriocin NB-C1, Bacteriocin PPK 34, Bacteriocin PsVP-10, Bacteriocin R 1333, Bacteriocin Rm-10, Bacteriocin S34, Bacteriocin SJ, Bacteriocin SM19, Bacteriocin Smb, Bacteriocin ST44AM, Bacteriocin ST 151BR, Bacteriocin ST 5Ha, Bacteriocin ST 23LD, Bacteriocin ST16 Pa, Bacteriocin T8, Bacteriocin TH14, Bacteriocin TN 635, Bacteriocin UO004, Bacteriocin UviB, 32,33,34,35-Bacteriohopanetetrol; (21βH,32R,33R,34S)-form, 32,33,34,35-Bacteriohopanetetrol; (21βH,32R,33R,34S)-form, 35-Deoxy, 35-amino, 32,33,34,35-Bacteriohopanetetrol; (21βH, 32R,33R,34S)-form, 35-Deoxy, 35-(ornithylamino), 32,33, 34,35-Bacteriohopanetetrol; (21βH,32R,33R,34S)-form, 35-Deoxy, 35-(tryptophanylamino), 32,33,34,35-Bacteriohopanetetrol; (21βH,32R,33R,34S)-form, 35-O-β-D-Glucuronopyranoside, 32,33,34,35-Bacteriohopanetetrol; (21βH,32R,33R,34S)-form, 35-Deoxy, 35-(N-hexadecanoylamino), 32,33,34,35-Bacteriohopanetetrol; (21βH,32R, 33R,34S)-form, 35-Deoxy, 35-(N-8Z-hexadecenoylamino), 32,33,34,35-Bacteriohopanetetrol; (21βH,32R,33R,34S)-form, 35-Carboxylic acid, (35→32)-lactone, 32,33,34,35-Bacteriohopanetetrol; (21αH,32ξ,33ξ,34ξ)-form, 32,33,34, 35-Bacteriohopanetetrol; (21βH,32R,33R,34R)-form, 32,33,34,35-Bacteriohopanetetrol; (21βH,22ξ,29ξ,30ξ,33ξ, 34ξ)-form, 32-Ketone, 35-O-(2-amino-2-deoxy-β-D-glucopyranoside), Bacteriophaeophorbide a, Bacteriorubein; 3"-Deoxy, 2",3"-didehydro, 3',4'-dihydro, Bacteriorubein; 3"-Deoxy, 2",3"-didehydro, 3',4'-epoxide, Bacteriorubein; 3",3"'-Dideoxy, 2",3":2"',3"'-tetradehydro, Bacteriorubein; 3',3"'-Dideoxy, 2",2"',3",3"'-tetradehydro,3,3',4,4'-tetrahydro, Bacteriorubein; 13Z-Isomer, Bacteriorubein; 5Z,9'Z-Isomer, Bacteriorubein; 5Z-Isomer, Bacteriorubein; 9Z-Isomer, Bacteroplanecin, Bacthuricins; Bacthuricins; Bacthuricin F103, Bactobolin A, Bactobolin A; Nω-(Alanylalanyl), Bactobolin A; Nω-Alanyl, Bactobolin A; 5-Deoxy, Bactobolin A; 5-Deoxy, Nω-alanyl, Bactobolin A; 5-Deoxy, Nω-(alanylalanyl), Bactobolin A; 5-Deoxy, dechloro, Bactobolin A; 5-Deoxy, dechloro, Nω-alanyl, BAF, Bagougeramine A, Bagougeramine B, Bamylocin A, Bavaricins, Bavaricins; Bavaricin A, Bavaricins; Bavaricin MN, BE 40644, Benastatin A; 5,6-Dihydro, 11-O-sulfate, Benastatin A; 11-O-Sulfate, Benzenecarbothioic acid; SH-form, Me ester, 1,2-Benzenedicarboxylic acid; Monobutyl ester, Benzene 1,2-dioxygenase, Benzeneethanethioic acid; SH-form, S-Me ester, Benzenesulfonamide; N-Butyl, 1,2-Benzisoxazole-3,6-diol, Benzoate oxygenases; Benzoate 1,2-dioxygenase, Benzoic acid, Benzophenone, p-Benzoquinone reductase, 2,6-Benzothiazolediol; NH-form, N-Me, 2(3H)-Benzothiazolethione, 2-Benzothiazolol, Benzoyl-CoA 3-monooxygenase, Benzoyl-CoA reductase, 5-Benzyl-3-hydroxy-2-isopropylpyrazine, 5-Benzyl-3-hydroxy-2-isopropylpyrazine; 4'-Hydroxy, 5-Benzyl-3-hydroxy-4-phenyl-2(5H)-furanone, 5-Benzyl-3-hydroxy-4-phenyl-2(5H)-furanone; (+)-form, 5-Benzyl-3-hydroxy-4-phenyl-2(5H)-furanone; (+)-form, Me ether, 2-Benzyl-3-hydroxypyrazine; OH-form, Me ether, 3-Benzylidene-6-isobutylidene-2,5-piperazinedione; (Z,Z)-form, 4"-Methoxy, 3-Benzylidene-6-isobutylidene-2,5-piperazinedione; (2Z,5E)-form, 4"-Methoxy, 4-Benzyl-3H-pyrrolo[2,3-c]quinoline, 4-Benzyl-3H-pyrrolo[2,3-c]quinoline; 4'-Hydroxy, 2-Benzyl-4(3H)-quinazolinone, Bergaptol; Me ether, Betaine reductase, Bi-(4'-O-3')-daidzein, Bifidobactern, Bifidocin B, 3',5-Bigenistein, Bile-acid-CoA hydrolase, Biocerin, Biostim, Biotin synthase, Biphenyl-2,3-diol 1,2-dioxygenase, Biphenyl 2,3-dioxygenase, N,N'-Bis(4-aminobutyl)-1,4-butanediamine, N,N-Bis(3-aminopropyl)-1,4-butanediamine, N,N-Bis(3-aminopropyl)-1,4-butanediamine; N4-Ac, 2,5-Bis(4-hydroxybenzyl)pyrazine, Bis(2-hydroxyethyl) trisulfide, 2,7-Bis(4-hydroxy-3-methyl-2-butenyl)-β,β-carotene, 2,2'-Bis(4-hydroxy-3-methyl-2-butenyl)-β,β-carotene; O-β-D-Glucopyranoside, 3,4-Bis(4-hydroxyphenyl)-1H-pyrrole-2,5-dicarboxylic acid, 3,4-Bis(4-hydroxyphenyl)-1H-pyrrole-2,5-dicarboxylic acid; 4'-Deoxy, 2,5-Bis(1H-indol-3-ylmethyl)pyrazine, 1,2-Bis(2-methoxyethoxy)ethane, 2,5-Bis(2-methylpropyl)pyrazine, 3,6-Bis(2-methylpropyl)-2(1H)-pyrazinone; OH-form, Me ether, Bisnorbiotin; (3S,4S,5S)-form, Bispolide A1, Bispolide A1; 13,13'-Di-Me ether, Bispolide A1; 2"-Hydroxy, Bispolide A1; 2"-Hydroxy, 13,13'-di-Me ether, Bispolide A1; 2"-Hydroxy, 13-Me ether, Bispolide A1; 2"-Hydroxy, 13'-Me ether, Bispolide A1; 13-Me ether, 2,5-Bis(1,2,3,4-tetrahydroxybutyl)pyrazine; (1'ξ,1"ξ,2'ξ,2"ξ,3'ξ,3"ξ)-form, 2',2"-Bis-O-(2-acetamido-2-deoxy-β-D-glucopyranoside), Bisucaberin, BK 101, BK 101; IBK 101C, Blasticidin S; 3"-N-Leucyl, Blastmycetin A, Blastmycetin B, Blastmycetin B; 3-Deoxy, Blastmycetin B; 3-Epimer, Blastmycetin B; 3-Epimer, 3-deoxy, Blastmycetin D, Blastmycetin E, Blastmycetin F, Blastolysin, Bleomycin; Bleomycin A5, Bleomycin hydrolase, Blood-group-substance endo-1,4-β-galactosidase, Blue copper proteins; Amicyanin, Blue copper proteins; Azurin, Blue copper proteins; Pseudoazurin, Blue copper proteins; Rusticyanin, Bogorol A, Bogorol B, Bogorol C, Bogorol D, Bogorol D; S-Oxide, Bohemamine, Boivin substance, Bongkrekic acid; (20E)-form, Bongkrekic acid; (20Z)-form, Boticins, Botrocidin, Botryticidin A, Bottromycin, Botulinum Toxins, Bovicins; Bovicin 255, Bovicins; Bovicin HC5, Bovicins; Bovicin HJ50, Boxazomycin A, Boxazomycin A; 1"-Deoxy, Boxazomycin A; 5-Deoxy, Bozacin 14, Bradyoxetin, Branched-chain amino acid transaminase, Branched-chain fatty acid kinase, Branched-dextran exo-1,2-α-glucosidase, Brassicanal B, Brassicanal C, Brassinin, Brassinin; N1-Methoxy, Brassinin; 4-Methoxy, Brassitin, Brassitin; 1-Methoxy, Bravomicin A, Bravomicin A; Et ester, Bravomicin A; 6-Hydroxy, Bravomicin A; 6-Hydroxy, Me ester, Bravomicin A; Me ester, Bravomicin D, Bravomicin D; Et ester, Bravomicin D; Me ester, Bresein, Brevicins; Brevicin 27, Brevicins; Brevicin 286, Brevicins; Brevicin 37, Brevicins; Brevicin 925A, Brevicins; Brevicin AF01, Brevicins; Brevicin SD-22, Brevicins; Brevicin SG1, Brevimycin, Brevin, Brevinic acid, Brevistin, Brevolin, Brochocin C, Bromoalterochromide A, 6-Bromo-1H-indole-3-carboxaldehyde, Brucellin, Bulbiformin, Bulgarican, Bulgecin A, Bulgecin B, Bulgecin C, Burkholdac A, Burkholdac B, Burkholdac B; 4"-De(methylthio), 4"-ethyl, Burkholdac B; 4"-S-Oxide, Burkholdine 1097, Burkholdine 1097; 7-O-β-D-Xylopyranoside, 1,4-Butanediamine, 1,4-Butanediamine; N-(2,3-Dihydroxybenzoyl), 1,4-Butanediamine; N-Hexadecanoyl, Butanethioic acid; SH-form, S-Me ester, 1-Butanol, 3-Butanoyl-1,4a,12,12a-tetrahydro-1,4,4a,6,7-pentahydroxy-2,5-naphthacenedione, 2-(2-Butenyl)benzenehexanoic acid, 2-(2-Butenyl)benzenehexanoic acid; 1',2'-Didehydro, 2-(2-Butenyl)benzenehexanoic acid; 1",4"-Didehydro, 2-(2-Butenyl)benzenehexanoic acid; Δ1"-Isomer(Z-), 1-Butoxy-2-methyl-1-(2-methylpropoxy)-2-propanol, Butyl methyl disulfide, 2-Butyl-5-propyl-1,3-benzenediol, Butyltrimethylpyrazine, Butyrate acetoacetate CoA-transferase, Butyrate kinase, Butyricin 7423, Butyrivibriocin, Butyrivibriocin; Butyrivibriocin AR10, Butyrivibriocin; Butyrivibriocin OR435, Butyrivibriocin; Butyrivibriocin OR79A, Cadeguomycin; Nitrile, Caerulomycin E; 1'-Carboxylic acid, amide, Caerulomycin E; 1'-Carboxylic acid, N-methoxyamide, Caerulomycin E; 1'-Carboxylic acid, nitrile, Caerulomycin E; O-De-Me, E-oxime, Caerulomycin E; 1'-Methanamine, O-de-Me, N—Ac, Caerulomycin E; 3-Methoxy, E-oxime, Caerulomycin E; E-Oxime, Caerulomycin E; Z-Oxime, Caerulomycin F, Caerulomycin F; 3-Methoxy, Caerulomycin K, Caffeate 3,4-dioxygenase, Calcimycin; De(methylamino), 3-hydroxy, Calcimycin; 14-Demethyl, de(methylamino), Caldarchaeol; O-[β-D-Galactofuranosyl-(1→6)-β-D-galactofuranoside], Caldarchaeol; O-[α-D-Glucopyranosyl-(1→2)-β-D-6-O-acetyl-β-D-galactofuranoside], Caldarchaeol; O-[α-D-Glucopyranosyl-(1→2)-β-D-galactofuranoside], Caldarchaeol; O-[α-D-Glucopyranosyl-(1→2)-β-D-galactofuranoside], O'-β-D-galactofuranoside, Caldarchaeol; O-(3-O-Phosphoglyceryl), Caldarchaeol; O-(3-O-Phosphoglyceryl), O'-[β-D-galactofuranosyl-(1→6)-β-D-galactofuranoside], Caldarchaeol; O-(3-O-Phosphoglyceryl), O'-[α-D-glucopyranosyl-(1→2)-β-D-galactofuranoside], Calditol, Calicheamicin, Camphor monooxygenases; Camphor 1,2-monooxygenase, Camphor monooxygenases; Camphor 5-monooxygenase, Candiplanecin, C5a peptidase, Capistruin, Capreomycin, Capsular-polysaccharide endo-1,3-α-galactosidase, Carbamate kinase, N6-(Carbamoylmethyl)-2'-deoxyadenosine, Carbazomycin G, Carbazomycin G; 6-Methoxy, 1-(β-Carbolin-1-yl)-3-hydroxy-1-propanone, Carbon monoxide dehydrogenases; Carbon monoxide dehydrogenase (acceptor), Carbon monoxide dehydrogenases; Carbon monoxide dehydrogenase (cytochrome b-561), Carbon monoxide dehydrogenases; Carbon monoxide dehydrogenase (ferredoxin), 1-(2-Carboxyanilino)-1-deoxyribulose; D-form, 2-Carboxy-2,5-dihydro-5-oxo-2-furanacetic acid; (R)-form, 7-Carboxy-8-(2,6-dihydroxybenzoyl)-4-oxo-2-propyl-4H-1-benzopyran-5-acetic acid, 3-Carboxyethylcatechol 2,3-dioxygenase, 3-O-(1-Carboxyethyl)glucuronic acid; D-(1'R)-form, 4-O-(1-Carboxyethyl)glucuronic acid; D-(1'S)-form, N6-(1-Carboxyethyl)lysine; (S,S)-form, N5-(Carboxyethyl)ornithine synthase, Carboxymethylenebutenolidase, Carboxypeptidase T, Carboxypeptidase Taq, Carnobacteriocins, Carnobacteriocins; Carnobacteriocin A, Carnobacteriocins; Carnobacteriocin B1, Carnobacteriocins; Carnobacteriocin B2, Carnobacteriocins; Carnobacteriocin BM1, Carnocins; Carnocin 54, Carnocins; Carnocin CP 5, Carnocins; Carnocin H, Carnocins; Carnocin KZ213, Carnocins; Carnocin UI 49, Carnocyclin A, Carnosin 44A, Carocin D, Carocin S2, Carolactone, β,β-Carotene-2,3-diol; (2R,3R)-form, β,ψ-Carotene-2,3-diol; (2R*,3R*)-form, β,ψ-Carotene-4,4'-dione, γ-Carotene; 1',2'-Dihydro, Carotovoricin, ι-Carrageenase, κ-Carrageenase, λ-Carrageenase, Caryophyllan, Caryophyllose, Caryose, Caseicin 80, Caseicins, Catacandin; Catacandin A, Catalase, Catechol dioxygenases; Catechol 1,2-dioxygenase, Catechol dioxygenases;

Catechol 2,3-dioxygenase, CDP-4-dehydro-6-deoxyglucose reductase, CDP-diacylglycerol-glycerol-3-phosphate 3-phosphatidyltransferase, CDP-diacylglycerol serine O-phosphatidyltransferase, CDP-glycerol glycerophosphotransferase, CDP-ribitol ribitolphosphotransferase, Cellobiose phosphorylase, Cellodextrin phosphorylase, Cellulase, Cellulose 1,4-β-cellobiosidase, Cellvibriocin, *Eubacterium saburreum* Cell-wall antigen, Cell wall protein, Cepaciachelin, Cepaciamide A, Cepaciamide B, Cepacian, Cepacidin A1, Cepacidin A1; 1″-Deoxy, Cepacin A, Cepacin B, Cepalycin, Cephabacin F; Cephabacin F4, Cephabacin F; Cephabacin F4, N27-L-Seryl, Cephabacin F; Cephabacin F4, N27-(L-Seryl-L-alanyl), Cephabacin F; Cephabacin F4, 28-Deoxy, N27-L-alanyl, Cephabacin F; Cephabacin F4, 28-Deoxy, N27-L-alanyl-L-alanyl), Cephabacin F; Cephabacin F4, 28-Deoxy, Cephabacin F; Cephabacin F7, Cephabacin F; Cephabacin F7, N27-L-Seryl, Cephabacin F; Cephabacin F7, N27-(L-Seryl-L-alanyl), Cephabacin H4, Cephabacin H4; 28-Deoxy, Cephabacin H4; 28-Deoxy, N27-L-alanyl, Cephabacin H4; 28-Deoxy, N27-(L-alanyl-L-alanyl), Cephabacin H4; N27-L-Seryl, Cephabacin H4; N27-(L-Seryl-L-alanyl), Cephabacin M; Cephabacin M1, Cephabacin M; Cephabacin M2, Cephabacin M; Cephabacin M3, Cephabacin M; Cephabacin M4, Cephabacin M; Cephabacin M5, Cephabacin M; Cephabacin M6, Cephalosporin-C deacetylase, Cephalosporin C transaminase, Cerein B2, Cereins, Cereins; Cerein 7, Cereins; Cerein 8A, Cereins; Cerein MRX1, Cereulide, Cereulide; Homologue (R═CH2CH3), Cerexins, Cervinomycin A1, Cervinomycin A1; 8,15-Quinone, Cervinomycin A1; 8,15-Quinone, O12-de-Me, Chaetomacin, Chandrananimycin C, Chejuenolide A, Chejuenolide A; 2-Epimer, Chinosporin S, Chitinovorin C, Chitinovorin D, Chitosanase, Chitovibrin, Chivosazole E, Chivosazole E; Aglycone, 20-Me ether, Chivosazole E; 2,3′-Di-Me ether, Chivosazole E; 6E-Isomer, 2′,3′,20-tri-Me ether, Chivosazole E; 20-Me ether, Chivosazole E; 3′-Me ether, Chivosazole E; 2′,3′,20-Tri-Me ether, Chivotriene, Chloramphenicol; (1R,2R)-form, Chloramphenicol O-acetyltransferase, Chlorate reductase, Chloridazon-catechol dehydrogenase, Chlorobactene, Chlorobactene; 1′,2′-Dihydro, 1′-hydroxy, Chlorobactene; 1′,2′-Dihydro, 1′-hydroxy, O-(6-dodecanoyl-β-D-glucopyranoside), Chlorobactene; 1′,2′-Dihydro, 1′-hydroxy, O-β-D-glucopyranoside, 2-Chlorobenzoate 1,2-dioxygenase, Chlorobiumquinone, 3-Chloro-4-(3-chloro-2-nitrophenyl)-1,5-dihydro-5-methoxy-2H-pyrrol-2-one; (−)-form, 4-Chloro-3-(3-chloro-2-nitrophenyl)-1,5-dihydro-5-methoxy-2H-pyrrol-2-one; (+)-form, 4-(2-Chloroethyl)-2,6-dinitrophenol, 2-Chloro-3-(4-hydroxy-3,5-dinitrophenyl) propanoic acid; (ξ)-form, 2-Chloro-3-(4-hydroxy-3-nitrophenyl)propanoic acid; (ξ)-form, 5-Chloro-6-methoxy-1-methyl-1H-indole-2,3-dione, 2-Chloro-1,6-phenazinediol, 4-Chlorophenylacetate 3,4-dioxygenase, 2-(4-Chlorophenyl)ethylamine; N,N-Dichloro, Chlorophyll a; 1‴,2″-Didehydro, Chlorophyll b; 1′,2′-Didehydro, Chloropolysporin B, Chloropolysporin B; Galactosyl, Chloropolysporin B; O-Derhamnosyl, 8-Chloro-7-propyl-4,7-octadienoic acid; (4E,7E)-form, Chlorotetaine, Chlorotetaine; Bromo analogue, Chlorothricin; 3B—O-Deacyl, 4B—O-(3-chloro-6-methoxy-2-methylbenzoyl), Chlorotonil A, 4-Chlorotryptophan; (S)-form, 5-Chlorotryptophan; (S)-form, Chlortetracycline; 8-Methoxy, Cholestan-3-one; 5β-form, Cholest-5-en-3-ol; 3β-form, O-(6-O-Hexadecanoyl-β-D-galactopyranoside), Choline kinase, Choline sulfatase, Choloyl-CoA hydrolase, Chondramide A, Chondramide A; 2′-Chloro, Chondramide A; 2′-Chloro, demethoxy, Chondramide A; Demethoxy, Chondrochloren A, Chondrochloren A; 2-O-De-Me, 2-Et ether, Chondro-4-sulfatase, Chondro-6-sulfatase, Chromoazepinone A; (ξ)-form, Chromoazepinone A; (ξ)-form, N,4-Didehydro, Chromoazepinone C, Chromoviridan, Chromoviridan; Deoxy, Chryseomonin, Chrysobactin, Chrysopine, Chuangxinmycin B, Chuangxinmycin C, Cinerubin B; 5C-Epimer, Cinerubin B; 10-Epimer, (E)-Cinnamoyl-CoA:(R)-phenyllactate CoA-transferase, Circularin A, Circulocin α, Circulocin α; 3′-Deoxy, Circulocin γ, Circulocin δ, Citramalate CoA-transferase, Citrate CoA-transferase, Citrate lyase deacetylase, Citrate lyase holo-[acyl-carrier-protein] synthase, Citrate synthases; Citrate (Re)-synthase, Citreamicin α, Citreamicin α; O2-De-Me, Citreamicin β, Citreamicin γ, Citreamicin η, Citromycetin, Citrusnin A, Cittilin A, Clausin, Closthioamide, Closthioamide D, Closthioamide F, Closthioamide F; 3″-Carboxylic acid, Closthioamide H, Closthioamide H; Nitrile, Closticin 574, Clostocins, Clostomicin C, Clostomicin D, Clostrhamnan, Clostridial aminopeptidase, Clostripain, CM 101, CoA-disulfide reductase, Coagulin, Cob(II) alamin reductase, Cobalt-factor II C20-methyltransferase, Cob(I)yrinic acid α,γ-diamide adenosyltransferase, Cob(II) yrinic acid a,c-diamide reductase, Cochinmicin I, Cochinmicin I; 5″-Chloro, Cochinmicin I; 2-Epimer, Cochinmicin I; 2-Epimer, 5″-chloro, Cochinmicin I; 2-Epimer, 17-hydroxy, 5″-chloro, Coenzyme B12, Coenzyme-B sulfoethylthiotransferase, Coenzyme Q; Coenzyme Q5, Coenzyme Q; Coenzyme Q8, Coenzyme Q; Coenzyme Q9, Colicin E3, Colicins, Coliformin, Colisan, Collagenase, Collagenase *clostridium histolyticum*, Columbicin A, CO-methylating acetyl-CoA synthase, Comirin, ComX168 pheromone, ComXRO-B-1 pheromone, ComXRO-B-2 pheromone, ComXRO-C-2 pheromone, ComXRO-E-2 pheromone, ComXRO-H-1 pheromone, Coproporphyrinogen oxidase, Corallolysin, Corallopyronin A, Corallopyronin B, Corallopyronin C, Cormycin A, Coronafacic acid, Coronafacic acid; L-Alloisoleucine amide, Coronafacic acid; L-Isoleucine amide, Coronafacic acid; L-Serine amide, Coronafacic acid; L-Threonine amide, Coronafacic acid; L-Valine amide, Coronatine, Corpeptins, Corrin-aminopropanol-phosphoribose, Corrugatin, Corrugatin; Homologue (R═CH2CH2CH2NH2), Corynicin JK, Corynomycolic acid; (2R,3R)-form, Corynomycolic acid; (2R,3R)-form, 11,12-Didehydro, Corynomycolic acid; (2R,3R)-form, 7′,8′,11,12-Tetradehydro, Creatinase, Creatininase, 4-Cresol dehydrogenase (hydroxylating), p-Cresolyldicyanocobamide, p-Cresolyldicyanocobamide; 4″-De-Me, Crisamicin A, Crisamicin A; 4′a,10′a-Epoxide, Crisamicin A; 1-Hydroxy, Crisamicin A; 9′-Hydroxy, Crispacin A, Crocacin A, Crocacin A; N10-De(aminoalkyl), Crocacin A; 5,6-Dihydro, Crocacin A; Parent acid, Crossover junction endodeoxyribonuclease, Cruentaren A, Cruentaren B, Cry45Aa, β-Cryptoxanthin; O-[9-Methyldecanoyl-(→6)-β-D-glucopyranoside], β-Cryptoxanthin; O-[11-Methyldodecanoyl-(→6)β-D-glucopyranoside], β-Cryptoxanthin; O-[13-Methyltetradecanoyl-(→6)-β-D-glucopyranoside], C-terminal processing peptidase, Cucumopine, Cucumopine; 4-Epimer, Curvacin A, Curvalicins, Curvaticins, Curvaticins; Curvaticin 13, Curvaticins; Curvaticin FS47, Curvaticins; Curvaticin L442, Cutinase, CW 5, 3-Cyano-1-(3,5-dichlor-2-hydroxyphenyl)-1-propanone, Cyano-5-hydroxybenzimidazolylcobamide, Cyano-5-hydroxybenzimidazolylcobamide; 5-Me ether, N-[1-Cyano-2-(4-hydroxyphenyl)ethenyl]formamide; (Z)-form, Cyano-5-methoxy-6-methylbenzimidazolylcobamide, Cyano-5-methylbenzimidazolylcobamide, 3-Cyanomethyl-3-hydroxyoxindole; (S)-form, Cyanophycinase, Cyanuric acid amidohydrolase, Cyclic-(1→2)-β-D-glucans, Cyclic-guanylate-specific phosphodiesterase, 2′,3-Cyclic-nucleotide 2'-phosphodiesterase, Cyclo(alanyl-4-hydroxyprolyl); (3S,7R,8aR)-form, Cyclo(alanyl-4-hydroxyprolyl); (3S,7R,8aS)-form, Cyclo(alanylisoleucyl); (1'S,3S,6S)-form, Cyclo(alanylisoleucylprolylleucyl), Cyclo(alanylleucyl); (3S,6S)-form, Cyclo(alanylprolyl); (3S,8aS)-form, Cyclo(arginylprolyl); (3S,8aR)-form, Cyclobrassinin, Cyclobrassinin; 5-Methoxy, 4,9-didehydro, Cyclocarbamide A, Cyclocarbamide A; N-Hexanoyl analogue, α-Cyclodextrin, β-Cyclodextrin, γ-Cyclodextrin, Cyclo(glutamylglycylprolyl), Cyclo(glutamylglycylserylprolyl), Cyclo(glutamylprolylglutamylprolyl), Cyclo(glycylprolyl); (S)-form, 3,5-Cycloheptadien-1-ol, 2,4,6-Cycloheptatrien-1-one, 10-Cycloheptyldecanoic acid, 13-Cycloheptyl-2-hydroxytridecanoic acid, 11-Cycloheptyl-2-hydroxyundecanoic acid; (R)-form, 11-Cycloheptyl-4-methylundecanoic acid; (S)-form, 9-Cycloheptylnonanoic acid, 13-Cycloheptyltridecanoic acid, 11-Cycloheptylundecanoic acid, Cyclohexane-1,2-diol dehydrogenase, Cyclohexanol dehydrogenase, Cyclohexanone monooxygenase, Cyclohexylamine oxidase, Cyclo(histidylproline); (S,S)-form, Cyclo(4-hydroyprolylleucyl-4-hydroxyproylleucyl); (2R,2'S,2''S,2'''S,4R,4''R)-form, Cyclo(4-hydroxyprolylphenylalanyl); (3S,7R,8aS)-form, Cyclo(4-hydroxyprolyltyrosyl); (3S,7R,8aR)-form, Cyclo(4-hydroxyprolyltyrosyl); (3S,7R,8aS)-form, Cyclo(isoleucylleucylisoleucylleucyl), Cyclo(isoleucylpipecolinyl); (3R,9aR)-form, Cyclo(isoleucylprolyl); (1'S,3S,8aS)-form, Cyclo(isoleucylprolylleucylprolyl); (all-L)-form, Cyclo(isoleucylvalyl); (1'S,3S,6S)-form, Cyclolaminarinose, Cyclolaminarinose, Cyclo(leucylphenylalanylleucylphenylalanyl), Cyclo(leucylpipecolinyl); (3S,9aR)-form, Cyclo(leucylprolyl); (3S,8aS)-form, Cyclo(leucylprolylleucylprolyl); (all-L)-form, Cyclo(leucylprolylphenylalanylprolyl), Cyclomaltodextrinase, Cyclomaltodextrin glucanotransferase, Cyclo(methionylprolyl); (3S,8aS)-form, Cyclopentanol dehydrogenase, Cyclopentanone monooxygenase, Cyclo(phenylalanylpipecolinyl); (3S,9aS)-form, Cyclo(phenylalanylprolyl); (3S,8aR)-form, Cyclo(phenylalanylprolyl); (3S,8aS)-form, Cyclo(phenylalanylproylphenylalanylprolyl) (all-L)-form, Cycloprodigiosin, Cyclo(prolylprolyl); (5aS,10aS)-form, Cyclo(prolyl-D-prolyltyrosyltyrosyl), Cyclo(prolyltryptophyl); (3S,8aS)-form, Cyclo(prolyltyrosyl); (3S,8aS)-form, Cyclo(prolyltyrosyl); (3ξ,8aξ)-form, 3'-Nitro, Cyclo(prolyltyrosylprolyltyrosyl), Cyclo(prolyltyrosylprolylvalyl), Cyclo(prolyltyrosylprolylvalyl); (all-L)-form, Cyclopropane-fatty-acyl phospholipid synthase, Cyclo(tryptophyltryptophyl); (3S,6S)-form, Cyclo(tryptophyltryptophyl); (3S,6S)-form, N1,N4-Di-Me, Cyclo(tryptophyltryptophyl); (3R,6S)-form, Cycloviracin B1, Cycloviracin B1; 20'-Ketone, Cymbimicin A, Cymbimicin B, Cyrmenin A, Cyrmenin B1, Cyrmenin B2, Cystathionine γ-synthase, Cysteine desulfurase, Cysteine synthase, Cystothiazole E, Cytidine deaminase, Cytidine 5'-diphosphate, 4-(Cytidine 5'-diphospho)-2-C-methyl-D-erythritol kinase, Cytidylate kinase, Cytoblastin, Cytochrome c 551, *Enterococcus faecalis* Cytolysin, Cytomycin, Cytophagin, Cytosine deaminase, Cytosol nonspecific dipeptidase, Dactylocycline A, Dactylocycline A; 3A-O—Ac, Dactylocycline A; Aglycone, Dactylocycline B, Dactylocycline C, Dactylocycline E, Dactylocycline F, Daitocidin, Dapdiamide A, Dapdiamide A; Isoleucine analogue, Dapdiamide A; Leucine analogue, Dapdiamide D, Dapdiamide D; 2ε,3ξ-Epoxide, Dapiramicin B, Dapiramicin B; 6'-Deoxy, Dapiramicin B; 1'-Epimer, 6'-deoxy, Datemycin, dATP(dGTP)-DNA purinetransferase, Daunomycin; 13ξ-Alcohol, O-de-Me, Daunomycin; O-De-Me, Daunomycin; 11-Deoxy, Daunomycin; 11-Deoxy, 13-alcohol, dCMP deaminase, dCTP deaminase, DCX, Deacetyl-[citrate-(pro-3S)-lyase] S-acetyltransferase, N-Deacylantibiotic A 40926, N-Deacylantibiotic A 40926; 6A-Ac, N2B-(10-methylundecanoyl), N-Deacylantibiotic A 40926; 6A-Ac, N2B-undecanoyl, N-Deacylantibiotic A 40926; N2B-Decanoyl, N-Deacylantibiotic A 40926; N2B-Dodecanoyl, N-Deacylantibiotic A 40926; N2B-(9-Methyldecanoyl), N-Deacylantibiotic A 40926; N2B-(10-Methylundecanoyl), N-Deacylantibiotic A 40926; N2B-Undecanoyl, N-Deacyltunicamycin, N-Deacyltunicamycin; N4''-(16-Methylheptadecanoyl), N-Deacyltunicamycin; N4''-(16-Methyl-2-heptadecenoyl), N-Deacyltunicamycin; N4''-(15-Methyl-2-hexadecenoyl), N-Deacyltunicamycin; N4''-14-Methyl-2-pentadecenoyl), N-Deacyltunicamycin; N4''-(13-Methyl-2-tetradecenoyl), N-Deacyltunicamycin; N4''-(2-Tetradecenoyl), 7-Deazainosine, N-Debenzoyllucentamycin A; N2'-Benzoyl, N-Debenzoyllucentamycin A; N2'-(3-Methylbutanoyl), N-Debenzoyllucentamycin A; N2'-(3-Methyl-2-butenoyl), 2,4-Decadienoic acid; (2E,4Z)-form, 1,2,7,7',8,8',11,11',12,12'-Decahydrolycopene, 14,22,26,29,33,50,58,62,65,69-Decamethyl-8,11,44,47-tetraoxaheptacyclo[68.2.1.12,5.118,21.134,37.138,41.154,57]octaheptacontane-10,46-dimethanol, Decaplanin, Decaprenoxanthin, Decaprenoxanthin; Deoxy, Decaprenoxanthin; Di-O-β-D-Glucopyranoside, Decaprenoxanthin; Mono-O-β-D-Glucopyranoside, 2-Decaprenyl-6-methoxy-1,4-benzoquinone, 2-Decaprenyl-6-methoxyphenol, 2-Decaprenylphenol, Decatromicin A; 30-Nor, 5''-chloro, 2-Decenoic acid; (Z)-form, 2-Decenoic acid; (E)-form, 2-Decyl-4-hydroxyquinoline, 2-Decyl-4-hydroxyquinoline; 1',2'-Didehydro(E-), 2-Decyl-4-hydroxyquinoline; 1',2'-Didehydro(Z-), 2-Decyl-4-hydroxyquinoline; N-Oxide, 2-Dehydro-3-deoxygalactonokinase, 2-Dehydro-3-deoxygluconokinase, 5-Dehydro-2-deoxygluconokinase, 2-Dehydro-3-deoxyglucuronate dehydrogenases, 2-Dehydro-3-deoxyglucuronate dehydrogenases; 2-Dehydro-3-deoxy-D-gluconate 6-dehydrogenase, Dehydrogluconokinase, 3-Dehydrogulonate 2-dehydrogenase, 2-Dehydropantolactone reductase; 2-Dehydropantolactone reductase (B-specific), Dehydrotryptamine; (E)-form, Na-Formyl, Dehydrothyptophan, Demethoxycoenzyme Q9, 4''-Demethylgentamicin C1, 4''-Demethylgentamicin C1; 6'-N-De-Me, 4''-Demethylgentamicin C1a, 2-Demethylvitamin K2(25), 2-Demethylvitamin K2(30), Dentigerumycin, Deoxyadenosine kinase, (Deoxy)adenylate kinase, 6-Deoxy-β-L-altropyranosyl-(1→2)-6-deoxy-β-L-altropyranosyl-(1→3)-6-deoxy-L-altrose, 6-Deoxyaltrose, 1-Deoxy-2,7-anhydroaltroheptulose; D-form, Deoxycytidine kinase, Deoxycytidylate 5-hydroxymethyltransferase, Deoxycytidylate C-methyltransferase, 1-Deoxy-1-(dimethylamino)pentitol 2-[2,3-bis[(3,7,11,15-tetramethylhexadecyl)oxy]propyl hydrogen phosphate, 1-Deoxy-1-(dimethylamino)pentitol 2-[2,3-bis[(3,7,11,15-tetramethylhexadecyl)oxy]propyl hydrogen phosphate; N-Me, 6-Deoxy-3-O-β-D-galactopyranosyl-D-gulose, 2-Deoxygluconate 3-dehydrogenase, 5'-Deoxyguanosine, Deoxyguanosine kinase, 6-Deoxygulose; D-form, 6-Deoxy-altro-heptose; D-form, 6-Deoxy-galacto-heptose; L-form, 6-Deoxy-guloheptose; L-form, 6-Deoxy-manno-heptose; D-form, 6-Deoxy-talo-heptose; D-form, 7-Deoxy-D-glycero-D-glucoheptose, 1-Deoxy-altro-2-heptulose; D-form, 3-Deoxy-threo-2-hexulosonic acid; D-form, 2-Deoxy-arabinohexuronic acid; D-form, 2-Deoxyinosine, 3-Deoxy-3-(methylamino)arabinose; L-form, 6-Deoxy-3-C-methylgulose; D-form, 6-Deoxy-3-C-methylgulose; 1-form, 6-Deoxy-3-C-methyl-2-O-methyltalose; L-form, 3-Deoxy-D-glycero-D-galacto-2-nonulosonic acid, Deoxynucleotide 3'-phosphatase, 3-Deoxy-α-D-manno-2-octulopyranosonosyl-(2→4)-3-deoxy-α-D-manno-2-octulopyranosonosyl-(2→6)-2-amino-2-deoxy-D-glucose, 3-Deoxy-α-D-manno-2-octulopyranosonosyl-(2→2)-β-D-ribofuranosyl-(1→2)-D-ribose, 3-Deoxy-α-D-manno-2-octulopyranosonosyl-(2→3)-[β-D-ribofuranosyl-(1→2)]-D-ribose, 3-Deoxy-manno-octulosonate cytidylyltransferase, 3-Deoxy-manno-octulosonate-8-phosphatase, 3-Deoxy-2-octulosonidase, 2-Deoxy-erythro-pentose; D-form, 5-Phosphate, 2-Deoxy-erythro-pentose; α-D-Pyranose-form, 2-Deoxy-erythro-pentose; β-D-Pyranose-form, 3-Deoxy-7-phosphoheptulonate synthase, 3-Deoxy-8-phosphooctulonate synthase, Deoxyribonuclease IV (phage-T4-induced), Deoxyribonuclease (pyrimidine dimer), Deoxyribonuclease V, Deoxyribonuclease X, 1-O-(6-Deoxy-6-sulfoglucopyranosyl)glycerol; α-D-form, 6-Deoxytalose; D-form, 6-Deoxytalose; D-form, 3-Me, 6-Deoxytalose; L-form, 1-Deoxyxylulose 5-phosphate reductoisomerase, 1-Deoxy-D-xylulose-5-phosphate synthase, Dephospho-CoA kinase, Desferriferribactin 13525, Destomycin A; 4',4"-Diepimer, N3-Me, Destomycin A; 4'-Epimer, N-de-Me, N3-Me, 3-Desvinyl-3-hydroxyethylphaeophorbide a, Dextran, Dextranase, Dextranicin 24, Dextran 1,6-α-isomaltotriosidase, Dextransucrase, Dextrin dextranase, dGTPase, Diabroticin A, Diabroticin A; 1'-Deoxy, Diacetin B, 2,4-Diacetyl-1,3,5-benzenetriol, Diacylglycerol kinase (ATP dependent), 1,2-Diacylglycerol 6-sulfoquinovosides, 1,2-Diacyl-3-(2,3,4,6-tetra-N-taurinamido-α-D-glucopyranosyl)glycerol, Diamine N-acetyltransferase, Diamine transaminase, 2,4-Diaminobutanoic acid; (S)-form, N2-(6-Methyloctanoyl), 1,4-Diamino-2-butanol; (S)-form, Diaminobutyrate transaminases; Diaminobutyrate 2-oxoglutarate transaminase, Diaminobutyrate transaminases; Diaminobutyrate pyruvate transaminase, 1,12-Diamino-4,8-diazadodecane, 1,13-Diamino-4,9-diazatridecane, 1,13-Diamino-5,9-diazatridecane, 4,4'-Diaminodibutylamine, 1,4-Diamino-1,4-dideoxyglucitol; D-form, 2,3-amino-2,3-dideoxyglucose; α-D-Pyranose-form, 2,3-Diamino-2,3-dideoxyglucuronic acid; D-form, 2N,3N-Di-Ac, 2,3-Diamino-2,3-dideoxyguluronic acid; L-form, 2,3-N-Di-Ac, 2,3-Diamino-2,3-dideoxymannuronic acid; D-form, N,N'-Di-Ac, 3,3'-Diaminodipropylamine, 3,3-Diaminodipropylamine; N3,N3'-Bis(2,3-dihydroxybenzoyl), L-erythro-3,5-Diaminohexanoate dehydrogenase, 3,5-Diaminohexanoic acid; (3S,6S)-form, 3,6-Diaminohexanoic acid; (S)-form, 2,6-Diamino-4-hexenoic acid; (S)-(E)-form, 2,6-Diamino-4-hexenoic acid; (±)-(E)-form, N2-Ac, 2,6-Diamino-3-hydroxyheptanedioic acid; (2RS,3SR,6SR)-form, 2,6-Diamino-5-hydroxy-5-(hydroxymethyl)hexanoic acid; N6-Ac, 2,6-Diamino-2-(hydroxymethyl)heptanedioic acid; (2S,6S)-form, N2-(2S-Carboxyethyl), 2,5-Diamino-3-hydroxypentanoic acid; (2R,3R)-form, 2,4-Diamino-3-methylbutanoic acid; (2R,3S)-form, 2,4-Diaminopentanoate dehydrogenase, 2,4-Diaminopentanoic acid; (2R,4S)-form, Diaminopimelate dehydrogenase, 1,20-Diamino-4,8,12,16-tetraazaeicosane, 1,20-Diamino-4,8,12,17-tetraazaeicosane, 1,20-Diamino-4,8,13,17-tetraazaeicosane, 1,16-Diamino-4,8,12-triazahexadecane, 1,16-Diamino-4,8,13-triazahexadecane, 2,4-Diamino-2,4,6-trideoxy-3-(α-D-galactopyranuronosyl)-D-galactose; N2-Ac, 2,4-Diamino-2,4,6-trideoxygalactose; D-form, 2-N—Ac, 2,4-Diamino-2,4,6-trideoxyglucose; D-form, 2,4-Diamino-2,4,6-trideoxyglucose; D-form, 4-N—Ac, 2,4-Diamino-2,4,6-trideoxyglucose; D-form, 4-N-(3S-Hydroxybutanoyl), 2-N—Ac, 2,3-Diamino-2,3,6-trideoxymannose; D-form, N2-Ac, N3-formyl, 2,3-Diamino-2,3,6-trideoxymannose; β-L-Pyranose-form, 2,3-Di-Ac, 5,7-Diamino-5,7,9-trideoxynon-2-ulosonic acid, 5,7-Diamino-4,6,8-trihydroxy-2-oxononanoic acid; (4S,5S,6S,7S,8S)-form, 5,7-Diamino-4,6,8-trihydroxy-2-oxononanoic acid; (4S,5S,6S,7S,8S)-form, N5-Ac, N7-formyl, 5,7-Diamino-4,6,8-trihydroxy-2-oxononanoic acid; (4S,5S,6S,7S,8S)-form, N5,N7-Di-Ac, 5,7-Diamino-4,6,8-trihydroxy-2-oxononanoic acid; (4S,5S,6S,7S,8S)-form, N7-(3-Hydroxybutanoyl), N5-Ac, 5,7-Diamino-4,6,8-trihydroxy-2-oxononanoic acid; (4R,5R,6S,7R,8R)-form, 5,7-Diamino-4,6,8-trihydroxy-2-oxononanoic acid; (4S,5R,6S,7R,8R)-form, 5,7-Diamino-4,6,8-trihydroxy-2-oxononanoic acid; (4S,5R,6S,7R,8S)-form, 5,7-Diamino-4,6,8-trihydroxy-2-oxononanoic acid; (4S,5R,6S,7R,8S)-form, N5-(1-Iminoethyl), N7-Ac, 2,5-Diaminovalerate transaminase, 4,4'-Diapo-4,4'-carotenedioic acid, 4,4'-Diapo-4,4'-carotenedioic acid; Dialdehyde, 4,4'-Diapo-4,4'-carotenedioic acid; [14-Methylpentadecanoyl-(→2)-β-D-xylopyranosyl] ester, 4,4'-Diapo-4,4'-carotenedioic acid; [12ξ-Methyltetradecanoyl-(→2)-β-D-xylopyranosyl] ester, 4,4'-Diapo-4,4-carotenedioic acid; [12-Methytridecanoyl-(→2)-β-D-xylopyranosyl] ester, 4,4'-Diapo-4,4'-carotenedioic acid; Monoaldehyde, 4,4'-Diapocaroten-4-oic acid, 4,4'-Diapocaroten-4-oic acid; 20,21-Dihydro, Diazepinomicin, 4-Diazo-3-(hydroxymethyl)phenol; 1-O-Sulfate, 3,6-Dibenzylidene-3,6-dihydro-5-methoxy-2-pyrazinone; (3Z,6Z)-form, 3,6-Dibenzylidene-2,5-piperazinedione; (Z,Z)-form, 3,6-Dibenzylidene-2,5-piperazinedione; (Z,Z)-form, N-Me, 2,3-Dibromo-4-(3-bromo-2-nitrophenyl)-1H-pyrrole, 2,3-Dibromo-4-(3-bromo-2-nitrophenyl)-1H-pyrrole; 2-Debromo, 2,3-Dibromo-4-(3-bromo-2-nitrophenyl)-1H-pyrrole, 3'-Debromo, 5'-bromo, 2,4-Dibromo-6-chlorophenol, 2-(3,5-Dibromo-2-hydroxyphenyl)-3,4,5-tribromopyrrole, 2-(3,5-Dibromo-2-hydroxyphenyl)-3,4,5-tribromopyrrole; Chloro analogue, N,N-Dichloro-2-(4-nitrophenyl)ethylamine, 2,3-Dichloro-4-nitro-1H-pyrrole, Dichrysobactin, 3',4'-Didehydro-β,ω-caroten-4-one, 3,4-Didehydro-1,2-dihydro-8'-apo-ψ-caroten-1-ol; (all-E)-form, 3',4'-Didehydro-1',2'-dihydro-1',2'-dihydroxy-β,ψ-caroten-4-one; (S)-form, 3',4'-Didehydro-1',2'-dihydro-1',2'-dihydroxy-β,ψ-caroten-4-one; (S)-form, 1'-O-β-D-Glucopyranoside, 3',4'-Didehydro-1',2'-dihydro-1',2'-dihydroxy-β,ψ-caroten-4-one; (S)-form, 1'-Deoxy, 2'-ketone, 3',4'-Didehydro-1',2-dihydro-1',2'-dihydroxy-β,ψ-caroten-4-one; (S)-form, 1'-O-[13-Methyltetradecanoyl-(→6)-β-D-glucopyranoside], 3,4-Didehydro-1,2-dihydro-1-hydroxy-8'-apo-ψ-caroten-8'-oic acid; (all-E)-form, Me ester, 3,4-Didehydro-1,2-dihydro-1-hydroxy-8'-apo-ψ-caroten-8'-oic acid; (all-E)-form, Me ester, 1-O-β-D-Glucopyranoside, 3',4'-Didehydro-1',2'-dihydro-3-hydroxy-1'-methoxy-β,ψ-caroten-19'-al; (9Z)-form, 3,4-Didehydro-1,2-dihydro-1-hydroxy-2-(3-methyl-2-butenyl)-ψ,ψ-carotene, 3,4-Didehydro-1,2-dihydrolycopene, 2,5-Didehydrogluconate reductase, 3,6-Dideoxy-erythro-hexopyranos-4-ulose, 3,6-Dideoxy-arabino-hexose; D-form, 3,6-Dideoxy-arabino-hexose; L-form, 3,6-Dideoxy-ribo-hexose; D-form, 3,6-Dideoxy-xylo-hexose; D-form, 3,6-Dideoxy-xylo-hexose; L-form, Difficol, Difficol; 6-Hydroxy, Difficol; 6-Hydroxy, 15-O-phosphate, Difficol; O-Phosphate, Di-β-D-fructofuranose 2,6':6,2'-dianhydride, Diguanidinobutanase, 5,6-Dihydro-5-azathymidine, 5,6-Dihydro-β,β-carotene-3,3',5-triol, 1',2'-Dihydro-γ-caroten-1'-ol; O-(6-O-Dodecanoyl-β-D-glucopyranoside), Dihydrocoumarin hydrolase, 3,4-Dihydro-6,8-dihydroxy-3-tridecyl-1H-2-benzopyran-1-one; (ξ)-form, 4,5-Dihydro-4,4-dimethyl-3H-pyrrolo[2,3-c]quinoline, 3-(2,3-Dihydro-3-hydroxy-1H-indol-3-yl)-2-oxopropanoic acid; (ξ)-form, 2,3-Dihydro-2-(hydroxymethyl)-4H-1-benzopyran-4-one; (ξ)-form, 5,6-Dihydro-8-hydroxynaphtho[1,8-bc]pyran-2(4H)-one, N-[5-[(1,6-Dihydro-2-hydroxy-5-octanamido-6-oxo-3-pyridyl)imino]-1,2,5,6-tetrahydro-2,6-dioxo-3- pyridyl]octanamide, 3,4-Dihydro-5-(1-hydroxy-2-phenylethyl)-2(5H)-furanone, 4,5-Dihydro-2-(2-hydroxyphenyl)-4-oxazolecarboxylic acid; (S)-form, Alcohol, Dihydrolipoyllysine-residue succinyltransferase, 1,2-Dihydrolycopene, 1,2-Dihydro-1-methoxy-ψ,ψ-caroten-4-one, 1,2-Dihydro-1-methoxy-ψ,ψ-caroten-4-one; 7',8'-Dihydro, 1,2-Dihydro-1-methoxy-ψ,ψ-caroten-4-one; 7',8',11',12'-Tetrahydro, Dihydro-3-(2-methyl-3-oxobutyl)-2(5H)-furanone, 2,5-Dihydro-3-methyl-5-oxo-2-furanacetic acid; (S)-form, Dihydro-2-methyl-3(2H)-thiophenone; (±)-form, 3,5-Dihydro-3-methyl-2H-thiopyrano[4,3,2-cd]indole-2-carboxylic acid; (2R,3S)-form, 1-[4,9-Dihydro-2-(methylthio)-1,3-thiazino[6,5-b]indol-4-yl]-2-propanone, 2-(1,3-Dihydro-3-oxo-2H-indol-2-ylidene)-7-hydroxycyclopent[g]indol-3(2H)-one, Dihydro-5-(8-oxotetradecyl)-2(3H)-furanone; (S)-form, Dihydropteroate synthase, 3,4-Dihydro-5-(2-pyridinyl)-2H-pyrrole-2-carboxylic acid, 3,4-Dihydro-5-(2-pyridinyl)-2H-pyrrole-2-carboxylic acid; (S)-form, 3,4-Dihydro-5-(2-pyridinyl)-2H-pyrrole-2-carboxylic acid; (S)-form, Fe complex (3:1), 3,4-Dihydro-5-(2-pyridinyl)-2H-pyrrole-2-carboxylic acid; (±)-form, Fe complex (3:1), 2,3-Dihydropyrrolo[2,1-b]quinazolin-9(1H)-one; 5-Hydroxy, 1,4-Dihydroquinoline; N-Me, 5,6-Dihydro-1,7,9,11-tetrahydroxy-3-methylbenzo[a]naphthacene-8,13-dione, 2,3-Dihydro-2-thioxo-4(1H)-pyrimidinone, 2,4'-Dihydroxyacetophenone dioxygenase, 1,5-Dihydroxyanthraquinone, 1,8-Dihydroxyanthraquinone, 2,3-Dihydroxybenzoate dioxygenases; 2,3-Dihydroxybenzoate 3,4-dioxygenase, 2,3-Dihydroxybenzoic acid, 2,6-Dihydroxy-1,4-benzoquinone; Di-Me ether, (2,3-Dihydroxybenzoyl)adenylate synthase, 2,3-Dihydroxybenzoylglycine, 2,3-Dihydroxy-β,β-carotene-4,4'-dione; (2R,3S)-form, 2,3-Dihydroxy-β,β-caroten-4-one; (2R,3R)-form, 2,3-Dihydroxy-β,ψ-caroten-4-one; (2R*,3S*)-form, 2,3-Dihydroxy-2,4,6-cycloheptatrien-1-one, 6,6'-Dihydroxy-α,α'-diisocyano-[1,1'-biphenyl]-3,3'-dipropanamide; (RS,RS)-form, 6,6'-Dihydroxy-α,α'-diisocyano-[1,1'-biphenyl]-3,3'-dipropanamide; (RS,SR)-form, 5,8-Dihydroxy-4,7-dimethoxy-2,6-dimethylisoquinolinium(1+), 3,4-Dihydroxy-1,2-dimethylcarbazole; Di-Me ether, 3,4-Dihydroxy-1,2-dimethylcarbazole; 3-Me ether, 7,9-Dihydroxy-8,10-dimethyl-2,4-dodecadienoic acid; (2Z,4E,7S,8S,9R,10S)-form, 9-O-(E-Cinnamoyl), amide, 7,9-Dihydroxy-8,10-dimethyl-2,4-dodecadienoic acid; (2Z,4E,7S,8S,9R,10S)-form, 7-O-(E-Cinnamoyl), amide, 7,9-Dihydroxy-8,10-dimethyl-2,4-tridecadienoic acid; (2Z,4E,7S,8S,9R,10S)-form, 9-O-Cinnamoyl(E-), amide, 3,4-Dihydroxy-1,7-dioxaspiro[4.4]nonan-8-one; 4-Hexanoyl, 3,4-Dihydroxy-1,7-dioxaspiro[4.4]nonan-8-one; 4-Octanoyl, 3,11-Dihydroxy-4,6-dodecadienoic acid; (3S,4E,6E,11R)-form, 1,3-Dihydroxy-2-hydroxymethylanthraquinone; 1,3-Di-Me ether, 6,8-Dihydroxy-3-hydroxymethyl-1H-2-benzopyran-1-one; 6-Me ether, 4,5-Dihydroxy-5-hydroxymethyl-2-cyclopenten-1-one; (4S,5S)-form, 1'-Ac, 3,5-Dihydroxy-2-hydroxymethyl-4H-pyran-4-one, 1,8-Dihydroxy-2-(3-hydroxy-1-oxo-2-hexenyl)-3-methylanthraquinone, 6,7-Dihydroxy-3-isocyano-2H-1-benzopyran-2-one, 4',7-Dihydroxyisoflavone, 4',7-Dihydroxyisoflavone; 3'-Nitro, 1-(3,5-Dihydroxy-4-isopropylphenyl)-2-phenylethylene, 1-(3,5-Dihydroxy-4-isopropylphenyl)-2-phenylethylene; 1',2'-Epoxide, 7,8-Dihydroxykynurenate 8,8a-dioxygenase, 5,7-Dihydroxy-4'-methoxyisoflavone, 3,6-Dihydroxy-4-methylhexanoic acid; (3ξ,4ξ)-form, 6-O-(1H-Indol-3-yl)ether, 3,5-Dihydroxy-6-methyl-7-(2-methyl-4-thiazolyl)-6-heptenoic acid, 3,5-Dihydroxy-6-methyl-7-(2-methyl-4-thiazolyl)-6-heptenoic acid; Homologue (R=CH3), 3,5-Dihydroxy-3-methylpentanoic acid; (±)-form, 1,5-Lactone, 3,5-Dihydroxy-8-methyl-8,10-undecadienoic acid; (3S,5R,8E)-form, Me ester, 3,5-Dihydroxy-8-methyl-8,10-undecadienoic acid; (3S,5R,8E)-form, δ-Lactone, 1,4-Dihydroxy-2-naphthalenecarboxylic acid, 1,4-Dihydroxy-2-naphthalenecarboxylic acid; 4-Me ether, 5,8-Dihydroxy-2-naphthalenecarboxylic acid; Di-Me ether, amide, (2,5-Dihydroxy-3-nitrophenyl)acetic acid; Me ester, 2,3-Dihydroxy-2-nor-β,β-carotene-3,4-dione, 7,10-Dihydroxy-8-octadecenoic acid; (7ξ,8E,10ξ)-form, 4,5-Dihydroxy-3-oxo-1-cyclohexenecarboxylic acid; (4S,5R)-form, 1,3-Dihydroxy-2-(2-oxopropyl)anthraquinone; Di-Me ether, 1,3-Dihydroxy-2-(2-oxopropyl)anthraquinone; 3-Me ether, 3,5-Dihydroxy-4-oxo-4H-pyran-2-carboxylic acid, 2,3-Dihydroxy-1-phenazinecarboxylic acid, 2,6-Dihydroxy-1-phenazinecarboxylic acid, 2,9-Dihydroxy-1-phenazinecarboxylic acid, 4,9-Dihydroxy-1,6-phenazinedicarboxylic acid; Di-Me ester, (2,5-Dihydroxyphenyl)acetic acid, (2,5-Dihydroxyphenyl)acetic acid; Me ester, (3,4-Dihydroxyphenyl)acetic acid, 1-(3,5-Dihydroxyphenyl)-2-(2-hydroxyphenyl)ethane; 3-Me ether, 1-(3,4-Dihydroxyphenyl)-3-hydroxy-1-propanone; 3'-Me ether, 1-(3,4-Dihydroxyphenyl)-3-hydroxy-1-propanone; 3'-Me ether, 3-O-β-D-glucopyranoside, 3,6-Dihydroxypregnan-20-one; (3α,5β,6α)-form, 1,2-Dihydroxy-1,2,3-propanetricarboxylic acid; (2S,3R)-form, 2,3-Dihydroxypropanoic acid; (S)-form, 2,3-Dihydroxypropanoic acid; (ξ)-form, 2-O-[α-D-Mannopyranosyl-(1→2)-α-D-glucopyranoside], 1,3-Dihydroxy-2-propanone, 3,8-Dihydroxy-1-propylanthraquinone, 3,8-Dihydroxy-1-propylanthraquinone-2-carboxylic acid; 3-Me ether, Me ester, 6-[2-(2,4-Dihydroxy-6-propylbenzoyl)-3,5-dihydroxybenzyl]-4-hydroxy-2H-pyran-2-one, 3,5-Dihydroxy-4H-pyran-4-one, 2,5-Dihydroxypyridine 5,6-dioxygenase, 2,6-Dihydroxypyridine 3-monooxygenase, 4,8-Dihydroxy-2-quinolinecarbothioic acid; 4-Me ether, 4,8-Dihydroxy-2-quinolinecarboxylic acid; 4-Me ether, 3,15-Dihydroxy-4,6,8,14-tetramethyl-5,9-dioxo-10,12-heptadecadienoic acid, 3,15-Dihydroxy-4,6,8,14-tetramethyl-5,9-dioxo-10,12-heptadecadienoic acid; 9S-Alcohol, 1,15-lactone, 3,15-Dihydroxy-4,6,8,14-tetramethyl-5,9-dioxo-10,12-heptadecadienoic acid; 1,15-Lactone, 5,13-Dihydroxy-4,6,10,14-tetramethyl-15-(2-methyl-1-thiazolyl)-10,14-pentadecadiene-3,7-dione, 5,13-Dihydroxy-2,4,6,14-tetramethyl-15-(2-methyl-4-thiazolyl)-10,14-pentadecadien-3-one, 2,4-Dihydroxy-3,3,4-trimethyl-5-oxo-2-pyrrolidinecarboxylic acid, 2,5-Dihydroxy-3,4,6-tris(methylthio)benzeneacetic acid, 2,5-Dihydroxy-3,4,6-tris(methylthio)benzeneacetic acid; Me ester, 3,3-Di-1H-indol-3-yl-2-butanone, 2-[2,2-Di(1H-indol-3-yl)ethyl]aniline, 2,2-Di-1H-indol-3-yl-4-methylpentanoic acid, 4-[(Di-1H-indol-3-yl)methyl]phenol, 2,2-Di-1H-indol-3-ylpropanoic acid, 1,1'-Di-myo-inosityl phosphate, Diisopropyl fluorophosphatase, 2,5-Diisopropyl-3-methoxypyrazine, 2,5-Diisopropylpyrazine, 2,6-Diisopropylpyrazine, 2,6-Diisopropylpyrazine; α-Hydroxy, 1,1'-Dimethoxy-3',4'-didehydro-1,1',2,2'-tetrahydro-ψ,ψ-caroten-4-one, N,N-Dimethyladenosine, Dimethylallyl transferases; Dimethylallyl-trans-transferase, Dimethylamine dehydrogenase, 2,7-Dimethyl-5,10-[2]butenophenazine-11,14-dione, 4,9-Dimethyldecanoic acid, Dimethyl disulfide, 4,10-Dimethyldodecanoic acid, 4,11-Dimethyldodecanoic acid, 15,16-Dimethyldotriacontanedioic acid, 2,20-Dimethyl-3-gammaceranol; (2β,3β,20α)-form, 2-[14-[3-(1,5-Dimethylhexyl)cyclopentyl]-3,7,11-trimethyltetradecyl]-3-methyl-1,4-naphthoquinone, 3,17-Dimethyl-29-hopanol, Dimethylmenaquinone, 2,5-Dimethyl-3-(2-methylbutyl)pyrazine, 2,5-Dimethyl-3-(methylthio)pyrazine, 13,14-Dimethyloctacosanedioic acid, 7,11-

Dimethyloctadecane, 2-(3,7-Dimethyl-2,6-octadienyl)-3-methyl-4(1H)-quinolinone; (E)-form, 2-(3,7-Dimethyl-2,6-octadienyl)-3-methyl-4(1H)-quinolinone; (E)-form, N-Me, 2-(3,7-Dimethyl-2,6-octadienyl)-3-methyl-4(1H)-quinolinone; (E)-form, N-(Methylthiomethyl), 2-(3,7-Dimethyl-2,6-octadienyl)-3-methyl-4(1H)-quinolinone; (E)-form, 6'ξ,7'ξ-Epoxide, N-Me, 2-(3,7-Dimethyl-2,6-octadienyl)-4(1H)-quinolinone; (E)-form, 2-(3,7-Dimethyl-2,6-octadienyl)-4(1H)-quinolinone; (E)-form, N-Me, 2-(3,7-Dimethyl-2,6-octadienyl)-4(1H)-quinolinone; (E)-form, 1'ξ-Hydroxy, N-Me, 2-(3,7-Dimethyl-2,6-octadienyl)-4(1H)-quinolinone; (E)-form, Δ1'-Isomer, 3'ξ-hydroxy, N-Me, 3,5-Dimethyl-2-propylpyrazine, 2,3-Dimethylpyrazine, 2,5-Dimethylpyrazine, 2,4-Dimethylquinazoline, 2,2-Dimethyl-4(1H,3H)-quinazolinone, 2,12-Dimethyltetradecanoic acid, 2,13-Dimethyltetradecanoic acid, 4,12-Dimethyltetradecanoic acid, 4,13-Dimethyltetradecanoic acid, Dimethyl tetrasulfide, 5,5-Dimethyl-1,2,3,4-tetrathiepane, 15,16-Dimethyltriacontanedioic acid, 2,12-Dimethyl-4-tridecanone, Dimethyl trisulfide, 4,4-Dimethyl-1,2,3-trithiolane, 2,5-Dinitro-1,3-benzenediol; 3-Me ether, 3,5-Dinitro-1,2-benzenediol; 1-Me ether, 3,5-Dinitro-1,2-benzenediol; 2-Me ether, 4,5-Dinitro-1,3-benzenediol; 3-Me ether, 34,35-Dinor-6,11-bacteriohopadiene-32,33-diol; (22R,32R)-form, 34,35-Dinor-6,11-bacteriohopadiene-32,33-diol; (22R,32R)-form, 11,12-Dihydro, 3,5-Dioxohexacosanoic acid, 3,5-Dioxooctacosanoic acid, 2,5-Dioxopiperazine hydrolase, Dioxybrassinin; (S)-form, Dipeptidyl peptidase IV, 3,4-Diphenyl-1H-pyrrole-2,5-dione; 3',3"-Dinitro, 4',4"-dihydroxy, 3,4-Diphenyl-1H-pyrrole-2,5-dione; 3',3"-Dinitro, 4',4"-dihydroxy, monoxime, 3,4-Diphenyl-1H-pyrrole-2,5-dione; 4'-Hydroxy, 3,4-Diphenyl-1H-pyrrole-2,5-dione; 3'-Nitro, 4',4"-dihydroxy, 3,4-Diphenyl-1H-pyrrole-2,5-dione; 3'-Nitro, 4'-hydroxy, 3,4-Diphenyl-1H-pyrrole-2,5-dione; 3'-Nitro, 4'-hydroxy, monoxime, Diphosphate serine phosphatransferase, 1,2-Diphytanylglycerol 3-phosphoethanolamine, 1,2-Diphytanylglycerol 3-phosphoethanolamine; 3'-Hydroxy, 1,2-Diphytanylglycerol 3-phosphoinositol; D-myo-Inositol-form, 3-Hydroxy, 1,2-Diphytanylglycerol 3-phosphinositol; L-myo-Inositol-form, 1,2-Diphytanylglycero-3-phosphoserine; 3'-Hydroxy, 1,2-Di-O-phytanyltetritol, Di-trans-poly-cis-decaprenyl-cis-transferase, Disorazole C1, Disorazole C2, Disorazole F1, Disorazole F1; O-De-Me, Disorazole F1; Demethoxy, 9,10:9',10'-diepoxide, 5',6'Z-didehydro, Disorazole F1; Demethoxy, 9',10'-dihydroxy, 9,10-epoxide 5',6'Z-didehydro, 9',10'-dihydro, Disorazole F1; Demethoxy, 9,9',10,10'-tetrahydroxy, 5',6'Z-didehydro, 9,9',10,10'-tetrahydro, Disorazole F1; 9R*,10S*:11R*,12S*-Diepoxide, Disorazole F1; 9R*,10R*:9'R,10'S*-Diepoxide, Disorazole F1; 9R*,10S*:9'R*,10'S*-Diepoxide, Disorazole F1; 9,10-Dihydroxy, 9,10-dihydro, Disorazole F1; 9,10-Dihydroxy, 9,10-dihydro, O10-Me, Disorazole F1; Epimer, 9,10-dihydroxy, 9,10-dihydro, Disorazole F1; 9R*,10R*-Epoxide, Disorazole F1; 9R*,10S*-Epoxide, Disorazole F1; 9R*,10S*-Epoxide, O-de-Me, Disorazole F1; 9R*,10S*-Epoxide, 16'-ketone, Disorazole F1; 9E,11E-Isomer, Disorazole F1; 7'Z-Isomer, demethoxy, 9,10:9',10'-diepoxide, 5',6'Z-didehydro, Disorazole F1; 7Z-isomer, 9R*,10R*:9'R*,10'S*-diepoxide, Disorazole F1; 11'E-Isomer, 9,10-dihydroxy, 9,10-dihydro, Disorazole F1; 11'E-Isomer, 9R*,10S*-epoxide, Disorazole F1; 5E-Isomer, 9R*,10S*-epoxide, Disorazole F1; 9'E,11'E-Isomer, 9R*,10S*-epoxide, Disorazole F1; 9'E-Isomer, 9R*,10S*-epoxide, Disorazole F1; 9'E,11'E-isomer, 10-methoxy, 9-hydroxy, 9,10-dihydro, Disorazole G1, Disorazole G2, Disorazole G3, Disulfoglucosamine-6-sulfatase, 1,4-Dithiane, Dithiocarbonic acid; Oxo-form, S,S-Di-Me ester, Divanchrobactin, Divercin V41, Divergicin 750, Divergicin A, Divergicin M35, Divericin, DKxanthenes, DKxanthenes; DKxanthene 504, DKxanthenes; DKxanthene 518, DKxanthenes; DKxanthene 530, DKxanthenes; DKxanthene 544, DKxanthenes; DKxanthene 556, Dnacin A1, DNA deoxyinosine glycosylase. DNA-directed DNA polymerase, DNA-directed RNA polymerase, DNA-formamidopyrimidine glycosylase, DNA glucosyltransferases; DNA α-glucosyltransferase, DNA glucosyltransferases; DNA β-glucosyltransferase, DNA glucosyltransferases; Glucosyl-DNA β-glucosyltransferase, DNA-3-methyladenine glycosylase I, DNA-3-methyladenine glycosylase II, 2,6,9,13,21,30,38,42,45,49,57,66-Dodecamethyl-24,27,60,63-tetraoxapentacyclo[68.2.1.114,17.134,37.150,53] hexaheptacontane-25,61-dimethanol, 2-Dodecenoic acid; (Z)-form, 2-Dodecyl-4-hydroxyquinoline, 2-Dodecyl-4-hydroxyquinoline; 1',2'-Didehydro(E-), 2-Dodecyl-4-hydroxyquinoline; 1',2'-Didehydro(Z-), 2-Dodecyl-4-hydroxyquinoline; N-Oxide, Dopastin; (S,E)-form, Dopsisamine, Dotriacolide, Dotriacolide; 3,4-Dihydro, dTDP-4-amino-4,6-dideoxygalactose transaminase, dTDP-4-amino-4,6-dideoxy-D-glucose transaminase, dTDP-4-Dehydro-6-deoxyglucose reductase, dTDP-6-Deoxytalose 4-dehydrogenase, dTMP kinase, Duramycin, Duramycin B, Duramycin C, Durancins; Durancin C102901, Durancins; Durancin GL, Durancins; Durancin L28-1A, Durancins; Durancin Q, Durancins; Durancin TW-49M, Durhamycin aglycone; 2-O-[2,6-Dideoxy-β-D-arabino-hexopyranosyl-(1→3)-4-O-acetyl-2,6-dideoxy-β-D-lyxo-hexopyranosyl-(1→3)-2,6-dideoxy-β-D-arabino-hexopyranoside], 7-O-[2,6-dideoxy-β-D-arabino-hexopyranosyl-(1→3)-2,6-dideoxy-β-D-arabino-hexopyranoside], Durhamycin aglycone; 2-O-[2,6-Dideoxy-3-D-arabino-hexopyranosyl-1→3)-2,6-dideoxy-β-D-arabino-hexopyranosyl-(1→3)-4-O-acetyl-2,6-dideoxy-β-D-lyxo-hexopyranosyl-(1→3)-2,6-dideoxy-β-D-arabino-hexopyranoside], 7-O-[2,6-dideoxy-β-D-arabino-hexopyranosyl-(1→3)-2,6-dideoxy-β-D-arabino-hexopyranoside], Dynemicin A, Dynemicin A; Aldehyde, Dynemicin A; 12-Deoxy, Dynemicin L, Dynemicin L; 4a-Dechloro, 4a-hydroxy, Dynemicin P, Dynemicin P; 3'-Hydroxy, 5-Me ether, Dynemicin P; 5-Me ether, Dynemicin P; 5-Oxo, Dysgalacticin, EAP, Echinenone; 3S-Hydroxy, Echinosporamicin, Ecomycin, Edeine, Ef 108 B, 4,5-Eicosanediamine, 1,2-Eicosanediol; (ξ)-form, 2-O-Hexadecanoyl, 1-O-β-D-glucopyranoside, 1,2-Eicosanediol; (ξ)-form, 2-O-Tetradecanoyl, 1-O-(6-O-tetradecanoyl-β-D-glucopyranoside), 1,2-Eicosanediol; (ξ)-form, 2-O-Hexadecanoyl, 1-O-(6-O-hexadecanoyl-β-D-glucopyranoside), Elansolide A3, Elansolide B1, Elansolide B1; 1→25-Lactone, Elansolide B1; 1→25-Lactone, atropisomer, Elansolide B1; Me ester, Elansolide D1, Elansolide D2, Elgicins, Eliamide, Empedopeptin, Enacyloxin IIa, Enacyloxin IIa; 15'S-Alcohol, Enacyloxin IIa; 18'-Dechloro, Enacyloxin IIa; 18'-Dechloro, 15'S-alcohol, Enacyloxin IIa; 13'-Me ether, Enacyloxin IIb, Enacyloxin IIb; 15'S-Alcohol, Enacyloxin IIb; 18'-Dechloro, Enacyloxin IIb; 18'-Dechloro, 15'S-alcohol, Enamidase, Endogalactosaminidase, Endoglycosylceramidase, Endopeptidase Clp, Endopeptidase La, Endopeptidase So, Endosubtilysin, *Bordetella pertussis* 1414 Endotoxin, *Bacillus thuringiensis* δ-Endotoxins, Endynamicin A, Endynamicin A; 4-Deoxy, 2-Enoate reductase, Enocin, Enterobactin, Enterocins, Enterocins; Enterocin 01, Enterocins; Enterocin 012, Enterocins; Enterocin 100, Enterocins; Enterocin 101, Enterocins; Enterocin 102, Enterocins; Enterocin 1146, Enterocins; Enterocin 3587, Enterocins; Enterocin 3915, Enterocins; Enterocin 626, Enterocins; Enterocin 81, Enterocins; Enterocin 900, Enterocins; Enterocin 96, Enterocins; Enterocin A, Enterocins; Enterocin 1071A, Enterocins; Enterocin 7A, Enterocins; Enterocin B, Enterocins; Enterocin 1071B, Enterocins; Enterocin 7B, Enterocins; Enterocin BC25, Enterocins; Enterocin C, Enterocins; Enterocin 388C, Enterocins; Enterocin CCM4231, Enterocins; Enterocin CRL 35, Enterocins; Enterocin CTC 492, Enterocins; Enterocin E760, Enterocins; Enterocin EIA, Enterocins; Enterocin EJ97, Enterocins; Enterocin EL1, Enterocins; Enterocin ESF100, Enterocins; Enterocin FH99, Enterocins; Enterocin HF, Enterocins; Enterocin HJ35, Enterocins; Enterocin I, Enterocins; Enterocin IT, Enterocins; Enterocin 416K1, Enterocins; Enterocin KP, Enterocins; Enterocin L50, Enterocins; Enterocin LR/6, Enterocins; Enterocin MC13, Enterocins; Enterocin 226NWC, Enterocins; Enterocin ON-157, Enterocins; Enterocin P, Enterocins; Enterocin RJ-11, Enterocins; Enterocin S37, Enterocins; Enterocin S760, Enterocins; Enterocin SD, Enterocins; Enterocin SE-K4, Enterocins; Enterocin U7, Enterocins; Enterocin UQ1, Enterocins; Enterocin V24, Enterocins; Enterocin W, Enterocins; Enterocin X, Enterococcins; Enterococcin A 2000, Enterococcins; Enterococcin EFS2, Enterococcins; Enterococcin V583, Enterocoliticin, Enterolysin A, Enterotoxin, Entianin, Entolysin A, Entomocin 110, Entomocin 420, Entomocin 9, EPF, Ephedrine dehydrogenase, Epicidin 280, Epidermicin NI 01, Epidermin, Epidermin; 1-Valine 6-leucine analogue, Epilancin K7, Epilancin 15X, Epothilone A, Epothilone A; 3-O-α-D-Arabinofuranoside, Epothilone A; 8-Demethyl, 3-O-α-D-arabinofuranoside, Epothilone A; 21-Hydroxy, Epothilone A; 27-Hydroxy, Epothilone A; Parent hydroxyacid, Epothilone A; Parent hydroxyacid, Me ester, Epothilone A1, Epothilone A1; 4-Epimer, Epothilone A8, Epothilone B, Epothilone B; 3-O-α-D-Arabinofuranoside. Epothilone B; 21-Hydroxy, Epothilone B; 21-Methyl, Epothilone C, Epothilone C; 3-O-α-D-Arabinofuranoside, Epothilone C; 16-Demethyl, Epothilone C; 4-Demethyl, 9-oxo, Epothilone C; 10,11-Didehydro(E-), Epothilone C; 8,9-Didehydro(E-), Epothilone C; 14α-Hydroxy, Epothilone C; 27-Hydroxy, Epothilone C; 27-Hydroxy, 3-O-α-D-arabinofuranoside, Epothilone C1, Epothilone C1; 4-Epimer, Epothilone C1; 4-Epimer, 12E-isomer, Epothilone C1; 12E-Isomer, Epothilone C3, Epothilone C4, Epothilone D, Epothilone D; 4-Demethyl, 10,11-didehydro(E-), Epothilone D; 6-Demethyl, 10,11-didehydro(E-), Epothilone D; 4-Demethyl, 9-oxo, stereoisomer 1, Epothilone D; 4-Demethyl, 9-oxo, stereoisomer 2, Epothilone D; 10,11-Didehydro(E-), Epothilone D; 8,9-Didehydro(E-), Epothilone D; 8-Epimer, 9-oxo, Epothilone D; Δ11,12-Isomer, 9-oxo, Epothilone D; 9-Oxo, Epothilone D; 9-Oxo, 10,11-didehydro(E-), Epothilone D1, Epothilone D1; 4-Epimer, Epothilone H1, Epothilone H1; 12α,13α-Epoxide, Epothilone H2, Epothilone H2; 12α,13α-Epoxide, Epothilone I1, Epothilone I2, Epothilone I3, Epothilone I4, Epothilone I5, Epothilone I5; 4-Epimer, Epothilone K, Epothilone M, Epothilone N, Epothilone tetrahydrofuran, Epoxomicin, 13,17-Epoxy-16-hydroxymacrolactin A, 15,17-Epoxy-16-hydroxymacrolactin A, 13,14-Epoxy-15-oxohexadecanoic acid, trans-Epoxysuccinate hydrolase, 9,11-Eremophiladiene-1,3-diol; (1β,3α,4α,5β)-form, Ericin A, Erwinicin, Erythrazole A, Erythrazole B, Erythritol kinase, Erythromycin, Esein, Esperin, Ethane, 1,2-Ethanediol, 2,2'-(1,2-Ethanediyl)bis[1-methyl-3-piperidinone]; (RS,SR)-form, Ethanolamine kinase, Ethanolamine oxidase, Ethoxyacetic acid, Ethylamine, Ethylbenzene hydroxylase, 3-(2-Ethyl-2-butenyl)-9,10-dihydro-1,6,8-trihydroxy-9,10-dioxo-2-anthracenecarboxylic acid, 2-Ethyl-1,8-dihydroxy-3-methylanthraquinone, 2-Ethyl-1,8-dihydroxy-3-methylanthraquinone; 8-Me ether, 1-(4-Ethyl-3,5-dihydroxyphenyl)-2-phenylethylene; (E)-form, 3-Ethyl-2,5-dimethylpyrazine, 2-Ethylmalate synthase, 3-Ethylmalate synthase, 2-Ethyl-4-methylquinazoline, 2-(1-Ethylpentyl)-2,3-dihydro-4(1H)-quinazolinone; (1'R,2R)-form, 2-(1-Ethylpentyl)-2,3-dihydro-4(1H)-quinazolinone; (1'R,2S)-form, 2-(1-Ethylpentyl)-2,3-dihydro-4(1H)-quinazolinone; (1'R,2S)-form, 1,2-Didehydro, 4-Ethyl-1H-pyrrole-2-carboxaldehyde, Etnangiene, 11-Eudesmene-1,4-diol; (1β,4α)-form, Eurocidin C, Eurocidin D, Eurocidin D; 7-Deoxy, Everninomicin A, Everninomicin A; 4A-O-De-Me, Everninomicin A; 3-Chloro, Everninomicin A; 3'-Dechloro, Everninomicin A; 3'-Dechloro, 2'-O-de-Me, Everninomicin A; 2H,3H-De-O-methylene, 3H—O-formyl, Everninomicin B, Everninomicin B; 2D-Deoxy, Everninomicin C, Exodeoxyribonuclease I, Exodeoxyribonuclease III, Exodeoxyribonuclease (lambda-induced), Exodeoxyribonuclease V, Exodeoxyribonuclease VII, Exo-poly-α-galacturonosidase, Exoribonuclease H, Exoribonuclease II, Exotoxin A, Factor S1, Factor S3, FAD synthetase, Faktor I, Faktor III, Farnesyl-transtransferase, Fatty acid synthase, Fengycin, Ferredoxin reductases; Ferredoxin-NADP(+) reductase, Ferredoxin reductases; Ferredoxin-NAD(+) reductase, Ferribactin 18.1, Ferribactin G173, Ferribactin G173; NGlu-Ac, Ferribactin G173; NGlu-Di-Ac, Ferribactin G173; NGlu-Hydroxy, Ferribactin PS 6.10-A, Ferricrocin, Ferrioxamine D2, Ferrocin, Ferroxidase; Rusticyanin, Feruloyl esterase, FIC, Figaroinic acid, Fijiolide A, Fijiolide A; N-De-Ac, Fla-P3, Fla-P3; 3-Chloro, Fla-P4, Fla-P4; 3-Chloro, Fla-P5, Flavocin, Flavolipids, Flavotoxin A, Flazine, Flexirubin, Flexirubin; 5-Chloro, Flexixanthin, Flexixanthin; 3-Deoxy, Flexixanthin; 3-Deoxy, O-β-D-glucopyranoside, Flexixanthin; 3-Deoxy, 2'R-hydroxy, Flexixanthin; 3-Deoxy, 2ξ-hydroxy, Flexixanthin; 3-Deoxy, O-[11-methyldodecanoyl-(→6)-β-D-glucopyranoside], Flexixanthin; 2'S-Hydroxy, Flexixanthin; 2'-Hydroxy, 1',3-di-Me ether, Flexixanthin; 2'S-Hydroxy, 1'-O-β-D-xylopyranoside, Flexixanthin; 2'S-Methoxy, Flexixanthin; 2'-Methoxy, 1',3-di-Me ether, Fluopsin B, Fluopsin C, Fluopsin N, 9-Fluorenol dehydrogenase, Fluvibactin, Fluviol D, Fluvirucin A; Fluvirucin A1, Fluvirucin A; Fluvirucin A1, 3'-N-Me, Fluvirucin A; Fluvirucin A1, 6-Demethyl, 3'-N-Me, Fluvirucin A; Fluvirucin A2, Fluvirucin B; Fluvirucin B0, Fluvirucin B; Fluvirucin B3, 4'-Epimer, 2'-O-[β-D-glucopyranosyl-(1→4)-α-D-glucopyranosyl], Fluvirucin B; Fluvirucin B3, 4'-Epimer, N3'-[[2-(2-phenylethyl)amino]carbonyl], Fluvirucin B; Fluvirucin B3, N3'-[[2-(2-Phenylethyl)amino]carbonyl], Fluvomycin, Formadicins, Formaldehyde dehydrogenases; Formaldehyde dehydrogenase, [Formate-C-acetyltransferase]-activating enzyme, Formate C-acetyltransferase, Formate dehydrogenases; Formate dehydrogenase (cytochrome-553), Formate dehydrogenases; Formate dehydrogenase (NADP(+)), Formate kinase, Formimidoylaspartate deiminase, Formimidoylglutamase, Formimidoylglutamate deiminase, Formyl-CoA hydrolase, Formyl-CoA transferase, Formylmethanofuran:tetrahydromethanopterin N-formyltransferase, 5-(Formyloxymethyl)uridine, 5-Formyl-1H-pyrrole-2-carboxylic acid, Fortimicin AH, Fortimicin AH; 3-Epimer, Fortimicin AK, Fortimicin AO, Fortimicin B, Fortimicin B; 1-N-(Aminoacetyl), Fortimicin B; 1-N-[(Aminocarbonylamino)acetyl], Fortimicin B; O-De-Me, 1-N-(aminoacetyl), Fortimicin B; O-De-Me, 4-N-(aminoacetyl), Fortimicin B; O-De-Me, 1-N-[[(aminocarbony) amino]acetyl], Fortimicin B; 1,6-Diepimer, Fortimicin B; 1,6-Diepimer, O-de-Me, Fortimicin B; 2,5-Diepimer, 1-N-[(formylamino)acetyl], Fortimicin B; 6-Epimer, Fortimicin B; 6-Epimer, 2'-N-(aminoacetyl), Fortimicin B; 1-Epimer, O-de-Me, Fortimicin B; 1-N-(Formylaminoacetyl), Fortimicin B; 1-N-(2-Hydroxyethyl), Fortimicin B; 1-N-[[(Iminomethyl)amino]acetyl], Fortimicin B; 1-N-Me, Fortimicin B; 1,3,6-Triepimer, Fortimicin KE, Fortimicin KE; 1-N-(Aminoacetyl), Fortimicin KE; O-De-Me, Fortimicin KF, Fortimicin KG, Fortimicin KG; 1-N-(Aminoacetyl), Fortimicin KG; O-De-Me, Fortimicin KG; 1,6-Diepimer, Fortimicin KG; 1,6-Diepimer, O-de-Me, Fortimicin KG; Stereoisomer, Fortimicin KK1, Fortimicin KL1, Fosfadecin, Fosfocytocin, Fosfoxacin, FR 183739, FR 183743, FR 252921, FR 252922, FR 252922; 5',6'-Didehydro, Fradicin, Fragilicin, Fragilomycin, Fragin; (−)-form, Frankobactin, Friulimicin, Friulimicin; Friulimicin A, 4'-Parent acid, Friulimicin; Friulimicin B, 4'-Parent acid, Friulimicin; Friulimicin D, 4'-Parent acid, Fructan β-(2,6)-fructosidase, Fructan β-fructosidase, 2,6-β-Fructan 6-levanbiohydrolase, β-D-Fructofuranosyl-(2→3)-β-D-glucopyranuronosyl-(1→3)-2-amino-2-deoxy-D-galactose, Fructokinase, Fructose 5-dehydrogenases; Fructose 5-dehydrogenase (acceptor), Fructose 5-dehydrogenases; Fructose 5-dehydrogenase (NADP(+)), 4-O-α-L-Fucopyranosyl-L-fucose, α-D-Fucopyranosyl-(1→2)-α-L-rhamnopyranosyl-(1→3)-D-mannose, Fucose; L-form, 3-Me, 1,2-α-L-Fucosidase, L-Fuculokinase, Fulvocin C, Fungicin M4, Fungistatin, 1-(2-Furanyl)-1,2-ethanediol; (R)-form, 2-Furoyl-CoA dehydrogenase, Fusaromycin A, Fuscopeptin A, Fuscopeptin B, Futalosine hydrolase, Galactan 1,3-β-galactosidase, Galactitol-1-phosphate 5-dehydrogenase, 2-O-β-D-Galactofuranosyl-D-galactose, 3-O-β-D-Galactofuranosyl-D-galactose, 5-O-β-D-Galactofuranosyl-D-galactose, 6-O-β-D-Galactofuranosyl-D-galactose, 1-O-β-D-Galactofuranosyl-D-glycerol, Galactokinase, β-D-Galactopyranosyl-(1→4)-2-amino-2-deoxy-β-D-glucopyranosyl-(1→3)-D-galactose, α-D-Galactopyranosyl-(1→6)-β-D-galactofuranosyl-(1→6)-D-galactose, α-D-Galactopyranosyl-(1→4)-α-D-galactopyranosyl-(1→3)-D-galactose, α-D-Galactopyranosyl-1→2)-α-D-galactopyranosyl-(1→2)-D-glucose, α-D-Galactopyranosyl-(1→3)-β-D-galactopyranosyl-(1→4)-D-glucose, β-D-Galactopyranosyl-(1→3)-β-D-galactopyranosyl-(1→4)-D-glucose, α-D-Galactopyranosyl-(1→3)-[α-D-galactopyranosyl(1→6)]-D-glucose, 2-O-α-D-Galactopyranosyl-D-galactose, 3-O-α-D-Galactopyranosyl-D-galactose, β-D-Galactopyranosyl-(1→4)-β-D-glucopyranosyl-(1→6)-2-amino-2-deoxy-D-glucose, β-D-Galactopyranosyl-(1→4)-[α-D-glucopyranosyl-(1→6)]-2-amino-2-deoxy-D-mannose; β-Pyranose-form, N—Ac, O-α-D-Galactopyranosyl-(1→2)-O-α-D-glucopyranosyl-(1→1)-D-glycerol, α-D-Galactopyranosyl-(1→3)-α-D-glucopyranosyl-(1→3)-L-rhamnose, α-D-Galactopyranosyl-(1→3)-[β-D-glucopyranuronosyl-(1→2)]-D-mannose, β-D-Galactopyranosyl-(1→4)-[β-D-glucopyranuronosyl-(1→3)]-L-rhamnose, 2-O-α-D-Galactopyranosylglycerol, α-D-Galactopyranosyl-(1→2)-α-D-mannopyranosyl-(1→4)-L-rhamnose, α-D-Galactopyranosyl-(1→6)-β-D-mannopyranosyl-(1→4)-L-rhamnose; α-Pyranose-form, 6''-Ac, β-D-Galactopyranosyl-(1→6)-β-D-mannopyranosyl-(1→4)-L-rhamnose, 6-O-β-D-Galactopyranosyl-D-mannose, 2-O-α-D-Galactopyranosyl-L-rhamnose, 2-O-β-D-Galactopyranosyl-L-rhamnose, 4-O-α-D-Galactopyranosyl-L-rhamnose, 4-O-β-D-Galactopyranosyl-L-rhamnose, Galactose 1-phosphate thymidylyltransferase, α-Galactosidase, Galactoside O-acetyltransferase, 1,3-β-Galactosyl-N-acetylhexosamine phosphorylase, Galantin I, Galantin II, Galbonolide A, Galbonolide A; 21-Hydroxy, Galbonolide B; 21-Hydroxy, Galbonolide B; Stereoisomer(?), Gallerin, Gallidermin, Galtamycinone; 4'-O-[2,3,6-Trideoxy-α-L-glycero-hex-2-enopyranos-4-ulosyl-(1→4)-2,3,6-trideoxy-α-L-threo-hexopyranosyl-(1→4)-2,6-dideoxy-α-L-lyxohexopyranosyl], Gamba A, Garamine, Garosamine; L-form, Garvicins, Garvicins; Garvicin L1-5, Garvicins; Garvicin ML, Garvicins; Garvicin Q, Gassericins, Gassericins; Gassericin A, Gassericins; Gassericin B1, Gassericins; Gassericin B2, Gassericins; Gassericin B3, Gassericins; Gassericin B4, Gassericins; Gassericin KT7, Gastric ulcer inhibitory substance, Gatavalin, Gavaserin, GDP Cobinamide, GDP-fucose synthase, GDP-Mannose 6-dehydrogenase, Gelatinase biosynthesis-activating pheromone, Gellan, Genimycin, Gentamicin A, Gentamicin A; 5-Deoxy, Gentamicin A; 4''-Epimer, Gentamicin A; 3''-N-Formyl, Gentamicin A2, Gentamicin A3, Gentamicin N-acetyltransferases; Gentamicin 3'-N-acetyltransferase, Gentamicin B, Gentamicin B; 3',4'-Dideoxy, Gentamicin B1, Gentamicin B1; 3',4'-Dideoxy, Gentamicin C1, Gentamicin C1; 3''-N-De-Me, Genitamicin C1; 6'-N-De-Me, Gentamicin C1; Di-N-de-Me, Gentamicin C1; 6'-Epimer, 6-N-de-Me, Gentamicin C1; 3-N-Me, Gentamicin C1a, Gentamicin C1a; 3''-N-De-Me, Gentamicin C1a; 3''-N-De-Me, 6'-N-Me, Gentamicin C1a; 5-Deoxy, 6',6'-N-di-Me, Gentamicin C1a; 5-Deoxy, 6-N-Me, Gentamicin C1a; 3,6'-N-Di-Me, Gentamicin C1a; 6'-N-Di-Me, Gentamicin C1a; 1-N-Et, Gentamicin C1a; 2S-Hydroxy, 6',6-N-di-Me, Gentamicin C1a; 2S-Hydroxy, 6'-N-Me, Gentamicin C1a; 3-N-Me, Gentamicin C1a; 6'-N-Me, Gentamicin C1a; 3,6',6'-N-Tri-Me, Gentamicin G 418, Gentamicin 2''-nucleotidyltransferase, Gentamicin X2, Gentamine C2, Gentamine C2; N6'-Me, 1-O-Gentiobiosylglucose; β-D-(2R)-form, Gentisate 1,2-dioxygenase, Gephyronic acid, Geranyl-trans-transferase, GGPL I, GGPL III, Gingipain K, Gingipain R, Glidobactamine, Glidobactamine; 13-Hydroxy, NThr-(2E,4E-dodecadienoyl), Glidobactamine; NThr-Acyl (?), Glidobactamine; NThr-(2E,4E-Decadienoyl), Glidobactamine; NThr-(2E,4E-Dodecadienoyl), Glidobactamine; NThr-(10ξ-Hydroxy-2E,4E-dodecadienoyl), Glidobactamine; NThr-(7ξ-Hydroxy-2E,4E-dodecadienoyl), Glidobactamine; NThr-(9-Methyl-2E,4E-decadienoyl), Glidobactamine; NThr-11-Methyl-2E,4E-dodecadienoyl), Glidobactamine; NThr-(2E,4E-Tetradecacienoyl), Glidobactamine; NThr-(2E,4E,8Z,11Z-Tetradecatetraenoyl), Glidobactamine; NThr-(2E,4E,8Z-Tetradecatrienoyl), Globicin, α-D-(1→3)-Glucan, β-D-(1→3)-Glucan; Curdlan, endo-1,3(4)-β-Glucanase, 1,4-α-Glucan branching enzyme, Glucan endo-1,2-β-glucosidase, Glucan endo-1,3-α-glucosidase, Glucan endo-1,6-β-glucosidase, Glucan 1,4-β-glucosidase, Glucan 1,6-α-glucosidase, Glucan 1,6-α-isomaltosidase, Glucan 1,4-α-maltohexaosidase, Glucan 1,4-α-maltohydrolase, Glucan 1,4-α-maltotetraohydrolase, Glucan 1,4-α-maltotriohydrolase, 4-α-Glucanotransferase, 4-α-D-[(1→4)-α-D-Glucano]trehalose trehalohydrolase, α-1,4-Glucan-protein synthase (ADP-forming), α-1,3-Glucan synthase, Glucoamylase, Gluconokinase, 1,4-Gluconolactone; D-form, α-D-Glucopyranosyl 2-amino-2-deoxy-β-D-glucopyranosyl-(1→6)-α-D-glucopyranoside; N-Hydroxymethyl, 6-O-α-D-Glucopyranosyl-D-fructofuranose, 5-O-α-D-Glucopyranosyl-D-fructose, 4-O-β-D-Glucopyranosyl-L-fucose, α-D-Glucopyranosyl-(1→3)-β-D-galactopyranosyl-(1→2)-L-rhamnose, β-D-Glucopyranosyl-(1→3)-α-D-galactopyranuronosyl-(1→3)-D-mannose; 4'-Ac, 2-O-α-D-Glucopyranosyl-D-galactose, 2-O-β-D-Glucopyranosyl-D-galactose, 3-O-β-D-Glucopyranosyl-D-galactose, 4-O-α-D-Glucopyranosyl-D-galactose, 4-O-β-D-Glucopyranosyl-D-galactose, 6-O-β-D-Glucopyranosyl-D-galactose, 4-O-Glucopyranosyl-D-gluconic acid; α-D-form, β-D-Glucopyranosyl-(1→2)-β-D-glucopyranosyl-(1→2)-β-D- glucose, α-D-Glucopyranosyl-(1→2)-β-D-glucopyranosyl-(1→4)-D-Glucose, α-D-Glucopyranosyl-(1→2)-[α-D-glucopyranosyl-(1→6)]-D-glucose, α-D-Glucopyranosyl-(1→2)-α-D-glucopyranosyl-(1→6)-D-glucose, α-D-Glucopyranosyl-(1→3)-α-D-glucopyranosyl-(1→3)-D-glucose, α-D-Glucopyranosyl-(1→3)-[α-D-glucopyranosyl-(1→-6)]-D-glucose, α-D-Glucopyranosyl-(1→3)-α-D-glucopyranosyl-(1→6)-D-glucose, α-D-glucopyranosyl-(1→6)-α-D-glucopyranosyl-(1→2)-D-glucose, α-D-Glucopyranosyl-(1→6)-β-D-glucopyranosyl-(1→2)-D-glucose, α-D-Glucopyranosyl-(1→6)-α-D-glucopyranosyl-(1→3)-D-glucose, α-D-Glucopyranosyl-(1→6)-β-D-glucopyranosyl-(1→3)-D-glucose, β-D-Glucopyranosyl-(1→6)-β-D-glucopyranosyl-(1→4)-D-glucose, α-D-Glucopyranosyl-(1→6)-β-D-glucopyranosyl-(1→6)-D-glucose, α-D-Glucopyranosyl-(1→2)-[β-D-glucopyranosyl-(1→3)]-L-rhamnose, α-D-Glucopyranosyl-(1→2)-α-D-glucopyranuronosyl-(1→3)-D-mannose, 2-O-α-D-Glucopyranosyl-D-glucose, 2-O-β-D-Glucopyranosyl-D-glucose, 6-O-α-D-Glucopyranosyl-D-glucose, 6-O-β-D-Glucopyranosyl-D-glucose, 3-O-α-D-Glucopyranosyl-D-mannose, 3-O-β-D-Glucopyranosyl-D-mannose; Pyranose-form, α-D-Glucopyranosyl-(1→4)-α-L-rhamnopyranosyl-(1→3)-2-amino-2-deoxy-β-D-glucose; N—Ac, α-D-Glucopyranosyl-(1→2)-[α-L-rhamnopyranosyl-(1→3)]-L-rhamnose, α-D-Glucopyranosyl-(1→3)-[α-L-rhamnopyranosyl-(1→2)]-L-rhamnose, α-D-Glucopyranosyl-(1→3)-α-L-rhamnopyranosyl-(1→2)-L-rhamnose, α-D-Glucopyranosyl-(1→3)-α-L-rhamnopyranosyl-(1→3)-L-rhamnose, 2-O-β-D-Glucopyranosyl-L-rhamnose, 3-O-α-D-Glucopyranosyl-L-rhamnose, 3-O-β-D-Glucopyranosyl-L-rhamnose, 4-O-α-D-Glucopyranosyl-L-rhamnose, 4-O-β-D-Glucopyranosyl-L-rhamnose, 3-O-α-D-Glucopyranosylribitol, 4-O-α-D-Glucopyranosyl-D-ribitol, 4-O-β-D-Glucopyranosyl-D-ribitol, 3-O-β-D-Glucopyranuronosyl-D-galactose, 4-O-β-D-Glucopyranuronosyl-D-galactose, β-D-Glucopyranuronosyl-(1→4)-β-D-glucopyranosyl-(1→4)-α-D-glucopyranosyl-(1→4)-D-galactose, β-D-Glucopyranuronosyl-(1→4)-β-D-glucopyranosyl-(1→4)-D-glucose, 4-O-β-D-Glucopyranuronosyl-D-glucose, 6-O-α-D-Glucopyranuronosyl-D-glucose, 2-O-β-D-Glucopyranuronosyl-D-mannose, 3-O-β-D-Glucopyranuronosyl-L-rhamnose, 4-O-β-D-Glucopyranuronosyl-L-rhamnose, Glucosamine kinase, Glucosamine-1-phosphate N-acetyltransferase, Glucose-1-phosphatase, Glucose 1-phosphate adenylyltransferase, Glucose 1-phosphate cytidylyltransferase, Glucose-6-phosphate 1-dehydrogenase, Glucose 1-phosphate phosphodismutase, Glucose 1-phosphate thymidylyltransferase, α-Glucosidase, β-Glucoside kinase, Glucuronic acid; D-form, 2-Me, α-Glucuronidase, β-Glucuronidase, Glucuronoarabinoxylan endo-1,4-β-xylanase, Glucuronosyldisulfoglucosamine glucuronidase, Glu-Glu dipeptidase, Glusun I, Glusun II, Glutacin, Glutaconate CoA-transferase, [Glutamate ammonia ligase]adenylyltransferase, Glutamate carboxypeptidase, Glutamate dehydrogenases; Glutamate dehydrogenase (NADP(+)), Glutamate 5-kinase, Glutamate syntheses; Glutamate synthase (NADH), Glutamate synthases; Glutamate synthase (NADPH), Glutamic acid; (S)-form, N-(3-Carboxypropanoyl), Glutaminase, Glutamine; (S)-form, N2-Carbamoyl, amide, Glutamine fructose-6-phosphate transaminase (isomerising), Glutamine scyllo-inositol transaminase, Glutamyl endopeptidase, D-Glutamyltransferase, γ-Glutamyltransferase, Glutathione; 1-Amide, Glyceofuran, Glyceraldehyde 3-phosphate dehydrogenases; Glyceraldehyde-3-phosphate dehydrogenase (ferredoxin), Glycerate dehydrogenases; Hydroxypyruvate reductase, Glycerate kinase, Glycerol 1-alkanoates; Glycerol 1-dodecanoate, Glycerol dehydrogenases; Glycerol dehydrogenase (acceptor), Glycerol 1,2-dialkanoates; Glycerol 1,2-dipentadecanoate, 3-O-[β-D-Glucopyranosyl-(1→6)-β-D-glucopyranoside], Glycerol 1,2-dialkanoates; Glycerol 1-heptadecanoate 2-pentadecanoate, 3-O-[β-D-Glucopyranosyl-(1→6)-β-D-glucopyranoside], Glycerol 1,2-dialkanoates; Glycerol 1-(9Z-heptadecenoate) 2-pentadecanoate, 3-O-[β-D-Glucopyranosyl-(1→6)-β-D-glucopyranoside], Glycerol 1,2-dialkanoates; Glycerol 1-hexadecanoate 2-(10Z-hexadecenoate), 3-O-[β-D-Glucopyranosyl-(1→6)-β-D-glucopyranoside], Glycerol 1,2-dialkanoates; Glycerol 1-hexadecanoate 2-(9Z-octadecenoate), 3-O-α-D-Galactopyranoside, Glycerol 1,2-dialkanoates; Glycerol 1-hexadecanoate 2-pentadecanoate, 3-O-[β-D-Glucopyranosyl-(1→6)-β-D-glucopyranoside], Glycerol 1,2-dialkanoates; Glycerol 1-(10Z-hexadecenoate) 2-pentadecanoate, 3-O-[β-D-Glucopyranosyl-(1→6)-β-D-glucopyranoside], Glycerol 1,2-dialkanoates; Glycerol 1-tetradecanoate 2-heptadecanoate, 3-O-[β-D-Glucopyranosyl-(1→6)-β-D-glucopyranoside], Glycerol 1,2-dialkanoates; Glycerol 1-tetradecanoate 2-hexadecanoate, 3-O-[β-D-Glucopyranosyl-(1→6)-β-D-glucopyranoside], Glycerol 1,2-dialkanoates; Glycerol 1-tetradecanoate 2-pentadecanoate, 3-O-[β-D-Glucopyranosyl-(1→6)-β-D-glucopyranoside], Glycerol kinase, Glycerol 3-phosphate cytidylyltransferase, Glycerone kinase, Glycerophosphocholine phosphodiesterase, Glycerophosphodiester phosphodiesterase, Glycero-3-phosphoglycerol; 2'-O-β-D-Glucopyranoside, Glycerophosphoinositol glycerophosphodiesterase, Glycine C-acetyltransferase, Glycinecin, Glycinecin; Glycinecin A, Glycine dehydrogenases; Glycine dehydrogenase (cyanide-forming), Glycine dehydrogenases; Glycine dehydrogenase (cytochrome), Glycine dehydrogenases; Glycine dehydrogenase (decarboxylating). Glycine dehydrogenases; Glycine oxidase, Glycine formimidoyltransferase, Glycine oxaloacetate transaminase, Glycine reductase, Glycolipid B, Glycopeptide α-N-acetylgalactosaminidase, Glycosulfatase, Glycothiohexide α, Glycothiohexide α; Stereoisomer, Glycylprolylphenylalanylprolylisoleucine, N-Glycylthreonine; L-form, N-(3,4-Dihydroxybenzoyl), Glycyrrhizinate β-glucuronidase, Glyphomicin, Glysperin A, Glysperin B, Glysperin C, Gonocin, Gonococcal growth inhibitor, Gordonin, Graceilin, Gramicidin K, Gramicidin S, Gramicidins A-D, Gratisin, Griseorhodin C; 3,4-Dideoxy, 3'-ketone, Griseusin D, GTP cyclohydrolase I, GTP diphosphokinase, Guanidinoacetase, Guanidinobutyrase, Guanidinopropionase, Guanine deaminase, Guanosine-3',5'-bis(diphosphate) 3'-diphosphatase, Guanosine deaminase, Guanosine diphosphate colitose, Guanylate kinase, Guaymasol, Guaymasol; 3-Epimer, Haem a; Deoxo, Haemocin, α-Haemolysin, Haliangicin A, Haliangicin A; 12,13-cis-Isomer, Haliangicin A; (2Z)-Isomer, Haliangicin A; (4E,6E)-Isomer, Haliangicin A; (4E)-Isomer, Halobacillin, Haloduracin, Halolitoralin A, Halolitoralin B, Halolitoralin C, Halomicin A, Halomicin A; 3-Deoxy, Halomicin A; 20-Hydroxy, 3-deoxy, Halomicin D, Halotoxin, Haloxanthin, Harveyicin, Haterumalide NE, Haterumalide NE; 3-Ac, Haterumalide NE; 3-Ac, (2-methylene-3-oxobutyl) ester, Haterumalide NE; 16Z-Isomer, 3-Ac, *Escherichia coli* Heat-stable enterotoxin STh, *Vibrio* Heat-stable enterotoxin, *Vibrio* Heat-stable enterotoxin; N1-L-Leucyl, Helveticins, Helveticins; Helveticin J, Helveticins; Helveticin V1829, δ-Hemolysins, δ-Hemolysin; N1-Deformyl, Hen egg-white lysozyme inhibitor, 5-Heneicosyl-1,3-benzenediol, 7-Hentriaconten-16-one; (Z)-form, Hepcin, 5-Heptacosyl-1,3-benzenediol, 6-Heptadecenoic acid; (Z)-form, 6-Heptadecenyl-6'-heptadecyl-4,4'-dihydroxy[3,3'-bi-2H-pyran]-2,2'-dione, Heptadepsin, 2-(3,7,11,15,19,23,27-Heptamethyl-2,6,10,14,18,22,26-octacosaheptaenyl)-1,4-naphthalenediol; 4-Me ether, Heptamycin B, Heptamycin B; N-De-Ac, N-propanoyl, Heptanedioic acid, 2-(2-Heptenyl)-3-methyl-4(1H)-quinolinone; (E)-form, 2-(2-Heptenyl)-3-methyl-4(1H)-quininone; (E)-form, 2',3'-Dihydro, D-glycero-D-manno-Heptitol, D-glycero-D-altro-Heptose, D-glycero-D-galacto-Heptose, D-glycero-D-manno-Heptose, D-glycero-L-manno-Heptose, L-glycero-D-ido-Heptose, L-glycero-D-manno-Heptose, L-glycero-D-manno-Heptose; 7-O-Carbamoyl, 6-Heptyl-3-hexyl-4-hydroxy-2H-pyran-2-one, 2-Heptyl-4-hydroxyquinoline, 2-Heptyl-4-hydroxyquinoline; 1',2'-Didehydro(E)-, 2-Heptyl-4-hydroxyquinoline; 1',2'-Didehydro(Z)-, 2-Heptyl-4-hydroxyquinoline; N-Oxide, 3-Heptyl-3-hydroxy-2,4(1H,3H)-quinolinedione, Herbicolacin 112Y, Herbicolin A, Herbicolin A; Aglycone, Herbicolin 2C, Herbicolin O, Heterobactin A, Heterobactin A; N2-Deacyl, 3,3',4,4',5,5'-Hexabromo-2,2'-bi-1H-pyrrole, 5-Hexadecenoic acid; (Z)-form, 1,1',2,2',7,8-Hexahydro-ψ,ψ-carotene-1,1'-diol; 11,12-Dihydro, di-Me ether, 1,1',2,2',7,8-Hexahydro-ψ,ψ-carotene-1,1'-diol; 11,12-Dihydro, 1'-Me ether, 1,1',2,2',7,8-Hexahydro-ψ,ψ-carotene-1,1'-diol; Di-Me ether, 1,1',2,2',7,8-Hexahydro-ψ,ψ-carotene-1,1'-diol; 1'-Me ether, 1,1',2,2',7,8-Hexahydro-ψ,ψ-carotene-1,1'-diol; 7,8',11',12'-Tetrahydro, 1"-Me ether, Hexahydro-4H-1,3-diazepin-4-one; N3-Me, Hexahydro-1,4-diazocine-2,5-dione, 4,4a,5,6,7,8-Hexahydro-4a,8-dimethyl-2(3H)-naphthalenone; (4aξ,8ξ)-form, 1,8-Dihydro, 2-alcohol, 4,4a,5,6,7,8-Hexahydro-4a,8-dimethyl-2(3H)-naphthalenone; (4aS,8S)-form, 4,4a,5,6,7,8-Hexahydro-4a,8-dimethyl-2(3H)-naphthalenone; (4aS,8S)-form, 1,8aβ-Dihydro, 1,2,3,4,7,8-Hexahydro-6-(4-hydroxyphenyl)-8-(2,3,4,5-tetrahydroxypentyl)-2,4,7-pteridinetrione; D-ribo-form, 1,1',2,2',7,8-Hexahydrolycopene, 1,2,7,7',8,8'-Hexahydrolycopene, 1,2,7,8,11,12-Hexahydrolycopene, 3,5,7,9,13,17-Hexamethyl-5,8,10,12,14,16,18-eicosaheptaene-2,4-diol; (2ξ,3ξ,4ξ,5ξ,7ξ,8E,10E,12E,14E,16E,18Z)-form, 2-Ac, 2,6,10,15,19,23-Hexamethyl-2,4,6,8,10,12,14,16,18,22-tetracosadecaen-1-al, 2,6,10,15,19,23-Hexamethyl-2,4,6,8,10,12,14,16,18,22-tetracosadecaen-1-ol, 2,6,10,15,19,23-Hexamethyl-2,4,6,8,10,12,14,16,18,22-tetracosadecaen-1-ol; O-D-Glucopyranoside, 2,6,10,15,19,23-Hexamethyl-2,4,6,8,10,12,14,16,18,20,22-tetracosaundecaen-1-al, 2,6,10,15,19,23-Hexamethyl-2,4,6,8,10,12,14,16,18,20,22-tetracosaundecaene, 2,6,10,15,19,23-Hexamethyl-2,4,6,8,10,12,14,16,18,20,22-tetracosaundecaene; 4,5-Dihydro, 2,6,10,15,19,23-Hexamethyl-2,4,6,8,10,12,14,16,18,20,22-tetracosaundecaene; 4,5,8,9,20,21-Hexahydro, 2,6,10,15,19,23-Hexamethyl-2,4,6,8,10,12,14,16,18,20,22-tetracosaundecaene; 4,5,8,9,16,17,20,21-Octahydro, 2,6,10,15,19,23-Hexamethyl-2,4,6,8,10,12,14,16,18,20,22-tetracosaundecaene; 4,5,20,21-Tetrahydro, 2,6,10,15,19,23-Hexamethyl-2,4,6,8,10,12,14,16,18,20,22-tetracosaundecaene; 4,5,8,9-Tetrahydro, 2,3-Hexanedione, 1,3,4,6-Hexanetetracarboxylic acid, 1,3,4,6-Hexanetetracarboxylic acid; (3RS,4SR)-form, 1,2,4,5-Hexanetetrol; (2R,4R,5R)-form, Hexanethioic acid; SH-form, Me ester, trans-Hexaprenyl-trans-transferase, α-L-threo-4-Hex-4-enopyranuronosyl-D-galacturonic acid, 3-(1-Hexenyl)-5-(hydroxymethyl)-2(5H)-furanone; (S)-form, 3-(1-Hexenyl)-5-hydroxy-5-methyl-2(5H)-furanone, 3-(1-Hexenyl)-5-methyl-2(5H)-furanone; (S)-(Z)-form, 3-(1-Hexenyl)-5-methyl-2(5H)-furanone; (ξ)-(Z)-form, ribo-Hexos-3-ulose; D-form, arabino-2-Hexulosonic acid; D-form, xylo-5-Hexulosonic acid; D-form, 2-Hexylcyclopropanedecanoic acid;

(1R,2S)-form, 3-Hexyl-4-hydroxy-6-pentyl-2H-pyran-2-one, 2-Hexyl-4-hydroxyquinoline, 2-Hexyl-4-hydroxyquinoline; 1',2'-Didehydro(E-), 2-Hexyl-4-hydroxyquinoline; 1',2'-Didehydro(Z-), 2-Hexyl-4-hydroxyquinoline; N-Oxide, 2-Hexyl-5-methyl-1,3-benzenediol, 2-Hexyl-5-pentyl-1,3-benzenediol, 2-Hexyl-5-propyl-1,3-benzenediol, 1-Hexyn-3-ol; (S)-form, Hibarimicin B, Hibarimicin B; 4A-O-Deglycosyl, 3Eβ-hydroxy, Hibarimicin B; 3Bβ,3Eβ-Dihydroxy, Hibarimicin B; 4D-O-Deglycosyl, Hibarimicin B; 1E-Epimer(?), Hibarimicin B; 3Eβ-Hydroxy, Hibarimicin C, Hibarimicin C; 4A-O-Deglycosyl, Hiracin JM79, Hiraecin S, Histidine kinase, Histidine transaminase, Histidinol phosphatase, Histidinol phosphate transaminase, HMP-Y6, HMP-Y6; Aglycone, Hobo-[acyl-carrier-protein] synthase, Hominicin, Homochainin, Homogentisate 1,2-dioxygenase, Homolanthionine; (S,S)-form, Homoserine O-acetyltransferase, Homoserine kinase, Homoserine O-succinyltransferase, Homospermidine synthases; Homospermidine synthase, 29-Hopanol; (21αH,22S)-form, 17(21)-Hopen-3-ol; 3β-form, 3-Ketone, HS 2, Hyaluronan synthase, Hydrogenobyrinic acid, Hydrogenobyrinic acid; a,b,c,d,e,g-Hexamide, 4-Hydroxyacetophenone monooxygenase, 12-Hydroxyandrosta-1,4-diene-3,17-dione; 12β-form, 17-Hydroxyandrosta-1,4-dien-3-one; 17β-form, 3-Hydroxy-12'-apo-β-caroten-12-al, N5-Hydroxyarginine; (S)-form, N-Hydroxyarylamine O-acetyltransferase, N-Hydroxyaspartic acid; (S)-form, 3-Hydroxybenzoate monooxygenases; 3-Hydroxybenzoate 2-monooxygenase, 3-Hydroxybenzoate monooxygenases; 3-Hydroxybenzoate 4-monooxygenase, 3-Hydroxybenzoate monooxygenases; 3-Hydroxybenzoate 6-monooxygenase, 4-Hydroxybenzoate monooxygenases; 4-Hydroxybenzoate 3-monooxygenase, 4-Hydroxybenzoate monooxygenases; 4-Hydroxybenzoate 3-monooxygenase [NAD(P)H], 2-Hydroxybenzoic acid, 2-Hydroxy-1,4-benzoquinone reductase, 7-Hydroxy-2H-1,4-benzothiazin-3(4H)-one, 6-Hydroxy-5-benzothiazoleacetic acid, 4-Hydroxybenzoyl-CoA thioesterase, 2-(4-Hydroxybenzyl)cycloprodigiosin, 2-(4-Hydroxybenzyl) prodigiosin, 2-(4-Hydroxybenzyl)prodigiosin; Homologue (n=5), 2-(4-Hydroxybenzyl)prodigiosin; Homologue (n=6), 2-(4-Hydroxybenzyl)prodigiosin; Lower homologue (n=3), 2-Hydroxybiphenyl 3-monooxygenase, Hydroxybutyrate-dimer hydrolase, 3-Hydroxybutyryl-CoA dehydrogenase, 3-Hydroxy-β,ψ-caroten-4-one, 6-Hydroxy-1,4-cycloheptanedione, 2-Hydroxycyclohexanone 2-monooxygenase, 9-Hydroxy-2,4-decadienoic acid; (2E,4E,9R)-form, 3-Hydroxydecanoic acid; (R)-form, O-[α-L-Rhamnopyranosyl-(1→2)-α-L-rhamnopyranoside], 3-Hydroxydecanoic acid; (R)-form, O-[3-(β-D-Glucopyranosyloxy)tetradecanoyl] 3-Hydroxydecanoic acid; (R)-form, 3-O-(3R-Hydroxydecanoyl), 3-Hydroxydecanoic acid; (R)-form, 3-O-(3R-Hydroxydodecanoyl), 3-Hydroxydecanoic acid; (R)-form, 3-O-(3R-Hydroxytetradecanoyl), 3-Hydroxydecanoic acid; (R)-form, 3-O-(3R-Hydroxyhexadecanoyl), 4'-Hydroxy-4,4'-diaponeurosporen-4-oic acid, 4'-Hydroxy-4,4'-diaponeurosporen-4-oic acid; O-β-D-Glucopyranoside, 1-Hydroxy-1,2-dihydrophytoene, 1-Hydroxy-1,2-dihydrophytoene; Me ether, 11-Hydroxy-4,12-dimethyl-13-(2-methyl-4-thiazolyl)-8,12-tridecadien-3-one, 11-Hydroxy-4,12-dimethyl-13-(2-methyl-4-thiazolyl)-8,12-tridecadien-3-one; Homologue (R=CH3), 9-Hydroxy-6,10-dimethyl-11-(2-methyl-4-thiazolyl)-6,10-undecadien-3-one, 3-Hydroxy-2,3-dimethyl-5-oxo-2-pyrrolidinecarboxylic acid, 9-Hydroxy-2,8-dimethyl-3-oxo-4,6-undecadienoic acid; (2S,4E,6E,8S,9R)-form, 2-Hydroxy-3,5-dimethylpyrazine; OH-form, Me ether, 3-Hydroxy-2,5-dimethylpyrazine; OH-form, Me ether, 4-Hydroxy-3,5-dinitrophenylacetic acid, 4-Hydroxy-3,5-dinitrophenylacetic acid; Me ester, 2-(4-Hydroxy-3,5-dinitrophenyl)ethanol, 2-(4-Hydroxy-3,5-dinitrophenyl)ethylamine; N—Ac, 3-(4-Hydroxy-3,5-dinitrophenyl)propanoic acid, 3-(4-Hydroxy-3,5-dinitrophenyl) propanoic acid; 3-Chloro, 3-(4-Hydroxy-3,5-dinitrophenyl) propanoic acid; Me ester, 2-Hydroxydodecanoic acid; (ξ)-form, 3-Hydroxydodecanoic acid; (R)-form, 3-Hydroxy-5-dodecenoic acid; (3R,5Z)-form, 3-Hydroxy-5-dodecenoic acid; (3ξ,5Z)-form, 12-Hydroxyeicosanoic acid; (ξ)-form, Me ether, 13-Hydroxyeicosanoic acid; (ξ)-form, Me ether, Hydroxyethylthiazole kinase, N-Hydroxyformamide, 2-Hydroxyglutarate synthase, 11-Hydroxyheptadecanoic acid; (ξ)-form, Me ether, 3-Hydroxyhexadecanoic acid; (ξ)-form, 3-Hydroxyhexadecanoic acid; (ξ)-form, Me ester, 6-Hydroxyhexanoate dehydrogenase, 2-Hydroxy-3-hexanone; (±)-form, 3-(1-Hydroxyhexyl)-5-methylene-2(5H)-furanone; (R)-form, 5-Hydroxy-3-(2-hydroxyethyl)-2-methyl-1, 4-naphthoquinone; 5-Deoxy, 9-Hydroxy-6-hydroxymethyl-1-phenazinecarboxylic acid; 9-Me ether, 9-Hydroxy-6-hydroxymethyl-1-phenazinecarboxylic acid; 9-Me ether, 1'-O-(aminoacetyl), 9-Hydroxy-6-hydroxymethyl-1-phenazinecarboxylic acid; 9-Me ether, 1'-O-(2-amino-3-hydroxy-3-methylbutanoyl)(S-), 9-Hydroxy-6-hydroxymethyl-1-phenazinecarboxylic acid; 9-Me ether, 1'-O-(2-amino-3-methylbutanoyl)(S-), 9-Hydroxy-6-hydroxymethyl-1-phenazinecarboxylic acid; 9-Me ether, 1'-O-(2-aminopropanoyl), 4-Hydroxy-6-(hydroxymethyl)-2H-pyran-2-one, 5-Hydroxy-2-(hydroxymethyl)-4H-pyran-4-one, 4-Hydroxy-5-hydroxymethyl-2-pyrrolidinecarboxylic acid; (2S,4S,5R)-form, 2-Hydroxy-3-(3-hydroxy-4-nitrophenyl)propanoic acid; (S)-form, Me ester, 2-Hydroxy-3-(4-hydroxy-3-nitrophenyl)propanoic acid; (ξ)-form, 3-Hydroxy-1-(4-hydroxyphenyl)-5-methyl-2-hexanone; (−)-form, 3-Hydroxy-4-(4-hydroxyphenyl)-1-phenyl-2-butanone; (S)-form, 3-Hydroxy-4-(4-hydroxyphenyl)-1-phenyl-2-butanone; (S)-form, 4'-Deoxy, 4"-hydroxy, 2-Hydroxy-3-(4-imidazolyl)propanoic acid, 3-Hydroxy-4-(1H-indol-3-yl)-2-butanone; (ξ)-form, 2-Hydroxy-1-(1H-indol-3-yl)-4-methyl-3-hexanone, 2-Hydroxy-1-(1H-indol-3-yl)-4-methyl-3-hexanone; O—Ac, 2-Hydroxy-1-(1H-indol-3-yl)-4-methyl-3-pentanone, 2-Hydroxy-1-(1H-indol-3-yl)-4-methyl-3-pentanone; O—Ac, 3-Hydroxy-4-(1H-indol-3-yl)-1-phenyl-2-butanone; (S)-form, 4"-Hydroxy, 2-Hydroxy-3-(3-indolyl)propanoic acid; (ξ)-form, 3-Hydroxy-2-isopropyl-5-(2-methylpropyl)pyrazine, 2-Hydroxy-3-isopropylpyrazine; OH-form, Me ether, 2-Hydroxy-3-isopropylpyrazine; OH-form, 1'-Hydroxy, Me ether, Hydroxyisourate hydrolase, Hydroxylamine oxidase, Hydroxylamine reductases; Hydroxylamine reductase, N6-Hydroxylysine N-acetyltransferase, 4-Hydroxymandelate oxidase, 2-Hydroxy-3-methoxy-2,4,6-cycloheptatrien-1-one, 4-Hydroxy-3-methoxy-2-methyl-9H-carbazole-1-carboxaldehyde, 4-Hydroxy-3-methoxy-2-methyl-9H-carbazole-1-carboxaldehyde; 6-Methoxy, 1-Hydroxy-5-methoxy-6-methyl-2(1H)-pyridinone, 1-Hydroxy-5-methoxy-6-methyl-2(1H)-pyridinone; Al complex (3:1), 1-Hydroxy-5-methoxy-6-methyl-2(1H)-pyridinone; Fe complex (3:1), 4-(Hydroxymethyl)benzenesulfonate dehydrogenase, Hydroxymethylbilane synthase, 7-Hydroxy-6-(3-methyl-2-butenyl)-2H-1-benzopyran-2-one, 4-Hydroxy-3-methyl-2-butenyl diphosphate reductase, 4-Hydroxy-3-methyl-2-butenyl diphosphate synthase, 2-(4-Hydroxy-3-methyl-2-butenyl)-2'-(3-methyl-2-butenyl)-3',4'-didehydro-1',2'-dihydro-ε,ψ-caroten-1'-ol, 2-(4-Hydroxy-3-methyl-2-butenyl)-2'-(3-methyl-2-butenyl)-3',4'-didehydro-1',2'-dihydro-ε,ψ-caroten-1'-ol; Δ5,6-Isomer, 2-(4-Hydroxy-3-methyl-2-butenyl)-2'-(3-methyl-2-butenyl)-3',4'-didehydro-1',2'-dihydro-ε,ψ-caroten-1'-ol; Δ5,6-Isomer, 3',4'-dihydro, 2-(4-Hydroxy-3-methyl-2-butenyl)-2'-(3-methyl-2-butenyl)-3',4'-didehydro-1',2'-dihydro-ε,ψ-caroten-1'-ol; Δ5,6-Isomer, 4"-O-β-D-glucopyranoside, 3-Hydroxy-2-methylbutyryl-CoA dehydrogenase, 5-(Hydroxymethyl)-5-cyclohexene-1,2,3,4-tetrol; (1S,2S,3S,4R)-form, 5-(Hydroxymethyl)-5-cyclohexene-1,2,3,4-tetrol; (1R,2S,3S,4R)-form, 5-(Hydroxymethyl)-2,3-dimethylpyrazine, 5-(1-Hydroxy-1-methylethyl)-2,8,12,16,21,25,29,33-octamethyl-2,6,8,10,12,14,16,18,20,22,24,26,28,32-tetratricontatetradecaene, Hydroxymethylglutaryl-CoA reductases; Hydroxymethylglutaryl-CoA reductase, 5-Hydroxy-4-methyl-2-heptenoic acid; (2E,4S,5R)-form, 5-Hydroxy-4-methyl-2-heptenoic acid; (2E,4S,5S)-form, 5-(6-Hydroxy-6-methylheptyl)-2(5H)-furanone, (S)-form, 5-Hydroxy-5-methyl-2-hexenoic acid; (E)-form, 3-C-(Hydroxymethyl) lyxose; L-form, 2-(Hydroxymethyl)-5-methylpyrazine, 4-(Hydroxymethyl)-6-methyl-2,3,5-pyridinetriol, 2-Hydroxymethyl-4-methylquinazoline, 5-Hydroxy-3-methylnaphtho[2,3-c]furan-4(9H)-one; 8-Hydroxy, 5-Hydroxy-3-methylnaphtho[2,3-c]furan-4(9H)-one; 9-Oxo, 6-hydroxy, 2-Hydroxy-3-methyl-1,4-naphthoquinone, 7-Hydroxy-6-methyl-2,4-nonadienoic acid; (2E,4E,6S,7R)-form, 5-(6-Hydroxy-6-methyloctyl)-2(5H)-furanone; (5S,6'ξ)-form, 5-(7-Hydroxy-6-methyloctyl)-2(5H)-furanone; (5S,6'R,7'R)-form, 5-(7-Hydroxy-6-methyloctyl)-2(5H)-furanone; (5S,6'R,7'S)-form, 2-Hydroxy-5-methyl-1-phenyl-3-hexanone; (S)-form, 2-Hydroxy-5-methyl-1-phenyl-3-hexanone; (S)-form, 4'-Hydroxy, 2-Hydroxy-5-methyl-1-phenyl-3-hexanone; (S)-form, 4'-Hydroxy, 2-Ac, 15-(3-Hydroxy-2-methylphenyl)-2,4,6,8,10,12,14-pentadecaheptaenoic acid; (all-E)-form, Me ester, 15-(3-Hydroxy-2-methylphenyl)-2,4,6,8,10,12,14-pentadecaheptaenoic acid; (all-E)-form, 4'-Chloro, Me ester, 2-(Hydroxymethyl)-3,4,5-piperidinetriol; (2R,3R,4R,5S)-form, 2-(1-Hydroxy-1-methylpropyl)-3-methoxypyrazine, 2-(1-Hydroxy-2-methylpropyl)-3-methoxypyrazine, 2-Hydroxy-3-methylpyrazine; OH-form, Me ether, 3-Hydroxy-2-methylpyridinecarboxylate dioxygenase, Hydroxymethylpyrimidine kinase, 4-Hydroxy-2-methylquinazoline, 3-Hydroxy-2-methyl-4(1H)-quinolinone 2,4-dioxygenase, 9-Hydroxy-8-methyl-4,6-undecadien-3-one; (4E,6E,8S,9R)-form, 1-Hydroxy-2-naphthalenecarboxylic acid, 1-Hydroxy-2-naphthoate 1,2-dioxygenase, 6-Hydroxynicotinate dehydrogenase, Hydroxynicotine oxidases, 6-Hydroxynicotine reductase, 4-Hydroxy-3-nitrobenzaldehyde, 4-Hydroxy-3-nitrobenzoic acid, (4-Hydroxy-3-nitrophenyl)acetic acid, (4-Hydroxy-3-nitrophenyl)acetic acid; Me ester, 2-(4-Hydroxy-3-nitrophenyl)ethanol, 2-(4-Hydroxy-3-nitrophenyl)ethylamine; N—Ac, 3-(4-Hydroxy-3-nitrophenyl)propanoic acid, 3-(4-Hydroxy-3-nitrophenyl)-2-propenoic acid, 13-Hydroxynonadecanoic acid; (ξ)-form, Me ether, 4-Hydroxy-2-nonylquinoline, 4-Hydroxy-2-nonylquinoline; 1',2'-Didehydro(E-), 4-Hydroxy-2-nonylquinoline; 1',2'-Didehydro(Z-), 4-Hydroxy-2-nonylquinoline; N-Oxide, 3-Hydroxy-3-nonyl-2,4(1H,3H)-quinolinedione, 18-Hydroxy-19-nor-8(14),15-isopimeradien-2-one, 27-Hydroxy-2,4,6,8,10,12,14,16,18,20,22,24-octacosadodecenoic acid; N2-Ornithine amide, 27-O-α-L-rhamnopyranoside, 6-Hydroxy-7,9-octadecadiene-11,13,15,17-tetraynoic acid; (7E,9E)-form, 6-Hydroxy-7,9-octadecadiene-11,13,15,17-tetraynoic acid; (7E,9Z)-form, 6-Hydroxy-7,9-octadecadiene-11,13,15,17-tetraynoic acid; (7Z,9E)-form, 16-Hydroxy-9,12-octadecadienoic acid; (9Z,12Z,16R)-form, 11-Hydroxyoctadecanoic acid; (ξ)-form, Me ether, 18-Hydroxyoctadecanoic acid; O-(2-O-Methyl-β-D-xylopyranoside), 16-Hydroxy-9-octadecenoic acid; (R,Z)-form, 3-(1-

Hydroxyoctyl)-5-methyl-2(5H)-furanone, 3-(1-Hydroxyoctyl)-5-methyl-2(5H)-furanone; 5,6-Didehydro, 4-Hydroxy-2-octylquinoline, 4-Hydroxy-2-octylquinoline; 1',2'-Didehydro(E-), 4-Hydroxy-2-octylquinoline; 1',2'-Didehydro(Z-), 4-Hydroxy-2-octylquinoline; N-Oxide, 25-Hydroxy-24-oxokibdelone C, 25-Hydroxy-24 oxokibdelone C; 3-Me ether, 3-Hydroxy-4-oxoquinoline 2,4-dioxygenase, 5-Hydroxypentanoate Co-transferase, 2-Hydroxy-3-pentanone, 4-Hydroxy-2-pentylquinoline, 4-Hydroxy-2-pentylquinoline; 1',2'-Didehydro(E-), 4-Hydroxy-2-pentylquinoline; 1',2'-Didehydro(Z-), 4-Hydroxy-2-pentylquinoline; N-Oxide, 2-Hydroxy-1-phenazinecarboxylic acid, 4-Hydroxy-1-phenazinecarboxylic acid, 6-Hydroxy-1-phenazinecarboxylic acid; Me ether, Me ester, 9-Hydroxy-1-phenazinecarboxylic acid, 4-Hydroxy-1,6-phenazinedicarboxylic acid; Di-Me ester, 4-Hydroxyphenethylamine; N-Butanoyl, 4-Hydroxyphenethylamine; N-(2ξ-Methylbutanoyl), 4-Hydroxyphenethylamine; N-(3-Methylbutanoyl), 4-Hydroxyphenethylamine; N-(3-Methyl-2-butenoyl), 4-Hydroxyphenethylamine; N-(4-Methylpentanoyl), 4-Hydroxyphenethylamine; N-(2-Methylpropanoyl), 4-Hydroxyphenethylamine; N-[3-(Methylthio)propanoyl], 4-Hydroxyphenethylamine; N-(Phenylacetyl), 4-Hydroxyphenethylamine; N-Propanoyl, 3-Hydroxyphenylacetate 6-hydroxylase, 4-Hydroxyphenylacetate monooxygenases; 4-Hydroxyphenylacetate 1-monooxygenase, 4-Hydroxyphenylacetate monooxygenases; 4-Hydroxyphenylacetate 3-monooxygenase, 4-Hydroxyphenylacetic acid; Amide, 2-(4-Hydroxyphenyl)ethanol, 2-(4-Hydroxyphenyl)ethenamine; (Z)-form, N-(2Z-Hexadecenoyl), O-α-L-rhamnopyranoside, 2-(4-Hydroxyphenyl)ethenamine; (Z)-form, N-(15-Methyl-2Z-hexadecenoyl), O-α-L-rhamnopyranoside, 5-Hydroxy-4-phenyl-2(5H)-furanone; ξ-form, D-4-Hydroxyphenylglycine transaminase, 1-(4-Hydroxyphenyl)-2-isocyanoethene; (E)-form, 1-(4-Hydroxyphenyl)-2-isocyanoethene; (E)-form, O-(6-Deoxyhexopyranoside), 5-[(4-Hydroxyphenyl)methylene]-2-thioxo-4-imidazolidinone; (Z)-form, 3-(4-Hydroxyphenyl)-2-oxopropanoic acid, 2-Hydroxy-3-phenylpropanoic acid; (S)-form, 2-Hydroxy-3-phenylpropanoic acid; (S)-form, Me ester, 3-(4-Hydroxyphenyl)propanoic acid, 3-(4-Hydroxyphenyl)propanoic acid; Methylamide, 2-(2-Hydroxyphenyl)thiazole, 2-(2-Hydroxyphenyl)-4-thiazolecarboxylic acid, 2-(2-Hydroxyphenyl)-4-thiazolecarboxylic acid; Alcohol, 2-(2-Hydroxyphenyl)-4-thiazolecarboxylic acid; Aldehyde, 2-(2-Hydroxyphenyl)-4-thiazolecarboxylic acid; 4S,5-Dihydro, 2-(2-Hydroxyphenyl)-4-thiazolecarboxylic acid; 4R,5-Dihydro, alcohol, 2-(2-Hydroxyphenyl)-4-thiazolecarboxylic acid; Me ester, 20-Hydroxypregn-4-en-3-one; (20S)-form, 3-Hydroxypropanal, 2-Hydroxypropanoic acid; (R)-form, 2-Hydroxypropyl-CoM dehydrogenases; 2-(R)-Hydroxypropyl-CoM dehydrogenase, 2-Hydroxypropyl-CoM dehydrogenases; 2-(S)-Hydroxypropy-CoM dehydrogenase, 9-Hydroxy-2-propyl-4H-pyrido[1,2-a]pyrimidin-4-one, 2-Hydroxypyridine 5-monooxygenase, 2-Hydroxy-4-quinolinecarboxaldehyde; NH-form, N-Mercapto, 4-Hydroxyquinoline 3-monooxygenase, 2-Hydroxyquinoline oxygenases; 2-Hydroxyquinoline 5,6-dioxygenase, 2-Hydroxyquinoline oxygenases; 2-Hydroxyquinoline 8-monooxygenase, 3-Hydroxysteroid dehydrogenases; 3α-Hydroxysteroid dehydrogenase (B-specific), 2-Hydroxytetradecanoic acid; (S)-form, 3-Hydroxytetradecanoic acid; (R)-form, 4-Hydroxythreonine-4-phosphate dehydrogenase, 3-Hydroxy-4-tridecanone; (S)-form, 4-Hydroxy-2-tridecylquinoline, 4-Hydroxy-2-tridecylquinoline; 1',2'-Didehydro(E-), 4-Hydroxy-2-tridecylquinoline; 1',2'-Didehydro(Z-), 4-Hydroxy-2-tridecylquinoline; N-Oxide, 8-Hydroxy-2,5,8-trimethyl-4-nonanone; (ξ)-form, 11-Hydroxy-2,4,10-trimethyl-5-oxo-6,8-tridecadienoic acid; (2S,4R,6E,8E,10S,11R)-form, Hydroxytropodithietic acid, 5-Hydroxytryptophan; (S)-form, 6-Hydroxytryptophan; (S)-form, 3-Hydroxyundecanoic acid; (ξ)-form, O-[α-L-Rhamnopyranosyl-(1→3)-3-hydroxyundecanoyl], 3-Hydroxyundecanoic acid; (±)-form, 3-Hydroxyundecanoic acid; (R)-form, 4-Hydroxy-2-undecylquinoline, 4-Hydroxy-2-undecylquinoline; 1',2'-Didehydro(E-), 4-Hydroxy-2-undecylquinoline; 1',2'-Didehydro(Z-), 4-Hydroxy-2-undecylquinoline; 3',4'-Didehydro, 4-Hydroxy-2-undecylquinoline; N-Oxide, Hygromycin A, Hygromycin A; 4''-Epimer, Hygromycin B 7''-O-kinase, Hyicin 3682, Hyicin M51, Hymenoptaecin, Hypeptin, Hypoxanthine phosphoribosyltransferase, IC 202A, IC 202B, IC 202C, Icumazole A, Icumazole A; 22-O-α-D-Arabinofuranoside, Icumazole A; 4β-α-D-Arabinofuranosyloxy, Icumazole F, Idonate dehydrogenases; L-Idonate 2-dehydrogenase, Idonate dehydrogenases; L-Idonate 5-dehydrogenase, Iduronic acid; L-form, IgA-specific serine endopeptidase, Imidazoleacetate 4-monooxygenase, Imidazole N-acetyltransferase, Imidazolonepropionase, 3-(Imidazol-5-yl)lactate dehydrogenase, N-(5-Imino-4-methyleneprolyl)threonine; (2S,2'S,3'R)-form, N-(5-Imino-4-methyleneprolyl)valine; (S,S)-form, N-(5-Iminoprolyl)threonine; (2'S,3'R)-form, 5-Imino-2H-pyrrol-2-ol, IMP cyclohydrolase, Imperatorin, 1H-Indazole-3-carboxaldehyde, Indigoidin, Indigoidin; N5,N5'-Didodecyl, Indochrome A, Indolactam I, 1H-Indole-3-acetaldehyde; Oxime, 1H-Indole-3-acetic acid; N-Methoxy, nitrile, 1H-Indole-3-carbothioic acid; SH-form, Me ester, 1H-Indole-3-carboxaldehyde, 1H-Indole-3-carboxaldehyde; N-Methoxy, 1H-Indole-2,3-dione, 1H-Indole-3-ethanol, 1H-Indole-3-ethanol; Me ether, Indolelactate dehydrogenase, 1H-Indol-2-ol, Indolo[2,1-b]quinazoline-6,12-dione, 4-(1H-Indol-3-yl)-3H-pyrrolo[2,3-c]quinoline, 6-(1H-Indol-3-yl)-8-(2,3,4,5-tetrahydroxypentyl)-2,4,7-(1H,3H,8H)-pteridinetrione; D-ribo-form, 5-(1H-Indol-3-yl)-2(3H)-thiazolethione, Inhibitory protein, Inosamycin E; 3''-Epimer, Inosine, Inosine kinase, Inosine nucleosidase, Inositol 3-kinase, Integramycin, Interferon; Interferon α, Alfa 2a, Interferon; Interferon β, Beta 1b, Interferon; Interferon γ, Gamma 1a, γ-Interferon-like protein, Inulinase, Inulosucrase, Invictolide; 1',3,6-Triepimer, Iron-cytochrome c reductase, Iron sulfur proteins; Rubredoxin, IS, Isoamylase, Isoapoptolidin A, Isoapoptolidin A; 6-Demethyl, Isobutyraldoxime O-methyltransferase, Isochorismatase, [Isocitrate dehydrogenase (NADP(+))] kinase, 3-(2-Isocyanoethenyl)-1H-indole; (Z)-form, 4-(2-Isocyanoethenyl)phenol; (ξ)-form, O-α-L-Rhamnopyranoside, Isoglutamine; (R)-form, Isohematinic acid; (±)-form, Isokibdelone A, Isokibdelone A; 6,7-Dihydro, Isokibdelone A; 11-O-α-Rhamnopyranoside, Isoleucylprolylisoleucine; L-L-L-form, Isomaltotriulose, Isoneoantimycin, 8(14),15-Isopimaradiene-2,3,18-triol; (2α,3β)-form, 2-Ketone, 2-Isopropenyl-5-isopropylpyrazine, 2-Isopropenyl-6-isopropylpyrazine, 2-Isopropylmalate synthase, 2-Isopropyl-3-methoxy-5-(1-methylpropyl)pyrazine, 2-Isopropyl-3-methoxy-5-(2-methylpropyl)pyrazine, 3-Isopropyl-6-methylene-2,5-piperazinedione; (S)-form, 2-Isopropyl-5-(1-methylpropyl)pyrazine, 2-Isopropyl-5-(2-methylpropyl)pyrazine, 2-Isopropyl-5-methylpyrazine, 2-Isopropyl-6-methylpyrazine, Isopropylpyrazine, Isopullulanase, Isopyoverdin Pp BTP 1, Isopyoverdin Pp CFML 90-33, Isopyoverdin Pp CFML 90-44, Isoquinocycline A, Isoquinocycline A; 2'-Epimer, 1''-ketone, Isoquinocycline A; 1''-Ketone, 1-Isoquinolinecarboxylic acid; Nitrile, Isozeaxanthin; Diketone, Iturin A, Iturin AL, Iturin D, Iturin E, Izenamicin B2, Izenamicin B2; Aglycone, Izenamicin B2; 23-Deoxy, 13α,14α-epoxide, Izumenolide, Izumenolide; 38,39-Dihydro, 39-sulfooxy, Izumenolide; 2,3,38,39-Tetrahydro, 39-sulfooxy, Janthinocin B, Janthinocin B; β-Deoxy, Janthinocin B; α,β-Dihydro, Jawsamycin, JBIR 78, JBIR 95, Jegathesan, Jenseniin G, Jenseniin P, Jerangolide A, Jerangolide A; 18-Deoxy, Jerangolide A; 18-Deoxy, 13,14ξ-dihydro, Jerangolide A; 18-Deoxy, 13,14ξ-dihydro, 14ξ-hydroxy, Jerangolide A; 13,14ξ-Dihydro, Jolipeptin, Juglone 3-monooxygenase, Juvenimicin B1, Juvenimicin B1; 20-Aldehyde, Juvenimicin B1; 20-Carboxylic acid, 12S,13S-epoxide, Juvenimicin B1; 20-Deoxy, Juvenimicin B1; 20-Deoxy, 12S,13S-epoxide, Juvenimicin B1; 12S,13S-Epoxide, Juvenimicin B1; 23-Hydroxy, Juvenimicin B1; 23-Hydroxy, 20-aldehyde, Juvenimicin B2, Juvenimicin B4, K 13, K 7/3, Kailuin; Kailuin E, Kalimantacin A, Kalimantacin A; 17ξ-Alcohol, Kalimantacin A; 17ξ-Alcohol, decarbamoyl, Kalimantacin A; Decarbamoyl, Kalimantacin A; 10E-Isomer, Kalimantacin C, Kanagawamicin, Kanamycin A; 3″-N-Me, Kanamycin B; 6″-O-Carbamoyl, Kanamycin B; 3′,4′-Dideoxy, 3″,6′-N,N-di-Me, Kanamycin B; 3′,4′-Dideoxy, 3″-N-Me, Kanamycin B; 3″-N-Me, Kanamycin kinase, Kanglemycin C; 6a,12a-Didehydro, Karalicin, Katanosin A, Katanosin B, Kayamycin, Kedarcidin, Kefiran, Kenyacin 404, Keratan-sulfate endo-1,4-β-galactosidase, Kibdelomycin, Kibdelone A, Kibdelone A; 6,7-Dihydro, Kibdelone A; 6,7-Dihydro, 12-O-α-L-rhamnopyranoside, Kibdelone A; 5,16-Hydroquinone, 6,7-dihydro, Kibdelone A; 5,16-Hydroquinone, 6,7-dihydro, 12-O-α-L-rhamnopyranoside, Kibdelone A; 10-Ketone, Kibdelone A; 12-O-α-L-Rhamnopyranoside, Kistamicin A, Kistamicin B, Klebicins, Klebocin, *Bacillus pumilus* KMM 1364 Lipodepsipeptides, *Bacillus subtilis* KMM 457 Peptide 1, *Bacillus subtilis* KMM 457 Peptide 2, Kojibiose phosphorylase, Kojic acid dimer, Kojihexaose, Kojitriose, Kokandomycin, Korkormicins, Korormicin A, Korormicin B, Korormicin C, Korormicin D, Kristenin, Kudzuisoflavone A; 5,5‴-Dihydroxy, Kudzuisoflavone A; 5-Hydroxy, Kurstacin 287, Kurstakins, Kusaya antibiotic, Kutzneride 1, Kutzneride 1; 4‴R-Chloro, Kutzneride 1; 3″″-Demethyl, Kutzneride 1; 3″″-Demethyl, 3′-epimer, Kutzneride 1; 2‴,3‴-Didehydro, Kutzneride 1; 3′-Epimer, Kutzneride 1; 3′-Epimer, 4‴R-chloro, Kutzneride 1; 3′-Epimer, 2‴,3‴-didehydro, Kutzneride 1; 3′-Epimer, 4‴R-hydroxy, 2‴,3‴-didehydro, Kyanomycin, Kynurenine 7,8-hydroxylase, L 654040, Lacidin A, Lactacins, Lactacins; Lactacin B, Lactacins; Lactacin F, β-Lactamase, Lactate dehydrogenases; D-Lactate dehydrogenase (cytochrome c-553), Lactate 2-monooxygenase, D-Lactate-2-sulfatase, Lacticins; Lacticin 3147, Lacticins; Lacticin 481, Lacticins; Lacticin BH5, Lacticins; Lacticin Q, Lacticins; Lacticin Z, Lactivicin, *Lactobacillus* polypeptide 2, Lacto-N-biosidase, Lactobrevin, Lactocepin, Lactocins, Lactocins; Lactocin 160, Lactocins; Lactocin 27, Lactocins; Lactocin 705, Lactocins; Lactocin A1, Lactocins; Lactocin C183, Lactocins; Lactocin D, Lactocins; Lactocin LC-09, Lactocins; Lactocin P 109, Lactocins; Lactocin S, Lactococcin, Lactococcin; Lactococcin 140, Lactococcin; Lactococcin 972, Lactococcin; Lactococcin A, Lactococcin; Lactococcin B, Lactococcin; Lactococcin BZ, Lactococcin; Lactococcin D53, Lactococcin; Lactococcin G, Lactococcin; Lactococcin K, Lactococcin; Lactococcin K3113, Lactococcin; Lactococcin M, Lactococcin; Lactococcin MMFII, Lactococcin; Lactococcin MMT24, Lactococcin; Lactococcin Q, Lactococcin; Lactococcin R, Lactocyclicin Q, Lactolin, 1,4-Lactonase, Lactostrepcins, Lactulosucrose, Lanthiopeptin, Lariatin A, Lariatin B, Laterocidin, Laterosporamine, Laterosporin, Latosillan, Lebstatin; 17-O-De-Me, Legiobactin, Lemonnierin, Leprotene, Leprotene; 3,3′-Dihydroxy, Leprotene; 3-Hydroxy, Leucine dehydrogenase, Leucocidin R1, Leucocins; Leucocin 4010, Leucocins; Leucocin A, Leucocins; Leucocin B, Leucocins; Leucocin B-TA33b, Leucocins; Leucocin C, Leucocins; Leucocin D La54a, Leucocins; Leucocin F10, Leucocins; Leucocin H, Leucocins; Leucocin K, Leucocins; Leucocin N, Leucocins; Leucocin OZ, Leucocins; Leucocin Q, Leucocyclicin Q, Leucylisoleucylargininal; N—Ac, Leucyltransferase, Leucylvalylargininal; N—Ac, Leuhistin, Leupyrrin C, Leupyrrin C; 2′,3-Didehydro, Leupyrrin C; 19,20-Didehydro, 21-Me ether, Leupyrrin C; 2′,3′-Didehydro, 21-Me ether, Leupyrrin C; 21-Me ether, Leupyrrin C; 2′,3′,19,20-Tetradehydro, 21-Me ether, Levan, Levansucrase, Levantilide A, Levantilide A; 23-Ketone, Lichenicidin, Lichenicidin VK21, Licheniformin A, Licheniformin B, Licheniformin C, Lichenin, Licheninase, Lichenysin A, Lichenysin G, Licoagroisoflavone; (R)-form, Lignostilbene αβ-dioxygenase, Limazepine B1, Limazepine B1; 11-Deoxy, 10,11-didehydro, Limazepine B1; 11-Deoxy, 1,10,11,11a-tetradehydro, Limazepine B1; 11-Epimer, Limazepine B1; Δ2,12-Isomer, 11-deoxy, 10,11-didehydro, Limazepine B1; 11-Ketone, Limazepine F, Limnazine, Limonene-1,2-epoxide hydrolase, Limonin-D-ring-lactonase, Linalool 8-monooxygenase, Lincomycin, Linecin A, Linenscin OC2, Linnocuicin 819, Lipiarmycin A; Lipiarmycin A3, Lipiarmycin A; Lipiarmycin A3, 4B-Deacyl, 3B-(2-methylpropanoyl), Lipiarmycin A; Lipiarmycin A3, 4B-Deacyl, 2B-(2-methylpropanoyl), Lipiarmycin A; Lipiarmycin A3, 4B-Deacyl, 2B-propanoyl, Lipiarmycin A; Lipiarmycin A3, 20-De(glycosyloxy), 18-deoxy, 4B-deacyl, 4B—Ac, Lipiarmycin A; Lipiarmycin A3, 3A-Aroyl isomer, 4A,4B-dideacyl, 2B-(2-methylpropanoyl), Lipiarmycin A; Lipiarmycin A3, 3″-Dechloro, Lipiarmycin A; Lipiarmycin A3, Didechloro, Lipiarmycin A; Lipiarmycin A3, 18-Deoxy, Lipiarmycin A; Lipiarmycin A3, 18-Deoxy, 4B-deacyl, Lipiarmycin A; Lipiarmycin A3, 18-Deoxy, 11-deglycosyl, Lipiarmycin A; Lipiarmycin A3, 18-Deoxy, 11-deglycosyl, 2A-O-de-Me, Lipiarmycin A; Lipiarmycin A3, 11-Deglycosyl, 11-O-[2-methylpropanoyl-(→4)-α-L-rhamnopyranoside], Lipiarmycin A; Lipiarmycin A3, 18-Deoxy, 20-deglycosyl, Lipiarmycin A; Lipiarmycin A3, 18-Deoxy, 20-deglycosyl, 4B-deacyl, Lipiarmycin A; Lipiarmycin A3, 18-Deoxy, 20-deglycosyl, 4B-deacyl, 4B—Ac, Lipiarmycin A; Lipiarmycin A3, 18-Deoxy, 20-deglycosyl, 4B-deacyl, 4B-propanoyl, Lipiarmycin A Lipiarmycin A3, 18-Deoxy, 11,20-dideglycosyl, Lipiarmycin A; Lipiarmycin A3, 18-Deoxy, 11,20-dideglycosyl, 20-O-β-D-mannopyranoside, Lipiarmycin A; Lipiarmycin A3, 20-De(glycosyloxy), 18-deoxy, 11-deglycosyl, Lipiarmycin A; Lipiarmycin A3, 20-De(glycosyloxy), 18-deoxy, Lipiarmycin A Lipiarmycin A3, 20-De(glycosyloxy), 18-deoxy, 4B-deacyl, Lipiarmycin A; Lipiarmycin A3, 20-De(glycosyloxy), 18-deoxy, 4B-deacyl, 4B-propanoyl, Lipiarmycin A; Lipiarmycin A3, 20-De(glycosyloxy), 18-deoxy, 18-methyl, Lipiarmycin A; Lipiarmycin A4, 4B-Deacyl, 2B-(2-methylpropanoyl), *Porphyromonas gingivalis* 381 Lipid A, Lipid A disaccharide synthase, Lipid X, Lipid X; 3′-O-Hexadecanoyl, Lipoate protein ligase, *Shewanella pacifica* Lipooligosaccharide, Lipopolysaccharide N-acetylglucosaminyltransferase, Lipopolysaccharide N-acetylmannosaminouronosyltransferase. Lipopolysaccharide 3-α-galactosyltransferase, Lipopolysaccharide glucosyltransferases; Lipopolysaccharide glucosyltransferase I, lipopolysaccharide glucosyltransferases; Lipopolysaccharide glucosyltransferase II, Lipoyl synthase, LIQ 4, Littorine; N-De-Me, Littorine; 3′ξ-Hydroxy, Lobatamide A; Stereoisomer (?), Loihichelins, Loloatins; Loloatin A, Loloatins; Loloatin B, Loloatins; Loloatin C, Lomaiviticin A, Lomaiviticin B, Long-chain-alcohol O-fatty-acyltransferase, LTA T, Lucentamycin B, Lumichrome, Luminchrome; N1-Me, Lumichrome; N1-α-Ribofuranosyl, Luminamicin, Lupinacidin A, Lupinacidin B, Lupinacidin C, Lutein, Lutoside, Lycogalic acid, 20-Lycopenal; (13Z)-form, Lycopene; (all-E)-form, 3,4-Didehydro(E-), 5',6'-dihydro, Lycophyll, Lyngbyatoxin A; N-De-Me, Lyngbyatoxin A; 19-Epimer, Lyngbyatoxin A; Me ether, Lysidine, Lysine carboxypeptidase, Lysine dehydrogenases; Lysine 6-dehydrogenase, Lysine monooxygenases; Lysine 2-monooxygenase, Lysine monooxygenases; Lysine 6-monooxygenase (NADPH), Lysine transaminases; L-Lysine 6-transaminase, Lysinomycin, Lysostaphin, Lysyl endopeptidase, N1-(N-Lysylphenylalanyl)cycloornithylvalyl, Lysyltransferase, Lyxuronic acid; D-form, Maackiain; (−)-form, O-β-Glucopyranoside, Macbecin II; O11-De-Me, Macbecin II; O12-De-Me, Macbecin II; O15-De-Me, Macbecin II; 18,21-Quinone, O11-de-Me, Macbecin II; 18,21-Quinone, O12-de-Me, Macbecin II; 18,21-Quinone, O15-de-Me, Macedocin, Macedocin ST91KM, Macquarimicin A, Macquarimicin B, Macquarimicin C, Macrolactin A, Macrolactin A; 7-Deoxy, 8,9-dihydro, 7,8-didehydro(E-), 9-hydroxy, Macrolactin A; 13-Deoxy, 16,17-dihydro, 15-ketone, Macrolactin A; 16,17-Dihydro, 15-ketone, 7-O-(3-carboxypropanoyl), Macrolactin A; 16,17-Dihydro, 15-ketone, 7-O-β-D-glucopyranoside, Macrolactin A; 18S,19S-Epoxide, Macrolactin A; 7-O-β-D-Glucopyranoside, Macrolactin A; 7-O-(4-β-D-Glucopyranosylsuccinoyl), Macrolactin A; 12S-Hydroxy, Macrolactin A; 20R-Hydroxy, Macrolactin A; 10E-Isomer, Macrolactin A; 18Z-Isomer, Macrolactin A; 10E-Isomer, 16,17-dihydro, 15-ketone, Macrolactin A; 10E-Isomer, 7-O-β-D-glucopyranoside, Macrolactin A; 18Z-Isomer, 7-O-β-D-glucopyranoside, Macrolactin A; 7-Malonyl, Macrolactin A; 7-Succinoyl, Macrolactin A; 7-O-(6-O-Succinoyl-β-D-glucopyranoside), Macrolactin H, Macrolactin L, Macrolactin M, Macrolactin M; 7-O-β-D-Glucopyranoside, Macrolactin U, Macrolide 2'-kinase, Madumycin II, Madumycin II; 13-Deoxy, Madurahydroxylactone, Madurahydroxylactone; 3-O-Butyl, Magnesidin, Magnesium-protoporphyrin IX methyltransferase, Maklamicin, Malate synthase, Malonate CoA-transferase, Maltophilin, Maltophilin; 20α-Alcohol, Maltophilin; Stereoisomer, Maltose O-acetyltransferase, Maltose-6'-phosphate glucosidase, Maltose phosphorylase, Mandelate 4-monooxygenase, Manilosporin, Mannan endo-1,6-α-mannosidase, Mannan exo-1,2-1,6-α-mannosidase, Mannan 1,4-mannobiosidase, Mannan 1,2-(1,3)-α-mannosidase, Mannan endo-1,4-β-mannosidase, Mannokinase, β-D-Mannopyranosyl-(1→4)-α-D-galactopyranosyl-(1→4)-L-rhamnose, 3-O-α-D-Mannopyranosyl-D-glucose, 2-O-α-D-Mannopyranosyl-myo-inositol; 1-Pentadecanoyl, 6'-heptadecanoyl, α-D-Mannopyranosyl-(1→2)-α-D-mannopyranosyl-(1→3)-D-galactose, 3-D-Mannopyranosyl-(1→2)-α-D-mannopyranosyl-(1→2)-D-mannose, β-D-Mannopyranosyl-(1→4)-α-D-mannopyranosyl-(1→3)-L-rhamnose; α-Pyranose-form, 3'-Ac, α-D-Mannopyranosyl-(1→4)-α-L-rhamnopyranosyl-(1→3)-D-galactose, β-D-Mannopyranosyl-(1→4)-α-L-rhamnopyranosyl-(1→3)-D-galactose, β-D-Mannopyranosyl-(1→2)-α-L-rhamnopyranosyl-(1→4)-L-rhamnose, 4-O-α-D-Mannopyranosyl-L-rhamnose 4-O-β-D-Mannopyranosyl-L-rhamnose, β-D-Mannopyranuronosyl-(1→4)-β-D-glucopyranosyl-(1→4)-D-galactose, 4-O-β-D-Mannopyranuronosyl-D-glucose, Mannose 1-phosphate guanylyltransferase, Mannose 1-phosphate guanylyltransferase (GDP), α-Mannosidase, β-Mannosidase, Mannosyl glycoprotein endo-β-N-acetylglucosaminidase, Mannosyl-oligosaccharide 1,2-α-mannosidase, Mannosyl-3-phosphoglycerate phosphatase, Mannosyl 3-phosphoglycerate synthase, Maracen A, Maracin A, Marcellomycin, Marcellomycin; N-De-Me, Marcellomycin; 10-Epimer, Marcescin, Maribasin A, Maribasin B, Maricin, Marihysin A, Marinobactins, Marinocine, Marinolic acid A, Marinolic acid A; 8'-Amide, Marinolic acid A4, Marinolic acid A6, Marinoquinoline F, Mannostatin, Massetolides, Massetolides; Massetolide A, Diastereoisomer, Massetolides; Massetolide C, Diastereoisomer, Matrucin; Matrucin 1, Matrucin; Matrucin 2, Maytansinol; 3-Butanoyl, Maytansinol; Dechloro, 4,5-deepoxy, 4,5-didehydro, N-de-Me, Maytansinol; 4,5-Deepoxy, 4,5-didehydro, N-de-Me, Maytansinol; 4,5-Deepoxy, 4E,5-didehydro, N-de-Me, 3-O-(2-methylpropanoyl), Maytansinol; 4,5-Deepoxy, 4,5-didehydro, O9-Me, N-de-Me, Maytansinol; N-De-Me, 3-Ac, Maytansinol; N22-De-Me, 3-Ac, N22-β-D-glucopyranosyl, Maytansinol; N-De-Me, 3-O-(3-methylbutanoyl), Maytansinol; N-De-Me, 3-O-(2-methylpropanoyl), Maytansinol; N22-De-Me, 3-O-propanoyl, N22-(4-O-carbamoyl-β-D-glucopyranosyl), Maytansinol; 15R-Hydroxy, Maytansinol; 15R-Hydroxy, 3-Ac, Maytansinol; 30-Hydroxy, 3-Ac, Maytansinol; 15R-Hydroxy, 3-O-(3-methylbutanoyl), Maytansinol; 30-Hydroxy, 3-O-(3-methylbutanoyl), Maytansinol; 3-O-(3-Hydroxy-3-methylbutanoyl), Maytansinol; 3-O-(4-Hydroxy-3-methylbutanoyl), Maytansinol; 3-O-(3-Hydroxy-3-methylbutanoyl), N-de-Me, Maytansinol; 15R-Hydroxy, 3-O-(2-methylpropanoyl), Maytansinol; 15R-Hydroxy, 3-propanoyl, Maytansinol; 30-Hydroxy, 3-propanoyl, Maytansinol; 3-O-(3-Methylbutanoyl), Maytansinol; 3-O-(2-Methylpropanoyl), Maytansinol; 3-Propanoyl, Mechercharstatin A, Mechercharstatin B, Mediolacin, Megacins, Megacins; Megacin A19213, Megacins; Megacin Cx, Megacins; Megacin FW337, Megalomicin A, Megalomicin A; 4A-Ac, Megalomicin A; 3A,4A-Di-Ac, Megalomicin A; 4A-Propanoyl, Megalomicin A; 4A-Propanoyl, 3A-Ac, Melaninocin, Melanocidin A, Melanocidin B, Melilotate 3-monooxygenase, Melithiazole B, Melithiazole B; O5-De-Me, Melithiazole B; 11α,12-Dihydro, Melithiazole B; 14,15-Dihydro, Melithiazole B; 14,15-Dihydro, O5-de-Me, Melithiazole B; 14,15-Dihydro, 14S,15-dihydroxy, Melithiazole B; 14,15-Dihydro, 14R,15-dihydroxy, O5-de-Me, Melithiazole B; 14,15-Dihydro, 14S,15-dihydroxy, O5-de-Me, Melithiazole B; 11α,12-Dihydro, 14,15-epoxide, Melithiazole B; 14,15-Dihydro, 14-hydroxy, Melithiazole B; 14,15-Dihydro, 1-hydroxy, Melithiazole B; 14,15-Dihydro, 14-hydroxy, O5-de-Me, Melithiazole B; 14,15-Epoxide, Melithiazole B; 11α,12,14,15-Tetrahydro, Melithiazole B; 11α,12,14,15-Tetrahydro, 15-methoxy, Melithiazole C, Melithiazole F, Melithiazole G, Melithiazole H, Melithiazole H; 14-Oxo, Melithiazole I, Membrane alanyl aminopeptidase, Membrane dipeptidase, Membrane-oligosaccharide glycerophosphotransferase, Menoxymycin B; 4-Deoxy, Menoxymycin B; 4-Deoxy, parent acid, 2-Mercapto-1H-indole-3-carboxaldehyde; S-Me, Mercury(II) reductase, Mersacidin, Mesenterocin 52, Mesenterocin ST99, Mesenterocin Y105, Methanesulfonic acid; Butyl ester, Methanesulfonothioic acid; Me ester, Methanethiol oxidase, Methanobactin, Methanofuran; 2-Hydroxy, Methanol-5-hydroxybenzimidazolylcobamide Co-methyltransferase, Methionaquinone, Methionine; (S)-form, N-Formyl, Methionine adenosyltransferase, Methionine-S-oxide reductase, Methionine synthase, Methionyl aminopeptidase, Methionylglycylmethionylisoleucine; N-Formyl, Methionylleucylphenylalanine; L-L-L-form, N-Formyl, Methionylmethionylisoleucylalanine; N-Formyl, Methionylphenylalanylleucine; N-Formyl, Methionylserylleucine; N-Formyl, Methionyl-tRNA formyltransferase, Methionylvalylphenylalanylisoleucylleucylleucine; N-Formyl, Methoxatin, 4-Methoxybenzoate monooxygenase (O-demethylating), Methoxybrassenin A, Methoxybrassenin B, 4-Methoxy-5-[(3-methoxy-5-pyrrol-2-yl-2H-pyrrol-2-ylidene)methyl]-2,2'-bipyrrole, 3-Methoxy-2-methyl-5-(1-methylpropyl)pyrazine; (ξ)-form, 3-Methoxy-2-methyl-5-(2-methylpropyl)pyrazine, 3-Methoxy-4-methyl-5-(2-methyl-4-thiazolyl)-4-pentenoic acid, 5-Methoxy-2-methyl-3-polyprenyl-1,4-benzoquinone, 5-Methoxy-2-methyl-3-polyprenyl-1,4-benzoquinone; 5-Methoxy-2-methyl-3-octaprenyl-1,4-benzoquinone, 3-Methoxy-2-(1-methylpropyl)-5-(2-methylpropyl)pyrazine, 2-Methoxy-3-(1-methylpropyl)pyrazine, 6-Methoxy-2-nonaprenyl(X—H2)-1,4-benzoquinone, 3-Methoxypyrazolo[4,3-e][1,2,4]triazine, 3-Methoxypyrazolo[4,3-e][1,2,4]triazine; 1H-form, N-Hydroxymethyl, 3-Methoxypyrazolo[4,3-e][1,2,4]triazine; 6H-form, N-Me, 3-Methoxypyrazolo[4,3-e][1,2,4]triazine; 7H-form, N-Me, 2-[[3-Methoxy-4-(1H-pyrrol-1-yl)-2H-pyrrol-2-ylidene]methyl]-5-methyl-1-pentyl-1H-pyrrole, Methoxyspheroidene, Methoxyspheroidene; 2'-Ketone, N-Methylalanine dehydrogenase, Methylamine-glutamate N-methyltransferase, 5-(Methylaminomethyl)-2-thiouridine, Methylated-DNA-[protein]-cysteine S-methyltransferase, 8-Methyl-8-azabicyclo[3.2.1]octane-3,6-diol; (1R,3S,5R,6R)-form, N-De-Me, 3-O-(2R-hydroxy-3-phenylpropanoyl), 2-Methylbenzothiazole, 2-Methylbutanal; (S)-form, 2-Methyl-1,2,3,4-butanetetrol; (2S,3R)-form, 2,4-Cyclic pyrophosphate, 3-Methylbutanethioic acid; SH-form, Me ester, 3-Methylbutanoic acid, 3-Methyl-1-butanol, 2-Methyl-2-butene-1,4-diol; (E)-form, 4-Diphosphate, 2-Methyl-2-butenoic acid; (E)-form, N-(3-Methyl-2-butenyl)adenosine; 5'-Deoxy, 4-Methylcholesta-8(14),24-dien-3-ol; (3β,4α,5α)-form, 4-Methylcholest-8-en-3-ol; (3β,4α,5α)-form, 5-Methylcytidine, 8-Methyldecanoic acid; (ξ)-form, 9-Methyldecanoic acid, 9-Methyl-3-decanol; (S)-form, 9-Methyl-3-decanone, 2-(9-Methyldecyl)-5-(4-methylpentyl)-1,3-benzenediol, 5-Methyldeoxycytidine 5'-phosphate kinase, [2-Methyl 7,12-diethenyl-3,8,13,17-tetramethyl-21H,23H-porphine-2,18-dipropanoato(2-)-N21,N22,N23,N24]magnesium, 3-Methyl-34,35-dinor-6,11-bacteriohopadiene-32,33-diol; (3β,22R,32R)-form, 3-Methyl-34,35-dinor-6,11-bacteriohopadiene-32,33-diol; (3β,22R,32R)-form, 6,7-Dihydro, 3-Methyl-34,35-dinor-6,11-bacteriohopadiene-32,33-diol; (3β,22R,32R)-form, 11,12-Dihydro, 2-Methyl-4,5-ditridecyl-1,4-cyclohexadiene-1-methanol, 11-Methyl-2,5-dodecadienoic acid; (Z,Z)-form, 11-Methyl-2-dodecenoic acid; (Z)-form, 3,3'-Methylenebisindole, 1,1'-Methylenebis[2-phenazinol], Methylenediurea deaminase, 3-Methylene-6-(1-methylpropyl)-2,5-piperazinedione; (S,S)-form, 3-Methylene-6-(2-methylpropyl)-2,5-piperazinedione; (S)-form, Methylenetetrahydrofolate-tRNA-(uracil-5)-methyltransferase (FADH2-oxidising), 2-C-Methyl-D-erythritol-4-phosphate cytidylyltransferase, 6-O-Methylgalactose; D-form, 20-Methyl-3-gammaceranol; (3β,20α)-form, 2-Methyl-3-gammaceranol; (2β,3β)-form, 6'-Methylgentamicin A, 6-Methylgentamicin A; 4''-Epimer, 3-O-Methylglucose; D-form, Methylglutamate dehydrogenase, Methylguanidinase, 20-Methyl-4,7,10,13,16-heneicosapentaenoic acid, 16-Methyl-6,9-heptadecadienoic acid, 16-Methyl-9,12-heptadecadienoic acid, 2-Methylheptadecanoic acid; Me ester, 16-Methyl-6,9,12-heptadecatrienoic acid, 16-Methyl-6-heptadecenoic acid; (Z)-form, 16-Methyl-8-heptadecenoic acid; (Z)-form, 6-Methyl-2-heptanone, 25-Methylhexacosanoic acid, 2-Methylhexadecanoic acid, 14-Methyl-9-hexadecenoic acid; (Z)-form, 15-Methyl-10-hexadecenoic acid; (Z)-form, 15-Methyl-11-hexadecenoic acid; (Z)-form, 15-Methyl-5-hexadecenoic acid; (Z)-form, 9-Methyl-10-hexadecenoic acid; (9ξ,10E)-form, 8-(5-Methylhexyl)-1H,3H-[1,3,4]oxadiazolo[3,4-a][1,2,4]triazin-1-one, 17-Methyl-3-hopanol; 3β-form, 2-Methyl-22-hopanol; (2α,21βH)-form, 2-Methyl-22-hopanol; (2β,21βH)-form, 2-Methyl-22-hopanol; (2ξ,21βH)-form, 3-Methyl-22-hopanol; 3β-form, 3-Methyl-29-hopanol; (3β,22S)-form, N-Methylhydantoinase (ATP-hydrolysing), 5-Methyl-2,4-imidazolidinedione; (S)-form, 3-Methyl-1H-indole-2-carboxylic acid, Methylmalonyl-CoA carboxytransferase, 3-O-Methylmannose; D-form, N-[15-Methyl-3-(13-methyl-4-tetradecenoyloxy)hexadecanoyl]glycine; (R)-(Z)-form, N-[15-Methyl-3-(13-methyl-4-tetradecenoyloxy)hexadecanoyl]glycine; (R)-(Z)-form, 4',5'-Dihydro, N-[14-Methyl-3-(13-methyl-4-tetradecenoyloxy)pentadecanoyl]glycine; (R)-(Z)-form, Methyl (methylthio)methyl disulfide, 28-Methylnonacosanoic acid, 18-Methyl-5,8,11,14-nonadecatetraenoic acid, 18-Methyl-8,11,14-nonadecatrienoic acid, 3-Methyl-2-(2-nonenyl)-4(1H)-quinolinone, 3-Methyl-2-(2-nonenyl)-4(1H)-quinolinone; NH-form, N-Hydroxy, 3-Methyl-2-(2-nonenyl)-4(1H)-quinolinone; 2',3'-Dihydro, 27-Methyloctacosanoic acid, 16-Methyloctadecanoic acid; (ξ)-form, Me ester, 11-Methyl-12-octadecenoic acid; (11β,12Z)-form, 12-Methyl-11-octadecenoic acid; (E)-form, 3-Methyl-2-(2-octenyl)-4(1H)-quinolinone; (E)-form, 4-Methyloxaloacetate esterase, (3-Methyloxiranyl)phosphonic acid; (2R,3S)-form, 3-Methyl-2-oxobutanoate hydroxymethyltransferase, 5-Methyl-2-oxo-4-imidazolidinehexanoic acid; (4R,5S)-form, Methylpendolmycin, 14-Methylpentadecanoic acid, 14-Methyl-5-pentadecenoic acid; (Z)-form, 3-Methyl-2-pentyl-4(1H)quinolinone, 9-Methyl-1-phenyl-1-decanone, 3-Methyl-2,5-piperazinedione; (±)-form, 2-Methyl-1,2-propanedithiol, 2-Methyl-1-propylamine; N-Propyl, 3-(2-Methylpropyl)-2,5-piperazinedione; (S)-form, 4-(2-Methylpropyl)-3H-pyrrolo[2,3-c]quinoline, Methylpyrazine, 4-Methyl-3H-pyrrolo[2,3-c]quinoline, 4-Methylquinazoline, 4-Methyl-2-quinazolinecarboxylic acid, 4-Methyl-2-quinazolinecarboxylic acid; Amide, 12-Methyltetradecanoic acid; (ξ)-form, 12-Methyltetradecanoic acid; (S)-form, 2-Methyl-4-tetradecanone, 12-Methyl-4-tetradecenoic acid; (Z)-form, 13-Methyl-4-tetradecenoic acid; (Z)-form, 5-Methyltetrahydropteroyltriglutamate-homocysteine S-methyltransferase, 3-Methyl-29-(2,3,4,5-tetrahydroxypentyl)-6,11-hopadiene; (3β,32R,33R,34R)-form, 3-Methyl-29-(2,3,4,5-tetrahydroxypentyl)-6,11-hopadiene; (3β,32R,33R,34S)-form, 3-Methyl-29-(2,3,4,5-tetrahydroxypentyl)hopane; (3β,32R,33R,34R)-form, 3-Methyl-29-(2,3,4,5-tetrahydroxypentyl)hopane; (3β,32R,33R,34S)-form, 3-Methyl-29-(2,3,4,5-tetrahydroxypentyl)-11-hopene; (3β,32R,33R,34R)-form, 3-Methyl-29-(2,3,4,5-tetrahydroxypentyl)-11-hopene; (3β,32R,33R,34S)-form, 3-Methyl-29-(2,3,4,5-tetrahydroxypentyl)-6-hopene; (3β,32R,33R,34S)-form, Methylthioadenosine nucleosidase, 1-(Methylthio)butane; S,S-Dioxide, 3-(Methylthio)propanoic acid, S-Methyl-5-thioribose kinase, 3-(Methylthio)rifamycin, 3-(Methylthio)rifamycin; 16,17,18,19,28,29-Hexahydro, 3-(Methylthio)rifamycin; 1,4-Quinone, 3-(Methylthio)rifamycin; 1,4-Quinone, 16,17,18,19,28,29-hexahydro, 2-Methyl-4-tridecanone, 3-Methyl-4-tridecanone; (ξ)-form, 2-Methyl-2-tridecen-4-one, Methylumbelliferyl-acetate deacetylase, 10-Methylundecanoic acid, 10-Methyl-2-undecanol; (ξ)-form, 10-Methyl-2-undecanone, 3-O-Methylxylose; L-form, 1'-Methylzeatin; (R)-form, 1'-Methylzeatin; (R)-form, 9-β-D-Ribofuranosyl, Met-Xaa dipeptidase, Mevalagmapeptide, Mevalonate kinase, M GCI, Micacocidins; Co complex, Micacocidins; Cu complex, Micacocidins; Fe complex, Micacocidins; Ni complex, Micacocidins; Zn complex, Michiganin A, Microbisporicin, Microcin B17, Microcin C, Microcin D93, Microcin E492, Microcin H47, Microcin J25, Microcin L, Microcin N, Microcin V, Micrococcal nuclease, Micrococcin GO5, Micrococcin M, Micrococcin P1, Micrococcin P1; 17'-Ketone, Micromonomycin, Micromonospolide A, Micromonospolide A; 21-O-Deacyl, Micromonospolide C, Micromonosporin A, Mildiomycin, Mildiomycin; 8'-Deoxy, Millericin B, Millipede protein, Mitomycin C; N1-(3-Oxobutyl), Mitomycin C; Stereoisomer, Miuraenamide A, Miuraenamide A; 3"-Chloro analogue, Miuraenamide A; O-De-Me, Miuraenamide A; 3R-Hydroxy, Miuraenamide A; 3"-Iodo analogue, Miuraenamide A; 13Z-Isomer, Mixirin A, Mixirin B, Mixirin C, MLI, Mocimycin, Moiramide A, Moiramide B, Monastatin, Monazomycin, Monazomycin; N-(Aminoiminomethyl), Monensin; Monensin B, 26-Deoxy, 3-O-de-Me, 3-propanoyl, Monensin; Monensin B, 3-O-De-Me, 3-propanoyl, Monicamycin, Monomethyl-sulfatase, Morganocin, Morphine 6-dehydrogenase, Morricin 269, MSA 13, Mundticin, Mundticin L, Mupirocin F2, Mupirocin H, Mupirocin W, Muramic acid; D-form, 1'-Epimer, N—Ac, Muraminomicins, Muramoylpentapeptide carboxypeptidase, Muramoyltetrapeptide carboxypeptidase, Musettamycin, Musettamycin; N-De-Me, Musettamycin; 10-Epimer, Mutacins; Mutacin B-Ny 266, Mutacins; Mutacin F-59.1, Mutacins; Mutacin GS5, Mutacins; Mutacin I, Mutacins; Mutacin II, Mutacins; Mutacin III, Mutacins; Mutacin IV, Mutacins; Mutacin K8, Mutacins; Mutacin MT6223, Mutacins; Mutacin N, Mutacins; Mutacin VSM43, Mutamicin 5, Mutanobactin A, Mutanobactin A; 25-Epimer, Mutanobactin A; 15-L-Isoleucine analogue, Mutanobactin D, Mycinamycin II, Mycinamycin II; 3B—O-De-Me, Mycinamycin II; 14-Deoxy, Mycinamycin II; 14-Deoxy, 3B—O-de-Me, Mycinamycin II; 14-Deoxy, 21-O-deglycosyl, Mycinamycin VI, Mycinamycin VI; Aglycone, Mycinamycin VI; Aglycone, 21-deoxy, Mycinamycin VI; 9ξ-Alcohol, 2",3"-di-Me ether, Mycinamycin VI; 21-O-Deglycosyl, Mycinamycin VI; 21-(Deglycosyloxy), Mycinamycin VI; 2",3"-Di-Me ether, Mycinamycin VI; 14α-Hydroxy, Mycinamycin VI; 14α-Hydroxy, 2",3"-di-Me ether, Mycinamycin VI; 14α-Hydroxy, 2"-Me ether, Mycinamycin VI; 2"-Me ether, Mycinamycin XI, Mycinamycin XI; 14-Deoxy, Mycinamycin XI; 11-Epimer, Mycinamycin XI; 11-Epimer, 14-deoxy, Mycinamycin XII, Mycinamycin XIII, Mycinamycin XIV, Mycinamycin XVII, Mycobacillin, Mycobactocidin, Mycocerein, Mycodextranase, Mycoheptin B, Mycopentene, Mycoplanecin, Mycoplasmal growth inhibitor, Mycosubtilin, Mycosubtilin B, Mycosubtilin C, Mycothiol bimane, Mycotrienol II; 20,23-Quinone, 19-hydroxy, 13-O-[[2-(cyclohexanecarbonyl)amino]propanoyl], Myomycin B, Myxalamides; Myxalamide A, Myxalamides; Myxalamide B, Myxalamides; Myxalamide C, Myxalamides; Myxalamide D, Myxalamides; Myxalamide D, 2'-Me ether, Myxalamides; Myxalamide D, 6E-Isomer, 7-Me ether, Myxalamides; Myxalamide D, 6E,10Z-Isomer, 2'-Me ether, Myxaline, Myxochelin A, Myxochelin A; 10-Deoxy, 10-amino, Myxochelin A; 10-Deoxy, 10-(2,3-dihydroxybenzoylamino), Myxochromide A, Myxochromide B, Myxochromide S, Myxocoxanthin, Myxocoxanthin; O-β-D-Glucopyranoside, Myxocoxanthin; Me ether, Myxocoxanthin; O-α-L-Rhamnopyranoside, Myxol, Myxopyronines; Myxopyronine A, Myxopyronines; Myxopyronine B, Myxothiazole A, Myxothiazole A; O3-De-Me, 2,3-dihydro, 3-ketone, Myxothiazole A; 17,18-Epoxide, Myxothiazole A; 17Z-Isomer, Myxothiazole A; Parent acid, Me ester, Myxovalargin, Myxovirescin A1, Myxovirescin A1; 9-Alcohol, Myxovirescin A1; 13-Deethyl, 13-methyl, Myxovirescin A1; 13-Deethyl, 13-methyl, 4-epimer, Myxovirescin A1; 13-Deethyl, 13-methyl, 4-epimer, 9-deoxo, Myxovirescin A1; 33-O-De-Me, Myxovirescin A1; 33-Demethoxy, Myxovirescin A1; 33-Demethoxy, 2,3-didehydro, Myxovirescin A1; 17-De(methoxymethyl), 17-carboxy, Myxovirescin A1; 33-Demethoxy, 5-oxo, Myxovirescin A1; 9-Deoxo, Myxovirescin A1; 9-Deoxo, 2,3-didehydro, Myxovirescin A1; 13-Dethyl, 13-methyl, 9-deoxo, Myxovirescin A1; 2,3-Didehydro, Myxovirescin A1; Epimer, Myxovirescn A1; 4-Epimer, 9-alcohol, Myxovirescin A1; 4-Epimer, 33-O-de-Me, Myxovirescin A1; 4-Epimer, 33-demethoxy, Myxovirescin A1; 4-Epimer, 9-deoxo, Myxovirescin A1; 5-Oxo, Myxovirescin G1, Myxovirescin G1; 4-Demethyl, 7-oxo, Myxovirescin G1; 4-Epimer, Myxovirescin K1, Myxovirescin K1; 4-Epimer, Myxovirescin N1, Myxovirescin N1; 4-Epimer, Myxovirescin P1, Myxovirescin P1; 4-Epimer, NAD(+):[dinitrogen reductase] (ADP-D-ribosyl)transferase, NADH peroxidase, NAD(+) kinase, NAD(+) nucleosidase, NADPH-cytochrome-c2 reductase, NADPH peroxidase, Nannochelin C, Nannochelin C; 1,1'-Di-Me ester, Nannochelin C; 1-Me ester, Naphthalene 1,2-dioxygenase, Naphthospironone A, Napyradiomycin A1, Napyradiomycin B1, Napyradiomycin B1; 3'-Dechloro, 3'-bromo, Napyradiomycin B1; 4a-Dechloro, 4,4a-didehydro, Napyradiomycin B4, Napyradiomycin C1, Napyradiomycin C1; A17(19)-Isomer, 16-chloro, Narine F, Nebularine, Neelaredoxin, Negamycin; (3R,5S)-form, 5-Deoxy, Neginamycin, α-Neoagaro-oligosaccharide hydrolase, Neoantimycin, Neobacillamide A; (R)-form, Neoberninamycin, Neocidin, Neoenactin; Neoenactin A, 10'-Alcohol, Neomycin A, Neomycin A; 3'-Deoxy, Neomycin A; 3,4'-Dideoxy, Neomycin A; 6'-N-Me, 1-N-(4-amino-2S-hydroxybutanoyl), Neomycin G; 6-Epimer, 6'-deamino, 6'-hydroxy, Neopullulanase, Neorustmicin B, Neorustmicin C, Neorustmicin D, Neosidomycin; 4-Methoxy, Neosidomycin; 4-Methoxy, 6'-parent acid, 6'-amide, Neosurugatoxin, 5,18-Neoverrucosanediol; (5β,13α)-form, 5,9-Neoverrucosanediol; (5β,9β,13α)-form, 5,9,18-Neoverrucosanetriol; (5β,9β,13α)-form, 5,9,18-Neoverrucosanetriol; (5β,9β,13α)-form, 18-Aldehyde, Neplanocin A, Neplanocin B, Neplanocin C, Neplanocin D, Neplanocin F, Ngercheumicin A, Ngercheumicin A; 4"',5"'-Dihydro, Ngercheumicin C, Ngercheumicin C; 3-Methionine analogue, Ngercheumicin C; 3-Phenylalanine analogue, Nicotinamide nucleotide adenylyltransferase, Nicotinate dehydrogenase, Nicotinate nucleotide adenylyltransferase, Nicotinate-nucleotide:dimethylbenzimidazole phospho-D-ribosyltransferase, Nicotinate-nucleotide diphosphorylase (carboxylating), Nicotinate phosphoribosyltransferase, Nicotine dehydrogenase, Nigrescin, Nisin A, Nisin A; 27-L-Asparagine analogue, Nisin F, Nisin Q, Nisin U, Nisin U; Variant, Nitric oxide dioxygenase, Nitric oxide reductase, 5-Nitro-1,3-benzenediol, Nitrogenases, 2-Nitroimidazole, 3-Nitroindazole, 2-Nitro-4-(2-nitroethenyl)phenol, 2-Nitro-4-(2-nitroethenyl)phenol; 6-Nitro, 4-Nitrophenol, 2-Nitrophenol 2-monooxygenase, Nitrosofungin, NMN nucleosidase, Nocamycin I, Nocamycin I; 8-Alcohol, Nocamycin I; N-Me, Nocapyrone A, Nocapyrone A; 5'-Deoxy, Nocapyrone C, Nocapyrone C; 6'-Deoxy, Nocapyrone F. Nocapyrone G, Nocapyrone G; 3'-Deoxy, Nocardamine, Nocardicin A; E-Isomer, Nocardicin E, Nocardicin E; E-Isomer, Nocardicin G, Nocardioazine A, Nocardioazine B, Nocardiopsin B, Nocardiopsin B; 28-Ketone, Nocardorubin, NodRf III, Nod Rm 1, 1,2-Nonadecanediol; (ξ)-form, 2-Tetradecanoyl, 1-O-β-D-glucopyranoside, 1,2-Nonadecanedol; (ξ)-form, 2-Hexadecanoyl, 1-O-β-D-glucopyranoside, 2-(3, 7,11,15,19,23,27,31,35-Nonamethyl-2,6,10,14,18,22,26,30,34-hexatriacontanonenyl)-1,4-benzoquinone, Nonaprenoxanthin, Nonaprenoxanthin; 11',12'-Didehydro, 2-Nonaprenylphenol, Nopaline; (R,S)-form, Norchainin, Norcoronatine, Noricumazole A, Noricumazole A; 18-O-α-D-Arabinofuranoside, Noricumazole A; 11-O-β-D-Glucopyranoside, Nosiheptide, Nostoxanthin, Nostoxanthin; 2'-Deoxy, 3'-sulfate, Nostoxanthin; 3-O-Sulfate, Nucleoside deoxyribosyltransferase, Nucleoside phosphotransferase, Nucleoside ribosyltransferase, Nucleoticidin, Nukacin ISK-1, Nukacin KQU-131, Nystatin; Nystatin A1, 28,29-Didehydro, 5-ketone, Oasomycin A, Oasomycin A; 46ξ-Alcohol (lactol), 22-O-α-D-mannopyranoside, Oasomycin A; 22-O-α-D-Mannopyranoside, Oasomycin A; Parent hydroxyacid, Oasomycin A; Parent hydroxyacid, 22-O-α-D-mannopyranoside, Oasomycin D, Oasomycin D; 22-O-α-D-Mannopyranoside, Obafluorin, Obutin, Occidiofungin A, Occidiofungin A; 3"ξ-Hydroxy, Ochramycin, Ochrobactin C, Ochrobactin C; N-Deacyl, N-octanoyl, Ochrobactin C; N-Deacyl, N-(2E-octenoyl), 6,11-Octadecadienoic acid; (6E,11Z)-form, 11-Octadecenoic acid; (Z)-form, [β-D-Glucopyranosyl-(1→2)-β-D-glucopyranosyl] ester, Octahydro-2-hydroxy-5H,10H-dipyrrolo[1,2-a:1',2'-d]pyrazine-5,10-dione; (2R,5aS,10aS)-form, 1,2,7,7',8,8',11,12-Octahydrolycopene, Octahydro-7a-methyl-1-(1-methyl-2-oxopropyl)-5-oxo-1H-indene-4-propanoic acid, Octamycin, Octanethioic acid; SH-form, S-Me ester, 5-Octanoylamino-2,3,6(1H)-pyridinetrione, Octapeptin A, Octapeptin B, Octapeptin B; Octapeptin B5, Octapeptin C, Octapeptin D, trans-Octaprenyl-trans-transferase, Octicidin, Octopinic acid, D-glycero-D-talo-2-Octulosonic acid, Okadaxanthin, Okenone, Oligo-1,6-glucosidase, Oligomycin A; 10-Demethyl, 7-alcohol, Oligomycin A; 10-Demethyl, 28-oxo, 7-alcohol, Oligonucleotidase, Oligopeptidase B, Oligosaccharide reducing-end xylanase, Olivoretin C, Olivoretin C; O-De-Me, Olivoretin E, Oncotoxin, Oomycin A, Opine dehydrogenase, Opines; Epileucinopine, 2-Epimer, Orcinol 2-monooxygenase, Orfamide A, Orfamide A; 10-N-Deacyl, 10-N-(3-hydroxydodecanoyl), Orfamide A; 7-Valine analogue, Ornibactin C4, Ornibactin C6, Ornibactin F, Ornithine aminotransferase, Ornithine carbamoyltransferase, Orotate phosphoribosyltransferase, Orthosomycin J, Oscillol; 2,2'-Diketone, 1,1'-di-Me ether, Oxalate CoA-transferase, Oxamate carbamoyltransferase, Oxamicetin, Oxaunomycin; 10,11-Dideoxy, 4-Me ether, Oxazinomycin, Oxetanocin, Oximidine II, Oximidine II; 12α,13α-Epoxide, Oximidine II; 17E-Isomer, 14-deoxy, 12α,13α-epoxide, 3-Oxoacyl-[acyl-carrier-protein] synthase, 3-Oxoadipate CoA-transferase, 3-Oxoadipate enol-lactonase, 3-Oxoadipyl-CoA thiolase, 7-Oxo-1-azabicyclo[3.2.0]heptane-2-carboxylic acid; (2R,5R)-form, 7-Oxo-1-azabicyclo[3.2.0]heptane-2-carboxylic acid; (2S,5R)-form, 7-Oxo-1-azabicyclo[3.2.0]hept-2-ene-2-carboxylic acid; (R)-form, α-Oxo-1-azetidineacetic acid, 4-Oxobutanoic acid, 6-Oxocineole dehydrogenase, [2-(5-Oxo-1-cyclopenten-1-yl)methyl]butanoic acid, (2-Oxoethyl)phosphonic acid, 2-Oxo-3-guaien-12,6-olide; (1β,5α,6α,10β,11α)-form, 27-Oxooctacosanoic acid, 2-Oxo-3-phenylpropanoic acid, 5-Oxoprolinase (ATP-hydrolysing), 2-Oxopropanal, 2-Oxopropyl-CoM reductase (carboxylating), 2-Oxo-2H-pyran-4,6-dicarboxylic acid, 3-Oxosteroid 1-dehydrogenase, 4,4'-Oxybis[benzenepropanoic acid], 1,1'-Oxybis[3-[4-(methylamino)phenoxy]-2-propanol], Paenibacillin, Paenibacillin N, Paenibacillin P, Paenibactin, Paenimacrolidin, Pantetheine; (R)-form, Pantetheine kinase, Pantetheine phosphate adenylyltransferase, Pantethine; (R,R)-form, Pantoate 4-dehydrogenase, Pantocin A, Pantocin A2, Pantocin B, Pantocin B; De(methylsulfonyl), Pantothenate kinase, Papulinone, Paracaseicin A, Paromamine, Paromamine; 3'-Deoxy, Paromamine; 5-O-β-D-Xylofuranosyl, Paromomycin; 3-N-Me, Pauciflorol F; 2,3-Didehydro, penta-Me ether, PAX Antibiotics; PAX 1, PAX Antibiotics; PAX 10, PAX Antibiotics; PAX 11, PAX Antibiotics; PAX 12, PAX Antibiotics; PAX 13, PAX Antibiotics; PAX 2, PAX Antibiotics; PAX 3, PAX Antibiotics; PAX 3', PAX Antibiotics; PAX 4, PAX Antibiotics; PAX 5, PAX Antibiotics; PAX 6, PAX Antibiotics; PAX 7, PAX Antibiotics; PAX 8, PAX Antibiotics; PAX 9, P CW, Pedein A, Pedein A; Dechloro, Pediocins, Pediocins; Pediocin 05-10, Pediocins; Pediocin 5, Pediocins; Pediocin A, Pediocins; Pediocin ACCEL, Pediocins; Pediocin ACM, Pediocins; Pediocin F, Pediocins; Pediocin ISK 1, Pediocins; Pediocin JD, Pediocins; Pediocin L50, Pediocins; Pediocin LB-B1, Pediocins; Pediocin N5p, Pediocins; Pediocin PA1, Pediocins; Pediocin PD1, Pediocins; Pediocin PO2, Pediocins; Pediocin SA131, Pediocins; Pediocin SJ-1, Pendolmycin, Penocin A, 1,11,19,27,35-Pentaamino-3-tetracontanol, 4,8,12,16,20-Pentaazatricosane-1,23-diamine, Pentachlorophenol monooxygenase, 5-Pentacosyl-1,3-benzenediol, 2,5,8,11,14-Pentadecanepentone, 1,2,3,5,7-Pentahydroxy-6-methylanthraquinone; 1,3-Di-Me ether, 29-(1,2,3,4,5-Pentahydroxypentyl)-29-hopanol; (22S,29R,31R,32R,33S,34S)-form, 35-O-[2-Deoxy-2-[(9-cyclohexylnonanoyl)amino]-β-D-mannopyranoside], 29-(1,2,3,4,5-Pentahydroxypentyl)-29-hopanol; (22S,29R,31R,32R,33S,34S)-form, 35-O-[2-Deoxy-2-[(11-cyclohexylundecanoyl)amino]-β-D-mannopyranoside], 29-(1,2,3,4,5-Pentahydroxypentyl)-29-hopanol; (22S,29R,31R,32R,33S,34S)-form, 35-O-[2-Deoxy-2-[(13-cyclohexylnonanoyl)amino)]-β-D-mannopyranoside], 29-(1,2,3,4,5-Pentahydroxypentyl)-29-hopanol; (22S,29R,31R,32R,33S,34S)-form, 35-O-[2-Deoxy-2-[(15-cyclohexylpentadecanoyl)amino]-β-D-mannopyranoside], 29-(1,2,3,4,5-Pentahydroxypentyl)-29-hopanol; (22S,29R,31R,32R,33S,34S)-form, 35-O-[2-Deoxy-2-[(17-cyclohexylheptadecanoyl)amino]-β-D-mannopyranoside], 29-(1,2,3,4,5-Pentahydroxypentyl)-29-hopanol; (22S,29R,31R,32R,33S,34S)-form, 35-O-[2-Deoxy-2-[(19-cyclohexylnonadecanoyl)amino]-β-D-mannopyranoside], 29-(1,2,3,4,5-Pentahydroxypentyl)-29-hopanol; (22S,29R,31R,32R,33S,34S)-form, 35-O-[2-Deoxy-2-[(21-cyclohexylheneicosanoyl)amino]-β-D-mannopyranoside], 29-(1,2,3,4,5-Pentahydroxypentyl)-29-hopanol; (22S,29R,31R,32R,33S,34S)-form, 35-O-[2-Deoxy-2-[(23-cyclohexyltricosanoyl)amino]-β-D-mannopyranoside], 2-O-(3,7,11,15,19-Pentamethyleicosyl)-1-O-(3,7,11,15-tetramethylhexadecyl) glycerol, Pentaneicin, trans-Pentaprenyl-trans-transferase, Pentocin TV35b, threo-2-Pentulose; D-form, PepB aminopeptidase, Peptidase Do, Peptidoglycan, Peptidoglycan β-N-acetylmuramidase, Peptidoglycan glycosyltransferase, Peptidyl dipeptidase A, Peptidyl dipeptidase Dcp, Peptin 31, Perfringocin 11105, Perillyl alcohol dehydrogenase, Permetin A, Permetin A; Analogue (1), Permetin A; Analogue (2), Permetin A; 2-L-Valine analogue, Persicomycin, Pertucin, Pesticin, Petrobactin, Petrobactin; 2',2"-Disulfo, Petrobactin; 2'-Sulfo, PGL Aglycone; 31-O-[β-D-Galactofuranosyl-(1→6)-β-D-galactofuranoside], PGL Aglycone; 31-O-[α-D-Glucopyranosyl-(1→2)-β-D-galactofuranoside], PGL Aglycone; N-Me, 31-O-[β-D-galactofuranosyl-(1→6)-β-D-galactofuranoside], PGL Aglycone; N-Me, 31-O-[α-D-glucopyranosyl-(1→2)-β-D-galactofuranoside], Phagicin, Pharacin, Phaseolotoxin, Phaseolotoxin; 3'-Hydroxy, Phenalamide A1, Phenalamide A1; 4Z,6E-Isomer, Phenalamide A1; 6E-Isomer, Phenalamide A1; 6E-Isomer, 10ξ,11ξ-epoxide, Phenalamide B, 2,3,5,7-Phenanthrenetetrol; 3,5-Di-Me ether, 2,3,5,7-Phenanthrenetetrol; 5,7-Di-Me ether, 1-Phenazinecarboxylic acid, 1-Phenazinecarboxylic acid; Amide, 1-Phenazinecarboxylic acid; 5,10-Dihydro, amide; amide (1:3 complex), 1,6-Phenazinedicarboxyhc acid, 1,6-Phenazinedmethanol, 1,6-Phenazinedimethanol; 1-Carboxylic acid, amide, 1,6-Phenazinediol, 1,6-Phenazinediol; 5,10-Dioxide, 1,6-Phenazinediol; Mono-Me ether, 5,10-dioxide, 1,6-Phenazinediol; 5-Oxide, 1,8-Phenazinediol, 1,8-Phenazinediol; 10-Oxide, 2,3-Phenazinediol, 2,3,7-Phenazinetriol, 1-Phenazinol, 1-Phenazinol; 10-Oxide, 2-Phenazinol, 2-Phenazinol; OH-form, O-(3ξ,7,11,15,19-Pentamethyl-6E,10E,14E,18-eicosatetraenyl), Phenazostatin B; Epimer, Phenol 2-monooxygenase, Phenomycin, Phenoxan, Phenylacetaldehyde, Phenylacetaldehyde; O-Methyloxime, Phenylacetic acid Amide, Phenylacetic acid; 2-Phenylethylamide, Phenylacetohydroxamic acid; N-Me, Phenylacetyl-CoA dehydrogenase, Phenylacetyl-CoA hydrolase, Phenylalanine N-acetyltransferase, Phenylalanine dehydrogenase, Phenylalanine monooxygenases; Phenylalanine 2-monooxygenase, Phenylalaninylarginal; N2-Ac, Phenylalaninylarginal; N2-(3-Methylbutanoyl), Phenylalaninylarginal; N2-(2-Methylpropanoyl), Phenylalaninylarginal; N2-Propanoyl, 4-Phenyl-3-buten-2-one; (E)-form, 10-Phenyldecanoic acid, 1-Phenyl-1-decanone, 12-Phenyldodecanoic acid, 2-Phenylethylamine; N—Ac, 2-Phenylethylamine; N-Butanoyl, 2-Phenylethylamine; N-Hexanoyl, 2-Phenylethylamine; N-(3-Methylbutanoyl), 2-Phenylethylamine; N-(13-Methyltetradecanoyl), 2-Phenylethylamine; N-Pentadecanoyl, 2-Phenylethylamine; N-Tetradecanoyl, N-(2-Phenylethyl)carbamic acid; Et ester, 4-Phenyl-2(5H)-furanone, 16-Phenylhexadecanoic acid, 3,3'-(Phenylmethylene)bis-1H-indole, Phenylnannolone A, Phenylnannolone A; 4'-Hydroxy, Phenylnannolone B, 1-Phenyl-1,2-propanedione, 3-Phenylpropanoic acid, 1-Phenyl-2-propanone, 14-Phenyltetradecanoic acid, 13-Phenyltridecanoic acid, Philipimycin, Pholipeptin, Pholipeptin; Stereoisomer, Phosphate acetyltransferase, Phosphate butyryltransferase, Phosphatidate cytidylyltransferase, Phosphatidylcholine synthase, Phosphatidylglycerol membrane-oligosaccharide glycerophosphotransferase, Phosphatidylglycerophosphatase, Phosphatidylinositol α-mannosyltransferase, Phospho-N-acetylmuramoyl-pentapeptide-transferase Phosphoenolpyruvate glycerone phosphotransferase, Phosphoenolpyruvate protein phosphotransferase, 1-Phosphofructokinase, 6-Phosphofructokinase, 6-Phosphofructo-2-kinase, 6-Phospho-β-galactosidase, 6-Phospho-β-glucosidase, Phosphoglycerate kinase, Phosphoglycerate phosphatase, 3-Phosphoglyceroyl phosphate polyphosphate phosphotransferase, Phospholipase C, Phosphomethylpyrimidine kinase, Phosphomevalonate kinase, Phosphonate dehydrogenase, Phosphopolyprenol glucosyltransferase. Phosphoramidate hexose phosphotransferase, Phosphoribokinase, Phosphoribosylglycinamide formyltransferase, Phosphoribulokinase, 3-Phosphoshikimate 1-carboxyvinyltransferase, Nδ-Phosphosulfamylornithine, α,α-Phosphotrehalase, Photobactin, Photolumazine B, Photolumazine B; 1'-Deoxy, Photopterin A, Phoxalone, Phthalate 4,5-dioxygenase, 3-Phytase, Phytoene synthase, Phytuberol; Ac, Piericidin; Piericidin A6, 11'R*,12'R*-Epoxide, Pipecolate dehydrogenases; L-Pipecolate dehydrogenase, Pipecolate dehydrogenases; L-Pipecolate oxidase, Piperazinomycin, Δ1-Piperideine-2-carboxylate reductase, Piscicocin CS526, Piscicolin 126, Planothiocin, Plantacin B, Plantaricins, Plantaricins; Plantaricin 1.25, Plantaricins; Plantaricin 149, Plantaricins; Plantaricin 423, Plantaricins; Plantaricin A, Plantaricins; Plantaricin AMA-K, Plantaricins; Plantaricin ASM1, Plantaricins; Plantaricin BN, Plantaricins; Plantaricin C, Plantaricins; Plantaricin C19, Plantaricins; Plantaricin D, Plantaricins; Plantaricin 35d, Plantaricins; Plantaricin EF, Plantaricins; Plantaricin F, Plantaricins; Plantaricin JK, Plantaricins; Plantaricin KW30, Plantaricins; Plantaricin LC74, Plantaricins; Plantaricin LP84, Plantaricins; Plantaricin MG, Plantaricins; Plantaricin NA, Plantaricins; Plantaricin NC8, Plantaricins; Plantaricin S, Plantaricins; Plantaricin SA6, Plantaricins; Plantaricin SIK83, Plantaricins; Plantaricin T, Plantaricins; Plantaricin UG1, Plantaricins; Plantaricin W, Plantazolicin A, Plantazolicin A; N,N-Di-de-Me, Platomycin A, Platomycin B, Pleuracin ML, Plusbacin A; Plusbacin A1, Plusbacin A; Plusbacin A1, 10-Deoxy, Plusbacin A; Plusbacin A2, Plusbacin A; Plusbacin A2, 10-Deoxy, Plusbacin A, Plusbacin A3, Plusbacin A; Plusbacin A3, 10-Deoxy, Plusbacin A; Plusbacin A4, Plusbacin A; Plusbacin A4, 10-Deoxy, Pneumocins, Polcillin, Polybromohydroxydiphenyl ethers; 2,3', 4,5'-Tetrabromo-2',6-dihydroxydiphenyl ether, 2-Me ether, Polyfermenticin SCD, Poly(glycerol-phosphate) α-glucosyltransferase, Poly(3-hydroxybutyrate) depolymerase, Poly (3-hydroxyoctanoate) depolymerase, Polymannuronate hydrolase, Polymyxin B1, Polymyxin B1; N-Deacyl, N-(6-methylheptanoyl), Polymyxin D1, Polymyxin D1; N-Deacyl, N-(6-methylheptanoyl), Polymyxin E, Polymyxin E; Ile-Polymyxin E1, Polymyxin E; Ile-Polymyxin E2, Polymyxin F, Polymyxin K, Polymyxin M, Polymyxin P; Polymyxin P1, Polymyxin P; Polymyxin P2, Polymyxin S1, Polymyxin T1, Polynitroxin, Polynucleotide 5'-phosphatase, Polypeptin A, Polypeptin B, Polyphosphate glucose phosphotransferase, Polyphosphate kinase, Polyprenol; Undecaprenol, Polyprenol; Undecaprenol, O-(2-Amino-2-deoxy-β-D-galactopyranosyl) phosphate, Poly(ribitol-phosphate) N-acetylglucosaminyltransferase, Poly(ribitol-phosphate) β-glucosyltransferase, Polyribonucleotide nucleotidyltransferase, *Achromobacter lyticus* Polysaccharide, *Bacillus laevolacticus* Polysaccharide, Polysaccharide RON F, Polysialic acid O-acetyltransferase, Portmicin, Portmicin; 21,25-Dideoxy, 21,25-epoxy, Pradimicin A, N-De-Me, Preacinetobactin, Preacinetobactin; 3'-Deoxy, Precorrin 2, Precorrin 4, Precorrin 5, Precorrin 3A, Precorrin 3B, Precorrin 6B, Precorrin-3B synthase, Precorrin methyltransferases; Precorrin-6A synthase (deacetylating), Precorrin methyltransferases; Precorrin-3B C17-methyltransferase, Precorrin methyltransferases; Precorrin-2 C20-methyltransferase, Precorrin methyltransferases; Precorrin-4 C11-methyltransferase, Precorrin methyltransferases; Precorrin-6Y C5,15-methyltransferase (decarboxylating), Precorrin 8x, Precorrin 6y, Precorrin 6y; 1,2-Didehydro, Pretaric acid, Pretubulysin D, Pretubulysin D; 4''-Hydroxy, Primycin, Proactinomycin; Proactinomycin A, Proactinomycin; Proactinomycin B, Proactinomycin; Proactinomycin C, Prochlorosins, Prodigiosan, Prodigiosene, Prodigiosin, Prodigiosin; O-De-Me, Prodigiosin; Demethoxy, Prodigiosin; Homologue (n=5), Prodigiosin; Homologue (n=6), Prodigiosin; Lower homologue (n=2), Prodigiosin; Lower homologue (n=3), Proferrorosamine B, Proferrorosamine B; Fe complex (2:1), Prohibicin, D-Proline reductase (dithiol), Prolyl oligopeptidase, Promysalin, Promysalin; 2-Deoxy, Promysalin; 2-Deoxy, 18,19-dihydro, Promysalin; 18,19-Dihydro, 1,3-Propanediamine, 2-Propenal, Propeptin, Propeptin; De(prolylseryl), Propionate CoA-transferase, Propionate kinase, Propionicins; Propionicin F, Propionicins; Propionicin GBZ 1, Propionicins; Propionicin PLG-1, Propionicins; Propionicin SM1, Propionicins; Propionicin T1, Propionin A, Propioxatin A, 3-Propylmalate synthase, [Protein ADP-ribosylarginine] hydrolase, Protein arginine deiminase, *Staphylococcus aureus* Protein A, Protein-glutamate methylesterase, Protein-glutamate O-methyltransferase, Protein- L-isoaspartate(D-aspartate) O-methyltransferase, Protein-methionine-S-oxide reductase, [Protein-PII] uridylyltransferase, Protescin, Proticin, Proticin 3, Protocatechuate dioxygenases; Protocatechuate 3,4-dioxygenase, Protocatechuate dioxygenases; Protocatechuate 4,5-dioxygenase, Protochelin, Protochlorophyllide, Protoporphyrinogen oxidase, Protylonolide, Protylonolide; 19,23-Dihydroxy, Protylonolide; 12,13-Epoxide, Protylonolide; 16-Hydroxy, Protylonolide; 19ξ-Hydroxy, Protylonolide; 23-Hydroxy, Proviolacein, Proviolacein; 5-Deoxy, Proximicin A, Proximicin A; N1-[2-(4-Hydroxyphenyl)ethyl], Proximicin A; N1-[2-1H-Indol-3-yl)ethyl], Prumycin, PSC A, Pseudoalterobactin A, Pseudoalterobactin B, Pseudobactin 589A, Pseudobactin B, Pseudobactin B; 5'-Amide, Pseudobactin B; Analogue (R=COCH2CH2CH-2NHCOOH), 5,6-dihydro, Pseudobactin B; Analogue (R=COCH2CH2CH2NHCOOH), 7-sulfo, 5,6-dihydro, Pseudobactin B; 5,6-Dihydro, 5'-amide, Pseudobactin B; 7-Sulfo, 5,6-dihydro, 5'-amide, Pseudobactin 7SR1, Pseudobactin 7SR1; 3'-Deoxy, Pseudodeoxyviolacein, Pseudodeoxyviolacein; 5-Hydroxy, Pseudodesmin A, Pseudodesmin B, Pseudofactin I, Pseudofactin II, Pseudomonic acid A, Pseudomonic acid A; 4',5'-Didehydro, Pseudomonic acid A; 5-Hydroxy, Pseudomonic acid A; 4-Ketone, Pseudomonic acid C, Pseudomonine, Pseudomonine; 3'-Hydroxy, Pseudomycin A, Pseudomycin A; 4'-Deoxy, Pseudomycin C, Pseudomycin C; 4'-Deoxy, Pseudotrienoic acid A, Pseudotrienoic acid B, Pseudouridine kinase, Psicofuranine, Pterin deaminase, Pteroylglutamic acid; Homologue (n=3), Pulcherriminic acid, Pulcherriminic acid; Fe complex, Pullulanase, Pulvomycin, Pumacin, Pumilicin 4, 2,6-Purinediamine, Purine nucleosidase, Purine-nucleoside phosphorylase, Pustulan, Putidolumazine, Putisolvin I, Putisolvin I; 2-Isoleucine or Leucine analogue, Putrescine carbamoyltransferase, Putrescine oxidase, Pyloricidin D, Pyloricidin D; N5-L-Leucyl, Pyloricidin D; N5-L-Valyl-L-isoleucyl-L-leucyl, Pyloricidin D; N5-L-Valyl-L-leucyl, Pyloricidin D; N5-L-Valyl-L-leucyl-L-leucyl, Pyloricidin D; N5-L-Valyl-L-valyl-L-leucyl, Pyochelin I, Pyochelin I; 2-Epimer, Pyocins, Pyocyanine, Pyo IV, Pyoluteorin, Pyoluteorin; 3'-Nitro, Pyoverdin 11370, Pyoverdin 18.1, Pyoverdin 18.1; Homologue (R=—COCH2CH2COCOOH), Pyoverdin 18.1; Homologue (R=—COCH2CH2COCOOH), 5,6-dihydro, Pyoverdin 2112, Pyoverdin 2908, Pyoverdin 90-51, Pyoverdin 90-51; 3'-Hydroxy, 4'-amide, Pyoverdin 95-275, Pyoverdin 96-312, Pyoverdin 96-312; Amide, Pyoverdin 96-312; Homologue (R=COOH), Pyoverdin 96-318, Pyoverdin 96-318; Homologue (R=COOH), Pyoverdin 96-318; 3'-Hydroxy, amide (R=NH2), Pyoverdin A1, Pyoverdin BTP 2, Pyoverdin BTP16G, Pyoverdin BTP7G, Pyoverdin C, Pyoverdin CFBP 2392, Pyoverdin CFBP 2461, Pyoverdin CFBP 2461; 3-Hydroxy, Pyoverdin CFML 96.188, Pyoverdin CFML 96.188; Homologue, amide, Pyoverdin CFML 96.188; Homologue (R=COOH), Pyoverdin CFML 96.188; 2-Ornithine homologue, amide, Pyoverdin CHAO, Pyoverdin CHAO; 4'-Amide, Pyoverdin C44H61N13O17. Pyoverdin C44H61N13O17; 4'-Amide, Pyoverdin C45H63N11O24, Pyoverdin C45H63N11O24; 4'-Amide, Pyoverdin C45H63N11O24; 5-Gly analogue, (17→34)-lactone, 4'-amide, Pyoverdin C45H63N11O24; (17→34)-Lactone, 4'-amide, Pyoverdin C52H75N15O23, Pyoverdin C52H75N15O23; 4'-Amide, Pyoverdin C55H83N17O21, Pyoverdin C57H85N17O24, Pyoverdin C57H85N17O24; (4'→4)-Lactam, Pyoverdin D, Pyoverdin D; Amide, Pyoverdin D-TR133A, Pyoverdin D-TR133A; Amide, Pyoverdin D-TR133A; 36-Nor, Pyoverdin D-TR133A; 36-Nor, amide, Pyoverdin G 173, Pyoverdin G 173; 3'''-Hydroxy, Pyoverdin GM II, Pyoverdin GM II; 3'-Amide, Pyoverdin G4RA, Pyoverdin G4RA; 4'-Amide, Pyoverdin I, Pyoverdin II, Pyoverdin II; Amide, Pyoverdin PaC, Pyoverdin Pa II, Pyoverdin Pa II; 3'-Amide, Pyoverdin Pa TII, Pyoverdin Pf, Pyoverdin Pf12, Pyoverdin Pf 1.3, Pyoverdin Pf 1547, Pyoverdin Pf3 17400, Pyoverdin Pf/3/2, Pyoverdin Pf/3/2; Amide, Pyoverdin Pf/3/2; 3'S-Hydroxy, Pyoverdin Pt CCM 2798, Pyoverdin Pt P19, Pyoverdin Pf P19; 3-Deoxy, Pyoverdin PL7, Pyoverdin PL8, Pyoverdin Pm, Pyoverdin Pp 1, Pyoverdin Pp 1; 4'-Amide, Pyoverdin Pp 1; 5,6-Dihydro, 4'-amide, Pyoverdin PpC 3B, Pyoverdin PpC 38; 4'-Amide, Pyoverdin PpC 3B; 3'-Hydroxy, Pyoverdin PpC 3B; 3'-Hydroxy, 4'-amide, Pyoverdin PS, Pyoverdin PS 6.10, Pyoverdin PS 6.10; 4'-Amide, Pyoverdin PS 6.10; 4'-Me ester, Pyoverdin PSS, Pyoverdin Pt A, Pyoverdin Pt A; Amide (R=NH2). Pyoverdin Pt A; Homologue (R=COOH), Pyoverdin R', Pyoverdin R'; 4'-Amide, Pyoverdin R'; Homologue (R=COOH), Pyoverdin Thai, Pyoverdin 51WA, Pyoverdin 51WA; 3'-Amide, Pyralomicin 1a, Pyralomicin 1b, Pyralomicin 2b, Pyrazinol; NH-form, 4-Oxide, 2,6-Pyridinedicarbothioic acid, 2,6-Pyridinedicarbothioic acid; Fe complex, 2,6-Pyridinedicarboxylic acid, 2,6-Pyridinedicarboxylic acid; Mono-Et ester, Pyridoxal kinase, Pyridoxal phosphatase, Pyridoxal 5'-phosphate synthase, Pyridoxamine phosphate transaminase, Pyridoxamine transaminases; Pyridoxamine pyruvate transaminase, 5-Pyridoxate dioxygenase, 4-Pyridoxolactonase, Pyrimidine-nucleoside phosphorylase, Pyrimido[5,4-e]-1,2,4-triazine-5,7-diol; 1,6-Di-Me, Pyrogallol hydroxytransferase, Pyrogallol 1,2-oxygenase, Pyroglutamyl peptidase I, 2-Pyrone-4,6-dicarboxylate lactonase, Pyrrolnitrin, Pyrrolnitrin; 2-Chloro, Pyrrolnitrin; 3-Dechloro, Pyrrolnitrin; 3-Dechloro, bromo analogue, Pyrrolnitrin; 3'-Dechloro, 2-chloro, Pyrrolnitrin; 4'-Fluoro, Pyrrolnitrin; 6'-Hydroxy, Pyrrolomycin B, Pyrrolomycin C, Pyrrolomycin C; 4-Chloro, Pyrrolomycin E, Pyrrolomycin F; Pyrrolomycin F1, Pyrrolomycin F; Pyrrolomycin F3, Pyrrolomycin F; Pyrrolomycin F2a, Pyrrolomycin F; Pyrrolomycin F2b, Pyrrolo[1,2-a]pyrazine-3,6(4H,7H)-dione, Pyrrolysine, Pyruvate kinase, Pyruvate phosphate dikinase, Pyruvate, water dikinase, Q 1047R-A, Q 1047R-A; 3-Epimer, Q 1047R-A; 3-Epimer, 1,4-quinone, Q 1047R-A; 1,4-Quinone, Quercetin 2,3-dioxygenase, Queuine tRNA-ribosyltransferase, Quinaldopeptin, Quinolidomicin A2, Quinolidomicin A2; Quinone, Quinolidomicin A2; Quinone, O-de-Me, 4-Quinolinecarboxaldehyde, 4-Quinolinecarboxaldehyde; Oxime, 4-Quinolinecarboxylic acid, 2-Quinolinemethanol, 2-Quinolinemethanol; Ac, Quorum-quenching N-acyl-homoserine lactonase, Rakicidin A, Rakicidin B, Ramoplanin, Ramoplanin; Ramoplanin A2, 4'E-Isomer, 3A-O-α-D-mannopyranoside, Ratjadone, Rectiplanin, Repressor LexA, Resorcinomycin A; (S)-form, Resorcinomycin B, Retymicin, Reutericyclin; (R)-form, Rg keto VII, α-L-Rhamnopyranosyl-(1→3)-2-amino-2-deoxy-β-D-glucopyranosyl-(1→2)-L-rhamnose, 2-O-α-L-Rhamnopyranosyl-D-galactose, 2-O-β-L-Rhamnopyranosyl-D-galactose, 3-O-α-L-Rhamnopyranosyl-D-galactose, β-L-Rhamnopyranosyl-(1→4)-β-D-glucopyranosyl-(1→3)-2-amino-2-deoxy-D-galactose; β-Pyranose-form, N—Ac, α-L-Rhamnopyranosyl-(1→2)-[β-D-glucopyranosyl-(1→4)]-D-galactose, β-L-Rhamnopyranosyl-(1→4)-β-D-glucopyranosyl-(1→4)-D-galactose, α-L-Rhamnopyranosyl-(1→3)-[α-D-glucopyranosyl (1→4)]-L-rhamnose, β-L-Rhamnopyranosyl-(1→4)-β-glucopyranosyl-(1→3)-L-rhamnose, α-L-Rhamnopyranosyl-(1→3)-[β-D-glucuronopyranosyl-(1→2)]-D-mannose, α-D-Rhamnopyranosyl-(1→2)-β-D-rhamnopyranosyl-(1→3)-D-rhamnose, α-L-Rhamnopyranosyl-(1→2)-α-L- rhamnopyranosyl-(1→3)-L-rhamnose, α-D-Rhamnopyranosyl-(1→3)-α-D-rhamnopyranosyl-(1→2)-D-rhamnose, α-L-Rhamnopyranosyl-(1→3)-α-L-rhamnopyranosyl-(1→2)-L-rhamnose, α-D-Rhamnopyranosyl(1→3)-α-D-rhamnopyranosyl-(1→3)-D-rhamnose, α-L-Rhamnopyranosyl-(1→3)-α-L-rhamnopyranosyl-(1→3)-L-rhamnose, α-L-Rhamnopyranosyl-(1→3)-[α-L-rhamnopyranosyl-(1→4)]-L-rhamnose, β-L-Rhamnopyranosyl-(1→4)-β-L-rhamnopyranosyl-(1→2)-L-rhamnose, β-L-Rhamnopyranosyl-(1→4)-α-L-rhamnopyranosyl-(1→3)-D-rhamnose, β-L-Rhamnopyranosyl-(1→4)-β-L-rhamnopyranosyl-(1→4)-L-rhamnose, 2-O-α-L-Rhamnopyranosyl-L-rhamnose, 3-O-α-L-Rhamnopyranosyl-L-rhamnose, 4-O-α-L-Rhamnopyranosyl-L-rhamnose, 4-O-β-L-Rhamnopyranosyl-L-rhamnose, Rhamnose; D-form, 2-Me, Rhamnose; L-form, 2-Me, Rhamnose; L-form, 2,4-Di-Me, Rhamnose; L-form, 3-Me, α-L-Rhamnosidase, β-L-Rhamnosidase, Rhamnosin A, Rhamnulokinase, Rhamsan, Rhizobacidin, Rhizobactin, Rhizobitoxin; (2S,2'R)-form, Rhizobitoxin; (2S,2'R)-form, Dihydro, Rhizocticin; Rhizocticin A, Rhizocticin; Rhizocticin B, Rhizocticin; Rhizocticin C, Rhizocticin; Rhizocticin D, Rhizoferrin; (S,S)-form, Rhizolotine, Rhizonin A, Rhizonin B, Rhizopodin, Rhizoxin D, Rhizoxin D; O-DO-Me, Rhizoxin D; 2R,3S; 11R,12R-Diepoxide, Rhizoxin D; 2R,3S; 11R,12R-Diepoxide, O-De-Me, Rhizoxin D; 11R,12R-Epoxide, Rhizoxin D; 11R,12R-Epoxide, O-de-Me, Rhizoxin D; 22Z-Isomer, 11R,12R-epoxide, Rhizoxin S1, Rhizoxin S1; Deepoxy, 11,12-didehydro(E-), Rhizoxin S1; 22Z-Isomer, 17-Me ether, Rhizoxin S1; 17-Me ether, Rhdobacterioxanthin, Rhodobactin, ε-Rhodomycinone, Rhodopeptin, Rhodopin, Rhodopin; 7',8'-Dihydro, Rhodopin; 7,7',8,8',11',12'-Hexahydro, Rhodopin; 7,7',8,8',11',12'-Hexahydro, Me ether, Rhodopin; Me ether, Rhodopin; 7',8',11',12'-Tetrahydro, Rhodopinol; 20-Aldehyde, Rhodopinol; 20-Aldehyde, 1-O-β-D-glucopyranoside, Rhodopinol; 20-Aldehyde, 1-Me ether, Rhodopinol; 1-Deoxy, 3,4-didehydro, 20-aldehyde, Rhodopinol; 3,4-Didehydro, 20-aldehyde, 1-Me ether, Rhodoquinone 10, Rhodostreptomycin A, Rhodostreptomycin A; 6-Epimer, Rhomboid protease, α-Ribazole phosphatase, Ribitol; 3,4-Di-O-α-D-glucopyranoside, Ribitol; 1-O-β-D-Ribofuranoside, D-Ribitol 5-phosphate cytidylyltransferase, Riboflavin kinase, Riboflavin phosphotransferase, Riboflavin synthase, 6-O-β-D-Ribofuranosyl-D-glucose, β-D-Ribofuranosyl-(1→3)-α-L-rhamnopyranosyl-(1→3)-L-rhamnose, 9-Ribofuranosyluric acid; β-D-form, 5-Ribofuranosyluridine; β-D-form, Ribokinase, *Bacillus subtilis* Ribonuclease, Ribonuclease D, *Enterobacter* Ribonuclease, Ribonuclease F, Ribonuclease III, Ribonuclease IV, Ribonuclease M5, Ribonuclease P, Ribonuclease P4, Ribonucleoside-diphosphate reductase, Ribonucleoside-triphosphate reductase, Ribose; D-form, Ribose; D-form, 3-Me, Ribose 1,5-bisphosphate phosphokinase, Ribosomal-protein-alanine N-acetyltransferase, Ribostamycin, Ribostamycin; 1-N-(4-Amino-2S-hydroxybutanoyl), Ribostamycin; 6'-Deamino, 6-hydroxy, 1-N-(4-amino-2S-hydroxybutanoyl), Ribostamycin; 4'-Deoxy, 1-N-(4-amino-2S-hydroxybutanoyl), Ribostamycin; 3',4'-Dideoxy, 1-N-(4-amino-2S-hydroxybutanoyl), Ribostamycin; 3',4'-Dideoxy, 6'-N-Me, 1-N-(4-amino-2S-hydroxybutanoyl), Ribostamycin; 3''-Epimer, Ribostamycin; 3''-Epimer, 1-N-(4-amino-2S-hydroxybutanoyl), Ribostamycin; 3''-Epimer, 6'-deamino, 6'-hydroxy, 1-N-(4-amino-2S-hydroxybutanoyl), Ribostamycin; 3''-Epimer, 4'-deoxy, 1-N-(4-amino-2S-hydroxybutanoyl), Ribostamycin; 3''-Epimer, 3'-deoxy, 3'-chloro, 1-N-(4-amino-2S-hydroxybutanoyl), Ribostamycin; 3''-Epimer, 3',4'-dideoxy, 1-N-(4-amino-2S-hydroxybutanoyl), Ribostamycin; 3''-Epimer, 3',4'-dideoxy, 6'-N-Me, 1-N-(4-amino-2S-hydroxybutanoyl), Ribostamycin; 3''-Epimer, 2S-hydroxy, 1-N-(4-amino-2S-hydroxybutanoyl), Ribostamycin; 6'-N-Me, 3-N-(4-amino-2S-hydroxybutanoyl), Ribosylnicotinamide kinase, Ribosylpyrimidine nucleosidase, Ribulokinase; D-form, Ribulokinase; L-form, Riburonic acid; D-form, Rifamycin, Rifamycin S, Ripostatin A, Ripostatin B, Ripostatin C, Ristomycin A, Ristomycin A; 2C-Deglycosyl, RNA III Activating protein, Rodaplutin, Roimatacene, Romidepsin, Rosamicin, Rosamicin; 20-(Acetylhydrazone), Rosamicin; 23-Hydroxy, Rosamicin; 6-Hydroxy(?), Rosecin, Roseobacticide A, Roseobacticide A; 4'-Deoxy, Royamicin A, RP 41200, rRNA N-glycosylase, rRNA methyltransferases; rRNA (adenine-N6)-methyltransferase, rRNA methyltransferases; rRNA (guanine-N1)-methyltransferase, rRNA methyltransferases; rRNA (guanine-N2)-methyltransferase, RU 41821, Rubixanthin; (all-E)-form, Rubixanthin; (all-E)-form, 7',8'-Dihydro, Rubradirin, Rubredoxin reductases; Rubredoxin-NAD(P)(+) reductase, Rubredoxin reductases; Rubredoxin-NAD(+) reductase, Rubrifacine, γ-Rubromycin; 3,3'-Dihydroxy, γ-Rubromycin; 4ξ-Hydroxy, γ-Rubromycin; 3'ξ-Hydroxy, 3,4-didehydro, 3ξ,4ξ-epoxide, γ-Rubromycin; 3,3',4-Trihydroxy, Rudolfomycin, Ruminococcin A, Ruminococcin C, S-657, S 365A, S 365A; 2'-Epimer, Safracin A, Safracin A; 7α-Hydroxy, Saframycin A; 25-Alcohol (1), Saframycin A; Decyano, 5α-methoxy, Saframycin Mx 1, Saframycin Mx 1; 7-Deoxy, Saframycin Mx 1; 7-Deoxy, 1,4-quinone, Saframycin Mx 1; 1,4-Quinone, Sakacins, Sakacins; Sakacin 674, Sakacins; Sakacin A, Sakacins; Sakacin B, Sakacins; Sakacin C2, Sakacins; Sakacin G, Sakacins; Sakacin K, Sakacins; Sakacin LSJ618, Sakacins; Sakacin M, Sakacins; Sakacin P, Sakacins; Sakacin Q, Sakacins; Sakacin T, Sakacins; Sakacin X, Salicylate 1-monooxygenase, Salivacin 140, Salivaricins, Salivaricins; Salivaricin 9, Salivaricins; Salivaricin A, Salivaricins; Salivaricin A2, Salivaricins; Salivaricin B, Salivaricins; Salivaricin CRL1328, Salivaricins; Salivaricin D, Salivaricins; Salivaricin G32, Salivaricins; Salivaricin P, Salmochelin 1, Salmochelin 2, Salmochelin 4, Salmochelin X, Saltavalin, Samandaridine, Sandramycin, Sanguicin, Saproxanthin, Saproxanthin; 1'-O-Glucoside, Saproxanthin; 1'-Me ether, Saproxanthin; 1'-O-Rhamnoside, Saquayamycin Z, Sarcinapterin, Sarcinaxanthin, Sarcinaxanthin; Di-O-β-D-Glucopyranoside, Sarcinaxanthin; 7,8-Dihydro, Sarcinaxanthin; Mono-O-β-D-Glucopyranoside, Sarcosine dehydrogenases; Sarcosine oxidase, Sarcosine reductase, SATS 6504, Sattazolin; (+)-form, Sattazolin; (+)-form, Me ether, Saxitoxin; N1-Hydroxy, SB 291071, SB 291071; Homologue (R=—C11H21), SB 291071; Homologue (R=—C13H25), SB 291071; Homologue (R=—C15H29), SB 291071; Homologue (R=—(CH2)10CH3), SB 291071; Homologue (R=—(CH2)12CH3), SB 315021, Sch 351448, Schizokinen, Schizokinen; N-De-Ac, N-(2-decenoyl), Schizokinen; N-Deoxy, Schizokinen A, 3,4,8,15-Scirpenetetrol; (3α,4β,8α)-form, 4,8-Di-Ac, Sedoheptulokinase, Sedolisin, Selenate reductase, Selenide, water dikinase, Selenomethionine; (S)-form, Selenomycin, Serine; (S)-form, N-(3-C-Glucosyl-5,6-dihydroxybenzoyl), Me ester, Serine O-acetyltransferase, Serine-type-D-Ala-D-Ala carboxypeptidase, Serracin P, Serrapeptase, Serratamic acid, Serratamolide A, Serratamolide B, Serratamolide C, Serratamolide D, Serratamolide E, Serratamolide F, Serratigen, Serratiochelin, Serratiomycin, Serrawettin W2, L-Seryl-tRNASec selenium transferase, N-Seryltyrosine; D-D-form, N-(6-

Methyloctanoyl), N-Seryltyrosine; D-D-form, N-(7-Methyloctanoyl), Sesbanimide A, Sesbanimide C, *Enterococcus faecalis* Sex pheromone cAD1, *Enterococcus faecalis* Sex pheromone cAM373, *Enterococcus faecalis* Sex pheromone cCF10, *Enterococcus faecalis* Sex pheromone cOB1, *Enterococcus faecalis* Sex pheromone cPD1, *Enterococcus faecalis* Sex pheromone inhibitor iAD1, *Enterococcus faecalis* Sex pheromone inhibitor iAM373, *Enterococcus faecalis* Sex pheromone inhibitor iCF10, *Enterococcus faecalis* Sex pheromone inhibitor iPD1, SF 2809, Sfericase, Shewanellose; D-form, Shigellacin 52, Shikimate kinase, Shikometabolin A, Shikometabolin B, Shikometabolin C, Shikometabolin D, Shikometabolin E, Sibiromycin, Sibiromycin; 1,11a-Didehydro, Sibiromycin; 1,11a-Didehydro, 9-O-(4,6-dideoxy-3-C-methyl-4-(methylamino)-α-L-mannopyranoside), Sibiromycin; 9-O-(4,6-Dideoxy-3-C-methyl-4-(methylamino)-α-L-mannopyranoside), Sibyllimycin, Siderochelin C, Signal peptidase I, *Escherichia coli* Signal peptide, Simaomicin β; N-Me, Simplexin, Simusan, Sinefungin VA; 4,5-Didehydro, Siolipin B; Deoxy, Siphonazole A, Siphonazole A; 3'-Me ether, Siroheme, Sirohydrochlorin, Sirohydrochlorin; Fe complex, Sirohydrochlorin; Octa-Me ester, Sisomicin, Sisomicin; N-De-Me, Sisomicin; 2'-N-Formyl, Sisomicin; 6'-N-Me, Sisomicin; N-De-Me, 6'-N-Me, Sisomicin B, Sisomicin B; 4"-Epimer, SmaPI, SML 91 Lectin, SNA 60-367, SNA 60-367; SNA 60-367-12, SNA 60-367; SNA 60-367-3, SNA 60-367; SNA 60-367-3, Stereoisomer, SNA 60-367; SNA 60-367-6, SNA 60-367; SNA 60-367-7, Solamacearicin M2, Sorangiadenosine, Sorangicin A, Sorangicin A; 22-Deoxy, Sorangicin A; O21-(6-Deoxy-β-D-glucopyranoside), Sorangicin A; 22-Deoxy, O21-β-D-Glucopyranoside, Sorangicin A; O21-β-D-Glucopyranoside, Sorangicin A; 37Z,39E-Isomer, Sorangicin A; 39E-Isomer, Sorangicin A; 41E-Isomer, Sorangicin A; 39E, 41E-Isomer, O21-(6-deoxy-β-D-glucopyranoside), Sorangicin C; (37E,39E,41E)-form, Sorangicin C; (37E,39E,41Z)-form, Sorangicin C; (37E,39Z,41E)-form, Sorangiolide A, Sorangiolide A; 6-Hydroxy, Soraphen A, Soraphen A; 10-O-De-Me, Soraphen A; 11-O-De-Me, Soraphen A; 11-O-De-Me, stereoisomer(?), Soraphen A; Derivative, Soraphen A; 10,11-Di-O-de-Me, Soraphen A; 10,11-Di-O-de-Me, stereoisomer(?), Soraphen A; 10,11-Di-O-de-Me, stereoisomer (?), Soraphen A; 10,11-Di-O-de-Me, stereoisomer(?), Soraphen A; 12,13-Dihydro, Soraphen A; 12,13-Dihydro, 11-O-de-Me, Soraphen A; 12,13-Dihydro, 18-O-de-Me, Soraphen A; 12,13-Dihydro, 13,14-didehydro, 12ξ-hydroxy, 10-O-de-Me, Soraphen A; 12,13-Dihydro, 7,8-didehydro, 13ξ-hydroxy, 11-O-de-Me, Soraphen A; 12,13-Dihydro, 10,11-di-O-de-Me, Soraphen A; 12,13-Dihydro, 13ξ-hydroxy, Soraphen A; 12,13-Dihydro, 13ξ-hydroxy, 10,11-bis-O-de-Me, Soraphen A; 12,13-Dihydro, 12ξ-hydroxy, 10-O-de-Me, Soraphen A; 12,13-Dihydro, 13ξ-hydroxy, 11-O-de-Me, Soraphen A; 12,13-Dihydro, 13ξ-hydroxy, 10,11-di-O-de-Me, 11-ketone, Soraphen A; 12ξ,13ξ-Epoxide, 11-O-de-Me, Soraphen A; 8ξ-Hydroxy, Soraphen A; 20-Hydroxy, 11-O-de-Me, Soraphen A; 8ξ-Hydroxy, 10-O-de-Me, Soraphen A; 8ξ-Hydroxy, 11-O-de-Me, Soraphen A; 3"-Hydroxy, di-O-de-Me, Soraphen A; 8ξ-Hydroxy, stereoisomer (?), Soraphen A; 8ξ-Hydroxy, stereoisomer(?), Soraphen A; 12-Methoxy(Z-), 11-O-de-Me, Soraphen A; Stereoisomer (?), Soraphen R, Soraphen R; 10,11-Di-Me ether, Soraphen R; 10-Me ether, Sorbistin D, Sorbistin D; 4'-N—Ac, Sorbistin D; 4'-N-Butanoyl, Sorbistin D; 4'-Deamino, 4'-hydroxy, Sorbistin D; 4'-N-Propanoyl, Sorbose; L-form, Sorbose dehydrogenases, Sorbose dehydrogenase-form, SP 127, SP 2259, Sperabillin C, Sperabillin C; 4'Z-Isomer, Sperabillin D, Sperabillin D; 4Z-Isomer, Spergualin, Spergualin; 15-Deoxy, Spermidine, Spermidine; N,N"-Bis(2,3-dihydroxybenzoyl), Spermidine dehydrogenase, Spermidine synthase, SPF 1010, SPF 140, SPF 100 FI, SPF 100 FII, SPF PCO 20, SPF PCO 30, Spheroidene, Spheroidene; (15Z, 15'Z)-form, Spheroidene; O-De-Me, Spheroidene; 11',12'-Dihydro, Spheroidene; 3,4,11',12'-Tetrahydro, Spheroidenone, Spheroidenone; O-De-Me, Spheroidenone; 1',2'-Dihydro, 1'-hydroxy, Sphingomyelin phosphodiesterase D, Spirangien A, Spirangien B, Spirillomycin; Spirillomycin 1655, Spirillomycin; Spirillomycin 1309 b, Spirobrassinol; Me ether, N-methoxy, Spirobrassinol; N-Methoxy, Spirodienal, Spirodienal; 4E-Isomer, Spirodienal B, Spiruchostatin A, Spiruchostatin B, SpoIVB peptidase, 13,15-Spongianediol; 13α-form, Sporacuracin A, Sporacuracin B, Sporamycin, Sporangirosomycin, Sporaviridin; Sporaviridin A1, Sporaviridin; Sporaviridin A1, 4D-Deoxy, 4D-amino, Sporaviridin; Sporaviridin A1, 6D-Hydroxy, Sporaviridin; Sporaviridin A2, Sporaviridin; Sporaviridin A2, 4D-Deoxy, 4D-amino, Sporaviridin; Sporaviridin A2, 6D-Hydroxy, Sporocuracin A, Sporocuracin B, Sporulene A, Sporulene A; 16,17-Dihydro, 17α-hydroxy, Sporulene A; Δ15-Isomer, Sporulene A; Δ17(35)-Isomer, Sporulene A; 16,17,24,27-Tetrahydro, 17α-hydroxy, Spoxazomicin A, Spoxazomicin A; 2-Epimer, SSL 91 Lectin, Stacopin P1, Stacopin P1; 4-Hydroxy, Stalobacin, Staphopain, Staphylococcal acid glycoprotein, Staphylococcins, Staphylococcins; Staphylococcin 414, Staphylococcins; Staphylococcin 462, Staphylococcins; Staphylococcin A, Staphylococcins; Staphylococcin Au-26, Staphylococcins; Staphylococcin BacR1, Staphylococcins; Staphylococcin C55, Staphyloferrin A, Staphyloferrin B, Staphylokinase, Starch synthase, Staurosporine; 5'α-Hydroxy, Staurosporine; 5'α-Hydroxy, N-Me, Staurosporine; 10-Methoxy, Staurosporinone, Staurosporinone; N13-(α-L-Rhamnopyranosyl), Steffimycin, Steffimycin; (Deglycosyloxy), 2-demethoxy, 10ξ-alcohol, Steffimycin; 2-Demethoxy, 10ξ-alcohol, Stellalysin, D-Stereospecific aminopeptidase, Stewartan, Stigmatellin A, Streptimidone, Streptin, Streptindole, Streptindole; O-De-Ac, O-butanoyl, Streptindole; Deacetoxy, Streptococcin A-M49, Streptococcin A-M57, Streptococcin Sal P, Streptodornase, Streptokinase, Streptomodulin, Streptomycin 3"-adenylyltransferase, Streptonigrin; N7-(1-Methyl-2-oxopropyl), Streptopain, Streptothricin; Streptothricin F, N5-Me, Strevertenes; Strevertene A, Strevertenes; Strevertene B, Strevertenes; Strevertene C, Strevertenes; Strevertene D, Strevertenes; Strevertene E, Strevertenes; Strevertene E, 7-Deoxy, 9-hydroxy, Strevertenes; Strevertene F, Sublancin 168, Subpeptin JM4, Subsporin A, Subsporin B, Subsporin C, Subtenolin, Subtilin, Subtilin; 6-Valine, 15-valine, 24-isoleucine, 29-histidine analogue, Subtilisins; Subtilisin BPN1, Subtilisins; Subtilisin Carlsberg, Subtilisins; Subtilisin ISP, Subtilosin A, Subtulene A, Succinamopine; (2R,2'S)-form, Succinamopine; (2S,2'S)-form, Succinate-citramalate CoA-transferase, Succinic acid, Succinic acid; Diamide, Succinoglycan, Succinopyoverdin 18.1, Succinopyoverdin G173, N-Succinylarginine dihydrolase, Succinyl-CoA:(R)-2-benzylsuccinate CoA-transferase, Succinyl-diaminopimelate transaminase, Sucrose:1,6-α-glucan 3(6)-α-D-glucosyltransferase, Sucrose phosphorylase, Sugar-phosphatase, Sugar-terminal-phosphatase, Sulcatone reductase, Sulfate adenylyltransferase, Sulfate adenylyltransferase (ADP), Sulfazecin, Sulfazecin; 2'-Epimer, Sulfite dehydrogenases; Sulfite dehydrogenase, Sulfite reductases; Sulfite reductase, Sulfite reductases; Sulfite reductase (NADPH), Sulfoacetaldehyde acetyltransferase, 4-Sulfobenzoate 3,4-dioxygenase, N-Sulfoglucosamine-3-sulfatase, Sulfolobusquinone, Sulfur dioxygenase, Sulfur reductase, Superoxide reductase, Surfactin, Surfactin; Surfactin B1, 4-L-Alanine analogue, Surfactin; Surfactin B2, 4-L-Alanine analogue, Surfactin; Surfactin B2, 1-Me ester, Surfactin; Surfactin C1, Surfactin; Surfactin C1, 4-L-Alanine analogue, Surfactin; Surfactin C1, 7-L-Isoleucine analogue, Surfactin; Surfactin C1, 7-L-Valine analogue, Surfactin; Surfactin C2, 4-L-Alanine analogue, Surfactin; Surfactin C2, 7-L-Valine analogue, 1-Me ester, Surfactin; Surfactin C2, 1-Me ester, Sutilains, Synpron, Syringacins, Syringacins; Syringacin 4A, Syringacins; Syringacin W1, Syringafactin A, Syringolide 1, Syringolide 2, Syringolide 3, Syringolin A, Syringolin A; 2,3-Dihydro, Syringolin C, Syringolin D, Syringolin D; 2,3-Dihydro, Syringolin F, Syringomycin, Syringopeptin 22A, Syringopeptin 25A, Syringopeptin 25A; 25-L-Phenylalanine analogue, Syringopeptin 22B, Syringopeptin 25B, Syringopeptin SC 1, Syringopeptin SC 2, Syringostatin, Syringostatin; Syringostatin A, 3-Glycine analogue, Syringostatin; Syringostatin F, 3-Glycine analogue, Szentiamide, Tabtoxin, Tagatose; D-form, Tagatose kinase, Tagatose 6-phosphate kinase, Tagetitoxin, Taitomycin, Takanawaenes; Takanawaene C, Tallysomycin; Tallysomycin A, Tallysomycin; Tallysomycin S1a, Tallysomycin; Tallysomycin S1a, Nω-Me, Tallysomycin; Tallysomycin S1a, Nω-(1-Phenylethyl), Tallysomycin; Tallysomycin S1a, Nω-(2-Hydroxyethyl), Tallysomycin; Tallysomycin S10a, Tallysomycin; Tallysomycin S2a, Tallysomycin; Tallysomycin S1b, Tallysomycin; Tallysomycin S1b, Nω,Nω-Di-Me, Tallysomycin; Tallysomycin S1b, Nω-(1-Phenylethyl), Tallysomycin; Tallysomycin S1b, Nω-Me, Tallysomycin; Tallysomycin S1b, Nω,Nω-Bis(2-hydroxyethyl), Tallysomycin; Tallysomycin S1b, Nω-(2-Hydroxyethyl), Tallysomycin; Tallysomycin S10b, Tallysomycin; Tallysomycin S12b, Tallysomycin; Tallysomycin S13b, Tallysomycin; Tallysomycin S2b, Tallysomycin; Tallysomycin S3b, Tallysomycin; Tallysomycin S3b, Nω-(2-Hydroxyethyl), Tallysomycin; Tallysomycin S3b, Nω-(2-Hydroxypropyl), Tallysomycin; Tallysomycin S4b, Tallysomycin K1, Tallysomycin K2, Tallysomycin K3, Tallysomycin K4, Tallysomycin K5, Tambjamine A; 1"-N-(3Z-Dodecenyl), TAN 1057A, TAN 1057A; 5-Epimer, Tartrolone A1, Tartrolone A1; Stereoisomer (1), Tartrolone A1; Stereoisomer (2), Tartrolone B, Tatiopterin, Tatiopterin 1, Tatiopterin; Tatiopterin O, Tatiopterin; Tatiopterin O, 2',5'-Dihydroxy, Tatumine, Tauramamide, Taurine dioxygenase, Taurine transaminases; Taurine 2-oxoglutarate transaminase, Taurine transaminases; Taurine pyruvate aminotransferase, Tecogalan, Teicoplanin, Teicoplanin; Teicoplanin A2-2, 15-Deamino, 15-oxo, Teicoplanin; Teicoplanin A2-3, 15-Deamino, 15-oxo, Teicoplanin; Teicoplanin A2-3, 4',5'Z-Didehydro, 15-deamino, 15-oxo, Teicoplanin; Teicoplanin A2-4, 15-Deamino, 15-oxo, Teicoplanin; Teicoplanin A2-5, 15-Deamino, 15-oxo, Teleocidin B1; 16,19-Diepimer, Teleocidin B1; 16-Epimer, Teleocidin B1; 19-Epimer, Teleocidin B1; 16-Epimer, N-de-Me, Teleocidin B1; 16-Epimer, Me ether, Teleocidin B1; Me ether, Tenacibactin B, Tenacibactin B; Me ester, Tenacibactin C, Tenacibactin D, Terephthalate 1,2-dioxygenase, [3,2':2(3'H),3"-Ter-1H-indol]-3'-one, [3,3':3'(2'H),3"-Ter-1H-indol]-2-one, Tetanolysin, 3,3',5,5'-Tetraacetyl-2,2',4,4',6,6'-hexahydroxydiphenylmethane, 4,8,12,16-Tetraazanonadecane-1,19-diamine, 2,3,5,7-Tetrabromo-1H-benzofuro[3,2-b]pyrrole, 3,3',5,5'-Tetrabromo[1,1'-biphenyl]-2,2'-diol, 3,3',5,5'-Tetrabromo[1,1'-biphenyl]-2,2'-diol; 3-Debromo, 2,3,4,5-Tetrabromo-1H-pyrrole, Tetrachloroethene reductive dehalogenase, 5-Tetradecenoic acid; (Z)-form, 3,3',4,4'-Tetradehydro-1',2'-dihydro-1'-hydroxy-β,ψ-carotene; O-β-D-Glucopyranoside, 3,3',4,4'-Tetradehydro-1',2'-dihydro-1'-hydroxy-β,ψ-caroten-2-one; O-β-D-Glucopyranoside, 3,3',4,4'-Tetradehydro-1,1',2,2'-tetrahydro-ψ,ψ-carotene-1,1'-diol, 3,3',4,4'-Tetradehydro-1,1',2,2'-tetrahydro-ψ,ψ-carotene-1,1'-diol; 3,4-Dihydro, di-Me ether, 3,3',4,4'-Tetradehydro-1,1',2,2'-tetrahydro-ψ,ψ-carotene-1,1'-diol; 3,4-Dihydro, 1'-Me ether, 3,3',4,4'-Tetradehydro-1,1',2,2'-tetrahydro-ψ,ψ-carotene-1,1'-diol; O-β-D-Glucopyranoside, 3,3',4,4'-Tetradehydro-1,1',2,2'-tetrahydro-ψ,ψ-carotene-1,1'-diol; O-[11-Methyldodecanoyl-(→6)-β-D-glucopyranoside], 3,3',4,4'-Tetradehydro-1,1',2,2'-tetrahydro-ψ,ψ-carotene-1,1'-diol; Mono-Me ether, 3,3',4,4'-Tetradehydro-1,1',2,2'-tetrahydro-ψ,ψ-carotene-1,1'-diol; O-(Tetradecanoyl-(→6)-β-D-glucopyranoside) 3,3',4,4'-Tetradehydro-1,1',2,2'-tetrahydro-ψ,ψ-carotene-1,1'-diol; 3,4,7,8-Tetrahydro, 1'-Me ether, Tetraethylene glycol; Di-Me ether, 1,1',2,2'-Tetrahydro-1,1'-dihydroxy-ψ,ψ-carotene-4,4'-dione; 1,1'-Bisdeoxy, 2,2'3,3'-tetradehydro, 1,1',2,2'-Tetrahydro-1,1'-dihydroxy-ψ,ψ-carotene-4,4'-done; Di-Me ether, 1,1',2,2'-Tetrahydro-1,1'-dihydroxylycopene, 3,4,5,10-Tetrahydro-5,10-dioxo-2H-naphtho[2,3-b]-1,4-thiazine-3-carbonyllysylvalylleucylarginylarginylhistidine, Tetrahydrodipicolinate N-acetyltransferase, 1,1',2,2'-Tetrahydrolycopene, 1,2,7,8-Tetrahydrolycopene, 7,8,11,12-Tetrahydrolycopene, 1,2,3,4-Tetrahydro-4-methoxy-2-methyl-8-quinolinecarboxylic acid; (2RS,4RS)-form, Tetrahydro-5-methyl-6-(1-methylbutyl)-3-(2-methylpropyl)-2H-pyran-2-one; (1'S,3S,5R,6R)-form, 1,4,5,6-Tetrahydro-2-methyl-4(6)-pyrimidinecarboxylic acid; (S)-form, 2,3,8,8a-Tetrahydro-3a-nitro-1H-pyrrolo[2,3-b]indole, 3,4,5,6-Tetrahydro-2-pyridinecarboxylic acid, 2,3,4,5-Tetrahydropyridine-2,6-dicarboxylate N-succinyltransferase, 3,3',4,4'-Tetrahydrospirilloxanthin-20-al, 2,2',3,3'-Tetrahydroxy-β,β-carotene-4,4'-dione, 2,2',3,3'-Tetrahydroxy-β,β-carotene-4,4'-dione; 4'-Deoxy, 2,2',3,3'-Tetrahydroxy-β,β-carotene-4,4'-dione; 4'-Deoxo, 2-deoxy, 3-O-sulfate, 2,2',3,3'-Tetrahydroxy-β,β-carotene-4,4'-dione; 4'-Deoxo, 3'-O-sulfate, 1,3,5,6-Tetrahydroxy-2-methylanthraquinone; 3,5-Di-Me ether, 1,3,5,6-Tetrahydroxy-2-methylanthraquinone; 5-Me ether, 2,5,7,8-Tetrahydroxy-1,4-naphthoquinone; 2,7-Di-Me ether, 29-(2,3,4,5-Tetrahydroxypentyl)-6,11-hopadiene; (32R,33R,34S)-form, 29-(2,3,4,5-Tetrahydroxypentyl)-6-hopene; (32R,33R,34R)-form, 29-(2,3,4,5-Tetrahydroxypentyl)-6-hopene; (32R,33R,34S)-form, 29-(2,3,4,5-Tetrahydroxypentyl)-6-hopene; (32R,33R,34S)-form, 35-Me ether, 11,17,20,21-Tetrahydroxypregn-4-en-3-one; (11β,17αOH,20R)-form, 2-(3,7,11,15-Tetramethyl-2,6,10,14-hexadecatetraenyl)benzene, 2,2,3,4-Tetramethylpentane, Tetramethylpyrazine, 3,3,7,7-Tetramethyl-1,2,5,6-tetrathiocane, 3,3,8,8-Tetramethyl-1,2,5,6-tetrathiocane, 3,3,6,6-Tetramethyl-1,2,5-trithiepane, 3,3,7,7-Tetramethyl-1,2,5-trithiepane, 4,4,6,6-Tetramethyl-1,2,5-trithiepane, Tetraprenyl-ar-curcumene, Tetraprenyl-ar-curcumene; 1,4-Dihydro, Tetraprenyl-β-curcumene, Tetraprenyl-β-curcumene; 1,4-Didehydro, Tetrenolin, Tetrocarcin A, Tetrocarcin A; 4A-De-Ac, 4A-(2-methylpropanoyl), Tetrocarcin A; 4A-Deacetoxy, 4A,5A-didehydro, 6A-aldehyde, Tetrocarcin A; 3A-Deglycosyl, Tetrocarcin A; 3A-Deglycosyl, 4A-de-Ac, 3A-Ac, Tetrocarcin A; Aglycone, Tetrocarcin A; 32-Alcohol, Tetrocarcin A; 4B,9-Dideglycosyl, 3B-hydroxy, 4B—Ac, Tetrocarcin A; 3B-Hydroxy, Tetrocarcin A; 3B-Hydroxy, 4B-deglycosyl, 4B—Ac, Tetrocarcin A; 4B-Hydroxy, 4C-deglycosyl, Tetrocarcin A; 32-Carboxylic acid, Tetrocarcin A; 4C-Deglycosyl, Tetrocarcin A; 23-Deformyl, 22,23-dihydro, Tetrocarcin A; 22,23-Dihydro, Tetrocarcin A; 3E-Denitro, 3E-amino, Tetrocarcin A; 3E-Denitro, 3E-amino, 4A-de-Ac, 4A-(2-methylpropanoyl), Tetrocarcin C, Tetrocarcin D, Tetrodotoxin, TF 130, TF 2, TF 300, Thailandamide A, Thailandamide A;

Stereoisomer, Thailandamide lactone, Thalassospiramide A, Thalassospiramide B, Thalassospiramide B; 4,7-Hydroxy, Thallusin, Thermitase, Thermocins, Thermocins; Thermocin 93, Thermoleovorin; Thermoleovorin NR 9, Thermoleovorin; Thermoleovorin S2, Thermolysin, Thermophilins; Thermophilin 1, Thermophilins; Thermophilin 110, Thermophilins; Thermophilin 1277, Thermophilins; Thermophilin 13, Thermophilins; Thermophilin 347, Thermophilins; Thermophilin 580, Thermophilins; Thermophilin 81, Thermophilins; Thermophilin 9, Thermophilins; Thermophilin A, Thermophilins; Thermophilin T, Thermorubin, Thermothiocin, Thiamine kinase, Thiamine phosphate diphosphorylase, Thiamine phosphate kinase, Thiangazole, Thiazocin A, Thiazocin B, 2,2'-Thiobis[7-hydroxy-2,4,6-cycloheptatrien-1-one], Thiobutacin, Thiochondrilline A, Thiochondrilline A; Conformational isomer, Thiochondrilline C, Thiocillin I; 34-Deoxy, 2-ketone, 26-Me ether, Thiocillin I; 34-Deoxy, 26-Me ether, Thiocillin I; 2-Ketone, Thiocillin I; 2-Ketone, 26-Me ether, Thiocillin I; 26-Me ether, Thiocoraline, Thiocoraline; 22-Deoxy, Thiocoraline; 17-S-Oxide, Thioformin, Thioglucosidase, Thiolstatin, Thiomarinol A, Thiomarinol A; 4-Deoxy, Thiomarinol A; 4,6-Dideoxy, 8-hydroxy, Thiomarinol A; 1″,1″-Dioxide, Thiomarinol A; 13-Ketone, Thiomarinol D, Thiomarinol E, Thiomarinol H, Thiomarinol H; 4-Deoxy, Thiomarinol H; Homologue (n=2), Thiomuracin C, Thiomuracin C; 45-Deoxy, Thiomuracin C; 83ξ,84-Dihydroxy, Thiomuracin C; 83ξ,84-Epoxide, Thiomuracin C; 83ξ-Hydroxy, Thiomuracin C; 84-Hydroxy, Thiomuracin C; 83-Oxo, Thiomuracin C; 83-Oxo, 84-hydroxy, Thiomuracin I, Thiophene-2-carbonyl-CoA monooxygenase, Thiosporamicin, Thiostrepton; 26-Thione, 1,2R-dihydro, Thiosulfate-dithiol sulfurtransferase, Thiosulfate sulfurtransferase, Thiosulfate-thiol sulfurtransferase, Thiothece 425, Thiothece 460, Thiothece 474, Thiothece 484, Thiothece-OH 484, Thiotropocin, 4-Thiouridine, Threonate 3-dehydrogenase, Thuggacin A, Thuggacin A; 13-Methyl, Thuggacin B, Thuggacin C, Thuggacin Cmc-A, Thuggacin Cmc-A; 17-Deoxy, Thuggacin Cmc-A; 32-Deoxy, Thuggacin Cmc-A; 17,32-Dideoxy, Thuggacin Cmc-A; (1→17)-Lactone isomer, Thuggacin Cmc-A; (1→18)-Lactone isomer, Thuricin CD, Thuricins, Thuricins; Thuricin 439, Thuricins; Thuricin 7, Thuricins; Thuricin S, Thuricin H, Thuringiensin, Thuringiensin; 6→3-Lactone, Thymidine 5'-diphosphate rhamnose, Thymidine phosphorylase, Thymidylate 5'-phosphatase, Thymidylate synthases; Thymidylate synthase, Tilivalline, T2-induced deoxynucleotide kinase, TM 64; (S)-form, TM 64; (S)-form, 1″-N—Ac, TM 64; (ξ)-form, 1″-N-Propanoyl, Tochicin, Tolaasin, Tolaasin; Tolaasin I, Ring-opened form, Toluene dioxygenase, Tolworthcin 524, Tomicid, Topostatin, Topostin B553, Topostin D 640, Topostin D654, Toxymycin, Trehalamine, Trehalamine; N2-β-D-Glucopyranosyl, 3-Trehalosamine, Trehalose 6-phosphate phosphorylase, α,α-Trehalose phosphate synthases, α,α-Trehalose; 6,6'-Bis-O-(2,4-dihydroxy-6-methylbenzoyl), Triacetate-lactonase, 2,4,6-Triacetyl-1,3,5-benzenetriol, 4,8,12-Triazapentadecane-1,15-diamine, 1,3,5-Triazine, 2,2,3-Tribromo-4,4'-biphenyldicarboxylic acid, 2,4,4'-Trichloro-2'-hydroxydiphenyl ether, Trichrysobactin (cyclic), Trichrysobactin (linear), 5-Tricosyl-1,3-benzenediol, Tridecaptin A, Tridecaptin B, Tridecaptin C, 2,3,6-Trideoxy-3-dimethylamino-ribo-hexose; L-form, Trifolitoxin, Trihexocin, 2',4',6'-Trihydroxyacetophenone, 1,3,8-Trihydroxyanthraquinone, 1,3,8-Trihydroxyanthraquinone; 1,3-Di-Me ether, 1,3,8-Trihydroxyanthraquinone; 3,8-Di-Me ether, 1,3,8-Trihydroxyanthraquinone; 1-Me ether, 1,4,5-Trihydroxyanthraquinone, 1,4,6-Trihydroxyanthraquinone; 4-Me ether, 3,4,5-Trihydroxybenzoic acid; Dodecyl ester, 3,4,5-Trihydroxybenzoic acid; Octyl ester, 3,4,5-Trihydroxybenzoic acid; Propyl ester, 3,7,12-Trihydroxycholan-24-oic acid; (3α,5α,7α,12α)-form, Me ester, 2,3,4-Trihydroxy-2,4,6-cycloheptatrien-1-one; 3,4-Di-Me ether, 3,4,6-Trihydroxy-1,2-dimethylcarbazole; 3,6-Di-Me ether, 3,4,6-Trihydroxy-1,2-dimethylcarbazole; Tri-Me ether, 3,4',7-Trihydroxyisoflavanone; (R)-form, 4',5,7-Trihydroxyisoflavone, 4',5,7-Trihydroxyisoflavone; 3',5'-Dinitro, 4',5,7-Trihydroxyisoflavone; 3'-Nitro, 4',7,8-Trihydroxyisoflavone; 7-O-α-D-Arabinofuranoside, 6,7,8-Trihydroxy-3-methyl-1H-2-benzopyran-1-one; 7-Me ether, 1,6,10-Trihydroxy-8-methyl-5,12-naphthacenedione, 2,3,5-Trihydroxy-6-methylpyridine, 2,5,8-Trihydroxy-1,4-naphthoquinone, 9,12,13-Trihydroxy-10,15-octadecadienoic acid; (9S,10E,12R,13S,15Z)-form, 3,4,5-Trihydroxy-2-pentanone; (3S,4R)-form, 2,3,9-Trihydroxy-1-phenazinecarboxylic acid, 2,3,7-Trihydroxy-1,6-phenazinedicarboxylic acid, 3,17,21-Trihydroxypregnane-11,20-dione; (3α,5β)-form, 4-(1,2,3-Trihydroxypropyl)-2(5H)-furanone; 3'-Hexanoyl, 4-(1,2,3-Trihydroxypropyl)-2(5H)-furanone; 3-Octanoyl, 1,1,3-Tri-(1H-indol-3-yl)butane; (ξ)-form, 1,1,1-Tri-(1H-indol-3-yl)ethane Tri-1H-indol-3-ylmethane, Trimethylamine N-oxide reductases; Trimethylamine-N-oxide reductase, 2-(3,7,11-Trimethyl-2,6,10-dodecatrienyl)-1H-indole; (E,E)-form, Trimethyloxazole, Trimethylpropylpyrazine, Trimethylsulfonium-tetrahydrofolate N-methyltransferase, 3,5,7-Trioxooctacosanoic acid, Tripeptide aminopeptidase, Triphosphoribosyl-dephospho-CoA synthase, Tripropeptin, Tris(3-aminopropyl)amine, Tris(3-aminopropyl)amine; N-(3-Aminopropyl), 2,3,5-Tris(methylthio)-1,4-benzenediol, 2,3,5-Tris(methylthio)-1,4-benzenediol; 6-(Methylthio), 2,3,5-Tris(methylthio)-1,4-benzenediol; 1,4-Quinone, 2,3,5-Tris(methylthio)-1,4-benzenediol; 1,4-Quinone, 6-(methylthio), Trivanchrobactin, tRNA isopentenyltransferase, tRNA methyltransferases; tRNA (cytosine-5)-methyltransferase, tRNA methyltransferases; tRNA (guanine-N1)-methyltransferase, tRNA methyltransferases; tRNA (guanine-N7)-methyltransferase, tRNA methyltransferases; tRNA guanosine-2'-O-methyltransferase, tRNA methyltransferases; tRNA (5-methylaminomethyl-2-thiouridylate)-methyltransferase, tRNA methyltransferases; tRNA (uracil-5)-methyltransferase, tRNA nucleotidyltransferase, tRNA sulfurtransferase, tRNA-uridine aminocarboxypropyltransferase, Tropinesterase, Tropodithietic acid, Tropolone, Troposulfenin, Troposulfenin; 8-S-Me, Tryptamine; Nb-Ac, Tryptamine; Nb-Di-Ac, Tryptamine; Nb-(2S-Hydroxy-3S-methylpentanoyl), Tryptamine; Nb-(3-Methylbutanoyl), Tryptamine; Nb-(3-Methyl-2-oxopentanoyl), Tryptophan; (S)-form, Nα-(9Z-Hexadecenoyl), Tryptophan; (S)-form, Nα-Hexadecanoyl, Tryptophan α,β-oxidase, Tryptophan oxygenases; Tryptophan 2-dioxygenase, Tryptophan oxygenases; Tryptophan 2-monooxygenase, Tryptophan transaminases; Tryptophan phenylpyruvate transaminase, Tryptophan transaminases; Tryptophan transaminase, Tubercidin, Tubulysins; Tubulysin A, Tubulysins; Tubulysin A, 4'-Deoxy, Tubulysins; Tubulysin B, 4'-Deoxy, Tubulysins; Tubulysin C, Tubulysins; Tubulysin C, 4'-Deoxy, Tubulysins; Tubulysin G, Tubulysins; Tubulysin I, Tubulysins; Tubulysin I, 4'-Deoxy, Turnagainolide A, Turnagainolide A; 15-Epimer, Tuscolide, Tuscorone B, Tuscorone B; 17-Deoxy, 17,18-didehydro, TV 110, TV 130, Tylosin B; 4A-Deoxy, 12α,13-dihydro, 20-alcohol, Tylosin B; 4A-Deoxy, 12α,13α-epoxide, 20-alcohol, Tylosin B; 20-Deoxo, 4A-deoxy, Type III site-specific deoxyribonuclease, Type II site-specific deoxyribonuclease, Type I site-specific deoxyribonuclease, Typhimuricin, Tyrocidine; 5-L-Lysinetyrocidine A, Tyrocidine; Tryptocidine A, Tyrocidine; Tryptocidine B, Tyrocidine; Tyrocidine A, Tyrocidine; Tyrocidine B, Tyrocidine; Tyrocidine B1, Tyrocidine; Tyrocidine C, Tyrocidine; Tyrocidine C1, Tyrocidine; Tyrocidine D, Tyrocidine; Tyrocidine E, Tyrosylvalylprolylleucine, Tyrothricin, Ubericin A, Uberolysin, UDP-2-acetamido-4-amino-2,4,6-trideoxyglucose transaminase, UDP-N-acetylglucosamine 1-carboxyvinyltransferase, UDP N-acetylglucosamine diphosphorylase, UDP-N-acetylmuramoylpentapeptide-lysine N6-alanyltransferase, UDP glucose hexose 1-phosphate uridylyltransferase, Ulbactin A, Ulbactin B, Ulbactin C, Ulbactin D, Ulbactin E, Ulceracin 378, UMP kinase, 14,22, 26,29,33,41,50,58,62,65,69-Undecamethyl-8,11,44,47-tetraoxahexacyclo[68.2.1.12,5.118,21.134,37.154,57]heptaheptacontane-10,46-dimethanol, Undecaprenol kinase, Undecaprenyldiphosphomuramoylpentapeptide β-N-acetylglucosaminyltransferase, Undecaprenyl-phosphate galactose phosphotransferase, Undecaprenyl-phosphate mannosyltransferase, Undecylprodigiosin, Unnarmicin A, Unnarmicin C, Uracil phosphoribosyltransferase, Ureidoglycolate dehydrogenase, Ureidoglycolate hydrolase, Uridine diphosphate mannose, Uridine kinase, Uridine phosphorylase, Urocanic acid; (E)-form, Uronate dehydrogenase, Uroporphyrin III, Uroporphyrinogen-Ill C-methyltransferase, Urukthapelstatin A, UTP glucose 1-phosphate uridylyltransferase, UTP hexose 1-phosphate uridylyltransferase, Valindolmycin, Valine transaminases; Valine pyruvate transaminase, Valylleucylprolylvalylprolylglutamine, Valylprolylisoleucine; L-L-L-form, Valylprolylleucine; L-L-L-form, Vanchrobactin, Vanillate monooxygenase, Variacin, Venturicidin B; 17-Hydroxy, 3'-carbamoyl, Verdamicin, Verdamicin; 1-N-Et, Verdamicin; 6'-N-Me, Vibriobactin, Vibriobactin; 3',3"-Dideoxy, Vibriocins, Vibrioferrin, Vicibactin, Vicibactin; N-De-Ac, Victomycin, Viilian, 1-Vinyl-β-carboline-3-carboxylic acid, Violacein, Violacein; Deoxy, Violacein; 3,3'-Dihydro, Violacein; 5-Hydroxy, Vioprolide A, Vioprolide B, Vioprolide C, Vioprolide D, Viridicin, Viridins; Viridin A, Viridins; Viridin B, Viridins; Viridin C, Viriplanin, Viscosin, Viscosin; 5-D-Leucyl epimer, Viscosinamide, Vitamin B12, Vitamin B12f; 176-Demethyl, Vitamin B12 monocarboxylic acid, Vitamin K2; Vitamin K2(40), Vomifoliol 4'-dehydrogenase, Vulnificin, Warnericin RB4, Warnericin RK, Warnerin, Warnerin, Weissellicins; Weissellicin 110, Weissellicins; Weissellicin M, Weissellicins; Weissellicin N23, Weissellicins; Weissellicin Y, Weissellin A, Welan, Xaa-Pro aminopeptidase, Xaa-Pro dipeptidase, Xaa-Pro dipeptidyl peptidase, Xaa-Xaa-Pro tripeptidyl peptidase, Xanthacin, Xanthan, Xanthellin, Xanthine oxidoreductases; Xanthine dehydrogenase, Xanthine phosphoribosyltransferase, Xanthobacidin, Xanthomonadin I, Xanthomonalisin, Xanthosine, Xanthotoxin, Xenematide A, Xenocoumacin 1, Xenocoumacin 2, Xenorhabdicin, Xenortide A, Xenortide B, Xenortide C, Xerosin, X-His dipeptidase, endo-1,4-β-Xylanase, Xylan endo-1,3-β-xylosidase, Xylan α-1,2-glucuronosidase, Xylan 1,3-β-xylosidase, Xylan 1,4-β-xylosidase, Xylitol kinase, Xylocandin, Xyloglucan-specific exo-β-1,4-glucanase, Xylono-1,4-lactonase, Xylose; D-form, 2,3-Di-Ac, Xylulokinase; D-form, Xylulokinase; L-form, Yersiniabactin, Yersiniose, YM 254890, YM 254890; 3"-O-Deacyl, YM 254891, YM 254892, YM 47141, YM 47142, Zafrin, Zanflo, Zeamine, Zeatin; (E)-form, 9-(2-Deoxy-β-D-ribofuranosyl), Zeatin; (E)-form, 2-Hydroxy, Zeatin; (E)-form, Deoxy, Zeatin; (E)-form, 7,3'-Dihydro, 9-β-D-ribofuranosyl, Zeatin; (Z)-form, Zeaxanthin; (3R,3'R, all-E)-form, 3-O-[11-Methyldodecanoyl-(→6)-β-D-glucopyranoside], Zeaxanthin; (3R,3'R, all-E)-form, 3-O-[13-Methyltetradecanoyl-(→6)-β-D-glucopyranoside], Zeaxanthin; (3R,3'R, all-E)-form, 3-O-[15-Methylhexadecanoyl-(→6)-β-D-glucopyranoside], Zeaxanthin; (3R,3'R, all-E)-form, 3,3'-Bis-O-[11-methyldodecanoyl-(→6)-β-D-glucopyranoside], Zeaxanthin; (3R,3'R, all-E)-form, 3-O-[11-Methyldodecanoyl-(→6)-β-D-glucopyranoside], 3'-O-[13-methyltetradecanoyl-(→6)-β-D-glucopyranoside], Zeaxanthin; (3R, 3'R, all-E)-form, 3,3'-Bis[13-methyltetradecanoyl-(→6)-β-D-glucopyranoside], Zeaxanthin; (3R,3'R, all-E)-form, Di-O-α-L-rhamnopyranoside, Zeaxanthin; (3R,3'R, all-E)-form, 3-O-α-L-Rhamnopyanoside, Zinc D-Ala-D-Ala carboxypeptidase, and Zoocin A.

In some embodiments, the desired compound is as listed below. In some embodiments, the desired compound is as listed below and obtainable from an *Actinomycetes*. Desired compounds include 1-(2-Acetamidophenyl)-2-hydroxy-1-propanone, Acetylesterase, Actinoidin; Actinoidin A, Actinoidin; Actinoidin A2, Actinoidin; Actinoidin B, Adenosine; 3-(Butyl hydrogen phosphate), Adenosine kinase, Aladapcin, Alkene monooxygenase, Altromycin A, Altromycin A; 2C-Deoxy, Altromycin A, 2C-Deoxy, N-Me, Altromycin A, N-De-Me, Altromycin A; 13-Deoxy, Altromycin A; 13-Deoxy, N-Me, Altromycin A; N-Me, Altromycin H, Altromycin H; N-Me, Amamistatin A, Amamistatin A; Demethoxy, 4-Amino-4,6-dideoxy-3-C-methylmannose; L-form, 2-Me, 4-Amino-4,6-dideoxy-3-C-methylmannose; L-form, 2-Me, N-(2-methoxypropanoyl), 2-Amino-3-hydroxybutanoic acid; (2R,3R)-form, 2-Amino-1,4-naphthoquinone, 2-Amino-1-(4-nitrophenyl)-1,3-propanediol; (1R,2R)-form, N—Ac, 2-Amino-1-(4-nitrophenyl-1,3-propanediol; (1R, 2R)-form, N-Propanoyl, 2-Amino-1-(4-nitrophenyl)-1,3-propanediol; (1R,2R)-form, N-(2-Methylpropanoyl), 2-Amino-3-oxo-3H-phenoxazine-1-carboxylic acid, 2-Amino-6-(1,2,3,4,5-pentahydroxypentyl)-4(1H)-pteridinone; 2'-O-β-D-Glucuronopyranoside, 2-Amino-3H-phenoxazin-3-one, 2-Amino-3H-phenoxazin-3-one; N-Me, Antibiotic 2326, Antibiotic 446, Antibiotic 1294B2, Antibiotic BE 32030, Antibiotic C 521C, Antibiotic 0089D, Antibiotic L 660631; (1'R,4S,5R)-form, Antibiotic LC 1202, Antibiotic LL-BM 123α, Antibiotic LL-BM 547β, Antibiotic M 3, Antibiotic M 4, Antibiotic PC 766B, Antibiotic PC 766B; 19-Me ether, Antibiotic SF 2457, Antibiotic YL 01641P-B2, Antibiotic YL 01641P-B2; 9-Ac, Antibiotic YL 01641P-B2; 1-Deoxy, 4-Me ether, 9-Ac, Antibiotic YL 01641P-B2; 4-Me ether, Antibiotic YL 01641P-B2; 4-Me ether, 9-Ac, α-D-Arabinofuranosyl-(1→5)-α-D-arabinofuranosyl-(1→5)-D-arabinose, α-D-Arabinofuranosyl-(1→5)-[β-D-galactofuranosyl-(1→6)]-D-galactose, N2-Asparaginyl-N2-hydroxyasparagine, Aspartyltransferase, Asterobactin, Avimycolic acid I; Me ester, Bacteriocin 14468, Benzanthrin A, Benzanthrin A; 4'-Epimer, Brasilicardin A, Brasilicardin A; 4'-Deacyl, 3'-deglycosyl, Brasilicardin A; 16-Demethoxy, Brasilicardin A; 16-Demethoxy, 4'-deacyl, 3'-deglycosyl, Brasilidine A, Brasilinolide aglycone; 37-O-(2,6-Dideoxy-α-D-lyxo-hexopyranoside), Brasilinolide aglycone; 23-Malonyl, 37-O-(2,6-dideoxy-3-O-pentanoyl-α-D-lyxo-hexopyranoside), Brasilinolide aglycone; 23-O-(2-Methoxycarbonylhexanoyl), 37-O-(2,6-dideoxy-3,4-dimethyl-α-D-lyxo-hexopyranoside), Brasiliquinone B, Brasiliquinone B; 8-O-(3-Acetamido-2,3, 6-trideoxy-α-L-ribo-hexopyranoside), Brasiliquinone B; 8-O-(3-Amino-2,3,6-trideoxy-α-L-ribo-hexopyranoside), Brasiliquinone B; 8-Me ether, β-Carboline, 1-(β-Carbolin-1-yl)-3-hydroxy-1-propanone, Carboxymycobactins, Cationomycin, Cephalosporin-C deacetylase, Cetocycline, Cetocycline; 4-Epimer, Chemomicin, Chloramphenicol; (1R,2R)-form, Cinodine I, Cinodine II, Coenzyme Q; Coenzyme Q9, Coformycin, Crustaxanthin; Tetraketone, Cyclo (alanylisoleucyl); (1'S,3S,6S)-form, Cyclo(alanylvalyl); (3S,6S)-form, Cyclo(leucylprolyl); (3S,8aS)-form, Decaplanin; 4A-Epimer, Decaplanin; 19-Chloro, 2B-derhamnosyl, Decaplanin; 19-Chloro, 2B-derhamnosyl, N56-Me, Decaplanin; 19-Chloro, 44-O-deglycosyl, 2-Dehydro-3-deoxygalactonokinase, 6-Deoxyaltritol; D-form, 3-Deoxy-7-phosphoheptulonate synthase, 6-Deoxy-2-O-α-L-rhamnopyranosyl-L-talose, 6-Deoxytalose; D-form, 6-Deoxytalose; L-form, 6-Deoxytalose; L-form, 3-Me, 3,6-Diaminohexanoic acid; (S)-form, 3,6-Dibenzylidene-2,5-piperazinedione; (Z,Z)-form, 1,1-Dichloro-4-ethyl-5-(4-nitrophenyl)-2-hexanone; (4S,5S)-form, 2,6-Dideoxy-arabino-hexose; α-D-Pyranose-form, Me glycoside, 4-Me, 13,18:12,15-Diepoxy-7,14,15-trihydroxy-3-cleroden-6-one, 1',2'-Dihydro-γ-caroten-1'-ol, 4',5-Dihydroxy-7-methoxyisoflavone, 1,8-Dihydroxy-3-methylbenz[a]anthracene-7,12-dione; 1'-Hydroxy, 3,4-Dihydroxy-9,10-secoandrosta-1,3,5 (10)-triene-9,17-dione 4,5-dioxygenase, 2,4-Dimethyldocosanoic acid; (2S,4S)-form, 2,4-Dimethyleicosanoic acid; (2S,4S)-form, 2,4-Dimethyl-2-eicosenoic acid; (2E,4S)-form, 3,6-Di-O-methylglucose; D-form, 4-(3,7-Dimethyl-2,6-octadienyl)-3-hydroxybenzoic acid; 1'-Alcohol, 4-(3,7-Dimethyl-2,6-octadienyl)-3-hydroxybenzoic acid; Me ester, 4-(3,7-Dimethyl-2,6-octadienyl)-3-hydroxybenzoic acid; Me ether, Me ester, 2,4-Dimethyltetradecanoic acid, Dnacin A1, Dnacin B1, DNA deoxyinosine glycosylase, dTMP kinase, Efrotomycin; N-De-Me, Efrotomycin B, 2-Eicosanol; (S)-form, 13,16-Epoxy-7,12,14,15-tetrahydroxy-3-cleroden-6-one, Erythromycin, Erythromycin; 12-Deoxy, 3"-O-de-Me, Erythromycin; 12-Deoxy, 3"-O-de-Me, 3"-Ac, Erythromycin; 12-Deoxy, 3"-O-de-Me, 3",4"-di-Ac, Erythromycin; 12-Deoxy, 3"-O-de-Me, 4"-propanoyl, 3"-Ac, Erythromycin E, Erythropterin, 2-Ethyl-6-hydroxybenzoic acid, Exochelin MN, Exochelin MS, Exo-1,4-β-D-glucosaminidase, Fatty acid O-methyltransferase, Fatty acid synthase, Ferrioxamine D2, Flexixanthin; 3-Deoxy, 3',4'-dihydro, Formobactin, Formycin A, Formycin B, Fortuitine, α-L-Fucopyranosyl-(1→3)-α-L-rhamnopyranosyl-(1→3)-L-rhamnose; α-Pyranose-form, Me glycoside, 2,2",3",4"-tetra-Me, β-D-Galactofuranosyl-(1→6)-β-D-galactofuranosyl-(1→5)-D-galactose, 5-O-α-D-Galactofuranosyl-D-galactose, 6-O-β-D-Galactofuranosyl-D-galactose, 1-O-Gentiobiosylglucose; β-D-(2R)-form, Glucolipsins; Glucolipsin B, 3-O-α-D-Glucopyranosyl-L-rhamnose, Glutamate dehydrogenases; Glutamate dehydrogenase (NADP(+)), Glycerol kinase, Glycerol trihexadecanoate, Glycine dehydrogenases; Glycine dehydrogenase, Glycocinnaspermicidin A, Glycocinnaspermicidin A; 4'-O-Deglycosyl, Glycolipid A1, *Mycobacterium avium* Glycopeptidolipid, Glycopeptidolipid X1, Guanosine-3',5'-bis(diphosphate) 3-diphosphatase, 5,13-Halimadien-15-ol; (ent-13E)-form, 2,4,6,8,10,12,14-Heptamethyltriacontanoic acid; (all-S)-form, Heptaprenylcycline, Heptaprenylcycline; 18-Oxo, Heterobactin A; N2-Deacyl, N2-(2,3-dihydroxybenzoyl), 2-(3,7,11,15,19,23-Hexamethyl-25-(2,6,6-trimethyl-2-cyclohexenyl)pentacosa-2,14, 18,22-tetraenyl-3-methyl-1,4-naphthoquinone, Histidomycin A, N-Hydroxyaspartic acid; (S)-form, 3-Hydroxyeicosanoic acid; (R)-form, Hydroxymethylglutaryl-CoA reductases; Hydroxymethylglutaryl-CoA reductase, 6-Hydroxy-1-phenazinecarboxylic acid, 4-(2-Hydroxyphenyl)butanoic acid, 5-Hydroxy-2-pyridinecarboxylic acid, 3-Hydroxy-2,4,6-trimethyltetracosanoic acid; (2S,3R,4S,6S)-form, Indisocin, Indisocin; N-Me, Isochelocardin, Isoglutamine; (R)-form, Isonargenicin A1, Isonocardicin synthase, 2-Isopropyl-malate synthase, Izupeptin, Kanglemycin A, Kanglemycin C, Kasugamycin, 4-Keto-γ-carotene, Lactate 2-monooxygenase, Luridomycin, Lysine; (S)-form, 6-N-Hydroxy, Macbecin II, Macbecin II; 18,21-Quinone, Maduramicin, Maduramicin; O5-De-Me, Maduramicin; 28-Epimer, Maduramicin; O29-Me, Malate synthase, Mannimositose, 6-O-α-D-Mannopyranosyl-D-mannose, Mannose 1-phosphate guanylyltransferase, β-D-Mannosylphosphodecaprenol:(1→6)-α-D-mannosyloligosaccharide (1→6)-α-D-mannosyltransferase, Mavioquinone, Maytansinol; 3-Ac, Maytansinol; 3-Butanoyl, Maytansinol; Dechloro, 4,5-deepoxy, 4,5-didehydro, Maytansinol; Dechloro, 4,5-deepoxy, 4,5-didehydro, N-de-Me, Maytansinol; 4,5-Deepoxy, 4,5-didehydro, N-de-Me, Maytansinol; N-De-Me, 3-Ac, Maytansinol; N-De-Me, 3-O-(3-methylbutanoyl), Maytansinol; N-De-Me, 3-O-(2-methylpropanoyl), Maytansinol; N-De-Me, 3-propanoyl, Maytansinol; 15R-Hydroxy, Maytansinol; 15R-Hydroxy, 3-Ac, Maytansinol; 30-Hydroxy, 3-Ac, Maytansinol; 15R-Hydroxy, 3-O-(3-methylbutanoyl), Maytansinol; 30-Hydroxy, 3-O-(3-methylbutanoyl), Maytansinol; 3-O-(3-Hydroxy-3-methylbutanoyl), Maytansinol; 3-O-(4-Hydroxy-3-methylbutanoyl), Maytansinol; 3-O-(3-Hydroxy-3-methylbutanoyl), N-de-Me, Maytansinol; 15R-Hydroxy, 3-O-(2-methylpropanoyl), Maytansinol; 15S-Hydroxy, 3-O-(2-methylpropanoyl), Maytansinol; 30-Hydroxy, 3-O-(2-methylpropanoyl), Maytansinol; 15R-Hydroxy, 3-propanoyl, Maytansinol; 30-Hydroxy, 3-propanoyl, Maytansinol; 3-O-(3-Methylbutanoyl), Maytansinol; 3-O-(2-Methylpropanoyl), Maytansinol; 3-Propanoyl, MD 011, Megalomicin A; 3A,4A-Di-Ac, Mercury(II) reductase, Mesenterin, Metacycloprodigiosin, 1-Methyl-β-carboline, Methylcyclodecylprodiginine, Methylene-fatty-acyl-phospholipid synthase, 4-Methy-3,9,11-hexacosanetriol; 3-Me ether, 8-Methylhexadecanoic acid; (ξ)-form, 10-Methyl-9-hexadecenoic acid, 11-Methyl-12-octadecenoic acid; (11ξ,12Z)-form, 14-Methylpentadecanoic acid, Muracein A, Muracein B, Muracein C, Mutactimycin A; 3A-O-De-Me, Mutactimycin A; 4A-Me ether, Mutactimycin A; Di-O-de-Me, Mycobacteriocin M 12, Mycobactin, Mycobactin; Mycobactin T, Mycocyclosin, Mycolactone A, Mycolactone A; 12'-Deoxy, Mycolactone A; 4'E-Isomer, Mycolactone A; 2'-Methyl, Mycolactone F, Mycolactone F; 14'-Methyl, Mycolactone F; 14'-Methyl, 13'-ketone, Mycolactone F; 17'-Oxo, 8',9'-dihydro, Mycoserosate synthase, Mycothiol, Mycothiol; N-De-Ac, N-(3-carboxypropanoyl), Mycothiol; N-De-Ac, N-formyl, Mycothiol bimane, Mycothione reductase, Myomycin A, Myomycin B, Myomycin B; Homologue (n=3), Myomycin B; Homologue (n=4), Myomycin B; Homologue (n=5), Myomycin C, NAD(+) kinase, Nanaomycin A; (−)-form, Nanaomycin A; (+)-form, Nargenicin B1, Nargenicin B2, Nargenicin B3, Neocitreamicin I, Neocitreamicin I; 2-O-(4-O-Acetyl-2,6-dideoxy-β-D-galactopyranoside), 2-Nitroimidazole, 4-Nitrophenol 2-monooxygenase, Nocamycin I, Nocamycin I; 8-Alcohol, Nocardamine, Nocardenone, Nocardianin, Nocardichelin A, Nocardichelin A; Lower homologue (n=10), Nocardicin A, Nocardicin A; E-Isomer, Nocardicin C, Nocardicin D, Nocardicin E, Nocardicin E; E-Isomer, Nocardicin G, Nocardicyclin A, Nocardicyclin A; 4'-Ac, Nocardicyclin A; Stereoisomer, 10-alcohol, Nocardimicin, Nocardimicin; Nocardimicin B, Ni-Deoxy, Nocardimicin; Nocardimicin D, N1-Deoxy, Nocardimicin; Nocardimicin D, 9',10'-Dihydro, N-de-Ac, N-formyl, Nocardimicin; Nocardimicin F, 9',10'-Dihydro, N-de-Ac, N-formyl, Nocardimicin; Nocardimicin F, N-De-Ac, N-formyl, Nocardimicin; Nocardimicin F, Homologue (R=—(CH2)16CH3), 9,10'-dihydro, N-de-Ac, N-formyl, Nocardione A; (S)-form, Nocardione A; (S)-form, Me ether, Nocardithiocin, Nocardodienone, Nocardorubin, Nocardotrienone, Nocarsine A, Nocobactin NA, Nodusmicin, Nodusmicin; 18-Ac, Nodusmicin; 19,20-Dimethoxy, 9-O-(1H-pyrrole-2-carboxylate), Nodusmicin; 9-O-(1H-Pyrrole-2-carboxylate), Nodusmicin; 9-O-(1H-Pyrrole-2-carboxylate), 18-Ac, Noformicin; (+)-form, Nonylprodigiosin, NS, N T 1, 9-Octacosenoic acid; (Z)-form, 2-Octadecanol; (+)-form, 3-Octadecyl-4-tridecyl-2-oxetanone; (3R*,4R*)-form, Octahydroheptaprenol, 7,7',8,8',11,11',12,12'-Octahydrolycopene, Ornithine carbamoyltransferase, 3-Oxosteroid 1-dehydrogenase, Pantothenate kinase, 4,8,12,16,20-Pentamethyl-1-heptacosanol; (all-S)-form, O-(β-D-Mannopyranosylphosphate), 4,8,12,16,20-Pentamethyl-1-pentacosanol; (all-S)-form, O-(β-D-Mannopyranosylphosphate), Peptidolipin NA; Peptidolipin NA, Peptidolipin NA; [Val6]Peptidolipin NA, 1,6-Phenazinediol, 1,6-Phenazinediol; Mono-Me ether, 1,6-Phenazinediol; 5-Oxide, Phenylalanine dehydrogenase, 1-Phenyl-3-buten-2-ol; (R)-form, Phosphatidylethanolamine; Glycerol 2-hexadecanoate 1-(10R-methyloctadecanoate) 3-phosphoethanolamine, Phospholipase C, 3-Phosphoshikimate 1-carboxyvinyltransferase, Plectaniaxanthin; (S)-form, 1'-O-β-D-Glucopyranoside, Plectaniaxanthin; (S)-form, 1'-O-(Hexadecanoyl-β-D-glucopyranoside), Polyphosphate glucose phosphotransferase, Polysaccharide O-methyltransferase, Primocarcin, Prodigiosin, Protorifamycin I-M1, Protorifamycin I-M1; 34a-Deoxy, Pseudouridine C; 3-Me, α-L-Rhamnopyranosyl-(1→2)-α-L-rhamnopyranosyl-(1→4)-L-rhamnose; 3-O-α-L-Rhamnopyranosyl-L-rhamnose; α-Pyranose-form, Me glycoside, 2-Me, Rhodonocardin A, Rhodonocardin A; 12b-O-Deglycosyl, Rifamycin, Rifamycin; O4-(Carboxymethyl), Rifamycin; 8-Deoxy, O4-(carboxymethyl), Rifamycin G, Rifamycin G; 16,17Z-Didehydro, Rifamycin P. Rifamycin Q, Rifamycin S; 8-Deoxy, Rifamycin S; 16,17-Dihydro, Rifamycin S; 16,17-Dihydro, 17-hydroxy, Rifamycin S; 3,31-Dihydroxy, Rifamycin S; 3-Hydroxy, Rifamycin S; 30-Hydroxy, Rifamycin S; 3-Hydroxy, 8-deoxy, Rifamycin verde, Rifamycin W, Rifamycin W; 35-Aldehyde, 35→25-hemiacetal, Rifamycin W; 35-Carboxylic acid, 35→25 lactone, Rifamycin W; 8-Deoxy, Rifamycin W; 8-Deoxy, 23-Ac, Rifamycin W; 8-Deoxy, 35-carboxylic acid, 35→25 lactone, Rifamycin W; 8-Deoxy, 13-hydroxy, Rifamycin W; 8-Deoxy, 20-hydroxy, Rifamycin W; 8-Deoxy, 30-hydroxy, Rifamycin W; 8-Deoxy, 23-ketone, Rifamycin W; 30-Hydroxy, Ristomycin A, Ristomycin A; 2C-Deglycosyl, Sakyomicin A, Sakyomicin A; 2-Deoxy, Sakyomicin B; (+)-form, Sakyomicin B; (+)-form, 5,6-Dihydro, Serine; (S)-form, N,O-Di-Me, Shikimate kinase, Siderochelin A, Siderochelin A; 4-Epimer, Smegmatocin, Steroid monooxygenases; Steroid 9α-monooxygenase, Streptomycin; 5'-Hydroxy, 4"-O-β-D-mannopyranosyl, Tagatose kinase, Tetracenomycin C; O12a-Me, 4,5,6,7-Tetrahydro-6,7-dihydroxy-1H-indol-4-one; (6R*,7R*)-form, Thiolactomycin, Thiolactomycin δ, Tomaymycin, Tomaymycin; 11-Demethoxy, 11-ethoxy, Transvalencin A, Transvalencin Z, Trehalose O-mycolyltransferase, Trehalosephosphatase, α,α-Trehalose; 6-Phosphate, α,α-Trehalose; 2-Sulfate, 3,5,7,8-Tridecatetraene-10,12-diynoic acid; (3E,5Z)-(R)-form, 1,6,10-Trihydroxy-3,9-dimethyl-5,12-naphthacenedione; 10-Me ether, 4',5,7-Trihydroxyisoflavone, Tubelactomicin A, Tubelactomicin A; 25-Hydroxy, Tubelactomicin A; 26-Hydroxy, Tubelactomicin B, Tuberculin, Undecaprenol kinase, Undecylprodigiosin, Undecylprodigiosin; Lower homologue (n=8), Vancomycin, and Vitamin K2; Vitamin K2(45).

In some embodiments, the desired compound is as listed below. In some embodiments, the desired compound is as listed below and obtainable from a *Streptomycetes*. Desired compounds include A 114, A 280, A 75943, A 58365A (S)-form, Aabomycin S, Aabomycin X, Abbeymycin, Abierixin, Abierixin; Δ3-Isomer, Abierixin; Δ3-Isomer, O-de-Me, Abierixin; 29-Me ether, Abikoviromycin, Abikoviromycin; 1,7a-Dihydro, Abikoviromycin; 1,7a-Dihydro, 7-hydroxy, Abkhazomycin, Ablastmycin, Aborycin, Aburatubolactam A, Aburatubolactam B, Aburatubolactam B; 25-Deoxy, Abyssomicin E, Abyssomicin I, Acanthomycin, ACDL 3172, 2-Acetamidobenzoic acid; Amide, (2-Acetamido-2-deoxy-α-D-glucopyranos-1-yl)(methyl 2-acetamido-2-deoxy-α-D-glucopyranosid-6-yl) phosphate, Acetomycin, N-Acetyl-S-[3-(carboxymethyl)-3,4,6,9-tetrahydro-10-hydroxy-7-(methylamino)-1-(3-methylbutyl)-6,9-dioxo-1H-naphtho[2,3-c]pyran-8-yl]cysteine, N-Acetyl-S-[3-(carboxymethyl)-3,4,6,9-tetrahydro-10-hydroxy-7-(methylamino)-1-(3-methylbutyl)-6,9-dioxo-1H-naphtho[2,3-c]pyran-8-yl]cysteine; 26-Epimer, 2-(N-Acetylcysteinyl) amido-2-deoxy-α-D-glucopyranosyl-D-myo-inositol disulfide, 2-Acetyl-2-decarboxamidotetracycline, 2-Acetyl-2-decarboxamidotetracycline; 7-Chloro, 2-Acetyl-2-decarboxamidotetracycline; 5-Hydroxy, 7-Acetyl-3,4-dihydro-3,6-dihydroxy-8-methyl-1(2H)-naphthalenone; (−)-form, 3-Acetyl-1,4-dihydro-5-hydroxy-β,4-dioxo-2-naphthalenebutanoic acid, 4-Acetyl-1,3-dihydro-2H-imidazo[4,5-c]pyridin-2-one, 3-Acetyl-4,5-dihydroxyanthraquinone-2-acetic acid, 3-Acetyl-4,5-dihydroxyanthraquinone-2-acetic acid; Me ester, 6-(2-Acetyl-3,5-dihydroxybenzyl)-4-hydroxy-2H-pyran-2-one, 1-Acetyl-4,5-dihydroxy-2-methylanthraquinone, 2-Acetyl-1,8-dihydroxy-3-methylanthraquinone, 3-Acetyl-1,8-dihydroxy-2-methylphenanthraquinone, 6-[2-(2-Acetyl-3,5-dihydroxyphenyl)-3-hydroxybenzyl]-4-hydroxy-2H-pyran-2-one, β-N-Acetylhexosaminidase, 5-(2-Acetylhydrazino)-2-hydroxybenzaldehyde, 7-Acetyl-8-hydroxy-2-methylnaphtho[1,8-bc]pyran, 7-Acetyl-8-hydroxy-2-(2-oxopropyl)naphtho[1,8-bc]pyran, 4-Acetyl-6-methyl-2(1H)-pyridinone, 2-Acetyl-3-propanoyl-1,8-naphthalenediol, 2-Acetyl-3-propanoyl-1,8-naphthalenediol; 8-O-β-D-Glucuronopyranoside, 2-Acetylpyrrole, 2-[(3-Acetyl-4,5,7-trihydroxy-2-naphthalenyl)methyl]-6-hydroxy-4H-pyran-4-one, Acidomycin; (−)-form, Acivicin, Acivicin; 4S-Hydroxy, Aclacinomycin G2, Aclacinomycin M, Aclacinomycin M; 2C,3C-Didehydro, 2C-amino, 4C-ketone, Aclacinomycin M; 2C,3C-Didehydro, 4C-ketone, Aclacinomycin M; 4C-Epimer, Aclacinomycin M; 5C-Epimer, 4C-ketone, Aclacinomycin M; 4C-Epimer, 1-hydroxy, Aclacinomycin M; 4C-Epimer, 2-hydroxy, Aclacinomycin M; 4C-Epimer, 8ξ-hydroxy, Aclacinomycin M; 4C-Epimer, 1-hydroxy, 3B-deoxy, Aclacinomycin M; 4C-Ketone, Aclacinomycin M; 4C-Ketone, N-de-Me, Aclacinomycin M; 4C-Ketone, N,N-di-de-Me, Aclacinomycin M; 1,11-Dihydroxy, 4C-ketone, Aclacinomycin M; 1-Hydroxy, Aclacinomycin M; 11-Hydroxy, Aclacinomycin M; 1-Hydroxy, 3B-deoxy, 2C,3C-didehydro, 4C-ketone, Aclacinomycin M; 11-Hydroxy, 3B-deoxy, 4C-ketone, Aclacinomycin M; 11-Hydroxy, 2C,3C-didehydro, 2C-amino, 4C-ketone, Aclacinomycin M; 1-Hydroxy, 2C,3C-didehydro, 4C-ketone, Aclacinomycin M; 11-Hydroxy, 4C-ketone, Aclacinomycin M; 1-Hydroxy, 4C-ketone, Aclacinomycin M; 2-Hydroxy, 4C-ketone, Aclacinomycin M; 1-Hydroxy, 4C-ketone, N-de-Me, Aclacinomycin M; 13-Methyl, 4C-ketone, Aclacinomycin ZIMET 33352, Aclidinomycin B, Aclidinomycin B; N-De-Me, Aclidinomycin B; 9-Deoxy, Aclidinomycin C, Acmycin, Actiketal, Actinobolin, Actinocarcin, Actinoflavoside, Actinofuranone A, Actinofuranone A; 2'-Deoxy, 2',3'-didehydro(E-), Actinogan, Actinolactomycin, Actinomycetin, Actinomycin Au6a, Actinomycin Au7a, Actinomycin C2, Actinomycin C3, Actinomycin C2a, Actinomycin D, Actinomycin D; 3-(2-Azetidinecarboxylic acid) homologue, Actinomycin D; 3α,3β-Bis(2-azetidinecarboxylic acid) homologue, Actinomycin D; 3α,3β-Bis-L-pipecolic acid homologue, Actinomycin D; 3α,3β-Bis-L-pipecolic acid homologue, hydroxy, Actinomycin D; 3α,3β-Bis-L-pipecolic acid homologue, oxo, Actinomycin D; N4α,N4β-Dide-Me, Actinomycin D; 43βR-Hydroxy, Actinomycin D; 43βS-Hydroxy, Actinomycin D; 3-(4-Hydroxy-L-pipecolic acid) homologue, Actinomycin D; 43β-Oxo, Actinomycin D; 3-(4-Oxo-L-pipecolic acid) homologue, Actinomycin D; 3-L-Pipecolic acid homologue, Actinomycin E1, Actinomycin E2, Actinomycin F2, Actinomycin F4, Actinomycin F8, Actinomycin F9, Actinomycin G1, Actinomycin G3, Actinomycin G3; 41β-Deoxy, Actinomycin G3; 41β-Deoxy, 41β-chloro, Actinomycin G3; 43βR-Hydroxy, 41β-deoxy, 41β-chloro, Actinomycin G3; 43β-Oxo, 41β-deoxy, 41β-chloro, Actinomycin G5, Actinomycin G6, Actinomycin K, Actinomycin P, Actinomycin S3, Actinomycin U, Actinomycin X, Actinomycin X1a, Actinomycin Y4, Actinomycin Y4; 4'-Ketone, Actinomycin Y5, Actinomycin Z1, Actinomycin Z; 41β-Deoxy, Actinomycin Z1; 41β-Deoxy, 41β-chloro, Actinomycin Z1; Dideoxy, Actinomycin Z1; Dideoxy, 41β-chloro, Actinonin, Actinoperylone, Actinopyrones, Actinoramide A, Actinoramide A; N28-Decarbamoyl, N28-Ac, Actinoramide C, Actinorhodin, α-Actinorhodin, β-Actinorhodin, γ-Actinorhodin, δ-Actinorhodin, ε-Actinorhodin, Actinorubin, Actinoxanthin, Actiphenamide, Actiphenol, Actiphenol; 1'''-Hydroxy, Actiphenol; 1'-Hydroxy, Actiphenol; 3-Hydroxy (3,4-trans-), A 88696D, Adecypenol, Adenomycin, Adenomycin; De-O-seryl, Adenosine; 5'-O-Sulfamoyl, Adenosyl fluoride synthase, Adiposin 1, Adiposin 2, Adiposin 2; Dihydro, Adriamycin, Adriamycin; 13S-Alcohol, Adriamycin; 11-Deoxy, O4-de-Me, Adriamycin; 4'-Epimer, Aestivophoenin A, Aestivophoenin B, Aestivophoenin B; Debenzoyl, A 88696F, A 88696F; 4-Deoxy, Aflastatin A, Aflastatin A; N-De-Me, Afragilimycin B, 2,4, 10-Africananetriol; (2α,3α,4α,6α,10β)-form, A 80915G acid, AH 2589, Ahpatinin A, Ahpatinin A; Stereoisomer, Ahpatinin E, Ahpatinin F, Ahpatinin G, AI 3688, AI 409, AI B, Akashine C, Akitamycin, Aklanonic acid, Aklavinone; 7-Deoxy, Aklavinone; 7-O-(2,6-Dideoxy-α-L-arabino-hexopyranoside), Aklavinone; 7,9-Diepimer, Aklavinone; 7-Epimer, Aklavinone; 9-Epimer, Aklavinone; 4-O-β-D-Glucuronopyranoside, Aklavinone; 2-Hydroxy, Aklavinone; 2-Hydroxy, 7-deoxy, Aklavinone; 7-Ketone, Aklavinone; 13-Methyl, Akrobomycin, Akrobomycin; 6-Deoxy, Akrobomycin; 13-Hydroxy, Akrobomycin; 13-Oxo, Akrobomycin; 13-Oxo, O4-Me, Alahopcin, Alahopcin; Dealanyl, Alanine dehydrogenase, Alanosine; (S)-form, Alazopeptin, Albidopyrone, Albocycline, Albocycline; O-De-Me, 7-O-α-D-glucopyranoside, Albocycline; O-De-Me, Albocycline; 7-Demethoxy, Δ7-isomer, 9-hydroxy, 2,3-dihydro, Albocycline; 7-Demethoxy, 7-oxo, Albocycline; 2,3-Dihydro, O-de-Me, Albocycline; 5,6-Dihydro, O-de-Me, Albocycline; 2,3-Dihydro O-de-Me, 7-O-α-D-glucopyranoside, Albocycline; 5,6-Dihydro, O-de-Me, 7-O-α-D-glucopyranoside, Albocycline; 8ξ,9ξ-Epoxide, Albocycline; 10ξ-Hydroxy, Albocycline; 11ξ-Hydroxy, Albocycline; 12ξ-Hydroxy, Albocycline; 18-Hydroxy, Albocycline; 18-Hydroxy, O-de-Me, Albocycline; 10ξ-Hydroxy, 2,3-dihydro, Albocycline; 11ξ-Hydroxy, 2,3-dihydro, Albocycline; 2,3,8, 9-Tetrahydro, O-de-Me, Albocycline K2, Albocycline K2; 9'-Ketone, Albocycline M8, Albofungin; 4-Chloro, Albomitomycin A, Albomitomycin A; 7-Demethoxy, 7-amino, Albomycin, Albomycin; Albomycin δ2, N-De-Me, Albopeptin A, Albopeptin B, Albopeptin B; N-Deoxy, Alborixin, Alborixin; 6-Demethyl, Albotetraene, Alboverticillin, Albucidin, Alchivemycin A, Aldecalmycin, Aldgamycin C, Aldgamycin C; 2,3-Didehydro(E-), Aleicide B, Aleicide C, Algacidins, Aliomycin, Alisamycin; (+)-form, Alisamycin; (−)-form, Alizarin 2-β-glucosyltransferase, 3-Alkanoyl-4-hydroxy-5-(hydroxymethyl)-2(5H)-furanones; 3-Hexadecanoyl-4-hydroxy-5-(hydroxymethyl)-2(5H)-furanone, 3-Alkanoyl-4-hydroxy-5-(hydroxymethyl)-2(5H)-furanones; 3-Hexadecyl-4-hydroxy-5-(hydroxymethyl)-2(5H)-furanone, Ca salt, 3-Alkanoyl-4-hydroxy-5-(hydroxymethyl)-2(5H)-furanones; 4-Hydroxy-5-<hydroxymethyl)-3-(10-methylpentadecanoyl)-2(5H)-furanone, 3-Alkanoyl-4-hydroxy-5-(hydroxymethyl)-2(5H)-furanones; 4-Hydroxy-5-(hydroxymethyl)-3-(11-methylpentadecanoyl)-2(5H)-furanone, 3-Alkanoyl-4-hydroxy-5-(hydroxymethyl)-2 (5H)-furanones; 4-Hydroxy-5-(hydroxymethyl)-3-(14-methylpentadecanoyl)-2(5H)-furanone, 3-Alkanoyl-4-hydroxy-5-(hydroxymethyl)-2(5H)-furanones; 4-Hydroxy-5-(hydroxymethyl)-3-(7-methylpentadecanoyl)-2(5H) furanone, 3-Alkanoyl-4-hydroxy-5-(hydroxymethyl)-2 (5H)-furanones; 4-Hydroxy-5-(hydroxymethyl)-3-(8-methylpentadecanoyl)-2(5H)furanone, 3-Alkanoyl-4-hydroxy-5-(hydroxymethyl)-2(5H)-furanones; 4-Hydroxy-5-(hydroxymethyl)-3-(9-methylpentadecanoyl)-2(5H)-furanone, 2-(3-Alkyl-5-chloro-2,6-dihydroxybenzoyl)-4,5-dichloro-1H-pyrroles; 2,3-Dichloro-5-[3-chloro-2,6-dihydroxy-3-(4-methylhexyl)benzoyl]-1H-pyrrole, 2-(3-Alkyl-5-chloro-2,6-dihydroxybenzoyl)-4,5-dichloro-1H-pyrroles; 2,3-Dichloro-5-[3-chloro-2,6-dihydroxy-5-(5-methylhexyl)benzoyl]-1H-pyrrole, 2-(3-Alkyl-5-chloro-2,6-dihydroxybenzoyl)-4,5-dichloro-1H-pyrroles; 2,3-Dichloro-5-[3-chloro-2,6-dihydroxy-5-(4-methylpentyl)benzoyl]-1H-pyrrole, 2-(3-Alkyl-5-chloro-2,6-dihydroxybenzoyl)-4,5-dichloro-1H-pyrroles; 2,3-Dichloro-5-(3-chloro-5-hexyl-2, 6-dihydroxybenzoyl)-1H-pyrrole, 2-Alkyl-3,4-dihydroxy-5-(hydroxymethyl)pyridines; 3,4-Dihydroxy-5-(hydroxymethyl)-2-isopropylpyridine, 2-Alkyl-3,4-dihydroxy-5-(hydroxymethyl)pyridines; 3,4-Dihydroxy-5-(hydroxymethyl)-2-(1-methylpropyl)pyridine, 2-Alkyl-3,4-dihydroxy-5-(hydroxymethyl)pyridines; 3,4-Dihydroxy-5-(hydroxymethyl)-2-(2-methylpropyl)pyridine, 2-Alkyl-3,4-dihydroxy-5-(hydroxymethyl)pyridines; 3,4-Dihydroxy-5-(hydroxymethyl)-2-propylpyridine, 2-Alkyl-4-(hydroxymethyl)-3-furancarboxylic acids; 2-Butyl-4-(hydroxymethyl)-3-furancarboxylic acid, 2-Alkyl-4-(hydroxymethyl)-3-furancarboxylic acids; 4-(Hydroxymethyl)-2-(3-methylbutyl)-3-furancarboxylic acid, 2-Alkyl-4-(hydroxymethyl)-3-furancarboxylic acids; 4-(Hydroxymethyl)-2-methyl-3-furancarboxylic acid, α-L-Rhamnopyranosyl ester, 2-Alkyl-4-(hydroxymethyl)-3-furancarboxylic acids; 4-(Hydroxymethyl)-2-(2-ethylpropyl)-3-furancarboxylic acid, 2-Alkyl-4-(hydroxymethyl)-3-furancarboxylic acids; 4-(Hydroxymethyl)-2-pentyl-3-furancarboxylic acid, 2-Alkyl-4-(hydroxymethyl)-3-furancarboxylic acids; 4-(Hydroxymethyl)-2-pentyl-3-furancarboxylic acid, Me ester, 2-Alkyl-4-(hydroxymethyl)-3-furancarboxylic acids; 4-(Hydroxymethyl)-2-propyl-3-furancarboxylic acid, 3-(2-Alkyl-5-oxazolyl)-1H-indoles; 3-(2-Ethyl-5-oxazolyl)-1H-indole, 3-(2-Alkyl-5-oxazolyl)-1H-indoles; 3-(2-Methyl-5-oxazolyl)-1H-indole, Allantoicase, Allosamidin, Allosamidin; N-De-Me, Allosamidin; N,N-Di-de-Me, Allosamidin; 3'-Epimer, 6''-Me ether, Allosamidin; 3'-Epimer, 6''-Me ether, N-de-Me, Allosamidin; 6''-Me ether, Allosamidin; 6''-Me ether, N-de-Me, Almarcetin, Alnumycin, Alnumycin; 7-Methoxy, Altamiramycin, Altamycin A, Altamycin B, Altemicidin, Altemicidin; 5'-N-(2S-Amino-3S-methylpentanoyl), Altemicidin; 5'-N-(2S-

Amino-3S-methylpentanoyl), 6-O-(2S-amino-3S-phenylbutanoyl), Althiomycin, Alveomycin, Amastatins, Ambomycin, Amethobottromycin, Amicenomycin A, Amicenomycin B, Amicetin, Amicetin; N-De-Me, Amicetin C, Amiclenomycin, Amidinomycin, 3-Amidino-2-propenoic acid; (Z)-form, Amidomycin, N-(2-Aminoacetyl)-2-(1-cyclohexen-3-yl)acetamide, 2-Amino-4-(2-aminoethoxy)-3-butenoic acid; (S)-(E)-form, 2-Amino-4-(aminooxy) 3-butenoic acid; (S,E)-form, N-(1-Methylethylidene), 2-Amino-4-(aminooxy)-3-butenoic acid; (S,E)-form, N-(Aminoiminomethyl), 2-Amino-3-(aminooxy)propanoic acid; (R)-form, 2-Amino-1,4-benzenediol; N-Me, N-nitroso, 2-Aminobenzoic acid; Amide, 2-Aminobenzoic acid; 6-Deoxy-α-L-talopyranosyl ester, 2-Aminobenzoic acid; α-L-Rhamnopyranosyl ester, 4-Aminobutanoic acid, 2-Amino-3-butynoic acid; (S)-form, 4-Aminobutyrate transaminase, 3-(Aminocarbonyl)-9,10-dihydro-4,5,9-trihydroxy-9-methyl-10-oxo-2-anthraceneacetic acid, 2-Amino-4-chloro-3-hydroxybutanoic acid, 2-Amino-4-chloropentanoic acid; (2S,4S)-form, 4-Amino-3-chloro-2-pentenedioic acid; (R,Z)-form, 5-Amino-1,3-cyclohexadiene-1-carboxylic acid; (S)-form, α-Amino-1,4-cyclohexadiene-1-propanoic acid; (S)-form, 2-Aminocyclopentanecarboxylic acid; (1R,2S)-form, 4-Aminodemethylaminoanhydrodemethylchlorotetracycline, 5-Amino-5-deoxygalactose; D-form, 2-Amino-2-deoxyglucose; D-form, N-Carbamoyl, 2-Amino-2-deoxyglucose; β-D-Pyranose-form, 2,3-Dihydroxypropyl glycoside, 3-Amino-3-deoxyglucose; D-form, 5-Amino-5-deoxyglucose; D-Pyranose-form, 2-Amino-2-deoxygulose; D-form, N-Me, 2-Amino-2-deoxylyxose; D-form, 2-Amino-2-deoxymannitol; D-form, 5-Amino-5-deoxymannose; D-Pyranose-form, 2-Amino-2-deoxymannuronic acid; D-form, N—Ac, 6-Amino-1,4-diazacyclononane-2,5-dione; (−)-form, 2-Amino-6-diazo-5-oxohexanoic acid; (S)-form, 2-Amino-6-diazo-5-oxohexanoic acid; (S)-form, N—Ac, 2-Amino-4,4-dichlorobutanoic acid; (S)-form, 4-Amino-1,13-diguanidino-5-tridecanone; N4-Ac, α-Amino-2,5-dihydro-5-oxo-4-isoxazolepropanoic acid; (S)-form, 3-Aminodihydro-2(3H)-thiophenone; (ξ)-form, N—Ac, 3-Aminodihydro-2(3H)-thiophenone; (ξ)-form, N-Propanoyl, 5-Amino-1,6-dihydro-7H-1,2,3-triazolo[4,5-d]pyrimidin-7-one, 2-Amino-3,6-dihydroxybenzoic acid; N—Ac, 2-Amino-3,4-dihydroxybutanoic acid; (2S,3S)-form, 2-Amino-4,5-dihydroxy-2-cyclohexen-1-one; (4S, 5R)-form, N—Ac, 2-Amino-3-(2,5-dihydroxyphenyl)propanoic acid; (S)-form, 2-Amino-3-(3,4-dihydroxyphenyl) propanoic acid; (S)-form, N—Ac, 6-Amino-4,5-dihydroxy-3-piperidinecarboxylic acid; (3S,4S,5R,6S)-form, N—Ac, 6-Amino-4,5-dihydroxy-3-piperidinecarboxylic acid; (3R*,4R*,5R*,6R*)-form, N—Ac, 6-Amino-4,5-dihydroxy-3-piperidinecarboxylic acid; (3R*,4S*,5R,6R*)-form, N—Ac, 6-Amino-4,5-dihydroxy-3-piperidinecarboxylic acid; (3R*,4R*,5S*,6S*)-form, N—Ac, 2-Amino-3-(dimethylamino) propanoic acid; (S)-form, 2-Amino-9,13-dimethylheptadecanoic acid, 6-Amino-2,3-dimethyl-5,8-quinolinedione; N-Me, 7-Amino-5,8-dioxo-3-isoquinolinecarboxylic acid; N-Me, Me ester, 3-(3-Amino-1,3-dioxopropyl)-4,5-dihydroxyanthraquinone-2-acetic acid, 6-Amino-1,2-dithiolo[4,3-b]pyrrol-5(4H)-one; N6-Ac, 6-Amino-1,2-dithiolo[4,3-b]pyrrol-5(4H)-one; N6-Formyl, 6-Amino-1,2-dithiolo[4,3-b]pyrrol-5(4H)-one; 4-Me, 6-Amino-1,2-dithiolo[4,3-b]pyrrol-5(4H)-one; 4-Me, N6-Ac, 6-Amino-1,2-dithiolo[4,3-b]pyrrol-5(4H)-one; N6-Me, N6-formyl, 6-Amino-1,2-dithiolo[4,3-b]pyrrol-5(4H)-one; 4-Me, N6-(2-methylpropanoyl), 6-Amino-1,2-dithiolo[4,3-b]pyrrol 5(4H)-one; 4-Me, N6-propanoyl, 6-Amino-1,2-dithiolo[4,3-b]pyrrol-5(4H)-one; N6-Propanoyl, (2-Aminoethyl) phosphinic acid, O-(2-Aminoethyl)serine; (S)-form, 2-Amino-4-fluoro-3-hydroxybutanoic acid; (2ξ,3ξ)-form, Aminoglycoside N6'-acetyltransferase, 2-Amino-5-guanidino-3-hydroxypentanoic acid; (2S,3R)-form, N2-(2-Carboxyethyl), 5-Amino-2-hexynedioic acid; 1-Monoamide, 2-Amino-3-hydroxybenzoic acid; N—Ac, amide, 2-Amino-5-hydroxybenzoic acid; 9-Methyldecyl ester, 2-Amino-5-hydroxybenzoic acid; 8-Methylnonyl ester, 2-Amino-5-hydroxybenzoic acid; 10-Methylundecyl ester, 3-Amino-2-hydroxybenzoic acid; N-Formyl, 2-Amino-3-hydroxybutanedioic acid; (2S,3S)-form, 2-Amino-1-hydroxy-1-cyclobutaneacetic acid; (1S,2S)-form, 6-Amino-5-hydroxy-1,3-cyclohexadiene-1-carboxylic acid; (5S,6S)-form, 6-Amino-5-hydroxy-1,3-cyclohexadiene-1-carboxylic acid; (5S,6S)-form, Aldehyde, 2-Amino-4-hydroxy-2-cyclohexen-1-one; (R)-form, N—Ac, 1-Amino-3-hydroxy-8-decen-5-one; (+)-(E)-form, N—Ac, 4-Amino-2-hydroxy-5-(hydroxymethyl)pyrimidine; OH-form, 2-Me ether, 2-Amino-3-hydroxy-4-methylbenzoic acid, 2-Amino-3-hydroxy-4-methylbenzoic acid; N—Ac, 2-Amino-4-hydroxy-3-methylbutanoic acid; (2R*,3S*)-form, Lactone, N—Ac, 4-Amino-6-(hydroxymethyl)-1,3-cyclohexanediol; (1S,3R,4S,6R)-form, 4-Amino-6-hydroxymethyl-1,2,3,5-cyclohexanetetrol; (1R,2S,3S,4S,5S,6S)-form, 4-Amino-6-hydroxymethyl-1,2,3-cyclohexanetriol; (1R,2S,3S,4S,6R)-form, 3-Amino-2-hydroxy-5-methylhexanoylvalylvaline, 2-Amino-8-(hydroxymethyl)-3H-phenoxazin-3-one; N—Ac, 2-Amino-8-(hydroxymethyl)-3H-phenoxazin-3-one; N-(Hydroxyacetyl), 2-Amino-4-hydroxy-3-methyl-4-(2-pyridin)butanoic acid, 3-Amino-5-hydroxy-7-oxabicyclo[4.1.0]hept-3-en-2-one; (1S,5S,6S)-form, 3-Amino-5-hydroxy-7-oxabicyclo[4.1.0]hept-3-en-2-one; (1S,5S,6S)-form, N—Ac, 2-Amino-5-hydroxy-4-oxopentanoic acid, 2-Amino-5-hydroxy-4-oxopentanoic acid; (S)-form, N-(3-Amino-2-hydroxy-1-oxo-4-phenylbutyl)valine, 2-Amino-4-hydroxypentanoic acid; (2S,4R)-form, 2-Amino-4-hydroxypentanoic acid; (2S,4R)-form, Lactone, 2-Amino-3-hydroxy-4-pentynoic acid; (2S,3R)-form, 3-Amino-2-hydroxy-4-phenylbutanoylvalylisoleucine, 3-Amino-3-(4-hydroxyphenyl)-1-propanol; (S)-form, N—Ac, 3-Amino-3-(4-hydroxyphenyl)-1-propanol; (S)-form, 4'-Me ether, N—Ac, 2-Amino-4-(hydroxyphosphinyl)butanoic acid; (S)-form, 2-Amino-4-(hydroxyphosphinyl)butanoic acid; (S)-form, N—Ac, 2-Amino-3-(hydroxyphosphinyl)propanoic acid; (R)-form, α-Amino-5-hydroxy-2-pyridinepropanoic acid; (S)-form, 3-Amino-5-hydroxy-5-vinyl-2-cyclopenten-1-one; (R)-form, 3-Amino-5-hydroxy-5-vinyl-2-cyclopenten-1-one; (R)-form, N-Methoxycarbonyl, 3-Amino-5-hydroxy-5-vinyl-2-cyclopenten-1-one; (R)-form, N-[2-(4-Hydroxyphenyl)ethyl], 2-Aminoimidazole, 2-Amino-3-(3-indolyl)butanoic acid; (2S,3R)-form, 2-Amino-3-(3-indolyl)-1-propanol; (S)-form, N—Ac, 4-Amino-3-isoxazolidinone; (R)-form, 2-Amino-4-methyl-5-hexenoic acid; (2S,4S)-form, 2-Amino-5-methyl-5-hexenoic acid; (S)-form, 8-Amino-2-methyl-7-oxononanoic acid; (2R,8S)-form, 2-Amino-4-methylpentanedioic acid; (2ξ,4ξ)-form, 5-Nitrile, 2-Amino-4-methyl-1-pentanol; (ξ)-form, N—Ac, 2-(Aminomethyl)-2-propenoic acid, 2-Amino-4-methylquinazoline, 2-Amino-12 methyl-1,3,12-tetradecanetriol; N-Hydroxy, N-nitroso, 4-Amino-5-(methylthio)-1,2,3-cyclopentanetriol; (1R,2R,3R,4S,5R)-form, 2-Amino-5-nitrobenzoic acid, 2-Amino-1-(4-nitrophenyl)-1,3-propanediol; (1R,2R)-form, N—Ac, 3-Amino-2-oxetanecarboxylic acid; (2R,3S)-form, 5-Amino-4-oxo-5-hexenoic acid; N—Ac, 2-Amino-3-oxo-3H-phenoxazine-8-carboxylic acid, 2-Amino-3-oxo-3H-phenoxazine-8-carboxylic acid; N2-Ac, 2-Amino-3-oxo-3H-phenoxazine-1,8-dicarboxylic acid; 8-Alcohol, N2-Ac, 2-Amino-3-oxo-3H-phenoxazine-1,8-dicarboxylic acid; 8-Alcohol, 1-amide, 2-Amino-3-oxo-3H-phenoxazine-1,8-dicarboxylic acid; 8-Alcohol, 1-nitrile, N2-Ac, 2-Amino-3-oxo-3H-phenoxazine-1,8-dicarboxylic acid; 1-Amide, 2-Amino-3-oxo-3H-phenoxazine-1,8-dicarboxylic acid; 1-Amide, 8-Me ester, 2-Amino-4-pentynoic acid; (S)-form, Aminopeptidase S, 2-Aminophenol, 2-Aminophenol; N—Ac, 2-Aminophenol oxidase, 2-Amino-3H-phenoxazin-3-one, 2-Amino-3H-phenoxazin-3-one; N—Ac, 2-Amino-3H-phenoxazin-3-one; N-(2-Hydroxyethyl), 1-(4-Aminophenyl)-2-dichloroacetamido-1,3-propanediol; (R,R)-form, 7-(4-Aminophenyl)-2,4-dimethyl-7-oxo-5-heptenoic acid, 12-(4-Aminophenyl)-10-hydroxy-6-(1-hydroxyethyl)-7,9-dimethyl-12-oxo-2,4-dodecadienoic acid, 2-(4-Aminophenyl)-4-hydroxyquinazoline; N4'-Me, 9-(4-Aminophenyl)-7-hydroxy-2,4,6-trimethyl-9-oxo-2-nonenoic acid, 5-(4-Aminophenyl)-2,4-pentadienoic acid, 5-(4-Aminophenyl)-2,4-pentadienoic acid; Amide, N2-[5-(4-Aminophenyl)-2,4-pentadienoyl]glutamine; (S)-form, 2-Amino-5-phosphono-3-pentenoic acid; (R)-form, 2-Amino-1,3-propanediol; N-(2-Hydroxybenzoyl), 2-Amino-1,3-propanediol; N-(2-Hydroxybenzoyl), 1-Ac, 1-Amino-1,2,3-propanetricarboxylic acid; (1ξ,2ξ)-form, 1''-Nitrile, 2-Amino-1-propanol; (S)-form, N-(2-Hydroxybenzoyl), N-(2-Aminopropanoyl)benzeneacetamide; (ξ)-form, 3-Amino-2-pyrazinecarboxylic acid; N—Ac, 2-Amino-3-(2-pyridinyl)propanoic acid; (S)-form, 3-Amino-3-(2-thiazolyl)propanoic acid, 2-Amino-3-(1H-1,2,4-triazol-3-yl)propanoic acid; (S)-form, Amipurimycin, Ammosamide B, Ammosamide B; 2-Thione analogue, Amphomycin, Amphotericin B, Amphotericin B; 16-Decarboxy, 16β-methyl, Amphotericin B; 16-Decarboxy, 16β-methyl, 8-deoxy, aglycone, Amphotericin B; 16-Decarboxy, 16β-methyl, 8-deoxy, 28,29-dihydro, 15-ketone, Amphotericin B; 16-Decarboxy, 16β-methyl, 15-ketone, Amphotericin B; 19-Deglycosyl, 19-O-(4-amino-4,6-dideoxy-β-D-mannopyranoside), Amphotericin B; 8-Deoxy, Amphotericin B; 8-Deoxy, 28,29-dihydro, Amphotericin B; 28,29-Dihydro, Amphotericin B; 28,29-Dihydro, 15-ketone, Amphotericin B; 28,29-Dihydro, 7-oxo, Amphotericin B; 13-Epimer, 13-Me ether, Amphotericin B; 15-Ketone, Amphotericin B; 13-Me ether, Amphotericin B; 7-Oxo, Amycin, Amylostatin, Amylostatin; Amylostatin B, Amylostatin; Amylostatin C, Amylostatin; Amylostatin D, Amylostatin; Amylostatin E, Amylostatin; Amylostatin F, Amylostatin; Amylostatin K, Amylostatin; Amylostatin L, Amylostatin; Amylostatin M, Amylostatin; Amylostatin N, Amylostatin; Amylostatin XG, Amylostreptin, AN 3, AN 5, AN 7, Anantin, Anantin; Des-Phe analogue, Ancovenin, Androstane-3,17-dione; 5α-form, Anguyclinone C, Angustmycin A, Anhydromaggiemycin, Anhydromaggiemycin; 12-Deoxy, Anhydromaggiemycin; 4,12-Dideoxy, Anhydromaggiemycin; 10-Hydroxy, 4,12-dideoxy, Anhydro-ε-pyrromycinone, Anhydrotetracycline monooxygenase, Anisomycin; (−)-form, Anisomycin; (−)-form, O-De-Ac, Anisomycin; (−)-form, O-De-Me, Anisomycin; (−)-form, O-De-Me, O-de-Ac, Anisomycin; (−)-form, O-De-Ac, 3-propanoyl, Anisomycin; (−)-form, O-De-Me, 3-propanoyl, O-de-Ac, Anisomycin; (−)-form, O-De-Ac, 3-butanoyl, Anisomycin; (−)-form, O-De-Ac, 3-(3-methylbutanoyl), 3-p-Anisylidene-6-benzylidene-2,5-piperazinedione; (3Z,6Z)-form, 3-p-Anisylidene-6-benzylidene-2,5-piperazinedione; (3Z,6Z)-form, N4-Me, 3-p-Anisylidene-6-benzylidene-2,5-piperazinedione; (3Z,6Z)-form, N1,N4-Di-Me, 3-p-Anisylidene-6-benzylidene-2,5-piperazinedione; (3Z,6Z)-form, 6,7-Dihydro, N4-Me, Annorumin, Ansaetherone, Ansalactam A, Ansathiazin, Ansatrienin B, Ansatrienin B; N-Deacyl, N-(4-methylpentanoyl), Ansatrienin B; N-Deacyl, N-tigloyl, Ansatrienin B; 23-Deoxy, Ansatrienin B; 1'',2''-Didehydro, Ansatrienin B; 20-Me ether, Ansatrienin B; 21-(Methylthio), Ansatrienin B; 19-(Methylthio), 20,23-quinone. Ansatrienin B; 20,23-Quinone, Ansatrienin B; 20,23-Quinone, N-deacyl, N-(2ξ-methylbutanoyl), Ansatrienin B; 20,23-Quinone, N-deacyl, N-(3-methylbutanoyl), Ansatrienin B; 20,23-Quinone, N-deacyl, N-(4-methylpentanoyl), Ansatrienin B; 20,23-Quinone, 1'',2''-didehydro, Anslimins, Anthelvencin A; (S)-form, Anthelvencin B, Anthracidins, Anthracyclinone blue B, Anthracyclinone blue B; 12-Deoxy, Anthracyclinone 58G, Anthramycin, Anthramycin; 11-Et ether, N3'-Me, Anthramycin; N3'-Me, Anthramycin; 11-Me ether, N3'-Me, Anthramycin; Stereoisomer(?), Antibiotic 1004, Antibiotic 1008, Antibiotic 1100-50, Antibiotic 11-98, Antibiotic 1308, Antibiotic 131-1, Antibiotic 144-3, Antibiotic 156, Antibiotic 1579, Antibiotic 1588, Antibiotic 165, Antibiotic 1695, Antibiotic 1728, Antibiotic 1762, Antibiotic 1904, Antibiotic 206, Antibiotic 207, Antibiotic 216, Antibiotic 2305, Antibiotic 232, Antibiotic 2339, Antibiotic 2381, Antibiotic 24010, Antibiotic 2789, Antibiotic 2844-31; Antibiotic 2844-31A, Antibiotic 2844-31; Antibiotic 2844-31B, Antibiotic 2844-31; Antibiotic 2844-31C, Antibiotic 2911-2, Antibiotic 29119, Antibiotic 2928, Antibiotic 32, Antibiotic 323-58, Antibiotic 362, Antibiotic 3671, Antibiotic 3738-36, Antibiotic 472, Antibiotic 5, Antibiotic 5102-2, Antibiotic 5590, Antibiotic 560, Antibiotic 58, Antibiotic 583, Antibiotic 6431 36, Antibiotic 661, Antibiotic 6734 21, Antibiotic 69, Antibiotic 713, Antibiotic 741, Antibiotic 768, Antibiotic 792, Antibiotic 80-258, Antibiotic 878-6, Antibiotic 9408, Antibiotic 991, Antibiotic A 110-1, Antibiotic 116A, Antibiotic 1176A, Antibiotic A 121, Antibiotic 13285A, Antibiotic 14A, Antibiotic A 1502, Antibiotic A 171-2, Antibiotic A 1787, Antibiotic A 19009, Antibiotic A 2121, Antibiotic A 2121; Antibiotic A 2121-1, 4DO-Deacyl, Antibiotic A 216, Antibiotic A 2201, Antibiotic A 221, Antibiotic 273a2; Antibiotic 273a2α, Antibiotic 273a2; Antibiotic 273a2β, Antibiotic A28, Antibiotic A 280, Antibiotic A 33853, Antibiotic A 35512, Antibiotic A 38533, Antibiotic 4181A, Antibiotic A 477, Antibiotic A 4993, Antibiotic A 54145, Antibiotic A 54145; Antibiotic A 54145D, 3'''-Deoxy, 3-O-de-Me, Antibiotic A 54145; Antibiotic A 54145D, 3-Demethoxy, Antibiotic A 54145; Antibiotic A 54145D, 3-Demethoxy, 3'''-deoxy, Antibiotic A 54145; Antibiotic A 54145E, 3-Demethoxy, 3'''-deoxy, Antibiotic A 54556, Antibiotic 549-A1, Antibiotic 593A, Antibiotic A 5945, Antibiotic A 60, Antibiotic A 6067, Antibiotic 67-121A; N-De-Me, Antibiotic A 74528, Antibiotic A 77951, Antibiotic A 80789, Antibiotic 859A, Antibiotic 875A, Antibiotic 927A, Antibiotic A 94964, Antibiotic A 9594, Antibiotic A 9828, Antibiotic A 011A, Antibiotic A 0341A, Antibiotic A 0341A; 3-Hydroxy, Antibiotic A 16886A, Antibiotic A 201A, Antibiotic A 201A; 2Bξ,3Bξ-Dihydro. Antibiotic A 201A; 1B—O-Deglycosyl, Antibiotic A 201A; 3''-Hydroxy, Antibiotic A 228A, Antibiotic A 39183A, Antibiotic A 41030A, Antibiotic A 41030A; 22,45-Bis(dechloro), Antibiotic A 41030A; 22-Dechloro, Antibiotic A 41030A; 45-Dechloro, Antibiotic A 41030A; 22-Dechloro, dibutyl, Antibiotic A 41030A; 11-O-[Galactosyl-(1→?)-galactoside], dibutyl, Antibiotic A 41030A; 11-O-[Galactosyl-(1→?)-galactoside], Antibiotic A 41030A; 011-Sulfate, Antibiotic A 500359A, Antibiotic A 500359A; 2'-O-Carbamoyl, Antibiotic A 500359A; O-De-Me, Antibiotic A 500359A; 2''-Deoxy, Antibiotic A 51493A, Antibiotic A 53868A, Antibiotic A 80915A, Antibiotic A 82548A, Antibiotic AB 021, Antibiotic AB 023; Antibiotic AB 023A, Antibiotic AB 023; Antibiotic AB 023B, Antibiotic AB 041, Antibiotic A 10255B, Antibiotic A 130B, Antibiotic A 130B; 27-De(glycosyloxy), Antibiotic A 1308; 28-Epimer, 27-de(glycosyloxy), Antibiotic AB 161-2, Antibiotic A 58365B, Antibiotic AB 650, Antibiotic AB 78, Antibiotic A 80915B, Antibiotic A 80915B; 7-Demethyl, Antibiotic AB 3217A, Antibiotic AB 3217A; 13-O-(6-Hydroxy-1-methylheptanoyl), Antibiotic AB 3217A; 13-O-(4-Methylpentanoyl), Antibiotic A 10255C, Antibiotic A 21978C, Antibiotic A 21978C; Antibiotic A 21978C1, 11-D-Asparagine analogue, Antibiotic A 21978C; Antibiotic A 21978C2, 11-D-Asparagine analogue, Antibiotic A 21978C; Antibiotic A 21978C3, 11-D-Asparagine analogue, Antibiotic A 39183C, Antibiotic A 58365C, Antibiotic A 80915C, Antibiotic AD 26-1, Antibiotic AD 26-1; 5-O-Carbamoyl. Antibiotic A 39183D, Antibiotic A 80915D, Antibiotic A 10255E, Antibiotic A 39183E, Antibiotic AE 56, Antibiotic AF 030, Antibiotic A 10255F, Antibiotic AF 1231, Antibiotic A 503083F, Antibiotic A 503083F; Me ester, Antibiotic AF 7368E, Antibiotic A 10255G, Antibiotic A 80915G, Antibiotic A 10255H, Antibiotic AH 272α2, Antibiotic AH 272β2, Antibiotic AH 758, Antibiotic AI 5662, Antibiotic A 6661I, Antibiotic A 10255J, Antibiotic AJI 9561, Antibiotic AJI 9561; Me ester, Antibiotic AK 164, Antibiotic AM 8402, Antibiotic A 39079S-1, Antibiotic ASK 753, Antibiotic AS-N-7A, Antibiotic A 6888X, Antibiotic A 6888X; 20-Aldehyde, Antibiotic A 6888X; 20-Aldehyde, 4B-ketone, Antibiotic A 6888X; 4"-Epimer, 20-aldehyde, Antibiotic A 418Z-4, Antibiotic AZ-SH 29, Antibiotic 011B, Antibiotic B 1000, Antibiotic 10381b2, Antibiotic 1401B, Antibiotic 17-41B, Antibiotic 24010B1, Antibiotic B 28963, Antibiotic 301B, Antibiotic 301B; 5-O-Deglycosyl, Antibiotic 301B; 5-O-Deglycosyl, N4-de-Me, Antibiotic 4181B, Antibiotic 834B1, Antibiotic B 15565A, Antibiotic B 1625a-410, Antibiotic BA 6903, Antibiotic BA 17039A, Antibiotic BA 181314A, Antibiotic B 2289An, Antibiotic B 15565B, Antibiotic BE 14106, Antibiotic BE 14106; 8-Deoxy, Antibiotic BE 16627, Antibiotic BE 19093, Antibiotic BE 22179, Antibiotic BE 23254, Antibiotic BE 39891, Antibiotic BE 48021, Antibiotic BE 51068, Antibiotic BE 52211, Antibiotic BE 54017, Antibiotic BE 54476. Antibiotic BE 55051. Antibiotic BE 67251. Antibiotic BE 19412A, Antibiotic BE 26554A. Antibiotic BE 40665A; 9,9'-Dichloro, Antibiotic BE 43472A, Antibiotic BE 43472A; 4-Deoxy, Antibiotic BE 43472A; 4-Deoxy, 8'-Me ether, Antibiotic BE 43472A; 8'-Me ether, Antibiotic BE 52440A, Antibiotic BE 52440A; Monoalcohol, Antibiotic BE 54238A, Antibiotic BE 54238A; 1α-Hydroxy, 2'→1-lactone, Antibiotic BE 24566B; (+)-form, Antibiotic BE 24566B; (−)-form, Antibiotic BE 24566B; (−)-form, 10,12-Dichloro, 3-Me ether, Antibiotic BE 41956B1, Antibiotic BE 41956B1; 4'-Epimer, Antibiotic BE 52211C, Antibiotic BE 52211C; Δ17-Isomer, Antibiotic BE 45985X, Antibiotic B 1625FA2β-1, Antibiotic B 2847αH, Antibiotic BI 32169, Antibiotic BK 217γ, Antibiotic B 2847αL, Antibiotic BL 580, Antibiotic BL 617, Antibiotic B1T20, Antibiotic BU 4726G, Antibiotic C 104, Antibiotic C 104; 4A-Deacyl, Antibiotic C 104; 6-Hydroxy, Antibiotic C 1051, Antibiotic C 13648, Antibiotic C 15462, Antibiotic C 15462; Antibiotic C 15462V, Antibiotic C2, Antibiotic 202C, Antibiotic C22-4, Antibiotic 301C, Antibiotic C4; 5'-Alcohol, Antibiotic 4018-1C, Antibiotic 5399C, Antibiotic 6904C, Antibiotic C 8030B, Antibiotic CBS 154-94A, Antibiotic CBS 154-94B, Antibiotic CBS 154-94B; Me ester, Antibiotic CC 10232, Antibiotic C 8030D, Antibiotic CDA, Antibiotic CDA; Antibiotic CDA 4B, 4',6-Deoxy, 3,3-O-phosphate, Antibiotic CDA; Antibiotic CDA 4B, 4',6-Deoxy, 4',6-fluoro, 3,3-O-phosphate, Antibiotic CDA; Antibiotic CDA 4B, 4',6-Deoxy, 4',6-fluoro, 2.1,3.1-didehydro(Z-), 3,3-O-phosphate, Antibiotic CDK 711A, Antibiotic CDK 711A; 1D-Deglycosyl, Antibiotic CE 108, Antibiotic CE 108, Antibiotic CE 108; Amide, Antibiotic CE 108; 14-Decarboxy, 14α-methyl, Antibiotic C 19393E5, Antibiotic CG 15B, Antibiotic CG 15B; 3B-Deoxy, Antibiotic CG 15B; 3B-Deoxy, N,N-di-Me, Antibiotic CG 15B; 3B-Deoxy, N-Me, Antibiotic CG 15B; 3B,10-Dideoxy, 13ξ-alcohol, Antibiotic CG 15B; 10-Deoxy, 13ξ-alcohol, Antibiotic CG 15B; 6-Deoxy, N,N-di-Me, Antibiotic CG 15B; N,N-Di-Me, Antibiotic CG 15B; N-Me, Antibiotic CG 17B, Antibiotic CG 17B; 38-Deoxy, Antibiotic CG 17B; 3B-Deoxy, 4-Me ether, Antibiotic CG 17B; 4-Me ether, Antibiotic CK 4416, Antibiotic CP 101765, Antibiotic CP 21635, Antibiotic CP 50833, Antibiotic CP 56064, Antibiotic CP 56064; 12,13-Epoxide, Antibiotic CP 73064, Antibiotic CP 91243; 30-Hydroxy, 4A,4B-di-Me ether, Antibiotic CRP 2504-1, Antibiotic CV 1, Antibiotic 17927D, Antibiotic D 788-10, Antibiotic D 788-10; Me ester, Antibiotic DC 102, Antibiotic DC 105, Antibiotic DC 14, Antibiotic DC 81; (S)-form, Antibiotic DC 79A, Antibiotic DC 8118A, Antibiotic DC 8118A; 8'-Ketone, Antibiotic DC 38B, Antibiotic DJ 7164, Antibiotic DJ 400B; Antibiotic DJ 400B1, Antibiotic DJ 400B; Antibiotic DJ 400B2, Antibiotic DMCJ 49, Antibiotic 5838-DNI-3, Antibiotic 5923 DNI, Antibiotic 1-81D-1S, Antibiotic DX 27, Antibiotic 289E, Antibiotic E 367, Antibiotic E 76, Antibiotic E 210A, Antibiotic ECO 02301, Antibiotic EI 1511-3, Antibiotic EI 1511-5, Antibiotic EI 1511-5; Deepoxy, 5R-hydroxy, Antibiotic EI 1625-2, Antibiotic EI 2346, Antibiotic EM 2487, Antibiotic EM 98, Antibiotic F 2787, Antibiotic F 40, Antibiotic F 1370A, Antibiotic FA 2713, Antibiotic FA 252C, Antibiotic F 1370B, Antibiotic F 10C, Antibiotic FCE 21424, Antibiotic FCE 21424; 1",3"-Di-Me, Antibiotic FCE 21424; 2"-Thioxo analogue, Antibiotic FD 594, Antibiotic FD 891, Antibiotic FD 891; Stereoisomer (?), Antibiotic FD 892, Antibiotic FK 156, Antibiotic FK 506 isomer, Antibiotic FK 520 isomer, Antibiotic FL 120B', Antibiotic FL 120B'; O-De-Ac, 4-O-(2-methylpropanoyl), Antibiotic FL 657B, Antibiotic 289FO, Antibiotic FR 112123, Antibiotic FR 32863, Antibiotic FR 33289; (R)-form, Antibiotic FR 3383, Antibiotic FR 66979, Antibiotic FR 900012, Antibiotic FR 900109, Antibiotic FR 900137, Antibiotic FR 900148, Antibiotic FR 900336, Antibiotic FR 900452, Antibiotic FR 900452; Dihydro (?), Antibiotic FR 900462, Antibiotic FR 900482, Antibiotic FR 900482; 1,7,9-Tri-Ac, Antibiotic FU 10; 6'-Deoxy, 6'-amino, Antibiotic G1, Antibiotic G 252, Antibiotic G 253, Antibiotic G 83, Antibiotic GAI, Antibiotic GE 1655, Antibiotic GE 81112, Antibiotic GE 37468A, Antibiotic GE 37468A; 6-N-De(alkylaminoalkyl), Antibiotic GE 37468A; 3-N-De(carboxyalkyl), Antibiotic GE 3B, Antibiotic GEX 103, Antibiotic GP III, Antibiotic 2814H, Antibiotic H 3787, Antibiotic 3874H3, Antibiotic 3874H4, Antibiotic 3874H5, Antibiotic 3874H6, Antibiotic H 668, Antibiotic H 85, Antibiotic HA-1-92, Antibiotic HA-2-91, Antibiotic HHM 15, Antibiotic H 88111, Antibiotic H 537SY2, Antibiotic I 22, Antibiotic 8510-I, Antibiotic IC 101, Antibiotic IC 101; N1-Deoxy, Antibiotic IN 183T, Antibiotic IT 62B, Antibiotic JA 4015, Antibiotic JA 4495, Antibiotic JBIR 06, Antibiotic JBIR 06; 9-Demethyl, Antibiotic JBIR 11, Antibiotic JBIR 88, Antibiotic JI 20B, Antibiotic K 502, Antibiotic K 502; Antibiotic K 502-7, Antibiotic K 502; Antibiotic K 502A, Aglycone, Antibiotic K 802-4, Antibiotic K97-0239A, Antibiotic K 252b; 3'-Deoxy, 3'-(methylamino), Me ester, Antibiotic K 252b; Me ester, Antibiotic K 41B, Antibiotic K 41B; 15-O-Deglycosyl, 15-Me ether, Antibiotic K 41B; 15-De(glycosyloxy), Antibiotic K97-0239B, Antibiotic KF 77AG6; (S,S)-form, Antibiotic KI 26A, Antibiotic KOSN 1633, Antibiotic KOSN 1633; 4,5-Dihydro, Antibiotic KT 151, Antibiotic L 11-1, Antibiotic L 156602, Antibiotic L 29-141, Antibiotic L 681217, Antibiotic L 72, Antibiotic LA 5352, Antibiotic LA 5937, Antibiotic LC 28, Antibiotic LIA 0331, Antibiotic LIA 0735, Antibiotic LIA 0832C, Antibiotic LIA 0832D, Antibiotic LL-A 491, Antibiotic LL-AB 664, Antibiotic LL-AB 664; N5-Me, Antibiotic LL-BH872α, Antibiotic LL-BH872α; 2ξ-Alcohol, Antibiotic LL-BH872α; 4'ξ-Hydroxy, 2ξ-alcohol, Antibiotic LL-BH 890α, Antibiotic LL-BH 890β, Antibiotic LL-BL 869β, Antibiotic LL-BM 27β, Antibiotic LL-BM 27β; 2-Deoxy, Antibiotic LL-BM 27β; 2-Deoxy, 2'-amino, Antibiotic LL-BM 726, Antibiotic LL-BO 2964, Antibiotic LL-C 08078, Antibiotic LL-D 49194β1, Antibiotic LL-D 49194β1; 17-Deoxy, 14,17-epoxide, Antibiotic LL-D 49194β1; 17-Deoxy, 14,17-epoxide, 4"-O-de-Ac, Antibiotic M 259, Antibiotic M 331, Antibiotic M 770, Antibiotic M 368A, Antibiotic MA 39, Antibiotic MA 144E1, Antibiotic MA 144 U7, Antibiotic MA 144 U7; 4B-Deglycosyl, Antibiotic MA 144 U7; 4B-Deglycosyl, 3B-deoxy, Antibiotic MA 144 U7; 1,2CR-Dihydroxy, 4C-ketone, 3A-O-carbamoyl, Antibiotic MA 144 U7; 4C-Epimer, 3B-deoxy, Antibiotic MA 144 U7; 4C-Epimer, 11-hydroxy, 3A,3B-dideoxy, Antibiotic MA 144 U7; 4C-Epimer, 1-hydroxy, 3A,3B-dideoxy, Antibiotic MA 144 U7; 4C-Epimer, 1-hydroxy, 3B-deoxy, Antibiotic MA 144 U7; 4C-Ketone, Antibiotic MA 144 U7; 1-Hydroxy, 3A-deoxy, 4C-ketone, Antibiotic MA 144 U7; 1-Hydroxy, 4C-ketone, Antibiotic M 3688, Antibiotic MC 637SY1, Antibiotic MC 696-SY2B, Antibiotic MD 129C2, Antibiotic ME 168, Antibiotic MF 722-02, Antibiotic MF-EA 705α, Antibiotic MF-EA 705α; (1"Z)-Isomer, 3",4"-dihydro, Antibiotic MH 850, Antibiotic MH 563-32F1, Antibiotic ML 449, Antibiotic MM 44785, Antibiotic MM 44786, Antibiotic MM 44787, Antibiotic MM 44788, Antibiotic MM 8, Antibiotic MR 387A, Antibiotic MR 387A; 4-Deoxy, Antibiotic MS 282, Antibiotic MSO 901809, Antibiotic MT 10, Antibiotic MYC 8005, Antibiotic NA 181, Antibiotic N 44A-21, Antibiotic NA 699, Antibiotic NA 22598A, Antibiotic NA 22598A1, Antibiotic NAT 13, Antibiotic NC-GAI, Antibiotic NK 1012-2, Antibiotic NK 1012-3, Antibiotic NK 86-0186, Antibiotic NK 30424A, Antibiotic NK 30424A; Stereoisomer, Antibiotic NK 170204B, Antibiotic NP 522, Antibiotic NRC 101, Antibiotic NRC 501, Antibiotic NRC-C7, Antibiotic NRCS 15, Antibiotic NS 5, Antibiotic NS 5; N—Ac, Antibiotic NS 5; 1',2'-Didehydro, N—Ac, Antibiotic NSC-C, Antibiotic N05WA963A, Antibiotic N05WA963A; 4A-Deglycosyl, Antibiotic N05WA963A; 2C,3C-Didehydro, Antibiotic NW-G01, Antibiotic NW-G01; 2",3"-Didehydro, Antibiotic O 2867α, Antibiotic OA 7653, Antibiotic OA 612981, Antibiotic OA 612981; 8-Deoxy, Antibiotic OA 6129B1; 6-Epimer, Antibiotic OA 6129B1; 8-O-Sulfate, Antibiotic OA 6129D, Antibiotic OA 6129E, Antibiotic O 611B, Antibiotic OS 1804, Antibiotic OS 3256B, Antibiotic P 125, Antibiotic P 15149, Antibiotic P 15149; 8,19-Didehydro, 8,19-epoxide, Antibiotic P 15149; 12-Hydroxy, Antibiotic P 15149; 8-Hydroxy, Antibiotic 1645 P1, Antibiotic 1645P2, Antibiotic 31668P, Antibiotic P 371; Antibiotic P 371A1, Antibiotic P 371; Antibiotic P 371A1, 4β-Acetoxy, Antibiotic P 371; Antibiotic P 371B1, Antibiotic P 371; Antibiotic P 371B2, Antibiotic P 6226, Antibiotic PA 108, Antibiotic PA 128, Antibiotic PA 150, Antibiotic PA 153, Antibiotic PA 166, Antibiotic PA 616, Antibiotic PA 86, Antibiotic PA 133A, Antibiotic PA 46101A, Antibiotic PA 46101A; O6-(2,4-Di-O-methyl-3-C-methyl-α-rhamnopyranoside), Antibiotic PA 133B, Antibiotic PA 155B, Antibiotic PA 32413-I, Antibiotic PD 116152, Antibiotic PD 116740, Antibiotic PD 116740; O-De-Me, 6-O-(2,3,6-trideoxy-α-L-threo-hexopyranoside), Antibiotic PD 118576, Antibiotic PD 118576A1, Antibiotic PD 118576A1; 19-Me ether, Antibiotic PD 118576A2, Antibiotic PDE I, Antibiotic PDE II, Antibiotic PI 080, Antibiotic PI 080; 3-O-Deglycosyl, Antibiotic PI 080; 3-O-Deglycosyl, 2C,3C-dihydro, Antibiotic PI 085, Antibiotic PI 087, Antibiotic PS 6, Antibiotic PS 8, Antibiotic 3543 R1, Antibiotic R 906, Antibiotic RES 701, Antibiotic RK 1441A, Antibiotic RK 1441A; 11-Ketone, 3-O-de-Me, Antibiotic RK 699A, Antibiotic RK 955A, Antibiotic Ro 09-0766, Antibiotic Ro 09-0767, Antibiotic Ro 09-0768, Antibiotic 11837 RP, Antibiotic RP 13252, Antibiotic RP 16511, Antibiotic RP 16978, Antibiotic RP 17967, Antibiotic RP 18061, Antibiotic RP 18887, Antibiotic 19402 RP, Antibiotic RP 23671, Antibiotic RP 63834, Antibiotic RP 6798, Antibiotic RP 7071, Antibiotic RP 9768, Antibiotic RP 9971, Antibiotic RPI 856A, Antibiotic RPI 856A; 3"-Epimer, Antibiotic RPI 856C, Antibiotic RPI 856C; 3"-Epimer, Antibiotic RS 10, Antibiotic S 19, Antibiotic S 383-0, Antibiotic S 433, Antibiotic S 541; Antibiotic S 541A, Antibiotic S 541; Antibiotic S 541A, 5-Ketone, Antibiotic S 541; Antibiotic S 541A, 7-Deoxy, 2,5,6,7-tetradehydro, Antibiotic S 541; Antibiotic S 541A, Δ2-Isomer, Antibiotic S 541; Antibiotic S 541A, O5-Me, Antibiotic S 541; Antibiotic S 541C, Antibiotic S 541; Antibiotic S 541C, O5-Me, Antibiotic S 541; Antibiotic S 541D, Antibiotic S 541; Antibiotic S 541D, O5-Me, Antibiotic S 685, Antibiotic S 728, Antibiotic SA16-10, Antibiotic SA 1795, Antibiotic SA5-10, Antibiotic SAB 711, Antibiotic SAX 10, Antibiotic SB 212305, Antibiotic SB 217452, Antibiotic SB 22484, Antibiotic S 583B, Antibiotic S 8878, Antibiotic SBR 22, Antibiotic S-4C 33, Antibiotic S 632C, Antibiotic S 3907C4B, Antibiotic S 3907C4B; 4"-O-Sulfate, Antibiotic Sch 212394, Antibiotic Sch 382582, Antibiotic Sch 382582; De(methylthio), Antibiotic Sch 47555, Antibiotic Sch 47555; 2,3"-Didehydro, 4"-ketone, Antibiotic Sch 538415, Antibiotic Sch 58450, Antibiotic SEN 143, Antibiotic SEN 315, Antibiotic SEN 366D1, Antibiotic SEN 366D1, 2,3-Dihydro, Antibiotic SEN 366D1; 2-Hydroxy, 2,3-dihydro, Antibiotic SEN 366F, Antibiotic SF 1130, Antibiotic SF 1195, Antibiotic SF 1223, Antibiotic SF 1508, Antibiotic SF 1623, Antibiotic SF 1739, Antibiotic SF 1771, Antibiotic SF 1774, Antibiotic SF 1902; Antibiotic SF 1902A1, Antibiotic SF 1902; Antibiotic SF 1902A2, Antibiotic SF 1902; Antibiotic SF 1902A3, Antibiotic SF 1902; Antibiotic SF 1902A5, Antibiotic SF 1902; Antibiotic SF 1902A4a, Antibiotic SF 1902; Antibiotic SF 1902A4b, Antibiotic SF 1999, Antibiotic SF 2012, Antibiotic SF 2059, Antibiotic SF 2068, Antibiotic SF 2077, Antibiotic SF 2330, Antibiotic SF 2354, Antibiotic SF 2398, Antibiotic SF 2425, Antibiotic SF 2437, Antibiotic SF 2543, Antibiotic SF 2547, Antibiotic SF 2575, Antibiotic SF 2575; 4'-O-Deacyl, 4'-O-(2-ethyl-2Z-butenoyl), Antibiotic SF 2575; 12a-O-De-Me, Antibiotic SF 2609, Antibiotic SF 2716, Antibiotic SF 2768, Antibiotic SF 2771, Antibiotic SF 2776, Antibiotic SF 701, Antibiotic SF 701; N2"-De-Me, N5-Me, Antibiotic SF 701; N2"-Me, Antibiotic SF 98, Antibiotic SF 1540A, Antibiotic SF 1670A, Antibiotic SF 1961A, Antibiotic SF 2050A, Antibiotic SF 2111A, Antibiotic SF 2415A1, Antibiotic SF 2415A2, Antibiotic SF 2415A3, Antibiotic SF 2415A3; 7-Demethyl, Antibiotic SF 2446A1. Antibiotic SF 2446A1; Aglycone, Antibiotic SF 2446A1; 6-Deoxy, Antibiotic SF 2446A1; 1'-Epimer, Antibiotic SF 2446A1; 1'-Epimer, 6-deoxy, Antibiotic SF 1306B, Antibiotic SF 1540B, Antibiotic SF 1961B, Antibiotic SF 2103B, Antibiotic SF 2111B, Antibiotic SF 2415B1, Antibiotic SF 2415B2, Antibiotic SF 241583, Antibiotic SF 689B, Antibiotic SF 2587C, Antibiotic SF 733C, Antibiotic SF 2012L, Antibiotic SH 50, Antibiotic SK 229, Antibiotic S 213L, Antibiotic SOB 7, Antibiotic SP 351. Antibiotic SR 1223, Antibiotic SR 1768C, Antibiotic SR 1768F, Antibiotic SR 1768G, Antibiotic SS 33410, Antibiotic SS 49, Antibiotic SS 70, Antibiotic SS 21020A, Antibiotic SS 5401A, Antibiotic SS 56A, Antibiotic SS 56A; 4'-Epimer, Antibiotic SS 8215A, Antibiotic SS 288B, Antibiotic SS 288B; 1,3B,3C,3E,3F-Pentadeoxy, Antibiotic SS 288B; 1,3B,3C,3E,3F-Pentadeoxy, 2C,3C-didehydro, 4C-ketone, Antibiotic SS 288B; 1,3B,3C,3E,3F-Pentadeoxy, 2C,2F,3C,3F-tetradehydro, 4C,4F-diketone, Antibiotic SS 288B; 3B,3C,3E,3F-Tetradeoxy, Antibiotic SS 288B; 3B,3C,3E,3F-Tetradeoxy, 2C,3C-didehydro, 4C-ketone, Antibiotic SS 288B; 1,3B,3C,3F-Tetradeoxy, Antibiotic SS 288B; 3B,3C,3F-Trideoxy, Antibiotic SS 288B; 1,3B,3C-Trideoxy, 2C,3C-didehydro, 4C-ketone, 4D-deglycosyl, Antibiotic SS 288B; 3C-Deoxy, 4C-ketone, 10-deglycosyl, Antibiotic SS 288B; 1,3C-Dideoxy, 4C-ketone, 4D-deglycosyl, Antibiotic SS 288B; 1,3C,3E,3F-Tetradeoxy, Antibiotic SS 288B; 1,3C,3E,3F-Tetradeoxy, 4C-ketone, Antibiotic SS 288B; 1,3C,3E,3F-Tetradeoxy, 4F-ketone, Antibiotic SS 288B; 3C,3E,3F-Trideoxy, Antibiotic SS 288B; 3C,3E,3F-Trideoxy, 4C-ketone, Antibiotic SS 288B; 3C,3E,3F-Trideoxy, 2F,3F-didehydro, 4C,4F-diketone, Antibiotic SS 288B; 3C,3F-Dideoxy, Antibiotic SS 288B; 1,3C,3F-Trideoxy, Antibiotic SS 288B; 1,3C,3F-Trideoxy, 4C,4F-diketone, Antibiotic SS 288B; 7-De(glycosyloxy), 1-deoxy, Antibiotic SS 288B; 1-Deoxy, Antibiotic SS 288B; 1-Deoxy, 10-deglycosyl, Antibiotic SS 288B; 1,3E,3F-Trideoxy, 2F,3F-didehydro, 4F-ketone, 4A-deglycosyl, Antibiotic SS 8201B, Antibiotic SS 82288. Antibiotic SS 9816B, Antibiotic SS 8228C, Antibiotic SS 9816C, Antibiotic SS 43405D, Antibiotic SS 21020E, Antibiotic SS 9816E, Antibiotic ST 906, *Streptomyces toyocaensis* Antibiotic, Antibiotic SW 163A, Antibiotic SW 163A; De(formylamino), 2"-deoxy, 1-ketone, Antibiotic SW 163A; N-Deformyl, Antibiotic SW 163A; 1-Ketone, Antibiotic SW 163B, Antibiotic SW 163C. Antibiotic TA 13, Antibiotic TA 146, Antibiotic TA 243, Antibiotic TA 52, Antibiotic TA 54, Antibiotic TA 5411, Antibiotic TA 435A, Antibiotic TAN 1171, Antibiotic TAN 1254, Antibiotic TAN 1280, Antibiotic TAN 1039A, Antibiotic TAN 1460 A, Antibiotic TAN 420A, Antibiotic TAN 420A; 21-Deoxy, 12,13-didehydro(Z-), 4,5-dihydro, O15-de-Me, O12-Me, Antibiotic TAN 420A; 21-Deoxy, 12,13-didehydro(Z-), 4,5-dihydro, 015-de-Me, 012-Me, 11-carbamoyl, Antibiotic TAN 420A; 21-Deoxy, 4,5-dihydro, O15-de-Me, 012-Me, Antibiotic TAN 420A; 21-Deoxy, 4,5-dihydro, O15-de-Me, O12-Me, decarbamoyl, Antibiotic TAN 420A; O11,O12-Di-Me, Antibiotic TAN 420A; O12-Me, Antibiotic TAN 420A; 18,21-Quinone, Antibiotic TAN 420A; 18,21-Quinone, 15-demethoxy, O12-Me, Antibiotic TAN 420A; 18,21-Quinone, O11,O12-di-Me, Antibiotic TAN 420A; 18,21-Quinone, O12-Me, Antibiotic TAN 1460B, Antibiotic TAN 1532B, Antibiotic TAN 1532B; Decarboxy, 5,6-didehydro, 6-hydroxy. Antibiotic TAN 1532B; 5,6-Didehydro, Antibiotic TAN 1532B; 5,6-Didehydro, 13-O-(6-deoxyhexopyranosyl), Antibiotic TAN 1532B; 5,6-Didehydro, 6-hydroxy, Antibiotic TAN 1532B; 13-Me ether, Antibiotic TAN 876B, Antibiotic TAN 950B, Antibiotic T 2636B, Antibiotic TG 379A, Antibiotic TH 818, Antibiotic T 2636K, Antibiotic TK 12A, Antibiotic T 2636L, Antibiotic TM 482A, Antibiotic TM 482B, Antibiotic TMC 66, Antibiotic TMC 135A, Antibiotic TMC 89A, Antibiotic TMC 89A; 2-Epimer, Antibiotic TMC 1B, Antibiotic TMC 135B, Antibiotic TOM 83A, Antibiotic TPU 0043, Antibiotic TPU 0043; Stereoisomer(2), Antibiotic TPU 0043; Stereoisomer(2), 1',14-dihydroxy, Antibiotic TPU 0043; Stereoisomer(2), 1'-hydroxy, Antibiotic TPU 0043; Stereoisomer(2), 14-hydroxy, Antibiotic Tu 3010, Antibiotic Tu 1718B, Antibiotic U 106305, Antibiotic U 13714, Antibiotic U 15774, Antibiotic 31668U, Antibiotic U 56407, Antibiotic U 56407; Deepoxy, 5R-hydroxy, Antibiotic U 60394, Antibiotic U 62162, Antibiotic U 64846, Antibiotic U 68204, Antibiotic U 77802, Antibiotic U 77802; 3'''-Demethyl, Antibiotic UCF 13, Antibiotic UCH 15A, Antibiotic UCH 15A; N4'-Hydroxy, Antibiotic UCK 14A1, Antibiotic UCK 14C, Antibiotic UK 2, Antibiotic UK 2; Antibiotic UK 2A, Demethoxy, Antibiotic UK 63052, Antibiotic UK 63052; Antibiotic UK 63052, Antibiotic UK 63052; Antibiotic UK 63598, Antibiotic UK 63052; Antibiotic UK 65662, Antibiotic UK 63052; Antibiotic UK 163E, Antibiotic UK 86956, Antibiotic VI 7501, Antibiotic VKPM 425, Antibiotic VM 44866, Antibiotic VM 44866; 13β,23β-Bis(2-methylpropanoyloxy), Antibiotic VM 44866; 13β,23β-Bis(2-methylpropanoyloxy), 5-Me ether, Antibiotic VM 44866; 22-Deoxy, Antibiotic VM 44866; 22-Deoxy, 13β-(2-methylpropanoyloxy), Antibiotic VM 44866; 26-(3-Furanylacetoxy), Antibiotic VM 44866; 13β-Hydroxy, 5-Me ether, Antibiotic VM 44866; 5-Me ether, Antibiotic VM 44866; 27α-Methoxy, 5-Me ether, Antibiotic VM 44866; 26-(3-Methylbutanoyloxy), Antibiotic VM 44866; 13β-(2-Methylbutanoyloxy), 23β-(2-methylpropanoyloxy), 5-Me ether, Antibiotic VM 44866; 26-(3-Methyl-2-butenoyloxy), Antibiotic VM 44866; 13β-(2-Methylpropanoyloxy), Antibiotic VM 44866; 23β-(2-Methylpropanoyloxy), Antibiotic VM 44866; 23β-(2-Methylpropanoyloxy), 13β-hydroxy, Antibiotic VM 44866; 23β-(2-Methylpropanoyloxy), 13β-hydroxy, 5-Me ether, Antibiotic VM 44866; 13β-(2-Methylpropanoyloxy), 5-Me ether, Antibiotic VM 44866; 23β-(2-Methylpropanoyloxy), 5-Me ether, Antibiotic VM 44866; 26-(Tigloyloxy), 5-Me ether, Antibiotic VM 54339, Antibiotic W 46, Antibiotic WA 3854; Antibiotic WA 3854A, Antibiotic WA 3854; Antibiotic WA 3854A, 1-Aldehyde, Antibiotic WA 3854; Antibiotic WA 38548, Antibiotic WA 3854; Antibiotic WA 3854C, Antibiotic WA 3854; Antibiotic WA 3854D, Antibiotic W 341C, Antibiotic WCM 302, Antibiotic WF 5027I, Antibiotic WF 5027I; Tautomer, Antibiotic WP 3688-3, Antibiotic WP 3688-4, Antibiotic WP 3688-5, Antibiotic WR 142, Antibiotic WS 1279, Antibiotic WS 1921, Antibiotic WS 7338, Antibiotic WS 7338; Antibiotic WS 7338A, Antibiotic WS 7338; Antibiotic WS 7338B, Antibiotic WS 5995A, Antibiotic WS 009B, Antibiotic WS 009B; 6-Deoxy, Antibiotic WS 5995B, Antibiotic WS 5995B; 3'-Hydroxy, Antibiotic WS 79089B; 1'R-Hydroxy, δ-lactone, Antibiotic X 1008, Antibiotic X 1019, Antibiotic X 1020, Antibiotic X 63, Antibiotic X 14885A, Antibiotic X 372A, Antibiotic X 148738, Antibiotic X 14881B; O-De-Me, Antibiotic X 14881B; 4β-Hydroxy, Antibiotic X 14881B; 4β-Hydroxy, 6a-deoxy, 6a,12a-didehydro, 6a,12a-epoxide, Antibiotic X 14873C, Antibiotic X 14873D, Antibiotic X 14889D, Antibiotic X 14873G, Antibiotic XK 211, Antibiotic XK 46, Antibiotic XK 33F2, Antibiotic XK 201IV, Antibiotic Y, Antibiotic Y; 1"-Deoxo, Antibiotic Y; 2"-Hydroxy, Antibiotic YA 56Y, Antibiotic YF 044P-D, Antibiotic YG 665G, Antibiotic Y 03762J, Antibiotic YL 02107Q-A; 2B-Epimer, 2'-hydroxy, Antibiotic YL 02107Q-A; 2'ξ-Hydroxy, 5-O-deglycosyl, Antibiotic YM 24074, Antibiotic YN 0165JA, Antibiotic Y 1801W-C, Antibiotic Zg, Antibiotic Zg; 1'-Ketone, Anticapsin, Antifilamentous phage substance, Antifongine 4915, Antifungalmycin 702, Antimycic acid; N-Formyl, Me ester, Antimycin A, Antimycin A; Antimycin A1, Antimycin A; Antimycin A11, Antimycin A; Antimycin A12, Antimycin A; Antimycin A13, Antimycin A; Antimycin A14, Antimycin A; Antimycin A15, Antimycin A; Antimycin A16, Antimycin A; Antimycin A17, Antimycin A; Antimycin A18, Antimycin A; Antimycin A19, Antimycin A; Antimycin A2, Antimycin A; Antimycin A20, Antimycin A; Antimycin A3, Antimycin A; Antimycin A3, De(3-methylbutanoyl), Antimycin A; Antimycin A4, Antimycin A; Antimycin A9, Antimycin A; Antimycin A10a, Antimycin A; Antimycin A5a, Antimycin A; Antimycin A6a, Antimycin A; Antimycin A10b, Antimycin A; Antimycin A5b, Antimycin A; Antimycin A6b, Antimycoin, Antiostatin A, Antiostatin B, Antipain, Antipain; 4"-Hydroxy, Antiphlei factor, Antitumour substance A 898, Antraformin, Antrimycin, Antrimycin; Antrimycin A, Antrimycin; Antrimycin D, Aphicidin, AP-I, API-2, Aplasmomycin, Aplasmomycin; 9-Ac, Aplasmomycin; 9,9'-Di-Ac, Apramycin, Apramycin; 3'β-Hydroxy, Apramycin; 3-N-(2-Hydroxyethyl), Aquayamycin, Aquayamycin; 3-Deoxy, 4a-O-[2,6-dideoxy-α-L-lyxo-hexopyranosyl-(1→4)-2,6-dideoxy-α-L-lyxo-hexopyranoside], Aquayamycin; 3-Deoxy, 4a-O-[2,6-dideoxy-α-L-lyxo-hexopyranosyl-(1→4)-3-(dimethylamino)-2,3,6-trideoxy-α-L-lyxo-hexopyranoside], Aquayamycin; 12b-O-(2,3,6-Trideoxy-β-L-erythro-hexopyranoside), Aquinomycin, Arabilin, α-N-Arabinofuranosidase, 9-Arabinofuranosyladenine; β-D-form, Aramycin, Aranciamycin E, Aranciamycin E; 7-Deoxy, Aranciamycin E; 1-Deoxy, 7-O-(2,6-dideoxy-3-C-methyl-α-L-xylo-hexopyranoside), Aranciamycin E; 1-Deoxy, 13-hydroxy, 7-O-(2,3,6-trideoxy-β-D-erythro-hexopyranoside), Aranciamycin E; 1-Deoxy, 7-O-(2,3,6-trideoxy-β-D-erythro-hexopyranoside), Aranciamycin E; 1-Deoxy, 7-O-(2,3,6-trideoxy-α-L-threo-hexopyranoside), Aranciamycin E; 7-O-(2,3,6-Trideoxy-β-D-erythro-hexopyranoside), Arcyriaflavin A; 1,11-Dihydroxy, Arenaric acid, Arginine; (S)-form, N2-(2-Carboxyethyl), Arginine 2-monooxygenase, Arginomycin, Arginylthreonine; (2S,2'S,3'R)-form, N2-(2,3-Dihydroxybenzoyl), Arglecin, Argvalin, Aristeromycin, Aristeromycin M, Aristeromycin M; 5'-Hydroxy, Arsimycin, Arugomycin, Arugomycin; 4D-O-Deglycosyl, Aruptine, Arylomycin A1, Arylomycin A1; N-Deacyl, N-dodecanoyl, Arylomycin A1; N-Deacyl, N-(10-methyldodecanoyl), Arylomycin A1; N-Deacyl, N-(12-methyltridecanoyl), Arylomycin A1; N-Deacyl, N-(10-methylundecanoyl), Arylomycin A1; 5"-Nitro, N-deacyl, N-dodecanoyl, Arylomycin A1; 5"-Nitro, N-deacyl, N-(9-methyldecanoyl), Arylomycin A1; 5"-Nitro, N-deacyl, N-(10-methyldodecanoyl), Arylomycin A1; 5"-Nitro, N-deacyl, N-(11-methyldodecanoyl), Arylomycin A1; 5"-Nitro, N-deacyl, N-(12-methyltetradecanoyl), Arylomycin A1; 5"-Nitro, N-deacyl, N-(12-methyltridecanoyl), Arylomycin A1; 5"-Nitro, N-deacyl, N-(10-methylundecanoyl), Ascamycin, Ascomycin, Ascomycin; 9-Deoxo, Ascomycin; Homologue (R=CH3), Ascomycin; Homologue (R=CH3), 31-O-de-Me, Ascomycin; 21S-Hydroxy, Ascorbic acid; L-form, 2-Octadecyl, Ascosin, Ashimycin A, Ashimycin B, Asparenomycin C, Asparenomycin C; 1',2'-Dihydro, S-oxide, Asparenomycin C; S-Oxide, Aspartocin, Aspartocin A, Asukamycin, Asukamycin; Deepoxy, 5R-hydroxy, Asukamycin; Stereoisomer, Atacamycin A, Atacamycin A; 9-Demethoxy, Atacamycin A; 9-Demethoxy, 14-deoxy, Atramycin A, Atramycin A; 6-Deoxy, Auramycin B, Auramycin B; 1-Hydroxy, Auramycin C, Auramycin C; De(dimethylamino), Auramycin C; 4'-Deglycosyl, Auramycin C; 3"-Deoxy, Auramycin F, Auramycin F; Aglycone, 11-hydroxy, Auramycin F; Aglycone, 1-hydroxy, stereoisomer (?), Auramycin F; 3B-Deoxy, Auramycin F; 4C-Epimer, Auramycin F; 4C-Ketone, Auramycin F; 7-De(glycosyloxy), Auramycin F; 7-De(glycosyloxy), 1-hydroxy, Auramycin F; 7-De(glycosyloxy), 11-hydroxy, Auramycin F; 9-Epimer, aglycone, Auramycin F; 10-Epimer, 7-de(glycosyloxy), Auramycin F; 9-Epimer, 1-hydroxy, 4A-deglycosyl, Auramycin F; 11-Hydroxy, 4C-ketone, Auramycin F; 1-Hydroxy, 4C-ketone, Aurantimycin A, Aurantimycin A; 2,3'-Didehydro, Aurantimycin A; 2',2",3',3"-Tetradehydro, Aurantimycin D, Aurantin, Aureofacin, Aureofungin, Aureofuscin, Aureonuclemycin, Aureonuclemycin; O9-Me, 4-Ac, Me ester, Aureonuclemycin; Me ester, Aureonuclemycin; O9-Me, O4-(2-hydroxymethylbutenoyl), Aureonuclemycin; O9-Me, O4-(2-hydroxymethyl-2E-butenoyl), Me ester, Aureonuclemycin; O9-Me, O4-(2-hydroxymethyl-2E-pentenoyl), Me ester, Aureonuclemycin; O9-Me, Me ester, Aureonuclemycin; O9-Me, O4-(2-methylpropanoyl), Me ester, Aureonuclemycin; O9-Me, O4-tigloyl, Me ester, Aureonuclemycin; O4-Tigloyl, Aureothin; (R)-form, Aureothin; (R)-form, 4'-Denitro, 4'-acetamido, Aureothin; (R)-form, 11Z-Isomer, Aureoverticillactam, Auromomycin, Auxofuran; (S)-form, Avermectin B1a, Avermectin B1a; 3A,3B-Di-O-de-Me, Avermectin B1a; 3AO-De-Me, Avermectin B1a; 3AO-De-Me, 4A-O-deglycosyl, Avermectin B1a; 3AO-De-Me, 5-Me ether, 4A-O-deglycosyl, Avermectin B1a; 3BO-De-Me, Avermectin B1a; 22,23-Dihydro, 22ξ,23S-dihydroxy, Avermectin B1a; 22,23-Dihydro, 22,23S-dihydroxy, 5-Me ether, Avermectin B1a; 22,23-Dihydro, 23S-hydroxy, Avermectin B1a; 22,23-Dihydro, 23S-hydroxy, 3A,3B-di-O-de-Me, Avermectin B1a; 22,23-Dihydro, 23S-hydroxy, 3AO-de-Me, Avermectin B1a; 22,23-Dihydro, 23S-hydroxy, 3BO-de-Me, Avermectin B1a; 22,23-Dihydro, 23S-hydroxy, 5-ketone, Avermectin B1a; 22,23-Dihydro, 23S-hydroxy, 5-Me ether, Avermectin B1a; 22,23-Dihydro, 5-Me ether, Avermectin B1a; 5-Ketone, Avermectin B1a; 5-Me ether, Avermectin B1b, Avermectin B1b; 22,23-Dihydro, 23S-hydroxy, Avermectin B1b; 22,23-Dihydro, 23S-hydroxy, 5-ketone, Avermectin B1b; 22,23-Dihydro, 23S-hydroxy, O5-Me, Avermectin B1b; 5-Ketone, Avermectin B1b; O5-Me, Avermectin B1d, Avermectin B1d; 22,23-Dihydro, 23S-hydroxy, Avermectin B1d; 22,23-Dihydro, 23S-hydroxy, O5-Me, Avermectin B1d; O5-Me, Avermitilol, Avoparcin, Avoparcin; β-Avoparcin, O-Demannosyl, Avoparcin; β-Avoparcin, 50-O-D-Galactopyranoside, Awamycin, Axenomycin A, Axenomycin B, Axenomycin D, Axenomycin F, Axenomycin X, Ayamycin A2, 2-Azabicyclo[2.1.0]pentane-3-carboxylic acid, Azacolutin, Azalomycin F; Azalomycin F1, Azalomycin F; Azalomycin F2, Azalomycin F; Azalomycin F3, Azalomycin F; Azalomycin F3, 4,5,30,31,40,41-Hexahydro, 31-hydroxy, Nω-Me, 25-O-demalonyl, 23-malonyl, Azalomycin F; Azalomycin F3, 4,5,30,31,40,41-Hexahydro, 31-hydroxy, 25-O-demalonyl, 23-malonyl, Azalomycin F; Azalomycin F3, Nw-Me, Azalomycin F; Azalomycin F3, Nω,Nω'-Di-Me, Azalomycin F; Azalomycin F3, 2-Demethyl, Nω-Me, 25-O-demalonyl, 23-malonyl, Azalomycin F; Azalomycin F3, 2-Demethyl, Nω,Nω'-di-Me, 25-O-demalonyl, 23-malonyl, Azalomycin F; Azalomycin F3, 2-Demethyl, 46-deimino, 46-oxo, 25-O-demalonyl, 23-malonyl, Azalomycin F; Azalomycin F3, 2-Demethyl, 46-deimino, 46-oxo, 17-Me ether, 25-O-demalonyl, 23-malonyl, Azalomycin F; Azalomycin F3, 2-Demethyl, 25-O-demalonyl, 23-malonyl, Azalomycin F; Azalomycin F3, Nω-Me, 2-ethylpentyl ester, Azalomycin F; Azalomycin F3, Nω,Nω'-Di-Me, 2-ethylpentyl ester, Azamerone, Azaserine, Azaserine; (S)-form, Azaspirofuran A, Azdimycin, Azepinomycin, Azetomycin III, Azinomycin A, Azinomycin B, Azinothricin, Azinothricin; Lower homologue (R=CH3), Azinothricin; Lower homologue (R=CH3), demethoxy, 2,3-Aziridinedicarboxylic acid; (2S,3S)-form, Azomultin, Azotomycin, Bacteriocin RB 72(T), Bafilomycin A1, Bafilomycin A1; 2-Demethoxy, 2-methyl, Bafilomycin A1; 2-Demethoxy, 2-methyl, O21-Me, Bafilomycin A1; 24-Demethyl, Bafilomycin A1; 24-Demethyl, 17-deoxy, 17,18-didehydro, O19,O21-di-Me, Bafilomycin A1; 24-Demethyl, O19,O21-di-Me, Bafilomycin A1; 24-Demethyl, O19-Me, Bafilomycin A1; 24-Demethyl, O21-Me, Bafilomycin A1; 24-Demethyl, 17,19,21-trideoxy, 17,18,19,20,21,22-hexadehydro, Bafilomycin A1; O19, O21-Di-Me, Bafilomycin A1; O21-Me, Bafilomycin A1; O19-Me, O21-(2-O-methyl-α-L-rhamnopyranoside) Bafilomycin A1; O7-(2-Methylpropanoyl), O21-(2-O-methyl-α-L-rhamnopyranoside), Bafilomycin A1; O21-(2-O-Methyl-α-L-rhamnopyranoside), Bafilomycin A1; O21-α-L-Rhamnopyranoside, Bafilomycin B1, Bafilomycin B1; 2-Demethoxy, 2-methyl, Bafilomycin C1, Bafilomycin C1; Amide, Bafilomycin C1; 2-Demethoxy, 2-methyl, Bafilomycin C1; 24-Demethyl, Bafilomycin C1; O19-Me, Bafilomycin D, Bafilomycin D; 24-Demethyl, Bafilomycin E, Bafilomycin F, Bafilomycin I, Bagacidin A, Bandamycin A, Bandamycin B, Bandunamide, Barmumycin, Basidifferquinone A, Basidifferquinone B, Basidifferquinone B; 7-Deoxy, BAY o 6997, BAY q 1313, BCI 03, BE 10988, Belactosin A, Belactosin B, Belactosin C, Bellenamine; (R)-form, Benastatin A, Benastatin A; 5,6-Dihydro, Benastatin A; 6-Hydroxy, Benastatin C, Benastatin E, Benastatin F, Benastatin F; 17-Deoxy, 16,17-didehydro, 5,6-dihydro, O1,O11-di-Me, Benastatin F; 5,6-Dihydro, Benastatin H, Benastatin H; 5,6-Dihydro, Benhamycin, Benthocyanin A, Benthocyanin A; 11-Carboxy isomer, Benthocyanin C, Benthophoenin, Benzastatin A, Benzastatin A; Demethoxy, Benzastatin A; Demethoxy, 10'-hydroxy, Benzastatin A; Demethoxy, 11'-hydroxy, Benzastatin F, Benzastatin F; 16-Methoxy, Benzastatin G, Benzastatin G; Parent acid, 1,2-Benzenedicarboxylic acid; Benzyl butyl ester, 1,2-Benzenedicarboxylic acid; Bis(2-ethylhexyl) ester, 1,2-Benzenedicarboxylic acid; Dibutyl ester, 1,2-Benzenedicarboxylic acid; Heptyl hydroxynonyl ester, 1,4-Benzenediol; O-(6-Deoxy-α-L-talopyranoside), 1,2,4-Benzenetriol; 2-Me ether, 1-O-(6-deoxy-α-L-talopyranoside), Benzo[c]cinnoline-1,10-diol; Di-Me ether, Benzoic acid, Benzoic acid; α-L-Rhamnopyranosyl ester, Benzopyrenomycin, Benzoxacystole, Benzoxazomycin, 3-Benzyl-6-benzylidene-2,5-piperazinedione; (R,Z)-form, Benzylcarbamic acid, 2-Benzyl-2-hydroxybutanedioic acid; (S)-form, 5-Benzyl-3-hydroxy-2-isopropylpyrazine, 5-Benzyl-4-hydroxy-2-pyrrolidinone; (4R*,5R*)-form, 3-Benzylidene-3,4-dihydro-2-oxo-2H-1,4-benzoxazine-5-carboxylic acid, 3-Benzylidene-6-isobutylidene-2,5-piperazinedione; (Z,Z)-form, 3-Benzylidene-6-isobutylidene-2,5-piperazinedione; (2E,5Z)-form, 1-N-Me, 3-Benzylidene-6-isobutylidene-2,5-piperazinedione; (E,E)-form, 1-N-Me, 3-Benzylidene-6-isobutylidene-2,5-piperazinedione; (E,E)-form, 4-N-Hydroxy, 1-N-Me, Bequinostatin A, Bequinostatin A; 6-Deoxy, Bequinostatin A; 6-Deoxy, 5,6-didehydro, Bequinostatin A; 5,6-Didehydro, Bequinostatin B, Bequinostatin B; 6-Deoxy, 5,6-didehydro, Bequinostatin B; 5,6-Didehydro, Beminamycin A, Beminamycin A; 14-Demethyl, Beminamycin A; 14-Demethyl, 1"-deoxy, Berninamycin A; 1"-Deoxy, Beminamycin C, Beminamycin D, Beromycin, Bestatin, Betaclamycin M; 2C-Amino, 2C,3C-didehydro, 4C-ketone, Betaclamycin M; 4C-Epimer, Betaclamycin M; 4C-Ketone, Betaclamycin M; 11-Deoxy, 4C-ketone, Betaclamycin M; 11-Deoxy, 1-hydroxy, 4C-ketone, Betaclamycin M; 6-Deoxy, 1-hydroxy, 4C-ketone, Bicycloamide, Bicyclomycin, Bihoromycin, Bilanafos, Bilanafos; P-De-Me, Bingchamide A, Bingchamide B, Bioxalomycin α1, Bioxalomycin α1; N-Me, Bioxalomycin α1; 10,13-Quinone, Bioxalomycin α1; 10,13-Quinone, N-Me, Biphenomycin A, Biphenomycin A; N25-(2-Amino-5-guanidinylpentanoyl), Biphenomycin A; 7-Deoxy, Biphenomycin C, Biquinazomycin, Bireticulol, 3,6-Bis[(aminooxy)methyl]-2,5-piperazinedione; (3R,6R)-form, 13,13'-Bis(13,13-dinorbenastatin A); (RS, RS)-form, 13,13'-Bis(13,13-dinorbenastatin A); (RS,SR)-form, 1,4-Bis(4-hydroxyphenyl)-2,3-butanediol; (2R*, 3R*)-form, 1,4-Bis(4-hydroxyphenyl)-2,3-butanediol; (2RS,3SR)-form, 4,9-Bis(3-methyl-2-butenyl)-1,6-phenazinediol, 4,9-Bis(3-methyl-2-butenyl)-1,6-phenazinediol; N-Oxide, N,N'-Bis(2-phenylethyl)urea, Bizelesin, Blanchaquinone, Blasticidin A, Blasticidin H, Blasticidin S, Blasticidin S; N-De-Me, Blasticidin S; 5-Fluoro, Blasticidin S; 5-Hydroxymethyl, Blasticidin S; 3"-N-Leucyl, Bleomycin, Bleomycin A2, Bleomycin; Bleomycin A2, S-De-Me, Bleomycin; Bleomycin A2, S-De-Me, S-oxide, Bleomycin; Bleomycin A2, 7S,8-Dihydro, Bleomycin; Bleomycin A5, Bleomycin; Bleomycin A5, N-De(2,3-diamino-3-oxopropyl), Bleomycin; Bleomycin A5, Nω-(2-Carbamoylethyl), Bleomycin; Bleomycin A6, Bleomycin; Bleomycin A6, Nω-Ac, Bleomycin; Bleomycin A2'a, Bleomycin; Bleomycin A2'b, Bleomycin; Bleomycin A2'c, Bleomycin; Bleomycin B1', Bleomycin; Bleomycin B2, Bleomycin; Bleomycin B2, 7S,8-Dihydro, Bleomycin; Bleomycin B4, Bleomycin; Bleomycin B4, 7S,8-Dihydro, Bleomycin; Bleomycin B6, Bleomycin; Bleomycin B6, 7S,8-Dihydro, Bluensomycin, Bohemamine, Bohemamine; Deepoxy, Bohemamine; Deepoxy, 6β-chloro, 7α-hydroxy, Bohemamine; Deepoxy, 6α-hydroxy, Bohemamine; Deepoxy, 7α-hydroxy, Boholmycin, Boromycin, Boromycin; N—Ac, Boromycin; O-Devalyl, Boromycin; N-Formyl, Borrelidin, Borrelidin; 12-Carboxylic acid, Borrelidin; 12-Decyano, 12-methyl, Bottromycin, Bottromycin B1, Bottrospicatol, BR 040, BR 040; 8-Me ether, Bramycin, Branimycin, Brasiliquinone B; 3α-Hydroxy, Bripiodionene, 2-Bromoadenosine; 5'-O-Sulfamoyl, 7-Bromo-5-(2-chlorophenyl)-1,3-dihydro-3-hydroxy-2H-1,4-benzodiazepin-2-one, Brunefungin, Bulgerin, Butalactin, 3-Butanoyl-4-(hydroxymethyl)-4,5-dihydro-2(3H)-furanone, 2-Butenoic acid; (E)-form, 5-(2-Butenylidene)-3-ethyl-1,2,3,4,5,7a-hexahydro-4aH-1-pyrindine-4,4a-diol, Butylcycloheptylprodigiosine, 7-Butyl-1,2-dichloro-6,8-dihydroxy-9H-pyrrolo[2,1-b][1,3]benzoxazin-9-one, 7-Butyl-1,2-dichloro-6,8-dihydroxy-9H-pyrrolo[2,1-b][1,3]benzoxazin-9-one; 1-Dechloro, 3-Butyldihydro-4-hydroxy-5-methyl-2(3H)-furanone; (3R,4R,5S)-form, 3-Butyl-5-methyl-5H-furan-2-one; (S)-form, 1-Butyl-3,4,6,9-tetrahydro-10-hydroxy-7-(methylamino)-6,9-dioxo-1H-naphtho[2,3-c]pyran-3-acetic acid, 1-Butyl-3,6,8-trihydroxyanthraquinone, 1-Butyl-3,6,8-trihydroxyanthraquinone-2-carboxylic acid, 1-Butyl-3,6,8-trihydroxyanthraquinone-2-carboxylic acid; 6-Deoxy, 2-Butynedioic acid; Diamide, Butyrolactol A, Butyrolactol B, Cadeguomycin, 4(15),5-Cadinadiene; (1β,7β,10α)-form, 4-Cadinene-10,11-diol; (1β,6β,7β,10β)-form, 4-Cadinene-10,11-diol; (1β,6β,7β,10β)-form, 15-Hydroxy, 4-Cadinene-10,15-diol; (1β,6β,7β,10β)-form, 4-Cadinen-1-ol; (1β,6β, 7β,10α)-form, Caerulomycin D, Caerulomycin E, Caerulomycin E; 3-Hydroxy, E-oxime, Caerulomycin E; 3-Methoxy, E-oxime, Caerulomycin E; E-Oxime, Caeseorhodomycin, Cafamycin, C 1027-AG, Cairomycin B, Cairomycin C, Calcimycin, Calcimycin; De(methylamino), Cammunocin, Canacelunin, Candihexin, Capacidin, Capoamycin, Caprazamycin, Caprazamycin; Caprazamycin A, 2"'-O-Sulfate, Caprazamycin; Caprazamycin B, 2"'-O-Sulfate, Caprazamycin; Caprazamycin E, 2"'-O-Sulfate, Caprazamycin; Caprazamycin F, 2"'-O-Sulfate, Capreomycin, Capuramycin, Capuramycin; 2'-O-Carbamoyl, Capuramycin; O-De-Me, O-Carbamoylserine; (R)-form, Carbazomycin G, Carbazoquinocin, β-Carboline-3-carboxylic acid; Me ester, β-Carboline, 4-(β-Carbolin-1-yl)-4-oxobutanoic acid; 2',3'-Didehydro, 4-(β-Carbolin-1-yl)-4-oxobutanoic acid; 2',3'-Didehydro, Me ester, 7-[2-(4-Carboxy-1,3-butadienyl)phenyl]-2,4,6-heptatrienoic acid; (all-E)-form, 7-[2-(4-Carboxy-1,3-butadienyl)phenyl]-2,4,6-heptatrienoic acid; (2E,2'E,4E,4'E,6Z)-form, 7-[2-(4-Carboxy-1,3-butadienyl)phenyl]-2,4,6-heptatrienoic acid; (2Z,2'E,4E,4'E,6Z)-form, N2-(2-Carboxyethyl)arginine synthase, (Carboxyphosphonoenol)pyruvic acid, Carboxyvinyl-carboxyphosphonate phosphorylmutase, Carcinomycin, Carminomycin III; 5"-Epimer, 4-Me ether, Carminomycin III; 5"-Epimer, 4-Me ether, 6"-aldehyde, Carminomycin III; Stereoisomer, 6"-carboxylic acid, 4-Me ether (1), Carminomycin III; Stereoisomer, 6"-carboxylic acid, 4-Me ether (2), Carminomycin III; Stereoisomer, 4-Me ether, Carpetimycin A, Carpetimycin A; S-Deoxy, Carpetimycin A; S-Deoxy, O-sulfate, Carpetimycin A; 1',2'-Dihydro, Carpetimycin A; 1',2'-Dihydro, S-deoxy, Carpetimycin A; 1',2'-Dihydro, S-deoxy, O-sulfate, Carpetimycin A; 1',2-Dihydro, O-sulfate, Carpetimycin A; O-Sulfate, Carpetimycin X, Carquinostatin A, Carquinostatin A; 10S-Hydroxy, Carriomycin, Carriomycin; 6,27α-Dimethoxy, Carzinocidin, Cationomycin, CC-preferring endodeoxyribonuclease, Celastramycin B, Celastramycin B; 10-Deoxy, Celastramycin B; 8,9-Didehydro, 10-ketone, Celastramycin B; 8-(Methylthio), 8,9-didehydro, 10-ketone, Celesticetin, Celesticetin; O7-De-Me, Celesticetin; N-De-Me, Celesticetin; N,O7-Di-de-Me, Cephalomycin, Cephalosporin C, Cephalosporin C; O-De-Ac, Cephalosporolide C, Cephamycin B, Cephamycin B; 4'-Deoxy, Cephamycin B; 3'-Hydroxy, Cephamycin B; O-Sulfate, Cephamycin C, Cerevioccidin, Cervicarcin, Cervimycin A, Cervimycin A; 4D-O-Deacyl, 4D-O-(methylmalonyl), Cervimycin C, Cervimycin C; 4D-Deacyl, 4D-(2-methylmalonoyl), Cervinomycin A1, Cervinomycin A1; 8,15-Quinone, Chalcomycin, Chalcomycin; 4B-Propanoyl, Chalcomycin; 8-Deoxy. Chalcomycin; 8-Deoxy, 12,13-deepoxy, 12,13-didehydro, 10,11-dihydro, Chalcomycin; 10,11-Dihydro, Chandramycin, Chantalmycin, Chartarin; 10-O-[2-O-Acetyl-6-deoxy-3-O-methyl-α-D-galactopyranosyl-(1→2)-6-deoxy-β-D-galactopyranoside], Chartarin; 10-O-[4-O-Acetyl-6-deoxy-3-O-methyl-α-D-galactopyranosyl-(1→2)-6-deoxy-β-D-galactopyranoside], Chartarin; 10-O-[6-Deoxy-α-D-galactopyranosyl-(1→2)-6-deoxy-β-D-galactopyranoside], Chartarin; 10-O-[6-Deoxy-3-O-methyl-α-D-galactopyranosyl-(1→2)-6-deoxy-β-D-galactopyranoside], Chartarin; 10-O-[6-Deoxy-3-O-methyl-α-D-galactopyranosyl-(1→2)-6-deoxy-β-D-galactopyranosyl-(1→2)-6-deoxy-β-D-galactopyranoside], Chartreusin B, Chaxalactin B, Chaxalactin B; 14-Deoxy, Chaxalactin B; 15-Me ether, Chaxamycin A, Chaxamycin A; 8-Deoxy, Chaxamycin A; 35-Hydroxy, Chaxamycin D, Chicamycin B, Chicamycin B; 10,11-Dihydro, 11α-methoxy, Chilaphylin, Chimeramycin A, Chimeramycin A; O-De-Ac, Chinikomycin A, Chinikomycin A; 1,4-Quinone, Chitinase, Chitobiose, Chloptosin, Chloquinomycin, Chloramphenicol; (1R,2R)-form, Chloramphenicol; (1R,2R)-form, 3-Ac, Chloramphenicol; (1R,2R)-form, Dibromo analogue, 2-Chloroadenosine, 2-Chloroadenosine; 5'-O-Sulfamoyl, Chlorobiocin, Chlorobiocin; 5-Demethyl, Chlorocarcin A, Chlorocarcin B, Chlorocarcin C, Chlorocyclinone B, Chlorocyclinone B; Deacetoxy, Chlorocyclinone B; 1"-Hydroxy, Chlorocyclinone D, 7-Chloro-5a,11a-didehydrotetracycline, 2-Chloro-7-ethyl-6,8-dihydroxy-9H-pyrrolo[1,2-b][1,3]benzoxazin-9-one, 2-Chloro-7-ethyl-6,8-dihydroxy-9H-pyrrolo[1,2-b][1,3]benzoxazin-9-one; 1-Chloro, 2-Chloro-7-ethyl-6,8-dihydroxy-9H-pyrrolo[1,2-b][1,3]benzoxazin-9-one; 6-Me ether, 2-Chloro-7-ethyl-8-hydroxy-6-methyl-9H-pyrrolo[1,2-b][1,3]benzoxazin-9-one, Chloropeptin I, Chloroquinocin; (ξ)-form, Chloroquinocin; (ξ)-form, Dechloro, 7-deoxy, 6-Chloro-2-quinoxalinecarboxylic acid; 1,4-Dioxide, Chlorostatin, 8-Chloro-3',4',5,7-tetrahydroxyisoflavone, Chlorothricin, Chlorothricin; 2Aα-Hydroxy, Chlorothricin; 2Aα-Hydroxy, 3B—O-deacyl, 4B—O-(3-chloro-6-hydroxy-2-methylbenzoyl), Chlorothricin; 2Aα-Hydroxy, O-de-Me, Chlorothricin; 3B—O-Deacyl, 4B—O-(3-chloro-6-hydroxy-2-methylbenzoyl), Chlorothricin; 3C-Dechloro, 3C-bromo, Chlorothricin; Dechloro, Chlorothricin; O-De-Me, 6-Chloro-4',5,7-trihydroxyisoflavone, 8-Chloro-4',5,7-trihydroxy-3-methylflavanone; (2S,3S)-form, 8-Chloro-4',5,7-trihydroxy-3-methylflavanone; (2RS,3SR)-form, Chlortetracycline, Chlortetracycline; Bromo analogue, Choughwamycin A, Chrolactomycin, Chromin, Chromocyclomycin, Chromomycin A1, Chromomycin A2, Chromomycin A2; 4A,4E-Dideacyl, Chromomycin A2; 4A,4E-Dideacyl, 4E-Ac, Chromomycin A2; Aglycone, Chromomycin A2; 4B—O-De-Me, Chromomycin A2; 4B—O-De-Me, 4E-deacyl, 4E-Ac, Chromomycin A2; 3D-Deglycosyl, Chromomycin A2; O-De-Ac, Chromomycin A2; 4E-Deacyl, Chromomycin A2; 4E-Deacyl, 4E-Ac, Chromomycin A5, Chromomycin Ap, Chromomycin SA, Chromomycin SA; 4E-De-Ac, Chromomycin SA; 4E-De-Ac, 4E-(2-methylpropanoyl), Chromomycin SK, Chromomycin SK; 2'-Ketone, Chromophenazine A, Chromophenazine B, Chromophenazine C, Chromophenazine E, Chromophenazine E; Amide, Chromotrienin, Chromoxymycin, Chrothiomycin, Chrymutin, Chrymutin; O-[α-D-Fucopyranosyl-(1→2)-β-D-fucopyranoside], Chrymutin; O-[3-O-Methyl-α-D-fucopyranosyl-(1→2)-β-D-fucopyranoside], Chrymutin; O-[3-O-Methyl-α-D-fucopyranosyl-(1→2)-α-D-fucopyranosyl-(1→2)-β-D-fucopyranoside], Chrysomal B, Chrysomal C, Chrysomycin A, Chrysomycin A; 6-Alcohol, Chrysomycin A; 1'-Epimer(?), Chrysomycin B, Chrysomycin B; 1'-Epimer (?), Chymostatin, Chymostatin; Chymostatin A, 1'-Alcohol, Chymostatin; Chymostatin B, 1'-Alcohol, Chymostatin; Chymostatin C, 1'-Alcohol CI 782, CI 783, C 112-III, C 112-III; 2 or 3-Methoxy, Me ester, C 112-III; 1'-Oxo, Cineromycin A, Cinerubin B, Cinerubin B; 5C-Epimer, Cinerubin B; 5C-Epimer, 1-deoxy, Cinerubin B; N-De-Me, Cinerubin B; 1-Deoxy, Cinerubin B; 1-Deoxy, 1-hydroxy, Cinerubin B; 1-Deoxy, 2-hydroxy, Cinerubin Y, Cinnabaramide D, Cinnabaramide D; 12-Deoxy, Cinnabaramide D; 12-Deoxy, (19→3)-lactone, Cinnabaramide D; 4,12-Dideoxy, (19→3)-lactone, Cinnabaramide D; (19→3)-Lactone, Cinnabaramide F, Cinnabaramide F; Me ester, Cirramycin A1, Citreamicin δ, Citreamicin δ; 6,17-Hydroquinone, 7,8-dihydro, Citrimycin, Citropeptin, Citropeptin; Demethoxy, Cladoniamide A, Cladoniamide A; 10-Chloro, Cladoniamide A; Dechloro, Cladoniamide D, Cladoniamide D; 10-Chloro, Cladoniamide F, Cladoniamide F; 10-Chloro, Clavalanine, Clavaminate synthase, Clavaminic acid, Clavaminic acid; N-[(Acetylamino)acetyl], Clavaminic acid; N—Ac, Clavaminic acid; N-(Aminoacetyl), Clavaminic acid; 1',3R-Dihydro, Clavamycin A, Clavamycin B, Clavamycin C, Clavamycin D, Clavamycin D; Stereoisomer (?), Clavamycin E, Clavamycin E; Stereoisomer (?), Clavamycin F, Clavulanic acid, Clavulanic acid; 3-Hydroxypropanoyl, Clazamycin; (2S,7aR)-form, Clazamycin; (2S,7aS)-form, Clecarmycin C, Clecarmycin C; 8-Ketone, Cleomycin; Cleomycin A2, Cleomycin; Cleomycin A2, S-De-Me, Cleomycin; Cleomycin A2, S-De-Me, S-oxide, Cleomycin; Cleomycin A5, Cleomycin; Cleomycin B1', Cleomycin; Cleomycin B2, Cleomycin; Cleomycin B4, Clethramycin, Clethramycin; N-De(aminoiminomethyl), desulfo, Clethramycin; N-De(aminoiminomethyl), Cochleamycin A, Cochleamycin A; O-De-Ac, 10-O-(2-methylpropanoyl), Cochleamycin B, Cochleamycin B; O-De-Ac, O-(2-methylpropanoyl), Coelibactin, Coelichelin, Coerulomycin, Coformycin, Colabomycin A, Colabomycin B, Colabomycin C, Colabomycin D, Coleimycin, Collinone, Collismycin C, Collismycin D, Collismycin D; S-Oxide, Collismycin E, Collismycin F, Collismycins A-B; (Z)-form, Collismycins A-B; (E)-form, Collismycins A-B; (E)-form, S-Oxide, Colubricidin A, Complestatin, Complestatin; 2',3'R-Dihydro, 2'-oxo, Complestatin; 2',3'-Dihydro, 2'-oxo, 3'S-hydroxy, Conagenin, Concanamycin A, Concanamycin A; 25-Dealkyl, 25-methyl, Concanamycin A; 4'-Decarbamoyl, Concanamycin A; 23-O-Deglycosyl, Concanamycin A; 23-O-Deglycosyl, 23-fumaroyl, Concanamycin A; 23-O-deglycosyl, 21-Me ether, Concanamycin A; 23-O-Deglycosyl, 23-O-α-L-rhamnopyranosyl, Concanamycin A; 21-Epimer, 23-O-deglycosyl, 23-fumaroyl, Concanamycin B, Concanamycin B; 4'-Decarbamoyl, Concanamycin E, Concanamycin G, Conglobatin, Copiamycin, Copiamycin; 21-O-Demalonyl, Copiamycin; N-De-Me, Copiamycin; 13-Deoxy, Copiamycin; 34,35E-Didehydro, Coprismycin A, Coprismycin A; Z-Isomer, Coproporphyrin III; Zn complex, Copsomycin, Coralinomycin, Corallomycin, Coronafacic acid; 4ξ,5-Dihydro, Coronamycin, Cosmomycin B, Cosmomycin B; 4B-Deglycosyl, Cosmomycin B; 3B-Deoxy, Cosmomycin B; 3B-Deoxy, 4B-deglycosyl, Cosmomycin B; 3B-Deoxy, 4C-ketone, Cosmomycin B; 1,7-Dihydroxy, 6-deoxy, 4C-ketone, Cosmomycin B; 1-Hydroxy, Cosmomycin B; 7α-Hydroxy, 3B-deoxy, Coumabiocin A, Coumabiocin A; 3'''-Deoxy, Coumabiocin D, Coumabiocin D; 2'''-Deoxy, CPI 9, Craterifermycin, Cremimycin, Cryomycin, Cryptocidin, Cryptomycin, Crystallomycin, Cuevaene A, Cuevaene B, Curromycin A, Curromycin A; 30-Demethoxy, C 122 VI, C 122 VI; 2-(or3-)-Hydroxy, C 122 VI; 2-(or3-) Hydroxy, O-de-Me, Cyanocycline D, Cyanonaphthyridinomycin, Cyanonaphthyridinomycin; N-De-Me, Cyanonaphthyridinomycin; Hydroquinone, Cyclamenol, Cyclizidine, Cyclo(alanyl-4-hydroxyprolyl); (3S,7R,8aS)-form, Cyclo(alanylprolyl); (3S,8aS)-form, Cyclo(argininylleucyl); (3S,6S)-form, Cycloheptamycin, Cyclo(homoleucylprolyl); (3ξ,8aξ)-form, Cyclo(4-hydroxyprolylleucyl); (3S,7R,8aR)-form, Cyclo(leucylphenylalanyl); (3S,6S)-form, Cyclo(leucylphenylalanyl); (3S,6S)-form, 1',3-Didehydro(Z-), Cyclo(leucylphenylalanyl); (3S,6S)-form, 1'',6-Didehydro(Z-), Cyclo(leucylprolyl); (3S,8aS)-form, Cyclomarin A, Cyclomarin A; 13,14-Deepoxy, 13,14-didehydro, Cyclomarin A; 53-Deoxy, Cyclomarin A; 18-Valyl analogue, 13,14-deepoxy, 13,14-didehydro, Cyclononactic acid; Homologue (R=CH2CH3), Cyclooctatin, Cyclooctatin; 17-Hydroxy, Cyclo(phenylalanylproyl); (3R,8aS)-form, Cyclo(phenylalanylprolylphenylalanylprolyl), Cyclo(phenylalanyltryptophyl); (3S,6S)-form, N4-Me, Cyclopolic acid; Me ether, Cyclo(prolyltryptophyl); (3S,8aS)-form, Cyclo(prolyltyrosyl); (3R,8aR)-form, Cyclo(prolyltyrosyl); (3S,8aS)-form, Cyclo(prolylvalyl); (3S,8aS)-form, Cyclo(prolylvalylvalyl), Cyclothialidines, Cyclothiazomycin, Cyclothiazomycin B1, Cyclothiazomycin B1; E-Isomer, Cyclo(tyrosyltyrosyl); (3S,6S)-form, N,N'-Di-Me, Cypemycin, Cysfluoretin, Cyslabdan A, Cyslabdan A; 19-Hydroxy, Cyslabdan A; Me ester, Cystamycin, Cytidine 5'-triphosphate, Cytomycin, Cytorhodin P, Cytorhodin P; 1-Hydroxy, Cytorhodin X, Cytosaminomycin A, Cytosaminomycin C, Cytosaminomycin D, Cytosine; 1H-form, 1-N-(3-Deoxy-β-D-galacturonopyranosyl), Cytosine; 1H-form, 1-N-β-D-Glucuronopyranosyl, Cytosinine, Cytostatin, Cytotetrin, Cytotrienin A, Cytotrienin A; 1'',2''-Dihydro, Cytotrienin A; 20,23-Quinone, Cytotrienin A; 20,23-Quinone, 1'',2''-dihydro, Cytovaricin, Cytovaricin, Cytovaricin; De(glycosyloxy), Cytovaricin; De(glycosyloxy), stereoisomer (?), Cytovaricin; 26a-Me ether, Cytoxazone, Dalomycin T, Damavaricin D, Damavaricin D; 14-Hydroxy, Danomycin, Danomycin; Danomycin B, Daptomycin, Daryamide A, Daryamide A; 5-Deoxy, 5,6-didehydro, Daryamide A; 5-Deoxy, 5,6-didehydro, N-deacyl, N-(6-methyl-2E,4E-heptadienoyl), Daunomycin, Daunomycin; N—Ac, Daunomycin; Aglycone, 13R-alcohol, Daunomycin; Aglycone, 7-deoxy, Daunomycin; Aglycone, 7-deoxy, 13ξ-alcohol, Daunomycin; Aglycone, 7,11-dideoxy, 13ξ-alcohol, Daunomycin; 13R-Alcohol, Daunomycin; 13ξ-Alcohol, O-de-Me, Daunomycin; 13ξ-Alcohol, N-formyl, Daunomycin; 11-Deoxy, 13-alcohol, Daunomycin; 11-Deoxy, 13-alcohol, O-de-Me, Daunomycin; 11-Deoxy, O-de-Me, Daunomycin; N-(Ethoxycarbonyl), Daunomycin; N-Formyl, Daunomycin; 1-Hydroxy, 13ξ-alcohol, Daunomycin; 1-Hydroxy, 13ξ-alcohol, N-formyl, Daunomycin; N-(Methoxycarbonyl), Daunosaminyldaunomycin, Daunosaminyldaunomycin; 3''-Epimer, Deacetoxycephalosporin C, Deacetoxycephalosporin-C synthase, Deacylflambamycin; 2-Dechloro, 23-deoxy, O3-de-Me, 45-O-(2-methylpropanoyl), Deacylflambamycin; 6-Dechloro, 23-deoxy, 45-O-(2-methylpropanoyl), Deacylflambamycin; 33-Demethyl, 23-deoxy, 45-O-(2-methylpropanoyl), Deacylflambamycin; 23-Deoxy, 45-Ac, Deacylflambamycin; 23-Deoxy, 59S-alcohol, O32-de-Me, 45-O-(2-methylpropanoyl), Deacylflambamycin; 23-Deoxy, 59S-alcohol, O3-de-Me, 45-O-(2-methylpropanoyl), Deacylflambamycin; 23-Deoxy, 59S-alcohol, O37-de-Me, 45-O-(2-methylpropanoyl), Deacylflambamycin; 23-Deoxy, 59S-alcohol, O42-de-Me, 45-O-(2-methylpropanoyl), Deacylflambamycin; 23-Deoxy, 59S-alcohol, O3,O32-di-de-Me, 45-O-(2-methylpropanoyl), Deacylflambamycin; 23-Deoxy, 59S-alcohol, O3,O37-di-de-Me, 45-O-(2-methylpropanoyl), Deacylflambamycin; 23-Deoxy, 59S-alcohol, O3,O42-di-de-Me, 45-O-(2-methylpropanoyl) Deacylflambamycin; 23-Deoxy, 59S-alcohol, 45-O-(2-methylpropanoyl), Deacylflambamycin; 23-Deoxy, 59S-alcohol, O3,O32,O42-tri-de-Me, 45-O-(2-methylpropanoyl), Deacylflambamycin; 23-Deoxy, O32-de-Me, 45-O-(2-methylpropanoyl), Deacylflambamycin; 23-Deoxy, O3-de-Me, 45-O-(2-methylpropanoyl), Deacylflambamycin; 23-Deoxy, O37-de-Me, 45-O-(2-methylpropanoyl), Deacylflambamycin; 23-Deoxy, O42-de-Me, 45-O-(2-methylpropanoyl), Deacylflambamycin; 23-Deoxy, O32,O37-di-de-Me, 45-O-(2-methylpropanoyl), Deacylflambamycin; 23-Deoxy, O3,O32-di-de-Me, 45-O-(2-methylpropanoyl), Deacylflambamycin; 23-Deoxy, O3,O37-di-de-Me, 45-O-(2-methylpropanoyl), Deacylflambamycin; 23-Deoxy, O0,O42-di-de-Me, 45-O-(2-methylpropanoyl), Deacylflambamycin; 23-Deoxy, 35-hydroxy, 45-O-(2-methylpropanoyl). Deacylflambamycin; 23-Deoxy, 45-O-(2-methylpropanoyl), Deacylflambamycin; 23-Deoxy, 45-O-(2-methylpropanoyl), 58-de-Ac, 58-formyl, Deacylflambamycin; 23-Deoxy, 45-pentanoyl, Deacylflambamycin; 23-Deoxy, 45-propanoyl. Deacylflambamycin; 23-Deoxy, O3,O32,O42-tri-d-Me, 45-O-(2-methylpropanoyl), Deacylflambamycin; Didechloro, 23-deoxy, 59S-alcohol, O3-de-Me, 45-O-(2-methylpropanoyl), Deacylflambamycin; Didechloro, 23-deoxy, O3-de-Me, 45-O-(2-methylpropanoyl), Deacylflambamycin; 37-Epimer, 23-deoxy, 59S-alcohol, O3,O37-di-de-Me, 45-O-(2-methylpropanoyl), Deacylflambamycin; 37-Epimer, 23-deoxy, O3O37-di-de-Me, 45-O-(2-methylpropanoyl), Deacylflambamycin; 45-O-(2-Methylpropanoyl), N-Deacyltunicamycin, N-Deacyltunicamycin; 5,6-Dihydro, N4"-(10-methyl-2-dodecenoyl), N-Deacyltunicamycin; 5,6-Dihydro, N4"-(11-methyl-2-dodecenoyl), N-Deacyltunicamycin; 5,6-Dihydro, N4"-(12-methyl-2-tetradecenoyl), N-Deacyltunicamycin; 5,6-Dihydro, N4"-(12-methyl-2-tridecenoyl), N-Deacyltunicamycin; 5,6-Dihydro, N4"-(10-methyl-2-undecenoyl), N-Deacyltunicamycin; N4"-(2-Heptadecenoyl), N-Deacyltunicamycin; N4"-(2-Hexadecenoyl), N-Deacyltunicamycin; N4"-(10-Methyl-2-dodecenoyl), N-Deacyltunicamycin; N4"-(15-Methyl-2-hexadecenoyl), N-Deacyltunicamycin; N4"-(13-Methyltetradecanoyl), N-Deacyltunicamycin; N4"-(12-Methyl-2-tetradecenoyl), N-Deacyltunicamycin; N4"-(13-Methyl-2-tetradecenoyl), N-Deacyltunicamycin; N4"-(2-Pentadecenoyl), N-Deacyltunicamycin; N4"-(2-Tetradecenoyl), O-Dealkylcyclipostin S; O-Hexadecyl, O-Dealkylcyclipostin T; Deoxo, O-Me, O-Dealkylcyclipostin T; O-Hexadecyl, O-Dealkylcyclipostin T; O-Me, O-Dealkylcyclipostin T; O-(14-Methylpentadecyl), O-Dealkylcyclophostin A; Deoxo, O-Me, O-Dealkylcyclophostin A; O-Heptadecyl, O-Dealkylcyclophostin A; O-Hexadecyl, O-Dealkylcyclophostin A; O-(12-Hydroxyhexadecyl), O-Dealkylcyclophostin A; O-(13-Hydroxyhexadecyl), O-Dealkylcyclophostin A; O-(14-Hydroxyhexadecyl), O-Dealkylcyclophostin A; O-(15-Hydroxyhexadecyl), O-Dealkylcyclophostin A; O-(16-Hydroxyhexadecyl), O-Dealkylcyclophostin A; O-(12-Hydroxy-14-methylpentadecyl), O-Dealkylcyclophostin A; O-Me, O-Dealkylcyclophostin A; O-(14-Methylhexadecyl), O-Dealkylcyclophostin A; O-(14-Methylpentadecyl), O-Dealkylcyclophostin A; O-(13-Methyltetradecyl), O-Dealkylcyclophostin A; O-(12-Oxohexadecyl), O-Dealkylcyclophostin A; O-(13-Oxohexadecyl), O-Dealkylcyclophostin A; O-(14-Oxohexadecyl), O-Dealkylcyclophostin A; O-Pentadecyl, O-Dealkylcyclophostin A; O-Tetradecyl, 7-Deazainosine, 6,8-Decadiene-1,3,5-triol; (3S,5R,6E,8E)-form, 6,8-Decadiene-1,3,5-triol; (3S,5R,6E,8E)-form, 5-Ketone, 6,8-Decadiene-1,3,5-triol; (3S,5R,6E,8E)-form, 6,7-Dihydro, 5-ketone, 2,4-Decadienoic acid; (2E,4Z)-form, Decahydro-7-(1-hydroxymethyl)-1a-(hydroxymethyl)oxireno[e]pyrrolo[2,1-b]benzoxazole-2,3,5,6-tetrol, 2,4,7-Decatrienoic acid; (2E,4Z,7Z)-form, 8-Decene-1,3,5-triol; (3S,5S,8E)-form, Dechromoneocarzinostatin, Decilorubicin, Decilorubicin; 3A,3B-Bis(denitro), 3A,3B-diamino, Deferoxamine, Dehexylantimycin, Dehexylantimycin A0, Dehexylantimycin; Dehexylantimycin A1, Dehexylantimycin; Dehexylantimycin A2, Dehydroaltenusinic acid, Delactonmycin, Delaminomycin A, Delaminomycin A; 5'-Deoxy, Delaminomycin A; 5'-Me ether, Deltamycin X, Deltamycin X; 4B—Ac, Deltamycin X; 4B-Butanoyl, Deltamycin X; 4B-(3-Methylbutanoyl), Deltamycin X; 4B-Propanoyl, Deltamycin X; 14ξ-Hydroxy, 4B-(3-methylbutanoyl), Demethylenenocardamine, Demethylmacrocin O-methyltransferase, 7-Demethylpiericidin A1, 7-Demethylpiericidin A1; 4'-O-α-L-Rhamnopyranoside, O-Demethylpuromycin O-methyltransferase, 3'-Demethylstaurosporine O-methyltransferase, 6-Demethyltetracycline, 6-Demethyltetracycline; 7-Bromo, 6-Demethyltetracycline; 7-Chloro, Demetric acid, 23-Demycinosyltylosin D, 23-Demycinosyltylosin D; 20-Aldehyde, 23-Demycinosyltylosin D; 20-Aldehyde, 4B—O-(3-methylbutanoyl), 3-Ac, 23-Demycinosyltylosin D; 20-Deoxy, 23-Demycinosyltylosin D; 23-Deoxy, 23-Demycinosyltylosin D; 23-Deoxy, 20-aldehyde, 23-Demycinosyltylosin D; 20,23-Dideoxy, Denamycin, Deoliosyl-3C-β-D-mycarosylmithramycin, Deoxyaureothin, Deoxyaureothin; 21-Carboxylic acid, Deoxyaureothin; 7,8-Didehydro(E-), Deoxyaureothin; 21-Hydroxy, Deoxyaureothin; 7R-Hydroxy, Deoxyaureothin; 21-Oxo, Deoxydehydrochorismic acid; 1-Amide, 3'-Me ester, 7-Deoxy-D-glycero-D-gluco-heptose, 7-Deoxy-L-glycero-D-gluco-heptose, 7-Deoxy-altro-2-heptulose, 5-Deoxy-3-C-hydroxymethyllyxose, 3-Deoxy-7-phosphoheptulonate synthase, 8-Deoxypremithramycinone; 4a-O-(2,6-Dideoxy-β-D-arabino-hexopyranoside), 8-Deoxypremithramycinone; 4a-O-[2,6-Dideoxy-β-D-lyxo-hexopyranosyl-(1→3)-2,6-dideoxy-β-D-arabino-hexopyranoside], 8-Deoxypremithramycinone; 4a-O-[2,6-Dideoxy-3-C-methyl-β-D-ribo-hexopyranosyl-(1→3)-2,6-dideoxy-β-D-lyxo-hexopyranosyl-(1→3)-2,6-dideoxy-β-D-arabino-hexopyranoside], 2'-Deoxyuridine; 3-Me, 1-Deoxy-D-xylulose-5-phosphate synthase, Depsidomycin, Derinamycin, Dermostatin; Dermostatin A, Dermostatin; Dermostatin B, Desalicetin, Desalicetin; 2'-Ac, Desalicetin; 2'-O-(2-Aminobenzoyl), Desalicetin; 2'-O-(4-Amino-2-hydroxybenzoyl), Desalicetin; 2'-Butanoyl, Desalicetin; S-Dealkyl, S-Me, Desalicetin; N-De-Me, 2'-O-(4-amino-2-hydroxybenzoyl), Desalicetin; O-De-Me, 2'-O-(4-amino-2-hydroxybenzoyl), Desalicetin; O,N-Di-de-Me, 2'-O-(4-amino-2-hydroxybenzoyl), Desalicetin; 2'-O-(2-Methylpropanoyl), Desdamethine, Desertomycin A, Desertomycin A; N-(Aminoiminomethyl), Desertomycin A; N-[Methylamino(methylimino)methyl], Desferroferrithiocin; (S)-form, Desferroferrithiocin; (S)-form, Fe complex, Desideus, Desotamide, Destomycin A, Destomycin A; N-De-Me, N3-Me, Destomycin A; N-De-Me, Destomycin A; 4',4"-Diepimer, N3-Me, Destomycin A; 2S-Hydroxy, N-de-Me, Destomycin A; N3-Me, Detoxin A1, Detoxin C1, Detoxin C2, Detoxin C3, Detoxin D1, Detoxin D1; O-De-Ac, O-butanoyl, Detoxin D1; O-De-Ac, O-(3-methylbutanoyl), Detoxin D1; O-De-Ac, O-(2-methylpropanoyl), Detoxin D1; O-De-Ac, O-propanoyl, Detoxin E1, Deutomycin, Dextrochrysin, DHQ 5, DHQ 6, 2,5-Dialkylpyrrolidines; 2-Butyl-5-heptylpyrrolidine, 2,4-Diaminobenzoic acid, 2,3-Diamino-2,3-bis(hydroxymethyl)-1,4-butanediol, 2,3-Diaminobutantedioic acid; (2S,3S)-form, 3,6-Diaminohexanoic acid, (S)-form, 2,6-Diamino-4-oxohexanoic acid; (S)-form, Dianemycin, Dianemycin; 3AR-Hydroxy, Dianemycin; De(glycosyloxy), Dianemycin; O-De-Me, Dianemycin; 10-Demethyl, Dianemycin; 6-Demethyl, Dianemycin; 30-Deoxy, Dianemycin; 19-Epimer, Dianemycin; 15β-Glycosyloxy isomer, Dianemycin; 27α-Glycosyloxy isomer, Dianemycin; 15β-Glycosyloxy isomer, 27α-methoxy, Dianemycin; Stereoisomer (?), Diazaquinomycin B, Diazaquinomycin B; Quinone, Diazaquinomycin C, 6-Diazo-5-oxo-1,3-cyclohexadiene-1-carboxylic acid, Dibenarthin, 3,6-Dibenzylidene-2,5-piperazinedione; (Z,Z)-form, 3,6-Dibenzyl-2,5-piperazinedione; (3S,6S)-form, 1,2-Dichloro-8-hydroxy-6-methyl-7-propyl-9H-pyrrolo[1,2-b][1,3]benzoxazin-9-one, 6,6'-Dichloroindigotin; N-(4-Acetamido-4,6-dideoxy-β-D-glucopyranosyl), 6,6'-Dichloroindigotin; N-(4-Amino-4,6-deoxy-3-β-D-glucopyranosyl), 3',6-Dichloro-4',5,7-trihydroxyisoflavone, 2,9-Dichloro-1,6,10-trihydroxy-7-methyl-5,12-naphthacenedione, 7,8-Didemethyl-8-hydroxy-5-deazariboflavin, 2,6-Dideoxy-ribo-hexose; D-form, Dienomycin C, Dienomycin C; O—Ac, Dienomycin C; O-(2-Methylpropanoyl), 3,6-Diethyl-4-hydroxy-5-methyl-2H-pyran-2-one, Differolide, 3,8-Dihexyl-4,9-dihydroxy-5,10-dimethyl-1,6-dioxecane-2,7-dione, 5,6-Dihydro-5-azathymidine, 2,3-Dihydro-8,9-dihydroxy-1H-benz[f]inden-1-one, 3,4-Dihydro-4,8-dihydroxy-3-hydroxymethyl-4-methyl-1(2H)-naphthalenone; (3R*,4R*)-form, 3,4-Dihydro-4,8-dihydroxy-3-hydroxymethyl-4-methyl-1(2H)-naphthalenone; (3R*,4R*)-form, 1'-O-α-

Glucopyranoside, 3,4-Dihydro-4,8-dihydroxy-3-hydroxymethyl-4-methyl-1(2H)-naphthalenone; (3R*,4R*)-form, 2,3-Didehydro, 3,4-Dihydro-6,7-dihydroxy-3-isoquinolinecarboxylic acid; (S)-form, 2,3-Dihydro-3,5-dihydroxy-6-methyl-4H-pyran-4-one; (S)-form, Me ether, 6,11-Dihydro-1,3,4,6,10,12-hexahydroxy-6-methyl-11-oxo-2-naphthacenecarboxamide; 4-Deoxy, 6,11-Dihydro-1,3,4,6,10,12-hexahydroxy-8-methyl-11-oxo-2-naphthacenecarboxamide; 4-O-(4-Deoxy-α-L-threo-hex-4-enopyranuronoside), 6,11-Dihydro-1,3,4,6,10,12-hexahydroxy-6-methyl-11-oxo-2-naphthacenecarboxamide; 4-O-(4-Deoxy-6-O-methyl-α-L-threo-hex-4-enopyranuronoside), Dihydro-5-(1-hydroxy-2-butenyl)-2(3H)-furanone, Dihydro-5-(1-hydroxy-2-butenyl)-2(3H)-furanone; 3,4-Didehydro, Dihydro-5-(1-hydroxy-2-butenyl)-2(3H)-furanone; 4ξ-Hydroxy, Dihydro-3-(1-hydroxy-2-butenylidene)-4-(hydroxymethyl)-2(3H) furanone; (2'E,3E,4ξ)-form, 1'-O-α-L-Rhamnopyranoside, Dihydro-3-(1-hydroxy-2-butenylidene)-4-(hydroxymethyl)-2(3H)furanone; (2E,3Z,4ξ)-form, 1'-O-α-L-Rhamnopyranoside, Dihydro-3-(1-hydroxybutyl)-4-(hydroxymethyl)-2(3H)-furanone, Dihydro-3-(1-hydroxyethyl)-4-methyl-2(3H)-furanone; (1'ξ,3ξ,4ξ)-form, Dihydro-3-(1-hydroxyethyl)-4-methyl-2(3H)-furanone; (1'ξ,3ξ,4ξ)-form, 5-Acetoxy, 2,3-Dihydro-2-(1-hydroxyethyl)-2-methylquinazolin-4(1H)-one; (1'R*,2R*)-form, 2,3-Dihydro-2-(1-hydroxyethyl)-2-methylquinazolin-4(1H)-one; (1'R*,2S*)-form, Dihydro-3-(1-hydroxyheptyl)-4-(hydroxymethyl)-2(3H)furanone, Dihydro-3-(1-hydroxyheptyl)-4-(hydroxymethyl)-2(3H)furanone; 1'-Epimer, Dihydro-5-(1-hydroxyhexyl)-2(3H)-furanone; (1'R,5S)-form, Dihydro-5-(1-hydroxyhexyl)-2(3H)-furanone; (1'S,5R)-form, Dihydro-3-(1-hydroxyhexyl)-4-(hydroxymethyl)-2(3H)-furanone, Dihydro-3-hydroxy-3-(1-hydroxy-2,4-hexadienyl)-4-(hydroxymethyl)-2(3H)-furanone, Dihydro-3-hydroxy-4-(hydroxymethyl)-2(3H)-furanone; (3S,4S)-form, 5-O-(4R,5S-Epoxy-2-hexenoyl)(E-), 3,6-Dihydro-2-hydroxy-6-hydroxymethyl-2-methyl-2H-pyran-4-carboxaldehyde; (2R*,6R*)-form, Dihydro-4-(hydroxymethyl)-3-(1-hydroxy-5-methylheptyl)-2(3H)-furanone; (1'ξ,3S,4S,5'ξ)-form, Dihydro-4-(hydroxymethyl)-3-(1-hydroxy-6-methyl-heptyl)-2(3H)-furanone, Dihydro-4-(hydroxymethyl)-3-(1-hydroxy-6-methylheptyl)-2(3H)-furanone; 1'-Epimer, Dihydro-4-(hydroxymethyl)-3-(1-hydroxy-4-methylhexyl)-2(3H)-furanone, Dihydro-4-(hydroxymethyl)-3-(1-hydroxy-5-methylhexyl)-2(3H)-furanone, Dihydro-4-(hydroxymethyl)-3-(1-hydroxy-6-methyloctyl)-2(3H)furanone; (1'ξ,3R,4S,6'ξ)-form, Dihydro-4-(hydroxymethyl)-3-(1-hydroxy-6-methyloctyl)-2(3H)-furanone; (1'ξ,3S,4S,6'ξ)-form, Dihydro-4-(hydroxymethyl)-3-(1-hydroxy-7-methyloctyl)-2(3H)-furanone, Dihydro-4-(hydroxymethyl)-3-(1-hydroxy-4-methylpentyl)-2(3H)furanone, Dihydro-4-(hydroxymethyl)-3-(1-hydroxyoctyl)-2(3H)-furanone, Dihydro-4-hydroxy-5-methyl-3-(2-methybutyl)-2(3H)-furanone; (2'ξ,3R,4R,5S)-form, Dihydro-4-hydroxy-5-methyl-3-(3-methylbutyl)-2(3H)-furanone; (3R,4R,5S)-form, Dihydro-4-hydroxy-5-methyl-3-(3-methylbutyl)-2(3H)-furanone; (3S,4R,5S)-form, 4,5-Dihydro-4-(hydroxymethyl)-3-methylene-2(3H)-furanone; (ξ)-form, 5-Methylhexanoyl, 4,5-Dihydro-4-(hydroxymethyl)-3-methylene-2(3H)-furanone; (ξ)-form, Hexanoyl, Dihydro-4-hydroxy-5-methyl-3-(5-methylhexyl)-2(3H)furanone; (3R,4R,5S)-form, Dihydro-4-(hydroxyethyl)-3-(6-methyl-1-oxoheptyl)-2(3H)furanone, 4,10-Dihydro-9-hydroxy-1-methyl-10-oxo-3H-naphtho[2,3-c]pyran-3-acetic acid; (S)-form, 9,10-Dihydro-9-hydroxy-9-methyl-5-(2-oxopropyl)-11H-naphtho[2,1-b:4,5-b'c']dipyran-11-one, Dihydro-5-(4-hydroxy-4-methylpentyl)-2(3H)-furanone; (R)-form, 4,5-Dihydro-2-(2-hydroxyphenyl)-4-methyl-4-thiazolecarboxylic acid; (S)-form, 2,3-Dihydro-5-imino-2-pyridinecarboxylic acid, 5,6-Dihydro-3-isopropyl-4H-pyrrolo[1,2-b]pyrazole, 3,4-Dihydro-1(2H)-isoquinolinone; NH-form, N-Hydroxy, Dihydro-5-(6-methylheptyl)-2(3H)-furanone; (ξ)-form, Dihydro-5-(4-methylhexyl)-2(3H)-furanone, Dihydro-5-(6-methyloctyl)-2(3H)-furanone; (ξ)-form, 3,5-Dihydro-3-methyl-2H-thiopyrano[4,3,2-cd]indole-2-carboxylic acid; (2R,3S)-form, 2,5-Dihydro-2-oxo-3(5H)-furanpropanoic acid, 2,3-Dihydro-1-oxo-1H-pyrrolizine-3-carboxylic acid, 5,6-Dihydro-2-(1,3-pentadienyl)-4(1H)-pyridinone; (E,E)-form, 6,11-Dihydro-1,3,5,10,12-pentahydroxy-6-methyl-11-oxo-2-naphthacenecarboxamide; 5-O-β-D-Glucuronopyranoside, 3,4-Dihydro-4-propylidene-2H-pyrrole-2-carboxylic acid, 3,4-Dihydro-5-(2-pyridinyl)-2H-pyrrole-2-carboxylic acid; (R)-form, Fe complex (3:1), Dihydrostreptomycin, Dihydrostreptomycin; 2'-O-Deglycosyl, Dihydrostreptomycin; 5-Hydroxy, 2''-N-de-Me, Dihydrostreptomycin 6-phosphate 3'α-kinase, 6,11-Dihydro-1,3,10,12-tetrahydroxy-6,11-dioxo-2-naphthacenecarboxamide, 6,11-Dihydro-3,6,10,12-tetrahydroxy-6-methyl-1,4,11-trioxo-2-naphthacenecarboxamide, 9,10-Dihydro-3,5,8-trihydroxy-1,10-dimethyl-9-oxo-2-anthracenecarboxylic acid, 9,10-Dihydro-3,6,8-trihydroxy-9,10-dioxo-1-(1-oxopropyl)-2-anthraceneacetic acid; Me ester, 3,4-Dihydro-4,6,9-trihydroxy-8-methyl-1(2H)-anthracenone; (S)-form, 3,4-Dihydro-4,6,9-trihydroxy-8-propyl-1(2H)-anthracenone; (S)-form, 2,7-Dihydro-2,5,7-trimethyl-5H-imidazo[4,5-e]-1,2,4-triazine-3,6-dione, 5,6-Dihydrouridine; 5'-O-(3,7-Dimethyl-2E,6-octadienyl), 4,5-Dihydroxy-1,3-benzenedicarboxylic acid, 2,3-Dihydroxybenzoic acid, 10, 15-Dihydroxy-4-cadinen-3-one; (1β,6β,7β,10βOH)-form, 2,3-Dihydroxy-2,4,6-cycloheptatrien-1-one, 4,9-Dihydroxy-5,10-dimethyl-3,8-bis(5-methylhexyl-1,6-dioxecane-2,7-dione, 3,4-Dihydroxy-1,2-dimethylcarbazole; Di-Me ether, 3,4-Dihydroxy-1,2-dimethylcarbazole; Di-Me ether, N-Me, 3,4-Dihydroxy-1,2-dimethylcarbazole; 3-Me ether, 3,4-Dihydroxy-1,2-dimethylcarbazole; 10-Methoxy, 3-Me ether, 4,5-Dihydroxy-3-(1,3-dioxobutyl)anthraquinone-2-acetic acid, 8,12-Dihydroxy-2,4-dodecadienoic acid; (+)-(E,E)-form, 4,5-Dihydroxyhexanoic acid; (4S,5S)-form, Me ester, 4-O-(2,3,6-trideoxy-L-threo-hexopyranoside), 3,8-Dihydroxy-1-hydroxymethylanthraquinone, 4,5-Dihydroxy-5-hydroxymethyl-2-cyclopenten-1-one; (4S,5S)-form, 4,5-Dihydroxy-5-hydroxymethyl-2-cyclopenten-1-one; (4S,5S)-form, 4-Ac, 4,5-Dihydroxy-5-hydroxymethyl-2-cyclopenten-1-one; (4S,5S)-form, 1'-Ac, 6-[2,4-Dihydroxy-6-[(4-hydroxy-2-oxo-2H-pyran-6-yl)methyl]benzoyl]-2,5-dihydroxy-7-methyl-1,4-naphthalenedione, 6-[2,4-Dihydroxy-6-[(4-hydroxy-2-oxo-2H-pyran-6-yl)methyl]benzoyl]-2,7-dihydroxy-5-methyl-1,4-naphthalenedione, 8,10-Dihydroxy-5-[(6-hydroxy-4-oxo-4H-pyran-2-yl)methyl]-2-methyl-4H-naphtho[1,2-b]pyran-4-one, 8,10-Dihydroxy-5-[(6-hydroxy-4-oxo-4H-pyran-2-yl)methyl]-2-methyl-4H-naphtho[1,2-b]pyran-4-one; 2,3-Dihydro, 2ξ-hydroxy, 2,7-Dihydroxy-6-(4-hydroxy-6-oxopyran-2-yl)-5-methyl-1,4-naphthoquinone, 2-[2,4-Dihydroxy-6-[(4-hydroxy-2-oxo-2H-pyran-6-yl)methyl]phenyl]-7-hydroxy-5-methyl-4H-1-benzopyran-4-one, 5,7-Dihydroxy-4-(4-hydroxyphenyl)-2H-1-benzopyran-2-one; Tri-Me ether, 3,5-Dihydroxy-2-(2-hydroxypropyl)-1,4-naphthoquinone; (R)-form, 2'-Ketone, 4',7-Dihydroxyisoflavone, 4',7-Dihydroxyisoflavone; 4',7-Di-O-(2-O-methyl-α-L-rhamnopyranoside), 4',7-Dihydroxyisoflavone; 3',5'-Dinitro, 4',7-Dihydroxyisoflavone; 4',7-Di-O-α-L-rhamnopyranoside, 4',7-Dihydroxyisoflavone; 7-O-(2-O-Methyl-α-L- rhamnopyranoside), 4',7-Dihydroxyisoflavone; 3'-Nitro, 4',7-Dihydroxyisoflavone; 7-O-α-L-Rhamnopyranoside, 1,8-Dihydroxy-3-(methoxycarbonylmethyl)-2-(3-oxopentyl)anthraquinone, 1,8-Dihydroxy-3-(methoxycarbonylmethyl)-2-(3-oxopentyl)anthraquinone; 4-Hydroxy, 1,8-Dihydroxy-3-(methoxycarbonylmethyl)-2-(1-oxopropyl) anthraquinone, 4',5-Dihydroxy-7-methoxyisoflavone, 2',4'-Dihydroxy-6'-methylacetophenone, 1,8-Dihydroxy-3-methylanthraquinone; 8-O-β-D-Glucuronopyranoside, 3,8-Dihydroxy-1-methylanthraquinone, 3,8-Dihydroxy-1-methylanthraquinone; 3-O-(2,6-Dideoxy-β-D-arabino-hexopyranoside), 3,8-Dihydroxy-1-methylanthraquinone; 3-Me ether, 1,8-Dihydroxy-3-methylanthraquinone-2-carboxylic acid, Amide, 3,8-Dihydroxy-1-methylanthraquinone-2-carboxylic acid, 1,8-Dihydroxy-3-methylbenz[a]anthracene-7,12-dione, 1,8-Dihydroxy-3-methylbenz[a]anthracene-7,12-dione; 7ξ-Alcohol, 8-Me ether, 1-O-α-L-rhamnopyranoside, 1,8-Dihydroxy-3-methylbenz[a]anthracene-7,12-dione; 11-Hydroxy, 1,8-Dihydroxy-3-methylbenz[a]anthracene-7,12-dione; 8-Me ether, 1,8-Dihydroxy-3-methylbenzo[b]phenanthridine-7,12-dione, 1,8-Dihydroxy-3-methylbenzo[b]phenanthridine-7,12-dione; 1-O-(2,3,6-Trideoxy-3-methylamino-α-D-ribo-hexopyranoside), 6,8-Dihydroxy-3-methyl-1H-2-benzopyran-1-one, 6,8-Dihydroxy-3-methyl-1H-2-benzopyran-1-one; Di-Me ether, 6,8-Dihydroxy-3-methyl-1H-2-benzopyran-1-one; 6-Me ether, 4-(2,4-Dihydroxy-6-methylbenzoyl)-3,4-dihydro-3,6,8-trihydroxy-3-[(4-hydroxy-2-oxo-2H-pyran-6-yl)methyl]-1(2H)-naphthalenone, 6-(2,4-Dihydroxy-6-methylbenzoyl)-2,5-dihydroxy-7-[(4-hydroxy-2-oxo-2H-pyran-6-yl)methyl]-1,4-naphthalenedione, 2-[2-(2,4-Dihydroxy-6-methylbenzoyl)-3-hydroxybenzyl]-6-hydroxy-4H-1-pyran-4-one, 2-[2-(2,4-Dihydroxy-6-methylbenzoyl)-3-hydroxybenzyl]-6-hydroxy-4H-1-pyran-4-one; 5'-Hydroxy, 6-[2-(2,4-Dihydroxy-6-methylbenzoyl)-3-hydroxybenzyl]-4-hydroxy-2H-pyran-2-one, 6-[2-(2,4-Dihydroxy-6-methylbenzoyl)-3-hydroxybenzyl]-4-hydroxy-2H-pyran-2-one; Analogue (R=CH2COCH3), 6-[2-(2,4-Dihydroxy-6-methylbenzoyl)-3-hydroxybenzyl]-4-hydroxy-2H-pyran-2-one; Homologue (R=CH2CH3), 6-[2-(2,4-Dihydroxy-6-methylbenzoyl)-3-hydroxybenzyl]-4-hydroxy-2H-pyran-2-one; Homologue (R=CH2CH3), 5'-hydroxy, 7-(2,4-Dihydroxy-6-methylbenzoyl)-8-hydroxy-2-methlynaphtho[1,8-bc]pyran, 1-[7-(2,4-Dihydroxy-6-methylbenzoyl)-8-hydroxynaphtho[1,8-bc]pyran-2-yl]-2-propanone, 6-[[3-(2,4-Dihydroxy-6-methylbenzoyl)-4,5,7-trihydroxy-2-naphthalenyl]methyl]-4-hydroxy-2H-pyran-2-one, 1,3-Dihydroxy-4-methyl-6,8-decadien-5-one, 4,10-Dihydroxy-10-methyldodecanoic acid; (4ξ,10ξ)-form, 4,10-Dihydroxy-10-methyldodecanoic acid; (4ξ,10ξ)-form, δ-Lactone, 1,6-Dihydroxy-9-methyl-5,12-naphthacenedione, 1,6-Dihydroxy-9-methyl-5,12-naphthacenedione; 1-Deoxy, 4-hydroxy, 5-(6,7-Dihydroxy-6-methyloctyl)-2(5H)-furanone, 6,7-Dihydroxy-8-methyl-4-oxo-4H-1-benzopyran-5-carboxylic acid, 7-[2-(2,4-Dihydroxy-6-methylphenyl)-2-oxoethyl]-2,5-dihydroxy-6-(4-hydroxy-2-oxo-2H-pyran-6-yl)-1,4-naphthalenedione, 3,4-Dihydroxy-2-methylpyridine, 2,4-Dihydroxy-5-methylquinazoline, 22,23-Dihydroxymilbemycin α1; 23-O-(2,4-Dimethylpentanoyl), 22,23-Dihydroxymilbemycin α1; 23-O-(2,4-Dimethyl-2-pentenoyl), 22,23-Dihydroxymilbemycin α1; O5-Me, 23-O-(2,4-dimethylpentanoyl), 22,23-Dihydroxymilbemycin α1; O5-Me, 23-O-(2,4-dimethyl-2-pentenoyl), 22,23-Dihydroxymilbemycin α1; O5-Me, 23-O-(2-methylbutanoyl), 22,23-Dihydroxymilbemycin α1; O5-Me, 23-O-(2-methylhexanoyl), 22,23-Dihydroxymilbemycin α1; 23-O-(2-Methylbutanoyl), 22,23-Dihydroxymilbemycin α1; 23-O-(2-Methylhexanoyl), 22,23-Dihydroxymilbemycin α1; 26-O-(2-Pyrrolecarbonyloxy), 23-(2,4-dimethylpentanoyl), 22,23-Dihydroxymilbemycin α1; 26-O-(2-Pyrrolecarbonyloxy), 23-O-(2-methylbutanoyl), 22,23-Dihydroxymilbemycin α3; 23-O-(2,4-Dimethylpentanoyl), 22,23-Dihydroxymilbemycin α3; O5-Me, 23-O-(2-methylhexanoyl), 22,23-Dihydroxymilbemycin α3; 23-O-(2-Methylbutanoyl), 22,23-Dihydroxymilbemycin α3; 23-O-(2-Methylhexanoyl), 1,4-Dihydroxy-2-naphthalenecarboxylic acid; 4-Me ether, 4,5-Dihydroxy-2,6-octadienoic acid; 2,3-Dihydroxypropyl ester, 4,23-Dihydroxy-22-oxo-3,4-seco-12-oleanen-3-oic acid, 3,6-Dihydroxy-1-phenazinecarboxylic acid, 5,7-Dihydroxy-4-phenyl-2H-1-benzopyran-2-one; Di-Me ether, 3,16-Dihydroxypregnan-20-one; (3β,5β,16α)-form, 1,2-Dihydroxy-1,2,3-propanetricarboxylic acid; (2S,3R)-form, 3,8-Dihydroxy-1-propylanthraquinone, 3,8-Dihydroxy-1-propylanthraquinone; 3-Me ether, 3,8-Dihydroxy-1-propylanthraquinone-2-carboxylic acid, 6-[[3,5-Dihydroxy-2-[[1,2,3,4-tetrahydro-2,5,7-trihydroxy-2-methyl-4-oxo-1-naphthalenyl]carbonyl]phenyl]methyl]-4-hydroxy-2H-pyran-2-one, 3,3-Di-1H-indol-3-yl-1,2-propanediol, Dilactonmycin, 2,3-Dimethoxybenzoic acid; Amide, 2,4-Dimethyl-3-furancarboxylic acid; α-L-Rhamnopyranosyl ester, 3,5-Dimethyl-2(5H)-furanone; (ξ)-form, 2,3-Dimethyl-5-methylene-4-oxo-2-cyclopentene-1-carboxylic acid; (ξ)-form, 1,4-Dimethyl-6-(4-nitro-1H-indol-3-ylmethyl)-2,3,5-piperazinetrione; (S)-form, 2-(3,7-Dimethyl-2,6-octadienyl)-5,7-dihydroxy-3-methyl-1,4-naphthoquinone, (E)-form, 2-(3,7-Dimethyl-2,6-octadienyl)-5,7-dihydroxy-3-methyl-1,4-naphthoquinone; (E)-form, 2,3-Epoxide, 4-(3,7-Dimethyl-2,6-octadienyl)-1H-pyrrole-2-carboxylic acid, 4-[2-(3,5-Dimethyl-2-oxocyclohexyl)-2-hydroxyethyl]-2,6-piperidinedione; (1R,3R,5S,αR)-form, 4-[2-(3,5-Dimethyl-2-oxocyclohexyl)-2-hydroxyethyl]-2,6-piperidinedione; (1R,3R,5S,αS)-form, 4-[2-(3,5-Dimethyl-2-oxocyclohexyl)-2-hydroxyethyl]-2,6-piperidinedione; (1R,3S,5S,αR)-form, 4-[2-(3,5-Dimethyl-2-oxocyclohexyl)-2-hydroxyethyl]-2,6-piperidinedione; (1S,3S,5S,αR)-form, 4-[2-(3,5-Dimethyl-2-oxocyclohexyl)-2-hydroxyethyl]-2,6-piperidinedione; (1S,3S,5S,αR)-form, α-Ketone, 4-[2-(3,5-Dimethyl-2-oxocyclohexyl)-2-hydroxyethyl]-2,6-piperidinedione; (1S,3S,5S,αR)-form, 1,6-Didehydro, 4-[2-(3,5-Dimethyl-2-oxocyclohexyl)-2-hydroxyethyl]-2,6-piperidinedione; (1S,3S,5S,αR)-form, 5R-Acetoxy, 4-[2-(3,5-Dimethyl-2-oxocyclohexyl)-2-hydroxyethyl]-2,6-piperidinedione; (1S,3S,5S,αR)-form, 4ξ-Hydroxy, 4-[2-(3,5-Dimethyl-2-oxocyclohexyl)-2-hydroxyethyl]-2,6-piperidinedione; (1S,3S,5S,αR)-form, 3R-Hydroxy, 4-[2-(3,5-Dimethyl-2-oxocyclohexyl)-2-hydroxyethyl]-2,6-piperidinedione; (1S,3S,5S,αR)-form, 5R-Hydroxy, 2,4-Dimethyl-1H-pyrrole-3-carboxylic acid; α-L-Rhamnopyranosyl ester, Dioctatin, Diolmycin A1, Diolmycin A1; 2'-Epimer, Dioxamycin, Dioxolamycin, Dioxolide A, Dioxolide A; O—Ac, Dioxolide A; 3a,4-Didehydro, Dioxolide A; 3a,4-Didehydro, O—Ac, 3,9-Dioxo-4-megastigmen-13-oic acid; (R)-form, Diperamycin, Diphenazithionin, 5H,10H-Dipyrrolo[1,2-a:1',2'-d]pyrazine-5,10-dione, Distamycin A, Distamycin B, Distamycin C, Ditrisarubicin A, Ditrisarubicin A; 10-O-Deglycosyl, Ditrisarubicin A; 10-O-Deglycosyl, 11-deoxy, Ditrisarubicin A; 6-Deoxy, Ditrisarubicin A; 4E-O-Deglycosyl, Ditrisarubicin A; 3E-Deoxy, Ditrisarubicin A; 3E-Deoxy, 4FS-alcohol, Ditrisarubicin A; 3E-Deoxy, 2F,3F-didehydro, Ditrisarubicin A; 4FS-Alcohol, Ditrisarubicin GR; Ditrisarubicin GR; 4B—O-Deglycosyl, Ditrisarubicin GR; 3B-Deoxy, 2C,3C-didehydro, 4C-ketone, Ditrisarubicin GR; 4C-Ketone, Dityromycin, Diumycin, Diumycin; Diumycin A, Diumycin; Diumycin A', Diumycin; Diumycin B, Diumycin; Diumycin B', Diumycin; Diumycin B", Diumycin; Diumycin U, Divergolide A, Divergolide B, Divergolide C, Divergolide D, DMI 3, Dodecaketide TW 93H, Doramectin, Doricin, Dorrigocin A, Dorrigocin A; 13-Epimer, Dorrigocin B, dTDP-L-dihydrostreptose:streptidine-6-phosphate dihydrostreptosyltransferase, Duamycin, Dunaimycin C1, Dunaimycin C1; 10-Deoxy, Duocarmycin A, Duocarmycin C1, Duocarmycin C1; Bromo analogue, Duocarmycin C2, Duocarmycin C2; Bromo analogue, Duocarmycin C2; Hydroxy analogue, Duocarmycin D; (R)-form, Duocarmycin SA, Duramycin, Duramycin B, Duramycin C, Durhamycin aglycone; 2-O-[2,6-Dideoxy-β-D-arabino-hexopyranosyl-(1→3)-4-O-methyl-2,6-dideoxy-β-D-arabino-hexopyranosyl-(1→3)-2,6-dideoxy-β-D-lyxo-hexopyranosyl-(1→3)-2,6-dideoxy-β-D-arabino-hexopyranoside], 7-O-(2,6-dideoxy-β-D-arabino-hexopyranoside), Dutomycin, Dysidine, E 492, E 492; Homologue, E 837, Ebelactone A, Ebelactone B, Echiguanine A, Echiguanine B, Echinoserine, Echinosporin, Echinosporin; Deoxy, Efomycin; Efomycin B, Efomycin; Efomycin C, Efomycin; Efomycin D, Efomycin; Efomycin F, Efrotomycin, Ehrlichin, Ekatetrone; (ξ)-form, Elaiomycin, Elaiomycin B, Elaiomycin B; 10',11'-Didehydro(Z-), Elaiophylin, Elaiophylin; 14-Deethyl, 14-Methyl, Elaiophylin; 11,11'-Di-Me ether, Elaiophylin; 11-Me ether, Elaiophylin; 3"-Me ether, Elasnin, Elastatinal A, Elastatinal B, Elastatinal C, Elmycin A, Elmycin A; 6a,12a-Diepimer, Elmycin A; 6a,12a-Diepimer, 6-deoxy, Elmycin A; 6a,12a-Diepimer, 4S-hydroxy, Elmycin B, Elmycin C, Elmycin C; 5,6-Dihydro, Emycin B, Emycin D, Emycin E, Emycin F, Enamidonin, Enaminomycin B, Enaminomycin C, Enaminomycin C; Amide, Enaminomycin C; 5-Ketone, Enaminomycin C; 5-Ketone, amide, Encalines, Endogalactosaminidase, Endomycin, Endophenazine B, Enduracidin A, Enduracidin A, Mono(dechloro), Enduracidin B, Enduracidin B; Mono(dechloro), Enduracidin C, Enduracidin D, Enkastine, Enomycin, Enopeptin A, Enopeptin A; 4-Demethyl, Ensanchomycin, Enshumycin, Enterocin, Enterocin; 8-Deoxy, Enterocin; 8-Deoxy, O-de-Me, Enterocin; 6-Epimer, 8-deoxy Enteromycin, Enteromycin; Amide, Epiderstatin, Epocarbazolin A, Epocarbazolin B, Eponemycin, Eponemycin; 1"-N-Deacyl, 1"-N-butanoyl, Eponemycin; 6"-Hydroxy, Epopromycin A, Epopromycin A; 6,7-Dihydro, Epostatin, 13,16-Epoxy-7,12-dihydroxy-6,14-dioxo-3-cleroden-15-al; (7β,8βH,12R,13R)-form, 13,16-Epoxy-7,12-dihydroxy-6,14-dioxo-3-cleroden-15-al; (7β,8βH,12R,13R)-form, 18-Hydroxy, 12,13-Epoxyleucomycin V; 4B-Butanoyl, 3-propanoyl, 12,13-Epoxyleucomycin V; 3,4B-Di-Ac, 12,13-Epoxyleucomycin V; 3,4B-Dipropanoyl, 12,13-Epoxyleucomycin V; 4B-(3-Methylbutanoyl), 3-Ac, 12,13-Epoxyleucomycin V; 4B-(3-Methylbutanoyl), 3-propanoyl, 12,13-Epoxyleucomycin V; 4B-Propenoyl, 3-Ac, 12,13-Epoxyleucomycin V; 3-Propanoyl, 4B—Ac, Erbstatin, Erbstatin; 1',2'-Dihydro, Erdacin, Ergostane-3,5,6-triol; (3β,5α,6β,24S)-form, 3-O-β-D-Glucopyranoside, Ericamycin, Erythromycin, Erythromycin; 12-Deoxy, 3"-O-de-Me, Erythromycin; 8-Fluoro, Erythromycin E, Erythronolide A, Erythronolide A; 12-Deoxy, Erythronolide A; 6,12-Dideoxy, Erythronolide A; Oxime, Erythronolide synthase, ESA 36, Esmeraldine A, Esmeraldine B, Espicufolin A; (ξ)-form, 13-Deoxy, 14-hydroxy, Espicufolin A; (R)-form, Espicufolin A; (R)-form, 8-Hydroxy, Espicufolin A; (R)-form, 13-Deoxy, Espicufolin A; (R)-form, 13-Deoxy, 14S-hydroxy, Espicufolin A; (R)-form, 13-Deoxy, 16S-hydroxy, Espinomycin B, Essramycin, Esterastin, Etabetacin, Etamycin A, Etamycin A; N9-De-Me, Etamycin A; 2-Epimer, Etamycin A; 12-Hydroxy, Etamycin A; 2-(N-Methyl-L-leucine) analogue, Etamycin A; 4Pro-Deoxy, Etamycin A; 4Pro-Deoxy, 4Pro-chloro, Etheromycin, Ethesdanine, 3-Ethyl-1,3-dihydro-3-methoxy-2H-indol-2-one, 1-Ethyl-3,8-dihydroxyanthraquinone; 3-O-(2,6-Dideoxy-β-D-arabino-hexopyranoside), 2-Ethyl-1,8-dihydroxy-3-methylanthraquinone, 8-Ethyl-1,11-dihydroxy-5,12-naphthacenedione, 8-Ethyl-1,11-dihydroxy-5,12-naphthacenedione; 13ξ-Hydroxy, 4-Me ether, 8-Ethyl-1,11-dihydroxy-5,12-naphthacenedione; 4-Me ether, 7-Ethyl-4,10-dihydroxy-7-undecene-3,6-dione, 7-Ethyl-4,10-dihydroxy-7-undecene-3,6-dione; 10-Deoxy, 7-Ethyl-4,10-dihydroxy-7-undecene-3,6-dione; 4-Deoxy, 7-Ethyl-4,10-dihydroxy-7-undecene-3,6-dione; 4,10-Dideoxy, 9-hydroxy, 7-Ethyl-4,9-dihydroxy-7-undecene-3,6-dione, 4-Ethyl-2,4-hexadienoic acid; (E,E)-form, Amide, 6-Ethyl-4-hydroxy-3,5-dimethyl-2H-pyran-2-one, 4-Ethyl-2-(hydroxyimino)-5-nitro-3-hexenamide, 3-Ethyl-4-hydroxy-6-isopropyl-2H-pyran-2-one, 3-Ethyl-4-hydroxy-6-(1-methylpropyl)-2H-pyran-2-one; (S)-form, 3-Ethyl-4-hydroxy-6-(2-methylpropyl)-2H-pyran-2-one, 3-Ethyl-4-hydroxy-6-propyl-2H-pyran-2-one, 2-Ethylidene-5,7-dihydroxy-1-phenyl-3-heptanone, 3-Ethylidene-6-(1H-indol-3-ylmethyl)-4-methyl-2,5-piperazinedione; (S,Z)-form, 3-Ethyl-5-methyl-2(5H)-furanone; (ξ)-form, 4-Ethyl-5-methylheptanoic acid; Amide, 6-Ethyl-3-(2-methylpropyl)-2H-pyran-2-one, 6-Ethyltetrahydro-4-hydroxy-3,5-dimethyl-2H-pyran-2-one; (3R,4S,5R,6R)-form, 3-Ethyl-3,4,4a,12b-tetrahydro-3,4a,7,8-tetrahydroxybenz[a]anthracene-1,6(2H,6H)-dione; 3-Deoxy, 2,3-didehydro, 8-Ethyl-1,6,10,11-tetrahydroxy-5,12-naphthacenedione, 8-Ethyl-1,6,10,11-tetrahydroxy-5,12-naphthacenedione; 7-Deoxy, 13-hydroxy, 4,13-di-Ac, 8-Ethyl-1,6,10,11-tetrahydroxy-5,12-naphthacenedione; 7-Deoxy, 4-Me ether, 13ξ-acetoxy, 3-Ethyl-1,6,8-trihydroxybenz[a]anthracene-7,12-dione, 3-Ethyl-1,6,8-trihydroxybenz[a]anthracene-7,12-dione; 13,14-Didehydro, 3-Ethyl-1,7,8-trihydroxybenz[a]anthracene-5,6-dione, 8-Ethyl-1,6,11-trihydroxy-5,12-naphthacenedione, 8-Ethyl-1,6,11-trihydroxy-5,12-naphthacenedione; 1-Me ether, 4(15),7(11)-Eudesmadiene-8,9-diol; (8β,9β)-form, 4(15),7(11)-Eudesmadien-9-ol; 9β-form, Eulicin, Eurocidin T, Eurotin A, Eurystatin; Eurystatin A, Eurystatin; Eurystatin B, Eurystatin; Eurystatin C, Eurystatin; Eurystatin D, Eurystatin; Eurystatin E, Eurystatin; Eurystatin F, Evericin, Exfoliamycin, Exfoliamycin; 3-Deoxy, 3,4-didehydro, Exfoliamycin; 3-Me ether, Exfoliatin, Ezomycin A1, Ezomycin A2, Ezomycin B1, Ezomycin B1; 1-Epimer, Ezomycin B2, Ezomycin B2; 1-Epimer, Ezomycin D1, Ezomycin D2, FA 1819, Factumycin, Factumycin; 14E-Isomer, Factumycin; 14E-Isomer, 5,6-dihydro, Factumycin; 14E-Isomer, 29-Me ether, Farinamycin, Fattiviracin A1, Fattiviracins, FCRC 53, Feglymycin, Feigrisolide A, Feigrisolide A; 8-Epimer, Feigrisolide A; 8-Epimer, 3-deoxy, 2,3-didehydro, Feigrisolide C, Feigrisolide C; Stereoisomer (?), Feigrisolide D, Feldamycin, Fermicidin, Ferramidochloromycin, Ferrimycin A1, Ferrimycin A2, Ferrioxamine A2, Ferrioxamine B, Ferrioxamine D2, Ferromycin, Ferropyrumycin, Ferroverdin, Ferroverdin; 8-Monocarboxy(Z-), Ferroverdin; 8-Monohydroxy(E-), Feruloyl esterase, Feudomycin B, Feudomycin B; O-De-Me, Feudomycin C, Feudomycin C; Aglycone, Feudomycin C; De(glycosyloxy), Feudomycin C; 10β-Hydroxy, Feudomycin C; 10β-Hydroxy, aglycone, Fibrostatins, Ficellomycin, Filipin; Filipin I, Filipin; Filipin II, Filipin; Filipin III, Filipin; Filipin III, 3- or 1'-Epimer, Flavacid, Flavensomycin, Flaveolin, Flavofungin; Flavofungin I, Flavofungin; Flavofungin I, Stereoisomer, Flavofungin; Flavofungin I, 14-Demethyl, 19,21-diepimer, Flavofungin; Flavofungin I, 28,29-Dihydro, 23-deoxy, 24,29-dihydroxy, Flavofungin; Flavofungin II, Flavofungin; Flavofungin II, Stereoisomer, Flavopentin, Flavoviridomycin, Flavucidin, Flazine; Me ester, Fluorin, Fluoroacetaldehyde, Fluoroacetic acid, Fluorothreonine transaldolase, Fluostatin A, Fluostatin A; 2,3-Dihydro, 3R-chloro, 2S-hydroxy, 1R-alcohol, Fluostatin A; 2,3-Dihydro, 2-hydroxy, 1ξ-alcohol, Fluostatin A; 2S,3S-Epoxide, 1R-alcohol, Fluostatin A; 2S,3S-Epoxide, 1R-alcohol, 1-O-(2-methylpropanoyl), Fluvirucin B; Fluvirucin B3, 4'-Epimer, Fogacin, Formadicins; Formadicin A, Formadicins; Formadicin C, Formycin A, Formycin B, 3-[(4-Formylphenyl)amino]-4,7-dihydroxy-5-octenoic acid; Me ester, Foromacidin A, Foromacidin A; 3-Ac, Foromacidin A; 4A,9-Dideglycosyl, 18-deoxo, 9-ketone, 3-propanoyl, Foromacidin A; 4A,9-Dideglycosyl, 18-deoxo, 3-propanoyl, Foromacidin A Aglycone, 18-deoxo, Foromacidin A; Aglycone, 18-deoxo, 9-ketone, Foromacidin A; 18-Alcohol, Foromacidin A; 4B-Butanoyl, 3-Ac, Foromacidin A, 4B-Butanoyl, 3-propanoyl, Foromacidin A 3,4B-Di-Ac, Foromacidin A; 3,4B-Dipropanoyl, Foromacidin A; 4B—O-(3-Methylbutanoyl), Foromacidin A; 4B—O-(3-Methylbutanoyl), 3-Ac, Foromacidin A; 4B—O-(3-Methylbutanoyl), 3-propanoyl, Foromacidin A; 4B—O-(2-Methylpropanoyl), 3-Ac, Foromacidin A 4B—O-(2-Methylpropanoyl), 3-propanoyl, Foromacidin A; 4B-Propanoyl, 3-Ac, Foromacidin A; 18-Deoxo, Foromacidin A; 17-Methylene, Foromacidin A; 3-Propanoyl, Foromacidin A; 3-Propanoyl, 4B—Ac, Foromacidin D, Foroxymithine, Fortimicin B; 4-Epimer, 1-N-[[(iminomethyl)amino]acetyl], Fortimicin KE; 5-Deoxy, 6'-N-Et, Fortimicin KE; 5-Deoxy, 6'-N-Et, 1-N-(aminoacetyl), Fortimicin KE; 5-Deoxy, 6'-N-Et, 1-N-(formylaminoacetyl), Fortimicin KE; 5-Deoxy, 6'-N-Me, Fortimicin KE; 5-Deoxy, 6'-N-Me, 1-N-(aminoacetyl), Fortimicin KE; 5-Deoxy, 6'-N-Me, 1-N-[[(aminocarbonyl)amino]acetyl], Fortimicin KE; 5-Deoxy, 6'-N-Me, 1-N-(formylaminoacetyl), Fortimicin KE; 5-Deoxy, 6'-N-Me, 1-N-[[(iminomethyl)amino]acetyl], Fortimicin KE; 6-Epimer, 5-deoxy, Fortimicin KE; 4-Epimer, 5-deoxy, 6'-N-Me, Fortimicin KE; 6-Epimer, 5-deoxy, 6'-N-Me, Fortimicin KE; 4-Epimer, 5-deoxy, 6'-N-Me, 1-N-(aminoacetyl), Fortimicin KE; 4-Epimer, 5-deoxy, 6'-N-Me, 1-N-(formylaminoacetyl), Fortimicin KE; 6-Epimer, 5-deoxy, 6'-N-Me, 1-N-(formylaminoacetyl), Fortimicin KE; 4-Epimer, 5-deoxy, 6'-N-Me, 1-N-[[(iminomethyl)amino]acetyl], Fortimicin KE; Stereoisomer, Fosfazinomycin A, Fosfazinomycin B, Fostriecin, Fostriecin; 13-Deoxy, Fostriecin; O-Dephospho, Fostriecin; 5S-Hydroxy, Fostriecin; 5S-Hydroxy, O-dephospho, Fostriecin; Parent hydroxyacid, 5S-hydroxy, FR 182876, FR 182877, Fradicin, Fredericamycin A, Fredericamycin B, Fredericamycin C, Fredericamycin C1, Fredericamycin E, Fredericamycin M1, Fredericamycin M1; 9,12-Quinone, Fredericamycin M1; 9,12-Quinone, 14-hydroxy, Fredericamycin M3, Fredericamycin M4, Fredericamycin MS, Frenolicin, Frenolicin; Deepoxy, 4a,10a-didehydro, 4β-hydroxy, Me ester, Frenolicin; Deepoxy, 4a,10a-didehydro, Frenolicin B, Frenolicin B; 5a,11a-Epoxide, Fridamycin E; (R)-form, Frigocyclinone, Friulimicin; Friulimicin A, 4'-Parent acid, Friulimicin; Friulimicin B, 4'-Parent acid, Friulimicin; Friulimicin D, 4'-Parent acid, Fructan β-(2,6)-fructosidase, 2,6-β-Fructan 6-levanbiohydrolase, Fuchurmycin B, Fucothricin, Fujianmycin A, Fujianmycin A; 4-Epimer, 8-Me ether, Fujianmycin A; 13-Hydroxy, 8-Me ether, Fujianmycin A; 8-Me ether, Fujimycin, Fujimycin; 9ξ-Alcohol, Fujimycin; 31-O-De-Me, Fujimycin; 31-O-De-Me, 31-ketone, Fujimycin; 25-Demethyl, Fujimycin; 9-De-oxo, 31-O-de-Me, Fujimycin; 2',3'-Dihydro, Fujimycin; Lower homologue, Fulvomycin, Fumanomycin, Fungichromatin, Fungichromin, Fungichromin; 32-Deethyl, 30-methyl, stereoisomer, Fungichromin; 33-Demethyl, stereoisomer, Fungichromin; Stereoisomer, 2,4-Furandicarboxylic acid; Di-Me ester, 2,5-Furandimethanol, 2,5-Furandimethanol; Di-Ac, 2,5-Furandimethanol; Mono-Ac, 2-Furanol; OH-form, Ac, Furanomycin, Furanonaphthoquinone I, Furanonaphthoquinone I; O-De-Me, Furanonaphthoquinone I; 6-Demethyl, Furaquinocin G, Furaquinocin H, Furaquinocin H; 5'-Deoxy, Furaquinocin H; 6'-Deoxy, Furaquinocin H; 6'-Deoxy, 5'-carboxylic acid, Furaquinocin H; 6'-Deoxy, 5'-carboxylic acid, amide, Furaquinocin H; 1',6'-Dideoxy, Furaquinocin H; 5',6'-Dideoxy, Furaquinocin H; 1',6'-Dideoxy, 1',2-didehydro(E-), Furaquinocin H; 1',5',6'-Trideoxy, Futalosine, Futalosine hydrolase, Galactan 1,3-β-galactosidase, Galbonolide A, Galbonolide B, Galbonolide C, Galbonolide D, Galirubin A, Galtamycinone; 4'-O-(2E,4E-Decadienoyl), Galtamycinone; 3'-O-[2,6-Dideoxy-β-D-arabino-hexopyranosyl-(1→4)-2,3,6-trideoxy-α-D-threo-hexopyranoside], Galtamycinone; 3'-O-(2,3,6-Trideoxy-α-D-threo-hexopyranoside), Galtamycinone; 3'-O-[2,3,6-Trideoxy-α-L-lyxo-hexopyranosyl-(1→3)-2,6-dideoxy-β-D-arabino-hexopyranosyl-(1→4)-2,3,6-trideoxy-α-L-lyxo-hexopyranosyl], Gancidin, Ganefromycin δ1, Ganefromycin δ1; 32-Deoxy, Ganefromycin δ1; 32-Deoxy, 13-Me ether, Ganefromycin δ1; 32-Deoxy, 13-Me ether, 23-O-(phenylacetyl), Ganefromycin δ1; 23,32-Dideoxy, Ganefromycin δ1; 32-O-(2,6-Dideoxy-α-L-galactopyranoside), Ganefromycin δ1; 23,32-Dideoxy, 13-Me ether, Ganefromycin δ1; 21-Epimer, 23,32-dideoxy, Ganefromycin δ1; 21-Epimer, 23,32-dideoxy, 13-Me ether, Ganefromycin δ1; 13-Me ether, Ganefromycin δ1; 13-Me ether, 32-O-(2,6-dideoxy-α-L-galactopyranoside), Ganefromycin δ1; 13-Me ether, 23-O-(phenylacetyl), 32-O-(2,6-dideoxy-α-L-galactopyranoside), Ganefromycin δ1; 13-Me ether, 24-O-(phenylacetyl), 32-O-(2,6-dideoxy-α-L-galactopyranoside), Ganefromycin 61; 23-O-(Phenylacetyl), 32-O-(2,6-dideoxy-α-L-galactopyranoside), Ganefromycin δ1; 24-O-(Phenylacetyl), 32-O-(2,6-dideoxy-α-L-galactopyranoside), Gangtokmycin, Gannibamycin, Garlandosus, Gastric juice inhibitory substance, Gaudimycin B, Gaudimycin B; 6-Deoxy, Gaudimycin B; 6-Epimer, Gelbecidin, Geldanamycin, Geldanamycin; 19-(2-Aminoacetyloxy), 4,5-dihydro, Geldanamycin; 19-(2-Aminoacetyloxy), 4,5-dihydro, decarbamoyl, Geldanamycin; Decarbamoyl, Geldanamycin; 17-O-De-Me, Geldanamycin; 17-Demethoxy, 17-C-formyl, 18,21-hydroquinone, Geldanamycin; 17-Demethoxy, 17-C-formyl, 18,21-hydroquinone, 011-Me, Geldanamycin; 17-Demethoxy, 17-hydroxymethyl, Geldanamycin; 8-Demethyl, Geldanamycin; 8-Demethyl, 4R*,5S*-epoxide, Geldanamycin; 4,5-Dihydro, Geldanamycin; 4,5-Dihydro, decarbamoyl, Geldanamycin; 4,5-Dihydro, 17-O-de-Me, decarbamoyl, Geldanamycin; 18,21-Hydroquinone, Geldanamycin; 15R-Hydroxy, Geldanamycin; 15R-Hydroxy, 4,5-dihydro, Geldanamycin; 19-(Methylthio), Geldanamycin; 19-(Methylthio), 4,5-dihydro, Geminimycin, Geomycin, Geosmin, Gephyromycin, 2-Geranyl-3,5,7-trihydroxy-6-methyl-1,4-naphthoquinone, 2-Geranyl-3,5,7-trihydroxy-6-methyl-1,4-naphthoquinone; 3-Deoxy, 2ξ,3ξ-epoxide, Gerfelin; 3'-Me ether, Me ester, 1(10),5-Germacradiene-2,11-diol; (1(10),E,2α,5E)-form, 1(10),5-Germacradiene-3,11-diol; (1(10)E,3β,5E)-form, 1(10),5-Germacradien-11-ol; (1(10)E,4S,5E,7R)-form, Gerobriecin, Gibbestatin A, Gibbestatin B, Gibbestatin B; 2-Hydroxyphenyl ester, Gilvocarcin M, Gilvocarcin M; 6-Alcohol, Gilvocarcin M; 4'-Hydroxy, Gilvocarcin V, Gilvocarcin V; Aglycone, Gilvocarcin V; Aglycone, 6-alcohol, Gilvocarcin V; Aglycone, 12-O-de-Me, Gilvocarcin V; 6-Alcohol, Gilvocarcin V; 1",2"-Dihydro, Gilvocarcin V; 4'-Hydroxy, Gilvocarcin V; 4'-Hydroxy, 1",2"-dihydro, Glaciapyrrole A, Glaciapyrrole B, Glaciapyrrole C, Globerin, Globismycin, Globopeptin, Globoroseomycin, Glomecidin, Glucan endo-1,3-D-glucosidase, Glucan endo-1,3-α-glucosidase, Glucan endo-1,6-β-glucosidase, Glucolipsins; Glucolipsin A, Glucomycin, Gluconimycin, 6-O-α-D-Glucopyranosyl-D-glucose, Glucose 1-phosphate guanylyltransferase, Glucose 1-phosphate thymidylyltransferase, Glutamate dehydrogenases; Glutamate dehydrogenase (NADP(+)), Glutamate dehydrogenases; L-Glutamate oxidase, Glutamine scyllo-inositol transaminase, Glycerinopyrin, Glycerol 1-alkanoates; Glycerol 1-(18-methyleicosanoate) Glycerol 1-alkanoates; Glycerol 1-(16-methylheptadecanoate), Glycerol 1-alkanoates; Glycerol 1-(15-methylhexadecanoate), Glycerol 1-alkanoates; Glycerol 1-(18-methylnonadecanoate), Glycerol 1-alkanoates; Glycerol 1-(16-methyloctadecanoate), Glycerol 1-alkanoates; Glycerol 1-(17-methyloctadecanoate), Glycerol 1-alkanoates; Glycerol 1-(14-methylpentadecanoate), Glycerol 1-alkanoates; Glycerol 1-(12S-methyltetradecanoate), Glycerol 1,3-dialkanoates; Glycerol 1(3)-(14,16-dimethyloctadecanoate)-3(1)-(9E,12E-octadecadienoate), Glycinocin; Glycinocin A, Glycopeptide α-N-acetylgalactosaminidase, Goadsporin, Gombapyrone A, Gombapyrone A; 20-Deoxy, Gombapyrone A; 20-Deoxy, O-de-Me, Gombapyrone A; Lower homologue (R=H), 20-deoxy, Gostatin, Gougerotin, Gougeroxymycin, Granatomycin D, Granatomycin D; 3-Epimer, Granatomycin D; 4-Hydroxy, Granatomycin D; 4-Hydroxy, 1→4-lactone, Granatomycin D; 4β-Hydroxy, 1→4-lactone, 19-O-(2,3,6-trideoxy-β-D-threo-hexopyranoside), Granatomycin D; 4β-Hydroxy, 1→4-lactone, 19-O-(2,3,6-trideoxy-α-L-threo-hexopyranoside), Granatomycin D; 4-Hydroxy, Me ester, Granatomycin D; 4-Hydroxy, 19-O-(2,3,6-trideoxy-β-D-threo-hexopyranoside), Granatomycin D; Me ester, Granatomycin D; 19-O-(2,3,6-Trideoxy-L-threo-hexopyranoside), Grecocycline A, Grecocycline A; Deepoxy, 6aβ-mercapto, 12aβ-hydroxy, Grecocycline C, Grecoketide A, Grecoketide A, 4A,5A-Diepimer, Grecomycin, Grisamine, Griselimycin, Griseobactin, Griseochelin, Griseochelin; 24,25-Didehydro, Griseococcin D, Griseolic acid, Griseolic acid; 7'-Deoxy, Griseolic acid; 4'α,5'-Dihydro, 7'-deoxy, Griseomycin, Griseophagin, Griseorhodin A, Griseorhodin A2, Griseorhodin B, Griseorhodin C, Griseorhodin C; 4-Deoxy, Griseorhodin C; 3,4-Dideoxy, Griseorhodin C; 4-Me ether, Griseorhodin K, Griseorhodin L, Griseoviridin, Griseoviridin; 20-Deoxy, Δ20,Δ22-isomer, 24ξ-methoxy, Griseoviridin; O20-Me, Griseusin B; (−)-form, Griseusin B; (−)-form, 4α-Hydroxy, lactone, Griseusin B; (−)-form, 4α-Hydroxy, lactone, O-de-Ac, Griseusin B; (+)-form, 4-Hydroxy, lactone, 3'-O-[α-D-2,3,4,6-tetradeoxy-4-(dimethylamino)-erythro-hexopyranoside], Grisonomycin, Grividomycin I, Grividomycin I; Diastereoisomer, Grixazone B, Grixazone B; 1'-Aldehyde, GTP diphosphokinase, Guadinomic acid, Guadinomine A, Guadinomine A; 1'-Deoxy, Guadinomine A; 1'-Deoxy, NT-Ac, Guadinomine C1, Guadinomine C1; 3'-Epimer, Gualamycin, Guamycin, Guanamycin, 1D-1-Guanidino-3-amino-1,3-dideoxy-scyllo-inositol transaminase, Guanidinodeoxy-scyllo-inositol-4-phosphatase, Guanidolide A, Guanidylfungin A, Guanidylfungin A; N-De-Me, Guanidylfungin A; Me ether, Guanine; N7-Oxide, Gutingimycin, Hachimycin, Hachimycin; Trichomycin A, 5-Deoxy, 9-hydroxy, Haim, Halawanone A, Halawanone B, Halicoblelide, Halichomycin, Halstoctacosanolide A, Halstoctacosanolide A; 4-Deoxo, Halstoctacosanolide A; 4-Deoxo, 32-deoxy, Hamycin X, Harimycin, Hatomarubigin C, Hatomarubigin C; O-De-Me, Hatomarubigin C; 11-Deoxy, 6-hydroxy, 1-ketone, Hatomarubigin C; 1-Ketone. Hatomarubigin D, Helvolic acid, Helvomycin, Heptaene 757, Heptafungin A, Heptamycin, Heptamycin B, Heptamycin B; N-De-Ac, N-propanoyl, Heptamycin B; 4"-Hydroxy, Heptamycin B; Ring-opened form, Heptamycin B; Ring-opened form, N-de-Ac, N-propanoyl, 1-Heptyl-3-hydroxy-2-methyl-9H-carbazole, 3-Heptyl-5-methyl-2(5H)-furanone; (ξ)-form, Herboxidiene, Herboxidiene; 17-O-De-Me, Herboxidiene; 12-Hydroxy, Herboxidiene; 21-Hydroxy, Herboxidiene; 5-Hydroxy, Hernandaline; (S)-form, 2'-Alcohol, Heronamide A, Heronamide B, Heronamide C, Hexacyclinic acid, Hexaene 80, Hexahydro-7a-hydroxy-3H-pyrrolizin-3-one; (±)-form, Hexahydro-7a-hydroxy-3H-pyrrolizin-3-one; (±)-form, Me ether, Hexahydro-7a-hydroxy-3H-pyrrolizin-3-one; (±)-form, (1-Ethoxyethyl) ether, 4,4a,8,9,10,12b-Hexahydro-4a,7,8,12,12b-pentahydroxy-3-methylbenz[a]anthracene-1,11-dione, 3,4,4a,5, 10,10a-Hexahydro-4a,9,10a-trihydroxy-1-methyl-5,10-dioxo-1H-naphtho[2,3-c]pyran-3-acetic acid; Me ester, 3,3',4,4',7',9-Hexahydroxy-7,9'-epoxylignan; (7S,7'S,8R,8'S)-form, 7'-Ketone, 3,4:3',4'-bis(methylene) ether, 1,3,4,10,11,12-Hexahydroxy-6-methyl-2-naphthacenecarboxamide, 1,3,4, 10,11,12-Hexahydroxy-6-methyl-2-naphthacenecarboxamide; 4-Deoxy, Hexamycin, 1,4,5-Hexanetriol; (4S,5S)-form, 1,4,5-Hexanetriol; (4S,5S)-form, 4-O-(2,3,6-Trideoxy-α-L-threo-hexopyranoside), 3-(1-Hexenyl)-5-hydroxy-5-(hydroxymethyl)-4-methyl-2(5H)-furanone; (E)-(+)-form, Hexin, 3-Hexyldihydro-4-hydroxy-5-methyl-2(3H)-furanone; (3R,4R,5S)-form, 3-Hexyl-5-methyl-2(5H)-furanone; (±)-form, Hikizimycin, Himalomycin A, Himalomycin A; 12-O-Deglycosyl, Himalomycin B, Himalomycin B; 4',12-Bis(deglycosyl), Himalomycin B; 4',12-Bis(deglycosyl), 3',4'-diepimer, Himastatin, Histargin, Histidinol; (S)-form, N—Ac, Histidinomycin, N-Histidylvaline; L-L-form, N1-Formyl, Hitachimycin, Hodydamycin, Homoabyssomicin A, Homoabyssomicin B, Homoalanosine; (S)-form, Homononactic acid, Homononactic nonactic dilactone, Homononactyl nonactoate, 44-Homooligomycin A, 44-Homooligomycin A; 20-Deethyl, 20-methyl, 28-oxo, 44-Homooligomycin A; 12-Deoxy, 44-Homooligomycin A; 28-Oxo, 44-Homooligomycin A; 28-Oxo, 26-hydroxy, Homoplatensimide A, Homoplatensimide A; Me ester, Hondamycin; Hondamycin A, Hondamycin; Hondamycin B, Hormaomycin, Hortesin, Humidin, Hybrimycin A1, Hybrimycin A1; 1-Deamino, 1-hydroxy, Hybrimycin A1; 6'''-Deamino, 6'''-hydroxy, Hybrimycin A1; 2,5'''-Diepimer, Hybrimycin A1; 2-Epimer, Hybrimycin A1; 5'''-Epimer, Hybrimycin A1; 5'''-Epimer, 6'''-deamino, 6'''-hydroxy, Hydantocidin, Hydramycin, *Streptomyces luteoreticuli* Hydrocarbon, Hydroheptin, Hydrohexin, Hydroisoflavone A, Hydroisoflavone B, Hydroisoflavone B; 3-Deoxy, Hydrostatin A, 3-[[(Hydroxyamino)carbonyl]amino]alanine; (S)-form, [3-(Hydroxyamino)-2-hydroxypropyl]phosphonic acid; (R)-form, N—Ac, [3-(Hydroxyamino)-1-propenyl]phosphonic acid; (E)-form, N-Formyl, 3-Hydroxyanthranilate 4-C-methyltransferase, 1-(3-Hydroxy-1-azetidinyl)-7-undecene-1,5-dione; (E)-form, 4-Hydroxybenzoic acid; 6-Deoxy-α-L-talopyranosyl ester, 4-Hydroxybenzoic acid; 6-Deoxy-α-L-talopyranosyl ester, O-(6-deoxy-α-L-talopyranoside), 4-Hydroxybenzoic acid; α-L-Rhamnopyranosyl ester, 8-Hydroxy-2H-1,3-benzoxazine-2,4(3H)-dione, 2-(4-Hydroxybenzyl)-4-oxo-2-azetidinecarboxylic acid; (S)-form, 2-Hydroxy-1,2,4-butanetricarboxylic acid; (S)-form, O-[α-D-Ribofuranosyl-(1→2)-α-D-ribofuranosyl-(1→3)-α-O-ribofuranoside], 6-[2-(1-Hydroxybutyl)-4-methylphenyl]-5-hexenamide; (E)-form, 11-Hydroxy-2,5-dimethyl-4H-anthra[1,2-b]pyran-4,7,12-trione, 9-Hydroxy-1,3-dimethylbenz[g]isoquinoline-5,10-dione, 2-Hydroxy-3,6-dimethylbenzoic acid, 6-Hydroxy-4,6-dimethyl-3-hepten-2-one, 3-(1-Hydroxy-2,4-dimethylpentyl)-4-methyl-2,5-furandione, 6-Hydroxy-2',4-dimethylspiro[benzofuran-2(3H),7'(8'H)-naphtho[1,8-bc]pyran]-3,8'-dione, 3-Hydroxy-2,5-dphenyl-1,4-benzoquinone, 3-Hydroxy-1,4-diphenyl-7-oxabicyclo[4.1.0]hept-3-ene-2,5-dione, 3-(2-Hydroxyethyl)-4-oxa-1-azabicyclo[3.2.0]heptan-7-one; (3S,5S)-form, 6-(1-Hydroxyethyl)-1-phenazinecarboxylic acid, 6-(1-Hydroxyethyl)-1-phenazinecarboxylic acid; 6-Deoxy-α-L-glucopyranos-2-yl ester, 6-(1-Hydroxyethyl)-1-phenazinecarboxylic acid; 6-Deoxy-α-L-glucopyranos-3-yl ester, 6-(1-Hydroxyethyl)-1-phenazinecarboxylic acid; O-Hexadecanoyl, 6-(1-Hydroxyethyl)-1-phenazinecarboxylic acid; O-(Hydroxyacetyl), 6-(1-Hydroxyethyl)-1-phenazinecarboxylic acid; O-(2-Hydroxy-6-methylbenzoyl), 6-(1-Hydroxyethyl)-1-phenazinecarboxylic acid; 1'-Ketone, 6-(1-Hydroxyethyl)-1-phenazinecarboxylic acid; Me ester, 6-(1-Hydroxyethyl)-1-phenazinecarboxylic acid; Me ether, 6-(1-Hydroxyethyl)-1-phenazinecarboxylic acid; Me ether, Me ester, 6-(1-Hydroxyethyl)-1-phenazinecarboxylic acid; O-(16-Methylheptadecanoyl), 6-(1-Hydroxyethyl)-1-phenazinecarboxylic acid; O-(14-Methylhexadecanoyl), 6-(1-Hydroxyethyl-1-phenazinecarboxylic acid; O-(14-Methylpentadecanoyl), 6-(1-Hydroxyethyl)-1-phenazinecarboxylic acid; O-(12-Methyltetradecanoyl), 6-(1-Hydroxyethyl)-1-phenazinecarboxylic acid; O-(12-Methyltridecanoyl), 6-(1-Hydroxyethyl)-1-phenazinecarboxylic acid; O-Tetradecanoyl, 3-(2-Hydroxyethyl)-6-prenylindole, 3-(2-Hydroxyethyl)-6-prenylindole; Aldehyde, oxime, 3-(2-Hydroxyethyl)-6-prenylindole; Carboxylic acid, nitrile, 2-Hydroxyhexanoic acid; (S)-form, 2-Hydroxy-2-hydroxyaminocarbonyl)-3-methylpentanedioic acid, 2-Hydroxy-2-(hydroxyaminocarbonyl)pentanedioic acid, 4-Hydroxy-6-[1-hydroxy-3,5-dimethyl-6-(4-nitrophenyl)-3,5-hexadienyl]-3,5-dimethyl-2H-pyran-2-one, 4-Hydroxy-6-[1-hydroxy-3,5-dimethyl-6-(4-nitrophenyl)-3,5-hexadienyl]-3,5-dimethyl-2H-pyran-2-one; 6-Deoxy, 5-Hydroxy-3-(1-hydroxy-2-methybutyl)-4-methyl-2(5H)-furanone; (1'S,2'S,5ξ)-form, 5-Hydroxy-3-(1-hydroxy-2-methylbutyl)-4-methyl-2(5H)-furanone; (1'S,2'S,5ξ)-form, 5-Deoxy, 2-Hydroxy-2-hydroxymethyl-4-cyclopentene-1,3-dione, 3-Hydroxy-6-(hydroxymethyl)-2,8-dimethyl-6,8-decadienoic acid; Amide, 3-Hydroxy-8-(hydroxymethyl)-2,6-dimethyl-6,8-decadienoic acid; Amide, 4-Hydroxy-2-[[5-(hydroxymethyl)-2-furanyl]methylene]-5-methyl-3(2H)-furanone, 9-Hydroxy-6-hydroxymethyl-1-phenazinecarboxylic acid, 9-Hydroxy-6-hydroxymethyl-1-phenazinecarboxylic acid; 5,10-Dihydro, 9-Me ether, N5-(hydroxyacetyl), 9-Hydroxy-6-hydroxymethyl-1-phenazinecarboxylic acid; 9-Me ether, 9-Hydroxy-&-hydroxymethyl-1-phenazinecarboxylic acid; 9-Me ether, 1'-O-(hydroxyacetyl), 2-Hydroxy-4-(3-hydroxy-5-methylphenoxy)-6-methylbenzoic acid; Me ester, 5-Hydroxy-3-(1-hydroxy-2-methylpropyl)-4-methyl-2(5H)-furanone; (1'S,5ξ)-form, 5-Hydroxy-3-(1-hydroxy-2-methylpropyl)-4-methyl-2(5H)-furanone; (1'S,5ξ)-form, 5-Deoxy, 2-Hydroxy-2-[(hydroxyphosphinyl)methyl]butanedioic acid; (S)-form, 2-Hydroxy-3-(hydroxyphosphinyl)propanoic acid; (S)-form, 6-Hydroxy-1H-indole-2,3-dione, 2-Hydroxy-3-(3-indolyl)propanoic acid; (ξ)-form, 4-Hydroxy-6-isopropyl-3-(2-methylpropyl)-2H-pyran-2-one, 4-Hydroxy-6-isopropyl-3-methyl-2H-pyran-2-one, 2-Hydroxy-3-isopropylpyrazine; OH-form, Me ether, 2-Hydroxy-4-mercaptopyrimidine, 6-Hydroxy-5-methoxy-1-methyl-2,3,4(1H)pyridinetrione, 3-Hydroxy-4-methoxyphenethylamine; N—Ac, 2-(3-Hydroxy-4-methoxyphenyl)ethanol, 8-Hydroxy-2-methyl-1H-benz[f]indole-4,9-dione, 2-Hydroxy-6-methylbenzoic acid, 4-Hydroxy-6-(3-methylbutyl)-2H-pyran-2-one, 3-Hydroxymethylcephem carbamoyltransferase, 2-Hydroxymethylclavam; (3R,5S)-form, Formyl, 2-Hydroxymethylclavam; (3R,5S)-form, 5-(Hydroxymethyl)-1,2,3,4-cyclohexanetetrol; (1S,2S,3S,4S,5R)-form, 5-(Hydroxymethyl)-1,2,3-cyclohexanetriol; (1α,2α,3β,5β)-form, 5-(Hydroxymethyl)-1,2,3-cyclohexanetriol; (1α,2β,3β,5β)-form, 5-(Hydroxymethyl)-5-cyclohexene-1,2,3,4-tetrol; (1R*,2R*,3R*,4S*)-form, 1',4-Bis-O-(2-methylpropanoyl), 5-(Hydroxymethyl)-5-cyclohexene-1,2,3,4-tetrol; (1R*,2S*,3S*,4R*)-form, 1'-Ac, 5-(Hydroxymethyl)-5-cyclohexene-1,2,3,4-tetrol; (1S,2S,3S,4R)-form, 5-(Hydroxymethyl)-5-cyclohexene-1,2,3,4-tetrol; (1S,2S,3S,4R)-form, 1-O-(2-Methylpropanoyl), 5-(Hydroxymethyl)-5-cyclohexene-1,2,3,4-tetrol; (1S,2S,3S,4R)-form, 3-O-(2-Methylpropanoyl), 4-(Hydroxymethyl)-4-cyclopentene-1,2,3-triol; (1S,2S,3R)-form, 5'-Hydroxymethylcytomycin, 2-Hydroxy-6-(9-methyldecyl)benzoic acid, 5-[[[5-(Hydroxymethyl)-2-furanyl]methoxymethoxy]methyl]-2-furancarboxaldehyde, 5-[[[5-(Hydroxymethyl)-2-furanyl]methoxymethoxy]methyl]-2-furancarboxaldehyde; Homologue (n=2), 5-(6-Hydroxy-6-methylheptyl)-2(5H)-furanone; (S)-form, 5-Hydroxy-5-methyl-3-hexen-2-one; (ξ)-form, 4-Hydroxy-3-methyl-6-(1-methylpropyl)-2H-pyran-2-one; (S)-form, 3-Hydroxy-5-methyl-1-naphthalenecarboxylic acid; Me ether, amide, 3-Hydroxy-5-methyl-1-naphthalenecarboxylic acid; Me ether, [1-(aminocarbonyl)-2,3-epoxy-2-methylpropyl] ester (1S,2S-), 3-Hydroxy-5-methyl-1-naphthalenecarboxylic acid; Me ether, Me ester, 5-(6-Hydroxy-6-methyloctyl)-2(5H)-furanone; (5S,6'ξ)-form, 5-(6-Hydroxy-6-methyloctyl)-2(5H)-furanone; (5ξ,6'ξ)-form, 5-(7-Hydroxy-6-methyloctyl)-2(5H)-furanone; (5S,6'R,7'R)-form, 5-(7-Hydroxy-6-methyloctyl)-2(5H)-furanone; (5S,6'R,7'R)-form, 7'-Ketone, 5-(7-Hydroxy-6-methyloctyl)-2(5H)-furanone; (5S,6'R,7'R)-form, 6'ξ-Hydroxy, 5-(7-Hydroxy-6-methyloctyl)-2(5H)-furanone; (5S,6'R,7'R)-form, 6'ξ-Hydroxy, 7'-ketone, 5-(7-Hydroxy-6-methyloctyl)-2(5H)-furanone; (5S,6'R,7'S)-form, 4-(2-Hydroxy-5-methyl-4-oxo-5-octenyl)-2,6-piperidinedione, 4-Hydroxy-4-methyl-2-pentanone, 3-Hydroxy-3-(2-methylphenyl)propanoic acid; (±)-form, Amide, 2-(Hydroxymethyl)-3,4,5-piperidinetriol; (2R,3R,4R,5R)-form, 2-(Hydroxymethyl)-3,4,5-piperidinetriol; (2R,3R,4R,5S)-form, 2-(Hydroxymethyl)-3,4,5-piperidinetriol; (2R,3R,4R,5S)-form, N-Me, 4-(Hydroxymethyl)-2-(1-propenyl)-3-furancarboxylic acid; (E)-form, α-L-Rhamnopyranosyl ester, 4-Hydroxy-6-(1-methylpropyl)-3-(2-methylpropyl)-2H-pyran-2-one, 8-Hydroxy-2-methyl-4(1H)-quinazolinone, 2-Hydroxy-6-(9-methylundecyl)benzoic acid; (S)-form, 8-Hydroxy-3-mycarosylerythronolide B, 8-Hydroxy-3-mycarosylerythronolide B; 8-Deoxy, 8-Hydroxy-3-mycarosylerythronolide B; 8-Epimer, 8-deoxy, (4-Hydroxy-3-nitrophenyl)acetic acid, 3-(4-Hydroxy-3-nitrophenyl)propanoic acid, 4-Hydroxy-3-nitrosobenzaldehyde, 4-Hydroxy-3-nitrosobenzoic acid; Amide, 4-Hydroxy-3-nitrosobenzoic acid; Fe complex (2:1), N-(3-Hydroxy-1-oxocyclopent-2-en-2-yl)-3-(4-hydroxy-3-methoxyphenyl)propenamide, 1-(6-Hydroxy-4-oxo-4H-1-pyran-2-yl)-4,5,7-trihydroxy-2-methylanthraquinone, 7-[2-Hydroxy-5-oxo-4-[(2,4,6-trimethyl-1-oxo-2,4-decadienyl)amino]-7-oxabicyclo[4.1.0]hept-3-en-2-yl]-2,4,6-heptatrienoic acid, 4-Hydroxy-2-(1,3-pentadienyl)piperidine; (1'E,2R,3'E,4R)-form, 4-Hydroxy-2-(1,3-pentadienyl)piperidine; (1'E,2S,3'E,4R)-form, 4-Hydroxy-2-(1,3-pentadienyl)piperidine; (1'E,2S,3'E,4S)-form, 4-Hydroxy-2-(1,3-pentadienyl)piperidine; (1'E,2S,3'E,4S)-form, 4-Deoxy, 6-Hydroxy-1-phenazinecarboxylic acid; Me ether, Me ester, 6-Hydroxy-1-phenazinecarboxylic acid; 4-(Methylthio), O-α-L-rhamnopyranoside, 6-Hydroxy-1-phenazinecarboxylic acid; O-α-L-Rhamnopyranoside, 2-Hydroxy-1,6-phenazinedicarboxylic acid; 1'-Me ester, (4-Hydroxyphenyl)acetaldehyde; Oxime, 2-(2-Hydroxyphenyl)-4-benzoxazolecarboxylic acid, 2-(4-Hydroxyphenyl)ethenamine; (ξ)-form, N—Ac, N-[2-(4-Hydroxyphenyl)ethenyl]formamide; Me ether, 2-(2-Hydroxyphenyl)-5-methyl-4-thiazolemethanol, 2-(2-Hydroxyphenyl)-5-methyl-4-thiazolemethanol; 1"-Aldehyde, 2-(2-Hydroxyphenyl)-5-methyl-4-thiazolemethanol; 1"-Carboxylic acid, amide, 2-(2-Hydroxyphenyl)-5-methyl-4-thiazolemethanol; 4R*,5R*-Dihydro, 2-(2-Hydroxyphenyl)-5-methyl-4-thiazolemethanol; 4R*,5S*-Dihydro, 2-(2-Hydroxyphenyl)-4-thiazolecarboxylic acid; Amide, 2-(2-Hydroxyphenyl)-4-thiazolecarboxylic acid; 4R,5-Dihydro, alcohol, 2-(2-Hydroxyphenyl)-4-thiazolecarboxylic acid; 4ξ,5-Dihydro, amide, 4-Hydroxyphthalide; Me ether, 16-Hydroxypregnane-3,20-dione; (5β,16α)-form, 16-Hydroxypregn-4-ene-3,20-dione; 16α-form, 20-Hydroxypregn-4-en-3-one; (20R)-form, N-(4-Hydroxyprolyl)leucine, 3-(2-Hydroxypropyl)cyclohexanone; (2'R,3S)-form, 2-(2-Hydroxypropyl)-4-methylfuran; (ξ)-form, 6-Hydroxy-4H-pyrano[3,2-b]pyridine-4-methanol; 1'-Propanoyl, 6-O-β-D-glucopyranoside, 3-Hydroxy-2-quinolinecarboxylic acid, 8-Hydroxystreptazolone, 13-Hydroxy-2,4,9-tetradecatrienoic acid; (2E,4E,9E,13S)-form, 2-Hydroxy-6-(1,2,3,4-tetrahydro-2,5-dihydroxy-2-methyl-4-oxo-1-naphthalenyl)-4H-pyran-4-one, 2-Hydroxy-6-(1,2,3,4-tetrahydro-2,5-dihydroxy-2-methyl-4-oxo-1-naphthalenyl)-4H-pyran-4-one; 2'-Deoxy, 1',2'-didehydro, 10-Hydroxy-1,4,6,9-tetramethylpyrido[3,2-g]quinoline-2,8(1H,9H)-dione, 2-Hydroxy-6-(3,6,8-trihydroxy-1-methyl-2-naphthalenyl)-4H-pyran-4-one, 2-Hydroxy-6-(3,6,8-trihydroxy-1-methyl-2-naphthalenyl)-4H-pyran-4-one; 2-Et ether, 2-Hydroxy-6-(3,6,8-trihydroxy-1-methyl-2-naphthalenyl)-4H-pyran-4-one; 2-Me ether, 1-Hydroxy-2-valylamido-1-cyclobutaneacetic acid, 5-Hydroxy-3-vinyl-2(5H)-furanone, Hygrobafilomycin, Hygrocin A, Hygrocin B, Hygrolidin, Hygrolidin; Amide, Hygrolidin; Defumaroyl, Hygrolidin K2, Hygrolidin K2; 19-Me ether, Hygromycin A, Hygromycin A; 5"S-Alcohol, Hygromycin A; 5"S-Alcohol, 1,2-O-demethylene, Hygromycin A; 5"S-Alcohol, 1,2-O-demethylene, 1-Me ether, Hygromycin A; 1,2-O-Demethylene, Hygromycin A; 1,2-O-Demethylene, 1-Me ether, Hygromycin A; 1,4"-Diepimer, 1,2-demethylene, 1-Me ether, Hygromycin A; 4"-Epimer, Hygromycin A; 1-Epimer, 1,2-demethylene, 1-Me ether, Hygromycin B 7"-O-kinase, Hygroscopin A, Hygroscopin B, Hygrostatin, Iaquirin III, I 2190B, I 1001 C, Ichthyomycin A; Ichthyomycin A1, Ichthyomycin A; Ichthyomycin A2, Ichthyomycin A; Ichthyomycin A3, Ikarugamycin, Ikarugamycin; 4,5-Epoxide, Ikarugamycin; 26S-Methoxy, 4α,5α-epoxide, Ikarugamycin; 26R-Methoxy, 16ξ-hydroxy, 4β,5β-epoxide, Ikarugamycin; 26-Oxo, Ikarugamycin; 26-Oxo, 16R-hydroxy, Ikutamycin, Ilamycins, Ilamycins; Ilamycin A, Ilamycins; Ilamycin B1, Ilamycins; Ilamycin B2, Ilamycins; Ilamycin C2, Ileumycin, Imacidinic acid; Imacidinic acid C, Imacidinic acid; Imacidinic acid C, Lactone, Imbricin, N5-(1-Iminoethyl)ornithine; (S)-form, 2-Iminopiperidine, 1-Imino-2-propen-1-amine, Inarmycin, Incednine, Indanomycin, Indanomycin; 16-Deethyl Indanomycin; 8,9-Dihydro, Indanomycin; Homologue (R═CH2CH3), Indanomycin; Homologue (R═CH2CH3), 4-methyl, Indocarbazostatin, Indocarbazostatin; 8-Amino, Indocarbazostatin; 8-Amino, Me ester analogue, Indocarbazostatin; Me ester analogue, Indochrome A, Indolactam V, Indolactam V; O—Ac, Indolactam V; N-De-Me, Indolactam V; 7-(3,7-Dimethyl-2,6-octadienyl), Indolactam V; O-Malonoyl, 1H-Indole-3-carboxylic acid; α-L-Rhamnopyranosyl ester, 1H-Indole-5-carboxylic acid, Indolepyruvate C-methyltransferase, Indolizomycin, Indolmycin, N-[2-(1H-Indol-3-yl)-2-oxoethyl]acetamide, N-[2-(1H-Indol-3-yl)-2-oxoethyl]acetamide; 1'-Hydroxy, Indomycin aglycone; Glycoside (1), Indomycin aglycone; Glycoside (2), Indomycin aglycone; Glycoside (3), Indomycin aglycone; 14E,17Z-Isomer, Indomycin aglycone; 14E-Isomer, Indomycin aglycone; 17Z-Isomer, 14ξ,16ξ-dihydro, 16ξ-hydroxy, Indomycin aglycone; 17Z-Isomer, 14ξ,16ξ-epoxide, β-Indomycinone, β-Indomycinone; 17,18-Dihydro, 18-hydroxy, Indophenazine A, Indophenazine B, Indosespene, Indoxamycin A, Indoxamycin A; 10-Hydroxy, Indoxamycin A; 11-Hydroxy, Indoxamycin A; 3"-Hydroxy, Indoxamycin A; 4"-Hydroxy, Indoxamycin A; Δ7,11-Isomer, 6S-hydroxy, Inomycin, scyllo-Inosamine 4-kinase, scyllo-Inosamine-4-phosphate amidinotransferase, Inosamycin A, Inosamycin A; 6'-Deamino, 6'-hydroxy, Inosamycin A; 6'''-Deamino, 6'''-hydroxy, Inosamycin A; 5'''-Epimer, Inosamycin E, myo-Inosose 2, Inostamycin, Inostamycin; Decarboxy, Inostamycin B, Interleukin-1 receptor inhibitor 139A, Inthomycin; (4E,6E,8E)-form, Inthomycin; (4Z,6E,8E)-form, Inthomycin; (4Z,6E,8E)-form, 10-Hydroxy, Inthomycin; (4Z,6Z,8E)-form, Inthomycin; (4Z,6Z,8E)-form, 10ξ-Hydroxy (1), Inthomycin; (4Z,6Z,8E)-form, 10ξ-Hydroxy (2), Ionomycin, Ipomicin, Iromycin A, Iromycin A; 7'-Hydroxy, Iromycin C, Iromycin C; 7'ξ-Hydroxy, Irumamycin, Irumamycin; 3'-O-Decarbamoyl, Isemycin, Islamomycin A, ε-Isoactinorhodin, Isoaureomycin, Isoaureothin, Isoblasticidin S, 3-(2-Isocyanoethenyl)-1H-indole; (Z)-form, Isolasalocid A, Isoleucine; (2S,3S)-form, N—Ac, Isoleucylamiclenomycin, Isoleucylamicenomycylglutamic acid; Amide, Isoleucylamiclenomycylglutamic acid; NIle-Me, amide, Isoleucylamiclenomycylglutamic acid; NIle-Me, N2-Isoleucylarginine; L-L-form, Isoleucylisoleucylargininal; N—Ac, Isoleucylleucylargininal; N—Ac, Isomigrastatin, Isomigrastatin; O-De-Me, Isomigrastatin; Demethoxy, Isomigrastatin; Demethoxy, 16,17-didehydro, Isomigrastatin; Demethoxy, 17R-hydroxy, Isomigrastatin; 9-Deoxy, 17R-hydroxy, Isomigrastatin; 16,17-Didehydro, Isomigrastatin; 16,17-Didehydro, O-de-Me, Isomigrastatin; 17R-Hydroxy, Isomigrastatin; 17R-Hydroxy, O-de-Me, Isomitomycin A, γ-Isonaphthocyclinone, Isoneoantimycin, Isopenicillin-N synthase, Isoprekinamycin, 3-Isopropyl-6-methylene-2,5-piperazinedione; (S)-form, Isoquinocycline A, Isoquinocycline A; 2'-Epimer, 1"-ketone, Isoquinocycline A; 1"-Ketone, Isovalertatins, Isovalertatins; Isovalertatin M03, O-Deacyl, O-butanoyl, Isovalertatins; Isovalertatin M13, O-Deacyl, O-butanoyl, 4-Isoxazolecarboxylic acid, Iyomycin A, Iyomycin B, Izumiphenazine A, Izumiphenazine B, Izumiphenazine C, Izumiphenazine D, Jadomycin A, Jadomycin A; 6-O-(6-Deoxy-α-L-altro-hexopyranoside), Jadomycin A; 6-O-(2,6-Dideoxy-α-L-ribo-hexopyranoside), Jadomycin Ala, Jadomycin F, Jadomycin L, Jadomycin L; Aglycone, Jadomycin S, Jadomycin T, Jadomycin V, Janiemycin, JBIR 23, JBIR 23; O12-De-Me, JBIR 34, JBIR 34; 5-Demethyl, JBIR 56, JBIR 57, JBIR 58, JBIR 69, JBIR 73, JBIR 92, JBIR 93, JBIR 96, Jenamidine B, Jenamidine B; 7a-Deoxy, Jenamidine B; 4'-Deoxy, 6'-hydroxy, Jietacin A, Jietacin B, Jingsimycin, Josamycin S, Juglochroman A, Juglochroman B, Juglochroman C, Juglochroman C; Diastereoisomer, Juglocombin A, Juglomycin A, Juglomycin A; 2S,3-Dihydro, Juglomycin A; 4'-Epimer, Juglomycin A; 4'-Epimer, 3-methoxy, Juglomycin D; (S)-form, Juglomycin D; (S)-form, 3-Deoxy, Juglomycin D; (S)-form, 7-Ketone, Juglomycin D; (S)-form, 3-Deoxy, 2'-Ac, Juglomycin D; (S)-form, 3-Deoxy, 6-hydroxy, Juglomycin H, Juglomycin H; 1-Epimer, Juglomycin Z, Juglorescein, Juglorescein; 2,3-Dideoxy, 2,3-didehydro, Juglorin, Juglorin; Stereoisomer (?), Juglorubin, Julichrome Q1.1, Julichrome Q1.2, Julichrome Q1.3, Julichrome Q1.3; 4a,9a-Diepimer, Julichrome Q1.3; 9-Ketone, Julichrome Q1.5. Julichrome Q1.6, Julichrome Q1.9, Julichrome Q2.2, Julichrome Q2.2; Mono-O-de-Ac, ketone, Julichrome Q2.3, Julichrome Q2.3; 11"-O-De-Ac, 10',11"-diketone, Julichrome Q2.3; 11"-O-De-Ac, 11"-ketone, Julichrome Q3.3, Julichrome Q3.3; 9-Ketone, Julichrome Q3.8, Julichrome Q5.5, Julichrome Q5.6, Julichrome Q6; 8-O-β-D-Glucuronopyranoside, Julichrome Q6.6, Julichrome Q6.6; 10,10'-Dihydroxy, Juvenimicin B1; 3-Ac, Juvenimicin B1; 20-Aldehyde, 3-Ac, KA 107, Kabicidin, Kaimonolide B, Kakadumycin, Kalafungin; (+)-form, Kalafungin; (−)-form, Kanamine, Kanamine; 5-Deoxy, Kanamycin A, Kanamycin A; 5-Deoxy, Kanamycin B, Kanamycin B; N—Ac, Kanamycin B; 6"-O-Carbamoyl, Kanamycin B; 4'-O-α-D-Glucopyranosyl, Kanamycin C, Kanamycin C; 3'-Deoxy, Kanamycin C; 3'-Deoxy, 6"-carbamoyl, Kanamycin C; 2S-Hydroxy, Kapurimycin A; Kapurimycin A1, Kapurimycin A; Kapurimycin A2, Kapurimycin A; Kapurimycin A3, Karabemycin, Kasugamycin, Kendomycin, Kesarirhodin A, Kesarirhodin A; 3"-Deoxy, Ketoanhydrokinamycin, 4-Ketoanhydrotetracycline, 17-Keto-o-thaxtomin A, Kexstatin I, Kidamycin, Kidamycin; 4"-Ac, Kidamycin; 1"-Epimer, Kidamycin; 14S,16S-Epoxide, Kijanimicin; 3B—O-Deglycosyl, Kijanimicin; 32-Deoxy, 3B,4B-di-O-deglycosyl, Kijanimicin; 32-Deoxy, 3B—O-deglycosyl, Kikumycin A, Kikumycin A; 4R-Hydroxy, Kikumycin A; Pyrrolo-N-Me, Kinafluorenone, Kinamycin F, Kinamycin F; 2-Ac, Kinamycin F; 3-Ac, Kinamycin F; 4-Ac, Kinamycin F; 2,4-Di-Ac, Kinamycin F; 4-O-(2-Methylpropanoyl), Kinamycin F; 3-O-(2-Methylpropanoyl), 2,4-di-Ac, Kinamycin F; 4-Propanoyl, 2-Ac, Kinamycin F; 1,2,4-Tri-Ac, Kinamycin F; 2,3,4-Tri-Ac, Kinobscurinone, Kirigamycin A, Kirigamycin B, Kirigamycin C, Kitamycin A, Kitamycin B, KL 4, Kobenomycin, Kobutimycin A, Kobutimycin B, Kokubumycin, Komamycin A, Komamycin B, Kotomycin, Kromycin, KSB 8200W, Kudzuisoflavone A; 5,5'''-Dihydroxy, Kudzuisoflavone A; 5-Hydroxy, Kundrymycin, Kuranomycin, Kuwaitimycin, L 156373; (all-L)-form, L 156373; (all-L)-form, 1-(N-Hydroxy-L-leucine), 6-L-valine analogue, L 156373; (all-L)-form, 1-(N-Hydroxy-L-leucine), 6-L-isoleucine analogue, L 156373; (all-L)-form, 1-(N-Hydroxy-L-valine) analogue, L 156373; (all-L)-form, 1-(N-Hydroxy-L-leucine) analogue, L 156373; 1L,2D,3L,4D,5L,6D-form, L 174580, L 681176, Lactacystin, β-Lactamase inhibiting protein, β-Lactamase inhibitor 6001, β-Lactamase, Lactimidomycin, Lactimidomycin; 8,9-Dihydro, Lactimidomycin; 8,9-Dihydro, 8R-hydroxy, Lactimidomycin; 8,9-Dihydro, 8S-hydroxy, Lacto-N-biosidase, Lactomycin, Lactonamycin, Lactonamycin; 4'-Epimer, 3'β-hydroxy, Lagunamycin, Lajollamycin, Landomycin A, Landomycin A; 4A-Deglycosyl, Landomycin A; Aglycone, Landomycin A; 3B-Deglycosyl, Landomycin A; 5B-Epimer, 3B-deglycosyloxy, Landomycin A; 5B-Epimer, 11-deoxy, 3B-deglycosyloxy, Landomycin A; 4C-Deglycosyl, Landomycin A; 4D-Deglycosyl, Landomycin A; 3D-Deoxy, Landomycin A; 3D,11-Dideoxy, Landomycin A; 3D,11-Dideoxy, 3E-deglycosyl, Landomycin A; 11-Deoxy, Landomycin A; 11-Deoxy, 4A-deglycosyl, Landomycin A; 11-Deoxy, aglycone, Landomycin A; 11-Deoxy, 3B-deglycosyl, Landomycin A; 11-Deoxy, 4C-deglycosyl, Landomycin A; 11-Deoxy, 4D-deglycosyl, Landomycin A; 6-Deoxy, 5,6-didehydro, Landomycin A; 6-Deoxy, 5,6-didehydro, 3B-deglycosyl, Landomycin A; 6-Deoxy, 5,6-didehydro, 4C-deglycosyl, Landomycin A; 6-Deoxy, 5,6-didehydro, 3E-deglycosyl, Landomycin A; 11-Deoxy, 3E-deglycosyl, Landomycin A; 6,11-Dideoxy, 5,6-didehydro, Landomycin A; 6,11-Dideoxy, 5,6-didehydro, 3B-deglycosyl, Landomycin A; 6,11-Dideoxy, 5,6-didehydro, 4C-deglycosyl, Landomycin A; 6,11-Dideoxy, 5,6-didehydro, 3E-deglycosyl, Landomycin A; 3D,6,11-Trideoxy, 5,6-didehydro, Landomycin A; 3E-Deglycosyl, Landomycin A; 5E-Epimer, 11-deoxy, 3E-deglycosyloxy, Landomycin A; 5E-Epimer, 3E-deglycosyloxy, Lankacidinol, Lankacidinol; 14-Ac, Lankacidinol; 16-Epimer, Lankacidinol; 2'-Epimer, Lankacidinol; 2'-Epimer, 14-Ac, Lankacidinol; 9ξ-Hydroxy, 2'-ketone, Lankacidinol; 9ξ-Hydroxy, 2'-ketone, 14-Ac, Lankacidinol; 2'-Ketone, Lankacidinol; 2'-Ketone, 14-Ac, Lankacidin T, Lankacidin T; Stereoisomer, Lankacyclinol, Lankacyclinol; 12-Ac, Lankamycin, Lankamycin; 15-Ac, Lankamycin; 15-O-(4-O-Acetyl-2,6-dideoxy-3-C-methyl-α-L-xylo-hexopyranoside), Lankamycin; 4A-O-De-Ac, Lankamycin; 4A-O-De-Ac, 15-Ac, Lankamycin; 3A-Demethoxy, 2A,3A-didehydro, Lankamycin; Aglycone, 8-deoxy, O-de-Ac, Lankamycin; Aglycone, 15-ketone, Lankamycin; 3B—O-De-Me, Lankamycin; 15-Deoxy, Lankamycin; 8-Deoxy, Lankamycin; 8,15-Dideoxy, Lankamycin; 15-Ketone, Lankamycin; 15-Ketone, 4A-O-de-Ac, Lankamycin; 15-Ketone, 3-O-deglycosyl, Lanopylins, Lansai A, Lansai A; N1-Me, α-Lapachone; 3R-Chloro, 8-methoxy, 6-hydroxy, Lapstatin, Largomycin, Largomycin; Largomycin F-II, Lasalocid A, Lasalocid B, Lasalocid C, Lasalocid D, Lasalocid E, Laspartomycin, Lateriomycin A, Lateriomycin B, Lateriomycin F, Lathumycin, Lavanducyanin, Lavanducyanin; 2-Chloro, Lavanduquinocin; (R)-form, Lavendamycin, Lavendofuseomycin, Lavendomycin, Lavendustin A, Lavendustin A; 5'-Deoxy, Lebstatin, Lebstatin; 17-O-De-Me, Lebstatin; 17-Demethoxy, Leinamycin, Leinamycin K1, Leinamycin K1; 1'Z-Isomer, Leinamycin K3, Leinamycin K3; 1'Z-Isomer, Leinamycin K3; 1'Z-Isomer, 11'-ketone, Leinamycin K3; 11'-Ketone, Leinamycin M1, Leinamycin M2, Lemacidin, Lemonomycin, Lenticulone, Leprotene; 3,3'-Dihydroxy, Leprotene; 3-Hydroxy, Leptofuranin A, Leptofuranin A; 24-Aldehyde, Leptofuranin B, Leptofuranin B; 24-Aldehyde, Leptomycin A, Leptomycin A; 24-Alcohol, Leptomycin A; 21-Demethyl, Leptomycin A; 21-Demethyl, 1-alcohol, Leptomycin A; 21-Demethyl, 1-alcohol, 1-deoxy, Leptomycin A; 30-Hydroxy, Leptomycin B, Leptomycin B; 21-Demethyl, Leptomycin B; 21-Demethyl, 1-alcohol, 1-deoxy, Leptomycin B; 30-Hydroxy, Leucemomycin, Leucinamycin, Leucine N-acetyltransferase, Leucocidin, Leucomycin A12, Leucomycin A13, Leucomycin A14, Leucomycin A15, Leucomycin A2, Leucomycin B; Leucomycin B1, Leucomycin B; Leucomycin B2, Leucomycin B; Leucomycin B3, Leucomycin B; Leucomycin B4, Leucomycin V, Leucomycin V; 3-Ac, Leucomycin V; 4A-Deglycosyl, 9-ketone, 3-propanoyl, Leucomycin V; 4A-Deglycosyl, 3-propanoyl, Leucomycin V; 4B—Ac, Leucomycin V; 4B-Butanoyl, Leucomycin V; 4B-Butanoyl, 3-Ac, Leucomycin V; 4B-Butanoyl, 3-propanoyl, Leucomycin V; 3,4B-Di-Ac, Leucomycin V; 3,4B-Dipropanoyl, Leucomycin V; 4B-(3-Methylbutanoyl), Leucomycin V; 4B-(3-Methylbutanoyl), 3-Ac, Leucomycin V; 4B-(3-Methylbutanoyl), 3-butanoyl, Leucomycin V; 4B-(3-

Methylbutanoyl), 3-propanoyl, Leucomycin V; 4B-(2-Methylpropanoyl), 3-propanoyl, Leucomycin V; 4B-Propanoyl, Leucomycin V; 4B-Propanoyl, 3-Ac, Leucomycin V; 10,11-Dihydro, 9-ketone, 4B-(3-methylbutanoyl), Leucomycin V; 14ξ-Hydroxy, 3-propanoyl, Leucomycin V; 9-Ketone, 4B-butanoyl, Leucomycin V; 9-Ketone, 4B-butanoyl, 3-propanoyl, Leucomycin V; 9-Ketone, 4B-(3-methylbutanoyl), Leucomycin V; 9-Ketone, 4B-(3-methylbutanoyl), 3-Ac, Leucomycin V; 9-Ketone, 4B-(3-methylbutanoyl), 3-butanoyl, Leucomycin V; 9-Ketone, 4B-(3-methylbutanoyl), 3-propanoyl, Leucomycin V; 9-Ketone, 3,4-dipropanoyl, Leucomycin V; 3-Propanoyl, Leucomycin V; 3-Propanoyl, 4B—Ac, Leucoplastin, N2-Leucylarginine; L-L-form, Leucylisoleucylargininal; N—Ac, Leucylvalylargininal; N—Ac, Leupeptin Ac-LL, Leupeptin Pr-LL, Leustroducsin H; 18-O-(Cyclohexanecarbonyl), Leustroducsin H; 18-O-(3-Cyclohexanepropanoyl), Leustroducsin H; 18-Deoxy, Leustroducsin H; 18-O-(2-Methylbutanoyl), Leustroducsin H; 18-O-(3-Methylbutanoyl), Leustroducsin H; 18-O-(5-Methylheptanoyl), Leustroducsin H; 18-O-(4-Methylhexanoyl), Leustroducsin H; 18-O-(5-Methylhexanoyl), Leustroducsin H; 18-O-(6-Methyloctanoyl), Leustroducsin H; 18-O-(7-Methyloctanoyl), Leustroducsin H; 18-O-(4-Methylpentanoyl), Leustroducsin H; 18-O-(2-Methylpropanoyl), Leustroducsin H; 18-Octanoyl, Levanase, Levorin A1, Levorin A2, Levorin A2; 3ξ-Alcohol, Levorin A2; 11-Deoxy, Levorin A2; 32Z-Isomer, Levorin A2; 26E,28E-Isomer, 18-decarboxy, 18-methyl, 3ξ-alcohol, Levorin A2; 26E-Isomer, 18-decarboxy, 18-methyl, 9-deoxy, Levorin A4, Levorin B, Libanomycin A, Libanomycin B, Libanomycin C, Lidamycin, Lidimycin, Lienomycin, Limamycin A, Limamycin B, Limazepine F; Deoxy, Limocrocin, Lincomycin, Lincomycin; N-De-Me, N-Et, Lincomycin; S-De-Me, S-Et, Lincomycin; N-De-Me, Lincomycin; 1-De(methylthio), 1-hydroxy, Lincomycin; N,S-Di-de-Me, N,S-di-Et, Lincomycin; N,S-Di-de-Me, S-Et, Lincomycin; S-Oxide, Lincomycin B, Linearmycin A, Linearmycin B, *Streptomyces* Lipoglycopeptides, α-Lipomycin, α-Lipomycin; Aglycone, Lipopeptin A, Liposidolide A, Liposidomycin, Liposidomycin; Liposidomycin A-I, 3-O-Deacyl, desulfo, Liposidomycin; Liposidomycin A-I, 3-O-Deacyl, Liposidomycin; Liposidomycin A-I, Desulfo, Liposidomycin; Liposidomycin A-I, 13,14-Didehydro, desulfo, Liposidomycin; Liposidomycin A-I, 7,8,10,11-Tetrahydro, Liposidomycin; Liposidomycin A-I, 7,8,10,11-Tetrahydro, desulfo, Liposidomycin; Liposidomycin A-I, 10,11-Dihydro, Liposidomycin; Liposidomycin A-I, 10,11-Dihydro, desulfo, Liposidomycin; Liposidomycin B-I, Desulfo, Liposidomycin; Liposidomycin H-I, Desulfo, Liposidomycin; Liposidomycin K-I, Desulfo, Liposidomycin; Liposidomycin K-I, 12,13-Dihydro, Liposidomycin; Liposidomycin K-I, 12,13-Dihydro, desulfo, Liposidomycin; Liposidomycin L-I, Desulfo, Liposidomycin; Liposidomycin X-I, Desulfo, Liposidomycin; Liposidomycin Y-I, Desulfo, Liposidomycin; Liposidomycin Y-I, 8,9-Dihydro, Liposidomycin; Liposidomycin Y-I, 8,9-Dihydro, desulfo, Liposidomycin; Liposidomycin Y-I, 5,6,8,9-Tetrahydro, Liposidomycin; Liposidomycin Y-I, 5,6,8,9-Tetrahydro, desulfo, Liposidomycin; Liposidomycin Y-I, 5,6,8,9-Tetrahydro, 3-deacyl, Liposidomycin; Liposidomycin Y-I, 5,6,8,9-Tetrahydro, 3-deacyl, desulfo, Lipoxamycin, Lipoxamycin; 10'-Alcohol, Lipstatin, Litmocidin, *Lividans* exported protein, Lomofungin, Longestin, Longicatenamycin, *Longisporus* trypsin inhibitor, Lonomycin A, Lonomycin A; 23,27-Bis(demethoxy), 11-O-de-Me, Lonomycin A; 23-Demethoxy, Lonomycin A; 23-Demethoxy, 29-Me ether, Lonomycin A; 2-Demethyl, Lonomycin A; 3-Epimer. Lonomycin A; 2-Epimer, 23,27-bis(demethoxy), 11-O-de-Me, Lonomycin A; 28-Epimer, 23,27-bis(demethoxy), 11-Ode-Me, Lorneic acid A, Lorneic acid A; 1",2"-Dihydro, 1"ξ-hydroxy, Louisianin C, Louisianin C; 1-Hydroxy, Louisianin C; 1-Hydroxy, 5ξ-alcohol, Louisianin C; 1'ξ-Hydroxy, 2',3'-dihydro, Louisianin C; Δ1'-Isomer(E)-, Lucensimycin B, Lucensimycin B; 24-Deoxy, 23,24-didehydro, Lucensimycin C, Lucensimycin D, Lucensimycin D; 30-Amide, N30-[myo-inosityl-(1→1)-2-amino-2-deoxy-α-L-idopyranos-2-yl], Lucensimycin D; 23-Epimer, Lucensimycin D; 23-Epimer, 30-amide, N30-[myo-inosityl-(1→1)-2-amino-2-deoxy-α-L-idopyranos-2-yl], Lucensomycin, Lucknowmycin, Luisol A, Luisol A; 2R-Hydroxy, Luisol B, Luminacins, Luminacins; Antibiotic SI 42280D, Luminacins; Antibiotic SI 4228E, Luminacins; Antibiotic SI 4228E, 8-Deoxy, Luridin III, Lustericin, Lustromycin, Luteomycin, Luteoreticulin, Lydiamycin A, Lydiamycin A; 7,8-Didehydro, Lydiamycin A; 5R-Hydroxy, Lydiamycin A; 7'ξ-Hydroxy, Lydicamycin, Lydicamycin; 30-Demethyl, Lydicamycin; 30-Demethyl, 8-deoxy, Lydicamycin; 8-Deoxy, Lydicamycin; 8-Deoxy, 14,15-didehydro, Lymphomycin, Lymphosarcin, Lymphostin, Lyngbyatoxin A, Lyngbyatoxin A; 14-O-(2-Acetamido-2-deoxy-β-D-glucopyranoside), Lyngbyatoxin A; N-De-Me, Lyngbyatoxin A; 2,3α-Dihydro, 2-oxo, Lysine transaminases; L-Lysine 6-transaminase, Lysocellin, Lysocellin; Decarboxy, 2-methyl, 22-demethyl, Lysocellin; 22-Demethyl, Lysocellin; 4-Demethyl, 4α-ethyl, decarboxy, 5α-hydroxy, Lysocellin; 4-Demethyl, 4α-ethyl, 5α-hydroxy, Lysocellin; 22-Demethyl, 2S-methyl, Lysocellin; 2S-Methyl, Lysocellin; Stereoisomer, Lysolipin I, Lysolipin X, Lysopeptin A, Lysopeptin B, Lysotoxin, Lystatin, M 6672, Macrasidemycin, Macrocin O-methyltransferase, Macrolide 2'-kinase, Macromomycin, Macrostatin, Macrotetrolides, Macrotetrolides; Macrotetrolide B, Macrotetrolides; Macrotetrolide C, Macrotetrolides; Macrotetrolide D, Macrotetrolides; Macrotetrolide G, Macroviracins, Madindoline A, Madindoline A; 1'-Epimer, Maduramicin δ, Maduramicin δ; 2-Demethyl, 2R-hydroxy, Magnopeptin, Malayamycin A, Malayamycin A; O-De-Me, Maleimycin; (+)-form, Malioxamycin, Mallotusinic acid, Malolactomycin A, Malolactomycin A; Bis-N-de-Me, Malolactomycin A; O-Demalonyl, 27-malonyl, Malolactomycin A; N-De-Me, Malonomicin, Maltophilin, Maltophilin; 20α-Alcohol, Maltophilin; 30,31-Didehydro, Maltophilin; 18-Hydroxy, 30,31-didehydro, Maltotetraose, Maniwamycin B, Maniwamycin B; 2-Ketone, Mannokinase, Mannopeptimycin β, Mannopeptimycin β; 4"-O-[α-L-Mannopyranosyl-(1→4)-α-L-mannopyranoside], Mannopeptimycin β; 4"-O-[3-Methylbutanoyl-(→2)-α-L-mannopyranosyl-(1→4)-α-L-mannopyranoside], Mannopeptimycin β; 4"-O-[3-Methylbutanoyl-(→3)-α-L-mannopyranosyl-(1→4)-α-L-mannopyranoside], Mannopeptimycin β; 4"-O-[3-Methylbutanoyl-(→4)-α-L-mannopyranosyl-(1→4)-α-L-mannopyranoside], Mannopeptin A, Mannopeptin B, 2-O-α-D-Mannopyranosyl-myo-inositol, Mannosylglucosaminide, Mannosyl glycoprotein endo-β-N-acetylglucosaminidase, Mannosylparomomycin, Mannosylparomomycin; 3'-Deoxy, Mannosylparomomycin; 3'-Deoxy, 6'-phosphate, Mansoquinone, Mansouramycin A, Mansouramycin B, Mansouramycin B; Dechloro, Mansouramycin D, Manumycin A, Manumycin B, Manumycin B; Deepoxy, 5α-hydroxy, Manumycin C, Manumycin C; Deepoxy, 5R-hydroxy, Manumycin C; Deepoxy, 5R-hydroxy, 4'ξ,5'-dihydro, Manumycin D, Manumycin E, Manumycin E; Deepoxy, Manumycin G, Manumycin G; Deepoxy, 5R-hydroxy, Marcellomycin, Marcellomycin; 1-Deoxy, Marcellomycin; 1-Deoxy, 11-hydroxy, Maremycin A, Maremycin A; 3'-Epimer, Maremycin A; 3'-Epimer, S-oxide(R-), Maremycin A; 3'-Epimer, S-oxide(S-), Maremycin D1, Maremycin D1; 3'-Epimer, Maremycin E, Maremycin F, Marimycin, Marinamycin, Marine *Streptomyces* C30H38N2O5 lactam, Marineosin A, Marineosin A; 7,8-Diepimer, Marinopyrrole A, Marinopyrrole A; 4-Bromo, Marinopyrrole A; 5"-Bromo, Marinopyrrole A; 5"-Chloro, Marinopyrrole A; 5"-Chloro, Marinopyrrole F, Marmycin A, Marmycin A; 11-Chloro, Martinomycin, Matchamycin, Mayamycin, Maytansinol; N-De-Me, 3-Ac, Maytansinol; N-De-Me, 3-O-(3-methylbutanoyl), Maytansinol; N-De-Me, 3-O-(2-methylpropanoyl), Maytansinol; N-De-Me, 3-propanoyl, Maytansinol; 15R-Hydroxy, Maytansinol; 15S-Hydroxy, Maytansinol; 15R-Hydroxy, 3-Ac, Maytansinol; 15S-Hydroxy, 3-Ac, Maytansinol; 15R-Hydroxy, 3-O-(3-methylbutanoyl), Maytansinol; 15S-Hydroxy, 3-O-(3-methylbutanoyl), Maytansinol; 15R-Hydroxy, 3-O-(2-methylpropanoyl), Maytansinol; 15S-Hydroxy, 3-O-(2-methylpropanoyl), Maytansinol; 15R-Hydroxy, 3-propanoyl, Medermycin, Medermycin; 4a,10a-Epoxide, Medermycin; 6-Hydroxy, Medermycin; N-Oxide, Mediocidin, Megacidin, Meilingmycin, Melanomycin, Melanosporin, Melanostatin, Melastin, Meleagrin D; 4',5'-Dihydro, 5'-hydroxy, Memomycin, Menoxymycin B, Menoxymycin B; 4-Deoxy, 6-hydroxy, parent acid, Menoxymycin B; Parent acid, Mensacarcin, Meridamycin, Meridamycin; Pyrrolidine analogue, Meroparamycin, Mescengricin, Metacycloprodigiosin, *Streptomyces* Metalloprotease inhibitor, Metenaticin C, Metenaticin C; 15-O-(2,3,6-Trideoxy-β-L-threo-hexopyranoside), 2-Methoxyaniline; N—Ac, 7-Methoxycephalosporin C, 7-Methoxycephalosporin C; Deacetoxy, 7-Methoxycephalosporin C; O-De-Ac, 1-Methoxy-8-hydroxymethyl-3H-phenoxazin-3-one, 4-Methoxy-5-[(3-methoxy-5-pyrrol-2-yl-2H-pyrrol-2-ylidene)methyl]-2,2'-bipyrrole, 2-Methoxy-3-(1-methylpropyl)pyrazine, 2-(Methylamino)benzoic acid; N-(3-Phenylpropanoyl), Methyl 3-(4-aminomethoxyphosphoryloxy)phenyl-2-propenoate; (S,E)-form, 7-(Methylamino)-3H-pyrrolo[2,3-c]isoquinoline-6,9-dione, 2-Methylarginine; (S)-form, 3-Methyl-2H-azirine-2-carboxylic acid, α-Methylbiotin; (9ξ)-form, 3-Methylbutanoic acid; 6-Deoxy-α-L-talopyranosyl ester, 6-(3-Methyl-2-butenyl)-1H-indole, 5-(3-Methyl-2-butenyl)-1H-indole-3-carboxylic acid, 6-(3-Methyl-2-butenyl)-1H-indole-2,3-dione, 6-(3-Methyl-2-butenyl)-1-phenazinecarboxylic acid, 6-(3-Methyl-2-butenyl)-1-phenazinecarboxylic acid; 6-Deoxy-α-L-talopyranosyl ester, 6-(3-Methyl-2-butenyl)-1-phenazinecarboxylic acid; Δ1"-Isomer(E-), 3"-hydroxy, 9-(3-Methy-2-butenyl)-1-phenazinecarboxylic acid, 9-(3-Methyl-2-butenyl)-1-phenazinecarboxylic acid; 5,10-Dihydro, N5-Me, 4-(3-Methyl-2-butenyl)-1,6-phenazinediol; 10-Oxide, 1-Methyl-β-carboline, α-Methyldethiobiotin, 2-Methylene-3-oxocyclopentanecarboxylic acid; (R)-form, Methylenomycin A, Methylenomycin B, 1-(5-Methyl-3-furanyl)-1,2,3-propanetriol; (1R,2R)-form, Methyl geldanamycinate, 6-Methyl-5-hepten-2-one, 5-(6-Methylheptyl)-2(3H)-furanone; (ξ)-form, 5-(6-Methylheptyl)-2(5H)-furanone; (ξ)-form, 2-Methyl-3-hexene-2,5-diol; (3ξ,5ξ)-form, 7-(4-Methylhexyl)-2-oxepanone; (6R,10S)-form, 3-O-Methylmannose; D-form, 2-Methyl-8-(3-methyl-2-butenyl)-4-quinolinecarboxylic acid; 2',3'-Dihydro, 3'-methoxy, Me ester, 5-Methyl-3-(2-methylbutyl)-2(5H)-furanone; (2'S,5S)-form, 5-Methyl-3-(3-methylbutyl)-2(5H)-furanone, 5-Methyl-3-(5-methylheptyl)-2(5H)-furanone; (5S,5'S)-form, 5-Methyl-3-(4-methylheptyl)-2(5H)-furanone; (4'S,5S)-form, 5-Methyl-3-(5-methylhexyl)-2(5H)-furanone, 5-Methyl-3-(7-methylnonyl)-2(5H)-furanone; (5S,7'S)-form, 5-Methyl-3-(6-methyloctyl)-2(5H)-furanone; (5S,6'S)-form, 5-Methyl-3-(3-methylpentyl)-2(5H)-furanone; (3'S,5S)-form, 5-Methyl-3-(4-methylpentyl)-2(5H)-furanone, 4-(Methyl-aci-nitro) crotonic acid, 7-Methyl-2,4-octadienoic acid; (2E,4E)-form, Amide, 5-(6-Methyloctyl)-2(3H)-furanone; (ξ)-form, 5-(6-Methyloctyl)-2(5H)-furanone; (ξ)-form, (3-Methyloxiranyl) phosphonic acid; (2R,3S)-form, 2-Methyl-4-oxo-2H-1-benzopyran-5-acetic acid, 2-Methyl-4-oxo-2H-1-benzopyran-5-acetic acid; 2,3-Dihydro, 2-hydroxy, 2-Methyl-4-oxo-2H-1-benzopyran-5-acetic acid; Me ester, 8-Methyl-2H-oxocin-2-one, 2-Methyl-3-oxocyclopentanecarboxylic acid; (1R,2S)-form, N5-(5-Methyl-4-oxo-2-imidazolin-2-yl)ornithine; (2S,5'ξ)-form, 8-Methylpentadecanoic acid, 14-Methyl-9-pentadecenoic acid; (Z)-form, 5-(13-Methylpentadecyl)-1,3-benzenediol; Di-O-sulfate, 5-(13-Methylpentadecyl)-1,3-benzenediol; Mono-O-sulfate, 5-(14-Methylpentadecyl)-1,3-benzenediol; Di-O-sulfate, 5-Methyl-3-pentyl-2(5H)-furanone; (ξ)-form, 7-(4-Methylpentyl)-2-oxepanone; (R)-form, 5-(2-Methylphenyl)-5-oxopentanoic acid, 3-(2-Methylphenyl)-3-oxopropanamide, 5-(2-Methylphenyl)-4-pentenoic acid; (E)-form, 3-(2-Methylphenyl)-2-propenoic acid; (E)-form, Amide, 5-Methyl-3-propyl-2(5H)-furanone, N-(2-Methylpropyl)-3-(3-oxo-1-cyclopenten-1-yl)propanamide, 4-Methyl-1 H-pyrrole-2-carboxylic acid; N-Hydroxy, 2-carboxyethylamide, 9-Methylstreptimidone, 9-Methylstreptimidone; 8ξ,9ξ-Epoxide, 9-Methylstreptimidone; 5-Hydroxy, 9-Methylstreptimidone; 8E-Isomer, 9-Methylstreptimidone; Stereoisomer, 8,9-epoxide, 12-Methyl-1-tetradecylamine; (S)-form, 5-(13-Methyltetradecyl)-1,3-benzenediol, 5-(13-Methyltetradecyl)-1,3-benzenediol; Di-O-sulfate, 5-(13-Methyltetradecyl)-1,3-benzenediol; Mono-O-sulfate, 3-(Methylthio)-2-propenoic acid; (E)-form, 3-(Methylthio)-2-propenoic acid; (E)-form, Amide, 3-(Methylthio)propylamine, 11-Methyl-2-tridecanone; (ξ)-form, 12-Methyl-1-tridecylamine, N-Methyltyrosyl-N-methyltyrosylleucylalanine; L-L-L-form, Methymycin, Methymycin; Aglycone, Methymycin; Aglycone, 10-deoxy, Methymycin; 10-Deoxy, Mevashuntin, Mezzanomycin, MH 194-hF2, Miamycin, Michicarcin, Michigazone, Michigazone; 4-Demethoxy, Migrastatin, Miharamycin A, Miharamycin A; N3-Deoxy, Milbemycin α16, Milbemycin α17, Milbemycin β17, Milbemycin β17; 23-Deoxy, 22,23-didehydro, Milbemycin β17; 23-Ketone, Milbemycin α1, Milbemycin α1; 26-Hydroxy, Milbemycin α1; 23S-Hydroxy, 5-Me ether, Milbemycin α1; 26-Hydroxy, 5-Me ether, Milbemycin α1; 5-Ketone, Milbemycin α1; 5-Me ether, Milbemycin α1; 26-(3-Methylbutanoyloxy), Milbemycin α1; 26-(3-Methyl-2-butenoyloxy), Milbemycin α1; 26-(3-Methyl-2-pentenoyloxy), Milbemycin α1; 26-(Propanoyloxy), Milbemycin α1; 26-(2-Pyrrolylcarbonyloxy), Milbemycin α1; 26-(Tigloyloxy), Milbemycin β1, Milbemycin β1; 28-Deoxy, O-de-Me, Milbemycin β1; 6S-Hydroxy, Milbemycin β1; 6S-Hydroxy, 28-deoxy, O-de-Me, Milbemycin β20, Milbemycin β20; 23-Deoxy, 22,23-didehydro, Milbemycin β20; 23-Ketone, Milbemycin β21, Milbemycin β2, Milbemycin β2; 5-O-De-Me, Milbemycin β2; 28-Deoxy, Milbemycin β2; 28-Deoxy, 5-O-de-Me, Milbemycin β2; 28-Deoxy, 5-O-de-Me, 5-ketone, Milbemycin β2; 6S-Hydroxy, Milbemycin α3, Milbemycin α3; 7-Deoxy, 2,5,6,7-tetradehydro, Milbemycin α3; 23S-Hydroxy, Milbemycin α3; 26-Hydroxy, Milbemycin α3; 23S-Hydroxy, 5-ketone, Milbemycin α3; 26-Hydroxy, 5-Me ether, Milbemycin α3; 5-Ketone, Milbemycin α3; 5-Me ether, Milbemycin α3; 26-(3-Methylbutanoyloxy), Milbemycin α3; 26-(3-Methyl-2-butenoyloxy), Milbemycin α3; 26-(Propanoyloxy), Milbemycin α3; 26-(2-

Pyrrolecarbonyloxy), Milbemycin α3; 26-(Tigloyloxy), Milbemycin β3, Milbemycin β3; Homologue (R=CH2CH3), 28-hydroxy, Milbemycin β3; 28-Hydroxy, Milbemycin D, Milbemycin D; O5-Me, Milbemycin D; 26-O-(2-Pyrrolecarbonyloxy), Milbemycin E, Milbemycin E; 28-Deoxy, O-de-Me, 5-ketone, Milbemycin IV, Milbemycin IV; 7-Deoxy, 2,5,6,7-tetradehydro, Milbemycin IV; 22α,28-Dihydroxy, O5-Me, Milbemycin IV; 6,22α-Dihydroxy, O5-Me, Milbemycin IV; 28-Hydroxy, 5-ketone, Milbemycin IV; 23α-Hydroxy, O5-Me, Milbemycin IV; 5-Ketone, Milbemycin IV; 28-Oxo, Milbemycin IV; 28-Oxo, 5-ketone, Milbemycin IV; 6,23α,27-Trihydroxy, O5-Me, Mimocin, Mimosamycin, Miniatomycin, Minomycin, Miromycin, Misionin, Mithramycin, Mithramycin; 6-O-Deglycosyl, Mithramycin SA, Mithramycin SK, Mithramycin SK; 3D-O-Deglycosyl, Mithramycin SK; 2'-Ketone, Mitiromycin A, Mitocromin, Mitomalcin, Mitomycin A, Mitomycin A; 8,15-Didehydro, 1-N-Me, de(carbamoyloxy), Mitomycin A; 8-Epimer, O7-de-Me, 1-N-Me, Mitomycin A; 8-Epimer, 1-N-Me, Mitomycin A; 1-N-Me, Mitomycin A; Stereoisomer, Mitomycin C, Mitomycin C; O-De-Me, N-Me, Mitomycin C; N-Me, Mitomycin C; Stereoisomer, Mitomycin G, Mitomycin H, Mocimycin, Mocimycin; 3'-Deoxy, N-Me, Mocimycin; 5,6-Dihydro, Mocimycin; N-Me, Moenocinol, Moenomycin, Moenomycin; Moenomycin C1, Moenomycin; Moenomycin C3, Moenomycin; Moenomycin C4, Moenomycin; Moenomycin C4, 6C-Hydroxy, Moldcidin A, Moldicidin, Momofulvenone A, Momofulvenone A; 4-Ac, Monamidocin, Monamycins, Monensin, Monensin; Monensin A, 3-O-De-Me, Monensin; Monensin A, 26-Deoxy, Monensin; Monensin A, 26-O-[(2-Phenylethyl)carbamoyl], Monensin; Monensin A, 26-O-β-D-Glucopyranoside, Monensin; Monensin A, 2-Demethyl, Monensin; Monensin B, Monensin; Monensin B, 3-O-De-Me, Monensin; Monensin B, 26-O-[(2-Phenylethyl)carbamoyl], Monensin; Monensin B, 26-Deoxy, Monensin; Monensin B, 2-Demethyl, Monensin; Monensin C, Monensin; Monensin D, Monilin, Monoketoorganomycin, Monopodialysin, Morimycin, Moromycin A, Moromycin A; 3-O-Deglycosyl, Moroyamycin, Moroyamycin; Moroyamycin B, Moyukamycin, Mucopeptin, Mucopeptin; Mucopeptin A, Mucopeptin; Mucopeptin B, Mucopeptin; Mucopeptin C, Mumbaistatin, Munumbicins, Muramoylpentapeptide carboxypeptidase, Murayaanthraquinone, Murayalactone, Murayaquinone, Muraymycin A; Muraymycin A1, Muraymycin A; Muraymycin A1, 13'''-N-Deoxy, Muraymycin A; Muraymycin A1, 2A-O-De-Me, Muraymycin A; Muraymycin A1, 3-O-Deglycosyl, Muraymycin A; Muraymycin A2, Muraymycin C1, Muraymycin C1; 2A-O-De-Me, Muraymycin C1; 2A-O-De-Me, 3''-O-(6-methylheptanoyl), Muraymycin C1; 2A-O-De-Me, 3''-O-(7-methyloctanoyl), Muraymycin C1; 2A-Demethoxy, Muraymycin C1; 2A-Demethoxy, 3''-deoxy, Muraymycin C1; 3-O-Deglycosyl, Muraymycin C1; 3''-Deoxy, Muraymycin C1; 3''-Deoxy, 2A-O-de-Me, Muraymycin C1; 3''-O-(6-Methylheptanoyl), Muraymycin C1; 3''-O-(8-Methylnonanoyl), Muraymycin C1; 3''-O-(6-Methyloctanoyl), Muraymycin C1; 3''-O-(7-Methyloctanoyl), Mureidomycin A, Mureidomycin A; 5'',6''-Dihydro, Mureidomycin A; N13-Glycyl, Mureidomycin A; N13-Glycyl, 5'',6''-dihydro, Mureidomycin E, Mureidomycin E; 8'-Deoxy, 6'-hydroxy, Mureidomycin E; 8'-Deoxy, 6'-hydroxy, 5'',6''-dihydro, Musacin B1, Musacin B1; 3-Epimer, Musacin C, Musacin H, Musacin H; Δ5'-Isomer, 6'-deoxy, 4'-hydroxy, Musacin I, Musacin I; Stereoisomer, Musacin K, Musashimycin, Musettamycin, Musettamycin; 1-Deoxy, Musettamycin; 1-Deoxy, 11-hydroxy, Mutactimycin A, Mutactimycin A; 3A-O-De-Me, Mutactimycin A; De(glycosyloxy), Mutactimycin A; Di-O-de-Me, Mutactimycin A; 14-Hydroxy, Mutactimycin C, Mutactimycin C; 11-Deoxy, Mutactimycin E; 5A-Demethyl, stereoisomer, Mutactin, MY 336a, Mycangimycin, 9-C-Mycarosylpremithramycinone, 9-C-Mycarosylpremithramycinone; O-De-Me, Mycelin, Mycelin IMO, Mycocidin, Mycodextranase, Mycomycetin, Mycopentene, Mycospocidin, Mycothiol, Mycothiol bimane, Mycothricin, Mycotrienol II, Mycotrienol II; 23-Deoxy, 13-O-[[2-(cyclohexanecarbonyl)amino]propanoyl], Mycotrienol II; 20,23-Quinone, N 61, NA 23063A, NADH peroxidase, NAD(P)(+) nucleosidase, Nagstatin, Nairomycin, Nanaomycin A; (−)-form, Nanaomycin A; (−)-form, Me ester, Nanaomycin A; (−)-form, Amide, Nanaomycin A; (−)-form, 2'-Alcohol, Nanaomycin A; (−)-form, 4a,10a-Dihydro, Nanaomycin A; (−)-form, 4aα,10aα-Epoxide, Me ester, Nanaomycin A; (−)-form, 4aα,10aα-Epoxide, 2'-alcohol, Nanaomycin A; (−)-form, 4aα,10aα-Epoxide, Nanaomycin B, Nanaomycin B; Me ester, Nanhumycin, Naphterpin, Naphterpin B, Naphterpin B; 2-Epimer, Naphthablin, Naphthablin; 3-O-Deacyl, 3-Ac, Naphthablin; 3-De(acyloxy), 1,2-didehydro, 1,3,6,8-Naphthalenetetrol, Naphthgeranine A, Naphthgeranine D, Naphthgeranine D; 4-Deoxy, Naphthgeranine D; 3,4-Dideoxy, Naphthgeranine E, Naphthgeranine F; (ξ)-form, β-Naphthocyclinone chlorohydrin, β-Naphthocyclinone epoxide, α-Naphthocyclinone, α-Naphthocyclinone; Parent acid, β-Naphthocyclinone, γ-Naphthocyclinone, δ-Naphthocyclinone, ε-Naphthocyclinone, Naphthomevalin, Naphthomycin A, Naphthomycin A; Dechloro, Naphthomycin A; Dechloro, 30-[(2-acetamidoethyl)thio], Naphthomycin A; Dechloro, 11-alcohol, Naphthomycin A; Dechloro, 30-hydroxy, Naphthomycin B, Naphthomycin B; Dechloro, Naphthomycin B; Dechloro, 30,37-dihydroxy, Naphthomycin B; Dechloro, 30-hydroxy, Naphthomycin B; Dechloro, 30-methoxy, Naphthomycin B; Dechloro, 30-(methylthio), Naphthomycin B; (4Z,6E)-Isomer, Naphthomycin B; (4Z,6E)-Isomer, dechloro, 30-amino, Naphthomycin B; (4Z,6E)-Isomer, dechloro, 30-hydroxy, Naphthomycin I, Naphthomycin I; Me ester, Naphthomycin I; Stereoisomer (?), Naphthomycin J, Naphthomycin J; Decarboxy, Naphthomycin J; (4Z,6E)-Isomer, Naphthomycin J; Me ester, Naphthomycin K, Naphthopyranomycin, Naphthostatin A, Naphthostatin A; 44-Epimer, Naphthostatin C, Naphthyridinomycin, Naphthyridinomycin B, Napsamycin B, Napsamycin B; 5'',6''-Dihydro, Napyradiomycin A1, Napyradiomycin A1; 18-Hydroxy, Napyradiomycin A1; Δ17-Isomer, 16R-hydroxy, Napyradiomycin A1; Δ17-Isomer, 16S-hydroxy, Napyradiomycin A1; Δ17-Isomer, 16-oxo, Napyradiomycin A1; 18-Oxo, Napyradiomycin B1, Napyradiomycin C1, Napyradiomycin C1; Δ17(19)-Isomer, 16ξ-hydroxy, Napyradiomycin SR, Narangomycin, Narasin A, Narasin A; 20-Deoxy, Narasin A; 17-Epimer, 20-deoxy, Narasin A; 20-Ketone, Narasin D, Narbosine A, Narbosine A; Me glycoside, Naseseazine A, Naseseazine B, Neaumycin, Nebramycin factor 3, Nebramycin factor 3; 3'-Deoxy, Nebularine, Negamycin; (3R,5R)-form, Negamycin; (3R,5R)-form, 6-N-Leucyl, Negamycin; (3R,5S)-form, 5-Deoxy, Negamycin; (3R,5S)-form, 5-Deoxy, 3-N-leucyl, Nemadectin α2, Nemadectin α2; 6-Deoxy, O5-Me, *Streptomyces microflavus* Nemadectin, Nemadectin ε, Nemadectin θ, Nemadectin ι, Neoantimycin, Neocarazostatin A, Neocarazostatin A; 1'-Deoxy, Neocarazostatin A; 1'-Me ether, Neocarzinostatin, Neocarzinostatin; 83[Aspartic acid] analogue, Neocid, Neoenactin; Neoenactin A, Neoenactin; Neoenactin A, 10'-Alcohol, Neoenactin; Neoenactin B1, Neoenactin; Neoenactin B1, 15'-Hydroxy, Neoenactin; Neoenactin B2, Neoenactin; Neoenactin B2, 15'-Hydroxy, Neoheptaene, Neohumidin, Neoindanomycin, Neomethymycin, Neomethymycin; Aglycone, Neomethymycin; 10-Hydroxy, Neomycin A, Neomycin A; 3'-Deoxy, Neomycin A; 4'-Deoxy, Neomycin B, Neomycin B; 6'''-Deamino, 6'''-hydroxy, Neomycin B; N-Diphosphate, Neomycin B; 5'''-Epimer, Neomycin B; 5'''-Epimer, 6'''-deamino, 6'''-hydroxy, Neomycin B; 5'''-Epimer, N-diphosphate, Neomycin B; N-β-D-Glucopyranoside, Neomycin G, Neomycin K, Neooxazolomycin, Neopentaene, Neopentalenoketolactone, Neopentalenolactone D, Neopeptin, Neopeptin; Neopeptin A, Neopeptin; Neopeptin B, Neopyrrolomycin, Neopyrrolomycin; 4'-Chloro, Neopyrrolomycin; 3-Dechloro, 4'-chloro, Neopyrrolomycin; 4-Dechloro, 4'-chloro, Neosidomycin, Neotelomycin, Neothramycin A, Neothramycin A; 3-Epimer, Neothricin, Neoviridogrisein III, Neoviridogrisein III; 4Pro-Deoxy, Neoviridogrisein MP, Netropsin, Neutramycin, Neutramycin; 5-O-Deglycosyl, Neutramycin; 5-O-Deglycosyl, 3''-O-de-Me, Neutramycin; 3'-O-De-Me, Neutramycin; 8-Deoxy, 3'-O-de-Me, Neutramycin; 8-Deoxy, 3',3''-di-O-de-Me, Neutramycin; 3',3''-Di-O-de-Me, NFAT 133, NFAT 68, Nigericin, Nigericin; 30-Ac, Nigericin; 30-Ac, Me ester, Nigericin; 30-Deoxy, Nigericin; 28-Epimer, Nigericin; 28-Epimer, 30-deoxy, Nigericin; 29-Me ether, 30-Ac, Me ester, Nigericin; Stereoisomer(?), Nigericin; Stereoisomer (?), 30-Ac, Nigericin; Stereoisomer(?), 29-deoxy, 30-aldehyde, Nigrifactin, Nigrofungin, Nikkomycin B, Nikkomycin Bx, Nikkomycin C, Nikkomycin Cx, Nikkomycin I, Nikkomycin J, Nikkomycin JH, Nikkomycin JH; 1''-Deoxy, Nikkomycin Kx, Nikkomycin Kx; 5''-Hydroxy, Nikkomycin Kz, Nikkomycin Kz; 5''-Hydroxy, Nikkomycin M, Nikkomycin N, Nikkomycin pseudo-J, Nikkomycin pseudo-Z, Nikkomycin PX, Nikkomycin Qx, Nikkomycin Qz, Nikkomycin RZ, Nikkomycin Sox, Nikkomycin Sox; 6-Deoxy, Nikkomycin Soz, Nikkomycin Soz; 6-Deoxy, Nikkomycin Wx, Nikkomycin Wz, Nikkomycin X, Nikkomycin X; 4-Carboxylic acid, Nikkomycin X; 5'''-Deoxy, Nikkomycin Z, Nikkomycin Z; 5'''-Deoxy, Nikkomycin ZH, Nikkomycin ZT, Nilemycin, Ningnanmycin, Niphimycin; Niphimycin A1, Niphimycin; Niphimycin A2, Niphimycin; Niphimycin B1, Niphimycin; Niphimycin B2, Niphimycin; Niphimycin II, Niphimycin; Niphimycin Iα, Niphimycin; Niphimycin Iα, 18(or 19)-O-Malonyl, Niphimycin; Niphimycin Iα, O-Demalonyl, Niphimycin; Niphimycin Iα, 19-O-Malonyl, Niphimycin; Niphimycin Iα, 4,5-Dihydro, Niphimycin; Niphimycin Iα, Imino-N-Me, Niphimycin; Niphimycin Iβ, Niphithricin B, Nisamycin, Nitracidomycin A, Nitracidomycin B, 4-(2-Nitroethenyl)-1,2-benzenediol; (E)-form, 4-(2-Nitroethyl)-1,2-benzenediol, N-Nitroglycine, 2-Nitroimidazole, Nitropeptin, 3-Nitropropanoic acid, Nitrosofungin, Nitrosoxacin A, Nitrosoxacin B, Nitrosoxacin C, Nitrosporin, 2-Nitro-4-(3,7,11-trimethyl-2,6,10-dodecatrienyl)-1H-pyrrole; 2',3'-Dihydro, 3'R-chloro, 2'R-hydroxy, 2-Nitro-4-(3,7,11-trimethyl-2,6,10-dodecatrienyl)-1H-pyrrole; 2',3'-Dihydro, 2'R,3'S-dihydroxy, 2-Nitro-4-(3,7,11-trimethyl-2,6,10-dodecatrienyl)-1H-pyrrole; 2'R,3'R-Epoxide, 2-Nitro-4-(3,7,11-trimethyl-2,6,10-dodecatrienyl)-1H-pyrrole; Δ3'-Isomer(E-), 2'R-hydroxy, 2-Nitro-4-(3,7,11-trimethyl-2,6,10-dodecatrienyl)-1H-pyrrole; 2',3',10',11'-Tetrahydro, 3'R-chloro, 2'R,10'R,11'-trihydroxy, 2-Nitro-4-(3,7,11-trimethyl-2,6,10-dodecatrienyl)-1H-pyrrole; 2',3',10',11'-Tetrahydro, 11'-methoxy, 2'S,3'ξ,10'R-trihydroxy, 2-Nitro-4-(3,7,11-trimethyl-2,6,10-dodecatrienyl)-1H-pyrrole; 2',3',10',11'-Tetrahydro, 2'S,3'ξ,10'R,11'-tetrahydroxy, 4-Nitrotryptophan; (S)-form, 4-Nitrotryptophan; (S)-form, N-Me, 4-Nitrotryptophan; (S)-form, N—Ac, NK 175203, Nobilamide C, Nobilamie D, Nobilamide F, Nobilamide F; N5-(1R-Methyl-2-oxopropyl), Nobilamide F; N5-(1S-Methyl-2-oxopropyl), Noboritomycin A, Noboritomycin A; 6-Chloro, Noboritomycin B, Nocardamine, Nocardamine; N6-Deoxy, Nocardicin A; 3'-Chloro, Nogalamycin, Nonactic acid, Nonactic acid trimer, Nonactic acid trimer; Homologue (R1=CH3, R2=CH2CH3), Nonactic acid trimer; Homologue (R1=R2=CH2CH3), Nonactic-trihomononactic cyclic lactone, Nonactin, Nonactin; Homologue (R1=CH2CH3, R2=R3=R4=CH3), Nonactin; Homologue (R1=R2=CH2CH3, R3=R4=CH3), Nonactin; Homologue (R1=R4=CH2CH3, R2=R3=CH3), Nonactin; Homologue (R1=R2=R3=CH2CH3, R4=CH3), Nonactin; Homologue (R2=R3=R4=CH2CH3, R1=CH3), Nonactin; Homologue (R1=R2=R3=R4=CH2CH3), Nonactyl nonactoate, 1,3,9,15,21,27,33,39-Nonatriacontaneoctacarboxylic acid, Nongkang 101-F, 15-Norerythromycin A; 3''-O-De-Me, Northienamycin, Nosiheptide, Nosokomycin C, Nosokomycin C; 6''''-Amide, Nosokomycin C; 6''''-Amide, 6''-O-β-D-glucopyranosyl, Nosokomycin C; 6''-O-β-D-Glucopyranosyl, Notonesomycin A, Novobiocin, Novobiocin; Aglycone, Δ3'''-isomer, 2'''ξ-hydroxy, Novobiocin; 3''-O-Decarbamoyl, 2''-O-carbamoyl, Novobiocin; O-Decarbamoyl, Novobiocin; 6''-Demethyl, Novobiocin; 8-Demethyl, Novobiocin; Δ3'''-Isomer, 2'''ξ-hydroxy, Novomycin, NS Antibiotic complex, Nucleocidin, Nucleotide diphosphokinase, Nursimycin, Nybomycin, Nybomycin; Deoxy, Nybomycin; 1'-Hydroxy, Nystatin, Nystatin; Nystatin A1, 10-Deoxy, 35-O-(2,6-dideoxy-L-ribo-hexopyranoside), Nystatin; Nystatin A1, 10-Deoxy, Nystatin; Nystatin A1, 35-O-(2,6-Dideoxy-3-C-methyl-α-L-ribo-hexopyranoside), Nystatin; Nystatin A1, 28,29-Didehydro, Nystatin; Nystatin A1, 28,29-Didehydro, 35-O-(2,6-dideoxy-3-C-methyl-α-L-ribo-hexopyranoside), Nystatin; Nystatin A1, 10-Deoxy, 35-O-(2,6-dideoxy-3-C-methyl-α-L-ribo-hexopyranoside), Nystatin; Nystatin A1, 10-Deoxy, 28,29-didehydro, Nystatin; Nystatin A1, 10-Deoxy, 19-deglycosyl, Nystatin; Nystatin A1, 28,29-Didehydro, hexaene homologue, Nystatin; Nystatin A1, 28,29-Didehydro, hexaene homologue, 10-deoxy, 19-deglycosyl, Nystatin; Nystatin A1, 28,29-Didehydro, hexaene homologue, 19-deglycosyl, Nystatin; Nystatin A1, 28,29-Didehydro, octaene homologue, Nystatin; Nystatin A1, 28,29-Didehydro, octaene homologue, 37-O-(2,6-dideoxy-3-C-methyl-α-L-ribo-hexopyranoside), Nystatin; Nystatin A1, 28,29-Didehydro, octaene homologue, 10-deoxy, 37-O-(2,6-dideoxy-3-C-methyl-α-L-ribo-hexopyranoside), Nystatin; Nystatin A1, 28,29-Didehydro, 7-ketone, 35-O-(2,6-dideoxy-L-erythro-hexos-3-ulopyranoside), Nystatin; Nystatin A1, 28,29-Didehydro, 5-ketone, Nystatin; Nystatin A1, 28,29-Didehydro, 7-ketone, Nystatin B, Oasomycin A, Oasomycin A; 46ξ-Alcohol (lactol), Oasomycin A; 46ξ-Alcohol (lactol), 22-O-α-D-mannopyranoside, Obelmycin G, Obelmycin G; 1-Deoxy, Obscurolide A3, Obscurolide A3; 1''-Aldehyde, Obscurolide A3; 1''-Carboxylic acid, Obscurolide A3; 1''-Me ether, Obscurolide B3, Obscurolide B3; 7'-Aldehyde, Obscurolide B3; 5-Epimer, 7'-aldehyde, Obscurolide B3; T-Me ether, Obscurolide C2α, Obscurolide C2α; 7-Epimer, Obscurolide D2, Ochromycinone; (S)-form, Ochromycinone; (S)-form, Me ether, Ochromycinone; (S)-form, 5,6-Dihydro, Ochromycinone; (S)-form, 13-Hydroxy, 11-Octadecenoic acid; (E)-form, Octalactin B, Octalactin B; 10β,11β-Epoxide, Octavalinomycin, Octosyl acid B, Octosyl acid B; 5-Carboxylic acid, Octosyl acid B; 5-Carboxylic acid, 5-ketone, Oganomycin D2, Oganomycin E, Oganomycin E; O-(4-Hydroxycinnamoyl), Oganomycin E; O-(4-Sulfooxycinnamoyl), Oganomycin F, Oganomycin G, Oganomycin GF, Oganomycin GG, Oganomycin GH, Oganomycin GI, Oganomycin H, Oganomycin I, Okaspirodiol, Okilactomycin, Okilactomycin; 9α,22-Dihydro, 22-hydroxy, Okilactomycin; 9α,22-Dihydro, 22-hydroxy, 22-O-(2ξ,3-dihydroxypropyl), Okilactomycin C, Okilactomycin D, Oleandomycin, Oleandomycin; 3'-O-De-Me, Oleandomycin; 11-Deoxy, 10,11-didehydro, Oleandomycin; 6-Hydroxy, 12-Oleanene-3,21,22,24-tetrol; (3β,21β,22β)-form, 22-O-α-L-Arabinopyranoside, 12-Oleanene-3,22,24-triol; (3β,22β)-form, Oleficin, Oligomycin A, Oligomycin A; 26-Demethyl, Oligomycin A; 10-Demethyl, 7-alcohol, Oligomycin A; 26-Demethyl, 12-deoxy, Oligomycin A; 10-Demethyl, 12-deoxy, 7-alcohol, Oligomycin A; 12-Deoxy, Oligomycin A; 21R-Hydroxy, Oligomycin A; 34-Methyl, Oligomycin A; 28-Oxo, Oligomycin A; 28-Oxo, 263-hydroxy, Oligostatin; Oligostatin C, Oligostatin; Oligostatin D, Oligostatin; Oligostatin E, Olimycin, Olivomycin A, Olivomycin A; 4A-De-Ac, Olivomycin A; 4B—O-De-Me, Olivomycin A; 4B—O-De-Me, 4E-deacyl, 4E-Ac, Olivomycin A; 3D-O-Deglycosyl, Olivomycin A; 4E-Deacyl, 4E-Ac, 9-C-Olivosylpremithramycinone, 9-C-Olivosylpremithramycinone; 4A-(2,6-Dideoxy-β-D-arabino-hexopyranosyl), 9-C-Olivosylpremithramycinone; O4-De-Me, Olivovariin; (ξ)-form, Onomycin I, Onomycin II, Orbuticin, Oridamycin A, Oridamycin A; 4-Epimer, Oridamycin A; 4-Epimer, 5-hydroxy, Oridamycin A; 4-Epimer, Me ester, Oridamycin A; 17-Hydroxy, Orinocin, Oryzoxymycin, Ossamycin, Ossamycin; Aglycone, Ossamycin; Aglycone, 19-deoxy, 18,19-didehydro, Ossamycin; 19-Deoxy, 18,19-didehydro, Ossamycin; 28-Methyl, Ossamycin; 28-Methyl, de(glycosyloxy), Ossamycin; 28-Methyl, de(glycosyloxy), 4-deoxy, Ossamycin; 28-Methyl, de(glycosyloxy), 19-deoxy, 18,19-epoxide, Ossamycin; 28-Methyl, 19-deoxy, 18,19-didehydro, Ossamycin; 28-Methyl, 19-Me ether, Ostreogrycin A, Ostreogrycin A; Deoxy, 14,15-didehydro, 14ξ,15ξ-epoxide, Ostreogrycin A; Deoxy, 14,15-didehydro, 14ξ,15ξ-epoxide, Ostreogrycin A; Deoxy, 14,15-didehydro, 14ξ,15ξ-epoxide, 16-alcohol, Ostreogrycin A; 26,27S-Dihydro, Ostreogrycin B, Ostreogrycin B; N-De-Me, Ostreogrycin B; 5pip-Hydroxy, Oxachelin, Oxamicetin, Oxanosine, Oxanthromicin; 3-O-α-D-Galactopyranoside, Oxanthromicin; 3-O-[α-D-Galactopyranosyl-(1→4)-α-D-galactopyranoside], Oxaunomycin, Oxaunomycin; 10-Deoxy, Oxaunomycin; 6-Deoxy, Oxaunomycin; 10-Deoxy, aglycone, Oxaunomycin; 11-Deoxy, N,N-di-Me, Oxaunomycin; 10-Deoxy, 1-hydroxy, Oxaunomycin; 10-Deoxy, 4-Me ether, Oxaunomycin; 10,11-Dideoxy, Oxaunomycin; 10,11-Dideoxy, N,N-di-Me, Oxaunomycin; 10,11-Dideoxy, 4-Me ether, Oxaunomycin; N,N-Di-Me, Oxaunomycin; 10-Epimer, Oxaunomycin; 10-Epimer, 11-deoxy, Oxaunomycin; 1-Hydroxy, Oxaunomycin; 1-Hydroxy, N,N-di-Me, Oxazinomycin, Oxazolomycin, Oxazolomycin; 13',16-Dimethyl, Oxazolomycin; 4'E,6'E-Isomer, Oxazolomycin; 6E-Isomer, Oxazolomycin; 16R-Methyl, Oxazolomycin; 16S-Methyl, Oxazolomycin; 16R-Methyl, 6'E-isomer, Oxazolomycin; 13'-Methyl, 16-(methoxymethyl), 3-(5-Oxazolyl)-1H-indole, 3-(5-Oxazolyl)-1H-indole; 4'-Chloro, 8-Oxocoformycin reductase, α-Oxo-3-cyclohexene-1-acetic acid; (R)-form, α-Oxo-3-cyclohexene-1-acetic acid; (R)-form, α-Alcohol, 9-Oxo-2,4,5,7-decatetraenoic acid, Oxohygrolidin, 4-Oxo-2-nonenoic acid; (E)-form, 7-Oxo-4-oxa-1-azabicyclo[3.2.0]heptane-3-carboxylic acid; (3R,5S)-form, 2-Oxo-3-phosphonopropanoic acid, Oxopropaline D; (R)-form, Oxopropaline D; (R)-form, 2'-O-α-L-Rhamnopyranoside, Oxopropaline D; (R)-form, 3'-O-α-L-Rhamnopyranoside, Oxopropaline D; (R)-form, 2'-Deoxy, Oxopropaline D; (R)-form, 2'-Deoxy, 3-O-α-L-rhamnopyranoside, 4-Oxo-2-propyl-4H-benzopyran-5-acetic acid, Oxytetracycline, Oxytetracycline; 7-Chloro, Oxytetracycline; N-De-Me, N-Et, Ozemycin A, Ozemycin B, Ozemycin C, Pacidamycin 1, Pacidamycin 2, Pacidamycin 3, Pacidamycin 4, Pacidamycin 5, Pacidamycin 6, Pacidamycin 7, Pacidamycin D, Pacidamycin 4N, Pacidamycin 5T, Pactamycate, Pactamycate; 8"-Hydroxy, Pactamycin, Pactamycin; 7-Deoxy, Pactamycin; 5"-Fluoro, Pactamycin; 8"-Hydroxy, Pactamycin; 2'-Me ether, Padanamide B, Paim, Paldimycin; Paldimycin A, Paldimycin; Paldimycin A2, Paldimycin; Paldimycin B, Paldimycin; Paldimycin B2, Pamamycin, Pamamycin; Pamamycin 593, Pamamycin; Pamamycin 607, Pamamycin; Pamamycin 607, N-De-Me, Pamamycin; Pamamycin 663, Pamamycin; Pamamycin 677, Pamamycin; Pamamycin 691, Pamamycin; Pamamycin 705, Pamamycin; Pamamycin 621A, Pamamycin; Pamamycin 621A, Homologue, Pamamycin; Pamamycin 635A, Pamamycin; Pamamycin 635A, Homologue, Pamamycin; Pamamycin 649A, Pamamycin; Pamamycin 593B, Pamamycin; Pamamycin 621B, Pamamycin; Pamamycin 635B, Pamamycin; Pamamycin 649B, Pamamycin; Pamamycin 621C, Pamamycin; Pamamycin 635C, Pamamycin; Pamamycin 621D, Pamamycin; Pamamycin 635D, Pamamycin; Pamamycin 635E, Pamamycin; Pamamycin 635F, Panclicins, Panglimycin D, Panglimycin D; 4-Deoxy, Pantomycin, Parimycin, Paromamine, Paromamine; 3'-Deoxy, Paromomycin, Paromomycin; 1-N—Ac, Paromomycin; 6'''-Deamino, 6'''-hydroxy, Paromomycin; 3'-Deoxy, Paromomycin; 6-Deoxy, Paromomycin; 5'''-Epimer, Paromomycin; 5'''-Epimer, 6'''-deamino, 6'''-hydroxy, Paromomycin; 5'''-Epimer, 6-deoxy, Partricin A, Partricin A; N-De-Me, Me ester, Partricin A, N-De-Me, Partricin A, 7-Deoxy, 5-alcohol, Partricin A; 7-Deoxy, 5-alcohol, N-de-Me, Partricin A; Me ester, Partricin C, Parvulomycin, Paulomycin A, Paulomycin A; 6'-O-De-Ac, 6'-propanoyl, Paulomycin A; 4'-O-Deacyl, Paulomycin A; 3"-O-De-Me, Paulomycin A2, Paulomycin B, Paulomycin B; 4'-O-Deacyl, Paulomycin B; 3"-O-De-Me, Paulomycin C. Paulomycin D, Paulomycin E, Paulomycin E; 3"-Epimer, Paulomycin F, Paulomycin F; 3"-Epimer, PD 125375, Pectinatone; (Z)-Isomer, Peliomycin, Penicillin N, Penicillin N; 3-De-α-methyl, Penicillin N; 3-De-α-methyl, 5'-epimer, Penicillin N; 5'-Epimer, Penicillin N; 5'-Epimer, 5'-N—Ac, 5-Pentadecyl-1,3-benzenediol, 5-Pentadecyl-1,3-benzenediol; Di-O-sulfate, 5-Pentadecyl-1,3-benzenediol; Mono-O-sulfate, Pentaene G8, Pentaene I, Pentafungin, 2,3',4,4',5-Pentahydroxy-7,9':7',9-diepoxylignan; (7S,7'S,8R,8'R)-form, 4,5-Methylene, 3'-Me ether, 1,3,5,7,10-Pentahydroxy-1,9-dimethyl-2H-benzo[cd]pyrene-2,6(1H)-dione, 2',3',4',5,7-Pentahydroxyisoflavone; 3'-Me ether, 3',4',5,6,7-Pentahydroxyisoflavone; 4',6-Di-Me ether, 3',4',5,7,8-Pentahydroxyisoflavone, 3',4',5,7,8-Pentahydroxyisoflavone; 4',8-Di-Me ether, 3',4',6,7,8-Pentahydroxyisoflavone; 4',6,7-Tri-Me ether, 2,3,5,7,10-Pentahydroxy-9-methyl-6H-benzo[cd]pyren-6-one, 1,3,10,11,12-Pentahydroxy-2-naphthacenecarboxamide, Pentalenene, Pentalenic acid, Pentalenic acid; 1-Deoxy, Pentalenic acid; 1-Deoxy, β-D-glucopyranosyl ester, Pentalenolactone, Pentalenolactone A, Pentalenolactone B, Pentalenolactone D, Pentalenolactone E, Pentalenolactone F, Pentalenolactone F; 9-Epimer, Pentalenolactone F; 1α-Hydroxy, Pentalenolactone F; 1-Oxo, Pentalenolactone I, Pentalenolactone O, Pentalenolactone P, Pentopyranine A, Pentopyranine A; 4'-Epimer, Pentopyranine C, Pentopyranine C; 4'-Epimer, Pentostatin, 2-Pentylpyridine, Pepstanone A, Pepstanone A; N1-Deacyl, N1-hexanoyl, Pepstanone A; N1-Deacyl, N1-(4-methylpentanoyl), Pepstatins; Pepsidin A, Pepstatins; Pepstatin A, Pepstatins; Pepstatin A, Me ester, Pepstatins; Pepstatin A, Hydroxy, Pepstatins; Pepstatin AC, Pepstatins; Pepstatin B, Pepstatins; Pepstatin BU, Pepstatins; Pepstatin C, Pepstatins; Pepstatin D, Pepstatins; Pepstatin E, Pepstatins; Pepstatin F, Pepstatins; Pepstatin G, Pepstatins; Pepstatin H, Pepstatins; Pepstatin I, Pepstatins; Pepstatin J, Pepstatins; Pepstatin PR, Pepthiomycin, Pepticinnamin, Peptide AN 2, Peptide P3A, Peptimycin, Perimycin A, Perlimycin, Perlolyrine, Persipeptide A, Persipeptide B, PF 6766, Phaeochromycin A, Phaeochromycin B, Phaeochromycin C, Phaeochromycin D, Phaeochromycin E, Phaeochromycin F, Phaeochromycin G, Phaeochromycin H, Phagomycin, Phalamycin, Phebestin, Pheganomycin, Pheganomycin D, Pheganomycin D; 1′1-Deoxy, Pheganomycin DGPT, Pheganomycin DR, Phenalinolactone A, Phenalinolactone A; 1-Deoxy, Phenalinolactone A; 6′-Methoxy, Phenalinolactone B, Phenamide; (S)-form, Phenatic acid A, Phenatic acid B, 1-Phenazinecarboxylic acid, 1-Phenazinecarboxylic acid; 5,10-Dihydro, carboxymethyl ester, 1-Phenazinecarboxylic acid; Me ester, 1,6-Phenazinedicarboxylic acid, 1,6-Phenazinedicarboxylic acid; 5,10-Dihydro, di-Me ester, 1,6-Phenazinedicarboxylic acid; Mono-Me ester, 1,6-Phenazinedicarboxylic acid; Mono-α-L-rhamnopyranosyl ester, 1,6-Phenazinediol, 1,6-Phenazinediol; Di-Me ether, 1,6-Phenazinediol; 5,10-Dioxide, 1,6-Phenazinediol; Mono-Me ether, 1,6-Phenazinediol; 5-Oxide, 1,2,6-Phenazinetriol; Tri-Me ether, 1-Phenazinol, 1-Phenazinol; Me ether, 1-Phenazinol; (Methoxycarbonylmethyl) ether, Phenazinoline A, Phenazinoline A; 11-Deoxy, Phenazinoline C, Phenazinoline D, Phenazinoline D; 6,11-Dideoxy, 9,14-dihydroxy, Phenazinomycin, Phenazostatin A, Phenazostatin B, Phenazostatin C, Phenelfamycin, Phenelfamycin; Phenelfamycin C, 23-De(phenylacetoxy), Phenelfamycin; Phenelfamycin C, 21-Epimer, 23-de(phenylacetoxy), Phenelfamycin; Phenelfamycin C, O-De-(phenylacetyl), Phenelfamycin; Phenelfamycin E, Phenelfamycin; Phenelfamycin E, 23-De(phenylacetoxy), Phenelfamycin; Phenelfamycin E, 21-Epimer, 23-de(phenylacetoxy), Phenelfamycin; Phenelfamycin E, O-De(phenylacetyl), Phenelfamycin; Phenelfamycin E, 31-Hydroxy, Phenelfamycin; Phenelfamycin F, Phenelfamycin; Phenelfamycin F, 31-Hydroxy, Phenocyclinone, Phenomycin, Phenylacetic acid, Phenylacetic acid; Amide, Phenylacetic acid; (6-Deoxy-α-L-talopyranosyl) ester, Phenylacetic acid; α-L-Rhamnopyranosyl ester, N-(Phenylacetyl)-2-butenediamide; (E)-form, Phenylalanylisoleucylargininal; NPhe-(3-Methylbutanoyl), 4-Phenyl-3-butenoic acid; (E)-form, 2-Phenylethylamine, 2-Phenylethylamine; N—Ac, 2-Phenylethylamine; N-(13-Methyltetradecanoyl), N-(2-Phenylethyl)carbamic acid; Butyl ester, N-Phenyl-1-naphthylamine, N-Phenyl-2-naphthylamine, 4-Phenyl-3-(2-pyridinyl)-2-buten-1-ol; (E)-form, Phepropeptin A, Phepropeptin A; 3-L-Isoleucine analogue, Phepropeptin A; 1-L-Phenylalanine analogue, Phepropeptin A; 1-L-Phenylalanine, 3-L-isoleucine analogue, Phosmidosine, Phosmidosine; O-De-Me, 1″-N-Me, Phosmidosine; O-De-Me, Phosmidosine; N-Deprolyl, Phosmidosine; 1″-N-Me, Phosphazomycin A, N-(Phosphinothricylalanylalanyl) phosphinothrcin, Phosphinothricylalanyl-2-aminobutanoic acid, Phosphinothricylalanylglycine, Phosphinothricylalanylserine, Phosphinothricylalanylvaline, Phosphinothricylglycylalanine, *Streptomyces* Phospholipase C inhibitor, Phospholipase D, N5-Phosphomethionine sulfoximine; (S,S)-form, N-Phosphomethionine S-sulfoximinylalanylalanine, Phosphophenylalanylarginine; L-L-form, Phostriecin, Phycomycin, Phyllomycin, Physostigmine, Physostigmine; N8-De-Me, Physostigmine; N1-De-Me, N1-Ac, Physostigmine; N1,N8-Di-de-Me, N1-Ac, Phytoactin, Phytophthoradiene, Phytostreptin, PI 201, PI 201; Lactone, PI 220, Piceamycin, Piceamycin; 2,3-Dihydro, N-acetylcysteine adduct (R=—SCH2CH(NHAc)COOH), Picromycin, Picromycin; 12-Deoxy, Picromycin; 12-Deoxy, aglycone, Picromycin; 12-Deoxy, 14R-hydroxy, Picromycin; 10,11-Dihydro, Picromycin; 14R-Hydroxy, Piericidin; Antibiotic IT143A, Piericidin; Antibiotic IT143A, 11S*,12S*-Epoxide, Piericidin; Antibiotic IT 143B, Piericidin; Antibiotic IT 143B, 5-Demethoxy, Piericidin; Antibiotic IT 143B, 11S*, 12S*-Epoxide, Piericidin; Piericidin A1, Piericidin; Piericidin A1, 11′,12′-Epoxide, Piericidin; Piericidin A1, 10′-Me ether, 11′,12′-epoxide, Piericidin; Piericidin A1, 4-O-D-Glucopyranoside, Piericidin; Piericidin A1, 10′-O-β-D-Glucopyranoside, Piericidin; Piericidin A1, 13′-Hydroxy, 10′-O-β-D-glucopyranoside, Piericidin; Piericidin A1, 4-O-L-Rhamnopyranoside, Piericidin; Piericidin A1, 4-O-(6-Deoxy-β-D-talopyranoside), Piericidin; Piericidin A1, 5-Demethoxy, Piericidin; Piericidin A1, O5-De-Me, Piericidin; Piericidin A1, 5-Demethoxy, 10′-O-β-D-glucopyranoside, Piericidin; Piericidin A2, Piericidin; Piericidin A2, 11′,12′-Epoxide, Piericidin; Piericidin A2, 10′-Me ether, 11′,12′-epoxide, Piericidin; Piericidin A3, Piericidin; Piericidin A3, 11′,12′-Epoxide, Piericidin; Piericidin A3, 10′-Me ether, 11′,12′-epoxide, Piericidin; Piericidin A3, 5-Demethoxy, Piericidin; Piericidin A4, Piericidin; Piericidin A4, 11′,12′-Epoxide, Piericidin; Piericidin A4, 10′-Me ether, 11′,12′-epoxide, Piericidin; Piericidin A5, 10′-Me ether, N-oxide, Piericidin; Piericidin A5, 11′R*,12′R*-Epoxide, Piericidinol A1; 3-Epimer, 10-O-β-D-glucopyranoside, Piericidinol A1; 10-O-β-D-Glucopyranoside, Pillaromycin A, Pillaromycin B1, Pillaromycin B2, Pillaromycin C, Pillarose; L-form, Piloquinone, Piloquinone; 4-Hydroxy, Pilosamycin, 9(11),15-Pimaradien-3-ol; (ent-3β,8α)-form, O-Carbamoyl, 9(11),15-Pimaradien-3-ol; (ent-3β,8α)-form, O-(2-Amino-2-oxoacetyl), 9(11),15-Pimaradien-3-ol; (ent-3β,8α)-form, O-(2-Hydroxyamino-2-oxoacetyl), 9(11),15-Pimaradien-3-ol; (ent-3β,8α)-form, O-[2-(Acetylhydroxyamino)-2-oxoacetyl], 9(11),15-Pimaradien-3-ol; (ent-3β,8α)-form, O—[N-[(2-Hydroxyethyl)aminocarbonyl] carbamoyl], 9(11),15-Pimaradien-3-ol; (ent-3β,8α)-form, 3-Ketone, Pimaricin, Pimaricin; Amide, Pimaricin; Deepoxy, 4,5-didehydro, Pinoresinol; (+)-form, Pinoresinol; (+)-form, 7′-Epimer, Piperastatin A, Piperastatin B, Piperazimycin A, Piperazimycin A; 8-Deoxy, Piperazimycin C, Pironetin, Pironetin; O-De-Me, Pitucamycin, Placetin, Pladienolide A, Pladienolide A; 7-Ac, Pladienolide A; 6-Deoxy, 7-Ac, Pladienolide A; 16ξ-Hydroxy, Pladienolide A; 20ξ-Hydroxy, Pladienolide A; 16ξ-Hydroxy, 7-Ac, Pladienolide A; 20ξ-Hydroxy, 7-Ac, Pladienolide A; 17-Hydroxy, 21-Me ether, 7-Ac, Pladienolide A; 21-Ketone, 7-Ac, Plasminostreptin, Platencin, Platencin; 15,16-Dihydro, 15R,16-dihydroxy, Platencin; 15,16-Dihydro, 15R-hydroxy, Platencin; 12S-Hydroxy, Platencin; 13R-Hydroxy, Platencin; 14S-Hydroxy, Platencin; 13R-Hydroxy, Me ester, Platencin; Methylthio ester analogue, 13R-hydroxy, 5′-O-β-D-glucopyranoside, Platencin A4, Platencin A4; 13R-Hydroxy, Platencin A4; 14S-Hydroxy, Platencin A7, Platencin A8, Platencinic acid; 2,3-Dihydroxypropyl ester, Platencinic acid; 12R-Hydroxy, Platencinic acid; 13R-Hydroxy, Platenocidin, Platenomycin A2, Platenomycin A2; 4B—O-Deacyl, 4B-propanoyl, Platenomycin W3, Platensimide A, Platensimide A; 14β-Hydroxy, 1-parent acid, Platensimide A; 14β-Hydroxy, 1-parent acid, Me ester, Platensimide A; 1-Parent acid, Platensimide A; 1-Parent acid, Me ester, Platensimycin, Platensimycin; Amide, Platensimycin; Decarboxy, Platensimycin; 6,7-Dihydro, 7β-hydroxy, Platensimycin; 5′-O-β-D-Glucopyranoside, Platensimycin; 12-Hydroxy, Platensimycin; 13β-Hydroxy, Platensimycin; 14β-Hydroxy, Platensimycin; 17-Hydroxy, Platensimycin;

14β-Hydroxy, Me ester, Platensimycin; Me ester, Platensimycin A5, Platensimycin B2, Pleomycin, Plicacetin, Plicacetin; N-De-Me, Plicacetin; 3'β-Hydroxy, Plicacetin; 3'β-Hydroxy, 4"-N-Me, Plumbemycin A, Plumbemycin A; 3'-Amide, Pluracidomycin A1, Pluracidomycin A2, Pluracidomycin B, Pluracidomycin C2, Pluracidomycin C3, Pluracidomycin D, Plurallin, Pluramycin B, PM 050463, PM 050463; 10'-O-β-D-Glucopyranoside, PM 060054, PM 060054; 10'-O-β-D-Glucopyranoside, Polyketoacidomycin, Polyketomycin, Polyketomycin; 4B-Debenzoyl, Polyketomycin; 3'''-Demethyl, Polyketomycin; 6-Demethyl, Polyketomycin IP3, ε-Polylysine, Polyoxin A, Polyoxin A; 5-Carboxylic acid, Polyoxin A; 5-De(hydroxymethyl), Polyoxin A; 5-Deoxy, Polyoxin B, Polyoxin B; 5-Carboxylic acid, Polyoxin B; 5-De(hydroxymethyl) Polyoxin B; 5-De(hydroxymethyl), 5-fluoro, Polyoxin B; 5-De(hydroxymethyl), 5-fluoro, 3"-deoxy, Polyoxin B; 5-De(hydroxymethyl), 5-methyl, Polyoxin B; 3"-Deoxy, Polyoxin B; 3"-Deoxy, 5-carboxylic acid, Polyoxin C, Polyoxin I, Polyoxin N, Polyoxin O, Polyoxypeptin A, Polyoxypeptin A; 4"-Deoxy, Polyribonucleotide nucleotidyltransferase, Porothramycin A, Porothramycin A; Me ether, Poststatin, Practomycin C, Prasinomycin, Prasinon A, Prasinon B, Prechrysophanol; (R)-form, 8-O-β-D-Glucuronopyranoside, Prefluostatin, Prejadomycin-2-carboxylic acid, Prekinamycin, Prelasalocid, Prelasalocid; 18β, 19β:22β,23β-Diepoxide, Premithramycin B, Premithramycin B; 3A-O-Deglycosyl, Premithramycin B; 3C,8-Di-O-deglycosyl, Premithramycin B; 3D,8-Di-O-deglycosyl, Premithramycin B; 3D,8-Di-O-deglycosyl, 4C-ketone, Premithramycin B; 8-O-Deglycosyl, Premithramycin B; 9-Demethyl, 3C,8-di-O-deglycosyl, Premithramycin B; 9-Demethyl, 3D,8-di-O-deglycosyl, Premithramycin B; 9-Demethyl, 3D,8-di-O-deglycosyl, 4C-ketone, Premithramycin B; 9-Demethyl, 8-O-deglycosyl, Premithramycinone, Premithramycinone; O-De-Me, Premithramycinone G, Premithramycinone H, Prenomycin, 3-Prenyltyrosine; (S)-form, 3-Prenyltyrosine; (S)-form, N—Ac, Primycin, Pristinamycin IC, Pristinamycin IC; N4'-De-Me, Probestin, Proceomycin, Procidin S 346, Procidin S 735, Proclavaminate amidinohydrolase, Proclavaminic acid, Prodigiosin, Prodigiosin R1, Promoinducin, Promothiocin A, Promothiocin B, Prostatin, Protactin, *Streptomyces chromofuscus* Protease inhibitor, *Streptomyces lividans* Protease inhibitor, Protein AN 1, Protetrone, Prothracarcin; (S)-form, Protocidin, Protostreptovaricin I, Protostreptovaricin I; O10-De-Me, Protostreptovaricin I; 14α-Hydroxy, Protostreptovaricin I; 14α-Hydroxy, 19-Me ether, Protostreptovaricin I; 19-Me ether, Protylonolide, Protylonolide; 5-O-(3,6-Dideoxy-3-dimethylamino-β-D-glucopyranoside), Protylonolide; 5-O-(2,6-Dideoxy-3-C-methyl-L-ribo-hexopyranoside), Protylonolide; 19ξ-Hydroxy, Protylonolide; 23-Hydroxy, Prumycin, Prunacetin A, Pseudostreptomycin, Pseudouridine C; 1-Me, Pseudoverticin, Psicofuranine, Pteridic acid A, Pteridic acid A; 6-Epimer, Pteridine 2096A, Pteridine 2096A; Stereoisomer, Pterocidin, Pulvomycin, 6-Purinol; 1,9-Dihydro-form, 9-β-D-Ribopyranosyl, Puromycin, Pyocyanine, Pyoluteorin; Deoxy, Pyracrimycin A; (E)-form, Pyracrimycin A; (E)-form, 1,2-Dihydro, Pyracrimycin B; (Z)-form, Pyrazinol; NH-form, 4-Oxide, Pyrazomycin; α-D-form, Pyrazomycin; β-D-form, Pyridazomycin, Pyridazomycin; 4-Parent acid, Pyridindolol; (R)-form, Pyridindolol; (R)-form, 14-O-β-D-Glucopyranoside, Pyridindolol; (R)-form, 15-O-β-D-Glucopyranoside, Pyridindolol; (R)-form, 16-O-β-D-Glucopyranoside, Pyridindolol; (R)-form, 16-Ac, Pyridindolol; (R)-form, 15,16-Di-Ac, 4-Pyridinecarboxylic acid; 2R-Methylheptyl ester, Pyridinopyrone A, Pyridinopyrone B, Pyridinopyrone C, Pyridomycin, Pyridomycin; 2',3'-Dihydro, 3'ξ-hydroxy, Pyrimidine-5'-nucleotide nucleosidase, Pyrimido[5,4-e]-1,2,4-triazine-5,7-diol; 6,8-Di-Me, Pyrimido[5,4-e]-1,2,4-triazine-3,5,7-triol; 2,6,8-Tri-Me, Pyrindicine; (q)-form, Pyrizinostatin, Pyrroindomycin A, Pyrroindomycin A; 5'-Chloro, 1H-Pyrrole-2-carboxylic acid, 1H-Pyrrole-2-carboxylic acid; (6-Deoxy-α-L-talopyranosyl) ester, 1H-Pyrrole-2-carboxylic acid; α-L-Rhamnopyranosyl ester, 1H-Pyrrole-3-propanoic acid; Amide, Pyrrolomycin B, Pyrrolomycin C, Pyrrolomycin C; 4-Chloro, Me ether, Pyrrolomycin C; Me ether, Pyrrolomycin G, Pyrrolomycin G; 2-Me ether, Pyrrolosine, 3-(1H-Pyrrol-3-yl)-2-propenoic acid; (E)-form, 3-(1H-Pyrrol-3-yl)-2-propenoic acid; (E)-form, Amide, Pyrromycin, Pyrromycin; 1-Deoxy, N-de-Me, Pyrromycin; 1-Deoxy, N,N-di-de-Me, Pyrromycin; 1-Deoxy, N,N-di-de-Me, parent acid, Pyrromycin; 1-Deoxy, 11-hydroxy, Pyrromycin; 1-Deoxy, 11-hydroxy, N,N-di-de-Me, Pyrromycin; 1-Deoxy, 11-hydroxy, N,N-di-de-Me, parent acid, Pyrromycin; 1-Deoxy, 11-hydroxy, 4-Me ether, Pyrromycin; 1-Deoxy, 4-Me ether, N,N-di-de-Me, Pyrromycin; 1-Deoxy, 4-Me ether, N,N-di-de-Me, parent acid, Pyrromycin; 7,9-Diepimer, Pyrromycin; 7-Epimer, Pyrromycin; 9-Epimer, η1-Pyrromycinone, η1-Pyrromycinone; 10-Deoxy, η1-Pyrromycinone; 10-Deoxy, 3,4-dihydro, ε-Pyrromycinone, ε-Pyrromycinone; 4-Deoxy, Pyrronamycin A, Pyrronamycin A; 7'-N-Hydroxy, Pyrroxamycin, Q 18627, Q 6402A, Q 6402A; Homologue (n=4), Qingfengcin, Qingjingmycin A, 4,8-Quinazolinediol, 2,4,8-Quinazolinetriol, Quinocarcin, Quinocarcinol, Quinomycin A, Quinomycin A; 7-S-Oxide, Quinomycin C, Quinomycin D, Quinomycin E, Quinomycin X, Quinquamycin, Racemomycin O, Rachelmycin, Rachelmycin; N-De(aminocarbonyl), N—Ac, Ractinomycin A, Radamycin, Rakicidin C, Rakicidin D, Rapamycin, Rapamycin; 32-O-De-Me, Rapamycin; 41-O-De-Me, Rapamycin; 7-O-De-Me, Rapamycin; 32-Demethoxy, Rapamycin; 32-Demethoxy, 7-O-de-Me, Rapamycin; 32-Demethoxy, 15-deoxo, 7,41-di-O-de-Me, Rapamycin; 15-Deoxo, Rapamycin; 7,32-Di-O-de-Me, Rapamycin; Lower homologue, Rapamycin; 46-Methyl, Rapamycin; 48-Methyl, Rapamycin; 51-Methyl, Rapamycin isomer, Raromycin, Ravidomycin, Ravidomycin; O-De-Ac, Ravidomycin; O-De-Ac, N-oxide, Ravidomycin; 10-O-De-Me, Ravidomycin; N-De-Me, O-de-Ac, N—Ac, Ravidomycin; N-De-Me, O-de-Ac, Ravidomycin; N-De-Me, Ravidomycin; N,N-Di-de-Me, N—Ac, Ravidomycin; 1",2"-Dihydro, 1"-hydroxy, Ravidomycin; 1",2"-Epoxide, Ravidomycin; N-Oxide, Ravidomycin M; O-De-Ac, Reductiline, Reductiomycin, Renastacarcin, Requinomycin, Resistoflavin, Resistoflavin; 11b-Me ether, Resistomycin, Resormycin, Resorthiomycin, Respinomycin A1, Respinomycin A1; 3A-Deamino, 3A-nitro, Respinomycin A1; 4'-O-Deglycosyl, Respinomycin A1; 4'-O-Deglycosyl, 3'-N-de-Me, Respinomycin A1; 7-De(glycosyloxy), Respirantin, Reticulomycin B, Retrostatin, Reveromycin A, Reveromycin B, Reveromycin C, Reveromycin D, Reveromycin E, Reveromycin E; 18-Deacyl, 18-O-(5-carboxy-3-furancarbonyl), Reveromycin E; 2',3'-Didehydro(E-), Reveromycin E; 4'-Me ester, Reveromycin F, Reveromycin G, Revistin, Rhamnosyllactone A, Rhizomycin, Rhodomycin A, Rhodomycin A; 3A-N-De-Me, Rhodomycin A; 3B—N-De-Me, Rhodomycin A; 7-O-Deglycosyl, Rhodomycin A; 10-O-Deglycosyl, 10-glycoside, Rhodomycin A; 7-O-Deglycosyl, 7-glycoside, Rhodomycin A; 7-Epimer, 7-O-deglycosyl, Rhodomycin A; 1-Hydroxy, Rhodomycin A; 1-Hydroxy, 7-O-deglycosyl, Rhodomycin A; 1-Hydroxy, 6-deoxy, Rhodomycin A; 1-Hydroxy, 6-deoxy, 10-O-deglycosyl, Rhodomycin A; 1-Hydroxy, 6-deoxy, 7-O-deglycosyl, Rhodomycin A; 1-Hydroxy, 4,6-dideoxy, Rhodomycin A; 1-Hydroxy, 4,6-dideoxy, 10-O-deglycosyl, Rhodomycin A; 1-Hydroxy, 4,6-dideoxy, 7-O-deglycosyl, β-Rhodomycin IV, γ-Rhodomycin IV, γ-Rhodomycin IV; 3C,7-Dideoxy, 4C—O-deglycosyl, γ-Rhodomycin IV; 7-Deoxy, 4C—O-deglycosyl, α1-Rhodomycinone, α1-Rhodomycinone; 10-Deoxy, α1-Rhodomycinone; 7-Deoxy, α1-Rhodomycinone; 10-Deoxy, 4-O-(3-dimethylamino-3,6-dideoxy-α-L-galactopyranoside), α-Rhodomycinone, α-Rhodomycinone; 7-Deoxy, α-Rhodomycinone; 7,10-Dideoxy, α-Rhodomycinone; 7,11-Dideoxy, α-Rhodomycinone; 7-Epimer, α-Rhodomycinone; 7-Epimer, 10-deoxy, α-Rhodomycinone; 7-Epimer, 6-deoxy, α-Rhodomycinone; 7-Epimer, 6,10-dideoxy, α-Rhodomycinone; 7-Epimer, 10-O-[2,6-dideoxy-α-L-lyxo-hexopyranosyl-(1→4)-2,6-dideoxy-α-L-lyxo-hexopyranosyl-(1→4)-3-(dimethylamino)-2,3,6-trideoxy-α-L-lyxo-hexopyranoside], α-Rhodomycinone; 7-Epimer, 1-hydroxy, α-Rhodomycinone; 7-Epimer, 1-hydroxy, 6-deoxy, α-Rhodomycinone; 1-Hydroxy, α-Rhodomycinone; 1-Hydroxy, 7-deoxy, δ-Rhodomycinone, ε-Rhodomycinone, ε-Rhodomycinone; 7-Deoxy, ε-Rhodomycinone; 7-Deoxy, 1-hydroxy, ε-Rhodomycinone; 10-Epimer, ε-Rhodomycinone; 4-O-β-D-Glucuronopyranoside, ε-Rhodomycinone; 1-Hydroxy, ε-Rhodomycinone; 7-Ketone, β-Rhodomycin S3, β-Rhodomycin S4, β-Rhodomycin S1B, β-Rhodomycin S1B; 7-Hydroxy, β-Rhodomycin V, β-Rhodomycin V; 3B-Deoxy, α-D-Ribofuranosyl-(1→2)-α-D-ribofuranosyl-(1→3)-D-ribose, Ribostamycin, Ribostamycin; 3-N—Ac, Ribostamycin; 3-N-(Carboxymethyl), Ribostamycin; 6'-Deamino, 6'-hydroxy, Ribostamycin; 3',4'-Dideoxy, Ribostamycin; 2R-Hydroxy, Ribostamycin; 2S-Hydroxy, Ribostamycin; 3-N-Me, Ribostamycin; 3',4',5"-Trideoxy, Rifamycin; O4-(Carboxymethyl), Rifamycin; O4-(Hydroxyacetyl), Rifamycin O, Rifamycin Y, Rimocidin, Rimocidin; Amide, Rimocidin; 14-Decarboxy, 14α-methyl, Rinamycin, Ripromycin, Rishirilide A, Rishirilide B, Robigocidin A, Rodaplutin, Roflamycoin, Roflamycoin; 32,33E-Didehydro, Rosamicin; 9ξ-Alcohol, Rosamicin; 9ξ-Alcohol, 3-Ac, Rosamicin; 9ξ-Alcohol, 3-propanoyl, Roseocitrin, Roseoflavin, Roseofungin, Roseolic acid, Roseophilin, Roseophilin; Dechloro, Roseorubicin A, Roseorubicin A; 4B-Deglycosyl, Roseothricin A, Rotihibin B, Rotihibin B; 2"-Amide, Routiennocin, Roxaticin, RP 31177, RP 34129, RP 66453, rRNA methyltransferases; rRNA (adenosine-2'-O)-methyltransferase, Rubidin, Rubiflavin C1, Rubiflavin C1; 14α,16α:17α,18α-Diepoxide, Rubiflavin C1; 17,18-Dihydro, Rubiflavin C1; 14,16-Dihydro, 14ξ,16ξ-dihydroxy, Rubiflavin C1; 14,16-Dihydro, 14-hydroxy, Rubiflavin C1; 14,16-Dihydro, 16ξ-hydroxy, Rubiflavin C1; 14α,16α-Epoxide, Rubiflavin C1; 14α,16α-Epoxide, 4"-Ac, Rubiflavin C1; 17E-Isomer, Rubiginone A1, Rubiginone A1; 4-Deoxy, Rubiginone A1; 4-Deoxy, O-de-Me, Rubiginone A1; 1-Ketone, 4-O-(2-methylpropanoyl), Rubiginone A1; 4-O-(2-Methylpropanoyl), Rubiginone D2, Rubiginone D2; 4-Ac, Rubiginone D2; 7ξ-Alcohol, 6a,12a-epoxide, 4-Ac, Rubiginone H, Rubomycin M, Rubomycin M; 3B-Deoxy, Rubomycin M; 3B-Epimer, Rubomycin M; 13-Deoxo, O-de-Me, Rubradirin, Rubradirin; Aglycone, Rubradirin; N-Deoxy, Rubradirin; 7E-Isomer, de(glycosyloxy), Rubradirin; 7E-Isomer, de(glycosyloxy), 3"-deoxy, Rubradirin D, Rubradirin D; Derivative, Rubrochlorin, Rubrolone, Rubrolone B, α-Rubromycin, α-Rubromycin; O5'-De-Me, β-Rubromycin, β-Rubromycin; 3'ξ-Hydroxy, γ-Rubromycin, γ-Rubromycin; 9'-Deoxy, γ-Rubromycin; 3R,3'R-Dihydroxy, 3'-O-(2,6-dideoxy-3-O-methyl-α-L-ribo-hexopyranoside), Rudolfomycin; 1-Deoxy, Rudolfomycin; 1-Deoxy, 11-hydroxy, Ruticin, Rutilantin, Sabaramycin A, SAF, Saframycin A, Saframycin A; Decyano, Saframycin A; Decyano, 5α-hydroxy, 1,4-hydroquinone, Saframycin A; Decyano, 5α-methoxy, Saframycin A; Decyano, 14-oxo, 1,4-hydroquinone, Saframycin A; 5α-Hydroxy, Saframycin A; 14-Oxo, 1,4-hydroquinone, Saframycin AD-1, Saframycin H, Saframycin R, Saframycin S, Saframycin Y3, Saframycin Y2b, Saframycin Y2b-D, Saframycin YD-1, Saframycin YD-2, Sakyomicin B; (+)-form, Stereoisomer (?), Sakyomicin B; (+)-form, 2-Deoxy, 5,6-dihydro, Sakyomicin B; (−)-form, Salbostatin, Salinamide A, Salinamide D, Salinamide E, Salinamide E; 20-O-[(4-Methy-2,4-hexadienoylamino)acetyl], Saliniketal A, Saliniketal A; 18-Hydroxy, Salinomycin, Salinomycin; 20-Deoxy, Salinomycin; 18,19-Dihydro, Salinomycin; 17-Epimer, 20-deoxy, Salinomycin; 5-Hydroxy, Salinomycin; 20-Ketone, Salinomycin A II, Salmycin B, Salmycin B; 2-Oxime, Salmycin C, Salmycin C; 2'-Oxime, Sangivamycic acid; Amide, Sangivamycic acid; 5'-Deoxy, nitrile, Sangivamycic acid; Nitrile, Sanglifehrin A, Sanglifehrin A; 35-Deoxy, 35,36-didehydro, Sanglifehrin C, Sanglifehrin C; 35-Deoxy, 35,36-didehydro, Sannamycin E, Sannamycin E; N-De-Me, Sannamycin E; 1-Epimer, O1-Me, Sannamycin E; 5-Epimer, O1-Me, 6-N-(aminoacetyl), Sannamycin E; O1-Me, Sannamycin K, Sannastatin, Sansanmycin A, Sansanmycin A; S-Oxide, Sansanmycin B, Sansanmycin E, Sansanmycin F, Sansanmycin G, Saptomycin B, Saptomycin B; 1'-Epimer, Saptomycin B; 1'-Epimer, 4'-Ac, Saptomycin D, Saptomycin D; 17,18-Epoxide, O-de-Ac, Saptomycin G, Saptomycin G; 1A-Epimer, 14ξ,16ξ-epoxide, Saptomycin G; 14ξ,16ξ-Epoxide, Sapurimycin, Saquayamycin A, Saquayamycin A; 2B,3B,2D,3D-Tetrahydro, Saquayamycin A; 3-O-Deglycosyl, Saquayamycin A; 3-O-Deglycosyl, 2D,3D-dihydro, Saquayamycin B, Saquayamycin B; 2C,3C-Dihydro, Saquayamycin B; 4Dβ-Alcohol, Saquayamycin B; 3-O-Deglycosyl, Saramycetin, Sarubicin A, Sarubicin B, Sceliphrolactam, Sclerothricin, Scopamycin A, Scopamycin B, Scopathricin, Scopathricin; Scopathricin I, Scopathricin; Scopathricin II, Secocycloheximide A, Secocycloheximide A; 3-Epimer, 6,8a-Seco-6,8a-deoxyavermectin A1a aglycone, 6,8a-Seco-6,8a-deoxyavermectin A1a aglycone; O-De-Me, 13-O-(2,6-dideoxy-3-O-methyl-α-L-arabino-hexopyranoside), 6,8a-Seco-6,8a-deoxyavermectin A1a aglycone; O-De-Me, 13-O-[2,6-dideoxy-3-O-methyl-α-L-arabino-hexopyranosyl-(1→4)-2,6-dideoxy-3-O-methyl-α-L-arabino-hexopyranoside], 6,8a-Seco-6,8a-deoxyavermectin A1a aglycone; O-De-Me, 5-ketone, 6,8a-Seco-6,8a-deoxyavermectin A1a aglycone; O-De-Me, 5-ketone, 13-O-(2,6-dideoxy-3-O-methyl-α-L-arabino-hexopyranoside), 6,8a-Seco-6,8a-deoxyavermectin A1a aglycone; O-De-Me, 6,8a-Seco-6,8a-deoxyavermectin A1a aglycone; 7-Deoxy, 2,5,6,7-tetradehydro, 22,23-dihydro, 23S-hydroxy, O-de-Me, 13-O-[2,6-dideoxy-3-O-methyl-α-L-arabino-hexopyranosyl-(1→4)-2,6-dideoxy-3-O-methyl-α-L-arabino-hexopyranside], 6,8a-Seco-6,8a-deoxyavermectin A1a aglycone; 13-O-(2,6-Dideoxy-3-O-methyl-α-L-arabino-hexopyranoside), 6,8a-Seco-6,8a-deoxyavermectin A1a aglycone; 22,23-Dihydro, 23S-hydroxy, 6,8a-Seco-6,8a-deoxyavermectin A1a aglycone; 22,23-Dihydro, 23S-hydroxy, O-de-Me, 13-O-(2,6-dideoxy-3-O-methyl-α-L-arabino-hexopyranoside), 6,8a-Seco-6,8a-deoxyavermectin A1a aglycone; 22,23-Dihydro, 23S-hydroxy, O-de-Me, 13-O-[2,6-dideoxy-3-O-methyl-α-L-arabino-hexopyranosyl-(1→4)-2, 6-dideoxy-3-O-methyl-α-L-arabino-hexopyranoside]6,8a-Seco-6,8a-deoxyavermectin A1a aglycone; 22,23-Dihydro, 23S-hydroxy, O-de-Me, 5-ketone, 6,8a-Seco-6,8a-deoxyavermectin A1a aglycone; 22,23-Dihydro, 23S-hydroxy, O-de-Me, 5-ketone, 13-O-(2,6-dideoxy-3-O-methyl-α-L-arabino-hexopyranoside), 6,8a-Seco-6,8a-deoxyavermectin A1a aglycone; 22,23-Dihydro, 23S-hydroxy, 13-O-(2,6-dideoxy-3-O-methyl-α-L-arabino-hexopyranoside), 6,8a-Seco-6,8a-deoxyavermectin A1b aglycone, 6,8a-Seco-6,8a-deoxyavermectin A1b aglycone; O-De-Me, 5-ketone, Secomilbemycin A, Secomilbemycin A; 8E-Isomer, Secomilbemycin C, Secomilbemycin C; 8E-Isomer, Seconemadectin, SEK 1005, SEK 34, SEK 34; 2-Deoxy, 2,3-didehydro, SEK 34; 7-Hydroxy, SEK 34; 7-Hydroxy, 2-deoxy, 2,3-didehydro, Sekazin, SEK 4B, SEK 4B; 2-Deoxy, 2,3-didehydro, Seldomycin 1, Seldomycin 1; 6'-Deoxy, 6'-amino, Seldomycin 5, SEN 128A, Senacarcin A, Senacarcin A; O-Deacyl, Senomycin, Seongomycin, Septacidin, Septacidin; 2'-Epimer, Septacidin; 2'-Epimer, 9''',10'''-didehydro(Z-), Septamycin, Septamycin; 27R-Hydroxy, Serine-type-D-Ala-D-Ala carboxypeptidase, Serinomycin, Serirubicin, Serirubicin; 7-De(glycosyloxy), Serirubicin; 1,6-Dihydroxy, Serirubicin; 1-Hydroxy, Serirubicin; 6-Hydroxy, Serirubicin; 6-Hydroxy, 4A-deglycosyl, Serirubicin; 6-Hydroxy, 4D-O-deglycosyl, Serpentemycin A, Serpentemycin A; (all-E)-Isomer, Serpentemycin D, Serpentemycin D; 1'Z-Isomer, Serpentene, Serpentene; (all-E)-Isomer, Sespenine, Setomimycin, Setomimycin; 1-Epimer, SFI, S Hemolysin, SHI, Shincomycin B, Showdomycin, Shurimycin A, Shurimycin A; N51-Me, SI 1 72, Siamycin I, Siamycin II, Siastatin A, Signermycin B, SIL, Silamycin A, Silamycin A; Lower homologue (R=CH3), Simocyclinone D4, Simocyclinone D4; 8'-Chloro, Simocyclinone D4; 6'-Methyl, Simocyclinone D4; Parent acid, Sinefungin, Sinefungin; 2-N-Carbamoyl, amide, Sinefungin; 4,5-Didehydro, Sinefungin; δ-Lactam, Sinefungin VA, Sinefungin VA; 4,5-Didehydro, Sinefungin VA; 4,5-Didehydro, 13-parent acid, Siolipin B, Siomycin A, Siomycin A; 49S,49'-Dihydro, 26-thione, 1'-parent acid, Siomycin A; 49S,49'-Dihydro, 26-thione, 1'-parent acid, Me ester, Siomycin A; 49S,49'-Dihydro, 26-thione, 4'-parent amide, Siomycin A; 49S,49'-Dihydro, 26-thione, 7'-parent amide, Siomycin A; 1'-Parent acid, Me ester, Siomycin A; 7'-Parent amide, Siomycin A; 1,2R,49S, 49'-Tetrahydro, 26-thione, 1'-parent acid, Siomycin A 1,2R, 49S,4'-Tetrahydro, 26-thione, 1'-parent acid, Me ester, Siomycin A; 1,2R,49S,49'-Tetrahydro, 26-thione, 4'-parent amide, Siomycin A; 1,2R,49S,49'-Tetrahydro, 26-thione, 7-parent amide, Siomycin D1, Sisomicin, Sistomycosin, Skyllamycin A, SNA 4606-1, SNF 4435C, SNF 4435C; 6-Epimer, Solumycin, Soulomycin, Sparsomycin, Sparsomycin; S15-Oxide (R-), Sparsomycin; S15-Oxide (S-), SP-Chymostatin B, SP-Chymostatin B; 1-Alcohol, SP-Chymostatin B; 2-Epimer, SP-Chymostatin B; 2-Epimer, 4'''-hydroxy, SP-Chymostatin B; 4''-Hydroxy, Spectinabilin, Spectinabilin; 2',3'-Didehydro, Spectinomycin, Spectinomycin; 4R-Alcohol, Spectomycin A2, Spectomycin A2; 8-Me ether, Spectomycin B1, Spenolimycin, Sphinin, Sphydrofuran, Spinamycin, Spiramycin S, Spiramycin S; 18-Aldehyde, Spiramycin S; 18-Aldehyde, 3-propanoyl, Spirodionic acid, Spirofungin A, Spirofungin A; 15-Epimer, Spirohexenolide A, Spirohexenolide A; 8-Deoxy, Spironaphthodione, Splenocin, Stambomycin, Staurosporine, Staurosporine; 4'-N-(Acetoxymethoxy), Staurosporine; 4'-N-Carbamoyl, Staurosporine; O-De-Me, Staurosporine; 4'α,5'α-Dihydroxy, 4'-de(methylamino), Staurosporine; 7-Epimer, 7-hydroxy, Staurosporine; 3'-Epimer, 4'-hydroxy, 4'-de(methylamino), Staurosporine; 4'-N-Formyl, Staurosporine; 7ξ-Hydroxy, Staurosporine; 4'-N-Hydroxy, 4'-N-de-Me, 4'-N-formyl, Staurosporine; 4'-Hydroxy, 4'-de(methylamino), Staurosporine; 4'-N-Me, Staurosporine; 4'α-Nitro, 4'-de(methylamino), Staurosporine; 7-Oxo, Staurosporinone, Staurosporinone; N13-(2,6-Dideoxy-α-D-ribo-hexopyranosyl), Staurosporinone; N6-[(1-Methylethoxy)methyl], Stawamycin, Stealthin A, Stealthin A; 12-Aldehyde, Stealthin C, Steffimycin, Steffimycin; Aglycone, 10ξ-alcohol, Steffimycin; 4A-Me ether, Steffimycin; De(glycosyloxy), 2-demethoxy, Steffimycin; 2-Demethoxy, Steffimycin; 8-Demethoxy, Steffimycin; 2-Demethoxy, 4A-O-[3-(2,5-dihydro-4-methyl-2,5-dioxo-3-furanyl)propanoyl], Steffimycin; 2-Demethoxy, 5-imine, Steffimycin; 10-Deoxo, Steffimycin; 10-Deoxo, 4A-Me ether, Steffimycin; 10-Deoxo, O2-de-Me, Steffimycin; 10-Deoxo, 8-demethoxy, Steffimycin; 10-Deoxo, 8-demethoxy, 2A-O-de-Me, Steffimycin; 10-Deoxo, 2,8-didemethoxy, 2A-O-de-Me, Stendomycin, Stenothricin, Stravidin S2, Stravidin S3, Strepin P1, Streptavidin, Streptazoline, Streptazoline; 13-Hydroxy, Streptazoline; 9R-Hydroxy, Streptazoline; 5-O-β-D-Xylopyranoside, Streptazone B1, Streptazone B1; 4ξ,4aξ-Epoxide, Streptazone B1; (E)-Isomer, Streptazone C, Streptimidone, Streptin, Streptin P1, Streptocidin A, Streptocidin A; 3-D-Tryptophan analogue, Streptocidin A; 3-L-Tryptophan analogue, Streptocidin A; 3-L-Tryptophan, 10-D-phenylalanine analogue, Streptofactin, Streptogan, Streptogrisin A, Streptogrisin B, Streptohexin, Streptoketol B, Streptolydigin, Streptomutin A, Streptomyceamide A, Streptomyceamide B, Streptomycin, Streptomycin; N-De-Me, Streptomycin; 2-Deoxy, Streptomycin; 5'-Hydroxy, Streptomycin; 5'-Hydroxy, 4''-O-β-D-mannopyranosyl, Streptomycin; 4''-O-[α-D-Mannopyranosyl-(1→6)-α-D-mannopyranosyl], Streptomycin; 4''-O-β-D-Mannopyranosyl, Streptomycin 3''-kinase, Streptomycin 6-kinase, Streptomycin-Park nucleotide antibiotic, Streptomycin-6-phosphatase, Streptonigrin, Streptonigrin; 10'-O-De-Me, Streptonigrin; 6-O-De-Me, Streptonigrin; 10'-Demethoxy, Streptonigrin F, Streptonigrin P1, Streptonigrin P2, Streptonigrone, Streptophenazine A, Streptophenazine A; 6'-Hydroxy, Streptophenazine A; 6-Parent acid, Streptophenazine B, Streptophenazine D, Streptophenazine E, Streptophenazine F, Streptophenazine G, Streptopyrrole, Streptopyrrole; Bromo analogue, Streptopyrrole; 1-Chloro, Streptopyrrole; 1-Chloro, 6-Me ether, Streptopyrrole; 6-Me ether, Streptorubin B, Streptothricin; Streptothricin A, Streptothricin; Streptothricin B, Streptothricin; Streptothricin B, 4'-O-Decarbamoyl, 6'-O-carbamoyl, Streptothricin; Streptothricin C, Streptothricin; Streptothricin C, Nβ-Ac, Streptothricin; Streptothricin C, 4'-O-Decarbamoyl, 6'-O-carbamoyl, Streptothricin; Streptothricin D, Streptothricin; Streptothricin D, Nβ-Ac, Streptothricin; Streptothricin D, N5-Me, Streptothricin; Streptothricin D, 4'-O-Decarbamoyl, 6'-O-carbamoyl, Streptothricin; Streptothricin E, Streptothricin; Streptothricin E, Nβ-Ac, Streptothricin; Streptothricin E, 6'-O-Carbamoyl, Nβ-Ac, Streptothricin; Streptothricin E, 4'-O-Decarbamoyl, 6'-O-carbamoyl, Streptothricin; Streptothricin F, Streptothricin; Streptothricin F, Nβ-Ac, Streptothricin; Streptothricin F, 4'-O-Decarbamoyl, 6'-O-carbamoyl, Streptothricin; Streptothricin F, 4'-Decarbamoyl, 6'-carbamoyl, Nβ-Ac, Streptothricin; Streptothricin F, 1'-Epimer, 4'-decarbamoyl, 6'-carbamoyl, Nβ-Ac, Streptothricin; Streptothricin F, 3a-Epimer, 4'-decarbamoyl, 6'-carbamoyl, Nβ-Ac, Streptothricin; Streptothricin X, Streptothricin acids, Streptothricin acids; Streptothricin C acid, Nβ-Ac, Streptothricin acids; Streptothricin D acid, Nβ-Ac, Streptothricin acids; Streptothricin D acid, 4'-Decarbamoyl, 6'-carbamoyl, Streptothricin acids; Streptothricin D acid, Nβ-Me, Nβ-Ac, Streptothricin acids; Streptothricin E acid, Nβ-Ac, Streptothricin acids; Streptothricin E acid, 6'-Carbamoyl, Nβ-Ac, Streptothricin acids; Streptothricin E acid, 4'-Decarbamoyl, 6'-carbamoyl, Streptothricin acids; Streptothricin F acid, 4'-Decarbamoyl, 6'-carbamoyl, Streptothricin acids; Streptothricin F acid, 4'-Decarbamoyl, 6'-carbamoyl, Nβ-Ac, Streptovaricin C, Streptovaricin C; 17-Ac, Streptovaricin C; 21-Ac, Streptovaricin C; 24-Deoxy, Streptovaricin C; 16-Hydroxy, Streptovaricin C; 16β-Hydroxy, 17-Ac, Streptovaricin C; 16β-Hydroxy, 21-Ac, Streptovaricin C; 17-Ketone, Streptovaricin F, Streptovaricin U, Streptoverticillin, Streptovitacin D, Streptozotocin, Strepturidin, Stresgenin B, *Streptomyces* Subtilisin inhibitor-like proteins, *Streptomyces* Subtilisin inhibitor, Succinimycin, Suidatrestin, Suinin, Suitamycin, Sulfinemycin, Sulfomycin, Sulfomycin; Sulfomycin I, Sulfomycin; Sulfomycin I, N49-Parent amide, Sulfomycin; Sulfomycin I, N52-Parent amide, Sulfomycin; Sulfomycin I, 21-Demethoxy, Sulfomycin; Sulfomycin I, 5-Methyl, Sulfomycin; Sulfomycin III, 65-Deoxy, 21-O-de-Me, Sulfomycin; Sulfomycin III, 65-Deoxy, 21-demethoxy, Sulfur, Sulfur (S8), Sulfurmycin B, Sulfurmycin B; 1-Hydroxy, Sulfurmycin B; 11-Hydroxy, Sulfurmycin C, Sulfurmycin C; 3B-Deoxy, Sulfurmycin D, Sulfurmycin D; 9-Epimer, 1-hydroxy, Sulfurmycin D; 11-Hydroxy, N-di-de-Me, Sulfurmycin F, Sulfurmycin F; Aglycone, Sulfurmycin F; Aglycone, 7-deoxy, Sulfurmycin F; Aglycone, 11-hydroxy, Sulfurmycin F; 3B-Deoxy, Sulfurmycin F; 4C-Epimer, Sulfurmycin F; 4C-Ketone, Sulfurmycin F; 7-De(glycosyloxy), 1-hydroxy, Sulfurmycin F; 11-Hydroxy, 4C-ketone, Sulfurmycin F; 1-Hydroxy, 4C-ketone, Sulphostin, Swalpamycin, Swalpamycin; 10,11-Dihydro, 12S,13S-epoxide, Swalpamycin; 12S,13S-Epoxide, Swalpamycin; 8β-Hydroxy, 12S,13S-epoxide, Syriamycin, T 76, TA 2590, Taitomycin, Taitomycin; Taitomycin B, Takamycin, Takanawaenes; Takanawaene A, Takanawaenes; Takanawaene B, Takanawaenes; Takanawaene C, Talopeptin, Talopeptin; 4A-Epimer, Tambjamine A; 1"-N-Dodecyl, TAN 1307, TAN 1030A, TAN 1030A; 4'-De(hydroxyimino), 4'-oxo, TAN 1030A; 3'-Epimer, 4'-de(hydroxyimino), 4'-oxo, TAN 1030A; 7ξ-Hydroxy, TAN 1030A; N6-(Isopropoxymethyl), TAN 1030A; N6-(Methoxymethyl), TAN 1030A; 7-Oxo, TAN 876A, Tartrolone B; 4,4'-Dihydroxy, Tartrolone D, Taurimycin A, Taurimycin B, Tautomycetin, Tautomycetin; 3'-Deoxy, Tautomycin, Tautomycin; 3'-Deoxy, Tautomycin, Tautomycin; 3'-Deoxy, 8R-hydroxy, Tautomycin; 3'-Deoxy, 4ξ-hydroxy, 2ξ-alcohol, Tbilimycin, Tejeramycin, Teleocidin B1, Teleocidin B1; N-De-Me, Teleocidin B1; 16-Epimer, Telomestatin, Telomycin, Tendamistat, Tendomycin, [1,1':4',1"-Terphenyl]-2',3',5'-triol; 2'-O-β-D-Glucopyranoside, [1,1':4',1"-Terphenyl]-2',3',5'-triol; 5'-Me ether, Terragine A, Terragine B, Terragine C, Terragine D, Tertiomycin A, Tertiomycin B, Tetracenomycin C, Tetracenomycin C; O8-De-Me, Tetracenomycin C; O8-De-Me, 8-O-(2,6-dideoxy-β-D-arabino-hexopyranoside), Tetracenomycin C; O8-De-Me, 8-O-(2,6-dideoxy-β-L-ribo-hexopyranoside), Tetracenomycin C; O8-De-Me, 8-O-(3,4-di-O-methyl-α-L-rhamnopyranoside), Tetracenomycin C; O3-De-Me, O3-Et, Tetracenomycin C; O8-De-Me, 8-O-β-D-glucopyranoside, Tetracenomycin C; O8-De-Me, O12a-Me, 8-O-(2,4-di-O-methyl-α-L-rhamnopyranoside), Tetracenomycin C; O8-De-Me, O12a-Me, 8-O-(3,4-di-O-methyl-α-L-rhamnopyranoside), Tetracenomycin C; O8-De-Me, O12a-Me, 8-O-(2,3,4-tri-O-methyl-α-L-rhamnopyranoside), Tetracenomycin C; 3,8-Di-O-de-Me, Tetracenomycin C; 6-Hydroxy, Tetracenomycin C; 6-Hydroxy, O8-de-Me, O12a-Me, 8-O-(2,3,4-tri-O-methyl-α-L-rhamnopyranoside), Tetracenomycin C; 4-Ketone, O8-de-Me, O12a-Me, 8-O-(2,3,4-tri-O-methyl-α-L-rhamnopyranoside), Tetracenomycin C; Stereoisomer, Tetracenomycin D3, Tetracenomycin D3; 6-Deoxo, Tetracenomycin D3; 6-Deoxo, 3-Me ether, Me ester, Tetracenomycin D3; 6-Deoxo, 8-Me ether, Me ester, Tetracenomycin D3; 3,8-Di-Me ether, Tetracenomycin D3; 3,8-Di-Me ether, Me ester, Tetracenomycin D3; Me ether, Tetracenomycin D3; 3-Me ether, Tetracenomycin D3; 3-Me ether, Me ester, Tetracenomycin D3; 8-Me ether, Me ester, Tetracenomycin F2, Tetracenomycin R1, Tetracycline, Tetracycline; N-De-Me, N-Et, Tetracycline; 6-Deoxy, Tetrafibricin, Tetrafungin, Tetrahexin, 5,6,7,8-Tetrahydro-5,7-dihydroxy-1H-azocin-2-one, 3a,4,7,7a-Tetrahydro-3a-hydroxy-2(3H)-benzofuranone; (3aS,7aR)-form, 1,2,3,9-Tetrahydro-3-hydroxy-1,2-dimethyl-4H-carbazol-4-one; (1R,2R,3R)-form, Tetrahydro-4-hydroxy-6-isopropyl-5-methyl-2H-pyran-2-one, 3,4,6,9-Tetrahydro-10-hydroxy-7-(methylamino)-1-(3-methylbutyl)-6,9-dioxo-1H-naphtho[2,3-c]pyran-3-acetic acid, Tetrahydro-4-hydroxy-5-methyl-6-(1-propenyl)-2H-pyran-2-one, 1,4,5,6-Tetrahydro-5-hydroxy-2-methyl-4(6)-pyrimidinecarboxylic acid, 5,6,7,7a-Tetrahydro-7a-hydroxy-3H-pyrrolizin-3-one; (ξ)-form, Tetrahydro-6-(5-methylheptyl)-2H-pyran-2-one; (ξ)-form, Tetrahydro-6-(5-methylhexyl)-2H-pyran-2-one; (ξ)-form, 1,4,5,6-Tetrahydro-2-methyl-4(6)-pyrimidinecarboxylic acid; (S)-form, 2,3,4,5-Tetrahydro-6-(1,3-pentadienyl)pyridine; (E,E)-form, 5,6,7,7a-Tetrahydro-3H-pyrrolizin-3-one; (R)-form, 5,6,8,13-Tetrahydro-1,7,9,11-tetrahydroxy-8,13-dioxo-3-(2-oxopropyl)benzo[a]naphthacene-2-carboxylic acid, 3,4,4a,12b-Tetrahydro-3,4a,7,8-tetrahydroxy-3-methylbenz[a]anthracene-1,6(2H,5H)-dione, 3,4,4a,12b-Tetrahydro-3,4a,7,8-tetrahydroxy-3-methylbenz[a]anthracene-1,6(2H,5H)-dione; 3-Deoxy, 2,3-didehydro, 3,4,4a,12b-Tetrahydro-3,4a,7,8-tetrahydroxy-3-methylbenz[a]anthracene-1,6(2H,5H)-dione; 4a-Deoxy, 4a,12b-didehydro, 3,4,7,12-Tetrahydro-7,8,12-trihydroxy-12-(hydroxymethyl)-3-methylbenz[a]anthracen-1(2H)-one, 3,4,5,6-Tetrahydroxy-1-cyclohexene-1-carboxaldehyde, 3,4,5,6-Tetrahydroxy-1-cyclohexene-1-carboxaldehyde; 6-Butanoyl, 3,4,5,6-Tetrahydroxy-1-cyclohexene-1-carboxaldehyde; 6-O-(2ξ-Methylbutanoyl), 3,4,5,6-Tetrahydroxy-1-cyclohexene-1-carboxaldehyde; 6-O-(3-Methylbutanoyl), 3,4,5,6-Tetrahydroxy-1-cyclohexene-1-carboxaldehyde; 6-O-(2-Methylpropanoyl), 3,4,5,6-Tetrahydroxy-1-cyclohexene-1-carboxaldehyde; 6-Pentanoyl, 3',4',5,7-Tetrahydroxyisoflavone, 3',4',5,7-Tetrahydroxyisoflavone; 3'-O-α-L-Rhamnopyranoside, 3',5,5',7-Tetrahydroxyisoflavone, 1,3,8,11-Tetrahydroxy-10-methyl-5,12-naphthacenedione, 1,3,8,11-Tetrahydroxy-10-methyl-5,12-naphthacenedione; 5-Deoxo, 1,3,8,11-Tetrahydroxy-10-methyl-5,12-naphthacenedione; 3-Me ether, 2,6,7,9-Tetrahydroxy-4-methyl-5,12-naphthacenedione, 2,3,5,8-Tetrahydroxy-6-methyl-1,4-naphthoquinone, 2,3,5,8-Tetrahydroxy-6-methyl-1,4-naphthoquinone; 6,7-Dihydro, 1,6,8,11-Tetrahydroxy-5,12-naphthacenedione; 1-Me ether, 2,5,7,8-Tetrahydroxy-1,4-naphthoquinone; 2,7-Di-Me ether, 1,2,7,7-Tetramethylbicyclo[2.2.1]heptan-2-ol; (1R,2R)-form, Tetrangomycin; (R)-form, Tetrangomycin; (R)-form, 6,9-Dihydroxy, Tetrangomycin; (R)-form, 6,11-Dihydroxy, Tetrangomycin; (R)-form, 9-Methoxy, 6-hydroxy, Tetrangomycin; (ξ)-form, 7ξ,12ξ-Dialcohol, O8-Me, Tetrangomycin; (ξ)-form, Stereoisomer (?), 1ξ-alcohol, O8-Me, Tetrangomycin; (ξ)-form, 6a,12a-Epoxide, 7ξ,12ξ-dialcohol, O8-Me, Tetrangomycin; (ξ)-form, 6a,12a-Epoxide, 1-ketone, 7-alcohol, O8-Me, Tetrangomycin; (ξ)-form, 11-Hydroxy, 1ξ-alcohol, O8-Me, Tetrangomycin; (ξ)-form, 1ξ,7ξ-Dialcohol, O8-Me, Tetrangomycin; (ξ)-form, 6-Hydroxy, O8-Me, Tetrangomycin; (ξ)-form, 3-Deoxy, 6-hydroxy, Tetrangomycin; (ξ)-form, O8-Me, Tetrangomycin; (ξ)-form, 1ξ-Alcohol, O8-Me, Tetrangomycin; (ξ)-form, 5,6-Dihydroxy, Tetrangomycin; (ξ)-form, 6-Hydroxy, Tetrangomycin; (ξ)-form, 7ξ-Alcohol, O8-Me, Tetrangomycin; (ξ)-form, 6-Hydroxy, 1ξ-alcohol, O8-Me, Tetrapetalone C, Tetrapetalone C; 17R-Acetoxy, Tetrapetalone C; 17R-Acetoxy, 2-deoxy, Tetrapetalone C; 2-Deoxy, Tetrin A, Tetrin A; 24-Demethyl, 24-ethyl, Tetrin A; 24-Demethyl, 24-ethyl, 4-hydroxy, Tetrin A; 5-Deoxy, 4,5-didehydro, 4,5-epoxide, Tetrin A, 4-Hydroxy, Tetrodecamycin, Tetrodecamycin; 4α,5-Dihydro, Tetromycin B, Tetromycin B; 9-Ac, Tetromycin C aglycone; 9-O-[4,6-Dideoxy-4-(2-hydroxy-4-methoxy-6-methylbenzoylamino)-3-C-methylhexopyranoside], Tetromycin C aglycone; 9-O-[2,4-Dimethoxy-6-methylbenzoyl-(→4)-6-deoxyhexopyranoside], Tetromycin C aglycone; 9-O-[2-Hydroxy-4-methoxy-6-methylbenzoyl-(→2)-6-deoxyhexopyranoside], Tetromycin C aglycone; 9-O-[2-Hydroxy-4-methoxy-6-methylbenzoyl-(→3)-6-deoxyhexopyranoside], Tetromycin C aglycone; 9-O-[2-Hydroxy-4-methoxy-6-methylbenzoyl-(→4)-6-deoxyhexopyranside], Tetronasin, Tetronomycin, Tetronothiodin, Thaimycin A, Thaimycin B, Thaimycin C, Thaxtomin A, Thaxtomin A; N1-De-Me, Thaxtomin A; N4-De-Me, Thaxtomin A; 3"Deoxy, Thaxtomin A; 3"-Deoxy, N4-de-Me, Thaxtomin A; 3"-Deoxy, 2"-hydroxy, Thaxtomin A; 3"-Deoxy, 4"-hydroxy, Thaxtomin A; 3,3"-Dideoxy, Thaxtomin A; 3,3"-Dideoxy, N4-de-Me, Thaxtomin A; 3,3"-Dideoxy, N1,N4-di-de-Me, Thaxtomin A; 3-Epimer, 3"-deoxy, 2"-hydroxy, Thaxtomin A; 4"-Hydroxy, Theiomycetin, Thermitase, Thermycetin, Thiazinotrienomycin A, Thiazinotrienomycin A; 33,34-Dihydro, Thiazinotrienomycin C, Thiazinotrienomycin D, Thiazinotrienomycin D; 33,34-Dihydro, Thiazinotrienomycin F, Thiazinotrienomycin F; 32,33-Dihydro, Thiazostatin A, Thiazostatin A, 2-Epimer, Thienamycin, Thienamycin; N—Ac, Thienamycin; 1',2'-Didehydro, N—Ac, Thienamycin; 6,8-Diepimer, N—Ac, Thienamycin; 6,8-Diepimer, N—Ac, O-sulfate, Thienamycin; 6,8-Diepimer, 1',2-didehydro, N—Ac, Thienamycin; 6,8-Diepimer, 1',2'E-didehydro, N—Ac, O-sulfate, Thienamycin; 6,8-Diepimer, 1',2'Z-didehydro, N—Ac, O-sulfate, Thienamycin; 6,8-Diepimer, 1',2'-didehydro, N—Ac, O-sulfate, S-oxide, Thienamycin; 6,8-Diepimer, 1',2'-didehydro, N-propanoyl, O-sulfate, Thienamycin; 6,8-Diepimer, O-sulfate, Thienamycin; 8-Epimer, Thienamycin; 8-Epimer, N—Ac, Thienamycin; 8-Epimer, N—Ac, O-sulfate, Thienamycin; 8-Epimer, 1',2'-didehydro, N—Ac, Thienamycin; 8-Epimer, 1',2'-didehydro, N—Ac, S-oxide, Thienodolin, Thioactin, Thiolactomycin, Thiomycin, Thiopeptin A2, Thiostrepton, Thiotetromycin, Thiotipin, 4-Thiouridine, Thioviridamide, Thioxamycin, Thraustomycin, Thrazarine, Threonylthreonylargininal; N—Ac, Thymidine; 3-Me, Thymidine 5'-diphosphate mannose, Thymidine 5'-diphosphate rhamnose, TI 9, Tirandalydigin, Tirandamycin A, Tirandamycin A; 10R-Alcohol, Tirandamycin A; 11,12-Deepoxy, 11,12-didehydro, Tirandamycin A; 11,12-Deepoxy, 11R-hydroxy, 10R-alcohol, Tirandamycin A; 8-Demethyl, 10R-alcohol, Tirandamycin A; 10-Deoxo, 11,12-deepoxy, 11,12-didehydro, Tirandamycin A; 18-Hydroxy, TMG-Chitotriomycin, Tobramycin, Tobramycin; 2'-N-Carbamoyl, Tobramycin; 6'-N-Carbamoyl, Tobramycin; 6"-O-Carbamoyl, TOD 4403, Tokimycin A, Tolypomycin R, Tolypomycin Y, Tomaymycin, Tomaymycin; 11-O-De-Me, Tomaymycin; 11-O-De-Me, 11-ketone, Tomaymycin; 11-Demethoxy, Tomaymycin; 11-Demethoxy, 10,11-didehydro, Toxifertilin, 2-Trehalosamine, 4-Trehalosamine, α,α-Trehalose; 6-Phosphate, Trestatin; Trestatin A, Trestatin; Trestatin B, Trestatin; Trestatin C, Triacsin B, Triacsin B; 6,9-Dihydro, Triacsin B; 8,9-Dihydro, Triacsin B; 6,7,8,9-Tetrahydro, Trialaphos, Tribenarthin, Tribenarthin; 3"→1 Lactone, 1,1,1-Trichloro-4-hydroxy-11-methyl-3,5,7,9-dodecatetraen-2-one, 1,1,1-Trichloro-4-hydroxy-11-methyl-3,5,7,9-dodecatetraen-2-one; 1-Dechloro, 1,1,1-Trichloro-4-hydroxy-11-methyl-3,5,7,9-dodecatetraen-2-one; Tridechloro, 1,1,1-Trichloro-4-hydroxy-11-methyl-3,5,7,9-tridecatetraen-2-one; (S)-form, 1,1,1-Trichloro-4-hydroxy-11-methyl-3,5,7,9-tridecatetraen-2-one; (S)-form, Tridechloro, Trichostatic acid, Trichostatin A, Trichostatin A; N-Deoxy, N-(1S-carboxy-2-hydroxyethyl), Trichostatin A; N-Deoxy, N-Me, Trichostatin A; N-Deoxy, Trichostatin A; Fe complex, Trichostatin A; O-α-D-Glucopyranoside, Trichostatin A; O-β-D-Glucopyranoside, Triculamine, Trienine, Trihomononactic acid, Trihomononactic acid; Lactone, Trihomononactic acid cyclic dimer, 2,3',4'-Trihydroxyacetophenone; 3'-Me ether, 3,4,5-Trihydroxybenzaldehyde, 5,10,11-Trihydroxy-3-cadinanone; (1β,4β,5α,6β,7α10α)-form, 2,3,4-Trihydroxy-2,4,6-cycloheptatrien-1-one, 1,4,6-Trihydroxy-5,8-dioxo-2,3-naphthalenedicarboxylic acid; 6-Me ether, di-Me ester, 1,3,5-Trihydroxy-2,4-diprenylxanthone, 8,10,12-Trihydroxy-2,4-dodecadienoic acid, 8,10,12-Trihydroxy-2,4-dodecadienoic acid; (2E,4E,8ξ,10ξ)-form, 4',5,7-Trihydroxyflavanone; (S)-form, 6,7,8-Trihydroxy-3-hydroxymethyl-1H-2-benzopyran-1-one; 6,7-Di-Me ether, 6,7,8-Trihydroxy-3-hydroxymethyl-1H-2-benzopyran-1-one; 7-Me ether, 4,5,6-Trihydroxy-2-hydroxymethyl-2-cyclohexen-1-one; (4R,5R,6R)-form, 4,5,6-Trihydroxy-2-hydroxymethyl-2-cyclohexen-1-one (4R,5R,6R)-form, 1'-O-(2-Butenoyl), 4,5,6-Trihydroxy-2-hydroxymethyl-2-cyclohexen-1-one; (4S,5S,6R)-form, 4,5,6-Trihydroxy-2-hydroxymethyl-2-cyclohexen-1-one; (4S,5S,6R)-form, 1'-Ac, 4,5,6-Trihydroxy-3-(hydroxymethyl)-2-cyclohexen-1-one; (4R,5S,6R)-form, 4,5,6-Trihydroxy-3-hydroxymethyl)-2-cyclohexen-1-one; (4R,5S,6S)-form, 4,5,6-Trihydroxy-3-(hydroxymethyl)-2-cyclohexen-1-one; (4R,5S,6S)-form, 1'-Ac, 4,5,6-Trihydroxy-3-(hydroxymethyl)-2-cyclohexen-1-one; (4R,5S,6S)-form, 1'-Deoxy, 1,3,6-Trihydroxy-2-hydroxymethyl-8-methylanthraquinone; 3,6-Di-Me ether, 1,3,6-Trihydroxy-2-hydroxymethyl-8-methylanthraquinone; 1',3,6-Tri-Me ether, 3',4',7-Trihydroxyisoflavone, 3',4',7-Trihydroxyisoflavone; 3'-O-α-L-Rhamnopyranoside, 3',5',7-Trihydroxyisoflavone; 3',5'-Di-Me ether, 4',5,7-Trihydroxyisoflavone, 4',5,7-Trihydroxyisoflavone; 3',5'-Dinitro, 4',5,7-Trihydroxyisoflavone; 4'-O-(2-Hydroxy-6-methylbenzoyl), 4',5,7-Trihydroxyisoflavone; 3'-Nitro, 4',5,7-Trihydroxyisoflavone; 5-O-α-L-Rhamnopyranoside, 4',5,7-Trihydroxyisoflavone; 5-O-α-L-Rhamnopyranoside, 7-O-(2-O-methyl-α-L-rhamnopyranoside), 4',6,7-Trihydroxyisoflavone; 6-Me ether, 7-O-(2-O-methyl-α-L-rhamnopyranoside), 4',6,7-Trihydroxyisoflavone; 6-Me ether, 7-O-α-L-rhamnopyranoside, 4',7,8-Trihydroxyisoflavone, 1,3,6-Trihydroxy-8-methylanthraquinone, 3,5,8-Trihydroxy-1-methylanthraquinone, 1,6,8-Trihydroxy-3-methylbenz[a]anthracene-7,12-dione, 1,6,8-Trihydroxy-3-methylbenz[a]anthracene-7,12-dione; 8-O-(2,6-Dideoxy-α-L-ribohexopyranosyl), 1,6,8-Trihydroxy-3-methylbenz[a]anthracene-7,12-dione; 5-Hydroxy, 1,7,8-Trihydroxy-3-methylbenz[a]anthracene-5,6-dione, 2,6,8-Trihydroxy-3-methylbenz[a]anthracene-1,4,7,12-tetrone, 1,10,12-Trihydroxy-methyl-6H-benzo[d]naphtho[1,2-b]pyran-6-one, 10-Me ether, 1,10,12-Trihydroxy-8-methyl-6H-benzo[d]naphtho[1,2-b]pyran-8-one; 10-Me ether, 12-O-α-L-rhamnopyranoside, 1,10,12-Trihydroxy-8-methyl-6H-benzo[d]naphtho[1,2-b]pyran-6-one; 12-O-α-L-Rhamnopyranoside, 1,10,12-Trihydroxy-8-methyl-6H-benzo[d]naphtho[1,2-b]pyran-6-one; 1-O-α-L-Rhamnopyranoside, 4,7,8-Trihydroxy-5-methyl-2H-1-benzopyran-2-one; 7-Me ether, 6,7,8-Trihydroxy-3-methyl- 1H-2-benzopyran-1-one, 6,7,8-Trihydroxy-3-methyl-1H-2-benzopyran-1-one; 6,7-Di-Me ether, 6,7,8-Trihydroxy-3-methyl-1H-2-benzopyran-1-one; 7-Me ether, 1,3,6-Trihydroxy-8-(3-methylbutyl)anthraquinone, 3,6,8-Trihydroxy-1-(3-methylbutyl)anthraquinone-2-carboxylic acid, 3,6,8-Trihydroxy-1-(3-methylbutyl)anthraquinone-2-carboxylic acid; 6-Deoxy, 2,3,4-Trihydroxy-6-methylcyclohexanone (2R,3R,4R,6S)-form, 2,3,4-Trihydroxy-6-methylcyclohexanone; (2R,3S,4S,6S)-form, 2,3,4-Trihydroxy-6-methylcyclohexanone; (2S,3R,4R,6R)-form, 2,5,6-Trihydroxy-3-methyl-2-cyclohexen-1-one; (5R,6R)-form, 4,5,6-Trihydroxy-2-methyl-2-cyclohexen-1-one; (4R,5R,6R)-form, 4,5,6-Trihydroxy-2-methyl-2-cyclohexen-1-one; (4R,5R,6S)-form, 4',5,7-Trihydroxy-3-methylflavanone; (2S,3S)-form, 4',5,7-Trihydroxy-3-methylflavanone; (2RS,3SR)-form, 1,2,6-Trihydroxy-2-methyl-4-heptanone; (−)-form, 1,3,8-Trihydroxy-7-methyl-2-methylene-4-nonanone, 1,10,11-Trihydroxy-8-methyl-5,12-naphthacenedione; 10-O-(2-O-Methyl-α-L-rhamnopyranoside), 1,6,11-Trihydroxy-8-methyl-5,12-naphthacenedione; 1-Me ether, 2,5,7-Trihydroxy-3-methyl-1,4-naphthoquinone; 2-Me ether, 2,5,7-Trihydroxy-6-methyl-1,4-naphthoquinone; 2,7-Di-Me ether, 2,5,7-Trihydroxy-6-methyl-1,4-naphthoquinone; 2-(O-(3,7-Dimethyl-2E,6-octadienyl), 7-Me ether, 2,5,7-Trihydroxy-6-methyl-1,4-naphthoquinone; 7-O-(3,7-Dimethyl-2E,6-octadienyl), 2-Me ether, 2,5,7-Trihydroxy-3-methyl-6-prenyl-1,4-naphthoquinone; 2-Me ether, β,γ,5-Trihydroxy-1,4-naphthoquinone-2-butanoic acid; Me ester, 3,22,24-Trihydroxy-11-oxo-12-oleanen-30-oic acid; (3β,22α)-form, 3,4,5-Trihydroxy-2-pentanone; (3S,4R)-form, 1,3,6-Trihydroxy-8-pentylanthraquinone, 1,3,6-Trihydroxy-8-propylanthraquinone, 1,6,10-Trihydroxy-2,8,10-trimethyl-9(10H)-anthracenone, 1,6,10-Trihydroxy-2,8,10-trimethyl-9(10H)-anthracenone; 1'-Hydroxy, 8,8,9-Trimethoxy-5-methylbenz[cd]isoindolo[2,1-a]indol-1(8H)-one, 8,8,9-Trimethoxy-5-methylbenz[cd]isoindolo[2,1-a]indol-1(8H)-one; 5-Demethoxy, 2,4,6-Trimethyl-2,4-decadienoic acid; (2E,4E,6R)-form, 2,4,6-Trimethyl-2,4-decadienoic acid; (2E,4E,6R)-form, Amide, 11,12,13-Trinor-2,5,9-eudesmanetriol; (2β,4α,5α,9α)-form, Triostin, Triostin; Triostin A, Triostin; Triostin B, Triostin; Triostin B0, Triostin; Triostin C, Trioxacarcin A, Trioxacarcin A; Aglycone, Trioxacarcin A; 7"-Alcohol, Trioxacarcin A; 4'-O-De-Ac, Trioxacarcin A; 14,17-Deepoxy, 14S,17-dihydroxy, Trioxacarcin A; O13-Deglycosyl, Trioxacarcin F, Trioxacarcin F; O13-Deglycosyl, Trisarubinicol, Trypanomycin, Trypsin, *Streptomyces* Trypsin inhibitor, STI 1, *Streptomyces* Trypsin inhibitor; STI 2, Tryptamine; Nb-Ac, Tryptophan 2-C-methyltransferase, Tselikomycin, Tsukubachelin, Tubercidin, Tubercidin; 5'-O-Sulfamoyl, Tubermycin A, Tumescenamide A, Tumescenamide B, Tumimycin, Tylonolide; 20-Alcohol, 5-O-(3,6-dideoxy-3-dimethylamino-β-D-glucopyranoside), Tylonolide; 20-Deoxo, 5-O-(3,6-dideoxy-3-dimethylamino-β-D-glucopyranoside), Tylonolide; 23-Deoxy, 5-O-(3,6-dideoxy-3-dimethylamino-β-D-glucopyranoside), Tylonolide; 5-O-(3,6-Dideoxy-3-dimethylamino-β-D-glucopyranoside), Tylosin, Tylosin; 2A-Deoxy, 20-alcohol, 12α,13α-epoxide, Tylosin; 2A-Deoxy, 12α,13α-epoxide, Tylosin; 20-Alcohol, Tylosin; 20-Alcohol, 2C,3C-di-O-de-Me, Tylosin; 20-Alcohol, 3C—O-de-Me, Tylosin; 4B—O-(3-Methylbutanoyl), 3-Ac, Tylosin; 2C,3C-Di-O-de-Me, Tylosin; 2C—O-De-Me, Tylosin; 3C—O-De-Me, Tylosin; 2C-Demethoxy, Tylosin; 2C-Demethoxy, 4B—O-(3-methylbutanoyl), 3-Ac, Tylosin; 3C-Demethoxy, 2C,3C-didehydro, Tylosin; 4C-Epimer, 2C-demethoxy, Tylosin; 20-Deoxo, 2A-deoxy, 12α,13α-epoxide, Tylosin; 9,20-Dialcohol, Tylosin B, Tylosin B; 2A-Deoxy, 12ξ,13ξ-epoxide, Tylosin B; 20-Alcohol, Tylosin B; 20-Alcohol, 2C,3C-di-O-de-Me, Tylosin B; 20-Alcohol, 3C—O-de-Me, Tylosin B; 2C,3C-Di-O-de-Me, Tylosin B; 3C—O-De-Me, UK 1, Ulufuranol, Umbrinomycin A, Umbrinomycin B, Unamycin A, Uncialamycin, Undecylprodigiosin, Undecylprodigiosin; Lower homologue (n=8), Uracil; 3-Oxide, Urauchimycin A, Urauchimycin B, Urauchimycin C, Urauchimycin D, Urauchimycin D; 8-O-(2-Methylpropanoyl), Urdamycin A, Urdamycin A; 3C-Deoxy, Urdamycin A; 3C-Deoxy, 4C-malonyl, Urdamycin A; 3C-Deoxy, 4C—O-(methylmalonyl), Urdamycin A; 5C-Epimer, 3C-deoxy, Urdamycin A; 3C-Ketone, Urdamycin A; 12b-O-Deglycosyl, Urdamycin A; 12b-O-Deglycosyl, 3C-deoxy, Urdamycin A; 12b-O-Deglycosyl, 3C-deoxy, 4C-malonyl, Urdamycin A; 12b-O-Deglycosyl, 3C-deoxy, 4C—O-(methylmalonyl), Urdamycin A; 5,6-Dihydro, 6β-hydroxy, Urdamycin A; 5-(Methylthio), Urdamycin B, Urdamycin B; 3A-Deglycosyl, Urdamycin B; 5B-Epimer, 4B-deglycosyl, Urdamycin B; 5C-Epimer, 3C-deoxy, Urdamycin B; 3-Deoxy, 3A-deglycosyl, Urdamycin B; 5-Hydroxy, Urdamycin B; 5-Hydroxy, 3A-deglycosyl, Urdamycin B; 6-Hydroxy, 3A-deglycosyl, Urdamycin B; Stereoisomer, 3C-deoxy, 4C—O-malonyl, Urdamycin C, Urdamycin D, Urdamycin G, Urdamycin H, Urdamycin I, Urdamycin I; 3-Deoxy, 2,3-didehydro, Urdamycin K, Urdamycin L; (R)-form, Urdamycin M, Urdamycin X, Usabamycin A, Usabamycin A; Demethoxy, Ushikulide A, Ushikulide A; Δ15-Isomer, Ussamycin, Vaccinocidin, Valanimycin, Valanimycin; 2,3-Dihydro, 3-hydroxy, Valclavam, Validoxylamine B, Validoxylamine B; 6-Deoxy, Validoxylamine B; 6-Deoxy, 4-O-β-D-glucopyranoside, Validoxylamine B; 6-Deoxy, 7-O-α-D-glucopyranoside, Validoxylamine B; 6-Deoxy, 4-O-β-D-glucopyranoside, 4'-O-α-D-glucopyranoside, Validoxylamine B; 6-Deoxy, 4-O-β-D-glucopyranoside, 7'-O-α-D-glucopyranoside, Validoxylamine B; 6-Deoxy, 4-O-[α-D-glucopyranosyl-(1→4)-β-D-glucopyranoside], Validoxylamine B; 6-Deoxy, 4-O-[β-D-glucopyranosyl-(1→6)-β-D-glucopyranoside], Validoxylamine B; 4-O-β-D-Glucopyranoside, Validoxylamine G, Validoxylamine G; 4-O-β-D-Glucopyranoside, Valienamine, Valilactone, Valindolmycin, Valinoctin, Valinomycin, Valiolamine, Valiolamine; 1-Epimer, Valiolamine; N-(2-Hydroxy-2-hydroxymethylethyl), Valistatin, Valylamiclenomycylglutamine, Valylamiclenomycylglutamine; ω-Carboxylic acid, N2-Valylarginine; L-L-form, Valylleucylargininal; N—Ac, Valylvalylargininal; N—Ac, Vanillobiocin, Vanillobiocin; Dechloro, Vanillobiocin; 2"-(5-Methyl-2-pyrrolecarbonyl) isomer, Variacyclomycin B; Dihydro, Variamycin B, Variapeptin, Variapeptin; Lower homologue (R=CH3), Varigomycin, Venezuelin, Venturicidin B, Venturicidin B; Aglycone, Venturicidin B; Aglycone, 17-hydroxy, Venturicidin B; Aglycone, 17-hydroxy, 23-deoxy, 23,24-didehydro, Venturicidin B; 3'-Carbamoyl, Venturicidin B; Homologue (R=CH2CH3), 17-hydroxy, 3'-carbamoyl, Venturicidin B; 17-Hydroxy, 3'-carbamoyl, Verotetrone, Versipelostatin, Versipelostatin; 4BO-Deglycosyl, Versipelostatin; 5B-Epimer, 4B—O-deglycosyl, 3B—O-de-Me, Versipelostatin; 5B-Epimer, 3B—O-de-Me, Versipelostatin; 2BR-Hydroxy, Versipelostatin; 1C-Epimer, Verticilactam, Verticillomycin, Vertimycin, Vicenistatin aglycone; O-(2,6-Dideoxy-3-C-methyl-β-D-ribo-hexopyranoside), Vicenistatin aglycone; O-(2,4,6-Trideoxy-4-methylamino-β-D-ribo-hexopyranoside), Vinacetin, Vineomycin A1, Vineomycin A1; 2C,3C,2E,3E-Tetrahydro, Vineomycin A2, Vineomycin B1, Vineomycin B2, Vineomycin B2; 12-O-Deglycosyl, Vinylamycin, 4-Vinylphenol; 3-Acetamido-4-hydroxybenzoyl, 4-Vinylphenol; 3-Amino-4-hydroxybenzoyl, Violacetin, Violacin, Violarin, Viomycin, Viomycin; N-Deacyl, Viomycin; 31-Deoxy, Viomycin; 31-Deoxy, 4'-hydroxy, Viomycin; 4'-Hydroxy, Viomycin kinase, Virantmycin, Virantmycin; Amide, Virantmycin; 3-Dechloro, 3β-hydroxy, Virantmycin; 3-Dechloro, 3β-hydroxy, amide, Virantmycin; 3-Dechloro, 3-methoxy, 2'ξ-hydroxy, Virantmycin; 2',5'-Didehydro, Virantmycin; 2'ξ-Hydroxy, Virginiaebutanolide F, Virginiamycin S1, Virginiamycin S1; 4'-Alcohol, N-de-Me, Virginiamycin S1; 5'-Hydroxy, Virginiamycin S4, Virginiamycin S5, Viridenomycin, Viridogrisein II, Viridomycin A, Viridomycin A; Monoalcohol, Viridomycin E, Virilemycin A, Virothricin A, Virusin 1609, Virustomycin A, Virustomycin A; Parent acid, Vitamin B12, Vitamin B12c, Vivomycin, WA 8242; WA 8242A1, WA 8242; WA 8242A2, WA 8242; WA 8242B, Wailupemycin A, Wailupemycin B, Wailupemycin C, Wailupemycin D, Wailupemycin D; 3-Epimer, Wailupemycin F, Wailupemycin G, Walkmycin A, Wassumycin, Watasemycin A, Watasemycin A; 2-Epimer, WJ 150, WJ 35, WJ 78, WJ 85, WJ 85; 5-Hydroxy, 5,10-quinone, WS 7622, WS 80130, WS 8242; Antibiotic WS 8242A, WS 8242; Antibiotic WS 8242B, WS 9326A, WS 9326A; 2"S,3"-Dihydro, Wuyiencin, X 2, Xaa-Xaa-Pro tripeptidyl peptidase, Xanthicin, Xanthocidin, Xantholipin, Xantholycin, Xanthomycin A, Xanthomycin B, Xanthostatin, Xialenone C, Xialenone C; 3a-Deoxy, Xialenone C; 3a-Deoxy, 4-ketone, Xialenone C; 6a-Deoxy, 4-ketone, Xialenone C; 3a,6a-Dideoxy, 3a,6a-didehydro, 2α,3α-dihydro, XK 19 2, endo-1,4-β-Xylanase, β-D-Xylopyranosyl-(1→3)-β-D-xylopyranosyl-(1→4)-D-xylose, Yakusimycin A, Yakusimycin B, Yakusimycin C, Yatakemycin, Yemenimycin, YM 216391, YM 47690, Yokonolide A, Yorophenazine, YS 221, YT 46, YT 46B, Yumimycin, Yunnanmycin, Z 24, Z 2685, Zaomycin, Zelkovamycin, Zhenggangmycin Z 902, Zhijiangjunsu, Zinc D-Ala-D-Ala carboxypeptidase, 5-Zizaen-4-one, Zorbamycin, Zorbonomycin B, and Zygomycin B.

In some embodiments, the desired compound is as listed below. In some embodiments, the desired compound is as listed below and obtainable from a cyanobacteria. Desired compounds include 2-Acetamido-2-deoxyglucose; D-form, Acutiphycin, Acutiphycin; 20,21-Didehydro, Acyclomicrocystin LR, Acyclonodularin, ADP-ribosyl-[dinitrogen reductase] hydrolase, Aerucyclamide A, Aerucyclamide A; 12,13-Didehydro, Aerucyclamide A; 2,3,12,13-Tetrahydro, Aerucyclamide C, Aerucyclamide D, Aeruginazole A, Aeruginoguanidines; Aeruginoguanidine 98A, Aeruginoguanidines; Aeruginoguanidine 988, Aeruginoguanidines; Aeruginoguanidine 98C, Aeruginopeptin 228A, Aeruginopeptin 228A; 1',2',3',4'-Tetrahydro, Aeruginopeptin 95A, Aeruginopeptin 95A; 1',2',3',4'-Tetrahydro, Aeruginopeptin 917S-A, Aeruginopeptin 917S-A; Stereoisomer, Aeruginopeptin 917S-A; 1',2',3',4'-Tetrahydro, Aeruginopeptin 917S-C, Aeruginosamide, Aeruginosin 102A, Aeruginosin 102A; 3-Epimer, Aeruginosin 102A; 2-Et ether, O-desulfo, Aeruginosin 205A, Aeruginosin 205A; 2,2',3-Triepimer, Aeruginosin 298A, Aeruginosin 298A; N1-De(argininolyl), Aeruginosin 298A; N1-De(argininolyl), stereoisomer, Aeruginosin 98A, Aeruginosin 98A 5'-Chloro, Aeruginosin 98A; 5'-Chloro, desulfo. Aeruginosin 98A; 3'-Dechloro, Aeruginosin 98A; 3'-Dechloro, 3'-bromo, Aeruginosin 98A; Desulfo, Aeruginosin 89B, Aeruginosin 89B; Diastereoisomer, Agardhipeptin A, Agardhipeptin B, Alotamide A, Ambigol A, Ambigol B, Ambigol B; 1-Deoxy, 4-hydroxy, Ambiguine B isonitrile, Ambiguine B isonitrile; Dechloro, Ambiguine B isonitrile; Dechloro, deoxy, Ambiguine B isonitrile; Deoxy, Ambiguine D isonitrile, Ambiguine D isonitrile; Dechloro, Ambiguine E isonitrile, Ambiguine E isonitrile; Dechloro, Ambiguine F isonitrile, Ambiguine F isonitrile; Dechloro, 25,26-dideoxy, 25,26-didehydro, Ambiguine F isonitrile; 25,26-Dideoxy, 25,26-didehydro, Ambiguine F isonitrile; 25-Epimer, dechloro, 26-deoxy, Ambiguine F isonitrile; 25-Epimer, 26-deoxy, Ambiguine F isonitrile; 26-Epimer, 25-ketone, Ambiguine G nitrile, Ambiguine G nitrile; Dechloro, Ambiguine G nitrile; Dechloro, decyano, 15α-hydroxy, 3-Aminodihydro-2(3H)-furanone; (S)-form, N-Butanoyl, 2-Amino-6-(1,2-dihydroxypropyl)-4(1H)-pteridinone; (1'R,2'S)-form, 2'-O-α-D-Glucopyranoside, 2-Amino-6-(1,2-dihydroxypropyl)-4(1H)-pteridinone; (1'R,2'S)-form, 2'-O-β-D-Glucopyranoside, 2-Amino-6-(1,2-dihydroxypropyl)-4(1H)-pteridinone; (1'R,2'S)-form, 2'-O-β-D-Ribofuranoside, 2-Amino-6-(1,2-dihydroxypropyl)-4(1H)-pteridinone; (1'R,2'R)-form, 2-Amino-6-(1,2-dihydroxypropyl)-4(1H)-pteridinone; (1'S,2'S)-form, 2-Amino-6-(1,2-dihydroxypropyl)-4(1H)-pteridinone; (1'S,2'S)-form, 2'-O-D-Mannopyranoside, 2-Amino-4-hydroxybutanoic acid; (S)-form, O-(2-O-Oxoethyl-β-D-altropyranoside), 2-Amino-6-(hydroxymethyl)-4(1H)-pteridinone; O-D-Glucopyranoside, 2-Amino-6-(hydroxymethyl)-4(1H)-pteridinone; O-[4-O-Methyl-α-D-glucuronopyranosyl-(1→6)-β-D-galactopyranoside], 3-Aminopentanedioic acid; N-Me, 2-Amino-1,3-propanediol; O,N-Di-Me, N-(4E-octadecenoyl), Anabaenopeptilide 202A, Anabaenopeptilide 202A; 3'-Chloro, 4'-O-de-Me, Anabaenopeptilide 90A, Anabaenopeptilide 90A; 3-Chloro, 4'-O-de-Me, Anabaenopeptin 908, Anabaenopeptin 915, Anabaenopeptin A, Anabaenopeptin B, Anabaenopeptin B; Me ester. Anabaenopeptin C. Anabaenopeptin D. Anabaenopeptin E, Anabaenopeptin F, Anabaenopeptin G, Anabaenopeptin H, Anabaenopeptin HU 892, Anabaenopeptin I, Anabaenopeptin J, Anabaenopeptin MM823, Anabaenopeptin MM913, Anabaenopeptin NZ825, Anabaenopeptin NZ825; 4',4"-Dihydroxy, Anabaenopeptin NZ825; 4'-Hydroxy, Anachelin 1, Anachelin 2, Anachelin H, Anatoxin a; (+)(HCl)-form, Anatoxin a(s), Anhydrohapaloxindole A, Anhydrohapaloxindole A; Dechloro, isothiocyanate, Anhydrohapaloxindole A; Isothiocyanate, Antanapeptin A, Antanapeptin A; 5,6-Dihydro, Antanapeptin A; 5,5,6,6-Tetrahydro, Antanapeptin D, Antibiotic A 90720A, Antibiotic BE 16627; Antibiotic BE 16627A, Antibiotic RPI 856A, Antibiotic RPI 856C, Antibiotic Sch 725424, Antibiotic SUAM 20007, Antibiotic SUAM 20008, Antibiotic SUAM 20010, Antibiotic SUAM 20010; 1-Me ester, Antibiotic SUAM 20012, Antibiotic SUAM 20012; Me ester, Antillatoxin, Antillatoxin B, Aphanorphine, Aphantoxin, Aplysiatoxin, Aplysiatoxin; 19-Bromo, Aplysiatoxin; 19-Bromo, 3-deoxy, 3,4-didehydro, Aplysiatoxin; Debromo, Aplysiatoxin; Debromo, 3-deoxy, 3,4-didehydro, Aplysiatoxin; 3-Deoxy, 3,4-didehydro, Aplysiatoxin; 19,21-Dibromo, 3-deoxy, 3,4-didehydro, Apramide A, Apramide A; Z-Demethyl, Apramide A; 7',8'-Dihydro, Apramide D, Apramide D; 2'-Demethyl, Apramide D; ',8'-Dihydro, Aparamide G, Apratoxin A, Apratoxin A; N12-De-Me, Apratoxin C, Apratoxin D, Apratoxin E, Argimicin B; Amide, [D-Asp3,(E)-Dhb7]Microcystin HtyHty, [D-Asp3,(E)-Dhb7]Microcystin HtyR, [D-Asp3,(E)-Dhb7]Microcystin HtyR; 9'-O-De-Me, 9'-Ac, [D-Asp3,(E)-Dhb7]Microcystin HtyR; 2"Z-Isomer, [D-Asp3,(E)-Dhb7]Microcystin HtyY, [D-Asp3,(E)-Dhb7] Microcystin LR, [D-Asp3,(E)-Dhb7]Microcystin LR; 9'-O-De-Me, 9'-Ac, [D-Asp3,(E)-Dhb7]Microcystin LR; Z-Isomer, [D-Asp3,(E)-Dhb7]Microcystin RR, [D-Asp3,(E)-Dhb7]Microcystin RR; 9'-O-De-Me, 9'-Ac, Aulosirazole, Aurilide B, Aurilide C, Bacteriochlorophyll a, 32,33,34,35-Bacteriohopanetetrol; (21βH,22R,32ξ,33ξ,34ξ)-form, 35-O-(3,6-Anhydro-β-D-galacturonopyranoside), 32,33,34, 35-Bacteriohopanetetrol; (21βH,22R,32ξ,33ξ,34ξ)-form, 35-O-α-D-Altruronopyranoside, 32,33,34,35-Bacteriohopanetetrol; (21βH,32R,33R,34S)-form, 35-O-(6-Amino-6-deoxy-β-D-glucopyranoside), 32,33,34,35-Bacteriohopanetetrol; (21βH,32R,33R,34S)-form, 35-O-β-D-Galacturonopyranoside, Bafilomycin B1, Bafilomycin C1, Bafilomycin C1; Amide, Banyascyclamide B, Banyascyclamide C, Banyaside A, Banyaside B, Banyasin A, Barbamide, Barbamide; Dechloro, Belamide A, 4-Benzyl-2-chlorophenol, Besarhanamide A, Besarhanamide B, Bisebromoamide, Biselyngbyaside, Biselyngbyolide A, Bistratamide A, Bistratamide A; 11,12-Didehydro, Blue copper proteins; Plastocyanin, Blue copper proteins; Pseudoazurin, Borophycin, 4-(Bromomethylene)-1,2-thiolane-3-methanol, Brunsvicamide C, Calophycin, 11-Carboxyanatoxin a, 4-O-(1-Carboxyethyl)mannose, Carmabin A, Carmabin A; 9,9,10,10-Tetrahydro, 9-oxo, Carotene 7,8-desaturase, γ-Carotene, Carriebowmide, Caylobolide A, Caylobolide A; 5-Deoxy, 7-hydroxy, 2,3-didehydro(E-), 6-Chloro-β-carboline; N2-Me, 7-Chloro-β-carboline; N-Me, 3-Chloro-11,12-dihydroindolo[2,3-a]carbazole, 3-Chloro-11,12-dihydroindolo[2,3-a]carbazole; N11-(6-Deoxy-β-D-gulopyranosyl), 3-Chloro-11,12-dihydroindolo[2,3-a]carbazole; N12-(6-Deoxy-β-D-gulopyranosyl), 3-Chloro-11,12-dihydroindolo[2,3-a]carbazole; N11-α-L-Rhamnopyrannosyl, 3-Chloro-11,12-dihydroindolo[2,3-a]carbazole; N12-α-L-Rhamnopyranosyl, 3-Chloro-11,12-dihydroindolo[2,3-a]carbazole; N11-β-D-Xyopyranosyl, 3-Chloro-11,12-dihydroindolo[2,3-a]carbazole; N12-β-D-Xyopyranosyl, 4-Chloromethylene-1,2,3,4-tetrahydro-8-methyl-6-quinolinol; (E)-form, O-(2,4-Di-O-methyl-β-D-xylopyranoside), Chlorophyll a, Chlorophyll synthase, 8-Chloro-7-propyl-4,7-octadienoic acid; (4E,7E)-form, 1-Chloro-1-tridecene-6,8-diol; (1E,6R,8R)-form, C49H76N10O13 Acyclic microcystin, C49H76N10O13 Acyclic microcystin; Analogue (R═—CH2Ph), Circinamide, Clavosolide A, Cocosamide A, Cocosamide A; 7,8-Didehydro, Coibamide A, Comnostin A, Comnostin A; 23-Aldehyde, Comnostin A; 23-Aldehyde, di-Me acetal, Comnostin A, 23-Carboxylic acid, Comnostin E, Convolutamydines; Convolutamydine C, 4-Debromo, Crossbyanol A, Crossbyanol A, 4',4"-Disulfate, Crossbyanol A; 4'-Sulfate, Crossbyanol A, 4"-Sulfate, Cryptophycin 18, Cryptophycin 18; 7β,8β-Epoxide, Cryptophycin 19, Cryptophycin 26, Cryptophycin 28, Cryptophycin 28; 7β,8β-Epoxide, Cryptophycin 29, Cryptophycin 29; 5'-Chloro, 7R,8R-epoxide, Cryptophycin 29; Dechloro, 7R,8R-epoxide, Cryptophycin 29; 7R,8R-Epoxide, Cryptophycin 29; 7R,8R-Epoxide, O-de-Me, Cryptophycin 4, Cryptophycin 4; 6'-Chloro, Cryptophycin 4; 6'-Chloro, O-de-Me, Cryptophycin 4; 6'-Chloro, 2,3-dihydro, 3α-hydroxy, Cryptophycin 4; 6'-Chloro, 7R,8R-epoxide, Cryptophycin 4; 6'-Chloro, 7S,8S-epoxide, Cryptophycin 4; 6'-Chloro, 7R,8R-epoxide, O-de-Me, Cryptophycin 4; O-De-Me, Cryptophycin 4; 6',8'-Dichloro, Cryptophycin 4; 6',8'-Dichloro, O-de-Me, Cryptophycin 4; 6',8'-Dichloro, 7R,8R-epoxide, Cryptophycin 4; 6',8'-Dichloro, 7R,8R-epoxide, O-de-Me, Cryptophycin 4; 2'-Epimer, 6'-chloro, Cryptophycin 4; 7R*,8R*-Epoxide, Cryptophycin 4; 2Z-Isomer, 6'-chloro, 7R,8R-epoxide, Cryptophycin 49, Cryptophycin 49; 7β,8β-Epoxide, Cryptophycin 5, Cryptophycin 6, Cryptophycin 7, Curacin A, Curacin A, 7Z-Isomer, Curacin A; 9Z-Isomer, Curacin D, Cyanobacterin, Cyanobacterin B, Cyanolide A, 5-Cyano-6-methoxyindolo[2,3-a]carbazole, 5-Cyano-6-methoxyindolo[2,3-a]carbazole; N11-Me, Cyanopeptolin 1020, Cyanopeptolin 880, Cyanopeptolin 880; 3'-Sulfate, Cyanopeptolin A, Cyanopeptolin 963A, Cyanopeptolin B, Cyanopeptolin B; NArg,NArg-Di-Me, Cyanopeptolin B; NArg-Me, Cyanopeptolin CB071, Cyanophycinase, Cyanostatin A, Cyanostatin B, Cyanovirin N, α-Cyclodextrin; 3",6-Di-Me ether, 6"'''-carbamoyl, 6"'-butanoyl, 6'-Ac, Cycloxazoline, Cylindrocyclophane A, Cylindrocyclophane A; 14-Ac, Cylindrocyclophane A, 30-Chloro, Cylindrocyclophane A; 34-Chloro, 1-deoxy, Cylindrocyclophane A; 30-Chloro, 1,14-di-O-carbamoyl, Cylindrocyclophane A; 14-Deoxy, Cylindrocyclophane A; 14-Deoxy, 1-Ac, Cylindrocyclophane A; 1,14-Di-Ac, Cylindrocyclophane A; 1,14-Di-O-carbamoyl, Cylindrocyclophane A; 30,30-Dichloro, Cylindrocyclophane A; 34,34-Dichloro, 1-deoxy, Cylindrocyclophane A; 30,30-Dichloro, 1,14-di-O-carbamoyl, Cylindrocyclophane A; 1,14-Dideoxy, Cylindrocyclophane A; 30,30,34,34-Tetrabromo, Cylindrocyclophane A, 30,30,34,34-Tetrachloro, Cylindrocyclophane A; 30,30,34,34-Tetrachloro, 1-deoxy, Cylindrocyclophane A; 30,30,34,34-Tetrachloro, 1,14-di-O-carbamoyl, Cylindrocyclophane A; 30,30,34,34-Tetrachloro, 1,14-dideoxy, Cylindrocyclophane A; 30,30,34-Trichloro, Cylindrocyclophane A; 30,34,34-Trichloro, 1-deoxy, Cylindrocyclophane A; 30,30,34-Trichloro, 1,14-di-O-carbamoyl, Cylindrospermopsin, Cylindrospermopsin; 7-Deoxy, Cylindrospermopsin; 7-Epimer, Cystargin, 9-Deazaadenosine, 9-Deazaadenosine; 5'-O-α-D-Glucopyranosyl, 3-[(2,3,3a,4,5,6,7,8,9,9b-Decahydro-2,9-dihydroxy-3,3,3a,6,7-pentamethyl-1H-benz[e]inden-6-yl)methyl]-4-hydroxybenzoic acid, Dendroamide A, Dendroamide B, Dendroamide B; S9-Oxide, 2-Deoxy-ribohexose; D-form, Deoxymalyngamide C, Deoxymalyngamide C; Deoxy, Deoxymalyngamide C; Deoxy, 4α,9α-epoxide, Deoxymalyngamide C; 8-Epimer, 4α,9α-epoxide, Deoxymalyngamide C; 8-Epimer, 4α,9α-epoxide, Ac, Deoxymalyngamide C; 4α,9α-Epoxide, Deoxymalyngamide C; 4α,9α-Epoxide, Ac, Deoxymalyngamide C; 2Z-Isomer, deoxy, 1,2-Diacylglycerol 3-glucosyltransferase, 1,2-Diacylglycerol 6-sulfoquinovosides, 1,2-Diacylglycerol 6-sulfoquinovosides; 2-O-Hexadecanoyl-1-O-(9-hexadecenoyl)glycerol 3-(6-deoxy-6-sulfo-α-D-glucopyranoside), 2,3-Diaminopropanoic acid; (S)-form, N3-Me, 3,4-Dibenzyl-5-benzylidene-2(5H)-furanone; (E)-form, 3,4-Dibenzyl-5-benzylidene-2(5H)-furanone; (Z)-form, 2,7-Dibromo-9H-carbazole, 3,6-Dibromo-9H-carbazole, 2,4-Dichlorobenzoic acid, 3,8-Dichloro-11,12-dihydroindolo[2,3-a]carbazole, 3,8-Dichloro-11,12-dihydroindolo[2,3-a]carbazole; N-(6-Deoxy-β-D-gulopyranosyl), 3,8-Dichloro-11,12-dihydroindolo[2,3-a]carbazole; N-β-D-Glucopyranosyl, 3,8-Dichloro-11,12-dihydroindolo[2,3-a]carbazole; N-α-L-Rhamnopyranosyl, 3,8-Dichloro-11,12-dihydroindolo[2,3-a]carbazole; N-β-D-Xylopyranosyl, 7,8-Dichloro-1-hydroxy-9-methyl-β-carboline, 7,8-Dichloro-9-methyl-β-carboline, 1,15-Dichloro-1,14-pentadecadiene-3,12-diyn-8-amine; (1E,14E)-form, N—Ac, 1,15-Dichloro-1,14-pentadecadiene-3,12-diyn-8-amine; (1E,14E)-form, 1-Chloro, N—Ac, 1,15-Dichloro-1,14-pentadecadiene-3,12-diyn-8-amine; (1E,14E)-form, 1-Chloro, 1,2,3,3,4,4-hexahydro, N—Ac, 1,15-Dichloro-1,14-pentadecadiene-3,12-diyn-8-amine; (1E,14E)-form, 1,15-Dichloro, 1,2-dihydro, N—Ac, 1,15-Dichloro-1,14-pentadecadiene-3,12-diyn-8-amine; (1E,14E)-form, 1,15-Dichloro, N—Ac, 1,15-Dichloro-1,14-pentadecadiene-3,12-diyn-8-amine; (1E,14Z)-form, 3Z,4-Dihydro, N—Ac, 3',4'-Didehydro-1',2'-dihydro-1',2'-dihydroxy-β,ψ-caroten-4-one; (S)-form, 2'-O-α-L-Fucopyranoside, Didmolamide A; Stereoisomer, Dihydro-4-hydroxy-2(3H)-furanone; (S)-form, 11,12-Dihydroindolo[2,3-a]carbazole; N-(6-Deoxy-β-D-gulopyranosyl), 11,12-Dihydroindolo[2,3-a]carbazole; N-α-L-Rhamnopyranosyl, 2,3-Dihydro-1-methoxy-6-methyl-3-oxo-1H- indene-4-carboxaldehyde, 2,5-Dihydro-4-methyl-5-oxo-3-furancarboxylic acid, 3,4-Dihydroxy-2,5-bis(hydroxymethyl)pyrrolidine; (2R,3R,4R,5R)-form, 3,4-Dihydroxy-2-(1-hydroxyethyl)pyrrolidine; (1'R,2R,3R,4S)-form, 3-O-[α-D-Glucuronopyranosyl-(1→2)-3,4-di-O-acetyl-α-L-arabinopyranosyl-(1→4)-3-O-methyl-α-D-glucopyranoside], 1,8-Dihydroxy-4-methylanthraquinone, 3,4-Dihydroxyplectaniaxanthin; 2'-O-L-Rhamnopyranoside, 3,6-Diiodo-9H-carbazole, 2,5-Dimethyldodecanoic acid, 2,5-Dimethyldodecanoic acid; (Z)-3-Acetoxy-3-bromo-1-propenyl ester, Dolabellin, Dolastatin 10, Dolastatin 10; Homologue (R=CH3), Dolastatin 11, Dolastatin 11; Demethoxy, 11-N-Me, Dolastatin 11; 15-Epimer, 31-methyl, 11-N-Me, Dolastatin 11; 11-N-Me, Dolastatin 11; 31-Methyl, demethoxy, 11-N-Me, Dolastatin 14, Dolastatin 14; Nγ(Asn)-Me, Dolastatin 16, Dolastatin 16; Homologue (R=—CH2CH3), Dolastatin 3, Dolastatin 3; Homologue (R=—CH2CH3), Dolastatin G; 55-Demethyl, Dolastatin G; 55-Demethyl, 37-O-de-Me, 1,3,29,31-Dotriacontanetetrol; (3R,29S,31R)-form, 1-O-α-D-Glucopyranoside, 1,3,29,31-Dotriacontanetetrol; (3R,29S,31R)-form, 1-O-α-D-Mannopyranoside, 1,3,29,31-Dotriacontanetetrol; (3R,29S,31R)-form, 29-Ketone, 1-O-α-D-glucopyranoside, 1,3,29,31-Dotriacontanetetrol; (3R,29S,31R)-form, 29-Ketone, 1-O-α-D-mannopyranoside, Dragomabin, Dragonamide A, Dragonamide A; 2',3'-Didehydro, Dragonamide B, Dragonamide C, Dragonamide D, Dysidenamide, Dysidenin; N-De-Me, N12-Me, Dysidenin; N-De-Me, Dysidenin; 13-Demethyl, 5-epimer, Dysiherbaine, Echinenone; 3'-Hydroxy, Enkephalins, 13,16-Epoxy-7,12-dihydroxy-6,14-dioxo-3-cleroden-15-al; (7β,8βH,12R,13R)-form, 2-Ethyl-3-methyl-2-butenedioic acid; (Z)-form, Imide, Eucapsitrione, Euhalothece 362, Ferintoic acid A, Ferintoic acid B, Ferredoxin reductases; Ferredoxin-NADP(+) reductase, Fischambiguine A, Fischambiguine A; 13β-Chloro, 25α,26-epoxide, Fischerellin A, Fischerellin B, Fischerindole L, Fischerindole L; 10,11-Didehydro, Fischerindole L; 10-Epimer, Fischerindole L; 10-Epimer, dechloro, Fischerindole L; 10-Epimer, dechloro, isothiocyanate, Flexixanthin; 2'-Hydroxy, 2-O-α-L-fucopyranoside, Flexixanthin; 2'-Hydroxy, 2'-O-α-L-rhamnopyranoside, Fontonamide, Fontonamide; Decloro, Fuzanine A, Fuzanine A; 3',4'-Dihydro, Fuzanine A; 3,4'-Dihydro, 5'-ketone, Fuzanine A; 3-Epimer, Fuzanine A; 3-Epimer, 3',4'-dihydro, Fuzanine A, 3-Epimer, 3',4'-dihydro, 5'-ketone, Fuzanine C, Fuzanine C; 5'-Epimer, Fuzanine I, Galactosylacylglycerol O-acyltransferase, Gallinamide A, Georgamide, 2-O-Glucopyranosylglycerol; α-D-form, Glucosylglycerol 3-phosphatase, Glucosylglycerol phosphate synthase, Glutamate dehydrogenases; Glutamate dehydrogenase (NADP(+)), Glutamate synthases; Glutamate synthase (ferredoxin), Glycerol 1-alkanoates; Glycerol 1-hexadecanoate, 3-O-β-D-Galactopyranoside, Glycerol 1-alkanoates; Glycerol 1-(9-hexadecenoate), 3-O-β-D-Galactopyranoside, Glycerol 2-alkanoates; Glycerol 2-hexadecanoate, 1-O-[6-O-Hexadecanoyl-α-D-galactopyranosyl-(1→6)-β-D-galactopyranoside], Glycerol 1,2-dialkanoates; Glycerol 1,2-di-(9Z,12Z,15Z-octadecatrienoate), 3-O-β-D-Galactopyranoside, Glycerol 1,2-dialkanoates; Glycerol 1,2-di-(9Z,12Z,15Z-octadecatrienoate), 3-O-[α-D-Galactopyranosyl-(1→6)-β-D-galactopyranoside], Glycerol 1,2-dialkanoates; Glycerol 1-hexadecanoate 2-tetradecanoate, 3-O-β-D-Galactopyranoside, Glycerol 1,2-dialkanoates; Glycerol 1-hexadecanoate 2-tetradecanoate, 3-O-[α-D-Galactopyranosyl-(1→6)-β-D-galactopyranoside], Glycerol 1,2-dialkanoates; Glycerol 1-(9Z-hexadecenoate) 2-hexadecanoate, 3-O-β-D-Galactopyranoside, Glycerol 1,2-dialkanoates; Glycerol 1-(9Z-hexadecenoate) 2-tetradecanoate, 3-O-β-D-Galactopyranoside, Glycerol 1,2-dialkanoates; Glycerol 1-(9Z-hexadecenoate) 2-tetradecanoate, 3-O-[α-D-Galactopyranosyl-(1→6)-β-D-glucopyranoside], Glycerol 1,2-dialkanoates; Glycerol 1-(9Z,12Z-octadecadienoate) 2-hexadecanoate, 3-O-β-D-Galactopyranoside, Glycerol 1,2-dialkanoates; Glycerol 1-(9Z,12Z-octadecadienoate) 2-hexadecanoate, 3-O-[α-D-Galactopyranosyl-(1→6)-β-D-galactopyranoside], Glycerol 1,2-dialkanoates; Glycerol 1-(9Z,12Z-octadecadienoate) 2-(4Z-hexadecenoate), 3-O-β-D-Galactopyranoside, Glycerol 1,2-dialkanoates; Glycerol 1-(9Z,12Z-octadecadienoate) 2-(9E-hexadecenoate), 3-O-β-D-Galactopyranoside(2S-), Glycerol 1,2-dialkanoates; Glycerol 1-(9Z,12Z-octadecadienoate) 2-(9E-hexadecenoate), 3-O-[α-D-Galactopyranosyl-(1→6)-β-D-galactopyranoside], Glycerol 1,2-dialkanoates; Glycerol 1-(9Z,12Z-octadecadienoate) 2-(9Z-hexadecenoate), 3-O-β-D-Galactopyranoside(2S-), Glycerol 1,2-dialkanoates; Glycerol 1-(9Z,12Z-octadecadienoate) 2-tetradecanoate, 3-O-β-D-Galactopyranoside, Glycerol 1,2-dialkanoates; Glycerol 1-(9Z,12Z-octadecadienoate) 2-tetradecanoate, 3-O-[α-D-Galactopyranosyl-(1→6)-β-D-galactopyranoside], Glycerol 1,2-dialkanoates; Glycerol 1-(9Z,12Z,15Z-octadecatrienoate) 2-hexadecanoate, 3-O-β-D-Galactopyranoside, Glycerol 1,2-dialkanoates; Glycerol 1-(9Z,12Z,15Z-octadecatrienoate) 2-hexadecanoate, 3-O-[α-D-Galactopyranosyl-(1→6)-β-D-galactopyranoside], Glycerol 1,2-dialkanoates; Glycerol 1-(9Z,12Z,15Z-octadecatrienoate) 2-(9E-hexadecenoate), 3-O-β-D-Galactopyranoside, Glycerol 1,2-dialkanoates; Glycerol 1-(9Z,12Z,15Z-octadecatrienoate) 2-(9Z-hexadecenoate), 3-O-β-D-Galactopyranoside, Glycerol 1,2-dialkanoates; Glycerol 1-(9Z,12Z,15Z-octadecatrienoate) 2-(9Z,12Z-octadecadientoate), 3-O-[α-D-Galactopyranosyl-(1→6)-β-D-galactopyranoside],
Glycerol 1,2-dialkanoates; Glycerol 1-(9Z,12Z,15Z-octadecatrienoate) 2-tetradecanoate, 3-O-β-D-Galactopyranoside, Glycerol 1,2-dialkanoates; Glycerol 1-(9Z,12Z,15Z-octadecatrienoate) 2-tetradecanoate, 3-O-[α-D-Galactopyranosyl-(1→6)-β-D-galactopyranoside], Glycerol 1,2-dialkanoates; Glycerol 1-(9Z-octadecenoate) 2-(9Z-hexadecenoate), 3-O-β-D-Galactopyranoside, Glycerol 1,2-dialkanoates; Glycerol 1-(9Z-octadecenoate) 2-tetradecanoate, 3-O-β-D-Galactopyranoside, Glycerol 1,2-dialkanoates; Glycerol 1-(9Z-octadecenoate) 2-tetradecanoate, 3-O-[α-D-Galactopyranosyl-(1→6)-β-D-glucopyranoside], Grassypeptolide A, Grassypeptolide A; 28-Epimer, Grassypeptolide B, Grassypeptolide F, Grassypeptolide G, Grassystatin A, Grassystatin B, Grassystatin C, Grenadamide B, Grenadamide B; 16-Chloro(E-), Guamamide, Guineamide A, Guineamide B, Guineamide C, Guineamide D, Guineamide E, Guineamide F, Hantupeptin A, Hantupeptin A; 7',8'-Dihydro, Hantupeptin A; 7',7',8',8'-Tetrahydro Hapalindole A, Hapalindole A; Dechloro, Hapalindole A; Dechloro, 8β-hydroxy, isothiocyanate, Hapalindole A; Dechloro, isothiocyanate, Hapalindole A; 10,10a-Didehydro, Hapalindole A; 6a,10a-Didehydro, Hapalindole A; 6a,9-Diepimer, Hapalindole A; 9,10a-Diepimer, Hapalindole A; 10a-Epimer, Hapalindole A; 6a-Epimer, Hapalindole A; 9-Epimer, Hapalindole A; 10a-Epimer, dechloro, Hapalindole A; 9-Epimer, dechloro, Hapalindole A; ?-Epimer, 20,21-epoxide, Hapalindole A, 20,21-Epoxide, Hapalindole A; 10aβ-Hydroxy, Hapalindole A, Isothiocyanate, Hapalindole E, Hapalindole E; Dechloro, Hapalindole E; Dechloro, isothiocyanate, Hapalindole E; 1',2'-Diepimer, dechloro, isothiocyanate, Hapalindole E, 5'-Epimer, Hapalindole E; 5'-Epimer, dechloro, Hapalindole E; 5'-Epimer, dechloro, isothiocyanate, Hapalindole E; 5'-Epimer, isothiocyanate, Hapalindole E; Isothiocyanate, Hapalindole E; 1',2',5'-

Triepimer, dechloro, Hapalindole T, Hapalindolinone A, Hapalindolinone A; Dechloro, Hapalonamide G, Hapalonamide G; 10,15-Diepimer, dechloro, Hapalonamide G; 10β-Hydroxy, Hapalosin, Hassallidin A, Hassallidin A; 39-O-α-L-Rhamnopyranoside, Hectochlorin, 1-Hentriacontene-4,6,8,10,12,14,16,18,20,22,24,26-dodecol; (4S,6S,8S,10S,12S,14S,16R,18R,20R,22R,24R,26R)-form, Dodeca-Me ether, 1-Heptacosene-4,6,8,10,12,14,16,18,20,22-decol; (4S,6S,8S,10S12S,14R,16R,18R,20R,22R)-form, Deca-Me ether, 1-Heptacosene-4,6,8,10,12,14,16,18,24-nonol; (4S,6S,8S,10S,12R,14R,16R,18R24R)-form, Nona-Me ether, 1-Heptadecene-4,6,8,10,12-pentol; (4S,6S,8R,10R,12R)-form, Penta-Me ether, 6-Heptadecyl-1,2,4-benzenetriol; 2,4-Di-Me ether, 2-Heptyl-1-cyclopropanepropanoic acid; (1R,2R)-form, 2-Phenylethylamide, 2-Heptyl-1-cyclopropanepropanoic acid; (1R*,2R*)-form, (5-Acetoxy-4-bromo-1,3-pentadienyl) ester (Z,Z-), 2-Heptyl-1-cyclopropanepropanoic acid; (1R*,2R*)-form, 5-Acetoxy-1,3-pentadienyl ester (1Z,3E-), Herbamide B, 2,2',3,4',5,5'-Hexabromo-1,3'-bi-1H-indole, 1,1,1,15,15,15-Hexachloro-3,12-pentadecadiyn-8-amine; (+)-form, N—Ac, 1,1,1,15,15,15-Hexachloro-3,12-pentadecadiyn-8-amine; (+)-form, Dechloro, N—Ac, 1,1,1,15,15,15-Hexachloro-3,12-pentadecadiyn-8-amine; (+)-form, 15-Dechloro, 3,3,4,4-tetrahydro, N—Ac, 1,1,1,15,15,15-Hexachloro-3,12-pentadecadiyn-8-amine; (+)-form, 1,15-Didechloro, 3,3,4,4-tetrahydro, N—Ac, 1,3,25-Hexacosanetriol; (3R,25R)-form, 1-O-α-D-Glucopyranoside, 1,3,25-Hexacosanetriol; (3R,25R)-form, 3-Ketone, 1-O-α-D-glucopyranoside, 1,3,25-Hexacosanetriol; (3S,25R)-form, 1-O-α-D-Glucopyranoside, 4,9-Hexadecadienoic acid; (Z,Z)-form, 4-Hexadecenoic acid; (Z)-form, 9-Hexadecenoic acid; (E)-form, Hofmannolin, Hoiamide A, Hoiamide B, Hoiamide C, Homoanatoxin a, Homoanatoxin a; 4S-Hydroxy, 131-A-Homo-131-A-oxa-132-hydroxychlorophyll a, Hormothamnione, 6-Hydroxy-4,8-dimethylquinoline, 6-Hydroxy-4,8-dimethylquinoline; O-(2,4-Di-O-methyl-β-D-xylopyranoside), 7-Hydroxy-4-dodecenoic acid; (4E,7S)-form, Me ether, (2-Hydroxyethyl)phosphonic acid; Hexadecanoyl, (2-Hydroxyethyl)phosphonic acid; 7,10,13-Hexadecatrienoyl, (2-Hydroxyethyl)phosphonic acid; 9,12,15-Octadecatrienoyl, (2-Hydroxyethyl)phosphonic acid; Tetradecanoyl, Hydroxyhomodolabellin 5-Hydroxy-5-(hydroxymethyl)hexadecanoic acid; (R)-form, 7-Hydroxy-9-methyl-4,8-hexadecadienoic acid; (4E,7ξ,8E)-form, Me ether, 4-Hydroxy-7-methyl-1-indanone, N-(1-Hydroxymethyl-2-methoxyethyl)-7-methoxy-4-eicosenamide; (1'R,4E,7S)-form, N-(1-Hydroxymethyl-2-methoxyethyl)-7-methoxy-4-eicosenamide; (1'R,4E,7S)-form, 2'-Ac, 9-Hydroxy-10,12-octadecadienoic acid; (9R,10E,12Z)-form, 9-Hydroxy-10,12,15-octadecatrienoic acid; (9R,10E,12Z,15Z)-form, 1-(4-Hydroxyphenyl)-3H-benzo[a]pyrrolo[2,3-c]phenazine, 11-Hydroxysaxitoxin; 11α-form, Decarbamoyl, 13-Ac, 11-O-sulfate, 11-Hydroxysaxitoxin; 11β-form, Decarbamoyl, 13-Ac, 11-O-sulfate, 11-Hydroxysaxitoxin; 11β-form, 12-Deoxy, decarbamoyl, O13-Ac, 11-O-sulfate, 7-Hydroxy-4-tetradecenoic acid; (4E,7S)-form, Me ether, Ichthyopeptin A, Ichthyopeptin B, 7H-Indolo[3,2-j]phenanthridine-7,13(12H)-dione, 7H-Indolo[3,2-j]phenanthridine-7,13(12H)-dione; N5-Oxide, Inosine kinase, Insulapeptolide A, Insulapeptolide A; Homologue (R=CH3), Insulapeptolide A; Homologue (R=CH3), 4"-Me ether, Insulapeptolide A, 4"-Me ether, Insulapeptolide F, Insulapeptolide F; 4"-Deoxy, Insulapeptolide F; Homologue (R=CH3), Insulapeptolide F; Homologue (R=CH3), 4"-deoxy, 18-Isocyano-4,6,8,10,12-pentamethoxy-13,15-dimethyl-1,13,15-nonadecatriene, 16-Isocyano-4,6,8,10-tetramethoxy-11,13-dimethyl-1,11,13,15-heptadecatetraene; (11E,13E,15E,all-S)-form, 16-Isocyano-4,6,8,10-tetramethoxy-11,13-dimethyl-1,11,13,15-heptadecatetraene; (11E,13Z,15E,all-S)-form, 16-Isocyano-4,6,8,10-tetramethoxy-11,13-dimethyl-1,11,13,15-heptadecatetraene; (11E,13E,15Z,all-S)-form, 16-Isocyano-4,6,8,10-tetramethoxy-11,13-dimethyl-1,11,13-heptadecatriene; (11E,13E,all-S)-form, 16-Isocyano-4,6,8,10-tetramethoxy-13-methyl-11-methylene-1,12,15-heptadecatriene; (12Z,15E,all-S)-form, Itralamide A, Itralamide B, Jamaicamide A, Jamaicamide A; Debromo, Jamaicamide A; Debromo, 19,20-dihydro, Kalkipyrone, Kalkitoxin, Kasumigamide, Kawaguchipeptin A, Kawaguchipeptin B, Kempopeptin A, Kempopeptin B, Kifunensine, Kimorexin A, Kororamide, Koshikalide, Lagunamide A, Lagunamide A; 40,41-Didehydro(E), Lagunamide C, Laingolide, Laingolide; 4-Demethyl, Laingolide B, Largamide A, Largamide B, Largamide C, Largamide D, Largamide D; 3"-Chloro analogue, Largamide D oxazolidine, Largamide F, Largamide G, Largamide H, Largazole, Laxaphycin A, Laxaphycin A; (Z)-Isomer, Laxaphycin B, Laxaphycin B; 5-Epimer, 3"-deoxy, Laxaphycin B; 4""R-Hydroxy, Laxaphycin C, Laxaphycin D, Laxaphycin E, Lobocyclamide A, Lobocyclamide B, Lobocyclamide C, Louludinium(1+), Lyngbouilloside, Lyngbyabellin A, Lyngbyabellin A; 27-Deoxy, Lyngbyabellin B, Lyngbyabellin C, Lyngbyabellin D, Lyngbyabellin E, Lyngbyabellin E; 21-Deoxy, Lyngbyabellin F, Lyngbyabellin F; 21-Deoxy, Lyngbyabellin G, Lyngbyabellin J, Lyngbyaloside, Lyngbyaloside; 2-Epimer, Lyngbyaloside B, Lyngbyaloside B; 6-Demethyl, O2-Me, Lyngbyaloside B; 18Z-Isomer, 6-demethyl, O2-Me, Lyngbyapeptin A, Lyngbyapeptin A; 15-O-De-Me, Lyngbyapeptin B, Lyngbyapeptin C, Lyngbyapeptin D, Lyngbyastatin 4, Lyngbyastatin 4; O-Desulfo, Lyngbyastatin 4; 11-Me ether, Lyngbyastatin 7, Lyngbyastatin 8, Lyngbyastatin 8; 30-Bromo, N-de-Ac, N-butanoyl, Lyngbyastatin 8; N-De-Ac, N-butanoyl, Lyngbyatoxin A, Lyngbyatoxin A; Δ24-Isomer, 26-hydroxy, Lyngbyatoxin A; Δ26-Isomer, 24ξ-hydroxy, Lyngbyazothrin C, Lyngbyazothrin C; 5"-Deacyl, Lyngbyazothrin C; 4""-Demethoxy, Lyngbyazothrin C; 4""-Demethoxy, 5"-deacyl, Maculalactone E, Maculalactone E; 4-Deoxy, Maculalactone E; 4-Epimer, 5-ketone, Maculalactone E; 3α,3aα-Epoxide, Maculalactone E; 3α,3aα-Epoxide, 1'ξ-hydroxy, Maculalactone I, Maculalactone I; 5-Ketone, Maculalactone J, Maculalactone L, Maculalactone M, Madangolide, Magnesium-protoporphyrin IX methyltransferase, Magnesium-protoporphyrin IX monomethyl ester (oxidative) cyclase, Majusculamide A, Majusculamide A; 2-Epimer, Majusculamide C, Majusculamide C; Demethoxy, Majusculamide C; 57-Nor, Majusculamide D, Majusculamide D; 4'-Deoxy, Majusculoic acid, Malevamide A, Malevamide B, Malevamide C, Malevamide D, Malyngamide 2, Malyngamide 3, Malyngamide A, Malyngamide A; 2'Z-Isomer, Malyngamide B, Malyngamide B; 2'Z-Isomer, Malyngamide E, Malyngamide E; 1',2'-Dihydro, 2'-hydroxy, Malyngamide F, Malyngamide F; Ac, Malyngamide G, Malyngamide H, Malyngamide I, Malyngamide J, Malyngamide L, Malyngamide Q, Malyngamide Q; 7-N-Me, Malyngamide T, Malyngamide U, Malyngamide U; 8-Epimer, Malyngamide W, Malyngolide; (3R,6S)-form, Malyngolide dimer, *Nostoc commune* Meroterpenoid, 3-Methoxy-2-methyl-1-phenyl-9H-carbazole, 3-Methoxy-2-methyl-1-phenyl-9H-carbazole; 6-Chloro, 2-Methyl-32,33,34,35-bacteriohopanetetrol; (2β,32R,33R,34S)-form, 2-Methyl-32,33,34,35-bacteriohopanetetrol; (2β,32R,33R,34S)-form, 35-O-β-D-Galacturonopyranoside, 2-Methyl-32,33,34,35-bacteriohopanetetrol; (2β,32R,33R,34S)-form, 35-O-α-D-Glucuronopyranoside, 2-Methyl-32,33,34,35-bacteriohopanetetrol; (2β,32ξ,33ξ,34ξ)-form, 35-O-α-D-Altruronopyranoside, 2-Methyl-32,33,34,35-bacteriohopanetetrol; (2β,32ξ,33ξ,34ξ)-form, 35-O-(3,6-Anhydro-β-D-galacturonopyranoside), 2-Methyl-2,6-eicosadienoic acid; (2E,6E)-form, (2-Hydroxyethyl)amide, 2-Methyl-2,6-eicosadienoic acid; (2E,6E)-form, (2-Acetoxyethyl)amide, 2-Methylheptadecane, 6-Methylheptadecane, 7-Methylheptadecane, 7-Methyl-1H-indole-3-carboxaldehyde; N-Me, 2-Methyl-29-(1,2,3,4,5-pentahydroxypentyl)hopane; (2β,22ξ,31S,32R,33S,34R)-form, 2-Methyl-29-(2,3,4,5-tetrahydroxypentyl)-29-hopanol; (2β,22ξ,29R,32R,33R,34R)-form, Microcin SF 608, Microcin SF 608; 2,2',2",3a,7a-Pentaepimer, Microcin SF 608; 2,2',2",3a,7a-Pentaepimer, 2"-Ac, Microcin SF 608; 2,2',3a,7a-Tetraepimer, Microcolin A, Microcolin A; Deoxy, Microcolin A; Deoxy, O-de-Ac, Microcydamide A, Microcydamide A; 21-Epimer, Microcydamide 7806A, Microcydamide 7806B, Microcydamide GL616, Microcyclamide GL628, Microcyclamide GL628; O-De-Me, Microcydamide GL546A, Microcyclamide GL546A; 21-Epimer, Microcydamide GL614A, Microcydamide GL614A; 21-Epimer, Microcystin, Microcystin; Microcystin EE, N7-De-Me, 4-Me ester, Microcystin; Microcystin EE, N7-De-Me, 2,4-di-Me ester, Microcystin; Microcystin EE, 3-D-Aspartic acid analogue, N7-de-Me, 4-Me ester, Microcystin; Microcystin EE, 3-D-Aspartic acid analogue, N7-de-Me, 2,4-di-Me ester, Microcystin; Microcystin EE, 7-L-Serine analogue, N7-de-Me, 4-Me ester, Microcystin; Microcystin EE, 7-L-Serine analogue, NT-de-Me, 2,4-di-Me ester, Microcystin; Microcystin EE, 3-D-Aspartic acid analogue, 7-L-serine analogue, N7-de-Me, 2,4-di-Me ester, Microcystin; Microcystin LR, 1-D-Leucine analogue, Microcystin; Microcystin LR, 3-D-Aspartic acid analogue, Microcystin; Microcystin LR, 3-D-Aspartic acid analogue, N7-de-Me, Microcystin; Microcystin LR, O-De-Me, Microcystin; Microcystin LR, N7-De-Me, Microcystin; Microcystin LR, 7-L-Serine analogue, N7-de-Me, Microcystin; Microcystin LR, 7-L-Serine analogue, Microcystin; Microcystin LR, 2-L-Homoisoleucine analogue, Microcystin; Microcystin LR, 7-L-Lanthionine analogue. Microcystin; Microcystin LR, 4-L-Phenylalanine analogue, Microcystin; Microcystin LR, 4-L-Tryptophan analogue, Microcystin; Microcystin RR, Microcystin; Microcystin RR, N7-De-Me, Microcystin; Microcystin RR, 3-D-Aspartic acid analogue, Microcystin; Microcystin RR, 3-D-Aspartic acid analogue, N7-de-Me, Microcystin; Microcystin RR, 7-L-Serine analogue, Microcystin; Microcystin RR, 3-D-Aspartic acid, 7-(N-methyl-L-serine) analogue, Microcystin; Microcystin RR, 3-D-Aspartic acid analogue, 6-Me ester, Microcystin; Microcystin YR, Microcystin; Microcystin YR, 2-[2-Amino-3-(4-hydroxy-2-cyclohexen-1-yl)propanoic acid] analogue, [D-Asp3,(E)-Dhb7]Microcystin HilR, (ADMAdda5)Microcystins, Microginin, Microginin 478, Microginin 299A, Microginin 299A; 1-Chloro, Microginin 299A; 1-Chloro, detyrosyl, Microginin 299A; Dechloro, Microginin 51A, Microginin 51A; N3-Me, Microginin 91A, Microginin 91A; 10-Chloro, Microginin 99A, Microginin 99A; 1-Chloro, Microginin AL584, Microginin 91C, Microginin 91C; 10-Chloro, Microginin 91C; 10,10-Dichloro, Microginin FR1, Microginin GH787, Microginin SD755, Microginin SD755; N3-De-Me, Microguanidine AL772, Micromide, Micropeptin 103, Micropeptin 90, Micropeptin A, Micropeptin A; N-Deoctanoyl, Nω-hexanoyl, Micropeptin 478A, Micropeptin 478A; Dechloro, Micropeptin 478A; Dechloro, 4"-deoxy, O-desulfo, Micropeptin 478A; Dechloro, 4"-deoxy, O-desulfo, 2'-O-sulfate, Micropeptin 478A; Dechloro, 4"-deoxy, 6""-Me ether, Micropeptin 478A; Dechloro, 4"-deoxy, 6""-Me ether, N-deacyl, Micropeptin 478A; Dechloro, 4"-deoxy, 6""-Me ether, O-desulfo, Micropeptin 478A; Dechloro, 4"-deoxy, 6""-Me ether, O-desulfo, 2'-O-sulfate, Micropeptin 478A; Dechloro, 4"-deoxy, 6""-Me ether, 2'-O-sulfate, Micropeptin 478A; Dechloro, 4"-deoxy, 2'-O-sulfate, Micropeptin 478A; Dechloro, 2'-O-sulfate, Micropeptin 478A; O-Desulfo, Micropeptin 478A; Lower homologue (R=—CH(CH3)2), 4",6""-di-Me ether, O-desulfo, Micropeptin 478A; Lower homologue (R=—CH(CH3)2), 4"-Me ether, Micropeptin 478A; Lower homologue (R=—CH(CH3)2), 4"-Me ether, O-desulfo, Micropeptin 478A; Lower homologue (R=—CH(CH3)2), 2'-O-sulfate, Micropeptin 478A; 4"-Me ether, Micropeptin 478A; 4"-Me ether, 2'-O-sulfate, Micropeptin 478A; 2'-O-Sulfate, Micropeptin 88A, Micropeptin 88B, Micropeptin C, Micropeptin 88C, Micropeptin 88C; 5"-Me ester, Micropeptin D, Micropeptin 88D, Micropeptin DR1006, Micropeptin DR1060, Micropeptin DR1060; 4",5",6",7"-Tetradehydro, Micropeptin E, Micropeptin 88E, Micropeptin EI 992, Micropeptin EI 992; N-Debutanoyl, N—Ac, Micropeptin F, Micropeptin GH979, Micropeptin GH979; 4"-Amide, Micropeptin HA983, Micropeptin K 139, Micropeptin MM836, Micropeptin MM836; 28-Hydroxy, 48-sulfo, Micropeptin MM836; 39-Me ether, Micropeptin MM836; 48-Sulfo, Micropeptin MM978, Micropeptin 88N, Micropeptin SD1002, Micropeptin SD944, Micropeptin SD979, Micropeptin SD999, Micropeptin SF909, Micropeptin SF995, Micropeptin T1, Micropeptin T2, Micropeptin T20, Micropeptin 88Y, Microphycin AL828, Microviridin A, Microviridin B, Microviridin C, Microviridin D, Microviridin E, Microviridin F, Microviridin H, Microviridin H; (1'"→3")-Lactone, O-de-Me, Microviridin I, Microviridin SD1684, Microviridin SD1684; Parent acid, [Glu-5→Ser][Asp→Thr] dilactone, Microviridin SD1684; Parent acid, [Glu-5→Ser] lactone, Microvirin, Microvirin, Minutissamide A, Minutissamide A; 12'-Chloro, Minutissamide C, Minutissamide C; 14'ξ-Alcohol, Mirabazole A; 4',5'-Didehydro, Mirabazole B, Mirabazole C, Mirabimide E, Mirabimides; Mirabimide A, Mirabimides; Mirabimide B, Mirabimides; Mirabimide C, Mirabimides; Mirabimide D, Molassamide, Mozamide A; Deoxy, Mozamide B; Deoxy, Mueggelone, Muscoride A, Mytilin A, Myxol; 2'-O-6-Deoxy-α-L-glucoside, Myxol; 2'-O-(2,4-Di-O-methyl-α-L-fucopyranoside), Myxol; 2'-O-α-L-Fucopyranoside, Myxol; 2'-O-(3-O-Methyl-α-L-fucoside), Myxol; 2'-O-α-L-Rhamnopyranoside, Nakienone A, Nakienone B, Nakienone C, Nakitriol, Nhatrangin A, Nhatrangin A; 9-Bromo, Nodulapeptin B, Nodulapeptin B; S-Oxide, Nodularin, Nodularin; 9-O-De-Me, Nodularin; 3'-Demethyl, Nodularin; Homoarginine analogue, Nodularin; 6Z-Isomer, 1-Nonacosene-4,6,8,10,12,14,16,18,20,22,24-undecol; (4S,6S,8S,10S,12S,14R,16R,18R,20R,22R,24R)-form, Undeca-Me ether, 1-Nonadecene-4,6,8,10,12,14-hexol; (4S,6S,8S,10R,12R,14R)-form, Hexa-Me ether, 20-Nor-5,7,9,11,13-abietapentaene-3,12-diol; 3α-form, 3-Ac, 20-Nor-5,7,9,11,13-abietapentaen-3-ol; 3α-form, Ac, Noscomin, Nostocine A, Nostoclide I, Nostoclide I; Monodechloro, Nostocyclamide, Nostocyclamide M, Nostocyclin, Nostocyclopeptide A1, Nostocyclopeptide A2, Nostocyclopeptide M1, Nostocyclophane C, Nostocyclophane C; 1-Me ether, Nostocyclophane C; 1-Me ether, 13,26-di-O-β-D-glucopyranoside, Nostocyclophane C; 1-Me ether, 13-O-β-D-glucopyranoside, Nostocyclyne A, Nostodione A, Nostoflan, Nostofungicidine, Nostoginin BN578, Nostopeptin A, Nostopeptin A; N-Debutanoyl, N—Ac, Nostopeptin BN920, Nostopeptin BN920; 3'-Chloro, Nostopeptolide A1, Nostopeptolide A1; 4'-Epimer, Nostopeptolide A2, Nostophycin, Nostotrebin 6, Nostoxanthin, Nostoxanthin; 2'-Deoxy, Obyanamide, 1,3,25,27-Octacosanetetrol; (3R,25S, 27R)-form, 1-O-α-D-Glucopyranoside, 1,3,25,27-Octacosanetetrol; (3R,25S,27R)-form, 3-Ketone, 1-O-α-D-glucopyranoside, 1,3,25,27-Octacosanetetrol; (3R,25S, 27R)-form, 1-O-α-D-Mannopyranoside, 1,3,25,27-Octacosanetetrol; (3R,25S,27R)-form, 25-Ketone, 1-O-α-D-glucopyranoside, 1,3,25,27-Octacosanetetrol; (3R,25S, 27R)-form, 25-Ketone, 1-O-α-D-mannopyranoside, 1,3,27-Octacosanetriol; (3S,27R)-form, 1-O-α-D-Glucopyranoside, 1,3,27-Octacosanetriol; (3R,27R)-form, 1-O-α-D-Glucopyranoside, 1,3,27-Octacosanetriol; (3R, 27R)-form, 27-Ketone, 1-O-α-D-glucopyranoside, 1,3,27-Octacosanetriol; (3R,27R)-form, 1-O-α-D-Galactopyranoside, 1,3,27-Octacosanetriol; (3R,27R)-form, 1-O-β-D-Glucopyranoside, 1,3,27-Octacosanetriol; (3R,27R)-form, 3-Ketone, 1-O-α-D-galactopyranoside, 1,3,27-Octacosanetriol; (3R,27R)-form, 3-Ketone, 1-O-α-D-glucopyranoside, 11-Octadecenoic acid; (Z)-form, Oscllacyclin, Oscillaginin A, Oscillaginin A; Dechloro, Oscillamide B, Oscillamide C, Oscillamide H, Oscillamide Y, Oscillapeptilide 97A, Oscillapeptilide 97A; O-De-Me, Oscillapeptin A, Oscillapeptin A; 72-Demethoxy, Oscillapeptin A; 75-Methyl, Oscillapeptin C, Oscillapeptin C; 11-O-De-Me, 28-O-sulfate, Oscillapeptin F, Oscillapeptin G, Oscillapeptin J, Oscillarin, Oscillariolide, Oscillatorin, Oscillatoxin A, Oscillatoxin A; 17-Bromo, Oscillatoxin A; 3-Deoxy, 3,4-didehydro, Oscillatoxin A; 17,19-Dibromo, Oscillatoxin B1, Oscillatoxin B1; 4-Epimer, Oscillatoxin D, Oscillatoxin D; 30β-Methyl, Oscillol; 2,2'-Bis-O-(3-O-methyl-α-L-fucopyranoside), Oscillol; 2,2'-Di-O-β-L-rhamnopyranoside, 2-Oxo-1,3-dioxolane-4,4-diacetic acid; Di-Me ester, Pahayokolide A, Pahayokolide A; 56-O-Deacyl, Palauamide, Palauimide, Palmyramide A, Palmyrolide A, Palmyrrolinone, Palythine; 3-N-(1Z-Propenyl), Parsiguine, 1-Pentacosene-4,6,8,10,12, 14,16,18,20-nonol; (4S,6S,8S,10S,12R,14R,16R,18R)-form, Nona-Me ether, 1-Pentacosene-4,6,8,10,12,14,16,18, 22-nonol; (4S,6S,8S,10S,12R,14R,16R,18R,22R)-form, Nona-Me ether, 1-Pentacosene-4,6,8,10,12,14,16,22-octol; (4S,6S,8S,10R,12R,14R,16R,22R)-form, Octa-Me ether, Pentadecane, 6-Pentadecyl-1,2,4-benzenetriol; 2,4-Di-Me ether, 29-(1,2,3,4,5-Pentahydroxypentyl)hopane; (22ξ,31S, 32R,33S,34R)-form, 2-Phenylethylamine; N-(7-Methoxy-4-tetradecenoyl)(4E,7S-), Phormidolide, Phosalacine, Phosphoribulokinase, Phycocyanobilin, Phycoerythrobilin, Pitiamide A, Pitipeptolide A, Pitipeptolide A; N-De-Me, Pitipeptolide A; 7,8-Dihydro, Pitipeptolide A; 7,7,8,8-Tetrahydro, Pitipeptolide E, Pitipeptolide F, Planktocyclin, Planktopeptin BL 1061, Planktopeptin BL 1125, Planktopeptin BL 843, Plectaniaxanthin; (S)-form, 2'-O-α-L-Rhamropyranoside, Plectaniaxanthin; (S)-form, 2'-O-α-L-Fucopyranoside, Plectaniaxanthin; (S)-form, 2'-O-(2,4-Di-O-methyl-α-L-fucopyranoside), Pompanopeptin A, Pompanopeptin B, Porphyra 334, Porpoisamide A, Porpoisamide A; 2-Epimer, Prenostodione, Prenylagaramide A, Prenylagaramide B, Propenediester, Propioxatin A, Propioxatin B, Pukeleimide; (E)-form, Pukeleimide; (E)-form, Me ether, Pukeleimide; (E)-form, 9,10-Dihydro, 10-hydroxy, Pukeleimide; (E)-form, 9,10-Dihydro, 10-methoxy, Pukeleimide; (E)-form, Δ10,13-Isomer, 13-deoxy, Pukeleimide; (Z)-form, Pukeleimide; (Z)-form, Me ether, Puwainaphycin A, Puwainaphycin B, Puwainaphycin C, Puwainaphycin D, Puwainaphycin E, 12-(2-Pyridinyl)-6,8-dodecadien-2-ol; (2R,6E,8E)-form, 12-(2-Pyridinyl)-6,8-dodecadien-2-ol; (2R,6E,8E)-form, Ac, 2-Pyrrolidinedione; Enol-form, Me ether, 2,4-Pyrrolidinedione; Enol-form, Me ether, N—Ac, Radiosumin, Radiosumin; 5,6-Didehydro, Radiosumin; 5,6-Didehydro, N4'-Me, Raocyclamide A, Raocyclamide B, Respirantin, Respirantin; N-Deformyl, Respirantin; Lower homologue (R=—CH (CH3)2), Retinoic acid; (7E,9E,11E,13E)-form, 7-Hydroxy (enol), Ribonuclease alpha, Sangivamycic acid; Nitrile, 5'-O-α-D-glucopyranoside, Saxitoxin; Decarbamoyl, 13-Ac, Saxitoxin; 12-Deoxy(12S-), decarbamoyl, Saxitoxin; 12-Deoxy(12S-), decarbamoyl, 13-O—Ac, Saxitoxin; N1-Hydroxy, Schizopeptin 791, Schizothrin A, Scyptolin A, Scyptolin A; 3"-O—(N-Butanoyl-L-alanyl), Scytonemide A, Scytonemide B, Scytonemin, Scytonemin A, Scytonine, Scytophycin C, Scytophycin C; 19-O-De-Me, Scytophycin C; 16,34-Didehydro, 16α,34-epoxide, Scytophycin C; 16,34-Didehydro, 16α,34-epoxide, 27ξ-alcohol, Scytophycin C; 6β,34-Dihydroxy, 7-Me ether, Scytophycin C; 16-Hydroxy, Scytophycin C; 34-Hydroxy, Scytophycin C; 6ξ-Hydroxy, 16,34-didehydro, 16α,34-epoxide, Scytophycin C; 6S-Hydroxy, 16,34-didehydro, 16α,34-epoxide, O7-Me, Scytoscalarol, Scytovirin, Seco[D-Asp3]microcystin RR, Semiplenamide C, Semiplenamide D, Semiplenamide E, Semiplenamide E; 2R*,3S*-Epoxide, Semiplenamide E; 2R*,3S*-Epoxide, O-de-Ac, Sepiapterin; (S)-form, Deoxy, Somamide A, Somamide B, Somocystinamide A, Spiroidesin, Spirulan, Spumigin B1, Spumigin B1; 1'-Alcohol, Spumigin B1; 2'-Epimer, Spumigin C, Stigmast-7-en-3-ol; (3β,5α,24S)-form, Suomilide, Swinholide A; 16-Demethyl, 7,7'-bis-O-(2,3-di-O-methyl-β-L-lyxopyranoside), Swinholide A; 16,16'-Didemethyl, 7,7'-bis-O-(2,3-di-O-methyl-β-L-lyxopyranoside) Symplocamide A, Symplostatin 2, Symplostatin 3, Synechobactin A, Synechobactin A; N1-Deacyl, N1-decanoyl, Synechobactin A; N1-Deacyl, N1-octanoyl, Synechoxanthin, Tanikolide dimer, Tantazole A, Tantazole A; 4"-Epimer, Tantazole B, Tantazole F, Tasiamide A, Tasiamide B, Tasihalide A, Tasihalide A; 7-Ac, Tasipeptin A, Tasipeptin A; N-Deacyl, N-butanoyl, Taveuniamide E, Taveuniamide E; 1-Chloro, 1,2-dihydro, Taveuniamide E; 1-Chloro, 12,12,13,13,14,15-hexahydro, Taveuniamide E; 1-Chloro, 1,2,3E,4-tetrahydro, Taveuniamide E; 12,12,13,13,14,15-Hexahydro, Tenuecyclamide A, Tenuecyclamide A; 12-Epimer, Tenuecyclamide C, Tenuecyclamide C; 14-S-Oxide, 2,2',5,5'-Tetrabromo-3,3'-bi-1H-indole, 2,2',6,6'-Tetrabromo-3,3'-bi-1H-indole, 2,3',5,5'-Tetrabromo-7'-methoxy-3,4'-bi-1H-indole; (+)-form, 2,3',5,5'-Tetrabromo-7'-methoxy-3,4'-bi-1H-indole; (+)-form, 2-Debromo, 2,3'5,5'-Tetrabromo-7'-methoxy-3,4'-bi-1H-indole; (+)-form, 3'-Debromo, 3,3',5,5'-Tetrabromo-7'-methoxy-1,4'-bi-1H-indole, 4,5,6,7-Tetrahydro-4,5-dihydroxy-1H-indole-3-carboxaldehyde; (4R*,5R*)-form, 5-Ac, Tetrahydro-6-hydroxymethyl-6-undecyl-2H-pyran-2-one; (R)-form, Tetrahydro-3-hydroxy-5-oxo-3-furanacetic acid; (ξ)-form, Me ester, 29-(2,3,4,5-Tetrahydroxypentyl)-29-hopanol; (22ξ,29R,32R,33R,34R)-form, Tetramethoxyscytonemin, Tetramethoxyscytonemin; 3,9-Didemethoxy, 3,9-didehydro, Thienamycin; 6,8-Diepimer, N—Ac, Thienamycin; 6,8-Diepimer, N—Ac, O-sulfate, Thienamycin; 6,8-Diepimer, 1',2'-didehydro, N—Ac, Thienamycin; 6,8-Diepimer, 1',2'E-didehydro, N—Ac, O-sulfate, Thienamycin; 6,8-Diepimer, 1',2'Z-didehydro, N—Ac, O-sulfate, Thiol sulfotransferase, Thiopalmyrone, Thiosulfate-dithiol sulfurtransferase, Tiglicamide A, Tiglicamide B, Tiglicamide C, Tjipanazole J, Tolybyssidin A, Tolybyssidin B, Tolypodiol, Tolypophycin, Tolyporphin D, Tolyporphin D; 2A-Ac, Tolyporphin D; 2A,2B-Di-Ac, Tolyporphin D; 2B—Ac, Tolyporphin D; 7,17-Bisdeglycosyl, 7-acetoxy, 17-hydroxy, Tolyporphin D; 7,17-Bisdeglycosyl, 7,17-diacetoxy, Tolyporphin D; 7,17-Bisdeglycosyl, 7-hydroxy, 17-acetoxy, Tolyporphin D; 7-Deglycosyl, 7-acetoxy, 2B—Ac, Tolyporphin D; 7-Deglycosyl, 7-hydroxy, 2B—Ac, Tolyporphin J, Tolyporphin K, 1,3,27,29-Triacontanetetrol; (3R,27S,29R)-form, 1-O-α-D-Galactopyranoside, 1,3,27,29-Triacontanetetrol; (3R,27S,29R)-form, 1-O-α-D-Glucopyranoside, 1,3,27,29-Triacontanetetrol; (3R, 27S,29R)-form, 3-Ketone, 1-O-α-D-galactopyranoside, 1,3, 27,29-Triacontanetetrol; (3R,27S,29R)-form, 3-Ketone, 1-O-α-D-glucopyranoside, 1,3,27,29-Triacontanetetrol; (3R,27S,29R)-form, 27-Ketone, 1-O-α-D-glucopyranoside, 3,4,5-Tribenzyl-2(5H)-furanone; (+)-form, 2,3,5-Tribromo-4-hydroxybenzaldehyde, 2,3,5-Tribromo-4-hydroxybenzyl alcohol, Trichamide, 1,1,1-Trichloro-5-undecylamine; (+)-form, N—Ac, 1-Tricosene-4,6,8,10,12,14,20-heptol; (4S, 6S,8S,10R,12R,14R,20R)-form, Hepta-Me ether, 1-Tricosene-4,6,8,10,12,14,16,18-octol; (4S,6S,8S,10S,12R, 14R,16R,18R)-form, Octa-Me ether, 6-Tridecylamine; (Ξ)-form, N—Ac, 4',5,7-Trihydroxyisoflavone; 7-O-(6-Deoxy-α-L-talopyranoside), 4',5,7-Trihydroxyisoflavone; 4',7-Di-O-(6-deoxy-α-L-talopyranoside), 9,12,13-Trihydroxy-10, 15-octadecadienoic acid; (9S,10E,12R,13S,15Z)-form, 2,6, 6-Trimethyl-1-cyclohexene-1-carboxaldehyde, Trungapeptin A, Trungapeptin A; 7,8-Dihydro, Trungapeptin A 7,7,8,8-Tetrahydro, Tryptamine; Nb-(7S-Methoxy-4E-tetradecenoyl), Tubercidin, Tubercidin; 5'-α-D-Glucopyranosyl, Tumonoic acid A, Tumonoic acid A; Et ester, Tumonoic acid A; Me ester, Tumonoic acid B, Tumonoic acid B; Me ester, Tumonoic acid C, Tumonoic acid D, Tumonoic acid E, Tumonoic acid F, Tumonoic acid G, Tumonoic acid H, Tumonoic acid I, Tychonamide A, Tychonamide A, 13-Demethoxy, Tyropeptin A, Tyropeptin B, Tyrostatin, Ulongamide B, Ulongamide B; 4"-Deoxy, Ulongamide C, Ulongamide D, Ulongamide E, Ulongamide F, Ulongapeptin, Venturamide A, Venturamide B, Veraguamide A, Veraguamide A; Debromo, Veraguamide A; Debromo, 35,35,36,36-tetrahydro, Veraguamide B, Veraguamide B; Debromo, Veraguamide B; Debromo, 35,35,36,36-tetrahydro, Veraguamide D, Veraguamide E, Veraguamide F, Viridamide A, Viridamide A; Lower homologue (R═CH3), Vitamin B12f, Welwitindolinone A isonitrile, Welwitindolinone B isothiocyanate, Welwitindolinone B isothiocyanate; 13,14-Didehydro, Welwitindolinone B isothiocyanate; 13,14-Didehydro, N-Me, Welwitindolinone B isothiocyanate; 13,14-Didehydro, N-Me, isocyanide, Welwitindolinone B isothiocyanate; 3-Hydroxy, 13,14-didehydro, N-Me, Welwitindolinone B isothiocyanate; 3-Hydroxy, 13,14-didehydro, N-Me, isocyanide, Welwitindolinone B isothiocyanate; N-Me, Welwitindolinone D isonitrile; N-Me, Wewakazole, Wewakpeptin A, Wewakpeptin A; 7,7, 8,8-Tetrahydro, Wewakpeptin C, Wewakpeptin C; 7,8-Tetrahydro, Yanucamide A, Yanucamide B, and Ypaoamide.

Additional compounds can be found in Blunt & Munro, *Dictionary of Marine Natural Products with CD-ROM*, Chapman and Hall/CRC (Sep. 19, 2007), the contents of which are incorporated by referwence in its entirety.

In some embodiments, an organism can selected for an increase in any of the compounds described above.

Based on knowledge of the desired chemical product (or compound), and the likely pathways involved (primary and secondary), the following strategies can be employed for creating mutant libraries.

First, several parameters may affect oligonucleotide (oligo) incorporation. These parameters include chemical modifications of oligonucleotides, the type of mismatch, and the number of bases between mismatches being introduced. General guidelines for optimizing allelic replacement include: (1) avoiding the MMR system; (2) using an oligo suitable for lagging-strand incorporation; (3) using saturating oligo concentrations; (4) using an appropriate size oligo as determined for the organism (approximately 70-90 bases, for example in *E. coli*); (5) placing altered bases more than about 9 bases from an oligo end.

In various embodiments, the oligonucleotide library includes one or more of the following features to induce genetic diversity in the host cell.

The oligonucleotide library may target the selected genes for varying promoter strength. In such embodiments, the oligonucleotide library contains, for each of the targeted genes, two, three, four, or five of the following promoters: T7, Trc, T3, T5, and/or any of the known *E. coli* endogenous promoters. See, e.g., Harley and Reynolds, Analysis of *E. coli* promoter sequences, *Nucleic Acids Res.* Vol. 15, No. 5, 2343-2361 (1987). Further, these promoters can include oligonucleotide degeneracy in the promoter region (e.g., from one to five degenerate positions) to provide a continuum of promoter strengths for screening.

Alternatively, or in addition, the oligonucleotide library may target the genes for varying translational efficiency. In such embodiments, the ribosomal binding site, or other sequence known to effect RNA turnover or translational efficiency, is made degenerate to provide a continuum of translational strengths. For example, the Shine-Dalgarno sequence may be rendered degenerate at from one to five positions in some embodiments.

In some embodiments that employ eukaryotic cells (e.g., yeast), one or more sites relating to splicing efficiency may be rendered degenerate at from one to five positions, to provide a continuum in splice efficiency for the targeted genes.

In some embodiments, the coding region of the genes is targeted for degeneracy, to provide a continuum of protein activity, so as to provide up and/or downregulation of key enzymes at the functional level. In these embodiments, the oligonucleotides contain from 1 to 20, or from 1 to 10, or from 1 to 5 degenerate positions, or combinations thereof at multiple locations in the oligo.

In some embodiments, the oligonucleotide library produces a premature stop codon in genes of potentially competing pathways, and/or screens seemingly unrelated metabolic genes for the effects of this inactivation on the desired phenotype (e.g., compound production).

In some embodiments, a tag refers to a protein that is fused to another protein to create a tagged protein. The tag sequence is often fused in-frame to the endogenous protein coding sequence such that a fusion protein is generated. In-frame means that the open reading frame (ORF) of the chromosomal sequence encoding the protein is maintained after the insertion of the tag sequence. In-frame insertions occur when the number of inserted nucleotides is divisible by three, which may be achieved by adding a linker of any number of nucleotides to the tag protein encoding sequence as applicable. A protein may be tagged anywhere within the protein polypeptide sequence provided the function of the protein is not affected. Generally, tagging is at the N- or C-terminus of the protein.

A tag sequence may be any peptide sequence encoded by a nucleic acid sequence. Tag sequence may encode a variety of tags including, but not limited to, epitope tags, affinity tags, reporters, or combinations thereof.

In some embodiments, the tag is an epitope tag. The epitope tag may comprise a random amino acid sequence, or a known amino acid sequence. A known amino acid sequence may have, for example, antibodies generated against it, or there may be no known antibodies generated against the sequence. The epitope tag may be an antibody epitope tag for which commercial antibodies are available. Non-limiting examples of suitable antibody epitope tags include but are not limited to myc, AcV5, AU1, AU5, E, ECS, E2, FLAG, HA, Maltose binding protein, nus, Softag 1, Softag 3, Strep, SBP, Glu-Glu, HSV, KT3, S, 51, T7, V5, VSV-G, 6×His, BCCP, and calmodulin.

In some embodiments, the tag is a reporter. Non-limiting examples of reporters include affinity tags, visual reporters or selectable-marker reporters. Non-limiting examples of affinity tags include chitin binding protein (CBP), thioredoxin (TRX), poly(NANP), tandem affinity purification (TAP) tag, and glutathione-S-transferase (GST). Visual reporters typically result in a visual signal, such as a color change in the cell, or fluorescence or luminescence of the cell. For instance, the reporter LacZ, which encodes 3-galactosidase, will turn a cell blue in the presence of a suitable substrate, such as X-gal. Other non-limiting examples of visual reporters include a fluorescent protein, luciferase, alkaline phosphatase, beta-galactosidase, beta-lactamase, horseradish peroxidase, and variants thereof. Selectable-marker reporters typically confer a selectable trait to the cell, such as drug resistance (e.g. antibiotic resistance).

In various embodiments, the tag is a fluorescent protein visual reporter. Non limiting examples of fluorescent protein visual reporters include green fluorescent proteins (e.g., GFP, GFP-2, tagGFP, turboGFP, EGFP, Emerald, Azami Green, Monomeric Azami Green, CopGFP, AceGFP, ZsGreen1), yellow fluorescent proteins (e.g. YFP, EYFP, Citrine, Venus, YPet, PhiYFP, ZsYellow1), blue fluorescent proteins (e.g. EBFP, EBFP2, Azurite, mKalama1, GFPuv, Sapphire, T-sapphire), cyan fluorescent proteins (e.g. ECFP, Cerulean, CyPet, AmCyan1, Midoriishi-Cyan), red fluorescent proteins (mKate, mKate2, mPlum, DsRed monomer, mCherry, mRFP1, DsRed-Express, DsRed2, DsRed-Monomer, HcRed-Tandem, HcRed1, AsRed2, eqFP611, mRaspberry, mStrawberry, Jred), and orange fluorescent proteins (mOrange, mKO, Kusabira-Orange, Monomeric Kusabira-Orange, mTangerine, tdTomato) or any other suitable fluorescent protein.

In various embodiments, a protein may be fused to the tag through a peptide linker. The sequence of the linker peptide is chosen based on known structural and conformational contributions of peptide segments to allow for proper folding and prevent possible steric hindrance of the protein to be tagged and the tag polypeptide. Linker peptides are commonly used and known in the art, and may be from about 3 to about 40 amino acids in length.

The protein also may be tagged with more than one tag. For instance, a protein may be tagged with at least one, two, three, four, five, six, seven, eight, or nine tags. More than one tag may be expressed as a single polypeptide fused to a protein of interest. More than one tag fused to a protein may be expressed as a single polypeptide which is cleaved into the individual tag polypeptides after translation.

In some embodiments the tags may promote synthetic scaffolding. Scaffolding of proteins can increase the local concentration of metabolites and alter the stoichiometry of the catalytic centers to balance flux through the metabolic pathway of interest. For instance SH3 domain(s) and their cognate peptides could be engineered with linkers to produce various specific ratios between two or more desired proteins such as enzymes. Methods which increase specific protein protein interactions can be used and include the use of SH3 domains and peptides, leucine zippers, PDZ domains and peptides, GBD domains and peptides, PhyB/Pif3, FKBP/FRB, or cohesin/dockerin In some embodiments, the tags may alter expression, folding, or degradation of recombinant proteins in the target host organism. Protein stability may be altered by tethering to an affinity tag. Tags, such as maltose binding protein, by way of illustration, may alter the folding properties of the nascent desired protein(s) preventing degradation or removal to, for instance, bacterial inclusion bodies.

In some embodiments, the invention can be used to conduct protein or peptide engineering on proteins or peptides such as enzymes, antibodies, or proteins and peptide hormones important to human health such as insulin. For instance, combinatorial mutations could be introduced into an enzyme to provide a library of related proteins which could be screened for improved physical or biochemical properties such as thermostability, feedback inhibition, substrate preference, pH optimum, $k_{cat}$ or $K_m$. Similarly, desired mutations could be introduced based structural, sequence, or biochemical knowledge to introduce specific desired changes singly or combinatorially.

These libraries can be further constructed as described herein or as synthetic allelic libraries, and employed with CRISPR-Cas9, TALENS, or other approach described herein based on production of double-strand breaks or single-stranded nicks in the host cell.

In various embodiments, the guide RNAs or crRNAs are elaborated with the approaches described above to create a library of different guide or crRNAs targeting different genetic sequences to explore different efficiencies of targeted cutting by the programmable nuclease. Alternatively or in addition, the DNA binding domain in TALEN restriction enzymes, or ZFNs, or BuDs is altered or modified by MAGE.

In these or other embodiments, PAM recognition sites for further engineering near the targeted locus is introduced with MAGE. If it is useful for a specific sequence to be cleaved by the Cas9 endonuclease, and there are no PAM recognition sites near this target, or if it desireable to avoid one, a new PAM recognition site may be introduced via MAGE to enable CRISPR to function on a desired locus in the genome. Similarly, PAM recognition sites may be ablated from a genomic sequence via MAGE.

In some embodiments, the biomolecule of interest is one or more RNA sequences, which may be altered to have optimal folding, stability or expression properties for therapeutic applications. The RNA sequence may be altered to change its binding affinity, catalytic activity, or regulation of its message. For example, in the case of mRNAs, the mRNAs may also be altered to have reduced or increased recognition efficiencies by host RNA-binding proteins or other host RNAs. In the case of mRNAs, the mRNAs may be altered to change translation of the message based on inter- or intra-molecular interactions. RNAs that are designed to contain unnatural or alternate chemistries may also be targeted by the invention.

These strategies allow for a large variety of compounds to be produced at higher levels (or other desired phenotype associated with industrial production of chemicals), and in diverse organisms.

Where the invention involves production of expression constructs, exemplary regulatory regions that can be included include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns. Exemplary promoter sequences that can be used in the expression constructs of the present invention include, e.g., promoter sequences capable of driving gene expression in target eukaryotic and/or prokaryotic cells. Specifically, constructs can include eukaryotic and prokaryotic promoters. An expression construct can include multiple copies of a single promoter or different promoters, e.g., two or more promoters. When two or more promoters are used in a single expression construct, the promoters can be selected to yield optimal expression of the encoded nucleic acids.

In some instances, expression constructs can include one or more prokaryotic promoter sequences and/or a Shine-Dalgarno sequence. Typically, prokaryotic promoter sequences contain two short consensus sequences at positions −10 and −35 upstream from the transcription initiation site. Prokaryotic promoter sequences that may be useful in the present invention include, but are not limited to, T7, T3, and T5 bacteriovirus promoter sequences.

Expression constructs can include one promoter per nucleic acid (e.g., operatively linked to a therapeutic nucleic acid). Expression constructs containing more than one promoter can contain multiple copies of the same promoter and/or different promoters. The choice of promoter or promoter combinations can be optimized to yield the highest expression level of the therapeutic nucleic acid of interest in the target cell.

The selected promoter will depend on the desired host cell. For example, promoters include but not limited to: viral promoters, bacterial promoters, animal promoters, mammalian promoters, synthetic promoters, constitutive promoters, tissue specific promoter, developmental specific promoters, inducible promoters, light regulated promoters; CYCI, HIS3, GALI, GAL4, GALIO, ADHI, PGK, PHOS, GAPDH, ADCI, TRPI, URA3, LEU2, ENO, TPI, alkaline phosphatase promoters (useful for expression in *Saccharomyces*); AOXI promoter (useful for expression in *Pichia*); b-lactamase, lac, ara, tet, trp, IPD IPR, T7, tac, and trc promoters (useful for expression in *Escherichia coli*); light regulated-, seed specific-, pollen specific-, ovary specific-, pathogenesis or disease related-, cauliflower mosaic virus 35S, CMV 35S minimal, cassava vein mosaic virus (CsVMV), chlorophyll alb binding protein, ribulose 1,5-bisphosphate carboxylase, shoot-specific, root specific, chitinase, stress inducible, rice tungro bacilliform virus, plant superpromoter, potato leucine aminopeptidase, nitrate reductase, mannopine synthase, nopaline synthase, ubiquitin, zein protein, and anthocyanin promoters (useful for expression in plant cells); animal and mammalian promoters known in the art include, but are not limited to, the SV 40 early (SV 40e) promoter region, the promoter contained in the 3 long terminal repeat (LTR) of Rous sarcoma virus (RSV), the promoters of the EIA or major late promoter (MLP) genes of adenoviruses (Ad), the cytomegalovirus (CMV) early promoter, the herpes simplex virus (HSV) thymidine kinase (TK) promoter, a baculovirus IEI promoter, an elongation factor 1 alpha (EF 1) promoter, a phosphoglycerate kinase (PGK) promoter, a ubiquitin (Ube) promoter, an albumin promoter, the regulatory sequences of the mouse metallothionein-L promoter and transcriptional control regions, the ubiquitous promoters (HPRT, vimentin, a-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis or disease related-promoters, and promoters that exhibit tissue specificity and have been utilized in transgenic animals, such as the elastase I gene control region which is active in pancreatic acinar cells; insulin gene control region active in pancreatic beta cells, immunoglobulin gene control region active in lymphoid cells, mouse mammary tumor virus control region active in testicular, breast, lymphoid and mast cells; albumin gene, Apo AI and Apo AII control regions active in liver, alpha-fetoprotein gene control region active in US 2008/0235816 AI liver, alpha I-antitrypsin gene control region active in the liver, beta-globin gene control region active in mycoid cells, myelin basic protein gene control region active in oligodendrocyte cells in the brain, myosin light chain-2 gene control region active in skeletal muscle, and gonadotropic releasing hormone gene control region active in the hypothalamus, pyruvate kinase promoter, villin promoter, promoter of the fatty acid binding intestinal protein, promoter of the smooth muscle cell a-actin, and the like. In addition, these expression sequences may be modified by addition of enhancer or regulatory sequences and the like.

Enhancer elements can increase transcription levels. Enhancer generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 base pairs in length, and they function in cis. Enhancers usually function to increase transcription from nearby promoters. Enhancers can also contain response elements that mediate the regulation of transcription. Exemplary enhancers that can be included in the constructs disclosed herein can include, but are not limited to, enhancer elements encoded by hepatitis B virus, BK virus, polyoma virus, rous Sarcoma virus (RSV), moloney murine leukemia virus (M-MuLV), SV40, TT virus, papilloma virus, and adenovirus.

Internal ribosomal entry site (IRES) elements are nucleotide sequences that allow for cap-independent translation initiation in the middle of a messenger RNA (mRNA). IRES elements can be usefully inserted, e.g., into bicistronic expression constructs to support the expression (translation) of a second therapeutic nucleic acid. IRES elements can be added intercistronicly to a construct to confer internal initiation of translation of an mRNA product independent of a 5' cap. Exemplary IRES elements include those present in, e.g., picornavirus, poliovirus, encephalomyocarditis virus, foot-and-mouth disease virus, flavivirus, hepatitis C virus, pestivirus, classical swine fever virus, retrovirus, murine leukaemia virus, lentivirus, simian immunodeficiency virus, insect RNA virus, and cricket paralysis virus.

Polyadenylation signals are useful for the synthesis of mRNA. Three elements define the core polyadenylation signal, (1) a hexanucleotide sequence AAUAAA found 10 to 30 nucleotides upstream of the cleavage site, (2) a U-rich or GU-rich element located downstream of the cleavage site and (3) the poly(A) site. Polyadenylation signals that can be useful include, e.g., the bovine growth hormone (BGH), herpes simplex virus-TK (HSV-TK), rabbit β-globin, simian virus 40 (SV40) late, hepatitis B virus (HBV), and human papilloma virus (HPV) polyadenylation signals.

Transcription initiation factors are useful for transcription. Transcription initiation factors can be included in the constructs described herein. Transcription initiation factors include. e.g., TFII-I, eukaryotic initiation factor 4G (eIF4G) and DAP5.

Kozak sequences are useful for promoting efficient translation, for example in eukaryotic cells. A kozak consensus sequence can be added to a expression vector to enhance the expression of the nucleic acid(s) of interest. Exemplary Kozak sequences include, for example, CCACCAUG (SEQ ID NO:1) and CCACCAUGG (SEQ ID NO:2).

Shine-Dalgarno Sequences are useful for promoting efficient translation, for example in prokaryotic cells. Shine-Dalgarno Sequences are typically located 6-7 nucleotides upstream from a start codon. The six-base consensus sequence is, for example, AGGAGG (SEQ ID NO: 3).

Termination control regions, i.e., terminator or polyadenylation sequences, may also be derived from various genes native to the preferred hosts. Optionally, a termination site may be unnecessary. In a preferred embodiment of the invention, the termination control region can comprise or be derived from a synthetic sequence, synthetic polyadenylation signal, an SV40 late polyadenylation signal, an SV40 polyadenylation signal, a bovine growth hormone (BGH) polyadenylation signal, viral terminator sequences, or the like.

In some instances, expression constructs can include species-specific DNA elements (e.g., flanking sequences) to facilitate integration of the construct or portions thereof into the genome of target cells and/or to promote episomal or plasmid maintenance (i.e., replication signals). Where integration is required, expression constructs can include loxP sequences flanking the integrating DNA sequence. Inclusion of such sequences allows subsequent removal (e.g., post-MAGE) of the integrated sequence from the genome via the standard practice of Cre expression, which is transformed and expressed from a separate vector. Where episomal expression is required, expression constructs can include species-specific origins of replication and one or more selectable markers. In such cases, the episome can be removed by discontinuing its selection. Exemplary origins of replication suitable for inclusion in the vectors are known in the art (see, e.g., Bryant et al., J Exp Bot., 52(355): 193-202 (2001); Edward et al., Basic Virology Third Edition, Blackwell publishing, ISBN 1-4051-4715-6 (2007); Mott and Berger, Nat. Rev. Microbial., 5 (5): 343-54 (2007); Huberman et al., Cell, 6; 51(3):473-81 (1987); Brewer and Fangman, Cell, November 6; 51(3):463-71 (1987); Kitai et al., J. Virol., 79(10): 5933-5942 (2005); Kelman, Trends Microbiol., 12: 399-401 (2004); Nasheuer et al., Prog. Nucleic Acid Res. Mol. Biol., 72: 41-94 (2002); Cheuk et al., Nucl. Acids Res. 40 (D1): D682-D686 (2012)). These include but are not limited to colE1/pMB1, oriC, f/oriV/oriS, oriN, oriT, oriH and oriL, p15A, pBR322, pSC101, R6K, RK2, RSF1010, cloDF13, colA, RSF1030, P1, rep/mob, pUB110, pRO1600/P, oriV, pWV0, 2 micron and CEN/ARS, and SV40.

In some instance, expression constructs can encode markers to facilitate selection of cells expressing the vector. Examples of selectable marker genes known and used in the art include: genes providing resistance to 5-Fluoro-2'-deoxyuridine, 5-Fluoroorotic Acid, acetamide, ampicillin, bialaphos, bleomycin, carbenicillin, coefotaxime, ceftriaxone, chloramphenicol, D-cycloserine, erythromycin, G418, gentamycin, herbicide, hygromycin, kanamycin, kasugamycin, nalidixic acid, neomycin, nourseothricin, puromycin, rifampicin, spectinomycin, streptomycin, sulfonamide, tetracycline, triclosan, trimethroprim, zeocin and the like; and genes that are used as phenotypic markers, i.e., anthocyanin, ccdB, gata1, isopentanyl transferase gene, mazF, lacY, regulatory genes, pir, pheS, rpsL, sacB, tetAR, tolC and the like. Use of such resistance markers allows identification of a cell when the cell is cultured under selective pressure (e.g., in the presence of the antibiotic). Selectable markers can also include nutritional and/or auxotrophic markers, for example, ade, arg, can, galK, his, met, phe, thr, thyA, leu, lys, proC, pyrF, trp, tyr, ura.

In some instances expression constructs can encode, in addition to the selectable markers, detection markers such as, for example, nucleic acids encoding enzymes and/or detectable proteins. In other instances, detectable markers may be included on separate vectors or may be chosen as genomic regions of the target cell. Exemplary detectable markers that can be encoded by vectors include, but are not limited to, chemiluminescent or fluorescent proteins, such as, for example, green fluorescent protein (GFP), enhanced green fluorescent protein (EGFP), Renilla Reniformis green fluorescent protein, GFPmut2, GFPuv4, yellow fluorescent protein (YFP), enhanced yellow fluorescent protein (EYFP), cyan fluorescent protein (CFP), enhanced cyan fluorescent protein (ECFP), enhanced blue fluorescent protein (EBFP), citrine and red fluorescent protein from discosoma (dsRED), luciferase, rhodamine, fluorescein and the like. In certain other embodiments, the detectable marker is an enzyme. In certain other embodiments, the detectable marker is a non-essential gene that can be assayed rapidly for genetic variation by qPCR. In certain other embodiments, the detectable marker is a drug resistance marker or nutritional marker that can be readily assessed for functionality by reverse selection.

As used herein, a vector (or plasmid) refers to discrete elements that are used to, for example, introduce heterologous nucleic acid into cells for expression or replication thereof. The vectors can remain episomal or can be designed to effect integration of a gene or portion thereof into a chromosome of the genome. Also contemplated are vectors that are artificial chromosomes, such as yeast artificial chromosomes and mammalian artificial chromosomes. Selection and use of such vehicles are well known to those of skill in the art. Included are vectors capable of expressing DNA that is operatively linked with regulatory sequences, such as promoter regions, that are capable of effecting expression of such DNA fragments (e.g. expression vectors). Thus, a vector refers to a recombinant DNA or RNA construct, such as a plasmid, a phage, recombinant virus or other vector that, upon introduction into an appropriate host cell, results in expression of the DNA. Appropriate vectors are well known to those of skill in the art and include those that are replicable in eukaryotic cells and/or prokaryotic cells and those that remain episomal or those that integrate into the host cell genome.

In some embodiments, the present compositions and methods can include vectors based and/or generated using commercially available expression constructs, which can optionally be adapted or optimized for use in certain species and/or cell types. Examples of such expression constructs include the GATEWAY cloning vector available from INVITROGEN, which is available for multiple species. Examples of other expression constructs suitable for use in various species are known in the art. By way of example, expression constructs suitable for use in, for example, *Pichia pastoris* include, for example, pAO815, pGAPZ, pGAPZa, pHIL-D2, pHIL-S1, pPIC3.5K, pPIC9K, pPICZ, and pPICZa. By way of example, expression constructs suitable for episomal maintenance in for example, *Kluyveromyces lactis* include, for example, pKD1. Expression constructs suitable for integration in *Kluyveromyces lactis* include, for example, pGB-HSb20 vector (Swinkels et al. Antonie van Leeuwenhoek, 64:187-201 (1993); Bergkamp et al., Current Genetics, 21(4-5):365-370 (1992); Rossolini et al. Gene, 21; 119(1):75-81 (1992); Domínguez et al., the Official Journal of the Spanish Society for Microbiology, 1:131-142 (1998)), pKLAC1 or pKLAC2 (Paul A. Colussi and Christopher H. Taron, Appl Environ Microbiol. 71(11): 7092-7098 (2005)).

The art provides a variety of vectors that find use in the present invention. By way of non-limiting illustration, phage vectors, plasmid vectors, phagemid vectors, phasmid vectors, cosmid vectors, virus vectors and YAC vectors may be used in the present invention.

In some embodiments, the following non-limiting illustrative phage vectors find use in the present invention: *E. coli* phage vector lambda EMBL3 left arm; *E. coli* phage vector lambda EMBL3 right arm; Bacteriophage f1; Bacteriophage fd; *E. coli* phage vector fd strain 478; *E. coli* phage vector fd-tet; *E. coli* phage vector fd fKN 16; *E. coli* phage vector f1 IR1; *E. coli* phage vector lambda (Styloviridae); *E. coli* phage vector M13; *E. coli* phage vector M13BM20; *E. coli* phage vector M13BM21; *E. coli* phage vector M13LH1; *E. coli* phage vector M13mc18; *E. coli* phage vector M13mIC7; *E. coli* phage vector M13mp1; *E. coli* phage vector M13mp10; *E. coli* phage vector M13mp11; *E. coli* phage vector M13mp18; *E. coli* phage vector M13mp19; *E. coli* phage vector M13mp2; *E. coli* phage vector M13mp7; *E. coli* phage vector M13mp8; *E. coli* phage vector M13mp9; *E. coli* phage vector M13plex00; *E. coli* phage vector M13plex01; *E. coli* phage vector M13plex05; *E. coli* phage vector M13plex06; *E. coli* phage vector M13plex07; *E. coli* phage vector M13plex10; *E. coli* phage vector M13plex13; *E. coli* phage vector M13plex17; *E. coli* phage vector M13plex18; *E. coli* phage vector M13plex19; *E. coli* phage vector M13plex20; *E. coli* phage vector M13tg130; *E. coli* phage vector M13tg131; *E. coli* phage vector M13WB23; *E. coli* phage vector M13WB2341; *E. coli* phage vector M13WB2342; *E. coli* phage vector M13WB2344 or M13WB2348; *E. coli* phage vector M13 PhageScript; *E. coli* plasmid vector pPop6 [tm]; *E. coli* phage vector f1 R199; *E. coli* phage vector f1 R208; *E. coli* phage vector f1 R229; *E. coli* phage vector lambda EMBL12; *E. coli* phage vector lambda EMBL3 AamBam; *E. coli* phage vector lambda EMBL3 cos; *E. coli* phage vector lambda EMBL3-cos-Not; *E. coli* phage vector lambda EMBL4; *E. coli* phage vector fd fBH 16; *E. coli* phasmid phage vector lambda 1059; *E. coli* phage vector lambda 2001; *E. coli* phage vector lambda amp3; *E. coli* phage vector lambda BLUEMID−; *E. coli* phage vector lambda BLUEMID+; *E. coli* phage vector lambda clKH100 (IS5); *E. coli* phage vector lambda DASH II; *E. coli* phage vector lambda DL10; *E. coli* phage vector lambda DL11; *E. coli* phage vector lambda DR2; *E. coli* phage vector lambda ExCell; *E. coli* phage vector lambda FIX II; *E. coli* phage vector lambda GEM11; *E. coli* phage vector lambda GEM12; *E. coli* phage vector lambda GEM2; *E. coli* phage vector lambda GEM4; *E. coli* phage vector lambda gt10; *E. coli* phage vector lambda gt102; *E. coli* phage vector lambda gt11; *E. coli* phage vector lambda gt11D; *E. coli* phage vector lambda gt11 SciI/NotI; *E. coli* phage vector lambda gt22A; *E. coli* phage vector lambda gtWES.lambdaB; *E. coli* phage vector lambda gtWES.lambda B'; *E. coli* phage vector lambda gtWES.T5-622; *E. coli* phage vector lambda MAX1; *E. coli* phage vector lambda MGU1; *E. coli* phage vector lambda MGU2; *E. coli* phage vector lambda N-cl857 r32; Vertebrate/*E. coli* phage vector lambda NMT; *E. coli* phage vector lambda plac Mu1; *E. coli* phage vector lambda placMu3; *E. coli* phage vector lambda pMu507; *E. coli* phage vector lambda pMu507.3; *E. coli* phage vector lambda Pop10; *E. coli* phage vector lambda Pop6; *E. coli* phage vector lambda SE4; *E. coli* phage vector lambda SE5; *E. coli* phage vector lambda SE6; *E. coli* phage lambdaSK17; *E. coli* phage lambdaSK20; *E. coli* phage lambdaSK22; *E. coli* phage lambdaSK23; *E. coli* phage vector lambda SurfZAP; *E. coli* phage vector lambda ZAP Express; *E. coli* phage vector lambda ZAP II; Vertebrate/*E. coli* phage vector lambda ZD31; Vertebrate/*E. coli* phage vector lambda ZD32; Vertebrate/*E. coli* phage vector lambda ZD35; *E. coli* phage vector lambda ZipLox; *E. coli* phage vector M13bla6; *E. coli* phage vector M13bla cat1; *E. coli* phage vector M13Gori1; *E. coli* phage vector M13K07; *E. coli* phage M13mp7-14; *E. coli* phage vector M13.SV.8; *E. coli* phage vector M13.SV.B11; *E. coli* phage vector M13.SV.B12; *E. coli* phage vector M13tg103; *E. coli* phage vector M13tg114; *E. coli* phage vector M13tg115; *E. coli* phage vector M13tg117; *E. coli* phage vector M13um20; *E. coli* plasmid vector pPop10; *E. coli* phage vector lambda Syrinx 2A; *Streptomyces* phage vector TG1; and *Streptomyces* phage vector TG2.

In some embodiments, plasmid vectors find use in the present invention. In some embodiments the vectors of the present disclosure are useful in, by way of non-limiting example, *E. coli*. In some embodiments, the following illustrative plasmids may be used in *E. coli* (or other suitable cells, including those disclosed herein): CFSN1; Charon 4; EZ-Tn5 pMOD-2; EZ-Tn5 pMOD-3; EZ-Tn5 pMOD-4; EZ-Tn5 pMOD-5; LITMUS28i; LITMUS38i; pACYC177; pACYC184; pACYCDuet-1; pAH153; pALTER-EX1; pALTER-EX2; p416; pBAC-2cp; pBACgus-2cp; pBAD-DEST49; pBAD-TOPO; pBAD-TOPO/LacZ; pBAD-TOPO/LacZ/V5-His; pBAD/gIII A; pBAD/gIII B; pBAD/gIII C; pBAD/gIII Calmodulin; pBAD/His A; pBAD/His B; pBAD/His C; pBAD/His/LacZ; pBAD/myc-His A; pBAD/myc-His B; pBAD/myc-His C; pBAD/Myc-His/lacZ; pBAD/Thio; pBAD/Thio-E; pBAD/Thio-TOPO; pBAD102/D-TOPO; pBAD102/D/LacZ; pBAD18; pBAD18-Cm; pBAD18-Kan; pBAD18s; pBAD202/D-TOPO; pBAD202/D/LacZ; pBAD24; pBAD28; pBAD30; pBAD33; pBADx53; pBEc-Q; pBEc-SBP; pBEc-SBP-Q; pBEc-SBP-SET1; pBEc-SBP-SET1-Q; pBEc-SBP-SET2; pBEc-SBP-SET2-Q; pBEc-SBP-SET3; pBEc-SBP-SET3-Q; pBEc-SET1; pBEc-SET2; pBEc-SET3; pBEn-SBP-SET1a; pBEn-SBP-SET1b; pBEn-SBP-SET1c; pBEn-SBP-SET2a; pBEn-SBP-SET2b; pBEn-SBP-SET2c; pBEn-SBP-SET3a; pBEn-SBP-SET3b; pBEn-SBP-SET3c; pBEn-SBPa; pBEn-SBPb; pBEn-SBPc; pBEn-SET1a; pBEn-SET1b; pBEn-SET1c; pBEn-SET2a; pBEn-SET2b; pBEn-SET2c; pBEn-SET3a; pBEn-SET3b; pBEn-SET3c; pBiEx-1; pBiEx-2; pBiEx-3; pBR322; pBS(Kan); pC194; pCA24N; pCAL-c; pCAL-kc; pCAL-n; pCAL-n-EK; pCAL-n-FLAG; pCC1BAC; pCDF-2 Ek/LIC; pCDFDuet-1; pCL1920/pCL1921; pCM251; pCM252; pCMV-GLuc; pCOLADuet-1; pCR2.1; pCRT7-E; pCX; pCX-TOPO; pDB130; pDEST14; pDEST15; pE194; pDEST17; pDEST24; pDEST565; pDESTR4-R3; pDONR201; pDONR207; pDONR221; pDONR223; pEpiFOS-5; pET-11a; pET-11b; pET-11c; pET-11d; pET-14b; pET-15b; pET-16b; pET-17b; pET-19b; pET-20b(+); pET-21(+); pET-21a (+); pET-21b(+); pET-21c(+); pET-21d(+); pET-22b(+); pET-23a(+); pET-23b(+); pET-23c(+); pET-23d(+); pET-24 (+); pET-24a(+); pET-24b(+); pET-24c(+); pET-24d(+); pET-25b(+); pET-26b(+); pET-27b(+); pET-28a(+); pET-28b(+); pET-28c(+); pET-29a(+); pET-29b(+); pET-29c(+); pET-30 Ek/LIC; pET-30 Xa/LIC; pET-30a(+); pET-30b(+); pET-30c(+); pET-31b(+) DNA; pET-32 Ek/LIC; pET-32 Xa/LIC; pET-32a(+) DNA; pET-32b(+) DNA; pET-32c(+) DNA; pET-33b(+); pET-39b(+); pET-3a; pET-3b; pET-3c; pET-3d; pET-40b(+); pET-41 Ek/LIC; pET-41a(+); pET-41b (+); pET-41c(+); pET-42a(+); pET-42b(+); pET-42c(+); pET-43.1 Ek/LIC; pET-43.1a(+); pET-43.1b(+); pET-43.1c (+); pET-44 Ek/LIC; pET-44a(+); pET-44b(+); pET-44c(+); pET-45b(+); pET-46 Ek/LIC; pET-47b(+); pET-48b(+);

pET-49b(+); pET-50b(+); pET-51 Ek/LIC; pET-51b(+); pET-52 3c/LIC; pET-52b(+); pET-5a; pET-5b; pET-5c; pET-9a; pET-9b; pET-9c; pET-9d; pET-DEST42; pET100/D-TOPO; pET100/D/LacZ; pET101/D-TOPO; pET101/D/LacZ; pET102/D-TOPO; pET102/D/LacZ; pET151/D-TOPO; pET151/D/LacZ; pET160-GW/CAT; pET160/GW/D-TOPO; pET161-GW/CAT; pET161/GW/D-TOPO; pET200/D-TOPO; pET200/D/LacZ; pETBlue-1; pETBlue-2; pETcoco-1; pETcoco-2; pETDuet-1; pF1A T7; pF1K T7; pF3A WG (BYDV); pF3K WG (BYDV); pF4A CMV; pF4K CMV; pF5A CMV-neo; pF5K CMV-neo; pF9A CMV hRluc-neo; pFC7A (HQ); pFC7K (HQ); pFC8A (HaloTag); pFC8K (HaloTag); pFN10A (ACT); pFN11A (BIND); pFN2A (GST); pFN2K (GST); pFN6A (HQ); pFN6K (HQ); pG5luc; pGEM-1; pGEM-11Zf(+); pGEM-11Zf(−); pGEM-13Zf(+); pGEM-15Zf(−); pGEM-2; pGEM-3; pGEM-3Z; pGEM-3Zf(+); pGEM-3Zf(−); pGEM-4 Vector; pGEM-4Z; pGEM-5Zf(+); pGEM-5Zf(−); pGEM-7Zf(+); pGEM-7Zf(−); pGEM-9Zf(−); pGEMEX-1; pGEMEX-2; pGEX-2T; pGEX-2TK; pGEX-3X; pGEX-4T-1; pGEX-4T-2; pGEX-4T-3; pGEX-5X-1; pGEX-5X-2; pGEX-5X-3; pGEX-6P-1; pGL2-Basic; pGL2-Control; pGL2-Enhancer; pGL2-Promoter pGlo; pGLuc-Basic Vector; pGPS1.1; pGPS2.1; pGPS3; pGPS4; pGPS5; pIndigoBAC-5; PinPoint Control; PinPoint Xa Control; PinPoint Xa-1; PinPoint Xa-2; PinPoint Xa-3; pJH370; pKD46; pKG116; pKLAC1; pKLAC1-malE; pKO500; pLacI; pLysE; pLysS; pMAL-c4E; pMAL-c4G; pMAL-c4X; pMAL-p4E; pMAL-p4G; pMAL-p4X; pMAL-pIII; pMMB277; pMutin4; pNEB193; pNEB206A; pNEBR-R1; pNEBR-X1; pNEBR-X1GLuc; pNEBR-X1Hygro; pOX38; pRS1274; pRS308; pRS414; pRS415; pRS475; pRS550; pRS551; pRS552; pRS577; pRS591; pRSET A; pRSET B; pRSET C; pRSET T7; pRSET-E; pRSET/LacZ; pRSF-2 Ek/LIC; pRSFDuet-1; pSC101; pSH47; pSIM5; pSIM6; pSIM7; pSIM8; pSIM9; pSIM10; pSIM17; pSIM18; pSIM19; pSP64; pSP64 Poly(A); pSP65; pSP70; pSP72; pSP73; pThioHis A; pThioHis B; pThioHis C; pTrcHis A; pTrcHis B; pTrcHis C; pTrcHis-TOPO; pTrcHis-TOPO/lacZ; pTrcHis/CAT; pTrcHis2 A; pTrcHis2 B; pTrcHis2 C; pTrcHis2-TOPO; pTrcHis2-TOPO/LacZ; pTrcHis2/LacZ; pTSC; pTWIN1; pTXB1; pTXB3; pTYB1; pTYB11; pUC-A1501; pUC19; pUC57; pUG6; pWEB; and pWEB-TNC.

In some embodiments, the following non-limiting illustrative phage vectors find use in the present invention: E. coli phagemid vector BSB; E. coli phagemid vector BSB+; E. coli phagemid vector pAcUW31; E. coli phagemid vector pAD3; E. coli phagemid vector pALTER-1 (formerly pSELECT-1); Cloning vector pALTER[R]-Ex1; Cloning vector pALTER[R]-Ex2; E. coli phagemid vector pAMP1; E. coli phagemid vector pAMP10; E. coli phagemid vector pAMP18; E. coli phagemid vector pAMP19; E. coli phagemid vector pAMP2; C. elegans phagemid vector pAST18a; C. elegans phagemid vector pAST18b; C. elegans phagemid vector pAST19a; C. elegans phagemid vector pAST19b; E. coli phagemid vector pAX4a; E. coli phagemid vector pAX4a+; E. coli phagemid vector pAX4b; E. coli phagemid vector pAX4b+; E. coli phagemid vector pAX4c; E. coli phagemid vector pAX4c+; E. coli phagemid vector pAX5; E. coli phagemid vector pAX5+; E. coli phagemid vector pBacPAK1; E. coli phagemid vector pBacPAK8; E. coli phagemid vector pBacPAK9; E. coli phagemid vector pBC KS(−); E. coli phagemid vector pBC KS(+); E. coli phagemid vector pBC SK(−); E. coli phagemid vector pBC SK(+); E. coli phagemid vector pBGS9; E. coli phagemid vector pBGS9+; Vertebrate/E. coli phagemid vector pBLCAT3.f1; E. coli phagemid vector pBluescript II KS(−); E. coli phagemid vector pBluescript II KS(+); E. coli phagemid vector pBluescript II SK(−); E. coli phagemid vector pBluescript II SK(+); E. coli phagemid vector pBluescript KS(−); E. coli phagemid vector pBluescript KS(+); E. coli phagemid vector pBluescript SK(−); E. coli phagemid vector pBluescript SK(+); E. coli phagemid vector pBP9; E. coli phagemid vector pBS; E. coli phagemid vector BlueScribe KS; E. coli phagemid vector BlueScribe KS+; E. coli phagemid vector pBS; E. coli phagemid vector pBSM13- or BlueScribe M13; E. coli phagemid vector pBSM13+ or BlueScribe M13+; E. coli phagemid vector pBS+; E. coli phagemid vector BlueScribe SK; E. coli phagemid vector BlueScribe SK+; E. coli phagemid vector pBTac1; E. coli phagemid vector pBT2; E. coli phagemid vector pCDM8; E. coli phagemid vector pcDNA3; E. coli phagemid vector pcDNAI; E. coli phagemid vector pcDNAIAmp; E. coli phagemid vector pcDNAII; E. coli phagemid vector pcDNAINeo; E. coli phagemid vector pCF20; Cloning vector pCI, mammalian expression vector; Cloning vector pCI-neo, mammalian expression vector; E. coli phagemid vector pCR1000; E. coli phagemid vector pCRII; E. coli phagemid vector pD4; E. coli phagemid vector pDW227; E. coli phagemid vector pDW229; E. coli phagemid vector pDW232; E. coli phagemid vector pEMBL18-Not (Sma−); Saccharomyces/E. coli phagemid vector pEMBLYe23; Saccharomyces/E. coli phagemid vector pEMBLYe24; Saccharomyces/E. coli phagemid vector pEMBLYi21; Saccharomyces/E. coli phagemid vector pEMBLYi22; Saccharomyces/E. coli phagemid vector pEMBLYi32; Saccharomyces/E. coli phagemid vector pEMBLYr25; E. coli phagemid vector pEX1; E. coli phagemid vector pEX2; E. coli phagemid vector pEX3; E. coli phagemid vector pExCell; E. coli phagemid vector pEZZ18; Saccharomyces/E. coli phagemid vector pFL59; Saccharomyces/E. coli phagemid vector pFL59+; Saccharomyces/E. coli phagemid vector pFL64; Saccharomyces/E. coli phagemid vector pFL64+; E. coli phagemid vector pGEM-1; E. coli phagemid vector pGEM-1Zf; E. coli phagemid vector pGEM-1Zf+; E. coli phagemid vector pGEM-13Zf+; E. coli phagemid vector pGEM-2; E. coli phagemid vector pGEM-3; E. coli phagemid vector pGEM-3Zf; E. coli phagemid vector pGEM-3Zf+; E. coli phagemid vector pGEM-4; E. coli phagemid vector pGEM-5Zf+; E. coli phagemid vector pGEM-7Zf; E. coli phagemid vector pGEM-7Zf+; E. coli phagemid vector pGEM-9Zf; E. coli phagemid vector pGEM-luc; E. coli phagemid vector pGEM-T; Broad host range/E. coli plasmid vector pGhost4; Broad host range/E. coli plasmid vector pGhost5; Broad host range/E. coli plasmid vector pGhost6; E. coli phagemid vector pGL2-Basic; E. coli phagemid vector pGL2-Enhancer; Cloning vector pGL3-Basic; Cloning vector pGL3-Control; Cloning vector pGL3-Enhancer; Cloning vector pGL3-Promoter; E. coli phagemid vector pGUSN358-S; E. coli phagemid vector PhageScript SK; E. coli phagemid vector pHph0; E. coli phagemid vector pHph-1; E. coli phagemid vector pHph+1; E. coli phagemid vector pICEM19H; E coil phagemid vector pICEM19H+; E. coli phagemid vector pICEM19R; E. coli phagemid vector pICEM19R+; Vertebrate/E. coli phagemid vector pJFCAT1; E. coli phagemid vector pKK161-8; E. coli phagemid vector pko; E. coli phagemid vector pKO-neo; E. coli phagemid vector pKSM710; E. coli phagemid vector pKSM711; E. coli phagemid vector pKSM713; E. coli phagemid vector pKSM715; E. coli phagemid vector pKUN9; E. coli phagemid vector pKUN9; E. coli phagemid vector pLH1; E. coli plasmid vector pMAL-c E. coli plasmid vector pMAL-c2 E. coli plasmid vector pMAL-cRI E. coli plasmid vector pMAL-p *E. coli* plasmid vector pMAL-p2 *E. coli* phagemid vector pMEX5; *E. coli* phagemid vector pMEX6; *E. coli* phagemid vector pMEX7; *E. coli* phagemid vector pNEB193; *E. coli* phagemid vector pON163; *E. coli* phagemid vector pPL-lambda; *E. coli* phagemid vector pRcCMV; *E. coli* phagemid vector pRcRSV; *E. coli* phagemid vector pRIT2T; Saccharomyces/*E. coli* phagemid vector pRS200; Saccharomyces/*E. coli* phagemid vector pRS303; Saccharomyces/*E. coli* phagemid vector pRS304; Saccharomyces/*E. coli* phagemid vector pRS305; Saccharomyces/*E. coli* phagemid vector pRS306; Saccharomyces/*E. coli* phagemid vector pRS313; Saccharomyces/*E. coli* phagemid vector pRS314; Saccharomyces/*E. coli* phagemid vector pRS315; Saccharomyces/*E. coli* phagemid vector pRS316; Saccharomyces/*E. coli* phagemid vector pRS403; Saccharomyces/*E. coli* phagemid vector pRS404; Saccharomyces/*E. coli* phagemid vector pRS405; Saccharomyces/*E. coli* phagemid vector pRS406; Saccharomyces/*E. coli* phagemid vector pRS413; Saccharomyces/*E. coli* phagemid vector pRS414; Saccharomyces/*E. coli* phagemid vector pRS415; Saccharomyces/*E. coli* phagemid vector pRS416; Saccharomyces/*E. coli* phagemid vector pRS423; Saccharomyces/*E. coli* phagemid vector pRS424; Saccharomyces/*E. coli* phagemid vector pRS425; Saccharomyces/*E. coli* phagemid vector pRS426; *E. coli* phagemid vector pRSETA; *E. coli* phagemid vector pRSETB; *E. coli* phagemid vector pRSETC; Saccharomyces/*E. coli* phagemid vector pRSS56; Cloning vector pSI; *E. coli* phagemid vector pSK222; *E. coli* phagemid vector pSK241; *E. coli* phagemid vector pSL1180; *E. coli* phagemid vector pSL1190; *E. coli* phagemid vector pSL301; *E. coli* phagemid vector pSP18; *E. coli* phagemid vector pSP19; *E. coli* phagemid vector pSP64; *E. coli* phagemid vector pSP64-f1; *E. coli* phagemid vector pSP64-f1+; *E. coli* phagemid vector pSP64 polyA; *E. coli* phagemid vector pSP65-f1+; *E. coli* phagemid vector pSP6-T3; *E. coli* phagemid vector pSP6-T7-19; *E. coli* phagemid vector pSP70; *E. coli* phagemid vector pSP71; *E. coli* phagemid vector pSP72; *E. coli* phagemid vector pSP73; *E. coli* phagemid vector pSPORT1; *E. coli* phagemid vector pSPORT2; *E. coli* phagemid vector pSPT18; *E. coli* phagemid vector pSPT19; *E. coli* phagemid vector pSPTbm20; *E. coli* phagemid vector pSPTbm21; *E. coli* phagemid vector pSS24; *E. coli* phagemid vector pSS25; *E. coli* phagemid vector pSVK3; *E. coli* phagemid vector pSV-SPORT1; *E. coli* phagemid vector pT3T7BM; *E. coli* phagemid vector pT3T7-lac; *E. coli* phagemid vector pT3T7-luc; *E. coli* phagemid vector pT7-0; *E. coli* phagemid vector pT7-1; *E. coli* phagemid vector pT7-2; *E. coli* phagemid vector pT7SP6; *E. coli* phagemid vector pTT7T3-18; *E. coli* phagemid vector pT7T3-18D; *E. coli* phagemid vector pT7T3-18U; *E. coli* phagemid vector pT7T3-19; *E. coli* phagemid vector pT7T3-19U; *E. coli* phagemid vector pT7T3alpha-18; *E. coli* phagemid vector pT7T3alpha-19; Vertebrate/*E. coli* phagemid vector pTF1; *E. coli* phagemid vector pTRXN; *E. coli* phagemid vector pTRXN+; *E. coli* phagemid vector pTZ18R; *E. coli* phagemid vector pTZ18U; *E. coli* phagemid vector pTZ19R; *E. coli* phagemid vector pTZ19U; *E. coli* phagemid vector pTZSV28; *E. coli* phagemid vector pUC118; *E. coli* phagemid vector pUC119; *E. coli* phagemid vector pUC12; *E. coli* phagemid vector pUC12c; *E. coli* phagemid vector pUC13; *E. coli* phagemid vector pUC13c; *E. coli* phagemid vector pUC18; *E. coli* phagemid vector pUC18c; Photinus pyralis pUC18-luciferase; *E. coli* phagemid vector pUC19; *E. coli* phagemid vector pUC1918; *E. coli* phagemid vector pUC19c; *E. coli* phagemid vector pUC3; *E. coli* phagemid vector pUC4; *E. coli* phagemid vector pUC5; *E. coli* phagemid vector pUC7; *E. coli* phagemid vector pUC7c; *E. coli* phagemid vector pUC8; *E. coli* phagemid vector pUC8-1; *E. coli* phagemid vector pUC8-2; *E. coli* phagemid vector pUC830; *E. coli* phagemid vector pUC8c; *E. coli* phagemid vector pUC9; *E. coli* phagemid vector pUC9-1; *E. coli* phagemid vector pUC9-2; *E. coli* phagemid vector pUC9c; *E. coli* phagemid vector pUC9tet; *E. coli* phagemid vector pUCbm20 or pUCPZ2; *E. coli* phagemid vector pUCbm21; *E. coli* phagemid vector pUCGM; *E. coli* phagemid vector pUCP18; *E. coli* phagemid vector pUCP20; *E. coli* phagemid vector pUCP22; *E. coli* phagemid vector pUCP24; *E. coli* phagemid vector pUCP26; *E. coli* phagemid vector pUR1; *E. coli* plasmid vector pWM521; Vertebrate/*E. coli* phagemid vector pXPRS- or pcDpolyB; Vertebrate/*E. coli* phagemid vector pXPRS+ or pcDpolyB+; *E. coli* phagemid vector pYES2; *E. coli* phagemid vector pYESHisA; *E. coli* phagemid vector pYESHisB; *E. coli* phagemid vector pYESHisC; Saccharomyces/*E. coli* phagemid pAS1; Yeast/*E. coli* phagemid vector pAS2; Saccharomyces/*E. coli* phagemid vector pASZ10 *E. coli* phagemid vector pBGS130-; *E. coli* phagemid vector pBGS130+; *E. coli* phagemid vector pBGS131-; *E. coli* phagemid vector pBGS131+; *E. coli* phagemid vector pBGS18-; *E. coli* phagemid vector pBGS18+; *E. coli* phagemid vector pBGS19-; *E. coli* phagemid vector pBGS19+; *E. coli* phagemid vector pBGS8-; *E. coli* phagemid vector pBI221; *E. coli* phagemid vector pBK-CMV; *E. coli* phagemid vector pBK-RSV; Trypanosoma/*E. coli* phagemid vector pBNsp-Neo-Alpha; *E. coli* phagemid vector pCR-Script SK(+); *E. coli* phagemid vector pDELTA2; *E. coli* phagemid vector pDK101; Saccharomyces/*E. coli* phagemid vector pEMBLYe30; Saccharomyces/*E. coli* phagemid vector pEMBLYe31; Saccharomyces/*E. coli* phagemid vector pEMBLYi27; *E. coli* phagemid pHis-Gal; Saccharomyces/*E. coli* phagemid vector pJA50; Saccharomyces/*E. coli* phagemid vector pJA51; Saccharomyces/*E. coli* phagemid vector pJA52; Saccharomyces/*E. coli* phagemid vector pJA53; Streptomyces/*E. coli* phagemid vector pKC1064; Vertebrate/*E. coli* phagemid vector pLUC; Vertebrate/*E. coli* phagemid vector pLUCS; *E. coli* phagemid vector pMA200U; Insect/*E. coli* phagemid vector pMbac; *E. coli* phagemid vector pMGU; Mammal/*E. coli* phagemid vector pOG44; Mammal/*E. coli* phagemid vector pOG45; *E. coli* plasmid vector pOK12; Mammal/*E. coli* phagemid vector pOPI3 CAT; Mammal/*E. coli* phagemid vector pOPRSVI CAT; Insect/*E. coli* phagemid vector pPbac; *E. coli* phagemid vector pRIT17; Saccharomyces/*E. coli* phagemid vector pRS166; Saccharomyces/*E. coli* phagemid vector pRS167; Saccharomyces/*E. coli* phagemid vector pRS169; Saccharomyces/*E. coli* phagemid vector pRS173; Saccharomyces/*E. coli* phagemid vector pRS202; Saccharomyces/*E. coli* phagemid vector pRS317; Saccharomyces/*E. coli* phagemid vector pRS318; Vertebrate/*E. coli* phagemid vector pRSVADH; Vertebrate/*E. coli* phagemid vector pRSVlacZII; Vertebrate/*E. coli* phagemid vector pRSVPAP; Vertebrate/*E. coli* phagemid vector pSHT; Vertebrate/*E. coli* phagemid vector pSV0Apap; Vertebrate/*E. coli* phagemid vector pSV232Apap; Vertebrate/*E. coli* phagemid vector pSV2Apap; *E. coli* phagemid vector pT7-7; *E. coli* phagemid vector pT7-7A; *E. coli* phagemid vector pT7-SCA; *E. coli* phagemid vector pT7-SCII; Vertebrate/*E. coli* phagemid vector pTAG-1; Vertebrate/*E. coli* phagemid vector pTAG4; *E. coli* plasmid vector pUC21; *E. coli* plasmid vector pUC6S; *E. coli* plasmid vector pUK21;

*Saccharomyces/E. coli* phagemid vector pUN30; *Saccharomyces/E. coli* phagemid vector pUN70; and *E. coli* phagemid vector pZL1;

In some embodiments, the following non-limiting illustrative phasmid vectors find use in the present invention: *E. coli* phasmid vector pEMBL18; *E. coli* phasmid vector pEMBL18+; *E. coli* phasmid vector pEMBL19-; *E. coli* phasmid vector pEMBL19+; *E. coli* phasmid vector pEMBL8-; *E. coli* phasmid vector pEMBL8+; *E. coli* phasmid vector pEMBL9-; *E. coli* phasmid vector pEMBL9+; and *E. coli* plasmid vector lambda SK.

In some embodiments, the following non-limiting illustrative bacterial artificial chromosomes (BACs) and cosmid vectors find use in the present invention: BAC pETcoco-1; BAC pETcoco-2; BAC pKLJ12; BAC pML31; *E. coli* cosmid vector Loric; *E. coli* cosmid vector Lorist2; *E. coli* cosmid vector LoristB; *E. coli* cosmid vector LoristE6; *E. coli* cosmid vector MUA-3; *E. coli* cosmid vector pAA113M; *E. coli* cosmid vector pDO184; *E. coli* cosmid vector pDO19; *E. coli* cosmid vector pDO2; *E. coli* cosmid vector pDO6; *Actinomycetes/E. coli* cosmid vector pFD666; *E. coli* cosmid vector pHC79; *E. coli* cosmid vector pIB8; *E. coli* plasmid vector pTL1; *E. coli* plasmid vector pTL3; *E. coli* plasmid vector pTL4; *E. coli* plasmid vector pTL5; *E. coli* cosmid vector pV34; Vertebrate/*E. coli* cosmid vector pWE15; *E. coli* cosmid vector pWE15A; *E. coli* cosmid vector sCos-1; Vertebrate/*E. coli* cosmid vector cos202; Vertebrate/*E. coli* cosmid vector cos203; *E. coli* cosmid vector cosKT1; Human/*E. coli* cosmid vector HDAB (1S149); *E. coli* cosmid vector HomerI; *E. coli* cosmid vector Lorist6; *E. coli* cosmid vector pAA3H; Broad host range/*E. coli* cosmid vector pAD22; *Saccharomyces/E. coli* cosmid vector pBTI-1; *Saccharomyces/E. coli* cosmid vector pBTI-10; *Saccharomyces/E. coli* cosmid vector pBTI-7; *Saccharomyces/E. coli* cosmid vector pBTI-9; Higher plants/*Agrobacterium/E. coli* cosmid vector pC22; *E. coli* cosmid vector pcos1EMBL; *E. coli* cosmid vector pcos2EMBL; *E. coli* cosmid vector pcos4EMBL; *E. coli* cosmid vector pcos5EMBL; *E. coli* cosmid vector pcos6EMBL; Broad host range/*E. coli* cosmid vector pCVD301; *Aspergillus/E. coli* cosmid vector pDG1; *E. coli* cosmid pDO192; *E. coli* cosmid pDO193; *E. coli* cosmid vector pHSG250; *E. coli* cosmid vector pHSG262; Broad host range/*E. coli* cosmid vector pHSG274; *E. coli* cosmid vector pJB8; Broad host range/*E. coli* cosmid vector pJRD215; *Aspergillus/E. coli* cosmid vector pKBY2; Broad host range/*E. coli* cosmid vector pLA2905; Broad host range/*E. coli* cosmid vector pLA2917; Broad host range/*E. coli* cosmid vector pLA2920; Broad host range/*E. coli* cosmid vector pLAFR1; *E. coli* cosmid vector pMF517; *E. coli* cosmid vector pMF7; Broad host range/*E. coli* cosmid vector pMMB33; Broad host range/*E. coli* cosmid vector pMMB34; *E. coli* cosmid vector pNO1517; *Actinomyces/E. coli* cosmid vector pOJ31; *Anacystis/E. coli* cosmid vector pPUC29; Broad host range/*E. coli* cosmid vector pUCD5; Broad host range/*Xanthomonas/E. coli* cosmid vector pUFR034; Broad host range/*E. coli* cosmid vector pVK100; Broad host range/*E. coli* cosmid vector pVK102; Vertebrate/*E. coli* cosmid vector pWE16; and *Drosophila/E. coli* cosmid vector smart2.

In some embodiments, vectors may be viral. Vectors of the invention comprise a nucleic acid encoding a gene of interest, or a complement thereof, operably linked to an expression control region, or complement thereof, that is functional in, for example, a mammalian cell. The expression control region is capable of driving expression of the operably linked blocking and/or stimulating agent encoding nucleic acid such that the blocking and/or stimulating agent is produced in a human cell transformed with the expression vector. In one aspect, the invention provides expression vectors that are viral vectors. Many viral vectors are known (see, e.g., Lundstrom, Trends Biotechnol., 21: 117, 122, 2003, the contents of which are hereby incorporated by reference in their entirety). In some embodiments, viral vectors illustrative include those selected from Antiviruses (LV), retroviruses (RV), adenoviruses (AV), adeno-associated viruses (AAV), and α viruses, though other viral vectors may also be used. For in vivo uses, viral vectors that do not integrate into the host genome are preferred, such as α viruses and adenoviruses, with α viruses being especially preferred. Exemplary types of α viruses include Sindbis virus, Venezuelan equine encephalitis (VEE) virus, and Semliki Forest virus (SFV), with SFV being especially preferred. For in vitro uses, viral vectors that integrate into the host genome are preferred, such as retroviruses, AAV, and Antiviruses.

In some embodiments, the following non-limiting illustrative YAC vectors find use in the present invention: *Saccharomyces*/vertebrate/*E. coli* YAC vector pNN414; *Saccharomyces/E. coli* YAC vector pYAC2; *Saccharomyces/E. coli* YAC vector pYAC3; *Saccharomyces/E. coli* YAC vector pYAC4; *Saccharomyces/E. coli* YAC vector pYAC5; *Saccharomyces/E. coli* YAC vector pYAC55; *Saccharomyces* YAC vector pYACneo; *Saccharomyces/E. coli* YAC vector pYAC-RC; and *Saccharomyces*/vertebrate/*E. coli* YAC vector pCGS966.

In some embodiments, kits comprising one or more constructs and/or host cells provided herein, or combinations thereof, are also provided. For example, if the kit comprises cells, the kit may also comprise cell culture medium. Optionally, the kit further comprises instructions for use.

This invention is further illustrated by the following non-limiting examples.

EXAMPLES

Example 1: Shuttle-MAGE Plasmid Construction to Engineer Cells with Modified Metabolic and Reporter Activity and Diverse Protein Products in a *Saccharomyces cerevisiae* Host The yeast 2u origin of replication and URA3 gene from the pYes2 plasmid (Plasmid 2, Table 4) was amplified using primers 1 and 2 from Table 1. This fragment was digested along with the pETcoco-2 plasmid (Plasmid 1, Table 4) with the restriction enzymes SacI & SphI, and inserted into the tunable copy number plasmid backbone pETcoco via DNA ligation using T4 DNA ligation. Resulting colonies were screened via colony PCR and the correct insert was verified by sequencing. This new 2u-pETcoco plasmid (Plasmid 3 in Table 4) was harvested from *E. coli* and transformed into *Saccharomyces cerevisiae* (strains BY4741 and BY4733, Strains 1 and 2 in Table 1) using a standard lithium acetate transformation protocol (Gietz R D, Schiestl R H. Nat Protoc. 2(1):31-4. (2007)) to confirm its ability to complement the uracil auxotrophy from those strains.

We next synthesized two constructs designed to target both endogenous (ADE2, Construct 1 in Table 3) and exogenous (Venus-YFP or vYFP, Construct 2) sequences in the yeast genome via the CRISPR genome editing system. The endogenous ADE2 target sequence was designed to include synonymous changes in the region recognized by the CRISPR guide RNA (FIG. 1A, blue lower case letters), while the exogenous YFP sequence [4] contained the identical sequence to that inserted into the genome. The vYFP construct contained the entire 717 base pair sequence of the gene, while the ADE2 construct comprised 400 bases encompassing the ade2-101 ochre mutation for red/white detection. The gRNAs contained on the synthesized sequences were preceeded by the yeast pSNR52 promoter and followed by the SUP4 terminator sequence, as described by DiCarlo J E, et al. (Nucleic Acids Res. 41(7):4336-43. (2013)). These synthesized constructs were PCR amplified (using Primers 5 and 6 from Table 1), digested with the PacI and PspXI restriction enzymes, then ligated as above into the 2u-pETcoco plasmid backbones (FIG. 1). These plasmids were confirmed via colony PCR and sequencing. These new shuttle plasmids are referred to as 2u-pETcoco-ADE2-gRNA-repair (Plasmid 4) and 2u-pETcoco-YFP-gRNA-repair (Plasmid 5).

Figure 2:
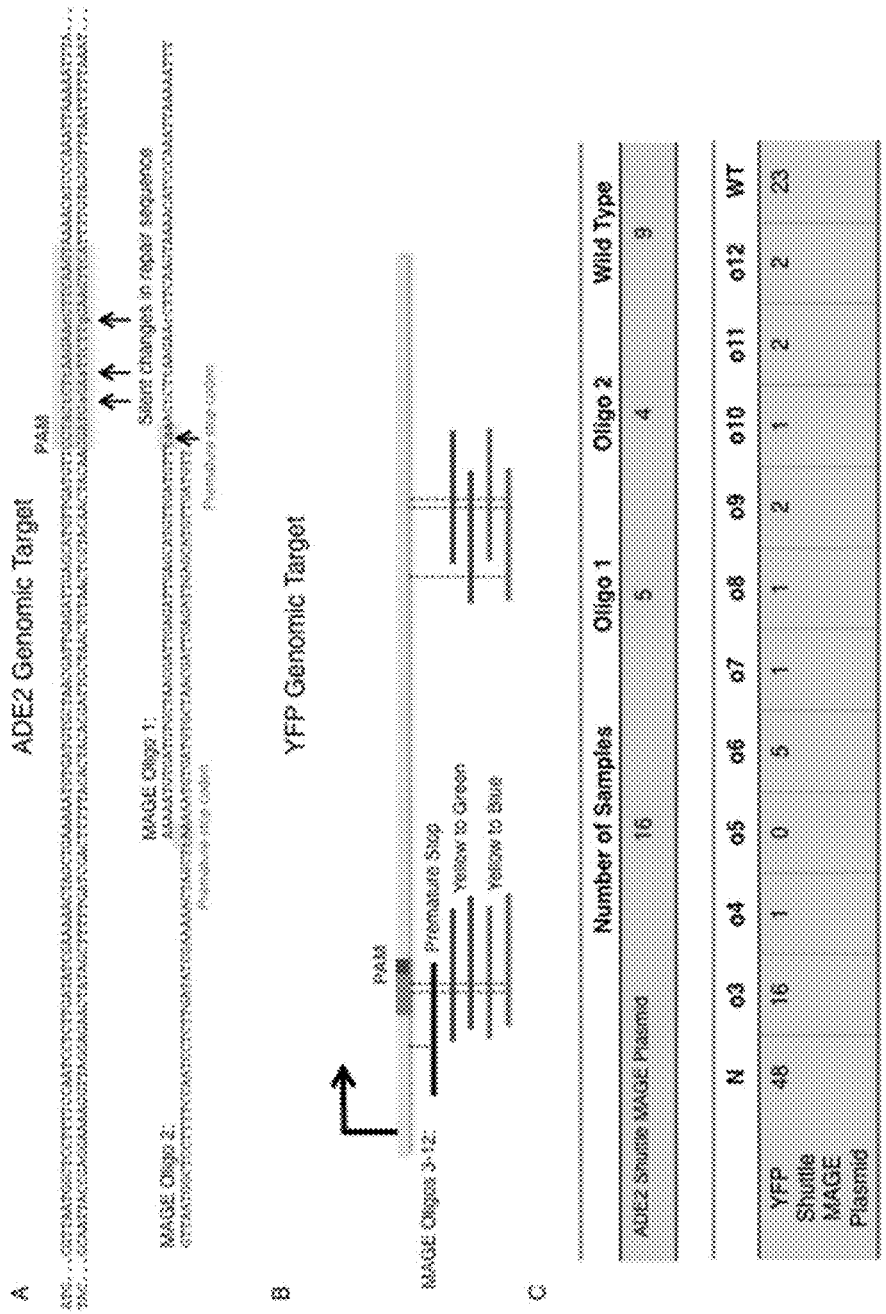
FIG. 2 shows modifying the shuttle-MAGE plasmid via MAGE. The repair sequences in the Shuttle-MAGE plasmid were targeted for modification by applying cycles of MAGE with oligos designed to introduce premature stop codons or new fluorescent properties to the target sequences. Panel A shows the ADE2 gene was targeted to be cleaved by Cas9 at the designated PAM recognition sequence. Two distinct MAGE oligos introduced premature stop codons in the encoding gene to render cells that utilize the given repair sequence to escape Cas9 cleavage unable to express a functional ADE2 allele. Panel B shows the fluorescent properties of the Venus-YFP gene introduced into the yeast genome were altered by the introduction of mutations in the sequence via MAGE. Oligos were designed to change the Venus-YFP sequence to that of either the Emerald (Yellow to Green) or Cerulean (Yellow to Blue) fluorescent proteins, or to contain a premature stop codon. The CRISPR gRNA target recognition sequence along the YFP target is shown in blue. Panel C shows after cycles of MAGE individual plasmids were sequenced to confirm that the desired mutations were incorporated.

Example 2: Shuttle-MAGE Plasmid Library Generation to Engineer Cells with Modified Metabolic and Reporter Activity and Diverse Protein Products in a *Saccharomyces cerevisiae* Host The 2u-pETcoco-gRNA-repair plasmids were transformed into MAGE-competent *E. coli* strains (EcM2.1, Strain 3 in Table 5). We performed 9 cycles of MAGE using oligos designed to introduce mutations in the ADE2 (Oligos 1 and 2, Table 2) or vYFP (Oligos 3-11, Table 2) sequences. For ADE2, each of the mutations was designed to introduce separate premature stop codons into the protein-encoding sequence (FIGS. 2, A and B). For vYFP, one oligo (Oligo 12) was similarly designed to introduce a premature stop codon, while the other oligos were designed to bestow the encoded fluorescent protein with alternative properties. This was engineered to alter the encoded Venus-YFP (vYFP) gene sequence to match that of either the Emerald fluorescent protein sequence (eGFP, Oligos 3-7) or Cerulean (CFP, oligos 3, 8-11). After MAGE cycling, single colonies were isolated from the plasmid-containing cultures on agar plates and the region of the plasmid that was targeted for mutagenesis was amplified by PCR using primers 3 and 4 (Table 1). The presence of the desired mutations was confirmed by sequencing (FIG. 2C). We were thus able to generate a combinatorial library containing up to 116 distinct fluorescent protein variants based on the vYFP sequence and 3 variants containing premature stop sequences in the ADE2 gene. Shuttle-MAGE plasmid libraries were induced to a high copy number and then harvested from the MAGE-competent *E. coli* hosts for future transformation into the target organism.

Example 3: Introducing Shuttle-MAGE Mutation Library into *Saccharomyces cerevisiae* Host to Engineer Cells with Modified Metabolic and Reporter Activity and Diverse Protein Products Two strains of the budding yeast *Saccharomyces cerevisiae* (BY4741 and BY4733) were modified to express the fluorescent protein vYFP from a constitutive promoter. The pTEF-driving vYFP sequence was transformed into the endogenous HO locus with a KanMX selectable marker surrounded by loxP recognition sites using a standard lithium acetate transformation protocol (Gietz R D, Schiestl R H. Nat Protoc. 2(1):31-4. (2007)). Proper integration of this cassette at the desired location in the genome was confirmed via PCR (primers 14 and 15). The KanMX marker was later removed from the genome by introducing and expressing the CRE-recombinase enzyme from the pSH47 plasmid (Plasmid 6), identifying drug sensitive colonies, and confirming the absence of the KanMX gene by PCR. In order to prepare strains to perform CRISPR-based genome editing, each strain was subsequently transformed to express Cas9 from the constitutive pTEF promoter episomally from a low-copy CEN plasmid containing the LEU2 auxotrophic marker (plasmid 7) (Dicarlo, et al. (2013). Genome engineering in *Saccharomyces cerevisiae* using CRISPR-Cas systems. *Nucleic Acids Research*. doi:10.1093/nar/gkt135). Introduction of this plasmid was selected for by growth in synthetic media absent of leucine, and Cas9 expression was confirmed via RT-PCR (primers 8 and 9).

Figure 3:
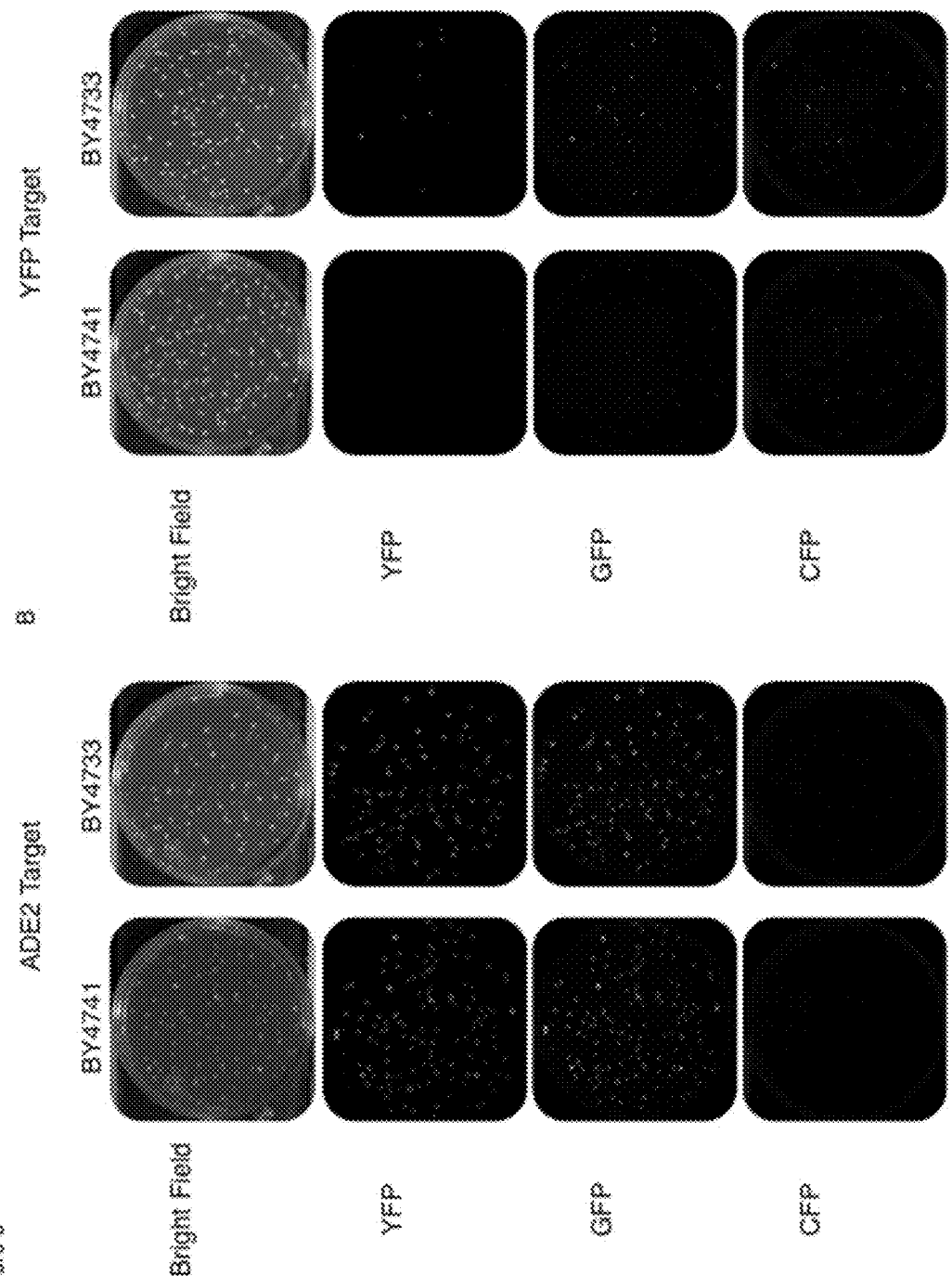
FIG. 3 shows imaging of yeast colonies to identify targeted changes. In order to confirm that the desired engineered mutations have been introduced into the target genomes, colonies of yeast strains were imaged after having undergone Shuttle-MAGE manipulation. Panel A shows the ADE2 Shuttle-MAGE plasmid was transformed into Cas9-expressing BY4741 and BY4733 cells. The resulting cultures were plated onto agar plates and photographed under different bright-field and fluorescent channels. The colonies that appear red have incorporated one of the premature stop codon mutations introduced by MAGE on the repair sequence in the Shuttle-MAGE plasmid. All colonies continue to express the Venus YFP protein. Panel B shows the YFP Shuttle-MAGE plasmid was transformed into Cas9-expressing cells. Under the fluorescent channels, most colonies appear to no longer be expressing the Venus YFP fluorescent protein, but rather an alternate fluorescent protein, pertaining either to Emerald (GFP) or Cerulean (CFP) fluorescent protein. The fluorescent spectra for the encoded YFP and GFP proteins largely overlap, so they appear very similar under the chosen imaging conditions.

Cas9-expressing strains were transformed with the harvested Shuttle-MAGE plasmid libraries containing either the introduced premature stop codons pertaining to the ADE2 locus or the changes to vYFP to alter its fluorescent properties as described above. Yeast strains with defective ADE2 genes will produce red colonies on agar plates [6]. The transformation cultures were grown on media without leucine and uracil, to select for the growth of only cells expressing both Cas9 and the guide RNAs and repair sequences from the Shuttle-MAGE plasmids. Transformation plates were then imaged to detect changes in colony color and or fluorescence (FIG. 3). All colonies that were targeted at the YFP locus produced white colonies, whereas the majority of the colonies targeted for ADE2 produced red colonies. Conversely, all ADE2-targeted colonies continued to express the vYFP fluorescent protein, but the colonies whose YFP-encoding sequences were targeted via CRISPR no longer appeared fluorescent in the same YFP spectrum but instead showed CFP or GFP properties (the spectra for GFP and YFP largely overlap, so there is some difficulty in distinguishing these colonies by plate imaging). Selected ADE2 and vYFP sequence fragments were amplified from the genomes (using primers 10 and 11 and 12 and 14, respectively) and sequenced to confirm that mutations that were introduced into the repair sequences of the plasmid were incorporated into the genome.

Example 4: Altering CRISPR gRNA Sequences Via MAGE

Figure 4:
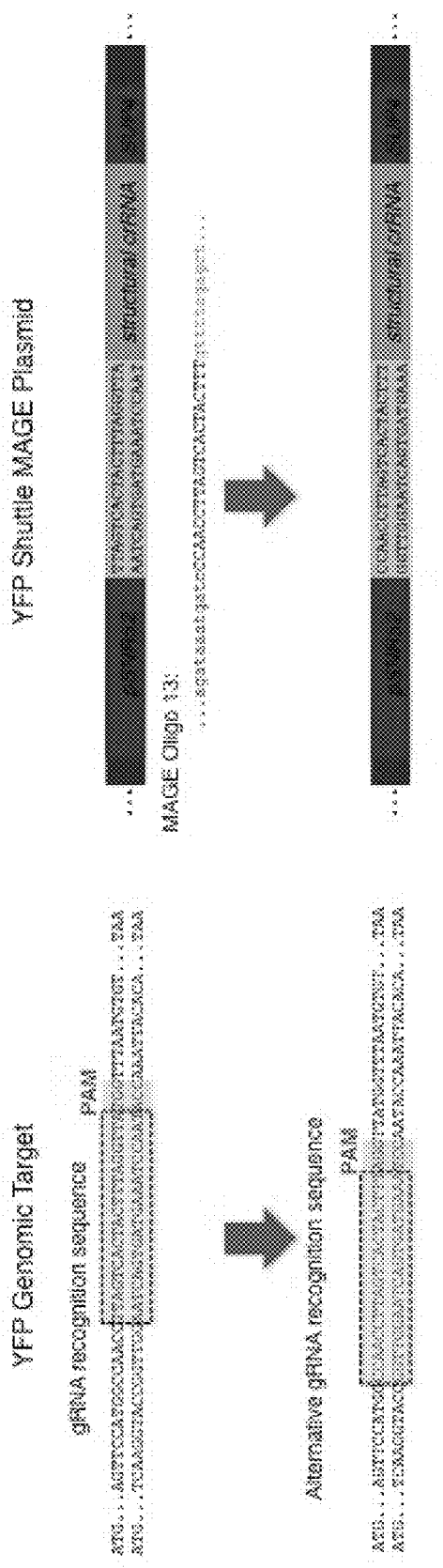
FIG. 4 shows changing CRISPR gRNAs on the shuttle-MAGE plasmid. In order to alter the Cas9 cleavage site along the genome (left), a MAGE oligo was designed to change the gRNA sequence in the Shuttle-MAGE plasmid (right). Cycles of MAGE were applied using Oligo 13, which contained homologous sequences to the regions up and downstream of the gRNA recognition sequence on the plasmid. The resulting library of plasmids is therefore capable of digesting and modifying the target genome at multiple sites.

In order to alter the target sequence determine by the CRISPR guide RNA, we performed MAGE cycling using an oligo designed to replace the 20-base gRNA recognition sequence on plasmid 5 with an alternative sequence homologous to the genomic target (oligo 13, FIG. 4). The oligo contained 35 bases homologous to the pSNR52 promoter followed by 20 bases of the new guide RNA target sequence followed by 35 bases homologous to the structural crRNA sequence. After five rounds of MAGE cycling, MAGE cultures were plated onto agar plates and the MAGE-targeted regions in selected colonies were amplified by colony PCR using primers 3 and 4. These PCR fragments were sequenced to confirm that the gRNA sequence had been altered via MAGE. Thus, the population of Shuttle-MAGE plasmids expressing CRISPR gRNAs was made into a library of heterogeneous CRISPR plasmids by MAGE.

TABLE 1

Primers used

| # | Name | Sequence |
|---|---|---|
| 1 | 2u-URA3F | TGTCGCTGTCGACGAGCTGAGCTCTGAAGCTCTAATTTGTGAGTTTAGT (SEQ ID NO: 4) |
| 2 | 2u-URA3R | CGTGATGGTGATGGTGATGCATGGCATGCATTATCAACCGGGGTGGAGC (SEQ ID NO: 5) |
| 3 | 2u-BB | AGGGAAGAAAGCGAAAGGAG (SEQ ID NO: 6) |
| 4 | 2u ori F | CAAGTTCAAGGAGCGAAAGG (SEQ ID NO: 7) |
| 5 | Misc-F | GCTAGATCATGCCGTGGATT (SEQ ID NO: 8) |
| 6 | Misc-R | GCTCTCACCATATCGGCATT (SEQ ID NO: 9) |
| 7 | TY1Rev | ATAATGCCTTTAGCGGCTTA (SEQ ID NO: 10) |
| 8 | Cas9 RT F | ATAAGGCTGACTGCGGTTG (SEQ ID NO: 11) |
| 9 | Cas9 RI R | GCTTTGGTGATCTCCGTGTT (SEQ ID NO: 12) |
| 10 | ADE2 F | ACCTTTTGATGCGGAATTGACTTT (SEQ ID NO: 13) |
| 11 | ADE2 R | ATTCCTTGCTTCTTGTTACTGGATA (SEQ ID NO: 14) |
| 12 | vYFP F | GAAGAATTATTCACTTGGTGTTGT (SEQ ID NO: 15) |
| 13 | vYFP R | TTATTTGTACAATTCATCCATACCA (SEQ ID NO: 16) |
| 14 | Internal HO cassette integration check | TCCTGATATGAATAAATTGCAGTTTCA (SEQ ID NO: 17) |
| 15 | External HO genome integration check | CAAGGCCATGTCTTCTCGTT (SEQ ID NO: 18) |

TABLE 2

MAGE Oligos used

| Number | Name | Sequence | Purpose |
|---|---|---|---|
| 1 | ADE2-101 | GTTAATGGCTCCTTTTCCAATCCTCTTGATATCGAAAAACTAGCTTAAAAATGTGATGTGCTAACGATTGAGATTGAGCATGTTGATGTT (SEQ ID NO: 19) | ADE2 premature stop |
| 2 | ADE2-2 | AAAAATGTGATGTGCTAACGATTGAGATTGAGCATGTTGATGTTTAAACTCTTAAGAACCTTCAAGTAAAACATCCCAAATTAAAAATTT (SEQ ID NO: 20) | ADE2 premature stop |
| 3 | YFP L46F | TGAAGGTGAAGGTGATGCTACTTACGGTAAATTGACCTTAAAATTTATTTGTACTACTGGTAAATTGCCAGTTCCATGGCCAACCTTAGT (SEQ ID NO: 21) | YFP L46F mutation |
| 4 | YFP2Em1 | TAAAATTGCCAGTTCCATGGCCAACCTTAGTCACTACTTTCCTTACTGGTGTAATGTGTTTTGCTAGATACCCAGATCATATGAAACAACA (SEQ ID NO: 22) | Venus to Emerald |
| 5 | YFP2Em2 | GACCTTAAAATTCATTTGTACTACTGGTAAATTGCCAGTTCCATGGCCAACCTTAGTCACTACTTTCCTTACTGGTGTAATGTGTTTTGC (SEQ ID NO: 23) | Venus to Emerald |
| 6 | YFP2EmDS1 | CAACTATAACTCTCACAAAGTTTACATCACTGCTGACAAACAAAAGAATGGTATCAAAGTTAACTTCAAAACTAGACACAACATTGAAGA (SEQ ID NO: 24) | Venus to Emerald |
| 7 | YFP2EmDS2 | GACAAACAAAAGAATGGTATCAAAGTTAACTTCAAAACTAGACACAACATTGAAGATGGTAGTGTTCAATTAGCTGACCATTATCAACAA (SEQ ID NO: 25s) | Venus to Emerald |
| 8 | YFP2Cer1 | TAAAATTGCCAGTTCCATGGCCAACCTTAGTCACTACTTTAACTTGGGGTGTAATGTGTTTTGCTAGATACCCAGATCATATGAAACAACA (SEQ ID NO: 26) | Venus to Cerulean |
| 9 | YFP2Cer2 | GACCTTAAAATTCATTTGTACTACTGGTAAATTGCCAGTTCCATGGCCAACCTTAGTCACTACTTTAACTTGGGGTGTAATGTGTTTTGC (SEQ ID NO: 27) | Venus to Cerulean |
| 10 | YFP2CerDS1 | AAGAAGATGGTAACATTTAGGTCACAAATTGGAATACAAGGCTAACTCTGACATTGTTTACATCACTGCTGACAAACAAAAGAATGGTA (SEQ ID NO: 28) | Venus to Cerulean |
| 11 | YFP2CerDS2 | GACAAACAAAAGAATGGTATCAAAGCTAACTTCAAATTAGACACAACATTGAAGATGGTAGTGTTCAATTAGCTGACCATTATCAACAA (SEQ ID NO: 29) | Venus to Cerulean |

TABLE 2-continued

MAGE Oligos used

| Number | Name | Sequence | Purpose |
|---|---|---|---|
| 12 | YFP2DARK | ACTACTGGTAAATTGCCAGTTCCATGGCCAACCTT AGTCACTTAATTAGGTTATGGTTTAATGTGTTTTGC TAGATACCCAGATCATATG (SEQ ID NO: 30) | Premature stop |
| 13 | YFP gRNA_2 | GTTCGAAACTTCTCCGCAGTGAAAGATAAATGATC CCAACCTTAGTCACTACTTTGTTTTAGAGCTAGAA ATAGCAAGTTAAAATAAGGC (SEQ ID NO: 31) | Replace YFP gRNA |

TABLE 3

Synthesized Constructs used

| | | |
|---|---|---|
| 1 | ADE2 repair and gRNA | GCTAGATCATGCCGTGGATTGCGATCGCCAAGCTTAA TTAAATGGATTCTAGAACAGTTGGTATATTAGGAGGG GGACAATTGGGACGTATGATTGTTGAGGCAGCAAACA GGCTCAACATTAAGACGGTAATACTAGATGCTGAAAA TTCTCCTGCCAAACAAATAAGCAACTCCAATGACCAC GTTAATGGCTCCTTTTCCAATCCTCTTGATATCGAAA AACTAGCTGAAAAATGTGATGTGCTAACGATTGAGAT TGAGCATGTTGATGTTCCTACTCTTAAGAACCTTCAA GTAAAACATCCCAAATTAAAAATTTACCCTTCTCCAG AAACAATCAGATTGATACAAGACAAATATATTCAAAA AGAGCATTTAATCAAAAATGGTATAGCAGTTACCCAA AGTGTTCCTGTGGAACAAGCCAGTGAGACGTCCCGGC GGCCGCTCTTTGAAAAGATAATGTATGATTATGCTTT CACTCATATTTATACAGAAACTTGATGTTTTCTTTCG AGTATATACAAGGTGATTACATGTACGTTTGAAGTAC AACTCTAGATTTTGTAGTGCCCTCTTGGGCTAGCGGT AAAGGTGCGCATTTTTTCACACCCTACAATGTTCTGT TCAAAAGATTTTGGTCAAACGCTGTAGAAGTGAAAGT TGGTGCGCATGTTTCGGCGTTCGAAACTTCTCCGCAG TGAAAGATAAATGATCACTTGAAGATTCTTTAGTGTG TTTTAGAGCTAGAAATAGCAAGTTAAAATAAGGCTAG TCCGTTATCAACTTGAAAAGTGGCACCGAGTCGGTG GTGCTTTTTTGTTTTTATGTCACTCGAGCATGCAA TGCCGATATGGTGAGAGC (SEQ ID NO: 32) |
| 2 | vYFP repair and gRNA | GCTAGATCATGCCGTGGATTGCGATCGCCAAGCTTGG ACGTCTTAATTAATAACAAAATGTCTAAAGGTGAAGA ATTATTCACTGGTGTTGTCCCAACTTTGGTTGAATTA GATGGTGATGTTAATGGTCACAAATTTTCTGTCTCCG GTGAAGGTGAAGGTGATGCTACTTACGGTAAATTGAC CTTAAAATTAATTTGTACTACTGGTAAATTGCCAGTT CCATGGCCAACCTTAGTCACTACTTAGGTTATCGTTT AATGTGTTTTGCTAGATACCCAGATCATATGAAACAA CATGACTTTTTCAAGTCTGCCATGCCAGAAGGTTATG TTCAAGAAAGAACTATTTTTTTCAAAGATGACGGTAA CTACAAGACCAGAGCTGAAGTCAAGTTTGAAGGTGAT ACCTTAGTTAATAGAATCGAATTAAAAGGTATTGATT TTAAAGAAGATGGTAACATTTTAGGTCACAAATTGGA ATACAACTATAACTCTCACAATGTTTACATCACTGCT GACAAACAAAAGAATGGTATCAAAGGTAACTTCAAA TTAGACACAACATTGAAGATGGTGGTGTTCAATTAGC TGACCATTATCAACAAAATACTCCAATTGGTGATGGT CCAGTCTTGTTACCAGACAACCATTACTTATCCTATC AATCTGCCTTATCCAAAGATCCAAACGAAAGAGAGA CCACATGGTCTTGTTAGAATTTGTTACTGCTGCTGGT ATTACCCATGGTATGGATGAATTGTACAAATAAGGCG CGCCATGCATGGCGGCCGCTCTTTGAAAAGATAATGT ATGATTATGCTTTCACTCATATTTATACAGAAACTTG ATGTTTTCTTTCGAGTATATACAAGGTGATTACATGT ACGTTTGAAGTACAACTCTAGATTTTGTAGTGCCCTC TTGGGCTAGCGGTAAAGGTGCGCATTTTTTCACACCC TACAATGTTCTGTTCAAAAGATTTTGGTCAAACGCTG TAGAAGTGAAAGTTGGTGCGCATGTTTCGGCGTTCGA AACTTCTCCGCAGTGAAAGATAAATGATCTTAGTCAC TACTTTAGGTTAGTTTTAGAGCTAGAAATAGCAAGTT AAAATAAGGCTAGTCCGTTATCAACTTGAAAAGTGG CACCGAGTCGGTGGTGCTTTTTTGTTTTTATGTCA CTCGAGCATGCAATGCCGATATGGTGAGAGC (SEQ ID NO: 33) |

TABLE 4

Plasmids used

| Number | Name | Purpose | Custom or Purchased |
|---|---|---|---|
| 1 | pETcoco-2 | Inducible plasmid | Purchased |
| 2 | pYes2 | Cloning 2u-URA3 | Purchased |
| 3 | 2u-pETcoco | Backbone for all Shuttle-MAGE plasmids described in this study | Custom |
| 4 | 2u-pETcoco-ADE2-gRNA-repair | | Custom |
| 5 | 2u-pETcoco-YFP-gRNA-repair | | Custom |
| 6 | pSH47 | Cre expression | Purchased |
| 7 | CEN pTEF-Cas9 | | Custom |

TABLE 5

Strains Used

| Name | Background | Genotype | Reference |
|---|---|---|---|
| BY4741 | *Saccharomyces cerevisiae* s288c | MATa his3delta1 leu2delta0 met15delta0 ura3delta0 | Brachmann C B, et al. Yeast. Jan 30; 14(2): 115-32. (1998) |
| BY4733 | *Saccharomyces cerevisiae* s288c | MATa his3delta200 leu2delta0 met15delta0 trp1delta63 ura3delta0 | Brachmann C B, et al. Yeast. Jan 30; 14(2): 115-32. (1998) |

TABLE 5-continued

Strains Used

| Name | Background | Genotype | Reference |
|---|---|---|---|
| EcM2.1 | E. coli | EcNR2.dtolC.xonA-.xseA-.exoX-.dnaG_Q576A.ec1.2556::tolQRA.mutS.KO (recJ+) | Gregg C J, et al. Nucleic Acids Res. 42(7): 4779-90 (2014) |

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

What is claimed is:

1. A method for multiplex engineering of a cell for production of a desired chemical or a desired phenotype, comprising:
   a) introducing an oligonucleotide library into a population of cells of a target organism,
      the cells expressing a single-stranded annealing protein (SSAP) system and/or a recombinase system that optionally promotes annealing of single stranded oligonucleotides at a lagging strand of a replication fork, and
      the oligonucleotide library targeting gene sequences of primary and secondary metabolic pathways and/or heterologous genes;
   b) targeting at least one locus with the SSAP system and/or the recombinase system and the oligonucleotide library, and
   c) selecting for cells having a desired mutation through altered expression of a selectable marker or reporter gene as a result of oligonucleotide incorporation or
      selecting against cells without a desired mutation with a site-specific programmable nuclease system; and
   d) selecting for cells having increased production of the desired chemical or the desired phenotype
   wherein the oligonucleotide library further targets at least one heterologously expressed gene, which is optionally an enzyme or a recombinant protein for purification.

2. The method of claim 1, wherein the SSAP system and/or the recombinase system comprises Beta protein of λ Red, RecT protein of RecET system, and/or proteins from the Rad52-like, Rad51-like, or Gp2.5-like superfamilies.

3. The method of claim 1, wherein the SSAP system and/or the recombinase system further comprises a deletion, inactivation, or inhibition of a mismatch repair protein.

4. The method of claim 1 wherein the cell has a deletion, repression, or inactivation of one or more single stranded DNA nucleases.

5. The method of claim 1, wherein the site-specific programmable nuclease system is a CRISPR/Cas9, BuD, ZFN, TALE, or TALEN.

6. The method of claim 1, wherein all or a portion of the site-specific programmable nuclease system is directly tethered on the same DNA to a repair or donor DNA sequence that is optionally either a synthetic DNA or elaborated with a multiplex genome engineering technique, which is optionally Multiplex Automated Genomic Engineering (MAGE).

7. The method of claim 1, wherein there is roughly a 1:1:1 ratio of DNA encoding selectable marker for the target organism, the site-specific programmable nuclease designed to cut the organism genome, and the repair or donor DNA.

8. The method of claim 1, wherein a vector suitable for replication in the target species and suitable for replication in a second species is co-transformed with the oligonucleotide library, wherein the vector expresses one or more components of the site-specific programmable nuclease system.

9. The method of claim 8, wherein the vector comprises one or more target sequence variants, gRNA, tracrRNA and/or crRNA components directing editing of a target sequence.

10. The method of claim 8, wherein the vector comprises one or more target sequence variants and gRNAs directing editing of the target sequence.

11. The method of claim 8, wherein the vector is engineered in a cell which is a MAGE-competent recombineering strain, which is optionally *E. coli*.

12. The method of claim 8, wherein the vector is exported to a target cell, which is not MAGE-competent or not recombineering.

13. The method of claim 8, wherein the vector is derived from a vector library that is transformed in a cyclical manner.

14. The method of claim 8, wherein the vector library targets more than one genomic locus, and optionally at least 10, at least 100, or at least 1000 loci.

15. The method of claim 1, wherein the selecting for the desired mutation is against a target sequence and in favor of target sequence variants.

16. The method of claim 1, wherein the selecting for the desired mutations is accomplished by providing relief from the site-specific programmable nuclease system or selection by repair of a selectable marker or gene encoding a fluorescent protein.

17. The method of claim 1, wherein the oligonucleotide library is introduced into the cells by one or more of electroporation, chemical transformation, ballistic transformation, pressure induced transformation, mechanical shear forces induced in microfluidics and carbon nanotubes, nanotube puncture, induced natural competence mechanisms of an organism, merging of protoplasts, and conjugation with *Agrobacterium*.

18. The method of claim 1, wherein modification of the target organism with the SSAP system and/or the site-specific programmable nuclease system is conducted in continuous fashion.

19. The method of claim 1, wherein the cell is a bacteria, yeast, filamentous fungi, algae, or plant cell.

20. The method of claim 1, wherein the target organism belongs to the bacterial genus selected from *Clostridium, Phytoplasma, Mycoplasma, Enterococcus, Lactococcus, Streptococcus, Staphylococcus, Listeria, Bacillus, Borrelia, Streptomyces, Corynebacterium, Mycobacterium, Acidobacterium, Geobacter, Campylobacter, Helicobacter, Wolbachia, Brucela, Agrobacterium, Chromobacterium, Neisseria, Bordetella, Xanthomonas, Psuedomonas, Xyella, Shewanella, Photobacterium, Vibrio, Haemophilus, Buchnera, Yersinia, Salmonella, Escherichia, Shigglea*, and *Lactobacillus* or an ascomycete yeast selected from *Saccharomyces cerevisiae, Yarrowia lipolytica, Pichia pastoris*, and *Pichia stipitis*.

21. The method of claim 1, wherein the desired phenotype is one or more of a change in carbon substrate utilization, increased cell growth rate, increased production of a desired chemical, redox cofactor balance, reduced production of one or more undesired byproducts, increased resistance to industrial fermentation, and increased recombinant protein production.

22. The method of claim 1, wherein cells with an improvement in the desired phenotype are selected in culture or in colonies and/or using a microfluidics system optionally with one or more of chromatographic analysis, spectroscopic analysis, extraction followed by an analytical chromatographic step, chemical chromogenic assay, flow cytometric analysis and sorting, enzymatic activity assay, zone of inhibition assay, and auxotrophic reporter strain growth assay.

23. The method of claim 1, wherein the metabolic pathway produces a natural or unnatural amino acid, nucleotide, lipid, fatty acid, antibiotic, pharmaceutical or intermediate thereof, therapeutic molecule or intermediate thereof, or a terpene or terpenoid.

* * * * *

SEQUENCE LISTING

```
<160> NUMBER OF SEQ ID NOS: 41

<210> SEQ ID NO 1
<211> LENGTH: 8
<212> TYPE: RNA
<213> ORGANISM: unknown
<220> FEATURE:
<223> OTHER INFORMATION: Kozak Sequence

<400> SEQUENCE: 1 ccaccaug                                                                8

<210> SEQ ID NO 2
<211> LENGTH: 9
<212> TYPE: RNA
<213> ORGANISM: unknown
<220> FEATURE:
<223> OTHER INFORMATION: Kozak sequence

<400> SEQUENCE: 2 ccaccaugg                                                               9

<210> SEQ ID NO 3
<211> LENGTH: 6
<212> TYPE: RNA
<213> ORGANISM: unknown
<220> FEATURE:
<223> OTHER INFORMATION: Shine dalgarno sequence

<400> SEQUENCE: 3 aggagg                                                                  6

<210> SEQ ID NO 4
<211> LENGTH: 49
<212> TYPE: DNA
<213> ORGANISM: artificial
<220> FEATURE:
<223> OTHER INFORMATION: oligonucleotide primer
```

-continued

```
<400> SEQUENCE: 4
tgtcgctgtc gacgagctga gctctgaagc tctaatttgt gagtttagt          49

<210> SEQ ID NO 5
<211> LENGTH: 49
<212> TYPE: DNA
<213> ORGANISM: artificial
<220> FEATURE:
<223> OTHER INFORMATION: oligonucleotide primer

<400> SEQUENCE: 5
cgtgatggtg atggtgatgc atggcatgca ttatcaaccg gggtggagc          49

<210> SEQ ID NO 6
<211> LENGTH: 20
<212> TYPE: DNA
<213> ORGANISM: artificial
<220> FEATURE:
<223> OTHER INFORMATION: oligonucleotide primer

<400> SEQUENCE: 6
agggaagaaa gcgaaaggag                                          20

<210> SEQ ID NO 7
<211> LENGTH: 20
<212> TYPE: DNA
<213> ORGANISM: artificial
<220> FEATURE:
<223> OTHER INFORMATION: oligonucleotide primer

<400> SEQUENCE: 7
caagttcaag gagcgaaagg                                          20

<210> SEQ ID NO 8
<211> LENGTH: 20
<212> TYPE: DNA
<213> ORGANISM: artificial
<220> FEATURE:
<223> OTHER INFORMATION: oligonucleotide primer

<400> SEQUENCE: 8
gctagatcat gccgtggatt                                          20

<210> SEQ ID NO 9
<211> LENGTH: 20
<212> TYPE: DNA
<213> ORGANISM: artificial
<220> FEATURE:
<223> OTHER INFORMATION: oligonucleotide primer

<400> SEQUENCE: 9
gctctcacca tatcggcatt                                          20

<210> SEQ ID NO 10
<211> LENGTH: 20
<212> TYPE: DNA
<213> ORGANISM: artificial
<220> FEATURE:
<223> OTHER INFORMATION: oligonucleotide primer

<400> SEQUENCE: 10
ataatgcctt tagcggctta                                          20

<210> SEQ ID NO 11
<211> LENGTH: 20
```

```
<212> TYPE: DNA
<213> ORGANISM: artificial
<220> FEATURE:
<223> OTHER INFORMATION: oligonucleotide primer

<400> SEQUENCE: 11
ataaggctga cttgcggttg                                              20

<210> SEQ ID NO 12
<211> LENGTH: 20
<212> TYPE: DNA
<213> ORGANISM: artificial
<220> FEATURE:
<223> OTHER INFORMATION: oligonucleotide primer

<400> SEQUENCE: 12
gctttggtga tctccgtgtt                                              20

<210> SEQ ID NO 13
<211> LENGTH: 24
<212> TYPE: DNA
<213> ORGANISM: artificial
<220> FEATURE:
<223> OTHER INFORMATION: oligonucleotide primer

<400> SEQUENCE: 13
accttttgat gcggaattga cttt                                         24

<210> SEQ ID NO 14
<211> LENGTH: 25
<212> TYPE: DNA
<213> ORGANISM: artificial
<220> FEATURE:
<223> OTHER INFORMATION: oligonucleotide primer

<400> SEQUENCE: 14
attccttgct tcttgttact ggata                                        25

<210> SEQ ID NO 15
<211> LENGTH: 23
<212> TYPE: DNA
<213> ORGANISM: artificial
<220> FEATURE:
<223> OTHER INFORMATION: oligonucleotide primer

<400> SEQUENCE: 15
gaagaattat tcactggtgt tgt                                          23

<210> SEQ ID NO 16
<211> LENGTH: 25
<212> TYPE: DNA
<213> ORGANISM: artificial
<220> FEATURE:
<223> OTHER INFORMATION: oligonucleotide primer

<400> SEQUENCE: 16
ttatttgtac aattcatcca tacca                                        25

<210> SEQ ID NO 17
<211> LENGTH: 27
<212> TYPE: DNA
<213> ORGANISM: artificial
<220> FEATURE:
<223> OTHER INFORMATION: oligonucleotide primer

<400> SEQUENCE: 17
```

```
tcctgatatg aataaattgc agtttca                                    27
```

```
<210> SEQ ID NO 18
<211> LENGTH: 20
<212> TYPE: DNA
<213> ORGANISM: artificial
<220> FEATURE:
<223> OTHER INFORMATION: oligonucleotide primer

<400> SEQUENCE: 18
caaggccatg tcttctcgtt                                            20
```

```
<210> SEQ ID NO 19
<211> LENGTH: 100
<212> TYPE: DNA
<213> ORGANISM: artificial
<220> FEATURE:
<223> OTHER INFORMATION: oligonucleotide primer

<400> SEQUENCE: 19
gttaatggct cctttccaa tcctcttgat atcgaaaaac tagcttaaaa atgtgatgtg  60
ctaacgattg ctaacgattg agattgagca tgttgatgtt                      100
```

```
<210> SEQ ID NO 20
<211> LENGTH: 90
<212> TYPE: DNA
<213> ORGANISM: artificial
<220> FEATURE:
<223> OTHER INFORMATION: oligonucleotide primer

<400> SEQUENCE: 20
aaaaatgtga tgtgctaacg attgagattg agcatgttga tgtttaaact cttaagaacc  60
ttcaagtaaa acatcccaaa ttaaaaattt                                  90
```

```
<210> SEQ ID NO 21
<211> LENGTH: 90
<212> TYPE: DNA
<213> ORGANISM: artificial
<220> FEATURE:
<223> OTHER INFORMATION: oligonucleotide primer

<400> SEQUENCE: 21
tgaaggtgaa ggtgatgcta cttacggtaa attgacctta aaatttattt gtactactgg  60
taaattgcca gttccatggc caaccttagt                                  90
```

```
<210> SEQ ID NO 22
<211> LENGTH: 90
<212> TYPE: DNA
<213> ORGANISM: artificial
<220> FEATURE:
<223> OTHER INFORMATION: oligonucleotide primer

<400> SEQUENCE: 22
taaattgcca gttccatggc caaccttagt cactactttc cttactggtg taatgtgttt  60
tgctagatac ccagatcata tgaaacaaca                                  90
```

```
<210> SEQ ID NO 23
<211> LENGTH: 90
<212> TYPE: DNA
<213> ORGANISM: artificial
<220> FEATURE:
<223> OTHER INFORMATION: oligonucleotide primer

<400> SEQUENCE: 23
```

```
gaccttaaaa ttcatttgta ctactggtaa attgccagtt ccatggccaa ccttagtcac    60
tactttcctt actggtgtaa tgtgttttgc                                     90

<210> SEQ ID NO 24
<211> LENGTH: 90
<212> TYPE: DNA
<213> ORGANISM: artificial
<220> FEATURE:
<223> OTHER INFORMATION: oligonucleotide primer

<400> SEQUENCE: 24
caactataac tctcacaaag tttacatcac tgctgacaaa caaagaatg gtatcaaagt     60 taacttcaaa actagacaca acattgaaga                                     90

<210> SEQ ID NO 25
<211> LENGTH: 90
<212> TYPE: DNA
<213> ORGANISM: artificial
<220> FEATURE:
<223> OTHER INFORMATION: oligonucleotide primer

<400> SEQUENCE: 25
gacaaacaaa agaatggtat caaagttaac ttcaaaacta gacacaacat tgaagatggt    60
agtgttcaat tagctgacca ttatcaacaa                                     90

<210> SEQ ID NO 26
<211> LENGTH: 90
<212> TYPE: DNA
<213> ORGANISM: artificial
<220> FEATURE:
<223> OTHER INFORMATION: oligonucleotide primer

<400> SEQUENCE: 26
taaattgcca gttccatggc caaccttagt cactacttta acttggggtg taatgtgttt    60
tgctagatac ccagatcata tgaaacaaca                                     90

<210> SEQ ID NO 27
<211> LENGTH: 90
<212> TYPE: DNA
<213> ORGANISM: artificial
<220> FEATURE:
<223> OTHER INFORMATION: oligonucleotide primer

<400> SEQUENCE: 27
gaccttaaaa ttcatttgta ctactggtaa attgccagtt ccatggccaa ccttagtcac    60
tactttaact tggggtgtaa tgtgttttgc                                     90

<210> SEQ ID NO 28
<211> LENGTH: 90
<212> TYPE: DNA
<213> ORGANISM: artificial
<220> FEATURE:
<223> OTHER INFORMATION: oligonucleotide primer

<400> SEQUENCE: 28
aagaagatgg taacattta ggtcacaaat tggaatacaa cgctaactct gacattgttt     60
acatcactgc tgacaaacaa aagaatggta                                     90

<210> SEQ ID NO 29
<211> LENGTH: 90
<212> TYPE: DNA
```

<213> ORGANISM: artificial
<220> FEATURE:
<223> OTHER INFORMATION: oligonucleotide primer

<400> SEQUENCE: 29
gacaaacaaa agaatggtat caaagctaac ttcaaaatta gacacaacat tgaagatggt   60
agtgttcaat tagctgacca ttatcaacaa                                    90

<210> SEQ ID NO 30
<211> LENGTH: 90
<212> TYPE: DNA
<213> ORGANISM: artificial
<220> FEATURE:
<223> OTHER INFORMATION: oligonucleotide primer

<400> SEQUENCE: 30
actactggta aattgccagt ccatggcca accttagtca cttaattagg ttatggttta    60
atgtgttttg ctagataccc agatcatatg                                    90

<210> SEQ ID NO 31
<211> LENGTH: 90
<212> TYPE: DNA
<213> ORGANISM: artificial
<220> FEATURE:
<223> OTHER INFORMATION: oligonucleotide primer

<400> SEQUENCE: 31
gttcgaaact tctccgcagt gaaagataaa tgatcccaac cttagtcact actttgtttt   60
agagctagaa atagcaagtt aaaataaggc                                    90

<210> SEQ ID NO 32
<211> LENGTH: 869
<212> TYPE: DNA
<213> ORGANISM: artificial
<220> FEATURE:
<223> OTHER INFORMATION: synthetic costruct

<400> SEQUENCE: 32
gctagatcat gccgtggatt gcgatcgcca agcttaatta aatggattct agaacagttg    60
gtatattagg aggggacaa ttgggacgta tgattgttga ggcagcaaac aggctcaaca   120
ttaagacggt aatactagat gctgaaaatt ctcctgccaa acaaataagc aactccaatg   180
accacgttaa tggctccttt tccaatcctc ttgatatcga aaaactagct gaaaaatgtg   240
atgtgctaac gattgagatt gagcatgttg atgttcctac tcttaagaac cttcaagtaa   300
aacatcccaa attaaaaatt tacccttctc cagaaacaat cagattgata caagacaaat   360
atattcaaaa agagcattta atcaaaaatg gtatagcagt tacccaaagt gttcctgtgg   420
aacaagccag tgagacgtcc cggcggccgc tctttgaaaa gataatgtat gattatgctt   480
tcactcatat ttatacagaa acttgatgtt ttctttcgag tatatacaag gtgattacat   540
gtacgtttga agtacaactc tagattttgt agtgccctct gggctagcg gtaaaggtgc    600 gcatttttttc acaccctaca atgttctgtt caaaagattt tggtcaaacg ctgtagaagt   660
gaaagttggt gcgcatgttt cggcgttcga aacttctccg cagtgaaaga taatgatca   720 cttgaagatt ctttagtgtg ttttagagct agaaatagca agttaaaata aggctagtcc   780
gttatcaact tgaaaagtg gcaccgagtc ggtggtgctt ttttgttttt ttatgtcact   840
cgagcatgca atgccgatat ggtgagagc                                    869

```
<210> SEQ ID NO 33
<211> LENGTH: 1216
<212> TYPE: DNA
<213> ORGANISM: artificial
<220> FEATURE:
<223> OTHER INFORMATION: synthetic construct

<400> SEQUENCE: 33
gctagatcat gccgtggatt gcgatcgcca agcttggacg tcttaattaa taacaaaatg      60
tctaaaggtg aagaattatt cactggtgtt gtcccaactt tggttgaatt agatggtgat     120
gttaatggtc acaaattttc tgtctccggt gaaggtgaag gtgatgctac ttacggtaaa     180
ttgaccttaa aattaatttg tactactggt aaattgccag ttccatggcc aaccttagtc     240
actactttag gttatggttt aatgtgtttt gctagatacc cagatcatat gaaacaacat     300
gactttttca gtctgccat gccagaaggt tatgttcaag aaagaactat tttttttcaaa     360 gatgacggta actacaagac cagagctgaa gtcaagtttg aaggtgatac cttagttaat     420
agaatcgaat taaaaggtat tgattttaaa gaagatggta acattttagg tcacaaattg     480
gaatacaact ataactctca caatgtttac atcactgctg acaaacaaaa gaatggtatc     540
aaagctaact tcaaaattag acacaacatt gaagatggtg tgttcaatt agctgaccat     600 tatcaacaaa atactccaat tggtgatggt ccagtcttgt taccagacaa ccattactta     660
tcctatcaat ctgccttatc caaagatcca acgaaaaga gagaccacat ggtcttgtta     720
gaatttgtta ctgctgctgg tattacccat ggtatggatg aattgtacaa ataaggcgcg     780
ccatgcatgg cggccgctct ttgaaaagat aatgtatgat tatgctttca ctcatattta     840
tacagaaact tgatgttttc tttcgagtat atacaaggtg attacatgta cgtttgaagt     900
acaactctag attttgtagt gccctcttgg gctagcggta aaggtgcgca ttttttcaca     960
ccctacaatg ttctgttcaa aagattttgg tcaaacgctg tagaagtgaa agttggtgcg    1020
catgtttcgg cgttcgaaac ttctccgcag tgaaagataa atgatcttag tcactactt    1080 aggttagttt tagagctaga aatagcaagt taaaataagg ctagtccgtt atcaacttga    1140
aaaagtggca ccgagtcggt ggtgcttttt ttgtttttta tgtcactcga gcatgcaatg    1200
ccgatatggt gagagc                                                    1216

<210> SEQ ID NO 34
<211> LENGTH: 141
<212> TYPE: DNA
<213> ORGANISM: unknown
<220> FEATURE:
<223> OTHER INFORMATION: ADE2 genomic target sequence

<400> SEQUENCE: 34
atgcgttaat ggctcctttt ccaatcctct tgatatcgaa aaactagctg aaaaatgtga      60
tgtgctaacg attgagattg agcatgttga tgttcctaca ctaaagaatc ttcaagtaaa     120
acatcccaaa ttaaaaattt a                                               141

<210> SEQ ID NO 35
<211> LENGTH: 90
<212> TYPE: DNA
<213> ORGANISM: artificial
<220> FEATURE:
<223> OTHER INFORMATION: oligonucleotide primer

<400> SEQUENCE: 35
aaaaatgtga tgtgctaacg attgagattg agcatgttga tgtttaaact cttaagaacc      60
```

```
ttcaagtaaa acatcccaaa ttaaaaattt                                              90

<210> SEQ ID NO 36
<211> LENGTH: 90
<212> TYPE: DNA
<213> ORGANISM: artificial
<220> FEATURE:
<223> OTHER INFORMATION: oligonucleotide primer

<400> SEQUENCE: 36
gttaatggct ccttttccaa tcctcttgat atcgaaaaac tagcttaaaa atgtgatgtg            60
ctaacgattg agattgagca tgttgatgtt                                             90

<210> SEQ ID NO 37
<211> LENGTH: 55
<212> TYPE: DNA
<213> ORGANISM: unknown
<220> FEATURE:
<223> OTHER INFORMATION: YFP genomic target sequence

<400> SEQUENCE: 37
atgagttcca tggccaacct tagtcactac tttaggttat ggtttaatgt gttaa                 55

<210> SEQ ID NO 38
<211> LENGTH: 55
<212> TYPE: DNA
<213> ORGANISM: unknown
<220> FEATURE:
<223> OTHER INFORMATION: YFP genomic target sequence

<400> SEQUENCE: 38
atgagttcca tggccaacct tagtcactac tttaggttat ggtttaatgt gttaa                 55

<210> SEQ ID NO 39
<211> LENGTH: 20
<212> TYPE: DNA
<213> ORGANISM: artificial
<220> FEATURE:
<223> OTHER INFORMATION: YFP Shuttle MAGE plasmid

<400> SEQUENCE: 39
ttagtcacta ctttaggtta                                                        20

<210> SEQ ID NO 40
<211> LENGTH: 43
<212> TYPE: DNA
<213> ORGANISM: artificial
<220> FEATURE:
<223> OTHER INFORMATION: oligonucleotide primer

<400> SEQUENCE: 40
agataaatga tcccaacctt agtcactact ttgttttaga gct                              43

<210> SEQ ID NO 41
<211> LENGTH: 20
<212> TYPE: DNA
<213> ORGANISM: artificial
<220> FEATURE:
<223> OTHER INFORMATION: YFP Shuttle MAGE plasmid

<400> SEQUENCE: 41
ccaaccttag tcactacttt                                                        20
```

UNITED STATES PATENT AND TRADEMARK OFFICE
CERTIFICATE OF CORRECTION

PATENT NO. : 9,944,925 B2
APPLICATION NO. : 14/909184
DATED : April 17, 2018
INVENTOR(S) : Jay H. Konieczka et al.

Page 1 of 1

It is certified that error appears in the above-identified patent and that said Letters Patent is hereby corrected as shown below:

In the Specification

On Column 1, Line 14, please add the following subheading and paragraph after the subheading "PRIORITY" and before the subheading "FIELD OF THE INVENTION":

-- GOVERNMENT INTEREST
This invention was made with government support under Grant No. 1315692, and Grant No. 1430813, each awarded by the National Science Foundation (NSF). The government has certain rights in the invention. --

Signed and Sealed this
Twenty-fifth Day of August, 2020

Andrei Iancu
*Director of the United States Patent and Trademark Office*